United States Patent
Nishimura et al.

(10) Patent No.: US 10,128,456 B2
(45) Date of Patent: *Nov. 13, 2018

(54) ORGANIC ELECTROLUMINESCENCE ELEMENT, AND MATERIAL FOR ORGANIC ELECTROLUMINESCENCE ELEMENT

(71) Applicant: IDEMITSU KOSAN CO., LTD., Chiyoda-ku (JP)

(72) Inventors: Kazuki Nishimura, Sodegaura (JP); Toshinari Ogiwara, Sodegaura (JP); Kumiko Hibino, Sodegaura (JP); Tetsuya Inoue, Sodegaura (JP); Mitsunori Ito, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 683 days.

This patent is subject to a terminal disclaimer.

(21) Appl. No.: 14/353,774

(22) PCT Filed: Oct. 26, 2012

(86) PCT No.: PCT/JP2012/077690
§ 371 (c)(1),
(2) Date: Apr. 24, 2014

(87) PCT Pub. No.: WO2013/062075
PCT Pub. Date: May 2, 2013

(65) Prior Publication Data
US 2014/0306207 A1    Oct. 16, 2014

(30) Foreign Application Priority Data

Oct. 26, 2011 (JP) .................................. 2011-235491

(51) Int. Cl.
  *H01L 51/54* (2006.01)
  *C09K 11/06* (2006.01)
  (Continued)

(52) U.S. Cl.
  CPC ........ *H01L 51/5028* (2013.01); *C07D 401/10* (2013.01); *C07D 401/14* (2013.01);
  (Continued)

(58) Field of Classification Search
  CPC .. C07D 209/82; C07D 401/00; C07D 401/02; C07D 401/10; C07D 401/14; C07D 403/00; C07D 403/02; C07D 403/10; C07D 403/14; C07D 471/00; C07D 471/02; C07D 471/04; C07D 407/12; C07D 405/00; C07D 405/02; C07D 405/10; C07D 405/14; C07D 409/00; C07D 409/02; C07D 409/10; C07D 409/14; C07D 487/00; C07D 487/02; C07D 487/04; C07D 491/048; C07F 7/0812; H05B 33/10; C09K 11/06; C09K 2211/1007; C09K 2211/1011; C09K 2211/1029; C09K 2211/1044; C09K 2211/1088; C09K 2211/1092;
  (Continued)

(56) References Cited

U.S. PATENT DOCUMENTS

| | | | |
|---|---|---|---|
| 7,358,661 B2 | 4/2008 | Kuma | |
| 2006/0099447 A1* | 5/2006 | Lee | ...... H01L 51/5016 428/690 |
| 2010/0084966 A1* | 4/2010 | Otsu | ...... C07D 405/14 313/504 |

(Continued)

FOREIGN PATENT DOCUMENTS

| | | |
|---|---|---|
| JP | 09-003448 | 1/1997 |
| JP | 2000-173774 | 6/2000 |

(Continued)

OTHER PUBLICATIONS

Machine translation of KR2011-048840. Date of publication: May 12, 2011.*
International Search Report for corresponding International Application No. PCT/JP2012/077690, dated Jan. 22, 2013.
International Preliminary Report on Patentability, dated Apr. 29, 2014 and Written Opinion for Corresponding Application No. PCT/JP2012/077690 dated Jan. 22, 2013, 9 pages.
Information Offer Form dated Jan. 11, 2017 in Japanese Application No. 2013-540840.

*Primary Examiner* — Andrew K Bohaty
(74) *Attorney, Agent, or Firm* — Oblon, McClelland, Maier & Neustadt, L.L.P.

(57) ABSTRACT

The organic electroluminescence device includes an anode, a cathode, and at least an emitting layer between the anode and the cathode. The emitting layer includes a first host material, a second host material, and a phosphorescent dopant material. The first host material is a compound represented by a formula (1) below and the second host material is a compound represented by a formula (2) below.

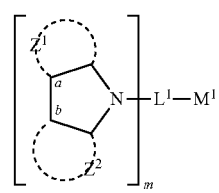

(1)

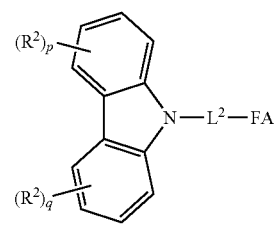

(2)

24 Claims, 5 Drawing Sheets

(51) Int. Cl.
*H01L 51/50* (2006.01)
*C07D 405/14* (2006.01)
*C07D 403/10* (2006.01)
*C07D 403/14* (2006.01)
*C07D 409/14* (2006.01)
*H01L 51/00* (2006.01)
*C07D 401/14* (2006.01)
*C07D 401/10* (2006.01)
*C07D 471/04* (2006.01)
*C07D 487/04* (2006.01)
*C07D 491/048* (2006.01)
*C07F 7/08* (2006.01)
*H05B 33/10* (2006.01)

(52) U.S. Cl.
CPC ......... *C07D 403/10* (2013.01); *C07D 403/14* (2013.01); *C07D 405/14* (2013.01); *C07D 409/14* (2013.01); *C07D 471/04* (2013.01); *C07D 487/04* (2013.01); *C07D 491/048* (2013.01); *C07F 7/0812* (2013.01); *C09K 11/06* (2013.01); *H01L 51/0052* (2013.01); *H01L 51/0054* (2013.01); *H01L 51/0067* (2013.01); *H01L 51/0072* (2013.01); *H01L 51/0073* (2013.01); *H01L 51/0074* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5016* (2013.01); *H01L 51/5044* (2013.01); *H01L 2251/5384* (2013.01)

(58) Field of Classification Search
CPC ............. H01L 51/0032; H01L 51/0052; H01L 51/0054; H01L 51/0067; H01L 51/0072; H01L 51/0073; H01L 51/0074; H01L 51/50; H01L 51/5012; H01L 51/5016; H01L 51/5024; H01L 51/5028; H01L 51/5044; H01L 2251/5384
USPC ....... 428/690, 691, 917, 411.4, 336; 427/58, 427/66; 313/500–512; 257/40, 88–104, 257/E51.001–E51.052; 252/301.16–301.35, 500
See application file for complete search history.

(56) References Cited

U.S. PATENT DOCUMENTS

| | | | |
|---|---|---|---|
| 2011/0272687 A1* | 11/2011 | Katakura | C07D 405/14 257/40 |
| 2012/0001158 A1* | 1/2012 | Asari | C07D 487/04 257/40 |
| 2012/0068170 A1* | 3/2012 | Pflumm | C07D 209/82 257/40 |

FOREIGN PATENT DOCUMENTS

| | | |
|---|---|---|
| JP | 2003-133075 A | 5/2003 |
| JP | 2005-255986 A | 9/2005 |
| JP | 2006-135295 | 5/2006 |
| JP | 2006-188493 | 7/2006 |
| JP | 2007-251097 | 9/2007 |
| JP | 2011-91355 A | 7/2009 |
| JP | 2009-267257 | 11/2009 |
| JP | 2011-051936 | 3/2011 |
| JP | 2011-509247 A | 3/2011 |
| JP | 2012-111853 | 6/2012 |
| WO | WO 2003/080760 | 10/2003 |
| WO | WO 2006/112265 A1 | 10/2006 |
| WO | WO 2007/063754 A1 | 6/2007 |
| WO | WO 2008/146839 A1 | 12/2008 |
| WO | WO2009/086028 A2 | 7/2009 |
| WO | WO2009/086028 A3 | 7/2009 |
| WO | WO 2009/136596 A1 | 11/2009 |
| WO | 2010/068865 | 6/2010 |
| WO | WO 2010090077 A1 * | 8/2010 ............ C07D 405/14 |
| WO | WO 2010/098246 | 9/2010 |
| WO | WO 2010/113755 A1 | 10/2010 |
| WO | WO 2010/134352 | 11/2010 |
| WO | WO 2010136109 A1 * | 12/2010 ............ C07D 209/82 |
| WO | WO 2011055934 A2 * | 5/2011 ............ C09K 11/06 |
| WO | WO 2011/081061 A1 | 7/2011 |
| WO | WO 2011/099374 A1 | 8/2011 |
| WO | WO 2011/122132 A1 | 10/2011 |
| WO | WO 2011/125680 A1 | 10/2011 |
| WO | WO 2012/153725 A | 11/2012 |

* cited by examiner

ORGANIC ELECTROLUMINESCENCE ELEMENT, AND MATERIAL FOR ORGANIC ELECTROLUMINESCENCE ELEMENT

CROSS-REFERENCE TO RELATED APPLICATIONS

This application is a National Stage of PCT/JP2012/077690, which was filed on Oct. 26, 2012. This application is based upon and claims the benefit of priority to Japanese Application No. 2011-235491, which was filed on Oct. 26, 2011.

TECHNICAL FIELD

The present invention relates to an organic electroluminescence device and a material for the organic electroluminescence device.

BACKGROUND ART

There has been known an organic electroluminescence device (hereinafter, referred to as an "organic EL device") that includes an emitting unit (in which an emitting layer is included) between an anode and a cathode and emits light using exciton energy generated by a recombination of holes and electrons that have been injected into the emitting layer.

A phosphorescent organic EL device using a phosphorescent dopant material as a luminescent material has been known as the organic EL device. The phosphorescent organic EL device can achieve a high luminous efficiency by using a singlet state and a triplet state of excited states of the phosphorescent dopant material. The reason is presumed as follows. When holes and electrons are recombined in the emitting layer, it is presumed that singlet excitons and triplet excitons are produced at a rate of 1:3 due to difference in spin multiplicity. Accordingly, luminous efficiency of the device using a phosphorescent material can reach three to four times as much as that of the device using only a fluorescent material.

Patent Literature 1 describes that a compound in which a nitrogen-containing heterocyclic group is bonded to an arylcarbazoyl group or a carbazoyl alkylene group is suitable to a phosphorescent host material usable in combination with a phosphorescent dopant material. An organic EL device driven at a low voltage and having a high color purity is obtainable by using the phosphorescent dopant material and this compound in the emitting layer.

CITATION LIST

Patent Literature

Patent Literature 1: International Publication No. WO2003/080760

SUMMARY OF THE INVENTION

Problems to be Solved by the Invention

However, since the phosphorescent host material described in Patent Literature 1 has a large HOMO, hole injection into the emitting layer is difficult. Accordingly, emission occurs at an interface of a hole transporting layer, resulting in a short lifetime.

An object of the invention is to provide a long-life organic electroluminescence device exhibiting a high luminous efficiency and a material for the organic electroluminescence device.

Means for Solving the Problems

After conducting concentrated studies in order to achieve the object, the inventors have found that a long-life organic electroluminescence device exhibiting a high luminous efficiency is obtainable in a combined use of a specific first host material and a specific second host material in an emitting layer. The invention has been achieved based on these findings.

An organic electroluminescence device according to an aspect of the invention includes an anode, a cathode, and at least an emitting layer between the anode and the cathode, the emitting layer including a first host material, a second host material, and a phosphorescent dopant material, in which the first host material is a compound represented by a formula (1) below and the second host material is a compound represented by a formula (2) below.

[Formula 1]

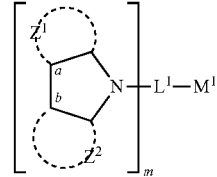

(1)

In the formula (1), $Z^1$ represents a cyclic structure fused at a of the formula (1) and represented by the formula (1-1) or (1-2); $Z^2$ represents a cyclic structure fused at b of the formula (1) and represented by the formula (1-1) or (1-2); at least one of $Z^1$ and $Z^2$ is represented by the formula (1-1); $M^1$ represents a substituted or unsubstituted nitrogen-containing heteroaromatic ring having 5 to 30 ring atoms; $L^1$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms; and m is 1 or 2.

[Formula 2]

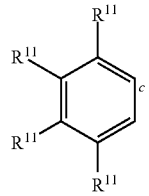

(1-1)

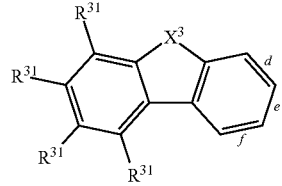

(1-2)

In the formulae (1-1) and (1-2): c, d, e, f are fused at a or b in the formula (1); $R^{11}$ and $R^{31}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms; a plurality of $R^{11}$ are mutually the same or different; a plurality of $R^{31}$ are mutually the same or different; adjacent groups of $R^{11}$ may be bonded with each other to form a ring; $X^3$ is a sulfur atom, an oxygen atom or $N-R^{32}$ or $C(R^{32})_2$; and $R^{32}$ represents the same as $R^{11}$ and $R^{31}$.

Herein, $N-R_2$ represents a bond of a single $R_2$ and a nitrogen atom (N) and $C(R_2)_2$ represents a bond of two $R_2$ and a carbon atom (C).

[Formula 3]

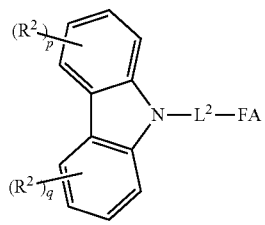

(2)

In the formula (2), $R^2$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

In the formula (2), p and q are independently an integer of 0 to 4; a plurality of $R^2$ are mutually the same or different.

Adjacent groups of $R^2$ may be bonded with each other to form a ring.

In the formula (2), $L^2$ represents a single bond or a linking group, the linking group being one or a combination of a substituted or unsubstituted aryl group having 6 to 30 ring carbon atoms, one or a combination of a substituted or unsubstituted heterocyclic group having 5 to 30 ring atoms, and a cycloalkyl group having 5 to 30 ring carbon atoms.

In the formula (2), FA represents a substituted or unsubstituted fused aromatic cyclic group having 10 to 30 ring carbon atoms, or a substituted or unsubstituted fused aromatic heterocyclic group having 9 to 30 ring atoms.

In the organic electroluminescence device according to the above aspect of the invention, the first host material is preferably represented by a formula (3) below.

[Formula 4]

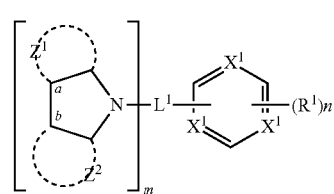

(3)

In the formula (3): $Z^1$ represents a cyclic structure fused at a of the formula (3) and represented by the formula (1-1) or a formula (1-2); $Z^2$ represents a cyclic structure fused at b of the formula (3) and represented by the formula (1-1) or (1-2); at least one of $Z^1$ and $Z^2$ is represented by the formula (1-1); $L^1$ represents the same as $L^1$ of the formula (1); $X^1$ is a nitrogen atom or $C-R^{10}$ and at least one of a plurality of $X^1$ is a nitrogen atom; $R^1$ and $R^{10}$ represent the same as $R^{11}$ of the formula (1-1); and m and n each are an integer of 1 to 2.

In the formulae (1-1) and (1-2), c, d, e, f are fused at a or b of the formula (3) in the formulae (1-1) and (1-2).

In the organic electroluminescence device according to the above aspect of the invention, the first host material is more preferably represented by a formula (4) below.

[Formula 4]

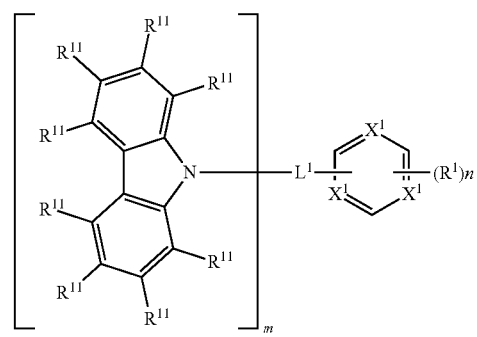

(4)

In the formula (4), $L^1$ represents the same as $L^1$ of the formula (1); $X^1$ is a nitrogen atom or $C-R^{10}$ and at least one of a plurality of $X^1$ is a nitrogen atom; $R^1$, $R^{10}$ and $R^{11}$ represent the same as $R^{11}$ of the formula (1-1); and m and n each are an integer of 1 to 2.

In the organic electroluminescence device according to the above aspect of the invention, the first host material is more preferably represented by a formula (5) below.

[Formula 6]

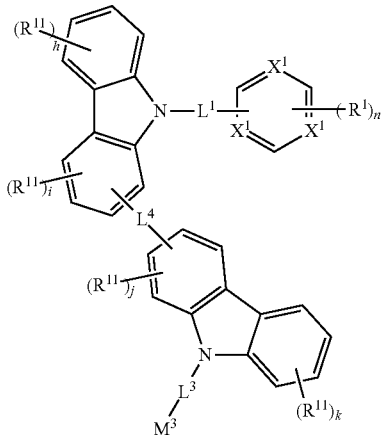

(5)

[Formula 8]

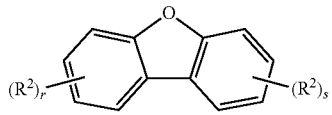

(2-1)

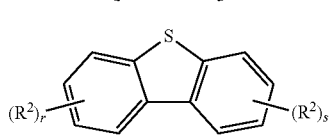

(2-2)

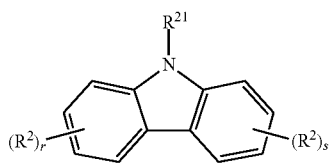

(2-3)

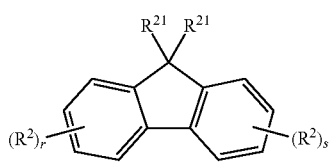

(2-4)

In the formula (5): $L^1$ and $R^1$ respectively represent the same as $L^1$ and $R^1$ of the formula (1); $R^{11}$ represents the same as $R^{11}$ of the formula (1-1); $L^3$ and $L^4$ represent the same as $L^1$ of the formula (1); $X^1$ is a nitrogen atom or C—$R^{10}$ and at least one of a plurality of $X^1$ is a nitrogen atom; $R^{10}$ represents the same as $R^{11}$ of the formula (1-1); n is an integer of 1 to 2; $M^3$ represents a substituted or unsubstituted aryl group having 6 to 30 ring carbon atoms, or a substituted or unsubstituted heterocyclic group having 5 to 30 ring atoms; h and k are an integer of 0 to 4; and i and j are an integer of 0 to 3.

In the organic electroluminescence device according to the above aspect of the invention, the second host material is preferably represented by the formula (2) in which FA is a substituted or unsubstituted fused aromatic cyclic group having 2 to 5 fused rings, or a substituted or unsubstituted fused aromatic heterocyclic group having 2 to 5 fused rings.

In the organic EL device according to the above aspect of the invention, the second host material is preferably represented by the formula (2) in which FA is represented by a formula (2-4) below.

[Formula 7]

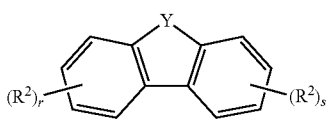

(2-A)

In the formula (2-A): Y represents O, S, $NR^{21}$ or $C(R^{21})_2$; and $R^2$ and $R^{21}$ represent the same as $R^2$ of the formula (2).

However, one of $R^2$ is a single bond to be bonded with $L^2$ in the formula (2). When Y is $C(R^{21})_2$, a plurality of $R^{21}$ are mutually the same or different.

r and s are an integer of 0 to 4.

In the organic EL device according to the above aspect of the invention, the second host material is preferably represented by the formula (2) in which FA is represented by any one of formulae (2-1) to (2-4).

In the formulae (2-1) to (2-4), $R^2$ and $R^{21}$ represent the same as $R^2$ of the formula (2).

However, one of $R^2$ is a single bond to be bonded with $L^2$ in the formula (2).

r and s are an integer of 0 to 4.

In the organic EL device according to the above aspect of the invention, the second host material is preferably represented by the formula (2) in which FA is represented by the formula (2-1) or (2-2).

In the organic EL device according to the above aspect of the invention, an emission peak wavelength of the phosphorescent dopant material is preferably in a range of 490 nm to 700 nm.

A material for an organic electroluminescence device according to another aspect of the invention includes a compound represented by the formula (1) and a compound represented by the formula (2).

In the material for the organic electroluminescence device according to the above aspect of the invention, the compound represented by the formula (1) is preferably represented by the formula (3).

Further, in the material for the organic electroluminescence device according to the above aspect of the invention, the compound represented by the formula (1) is preferably represented by the formula (4).

In the material for the organic electroluminescence device according to the above aspect of the invention, the compound represented by the formula (1) is more preferably represented by the formula (5).

In the material for the organic electroluminescence device according to the above aspect of the invention, the second host material is preferably represented by the formula (2) in which FA is a substituted or unsubstituted fused aromatic cyclic group having 2 to 5 fused rings, or a substituted or unsubstituted fused aromatic heterocyclic group having 2 to 5 fused rings.

In the material for the organic EL device according to the above aspect of the invention, the second host material is preferably represented by the formula (2) in which FA is represented by a formula (2-A) below.

In the material for the organic electroluminescence device according to the above aspect of the invention, the second host material is preferably represented by the formula (2) in which FA is represented by any one of the formulae (2-1) to (2-4).

In the material for the organic EL device according to the above aspect of the invention, the second host material is more preferably represented by the formula (2) in which FA is represented by the formula (2-1) or (2-2).

According to the invention, a long-life organic electroluminescence device exhibiting a high luminous efficiency and a material for the organic electroluminescence device can be provided.

DESCRIPTION OF EMBODIMENTS

First Exemplary Embodiment
Arrangement of Organic EL Device

Arrangement(s) of an organic electroluminescence device (hereinafter referred to as an organic EL device) of the invention will be described below.

The following are representative arrangement examples of the organic EL device:
(1) anode/emitting layer/cathode;
(2) anode/hole injecting layer/emitting layer/cathode;
(3) anode/emitting layer/electron injecting•transporting layer/cathode;
(4) anode/hole injecting layer/emitting layer/electron injecting•transporting layer/cathode; and
(5) anode/hole injecting•transporting layer/emitting layer/ electron injecting•transporting layer/cathode.

While the arrangement (5) is preferably used among the above, the arrangement of the invention is not limited to the above arrangements.

Note that the aforementioned "emitting layer" is an organic layer including a host material and a dopant material typically through a doping system. Typically, the host material promotes a recombination of electrons and holes and transmits exciton energy generated by the recombination to the dopant material. The dopant material is preferably a compound having a high quantum yield. The dopant material exhibits a high luminescent performance after receiving exciton energy from the host material.

The "hole injecting/transporting layer (or hole injecting•transporting layer)" means "at least one of a hole injecting layer and a hole transporting layer" while the "electron injecting/transporting layer (or electron injecting•transporting layer)" means "at least one of an electron injecting layer and an electron transporting layer."

Herein, when the hole injecting layer and the hole transporting layer are provided, the hole injecting layer is preferably closer to the anode. When the electron injecting layer and the electron transporting layer are provided, the electron injecting layer is preferably closer to the cathode.

Figure 1:
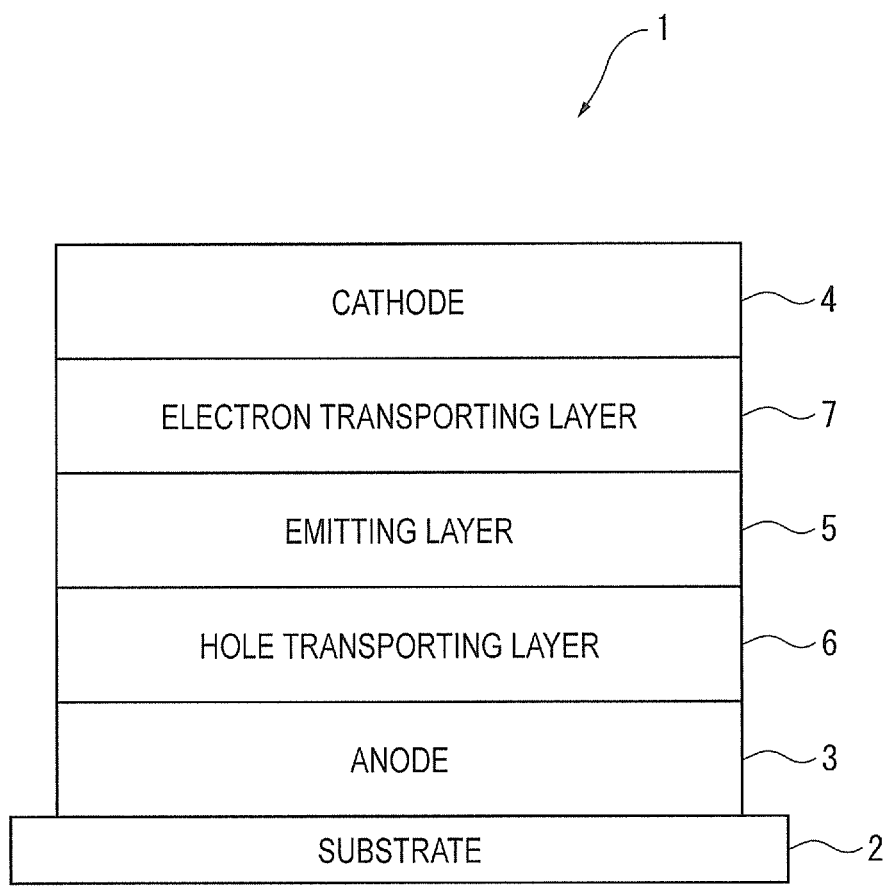
FIG. 1 schematically shows an exemplary arrangement of an organic EL device according to a first exemplary embodiment of the invention.

Next, an organic EL device 1 according to a first exemplary embodiment will be shown in FIG. 1.

The organic EL device 1 includes a transparent substrate 2, an anode 3, a cathode 4, a hole transporting layer 6, an emitting layer 5 and an electron transporting layer 7.

The hole transporting layer 6, the emitting layer 5, the electron transporting layer 7 and the cathode 4 are sequentially laminated on the anode 3.

Emitting Layer

The emitting layer 5 contains a first host material, a second host material and a phosphorescent dopant material.

It is preferable that the first host material is set in a range of 10 mass % to 90 mass %, the second host material is set in a range of 10 mass % to 90 mass %, and the phosphorescent dopant material is set in a range of 0.1 mass % to 30 mass % such that a total mass percentage of the materials contained in the emitting layer 5 is equal to 100 mass %. More preferably, the first host material is set in a range of 40 mass % to 60 mass %.

First Host Material

As the first host material used in the organic EL device of this exemplary embodiment, a compound represented by the above formula (1) is usable.

The "nitrogen-containing heteroaromatic ring" represented by $M^1$ in the formula (1) includes an azine ring.

Examples of the nitrogen-containing heteroaromatic ring represented by $M^1$ in the formula (1) are pyridine, pyrimidine, pyrazine, triazine, aziridine, azaindolizine, indolizine, imidazole, indole, isoindole, indazole, purine, pteridine, β-carboline, naphthyridine, quinoxaline, terpyridine, bipyridine, acridine, phenanthroline, phenazine and imidazopyridine.

Particularly, pyridine, pyrimidine and triazine are preferable. The first host material is preferably represented by the formula (3).

Here, a compound to which the cyclic structures represented by the formulae (1-1) and (1-2) are fused at a and b in the formula (3) is exemplified by compounds represented by the following formulae.

[Formula 9]

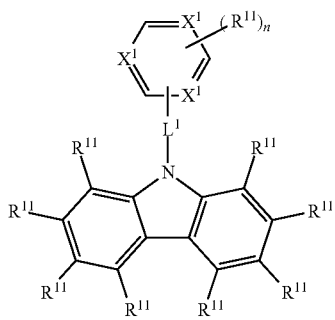

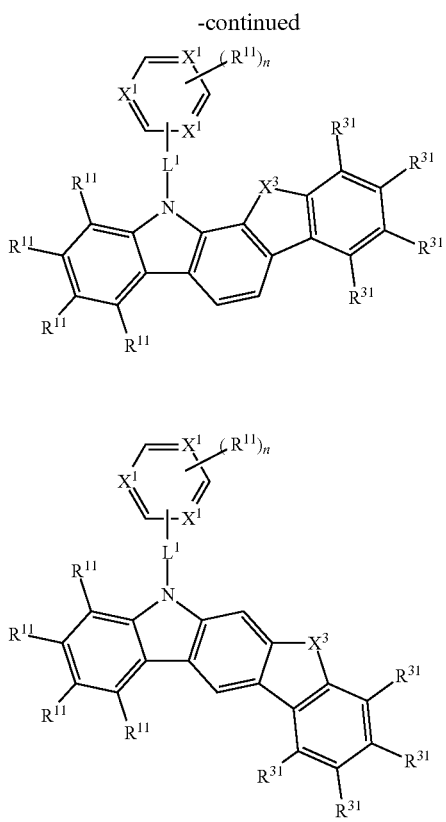

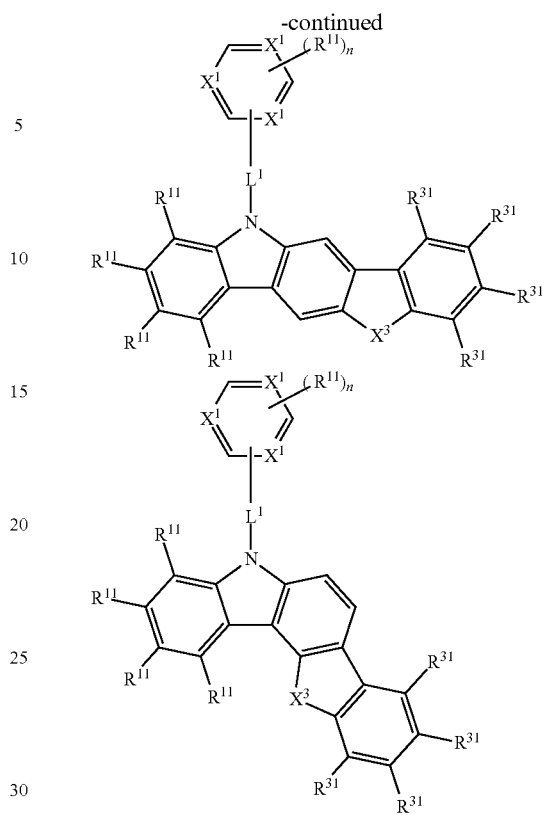

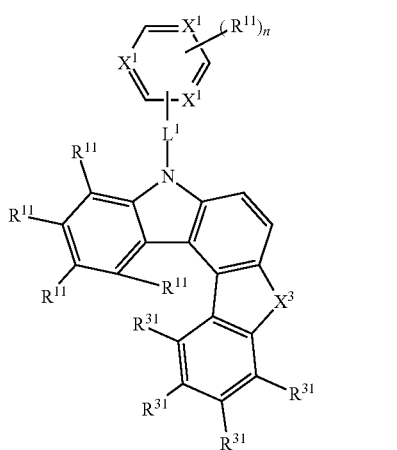

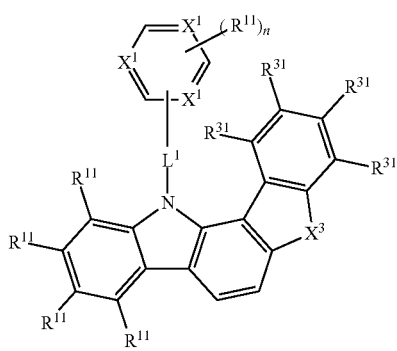

The first host material is more preferably represented by the formula (4), particularly preferably represented by the formula (5).

Groups represented by $R^1$, $R^{10}$ to $R^{11}$ and $R^{31}$ to $R^{32}$ in the formulae (1), (3) to (5), (1-1) and (1-2) will be described.

Examples of the aryl group having 6 to 30 ring carbon atoms are a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphehyl-3-yl group, a p-terphenyl-2-yl group, an m-quarterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, and a 4"-t-butyl-p-terphenyl-4-yl group.

The aryl group preferably has 6 to 20 ring carbon atoms, more preferably 6 to 12 ring carbon atoms. Among the aryl group, a phenyl group, a biphenyl group, a naphthyl group, phenanthryl group, a terphenyl group and a fluorenyl group are particularly preferable. With respect to a 1-fluorenyl group, a 2-fluorenyl group, a 3-fluorenyl group and a 4-fluorenyl group, a carbon atom at a position 9 is preferably substituted by a substituted or unsubstituted alkyl group having 1 to 30 carbon atoms.

Examples of the heterocyclic group having 5 to 30 ring atoms are a pyroryl group, a pyrazinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiophenyl group, and a group formed from a pyridine ring, a pyrazine ring, a pyrimidine ring, a pyridazine ring, a triazine ring, an indol ring, a quinoline ring, an acridine ring, a pyrrolidine ring, a dioxane ring, a piperidine ring, a morpholine ring, a piperadine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyrane ring and a dibenzofuran ring.

More specifically, the examples of the heterocyclic group having 5 to 30 ring atoms include a 1-pyroryl group, a 2-pyroryl group, a 3-pyroryl group, a pyrazinyl group, a 2-pyridinyl group, a 2-pyrimidinyl, a 4-pyrimidinyl, a 5-pyrimidinyl group, a 6-pyrimidinyl group, a 1,2,3-triazine-4-yl group, a 1,2,4-triazine-3-yl group, a 1,3,5-triazine-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, azacarbazolyl-8-yl group, an azacarbazolyl-9-yl group, a 1-phenanthrydinyl group, a 2-phenanthrydinyl group, a 3-phenanthrydinyl group, a 4-phenanthrydinyl group, a 6-phenanthrydinyl group, a 7-phenanthrydinyl group, an 8-phenanthrydinyl group, a 9-phenanthrydinyl group, a 10-phenanthrydinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group and a 4-germafluorenyl group.

The heterocyclic group preferably has 5 to 20 ring atoms, more preferably 5 to 14 ring atoms. Among the above heterocyclic group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-carbazolyl group, a 2-carbazolyl group, a 3-carbazolyl group, a 4-carbazolyl group, and a 9-carbazolyl group are preferable. With respect to a 1-carbazolyl group, a 2-carbazolyl group, a 3-carbazolyl group, and a 4-carbazolyl group, a nitrogen atom at a position 9 is preferably substituted by a substituted or unsubstituted aryl group having 6 to 30 ring carbon atoms or a substituted or unsubstituted heterocyclic group having 5 to 30 ring atoms.

The alkyl group having 1 to 30 carbon atoms may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group and 1,2,3-trinitropropyl group.

Examples of the cyclic alkyl group (cycloalkyl group) are a cyclopropyl group, a cyclobutyl group, a cyclopentyl group, a cyclohexyl group, a 4-methylcyclohexyl group, a 3,5-tetramethylcyclohexyl group, a cycloheptyl group, a cyclooctyl group, a 1-adamantyl group, a 2-adamantyl group, a 1-norbornyl group, and a 2-norbornyl group.

The linear or branched alkyl group preferably has 1 to 10 carbon atoms, more preferably 1 to 6 ring atoms. Among the linear or branched alkyl group, a methyl group, an ethyl group, a propyl group, an isopropyl group, an n-butyl group, an s-butyl group, an isobutyl group, a t-butyl group, an n-pentyl group and an n-hexyl group are preferable.

The cycloalkyl group preferably has 3 to 10 ring carbon atoms, more preferably 5 to 8 ring carbon atoms. Among the cycloalkyl group, a cyclopentyl group and a cyclohexyl group are preferable.

A halogenated alkyl group provided by substituting an alkyl group with a halogen atom is exemplified by one provided by substituting an alkyl group having 1 to 30 carbon atoms with one or more halogen groups. Examples of the halogenated alkyl group are a fluoromethyl group, a difluoromethyl group, a trifluoromethyl group, a fluoroethyl group and a trifluoromethylethyl group.

The alkenyl group having 2 to 30 carbon atoms may be linear, branched or cyclic. Examples of alkenyl group having 2 to 30 carbon atoms are a vinyl group, a propenyl group, a butenyl group, an oleyl group, an eicosapentaenyl group, a docosahexaenoyl group, a styryl group, a 2,2-diphenylvinyl group, a 1,2,2-triphenylvinyl group and a 2-phenyl-2-propenyl group. Among the alkenyl group, the vinyl group is preferable.

The alkynyl group having 2 to 30 carbon atoms may be linear, branched or cyclic. Examples of the alkynyl group having 2 to 30 carbon atoms are an ethynyl group, a propynyl group and a 2-phenylethynyl group. Among the alkenyl group, the ethynyl group is preferable.

The alkylsilyl group having 3 to 30 carbon atoms is exemplified by an alkylsilyl group having the alkyl group listed as the examples of the alkyl group having 1 to 30 carbon atoms. Specifically, examples of the alkylsilyl group are a trimethylsilyl group, a triethylsilyl group, a tri-n-butylsilyl group, a tri-n-octylsilyl group, a triisobutylsilyl group, a dimethylethylsilyl group, a dimethylisopropylsilyl group, a dimethyl-n-propylsilyl group, a dimethyl-n-butylsilyl group, a dimethyl-t-butylsilyl group, a diethylisopropylsilyl group, a vinyldimethylsilyl group, a propyldimethylsilyl group and triisopropylsilyl group. The three alkyl groups may be mutually the same or different.

Examples of the arylsilyl group having 6 to 30 ring carbon atoms are a dialkylarylsilyl group, an alkyldiarylsilyl group and a triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms. The two alkyl groups may be mutually the same or different.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms. The two aryl groups may be mutually the same or different.

The triarylsilyl group is exemplified by a triarylsilyl group including three of the aryl group listed as the examples of the aryl group having 6 to 30 ring carbon atoms. The triarylsilyl group preferably has 18 to 30 carbon atoms. The three aryl groups may be mutually the same or different.

Examples of the arylsilyl group are a phenyldimethylsilyl group, a diphenylmethylsilyl group, a diphenyl-t-butylsilyl group and a triphenylsilyl group.

The alkoxy group having 1 to 30 carbon atoms is represented by —OY. Y is exemplified by the alkyl group having 1 to 30 carbon atoms. The alkoxy group is preferably an alkoxy group having 1 to 6 carbon atoms, examples of which are a methoxy group, an ethoxy group, a propoxy group, a butoxy group, a pentyloxy group, and a hexyloxy group.

A halogenated alkoxy group provided by substituting an alkoxy group with a halogen atom is exemplified by one provided by substituting an alkoxy group having 1 to 30 carbon atoms with one or more halogen groups.

The aralkyl group having 6 to 30 ring carbon atoms is represented by —Y—Z. Y is exemplified by an alkylene group formed from the alkyl group having 1 to 30 carbon atoms. Z is exemplified by the aryl group having 6 to 30 ring carbon atoms. The aralkyl group is preferably an aralkyl group having 7 to 30 carbon atoms, in which an aryl portion has 6 to 30 carbon atoms, preferably 6 to 20 carbon atoms, more preferably 6 to 12 carbon atoms, and an alkyl portion has 1 to 30 carbon atoms, preferably 1 to 20 carbon atoms, more preferably 1 to 10 carbon atoms, further preferably 1 to 6 carbon atoms. Examples of the aralkyl group include: a benzyl group, a 2-phenylpropane-2-yl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrorylmethyl group, a 2-(1-pyroryl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group and a 1-chloro-2-phenylisopropyl group.

The aryloxy group having 6 to 30 ring carbon atoms is represented by —OZ. Z is exemplified by the aryl group having 6 to 30 ring carbon atoms or a monocyclic group and a fused cyclic group described below. The aryloxy group is exemplified by a phenoxy group.

Examples of the halogen atom are a fluorine atom, a chlorine atom, a bromine atom and a iodine atom, among which the fluorine atom is preferable.

The aryl group having 6 to 30 ring carbon atoms and the heterocyclic group having 5 to 30 ring carbon atoms, which are represented by $L^1$, $L^3$ and $L^4$ in the above formulae (1) and (3) to (5), are exemplified by a divalent group formed from the above groups.

Examples of the cycloalkyl group having 5 to 30 ring carbon atoms are a cyclopentylene group, a cyclohexylene group, and a cyclohepthylene group.

The aryl group having 6 to 30 ring carbon atoms and the heterocyclic group having 5 to 30 ring carbon atoms, which are represented by $M^3$ in the above formula (5), are exemplified by the above groups.

In the invention, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, an unsaturated ring, or an aromatic ring.

Examples of a substituent which may be used in a case of being "substituted or unsubstituted" are an hydroxyl group, a nitro group and a carboxy group in addition to an aryl group, a heterocyclic group, an alkyl group (a linear or branched alkyl group, a cycloalkyl group and a halogenated alkyl group), an alkenyl group, an alkynyl group, an alkylsilyl group, an arylsilyl group, an alkoxy group, a halogenated alkoxy group, an aralkyl group, an aryloxy group, a halogen atom, and a cyano group as described above. Among the above substituents, an aryl group, a heterocyclic group, an alkyl group, a halogen atom, an alkylsilyl group, an arylsilyl group and a cyano group are preferable. More preferable substituents are one listed as the preferable substituents described for each substituent. The substituents may be further substituted by the aforementioned substituents.

The same applies to the substituents of "substituted or unsubstituted" in compounds or a partial structure thereof described below.

In the invention, a hydrogen atoms encompasses isotopes having different numbers of neutrons, specifically, protium, deuterium and tritium.

Examples of the compounds represented by any one of the formulae (1) to (5) are as follows. Note that a bond without a formula (e.g., Ph, CN and a benzene ring) at an end represents a methyl group in the following structures.

[Formula 10]

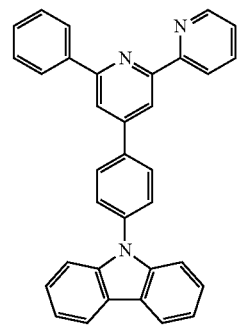

(A1)

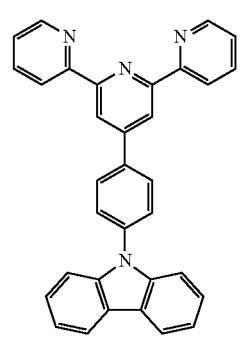

(A2)

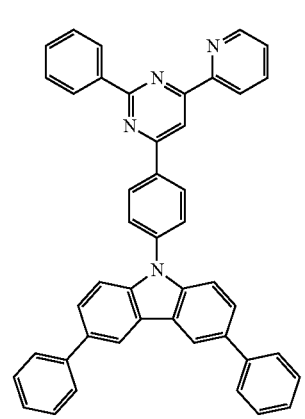

(A3)

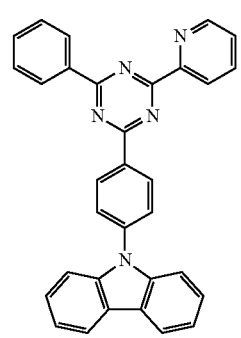

(A4)

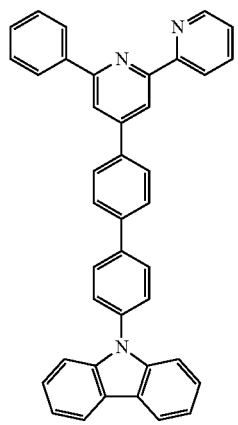
(A7)
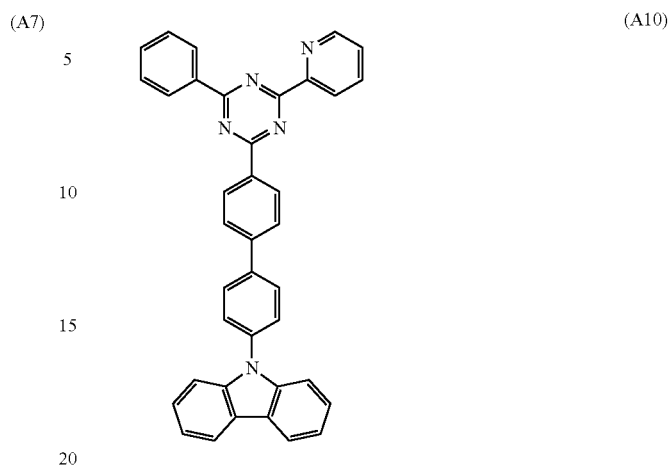
(A10)
(A8)
(A13)
(A9)
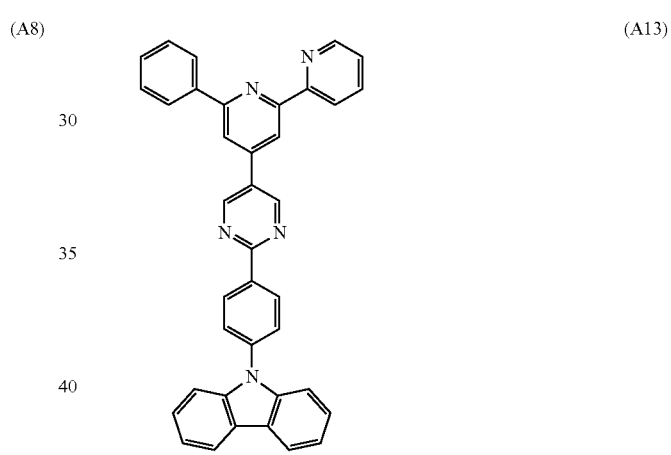
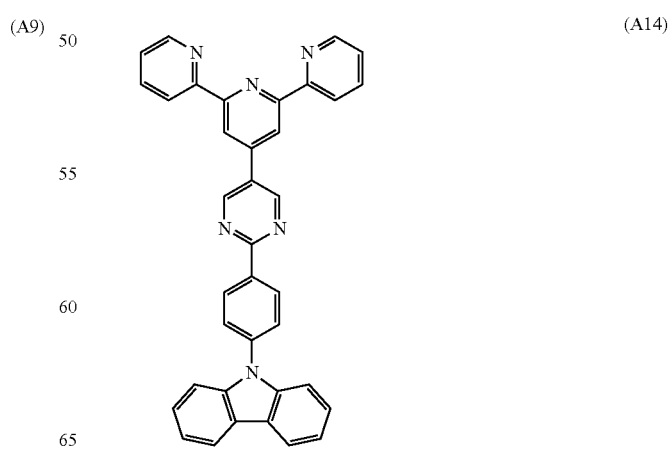
(A14)

(A15)
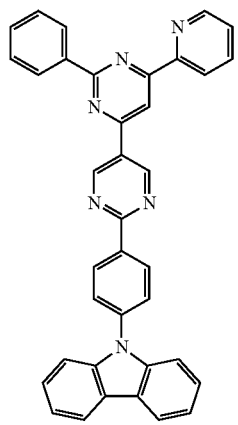
(A16)
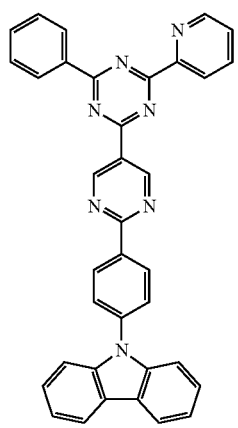
(A19)
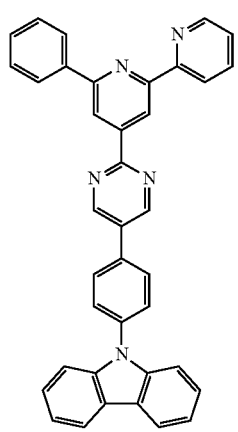
(A20)
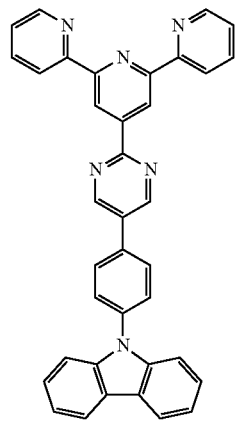
(A21)
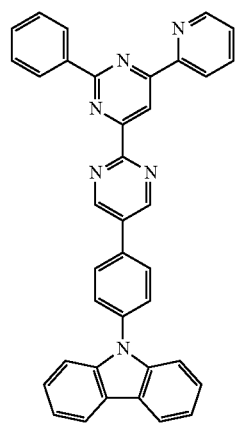
(A22)
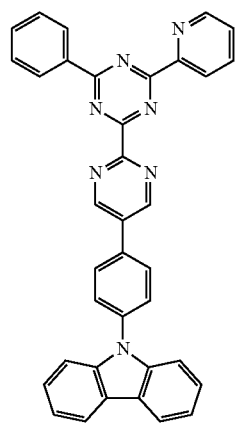
[Formula 11]
(A31)
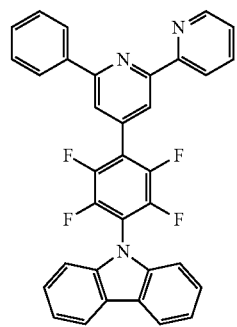

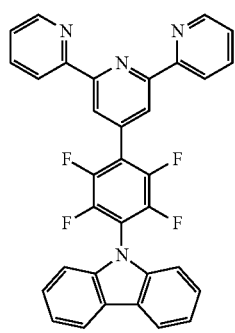 (A32)
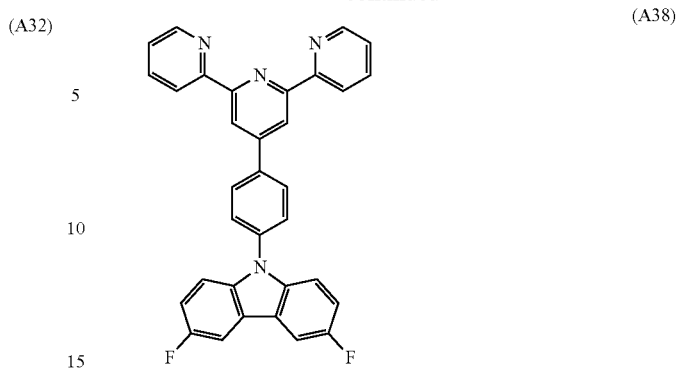 (A38)
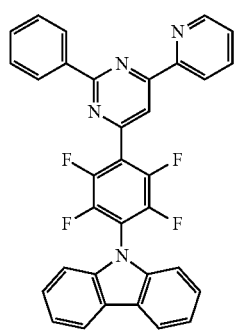 (A33)
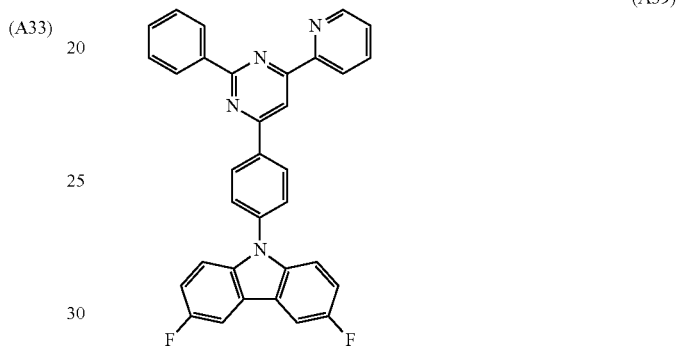 (A39)
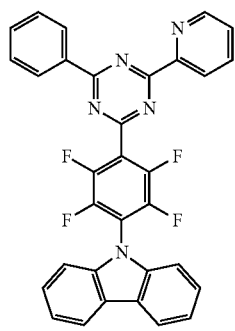 (A34)
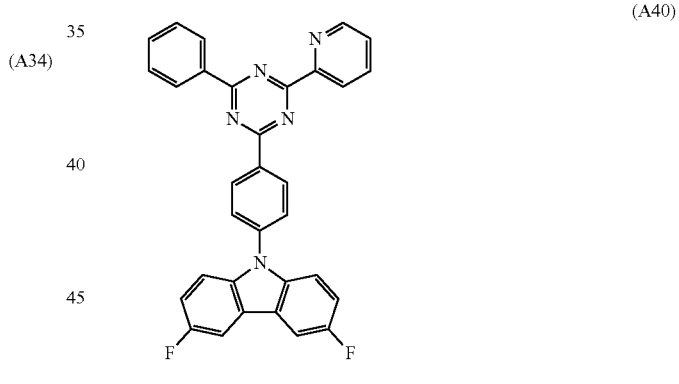 (A40)
[Formula 12]
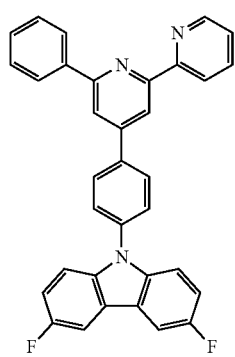 (A37)
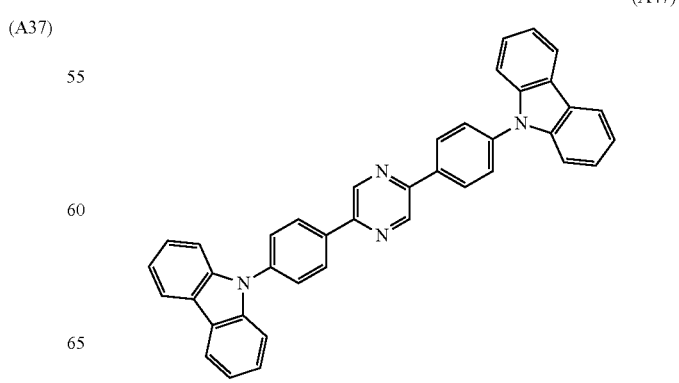 (A47)

(A48) 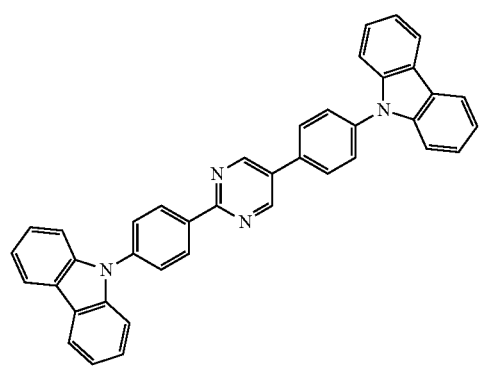
(A49) 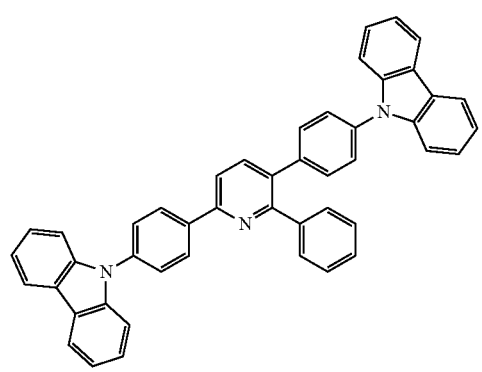
(A50) 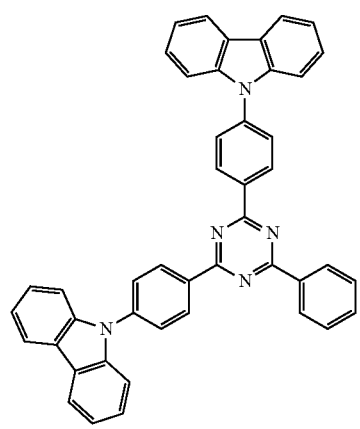
(A51) 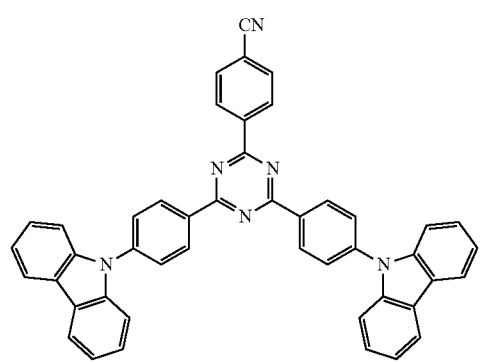
(A52) 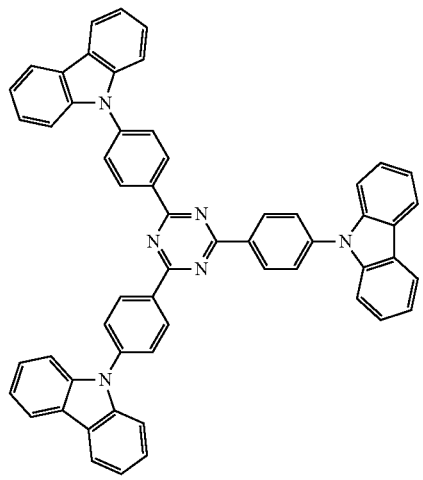
(A53) 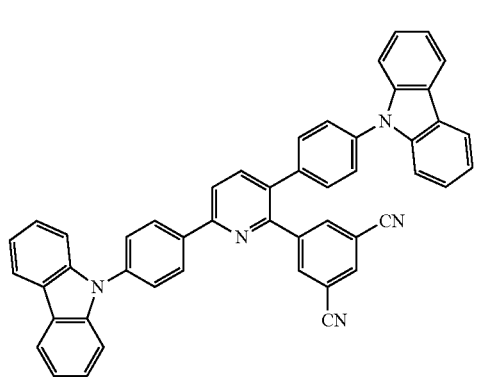
(A54) 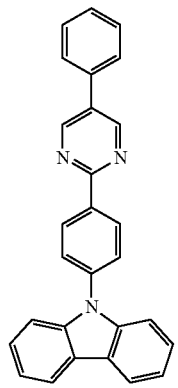
(A55) 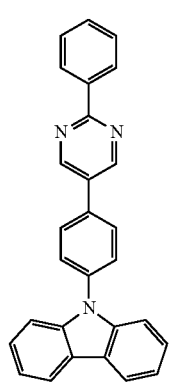

(A56)
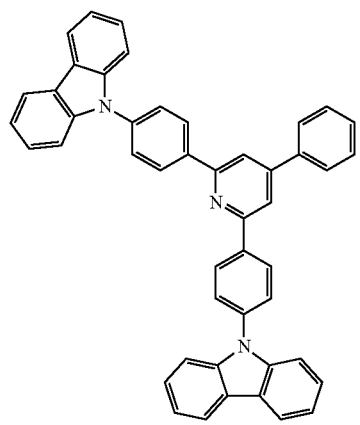
(A57)
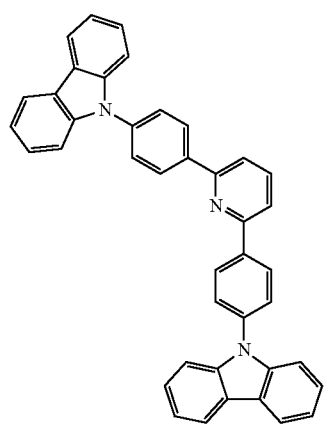
[Formula 13]
(A59)
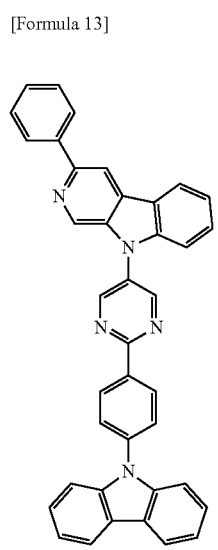
(A62)
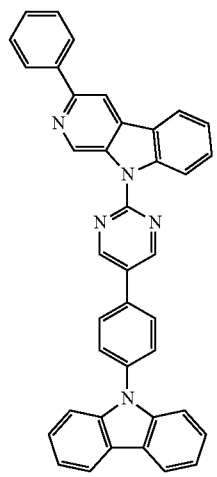
(A64)
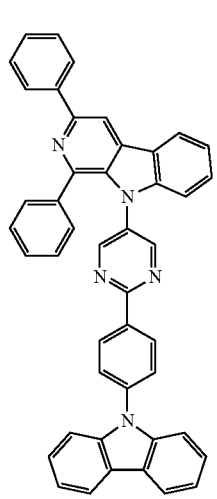
(A67)
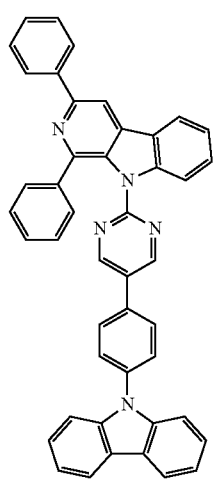

[Formula 14]
(A68)
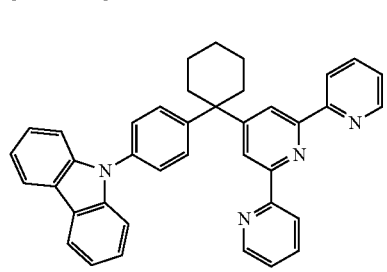
(A71)
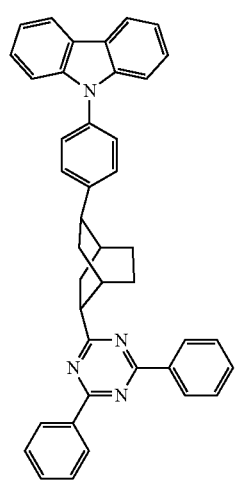
[Formula 15]
(A72)
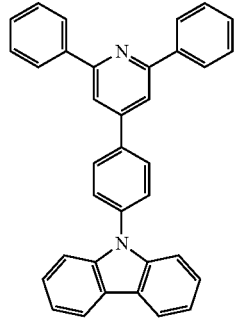
(A73)
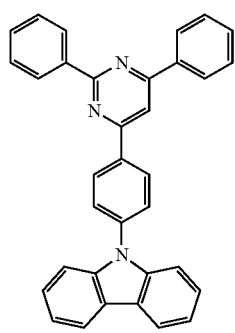
(A74)
(A75)
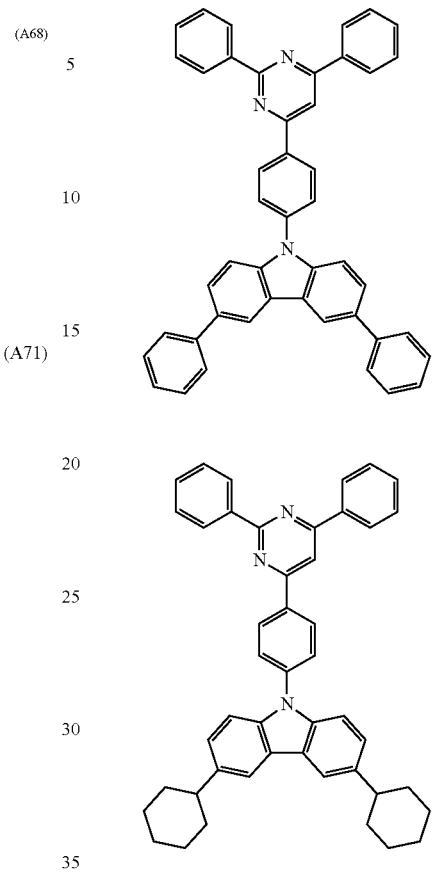
(A76)
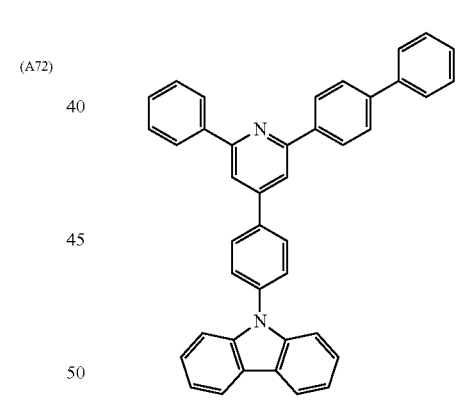
(A77)
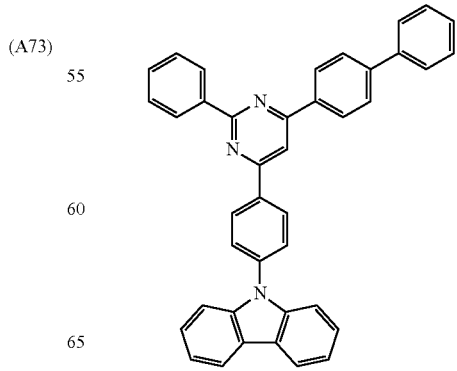

(A78) 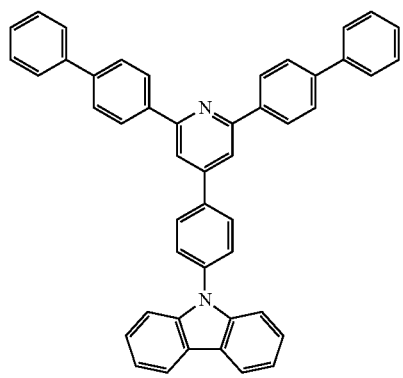
(A79) 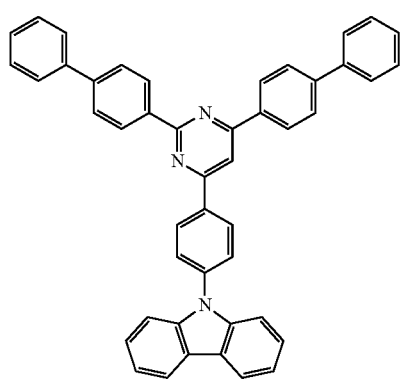
(A80) 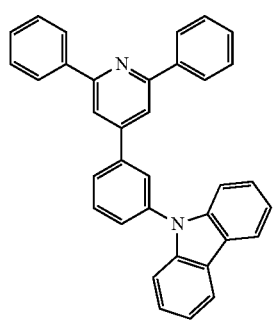
(A81) 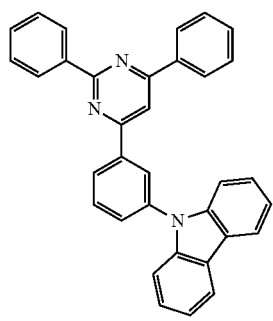
(A82) 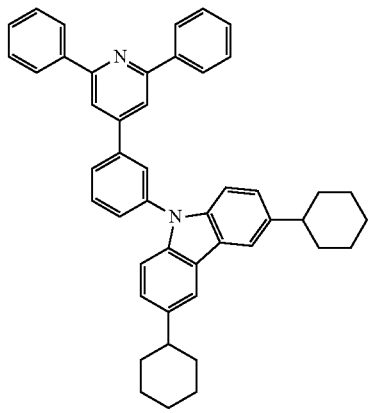
(A83) 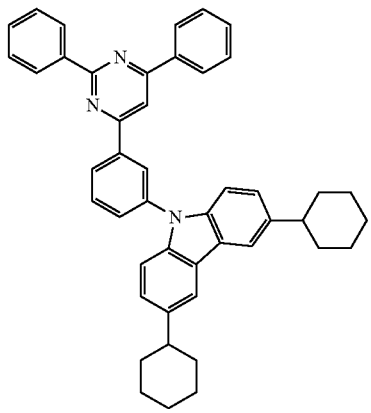
(A84) 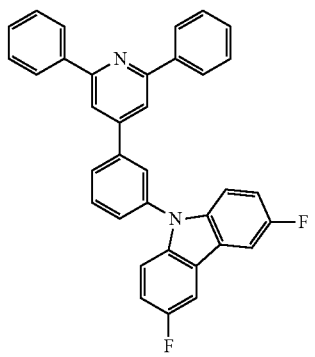
[Formula 16]
(A93) 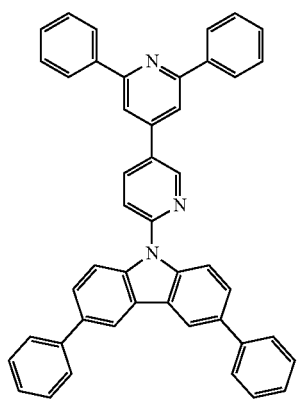

(A94)
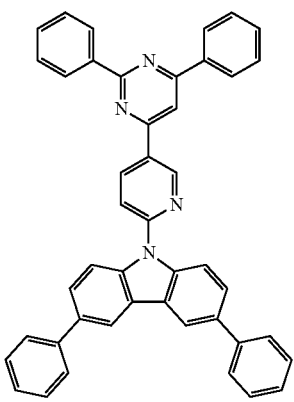
(A95)
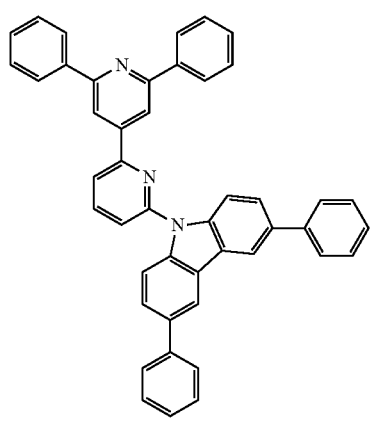
(A96)
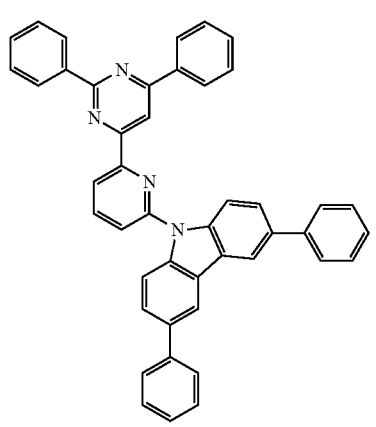
(A97)
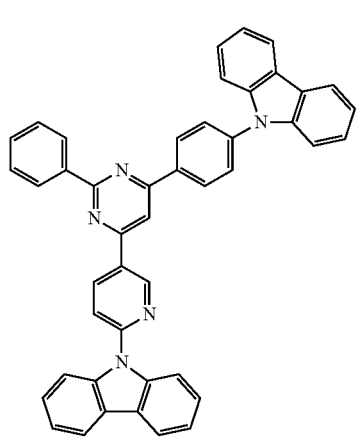
[Formula 17]
(A98)
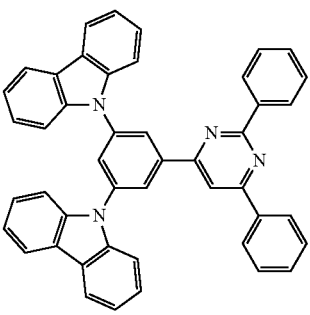
(A99)
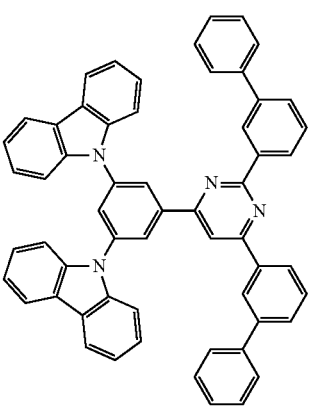
(A100)
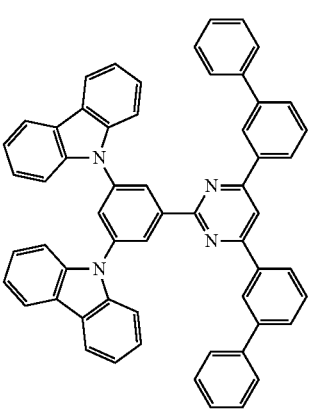
(A105)
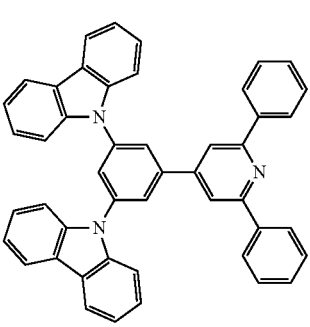

-continued
(A106)
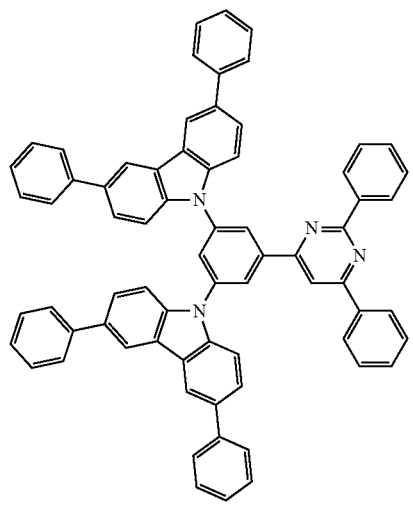
[Formula 18]
(A110)
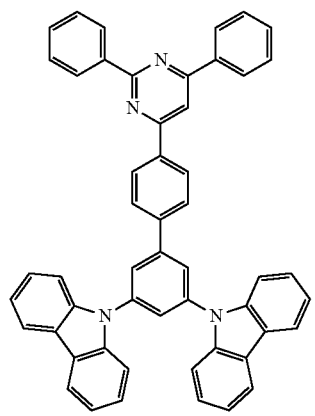
(A111)
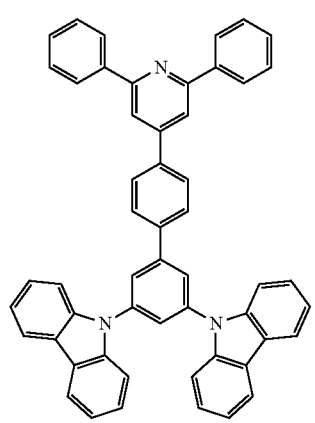
-continued
(A113)
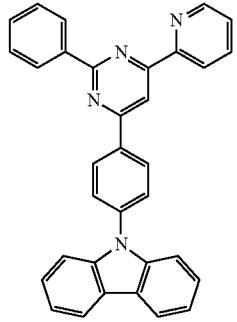
(A114)
[Formula 19]
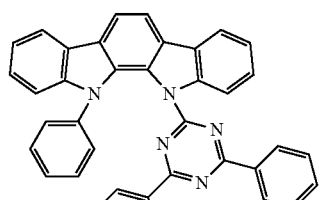
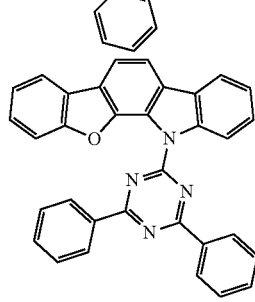
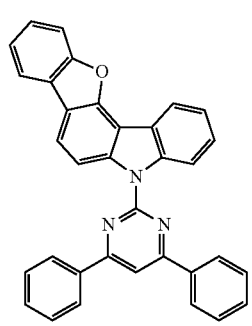

[Formula 20]
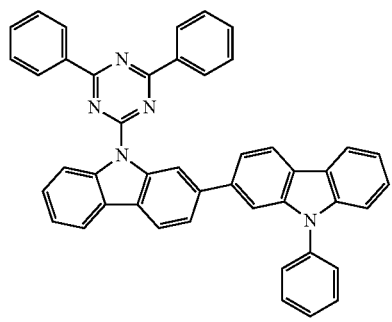
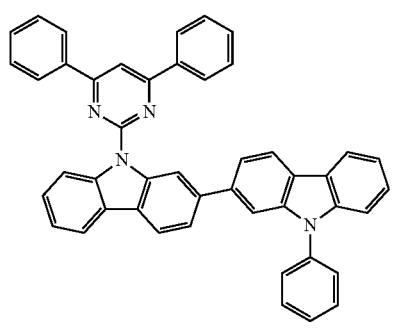
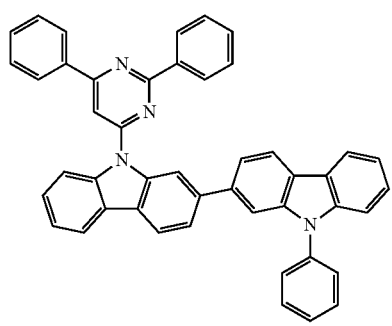
[Formula 21]
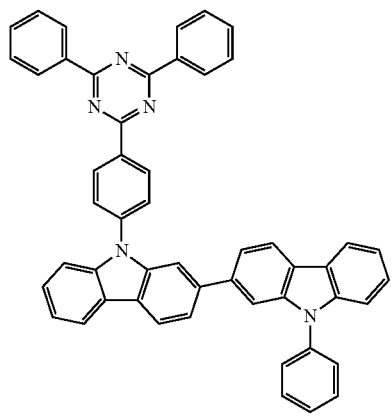
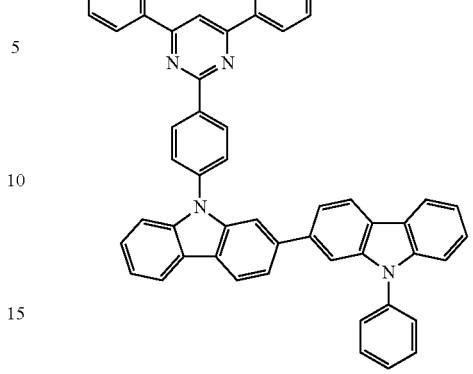
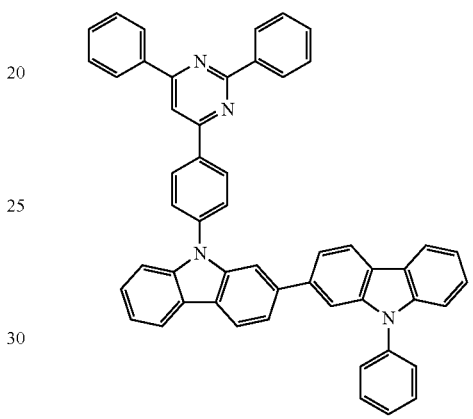
[Formula 22]
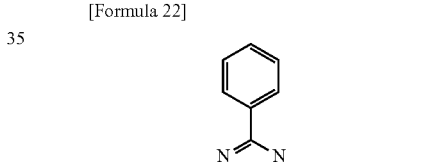
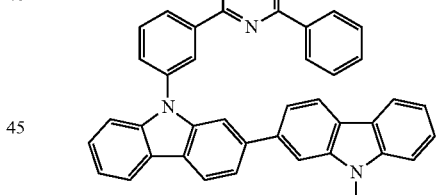

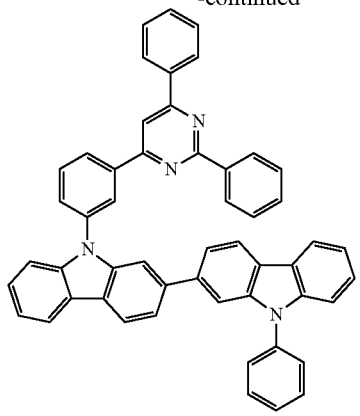
[Formula 23]
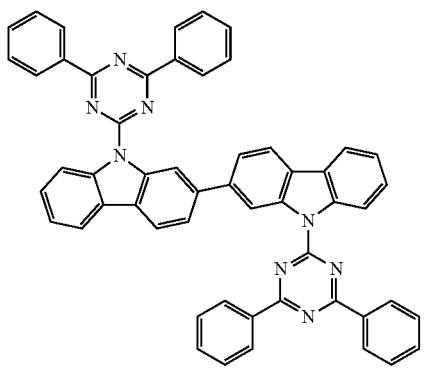
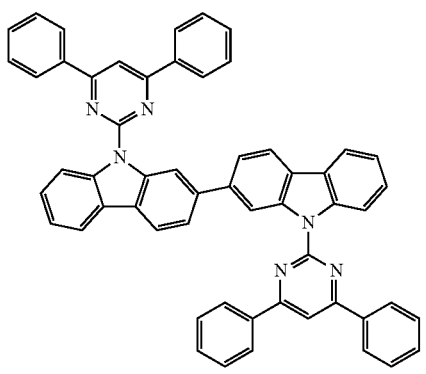
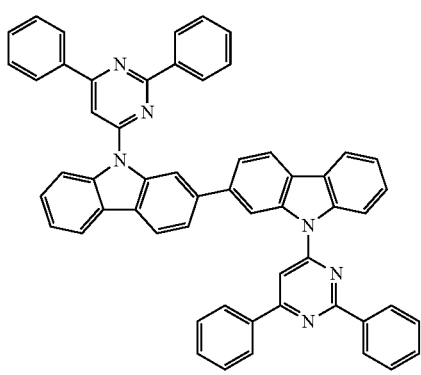
[Formula 24]
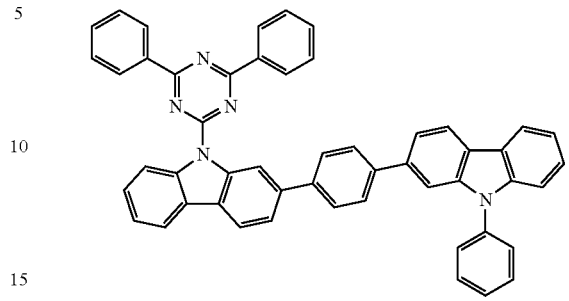
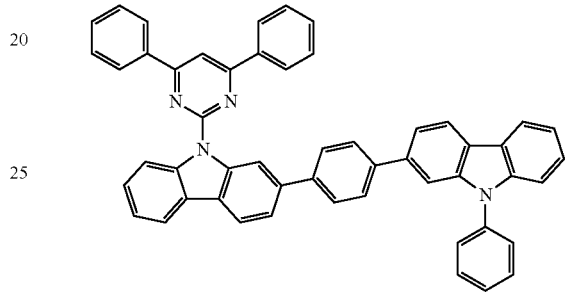
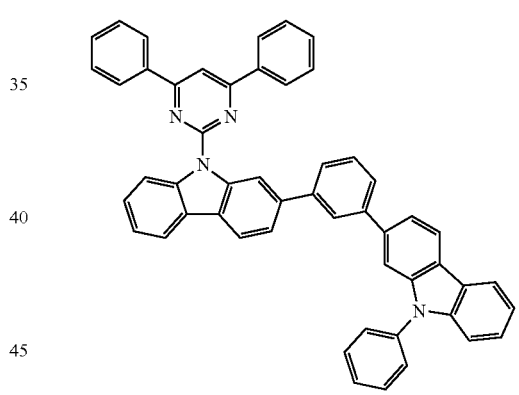
[Formula 25]
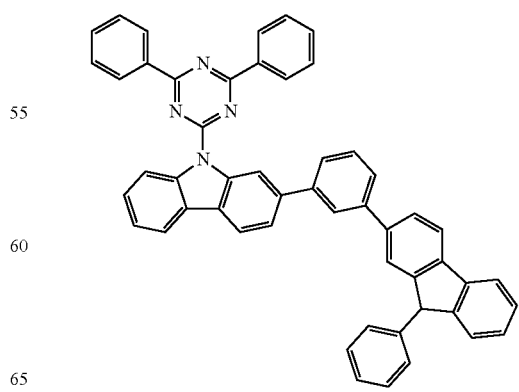

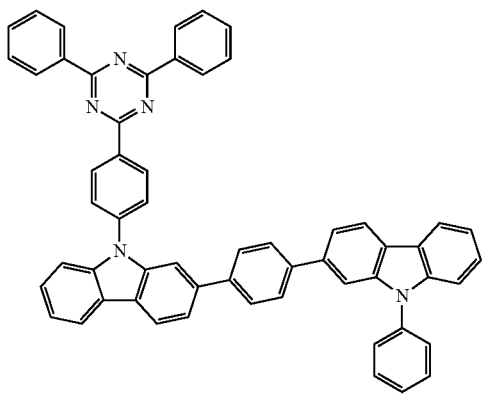
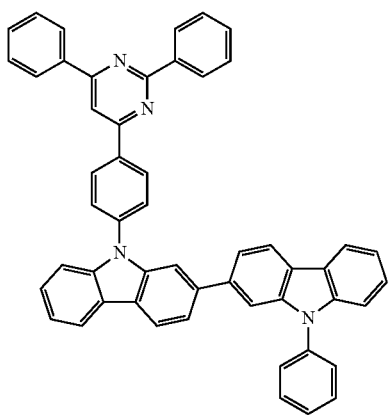
[Formula 26]
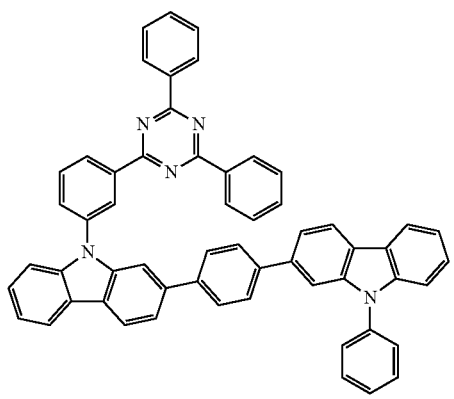
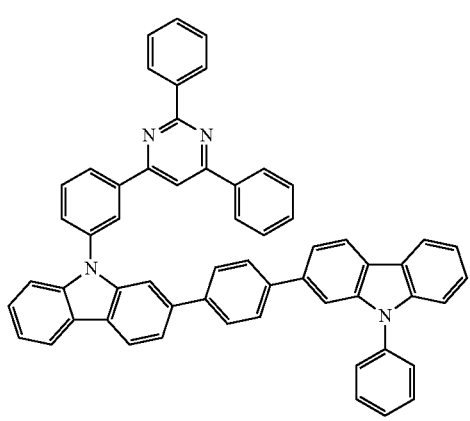
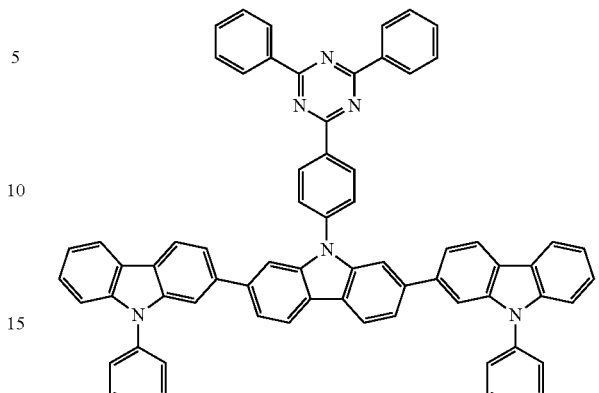
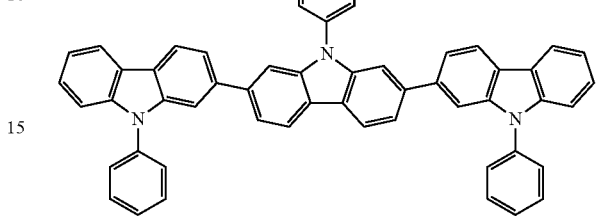
[Formula 27]
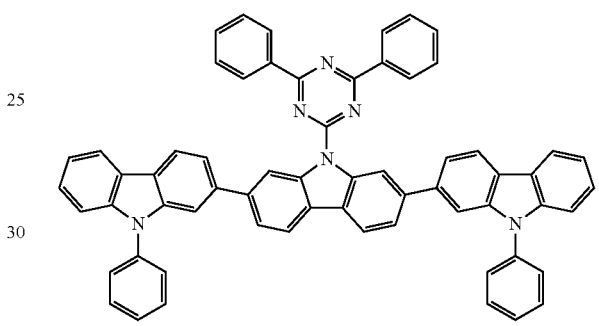
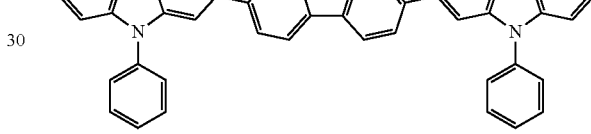
[Formula 28]
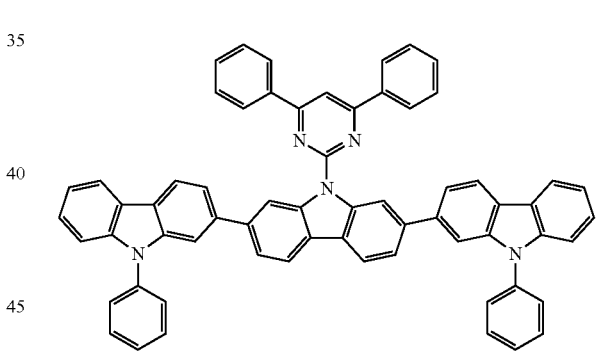
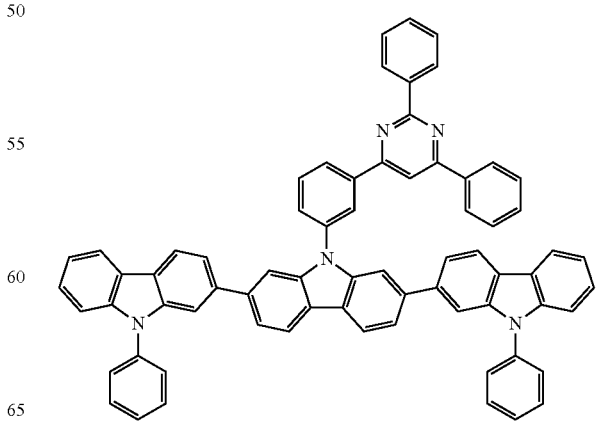

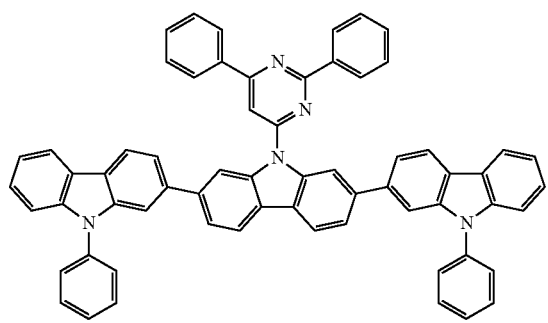
[Formula 29]
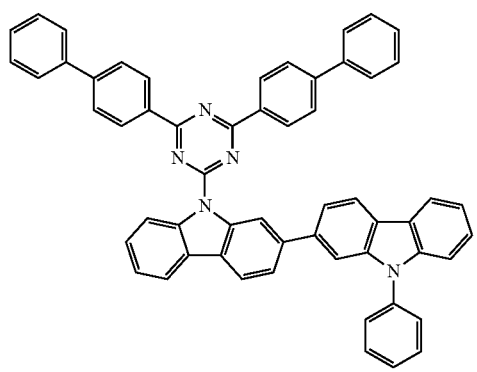
[Formula 30]
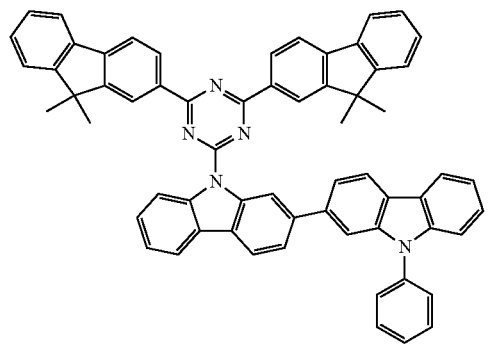
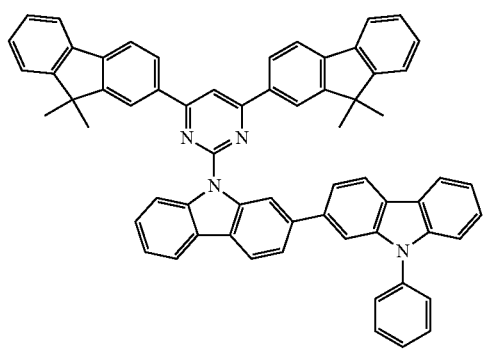
[Formula 31]
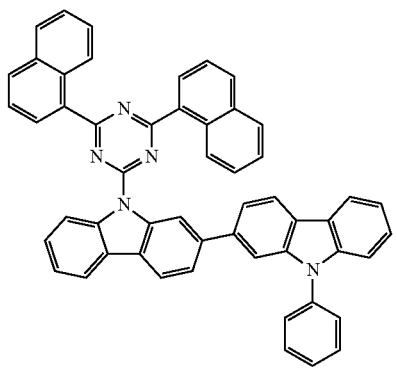
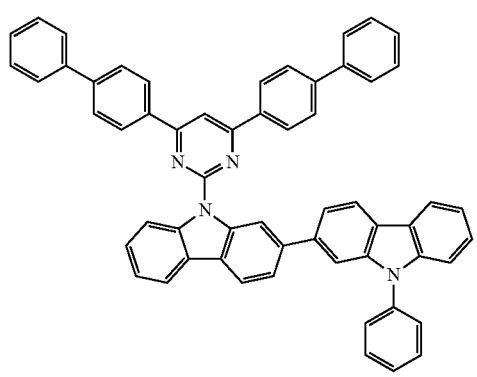
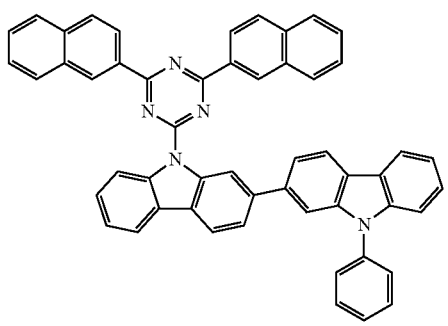

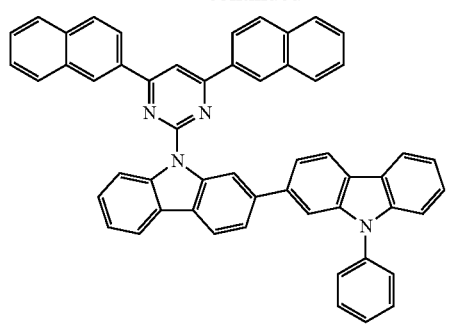
[Formula 32]
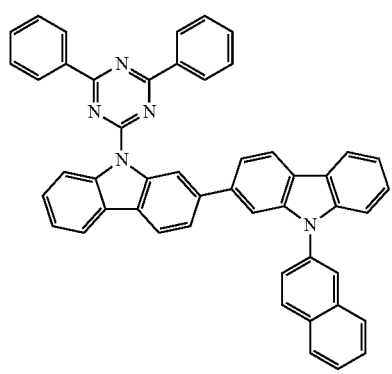
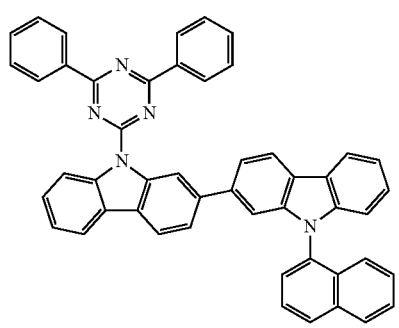
[Formula 33]
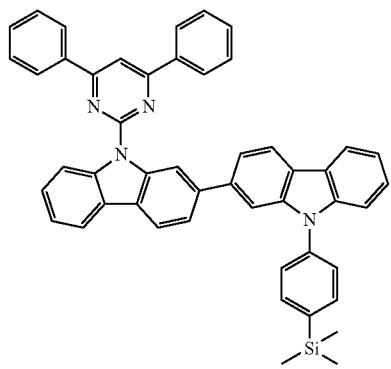
[Formula 34]
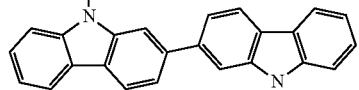

[Formula 35]
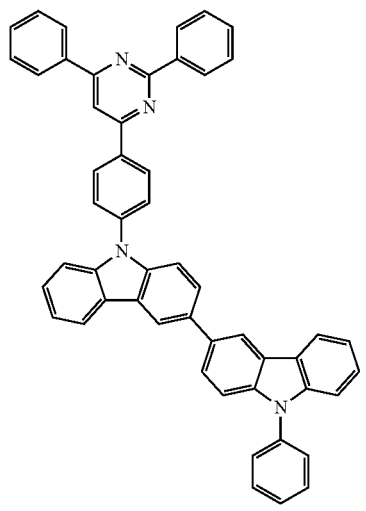
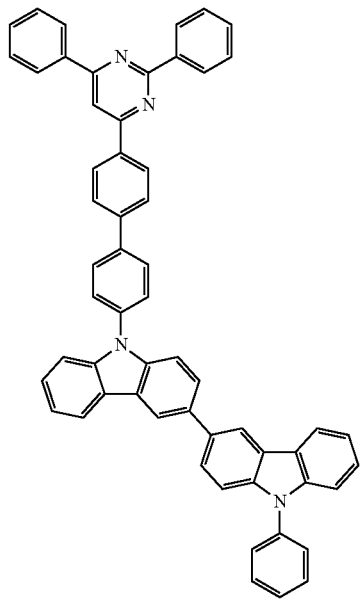
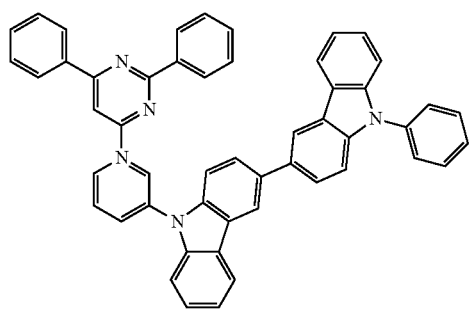
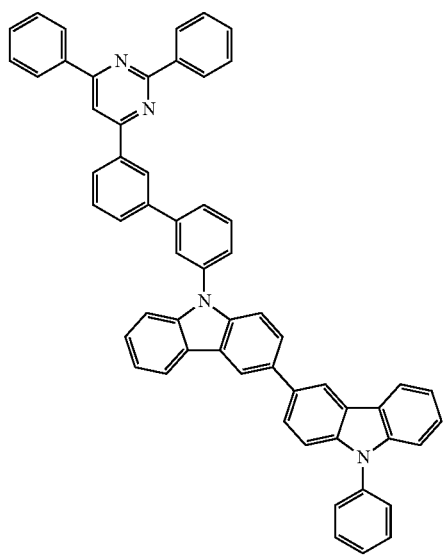
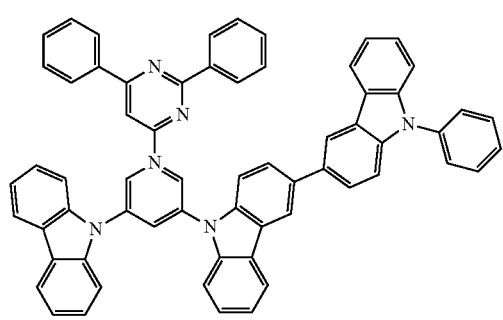

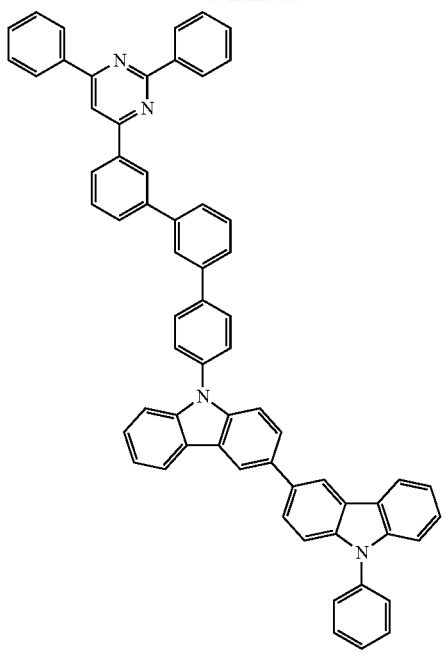
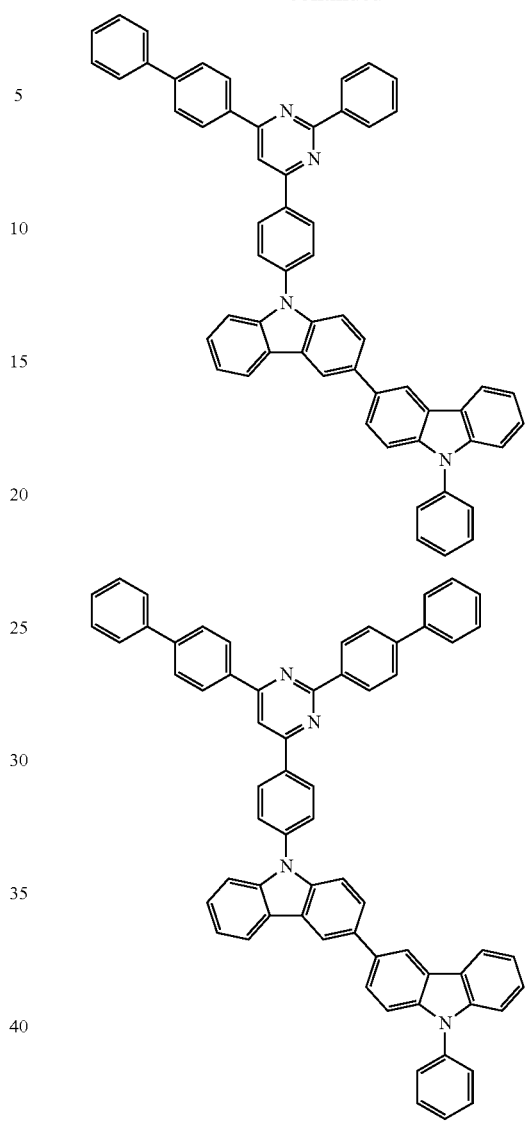
[Formula 36]
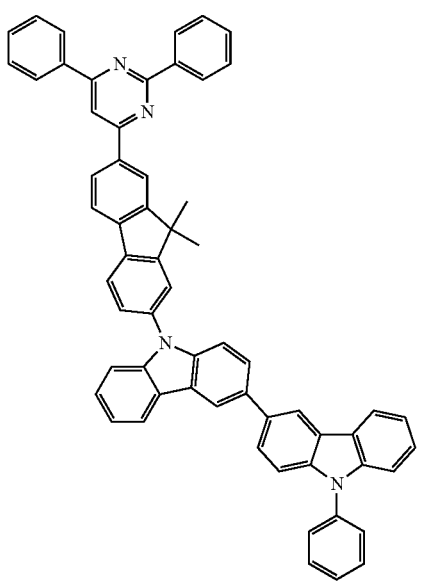

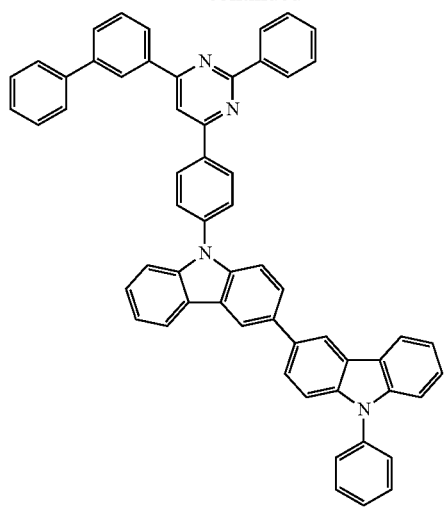
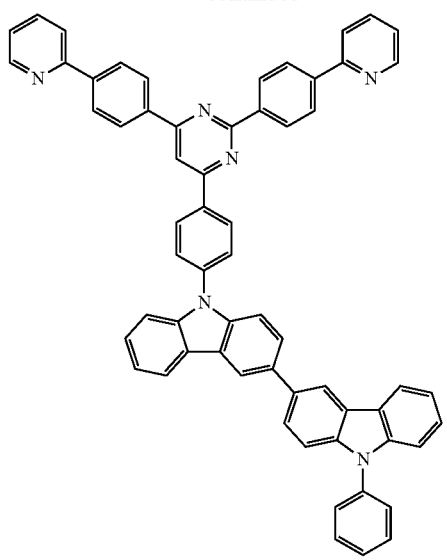
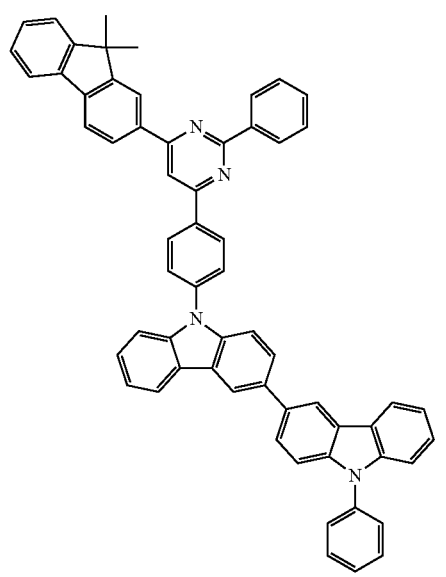
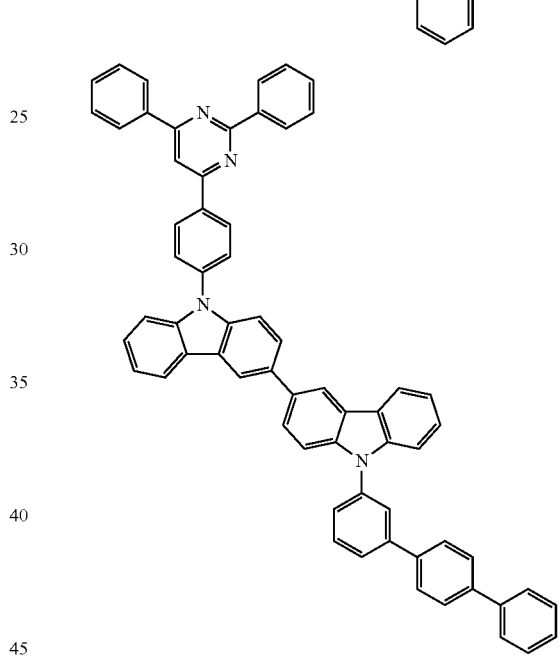
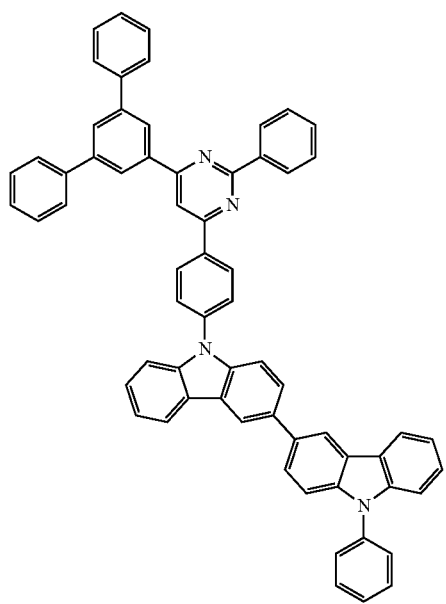
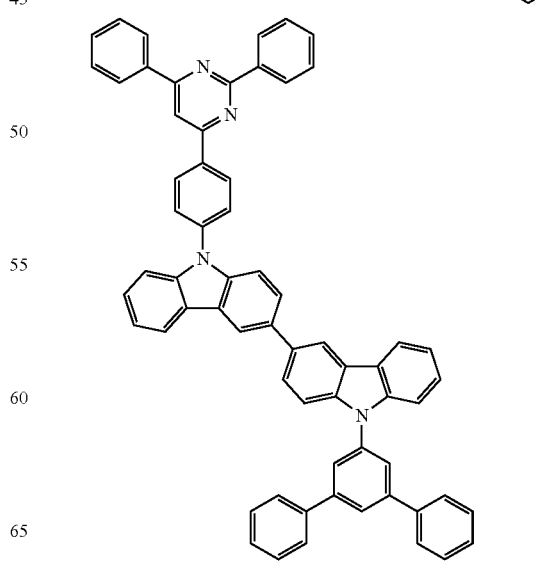

[Formula 37]
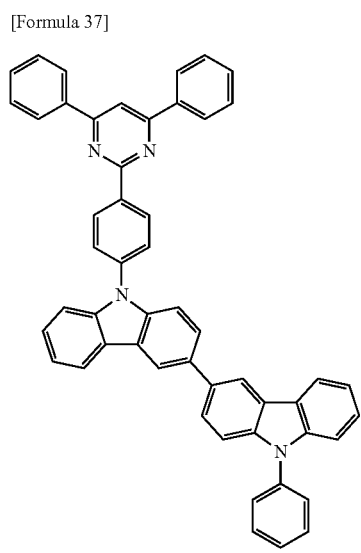
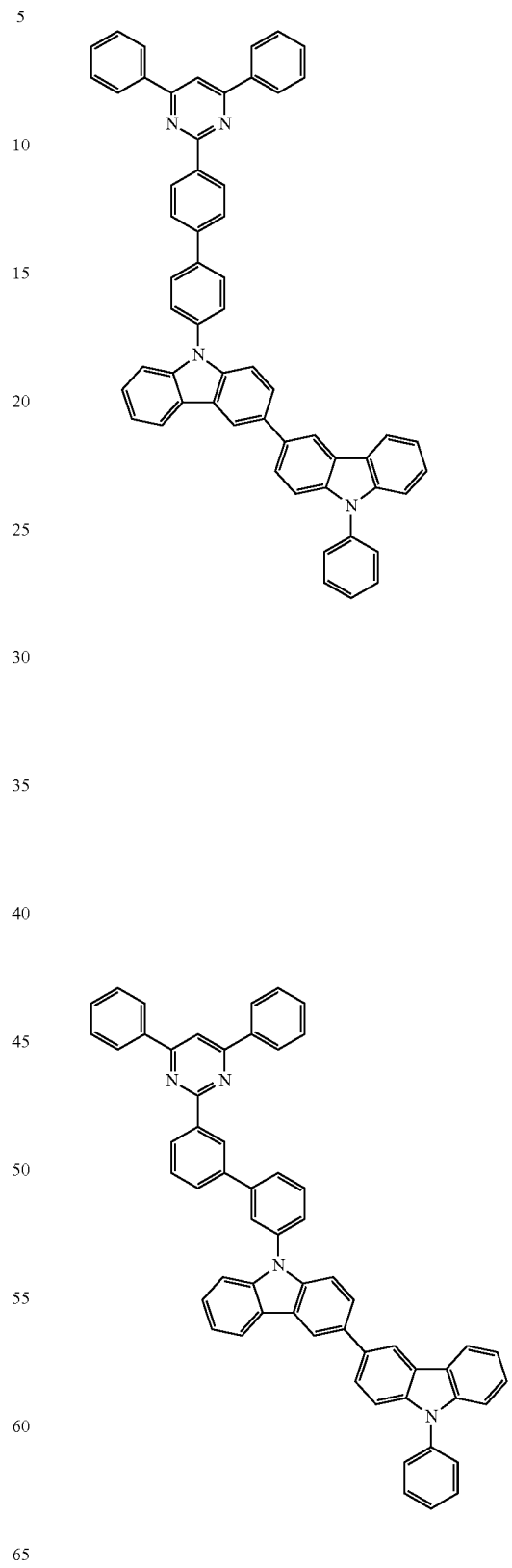

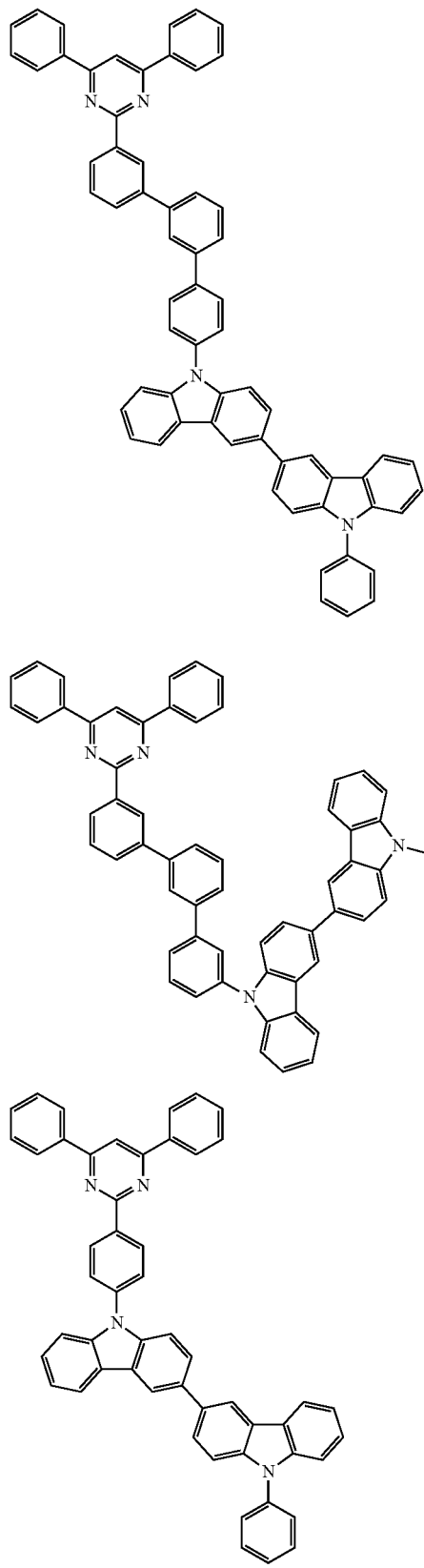
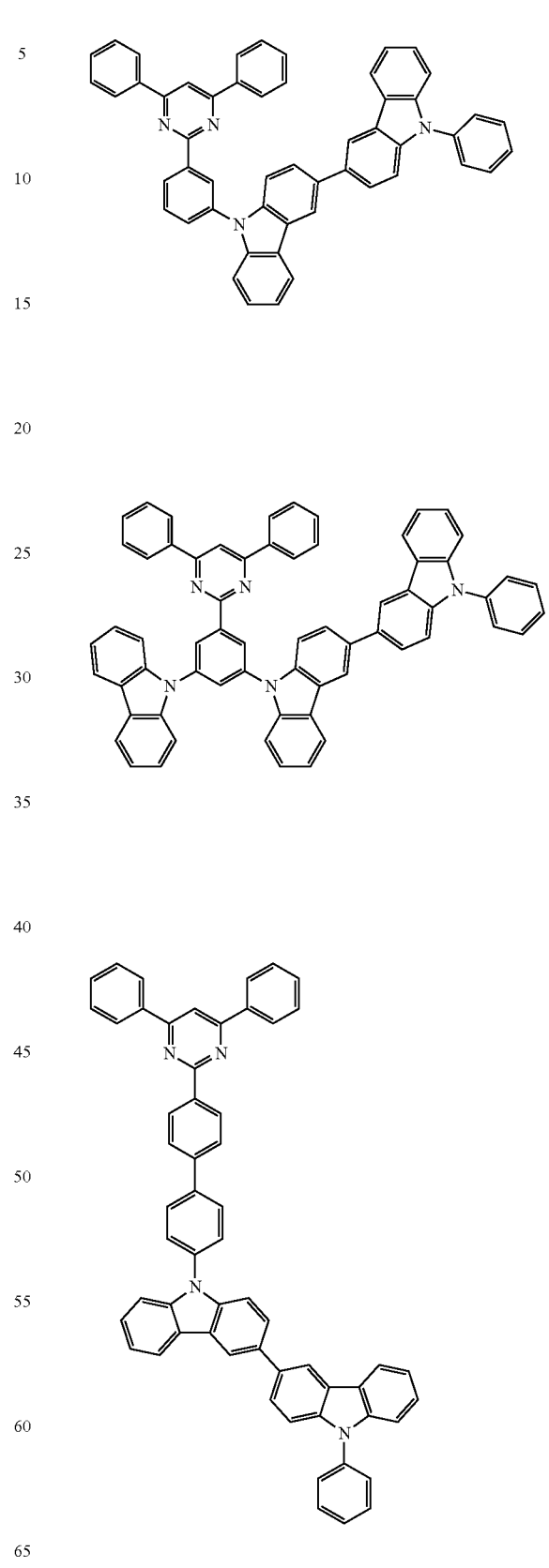

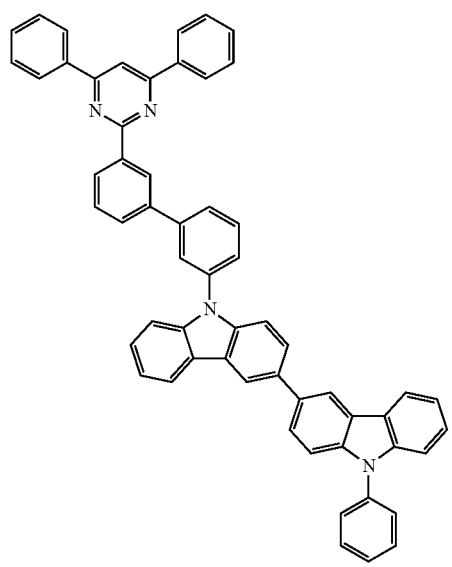
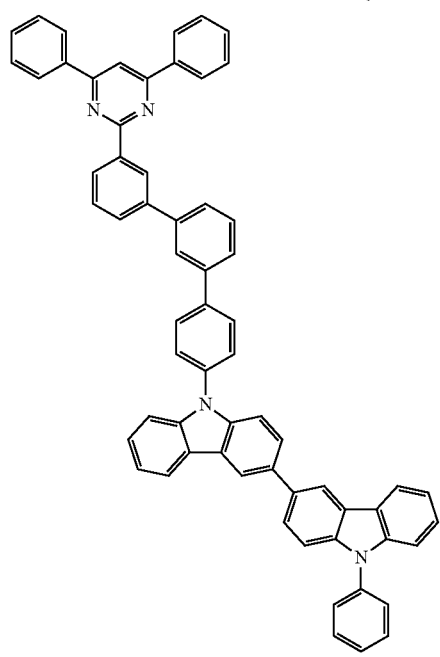
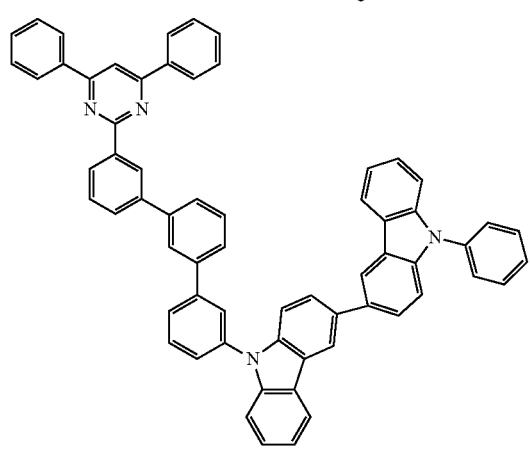
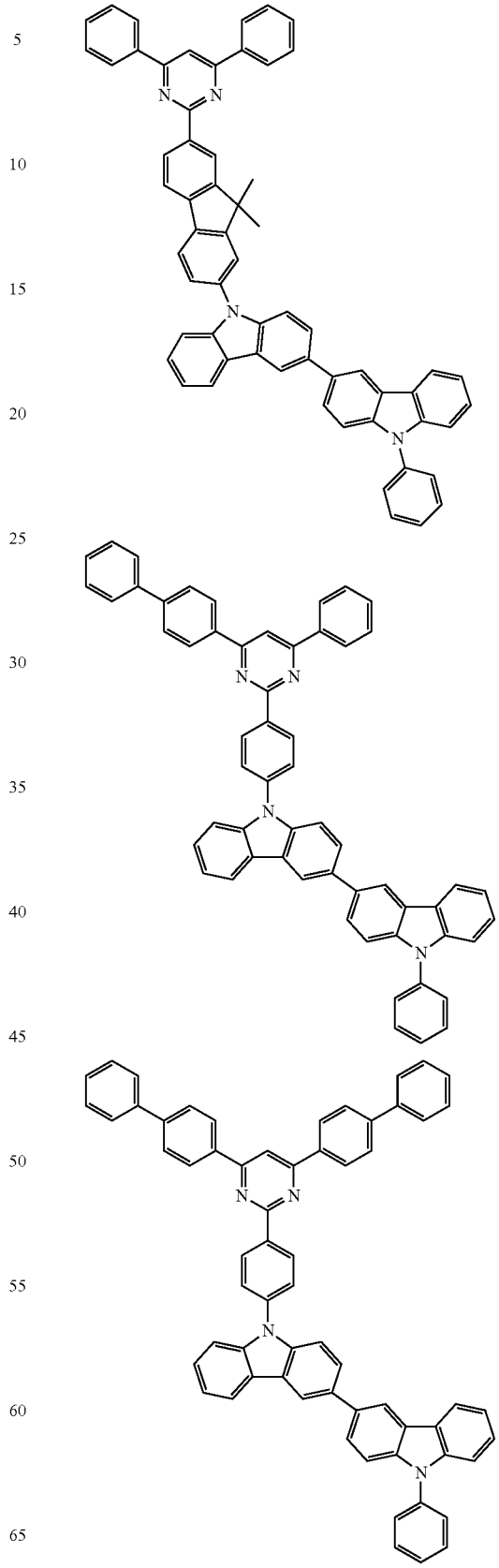

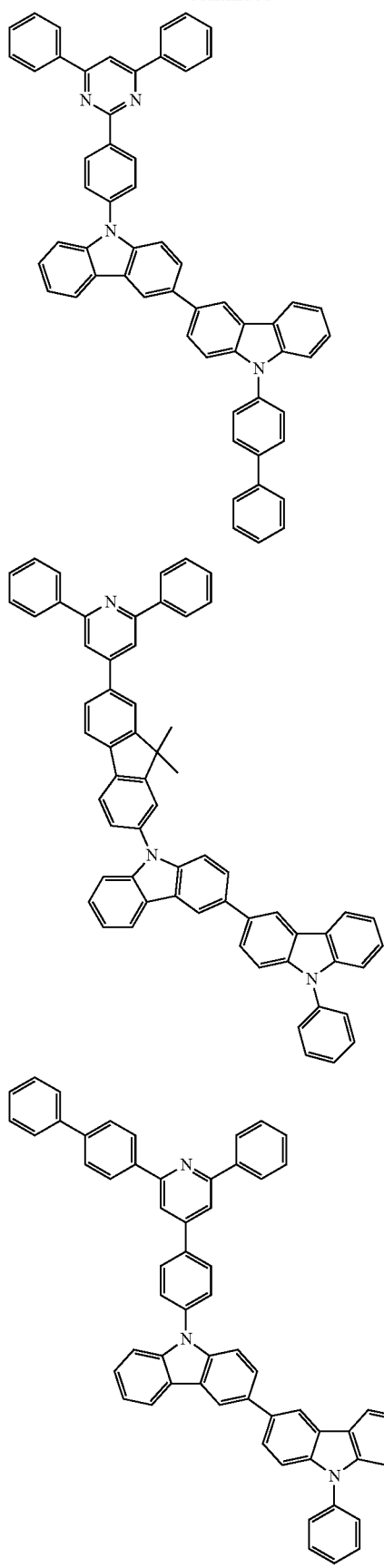
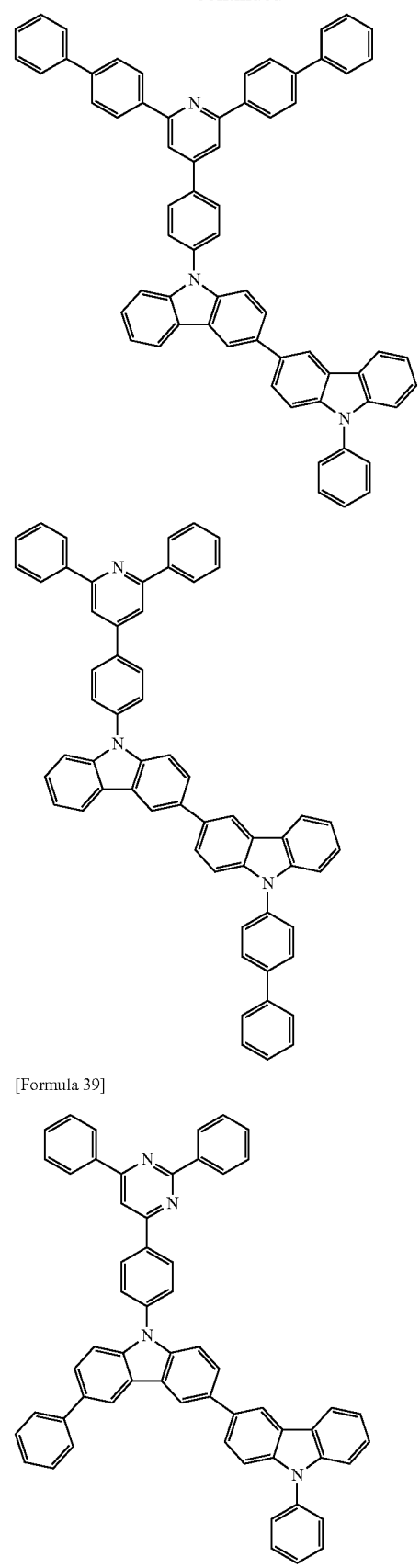
[Formula 39]

-continued
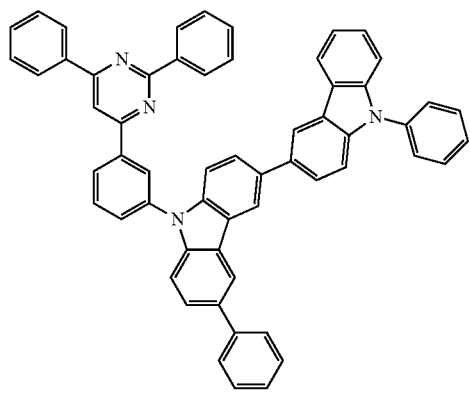
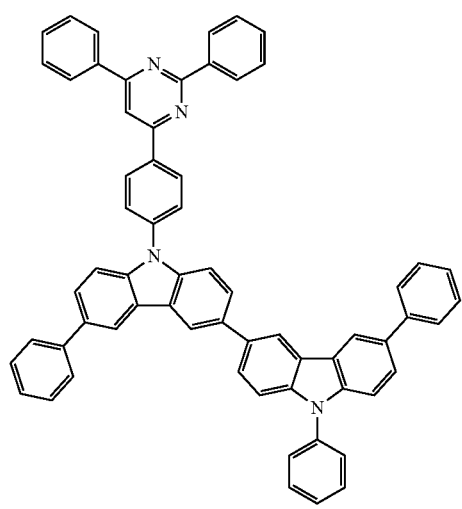
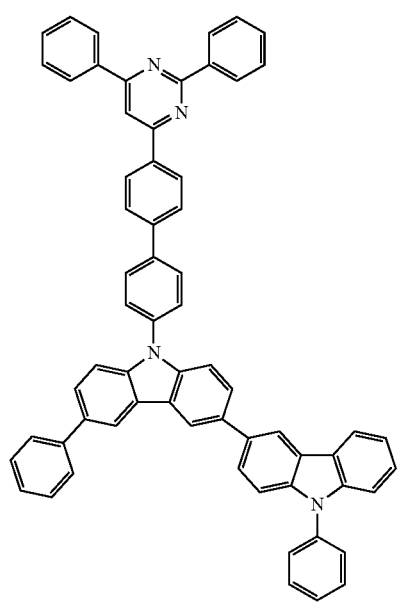
-continued
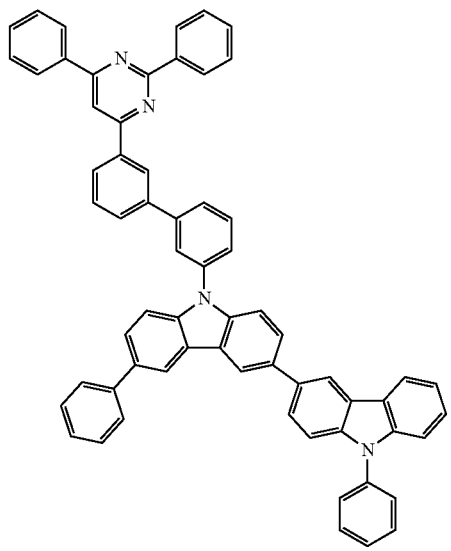
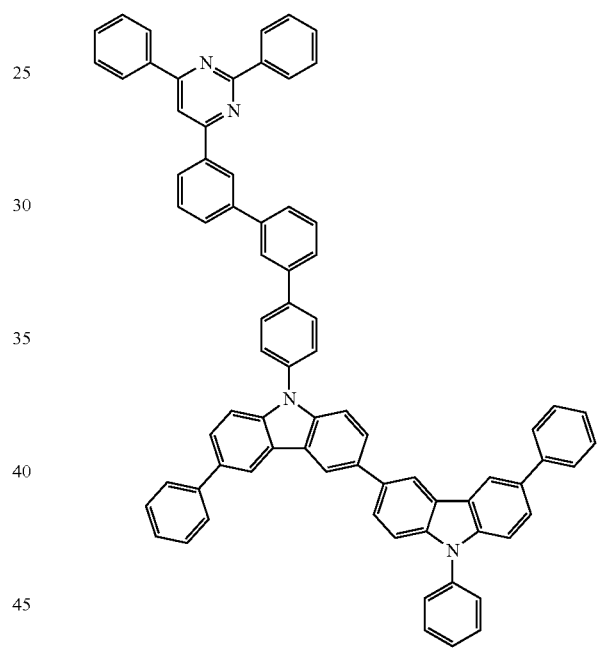
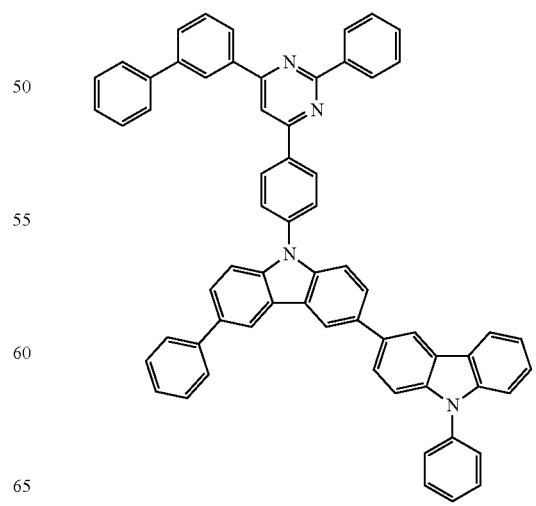

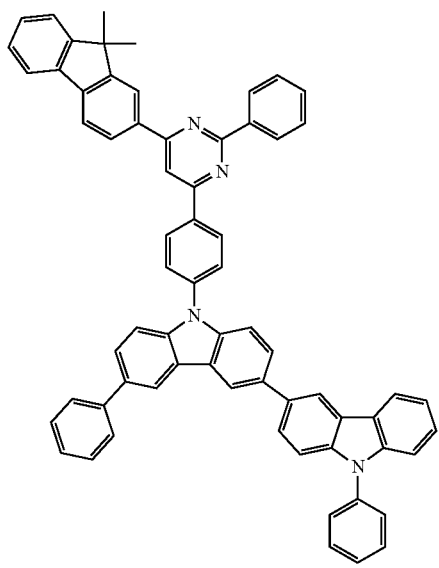
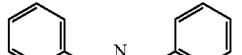
[Formula 40]
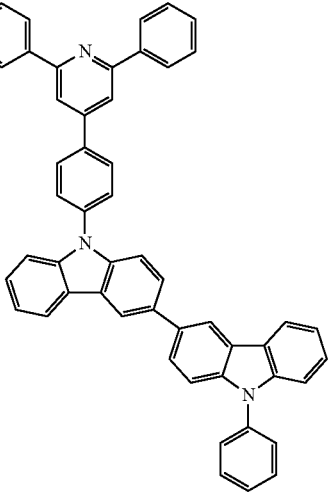
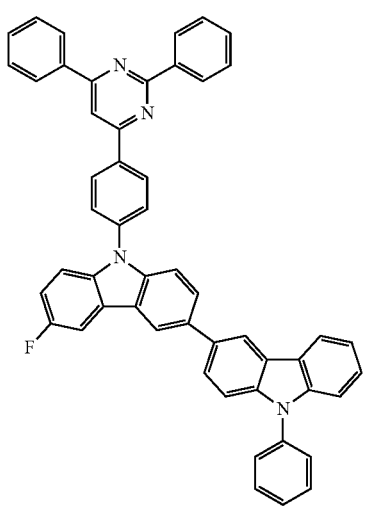
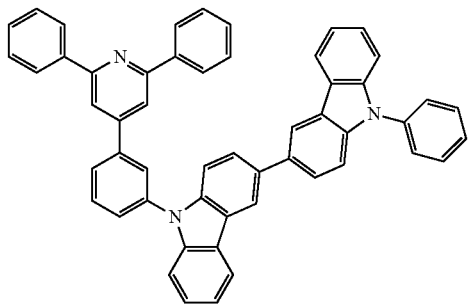
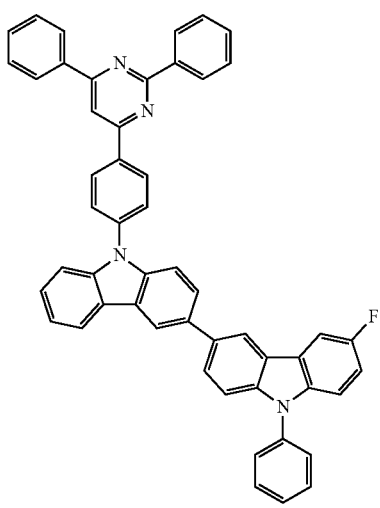
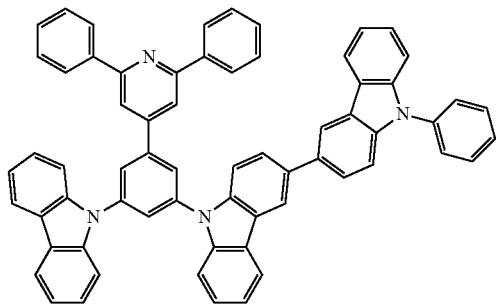

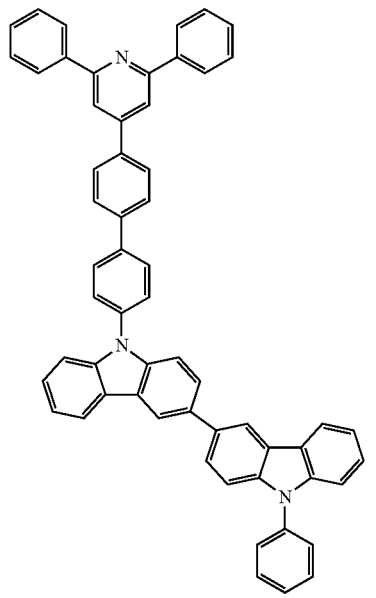
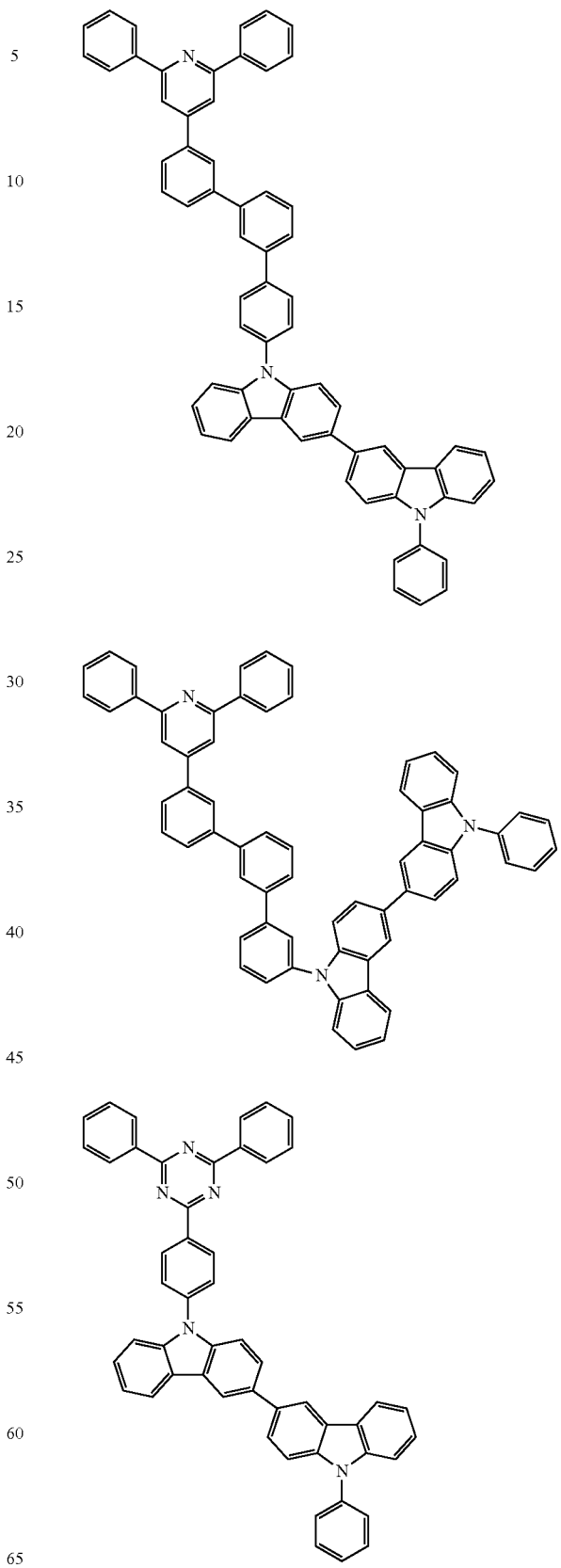

-continued
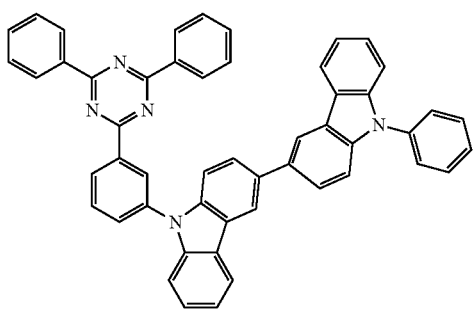
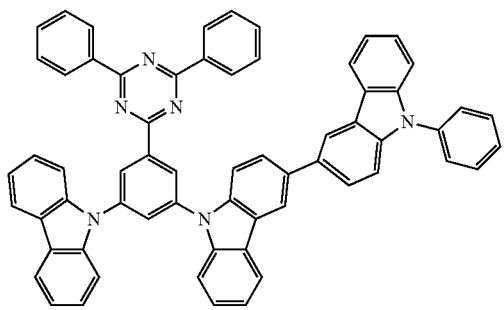
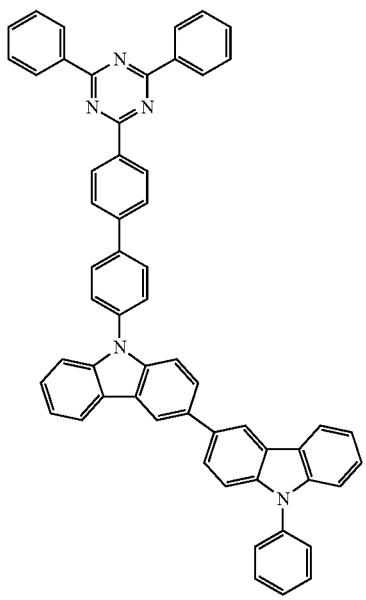
-continued
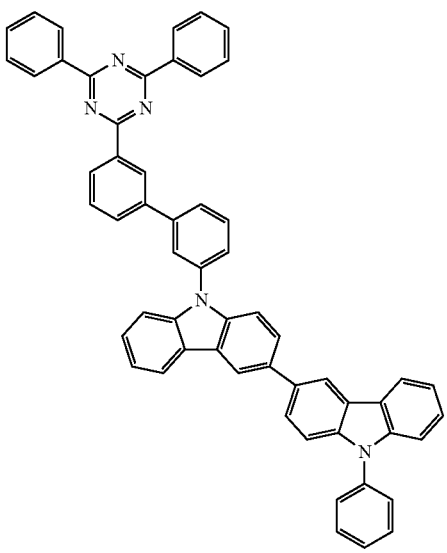
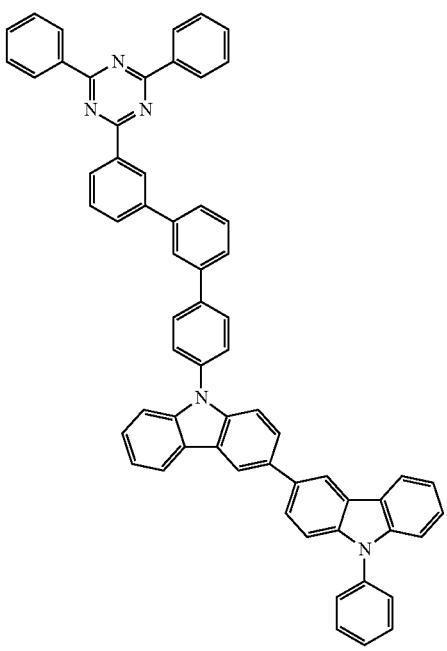
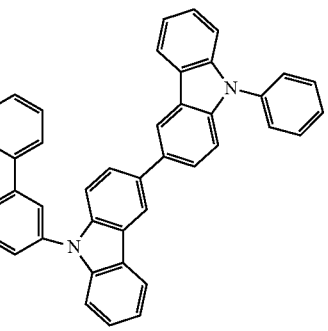

[Formula 41]
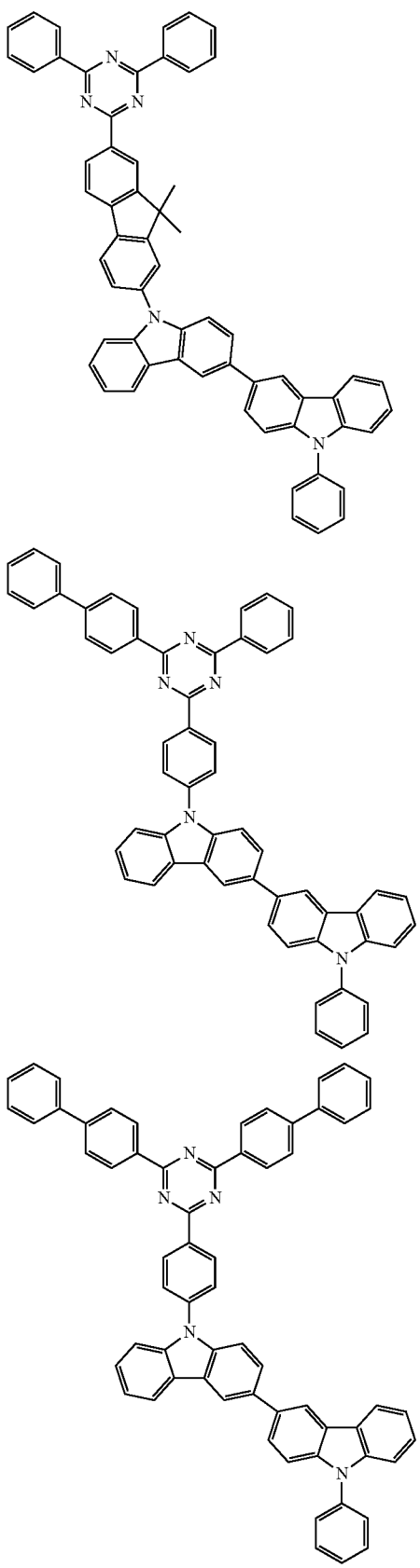
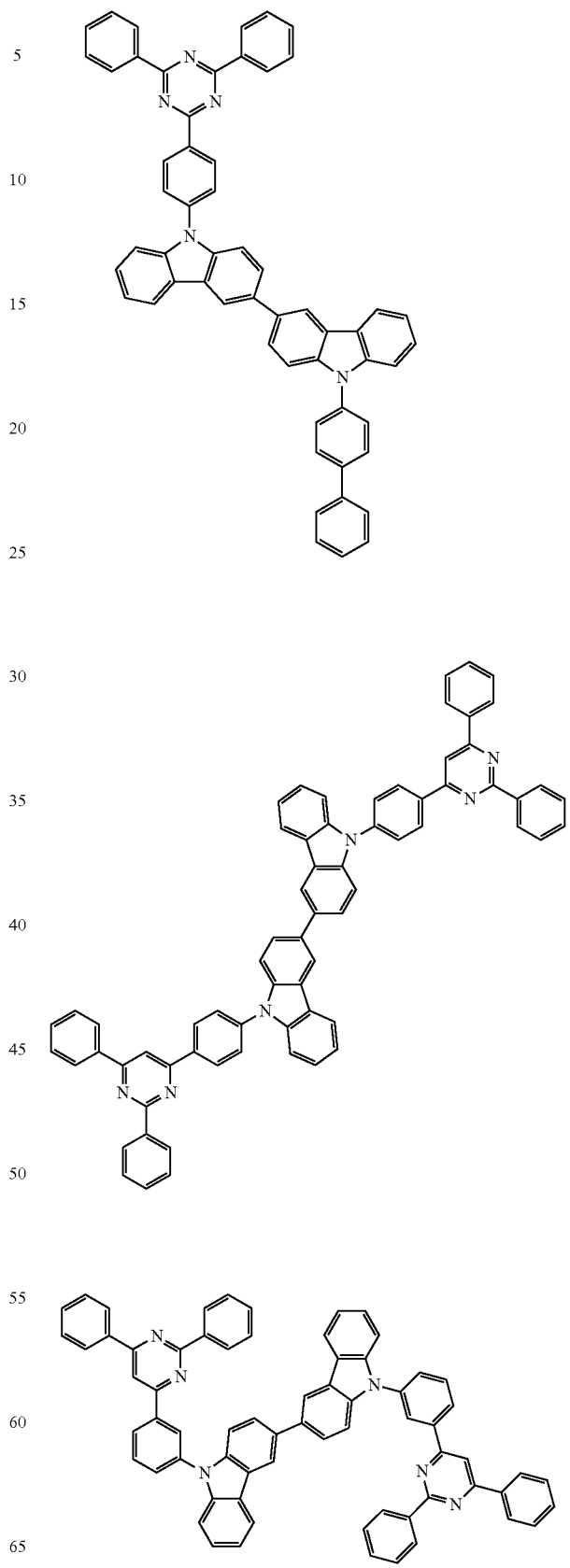

69
-continued
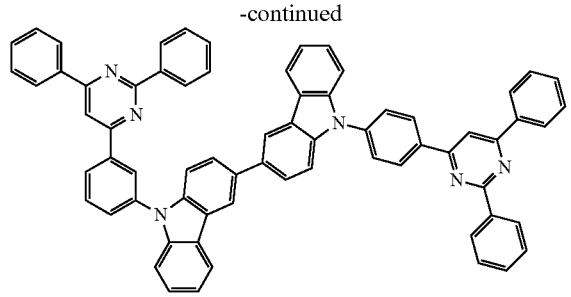
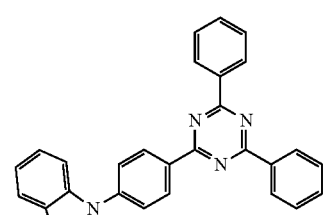
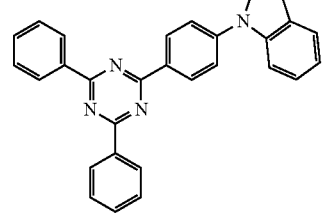
70
-continued
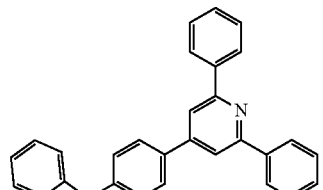
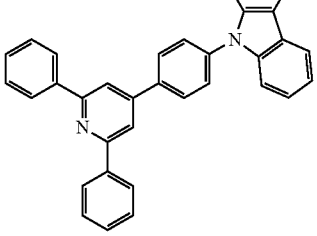
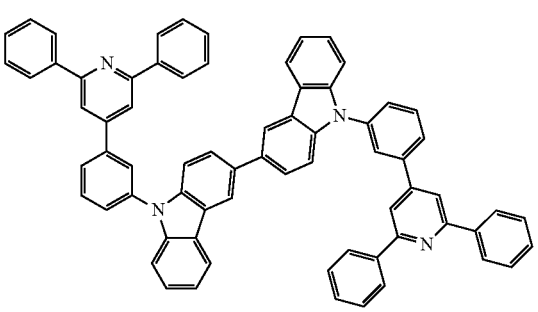
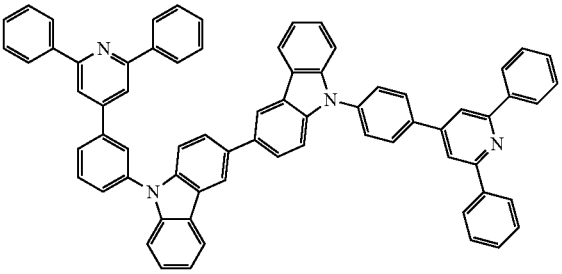
[Formula 42]
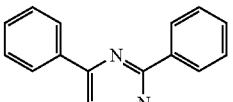
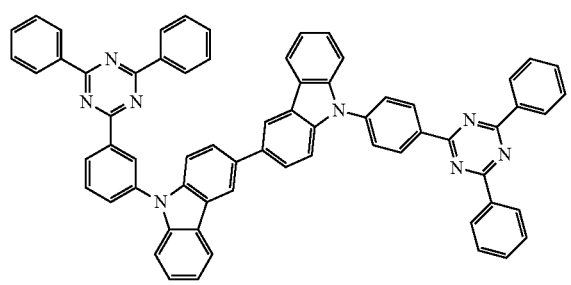

71
-continued
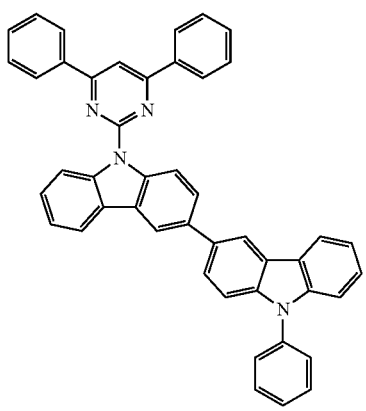
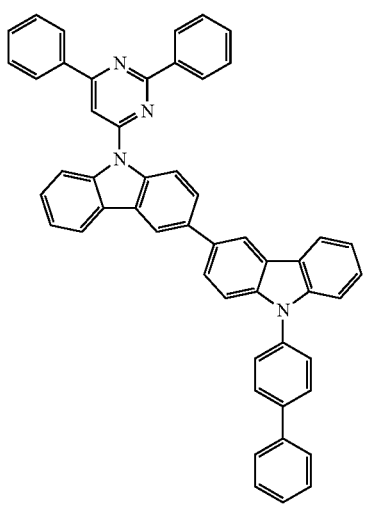
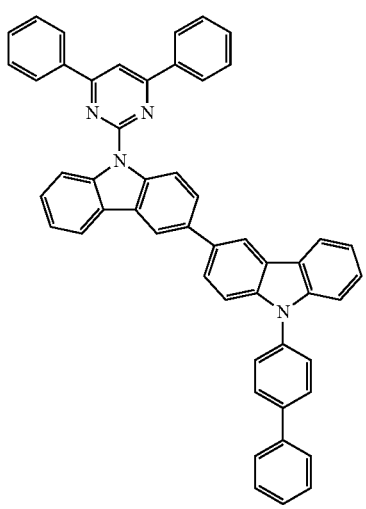
72
-continued
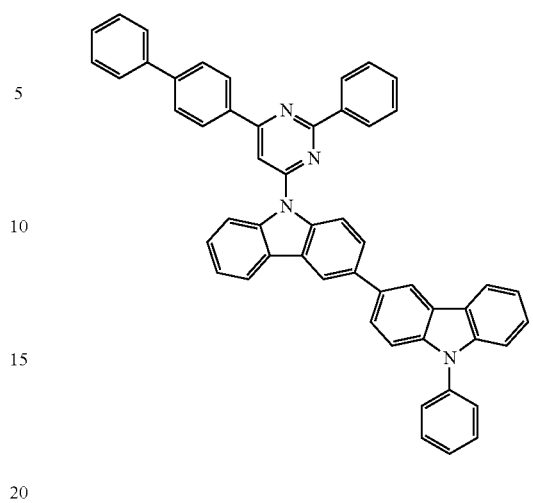
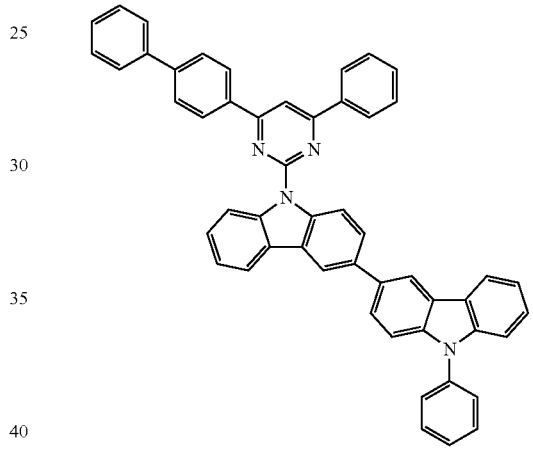
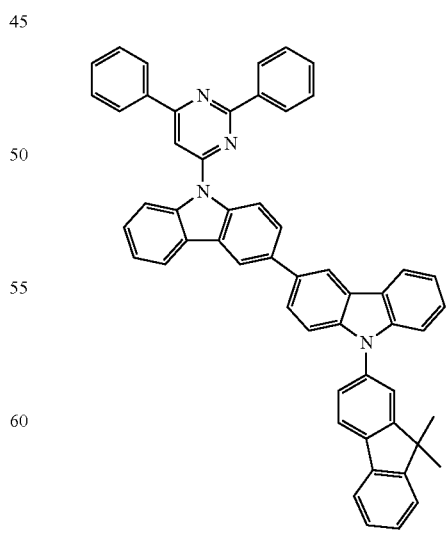

73
-continued
74
-continued
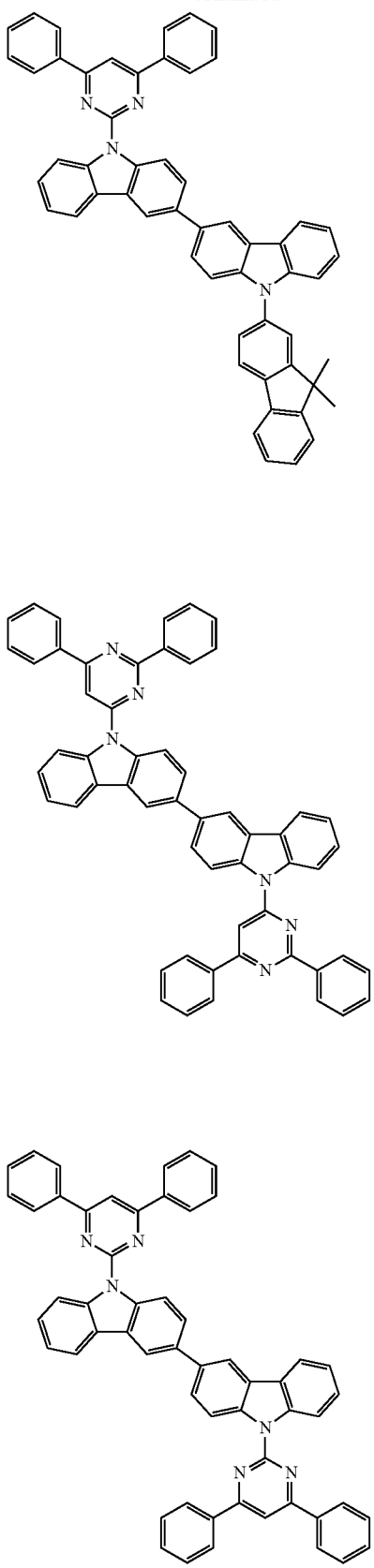
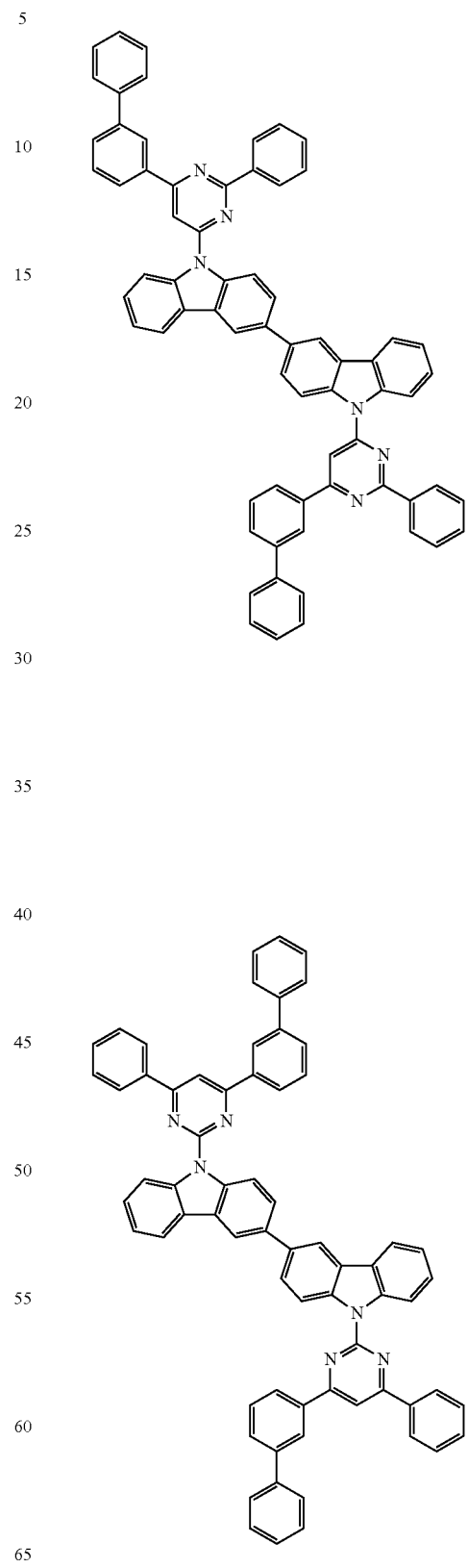

[Formula 43]
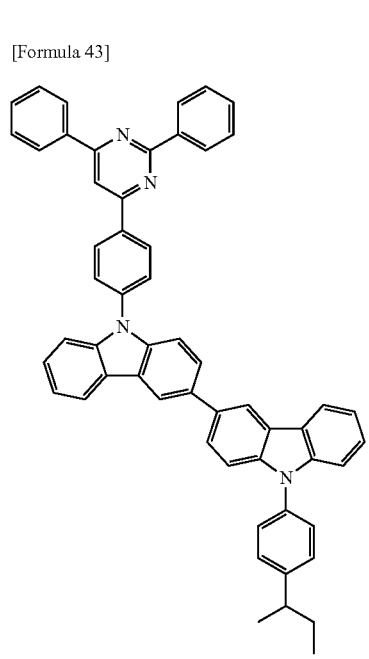
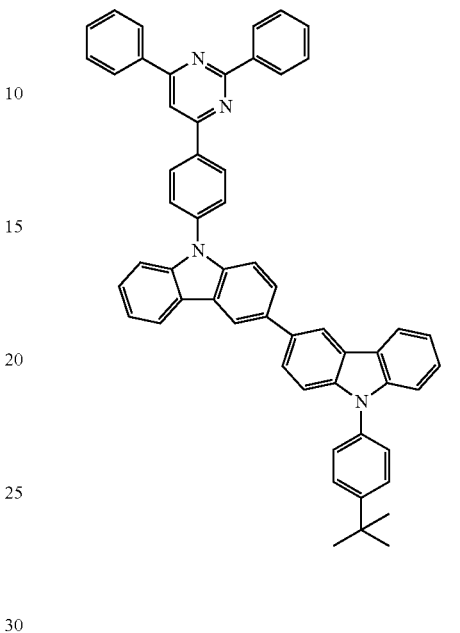
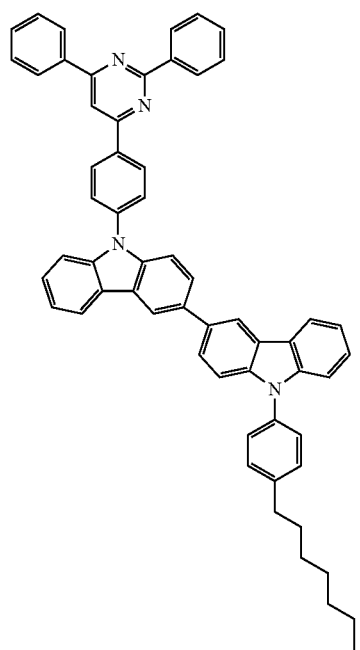
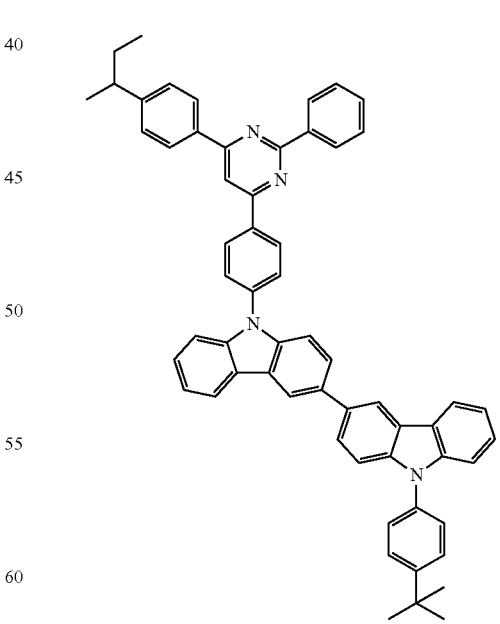

77
-continued
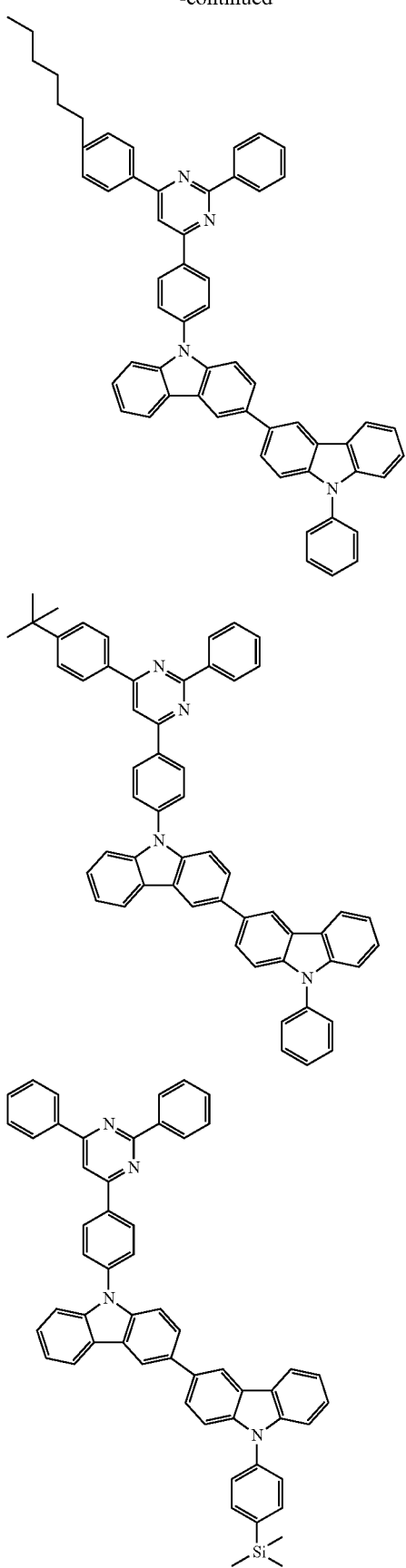
78
-continued
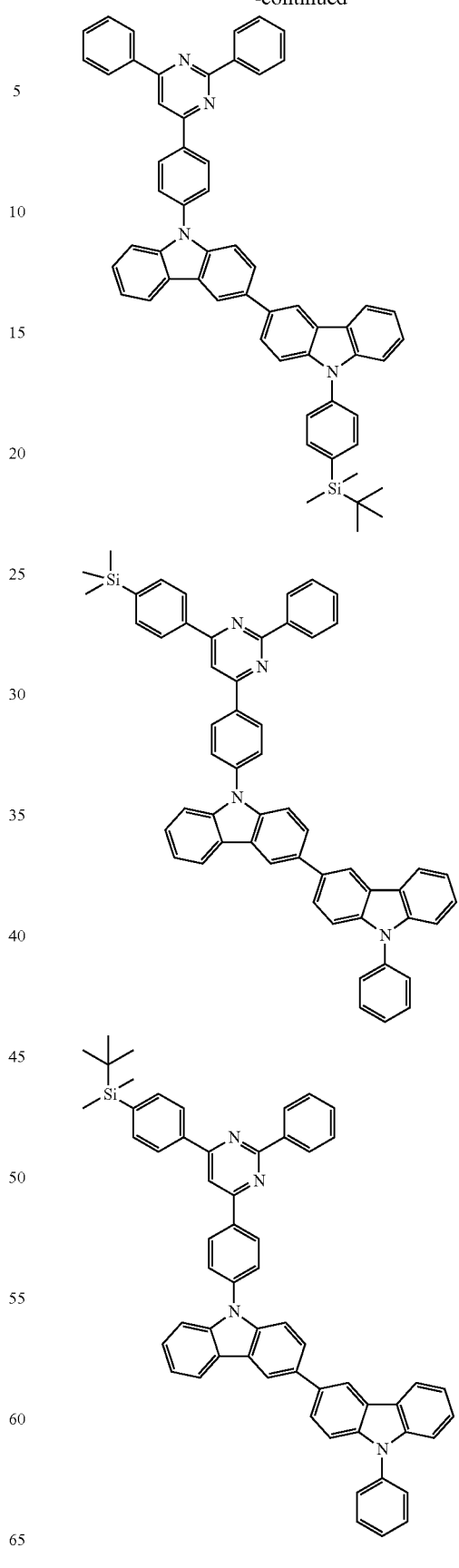

[Formula 44]
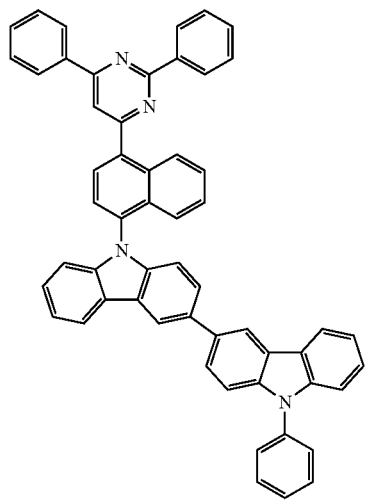
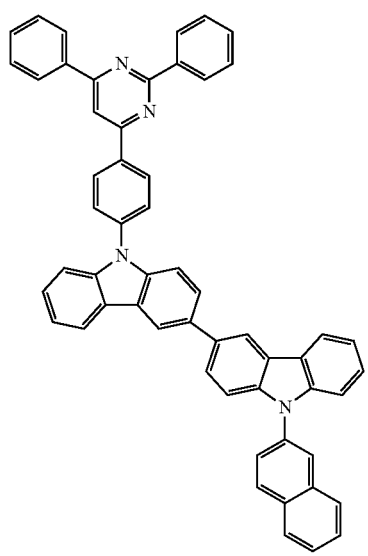
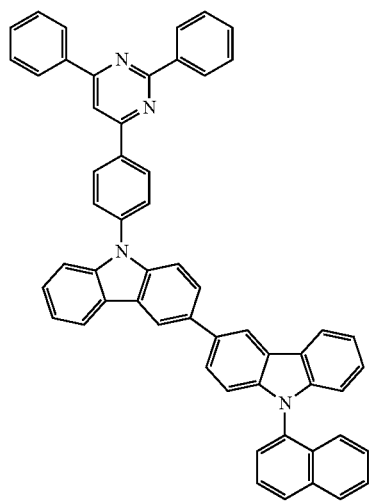
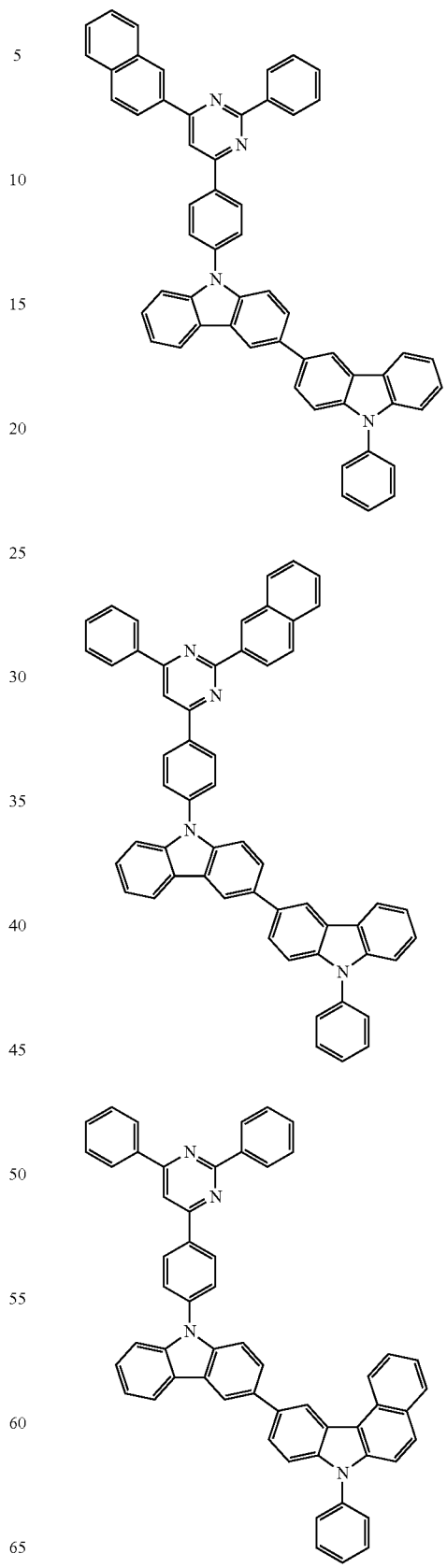

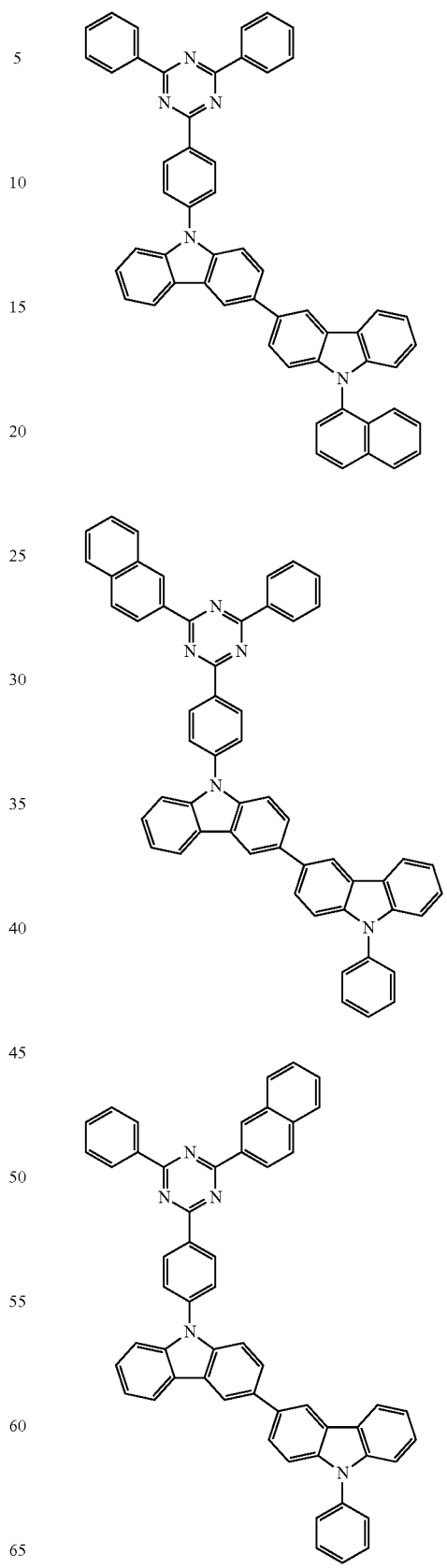

-continued
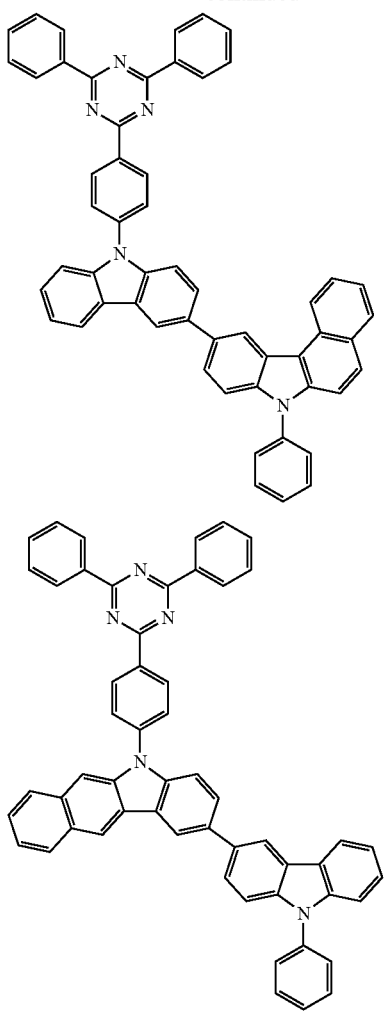
[Formula 45]
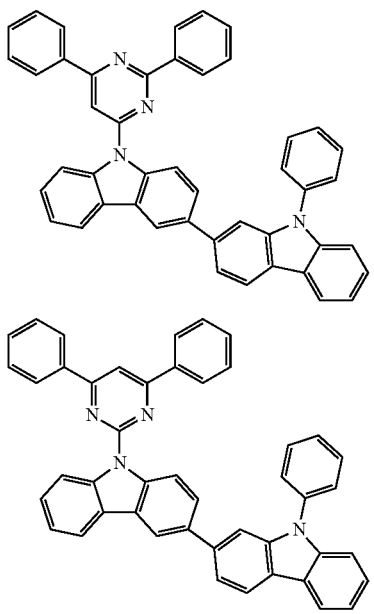
-continued
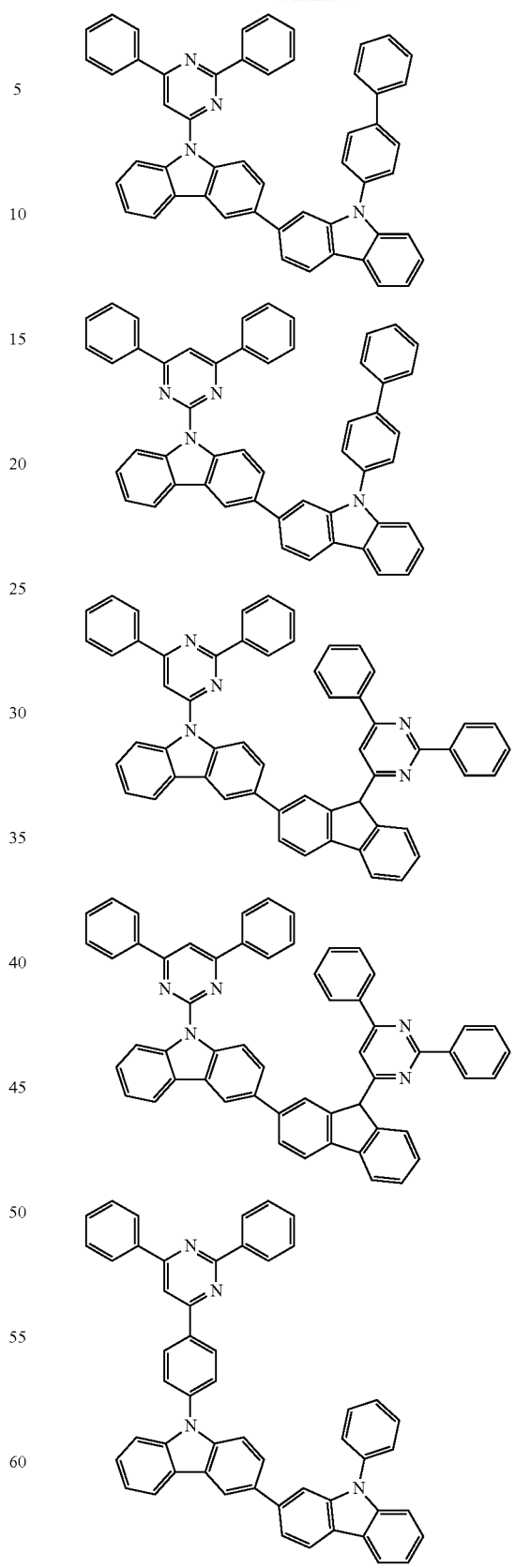

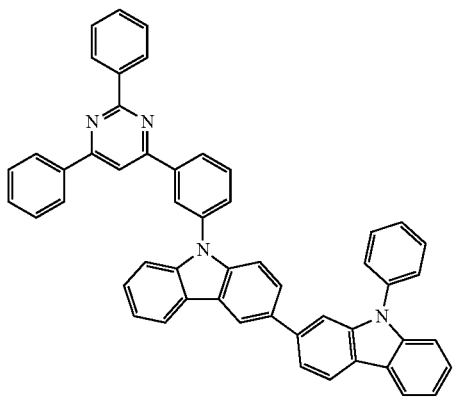
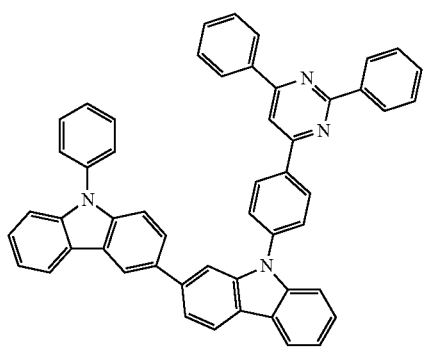
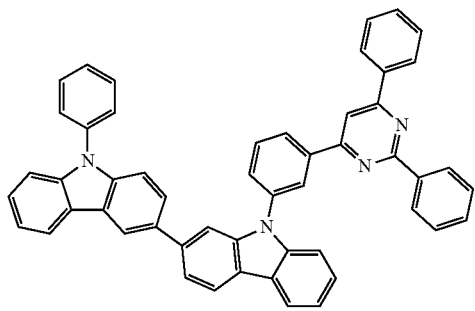
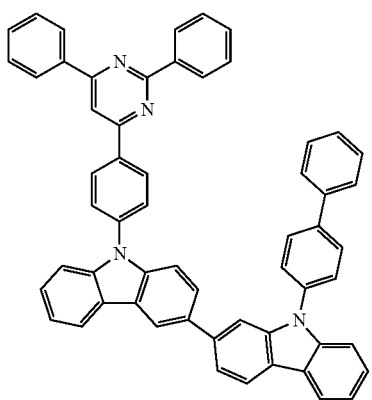
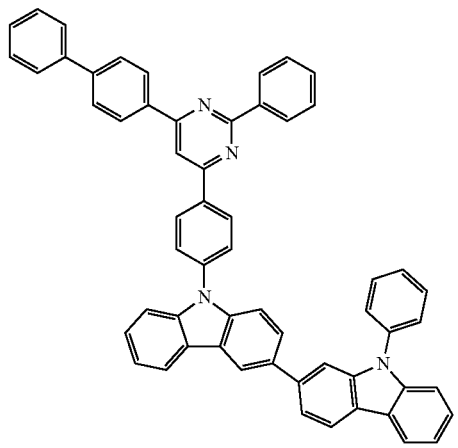
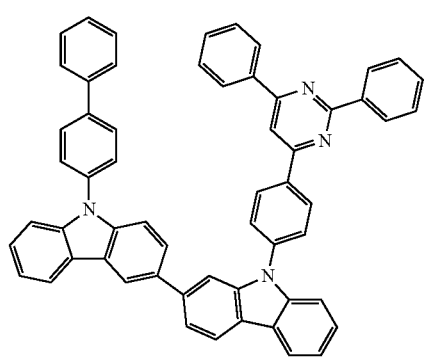
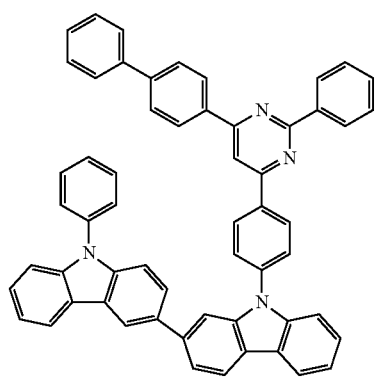
[Formula 46]
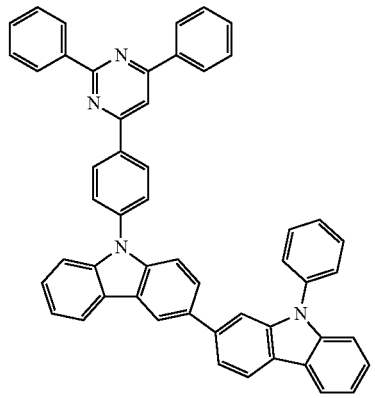

-continued
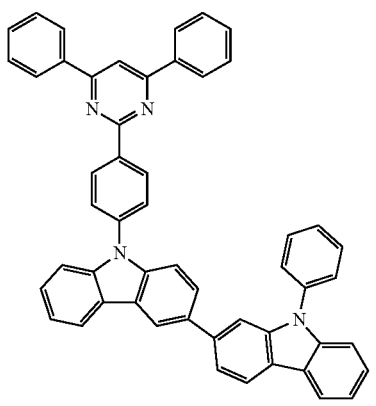
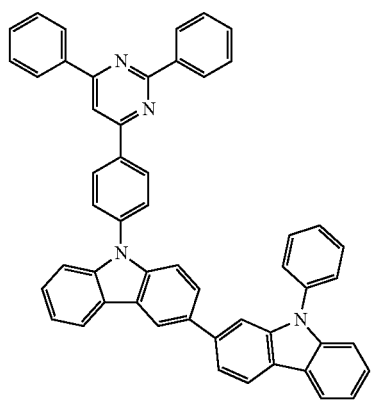
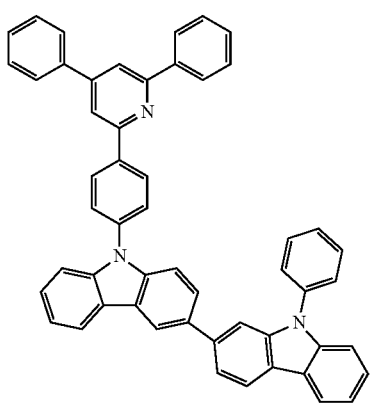
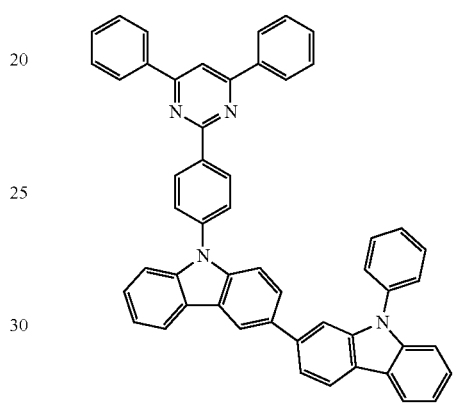
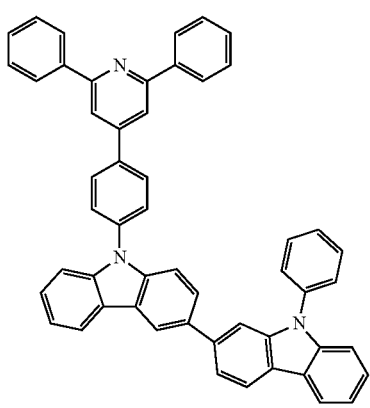
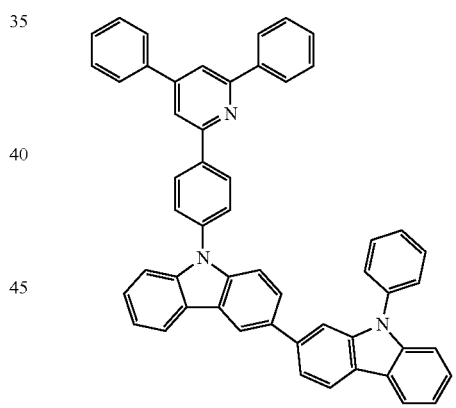
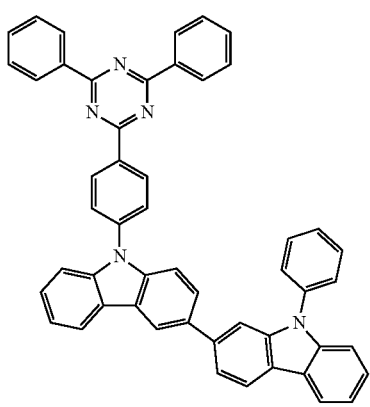
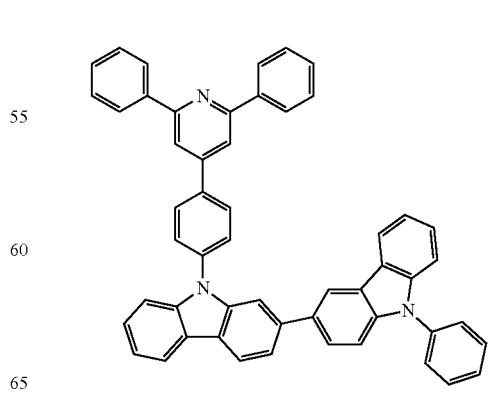

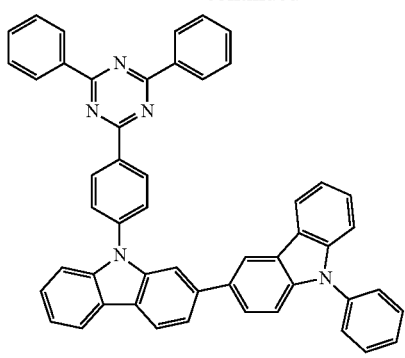
[Formula 47]
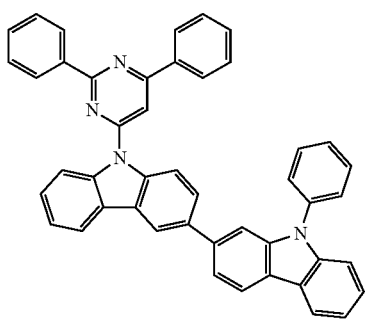
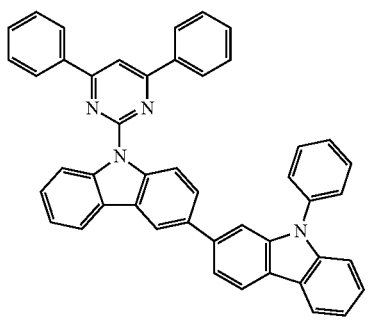
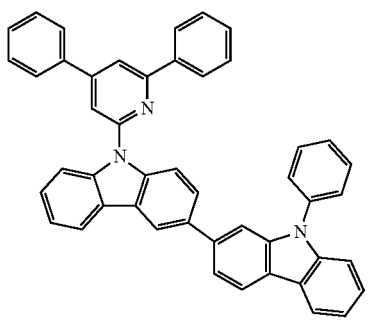
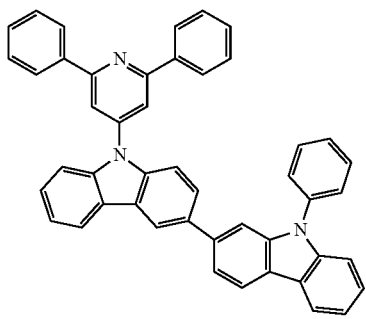
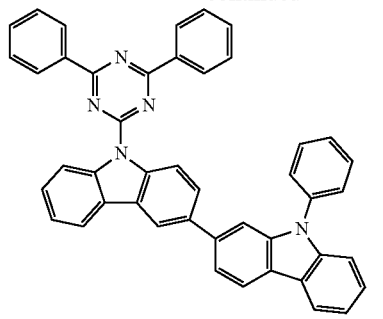
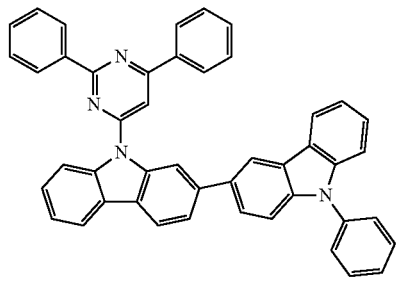
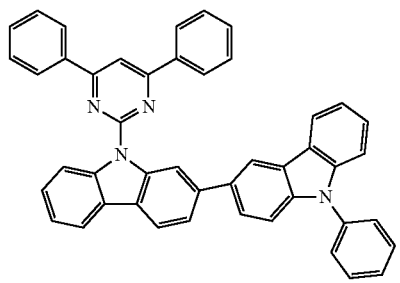
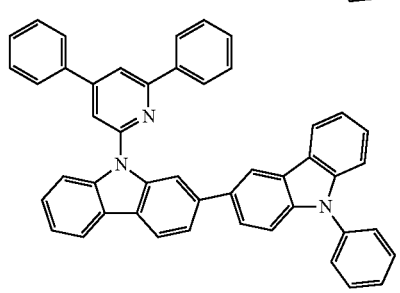
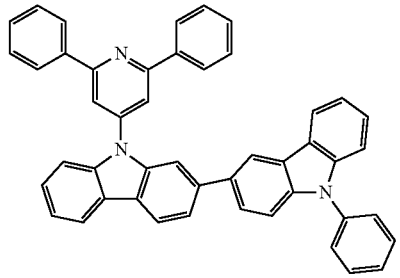
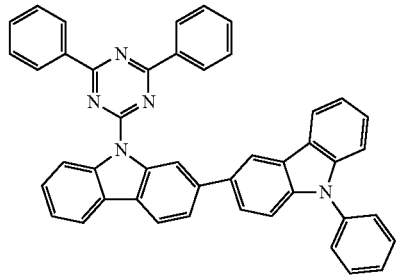

[Formula 48]
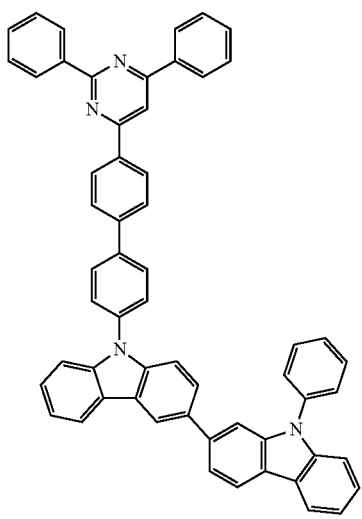

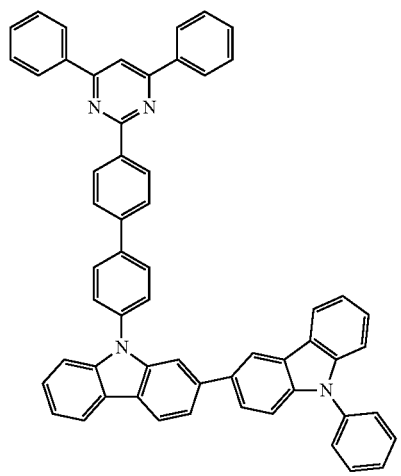
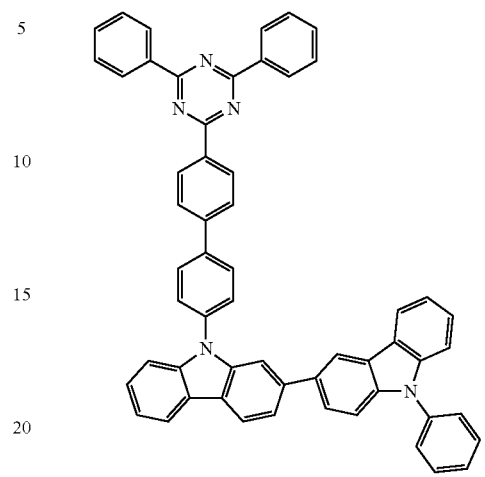
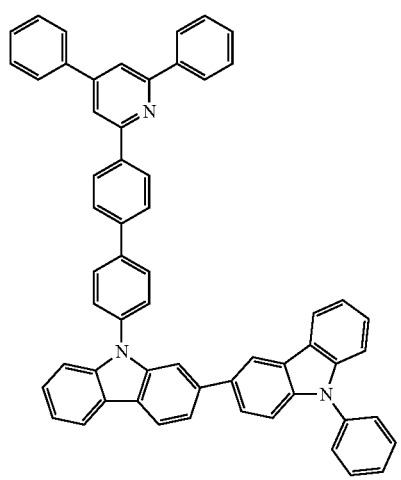
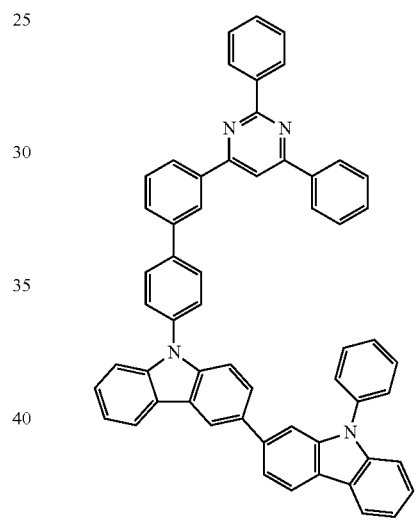
[Formula 49]
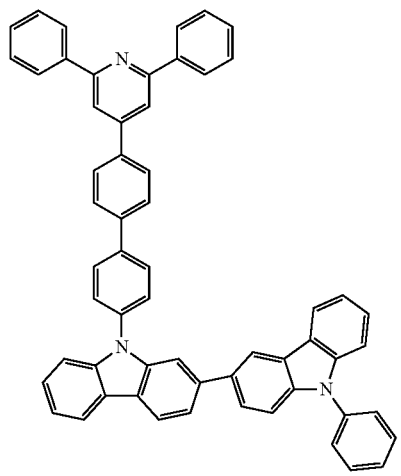
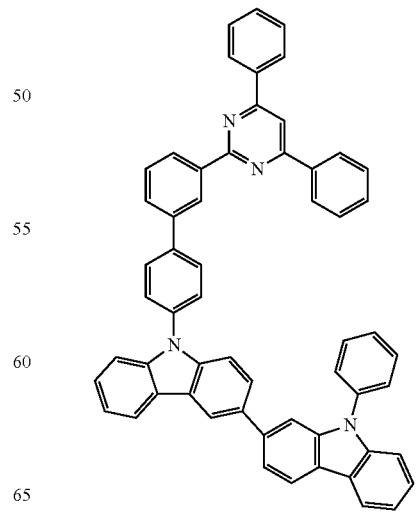

95
-continued
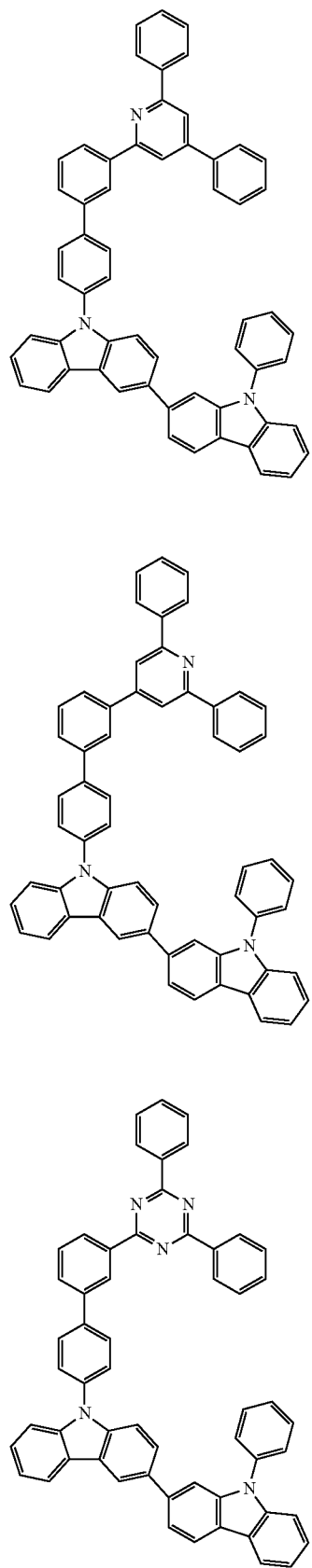 [SMILES: c1ccc(-c2cc(-c3cccc(-c4ccc(-n5c6ccccc6c6cc(-c7ccc8c9ccccc9n(-c9ccccc9)c8c7)ccc65)cc4)c3)nc(-c3ccccc3)n2)cc1 ; c1ccc(-c2cc(-c3ccccc3)nc(-c3cccc(-c4ccc(-n5c6ccccc6c6cc(-c7ccc8c9ccccc9n(-c9ccccc9)c8c7)ccc65)cc4)c3)n2)cc1 ; c1ccc(-c2cc(-c3ccccc3)nc(-c3cccc(-c4ccc(-n5c6ccccc6c6cc(-c7ccc8c9ccccc9n(-c9ccccc9)c8c7)ccc65)cc4)c3)c2)cc1]
96
-continued
[Formula 50]
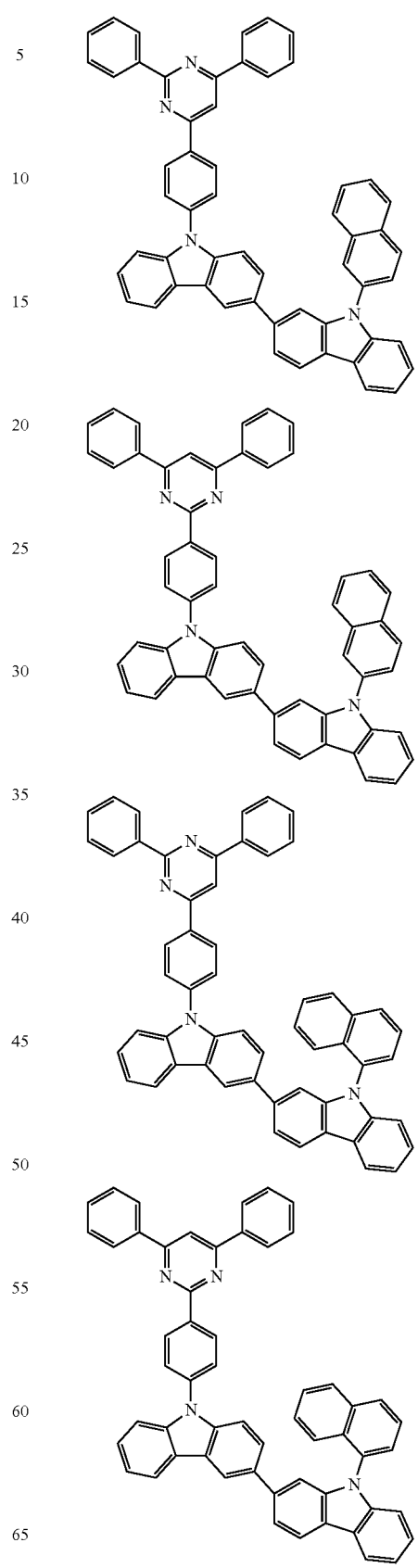

97
-continued
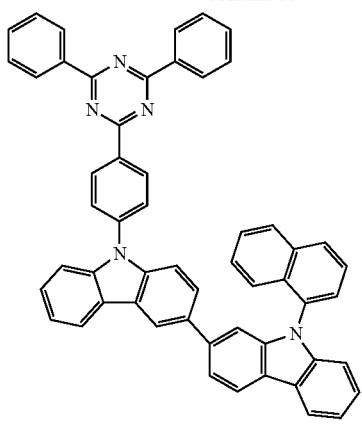
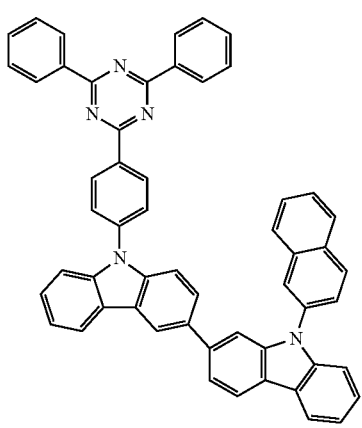
[Formula 51]
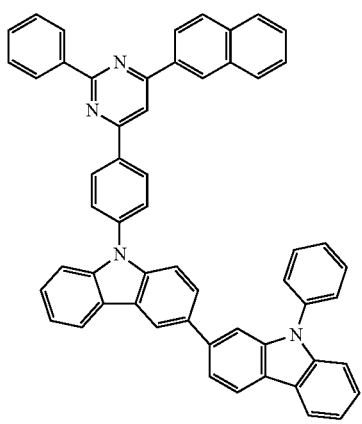
98
-continued
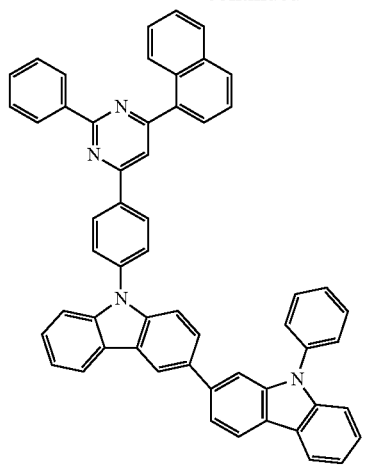
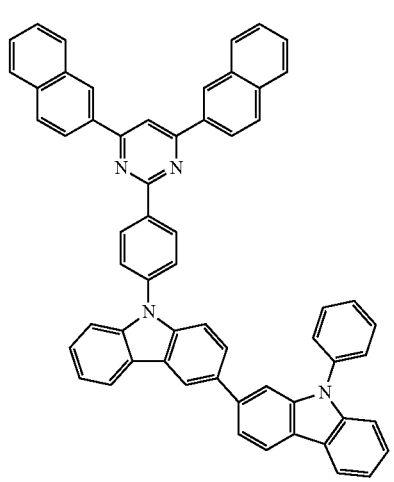
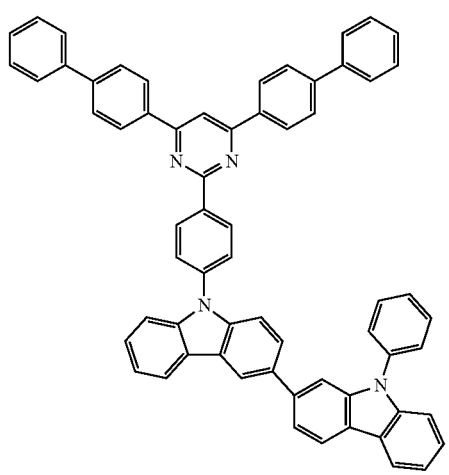

99
-continued
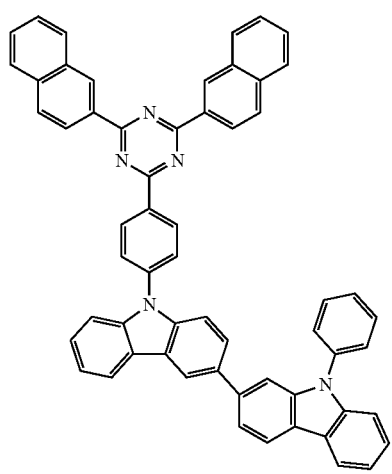
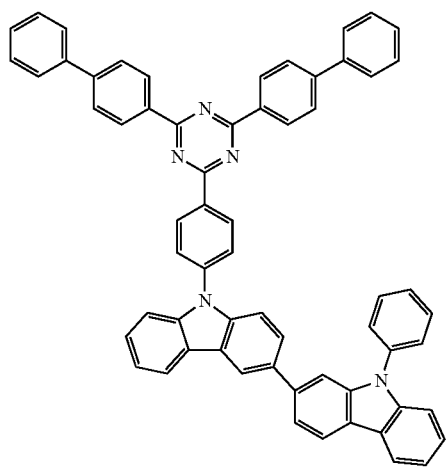
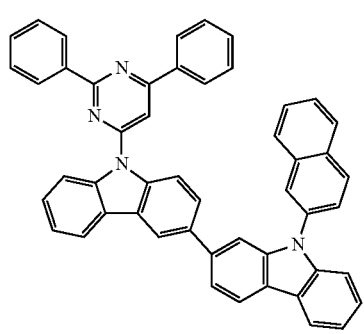
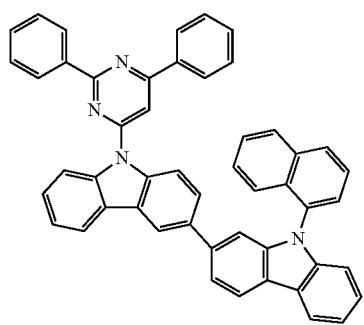
100
-continued
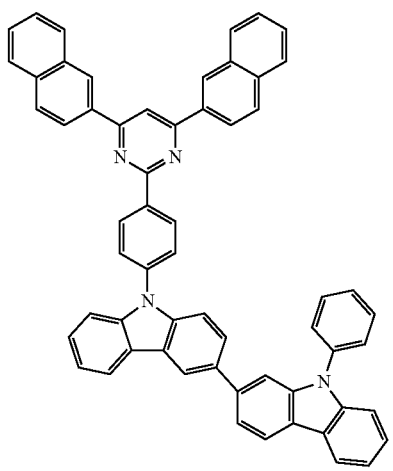
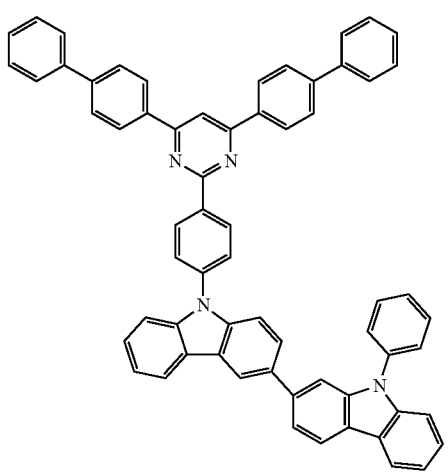
[Formula 52]
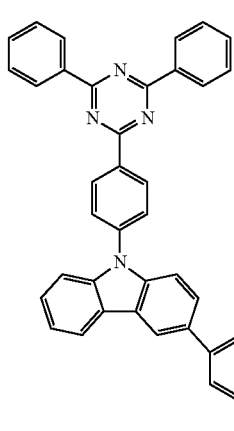

101
-continued
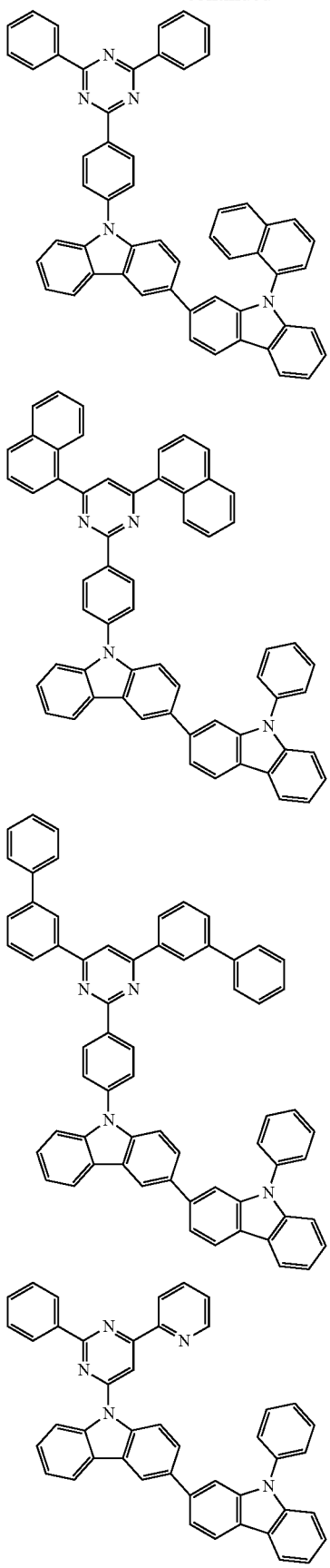
102
-continued
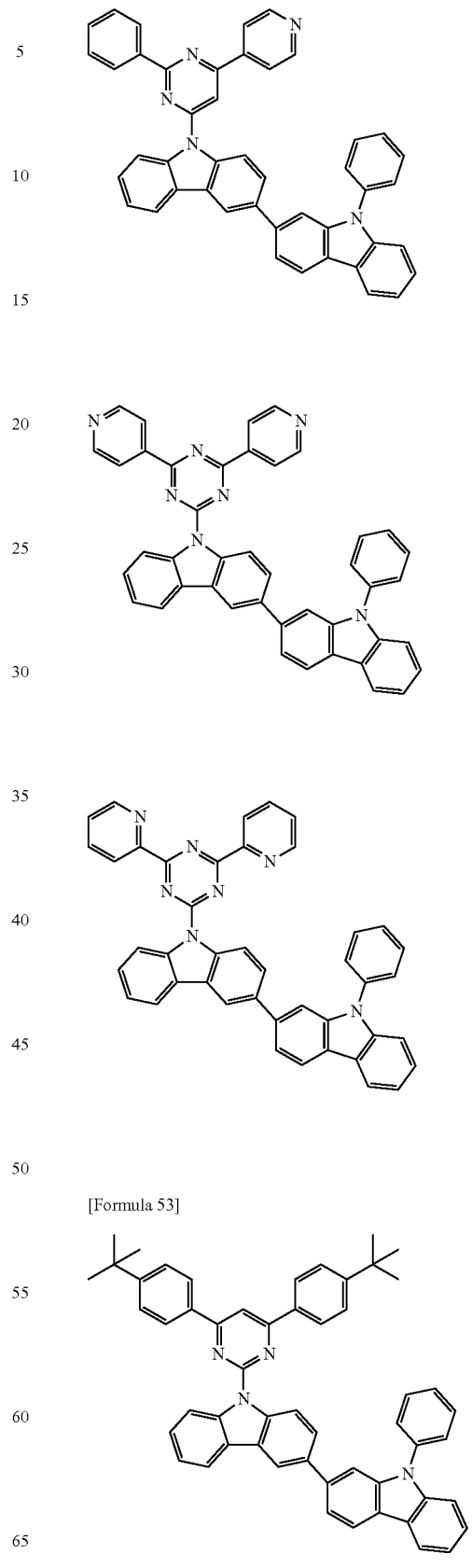
[Formula 53]

-continued
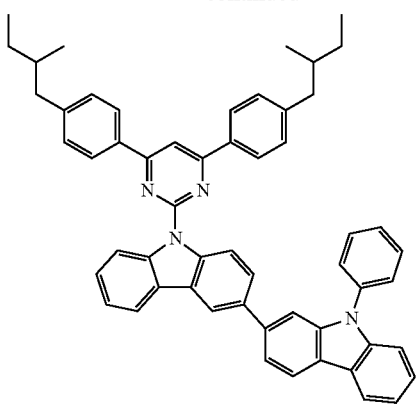
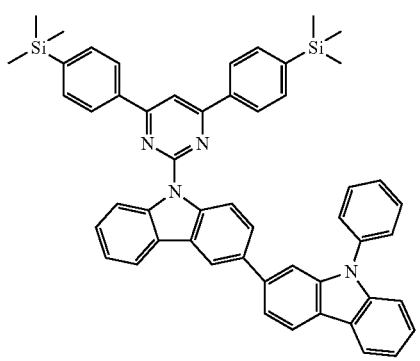
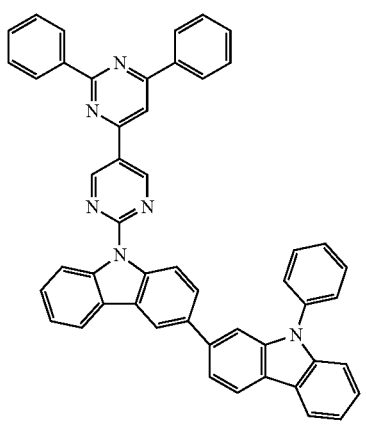
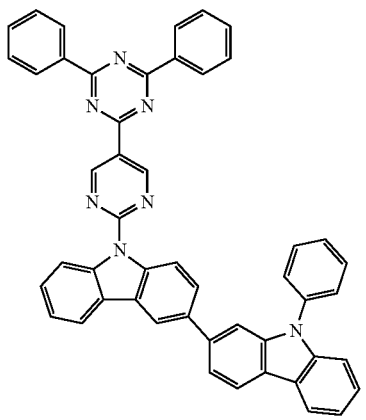
-continued
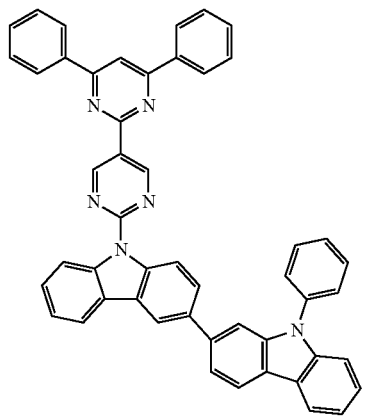
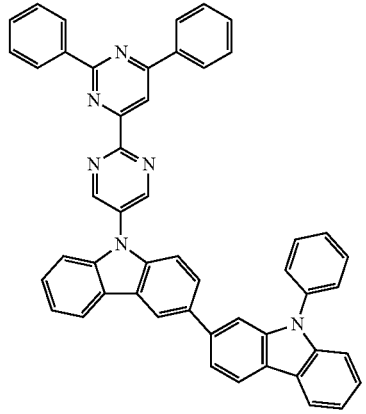
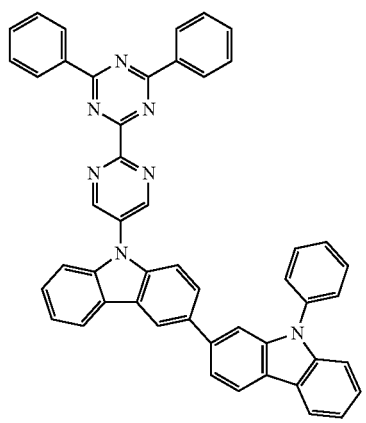
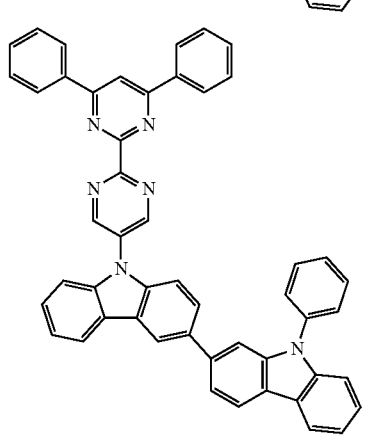

[Formula 54]
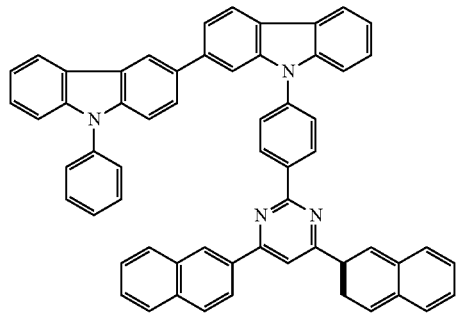
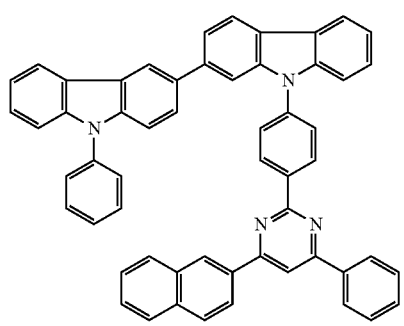
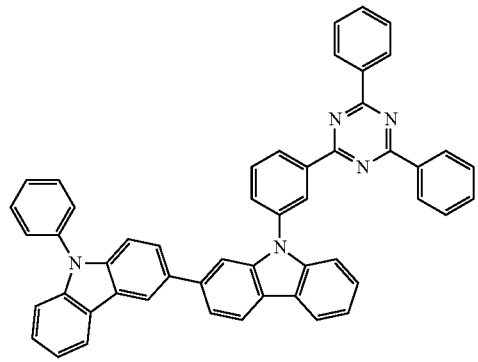
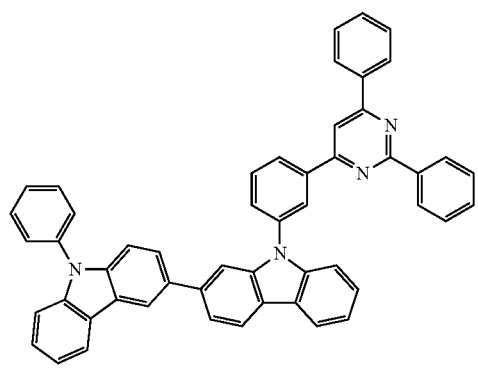
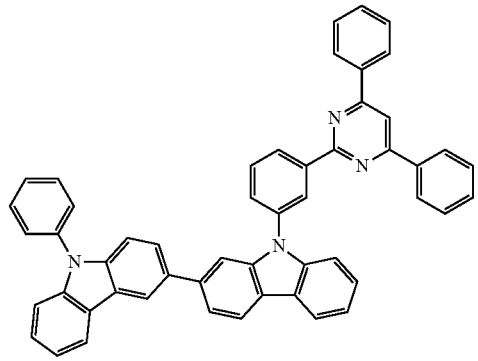
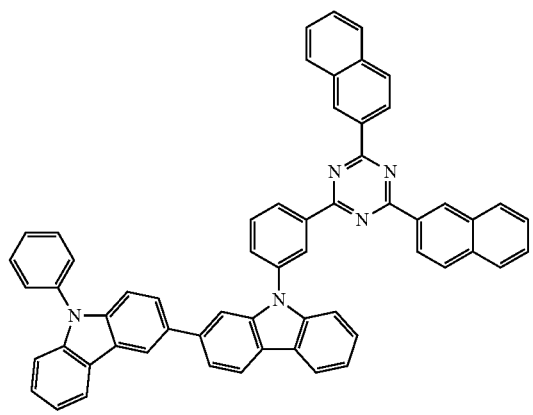
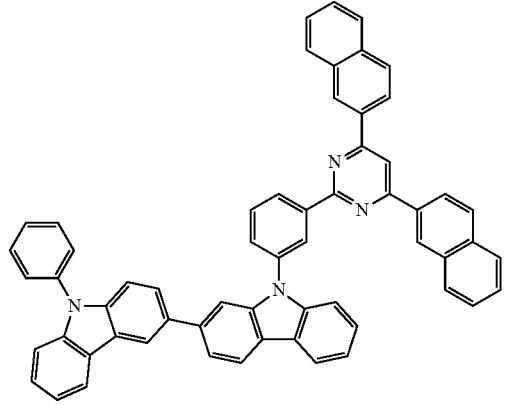
[Formula 55]
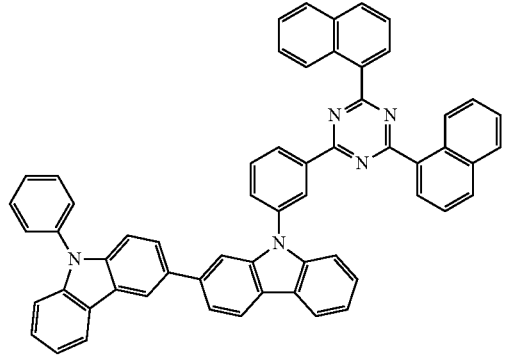

-continued
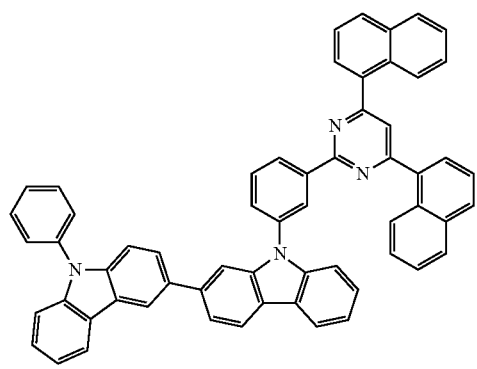
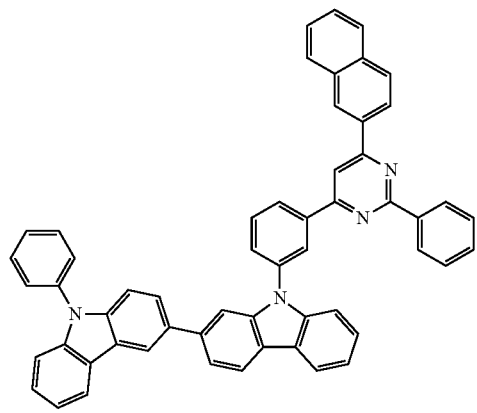
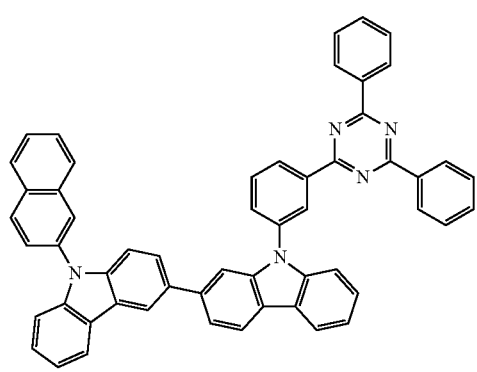
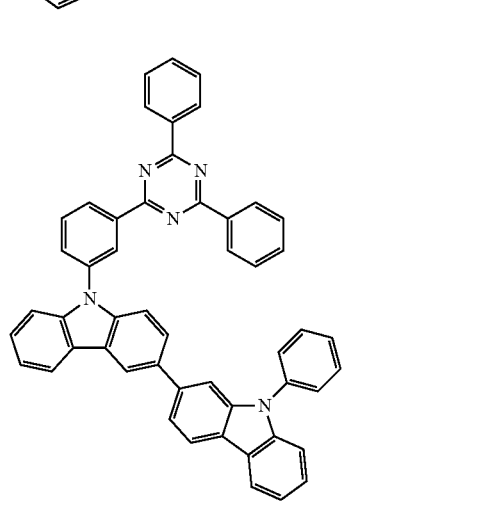
-continued
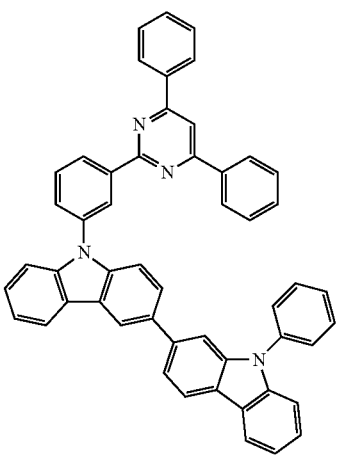
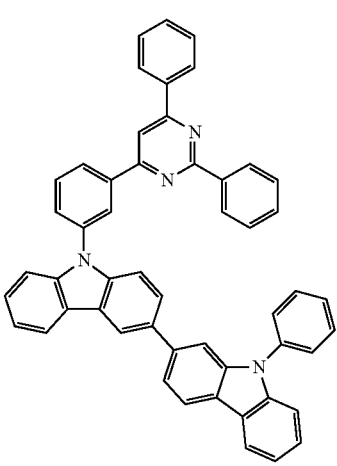
[Formula 56]
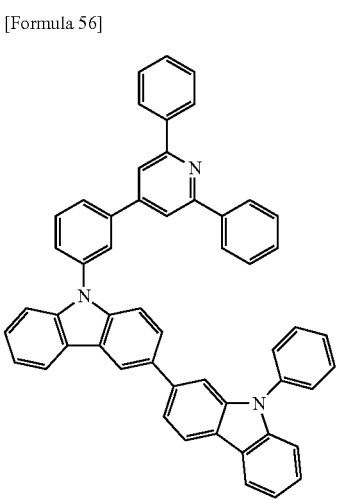

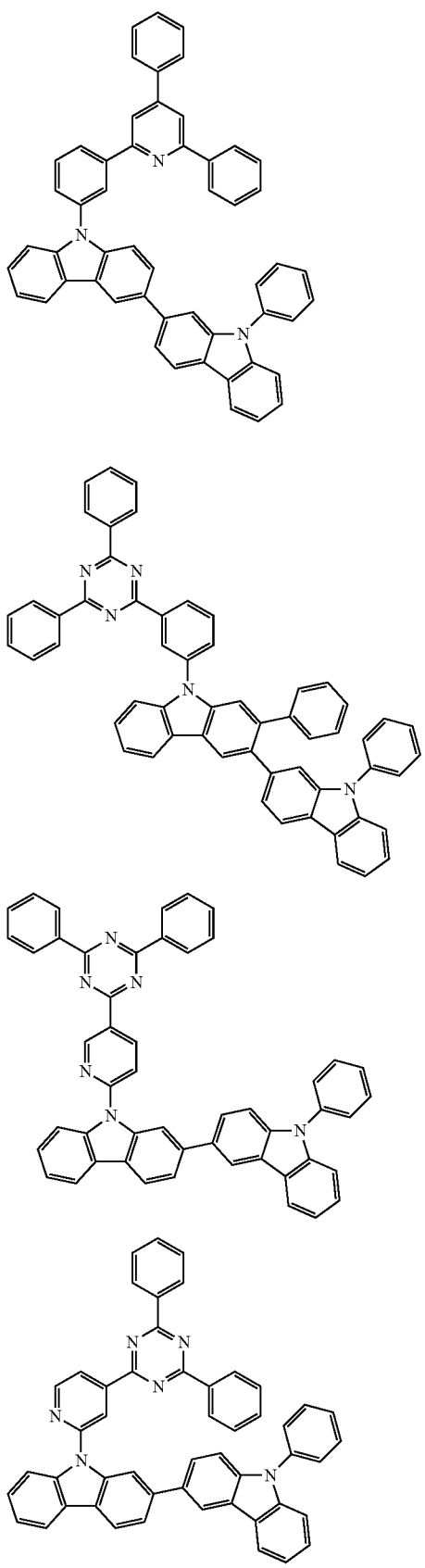
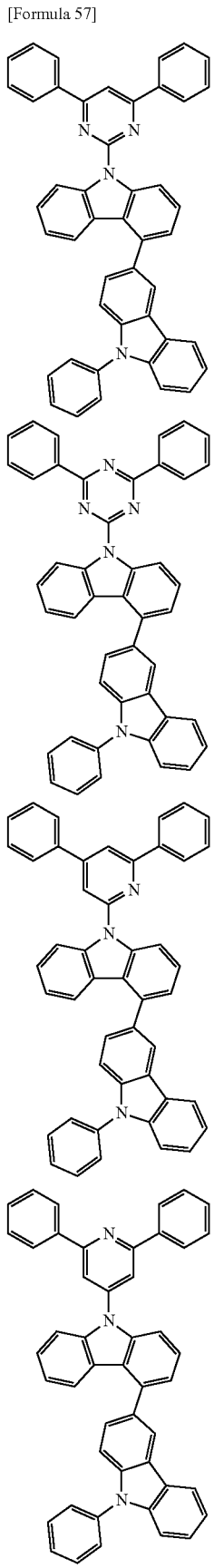
[Formula 57]

111
-continued
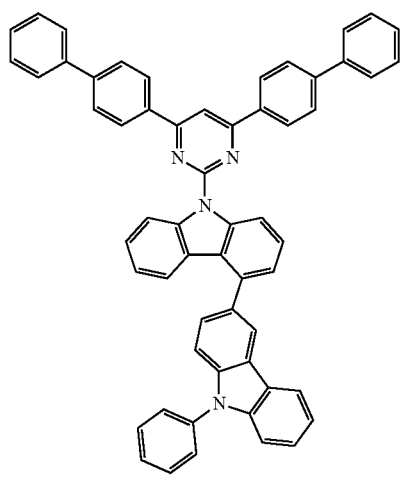
[Formula 58]
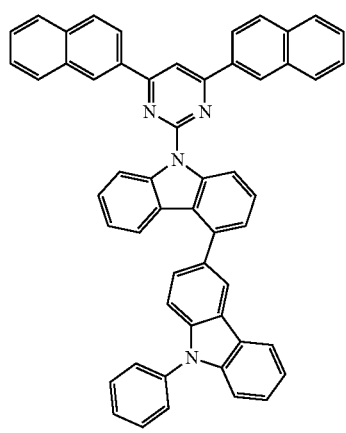
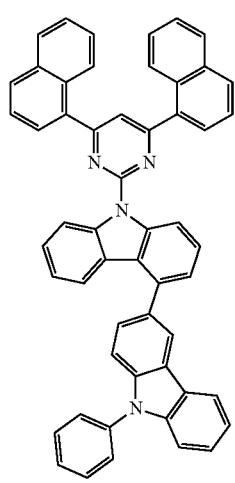
112
-continued
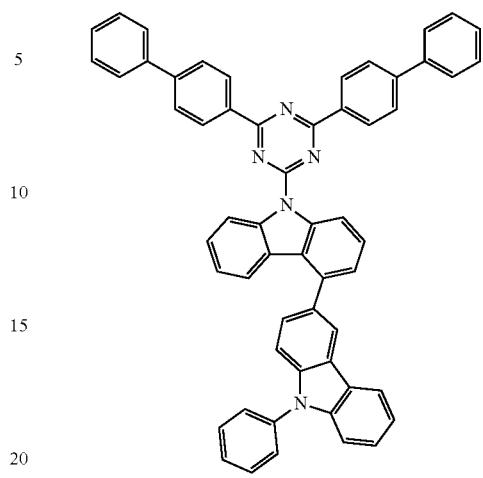
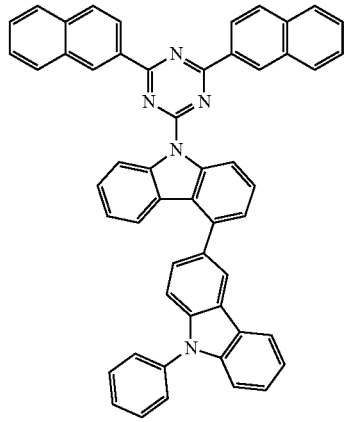
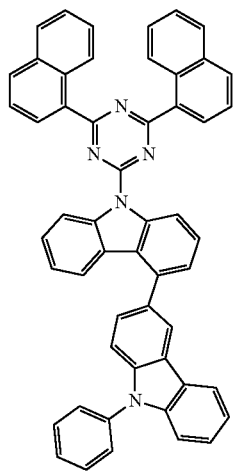

[Formula 59]
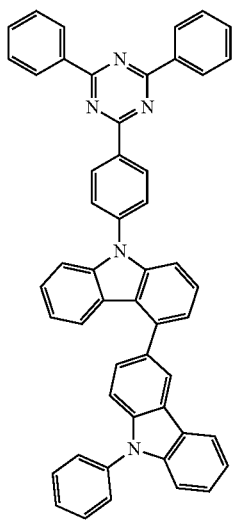
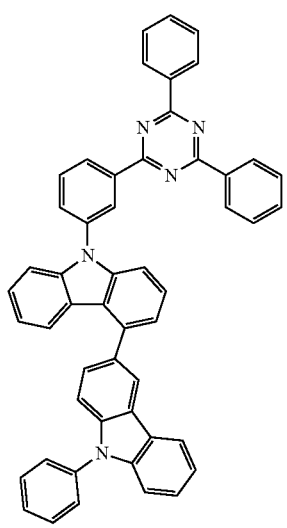
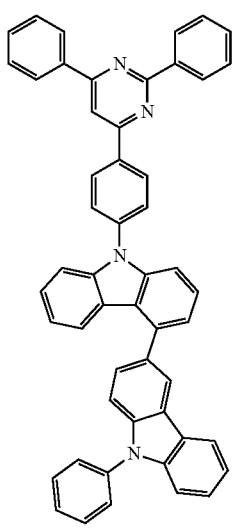
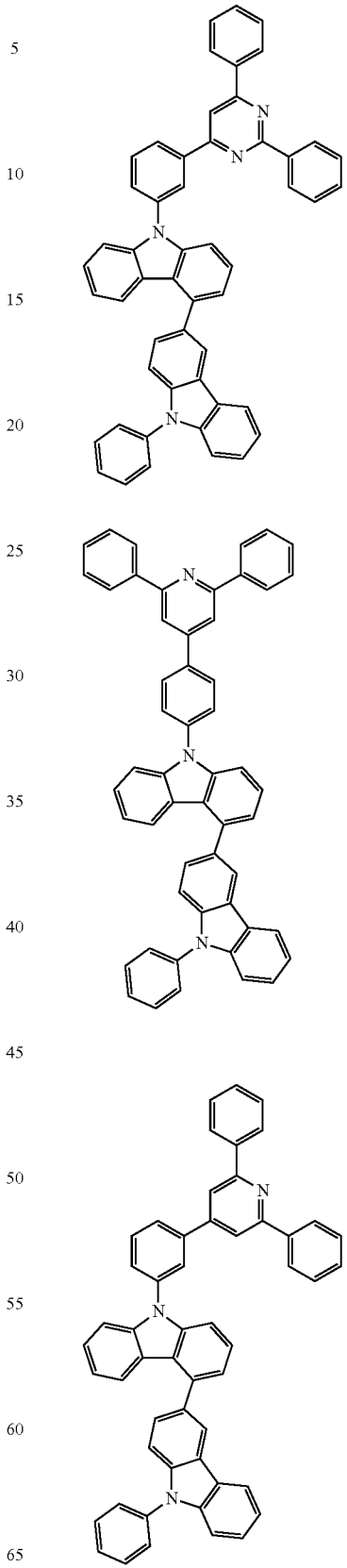

[Formula 60]
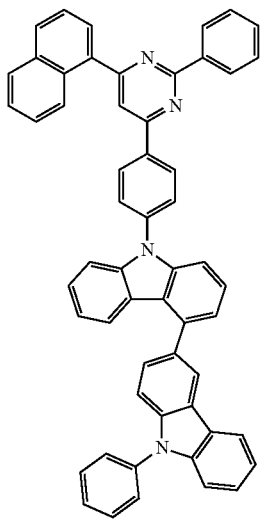
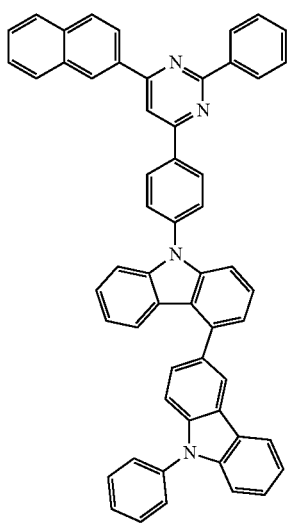
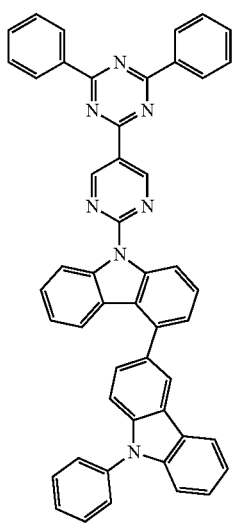
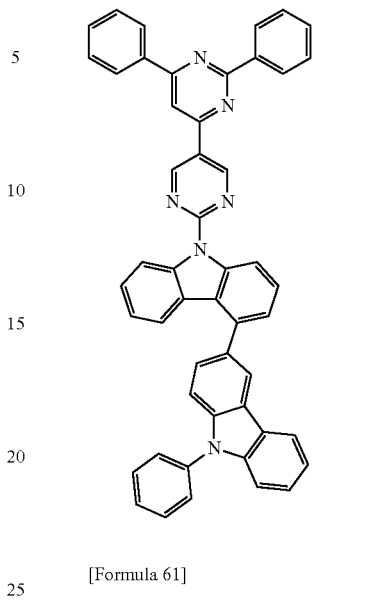
[Formula 61]
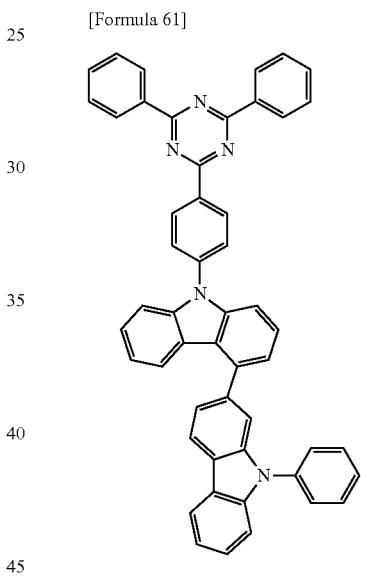
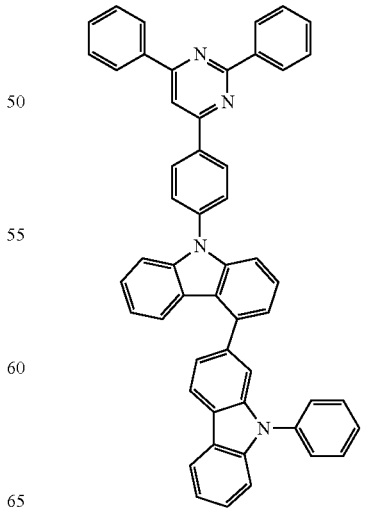

-continued
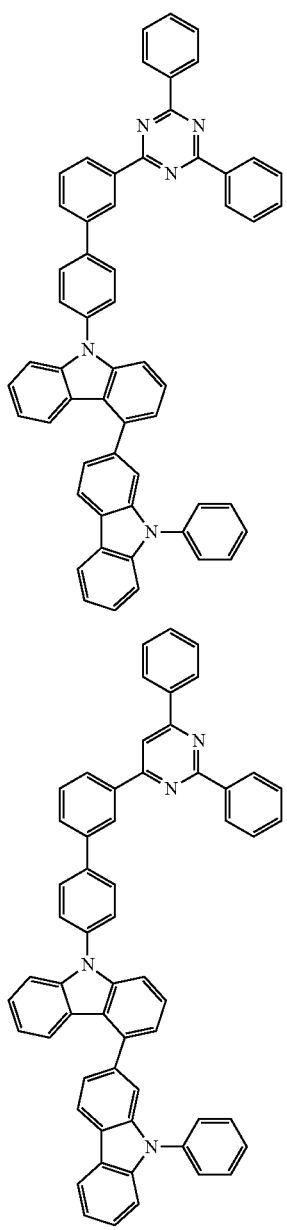
[Formula 62]
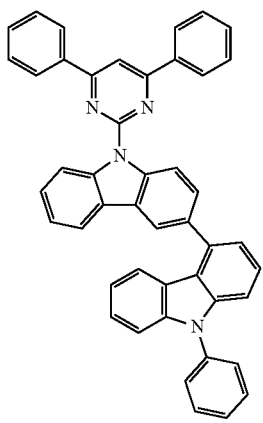
-continued
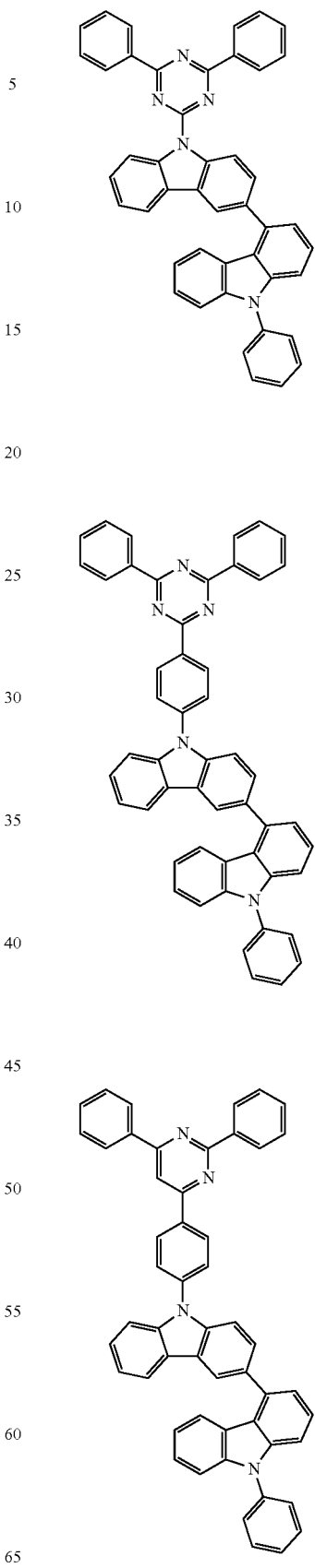

-continued
[Formula 63]
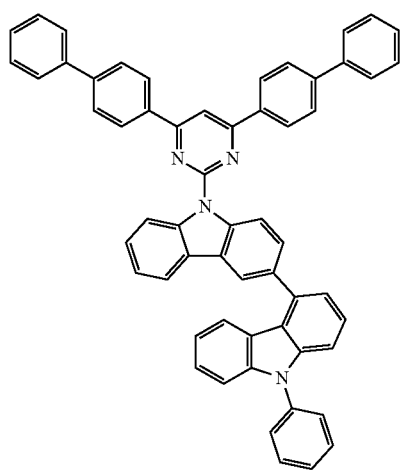
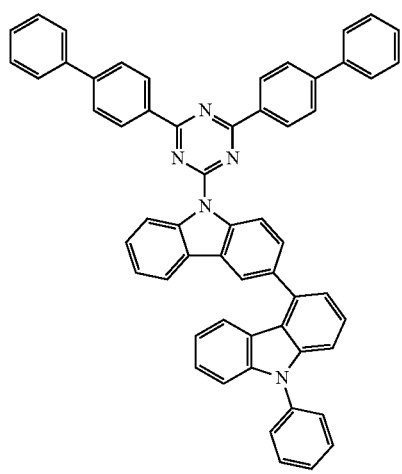
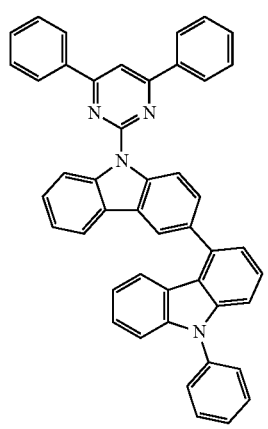
-continued
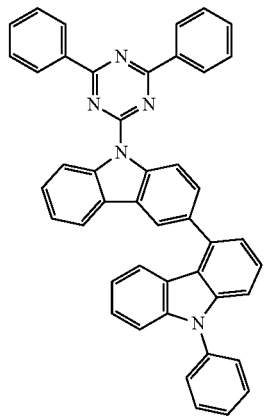
[Formula 64]
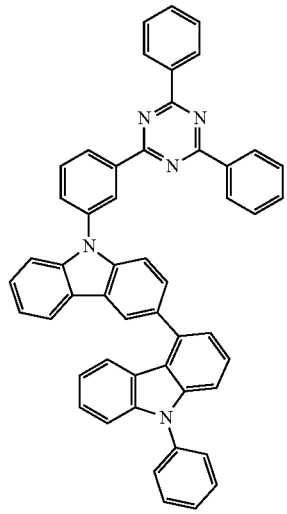
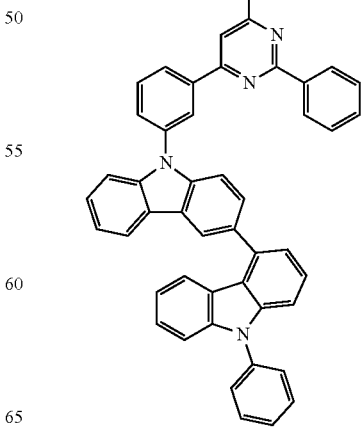

121
-continued
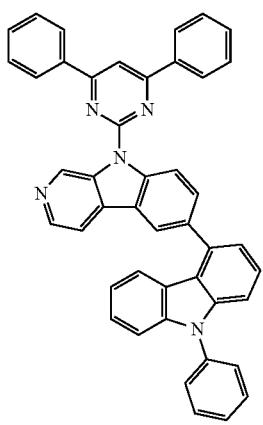
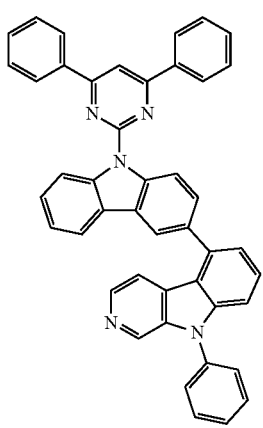
[Formula 65]
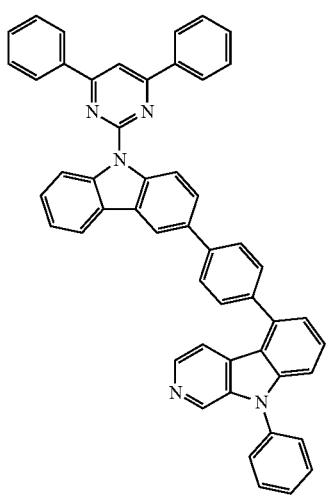
122
-continued
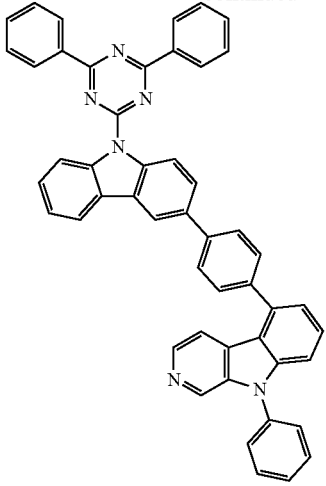
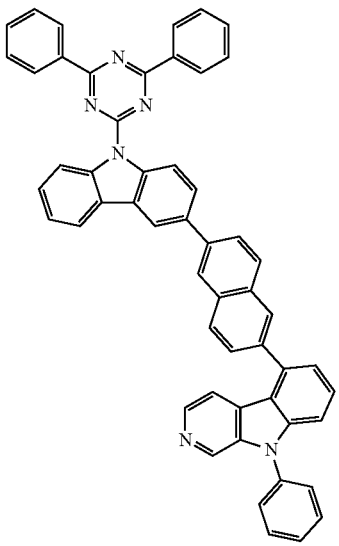
[Formula 66]
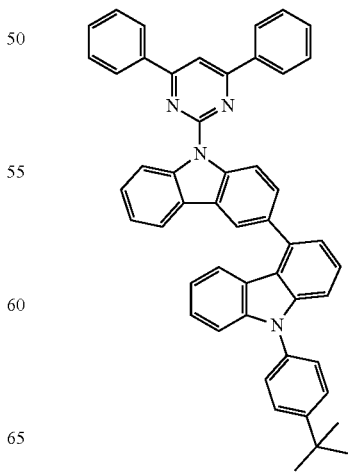

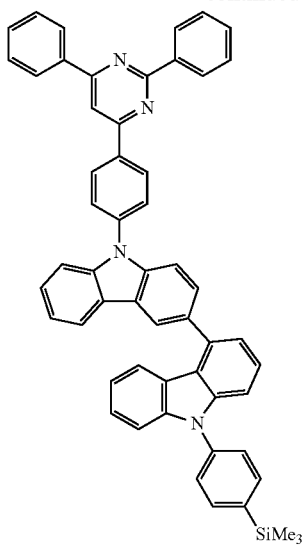
[Formula 67]
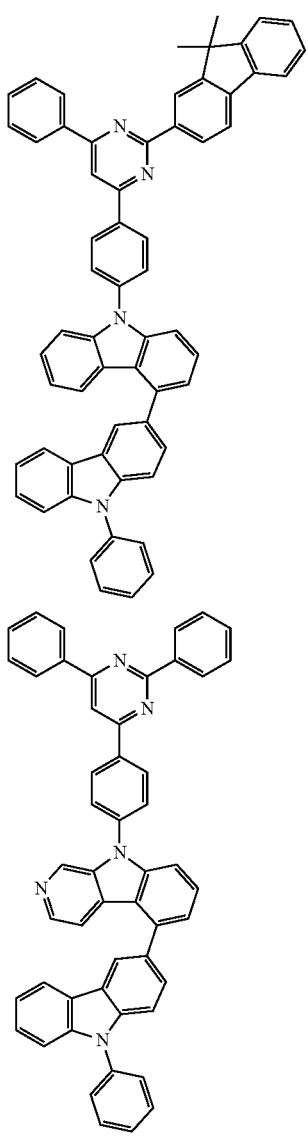
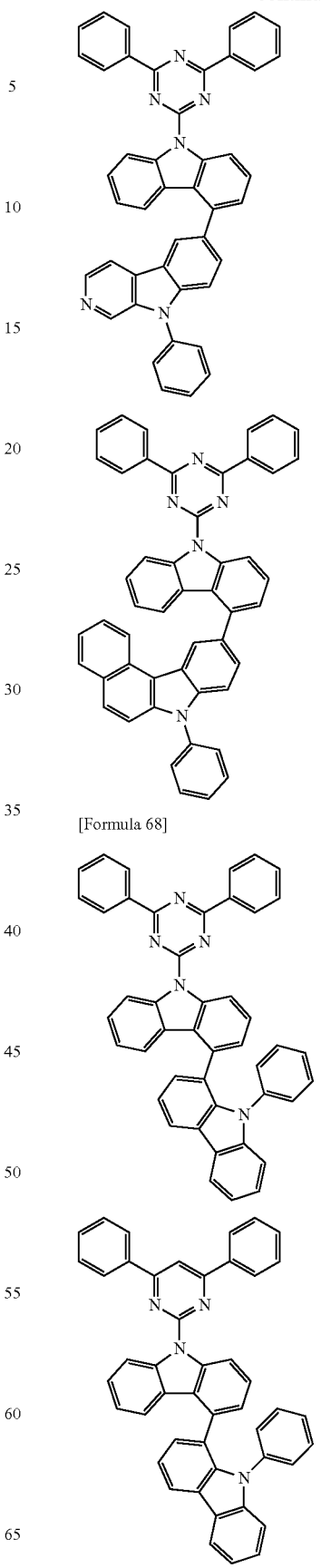
[Formula 68]

-continued
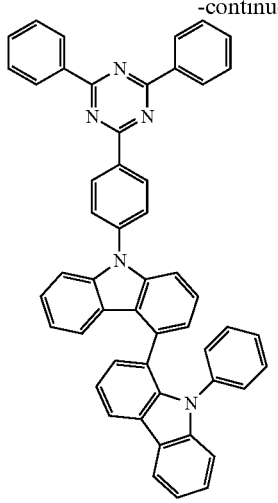
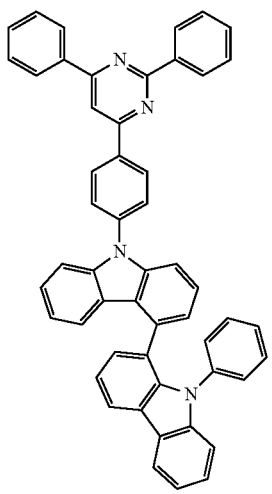
[Formula 69]
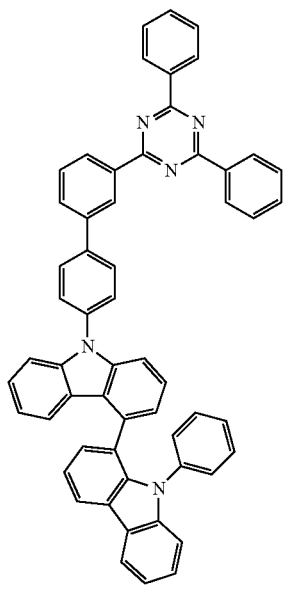
-continued
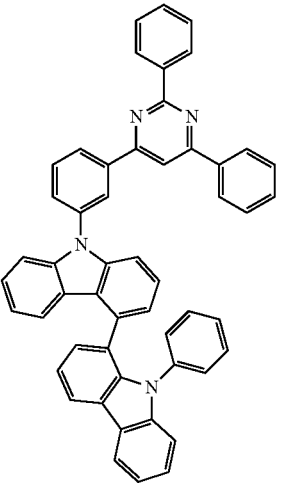
[Formula 70]
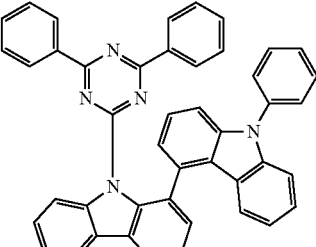
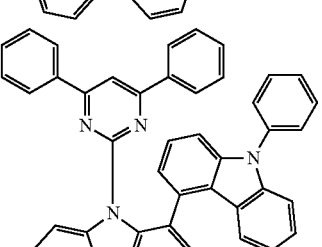
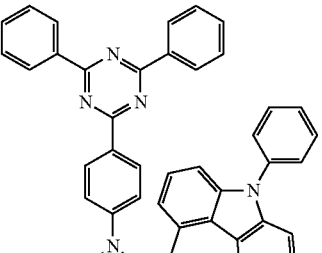
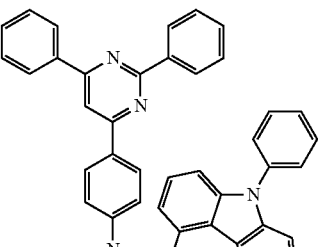

[Formula 71]
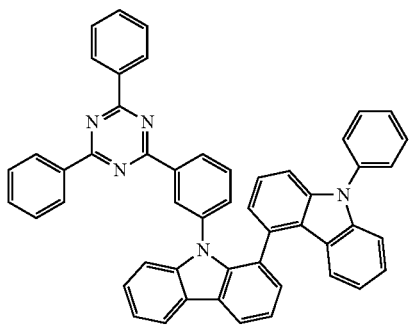
[Formula 72]
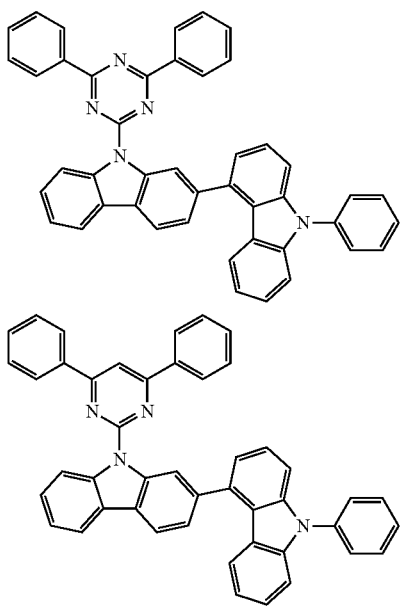
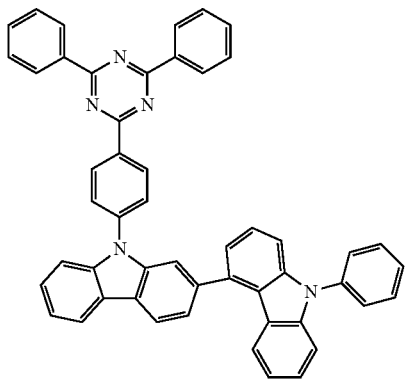
[Formula 73]
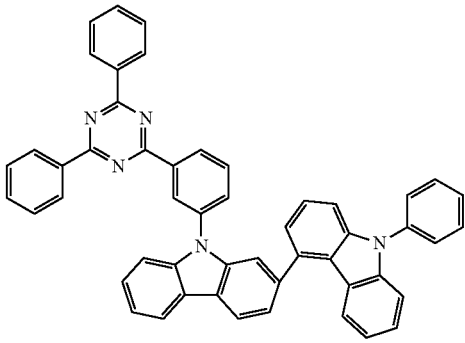
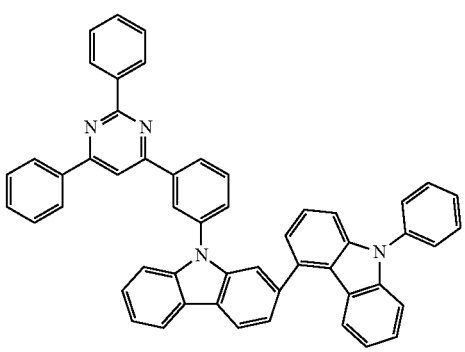
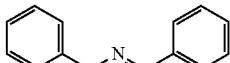
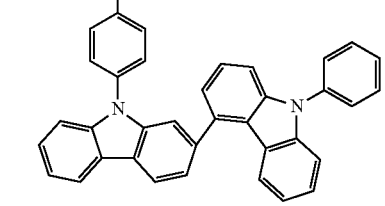
[Formula 74]
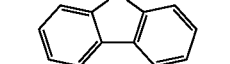
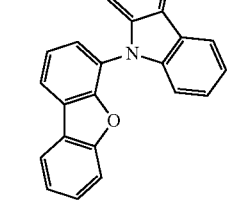

-continued
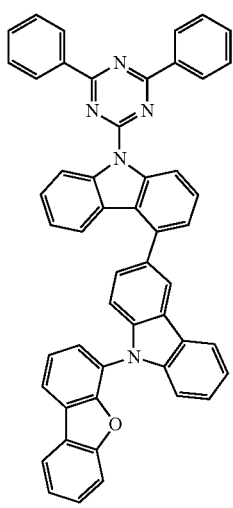
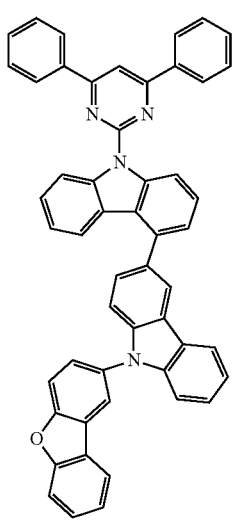
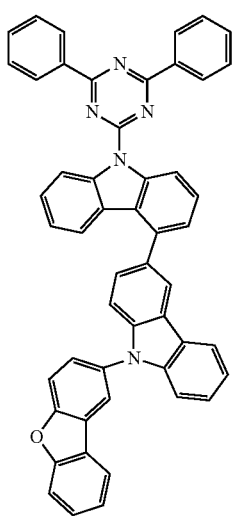
-continued
[Formula 75]
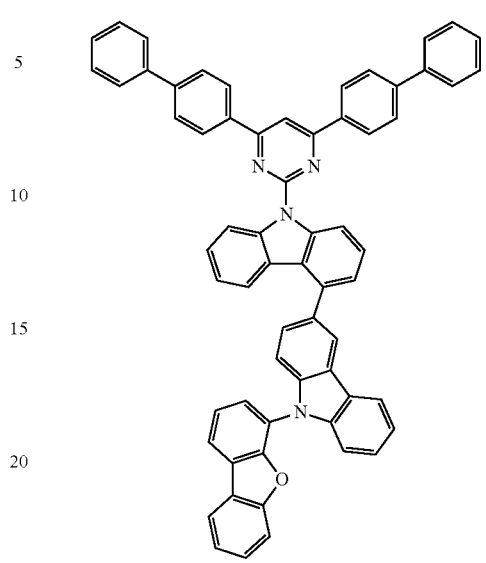
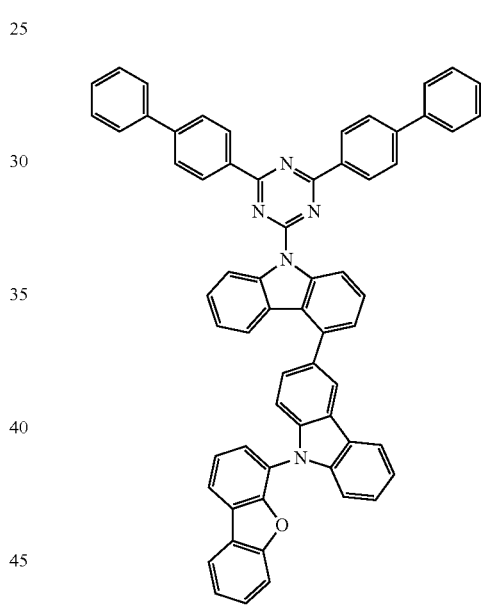
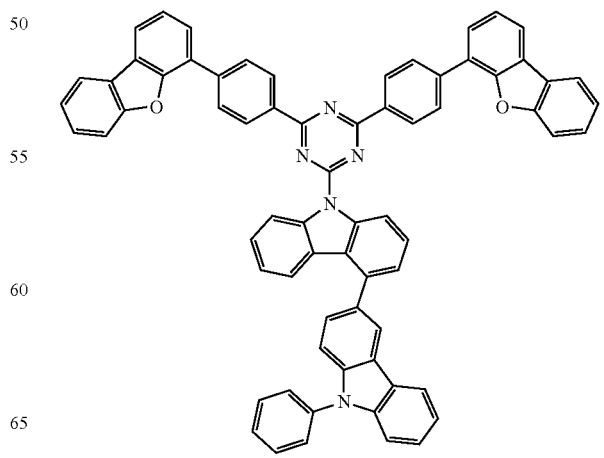

[Formula 76]
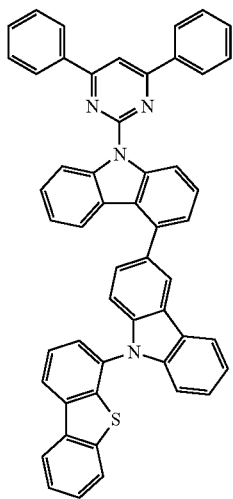
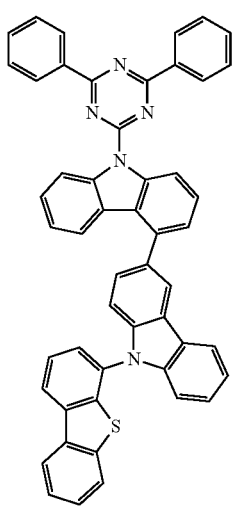
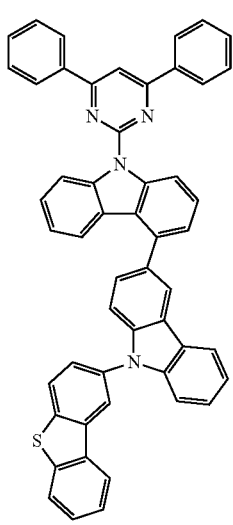
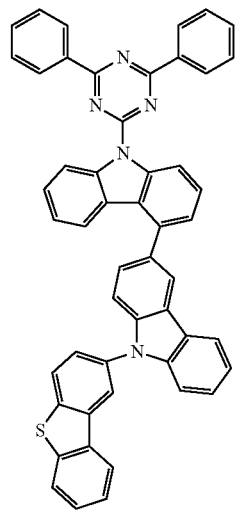
[Formula 77]
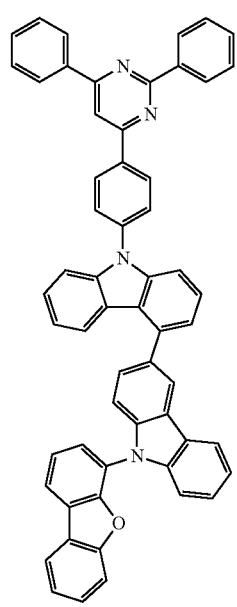

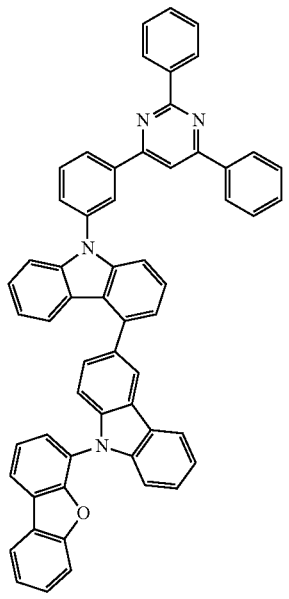
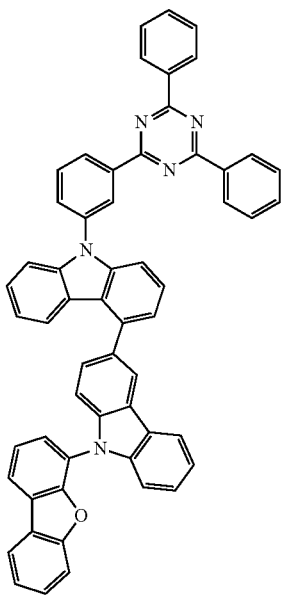
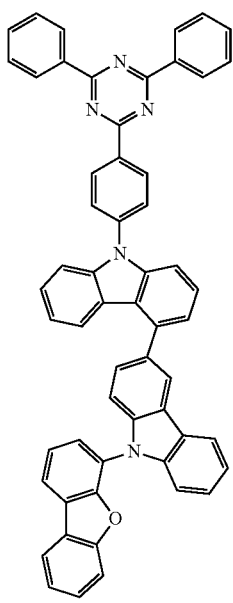
[Formula 78]
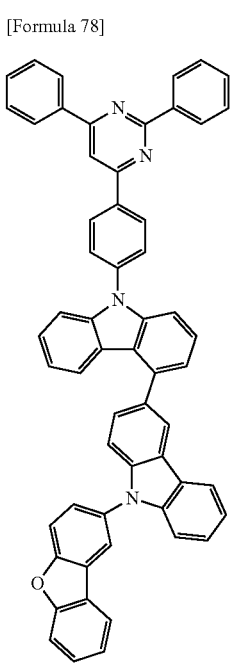

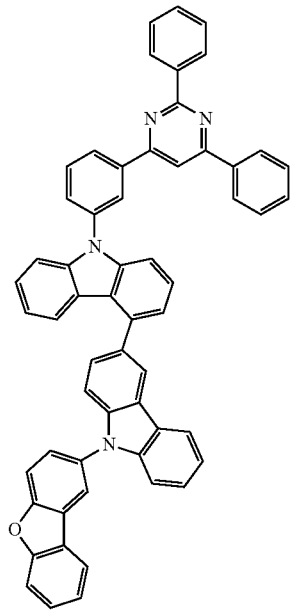
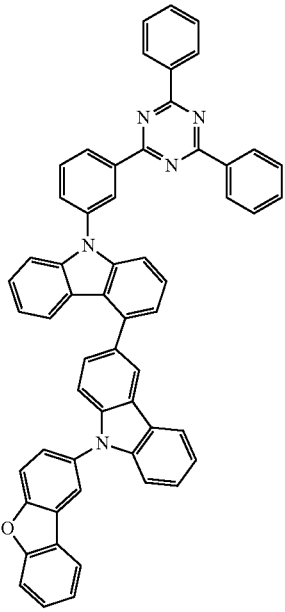
[Formula 79]
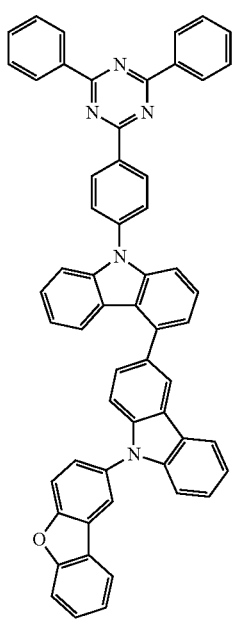
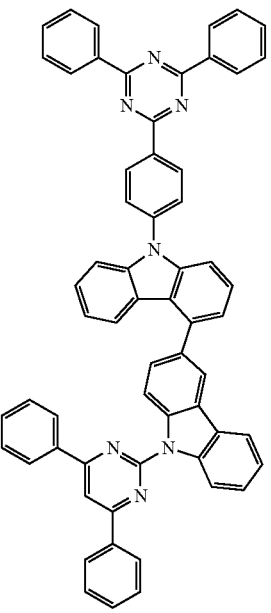

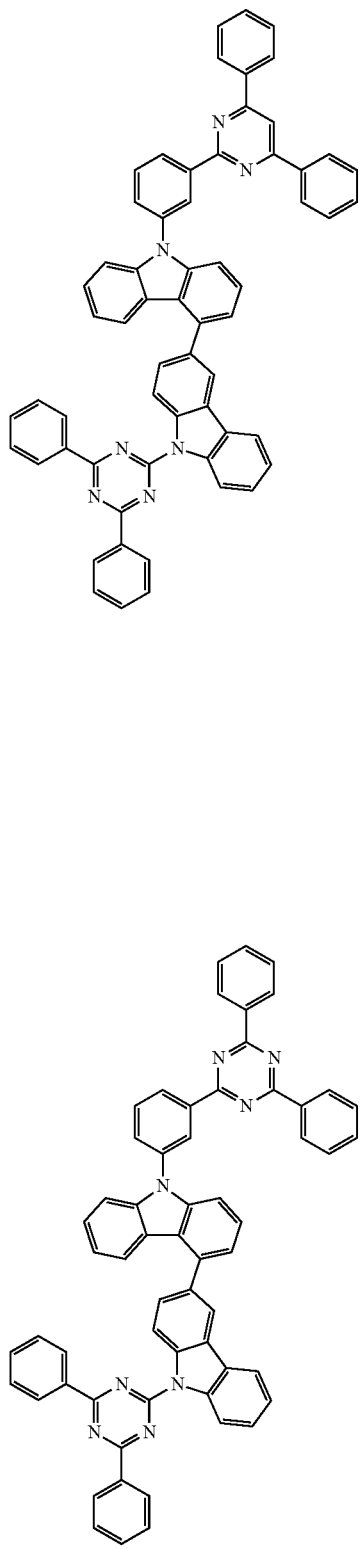
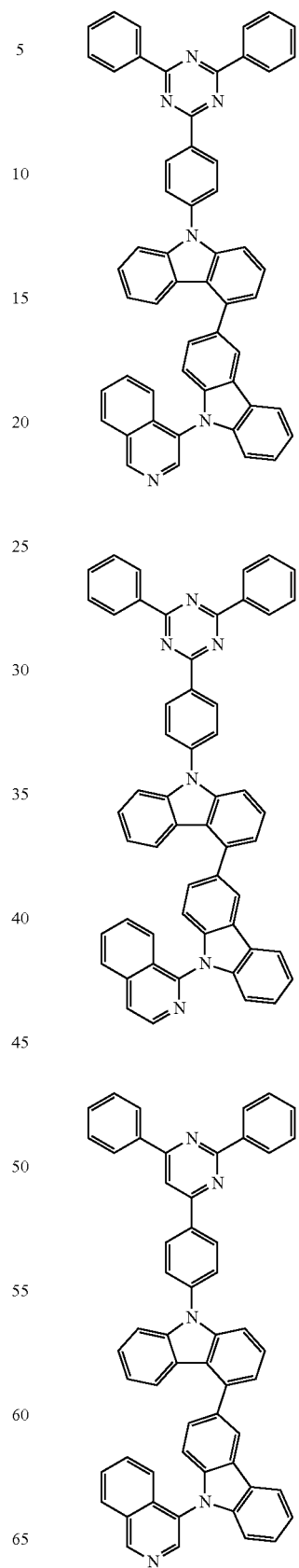
[Formula 80]

[Formula 81]

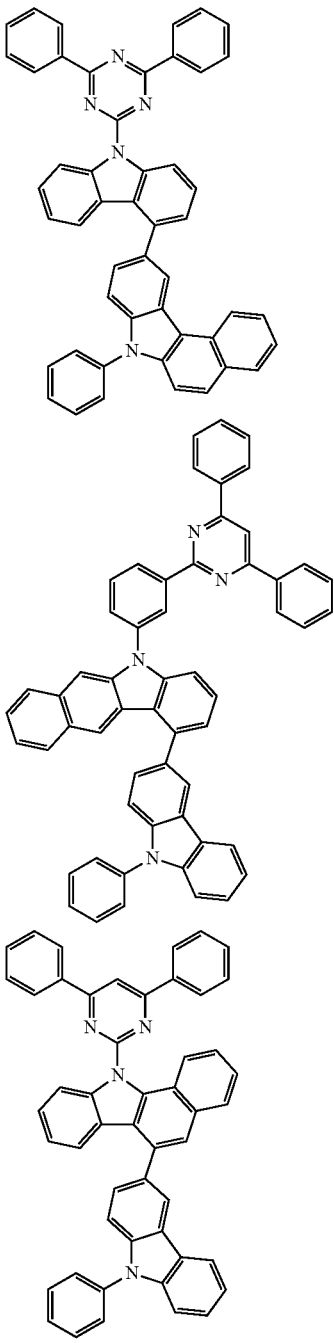

Second Host Material

As the second host material used in the organic EL device of this exemplary embodiment, a compound represented by the above formula (2) is preferable.

In the formula (2), an aryl group, an heterocyclic group, an alkyl group, an alkenyl group, an alkynyl group, an alkylsilyl group, an arylsilyl group, an alkoxy group, an aralkyl group and an aryloxy group represented by $R^2$ are the same as those described in relation to $R^1$, $R^{10}$ to $R^{11}$ and $R^{31}$ to $R^{32}$ in the formula (1) and the like.

In the formula (2), an aryl group, a heterocyclic group and a cycloalkyl group represented by $L^2$ are the same as those described in relation to $L^1$ in the formula (1).

In the formula (2), FA represents a substituted or unsubstituted fused aromatic cyclic group having 6 to 30 ring carbon atoms, or a substituted or unsubstituted fused aromatic heterocyclic group having 5 to 30 ring atoms.

FA is preferably a substituted or unsubstituted fused aromatic cyclic group having 10 to 30 ring carbon atoms, or a substituted or unsubstituted fused aromatic heterocyclic group having 9 to 30 ring atoms, more preferably a substituted or unsubstituted fused aromatic cyclic group having 2 to 5 fused rings, or a substituted or unsubstituted fused aromatic heterocyclic group having 2 to 5 fused rings.

FA is further preferably represented by a formula (2-A) below.

[Formula 82]

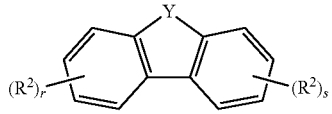

(2-A)

In the formula (2-A): Y represents O, S, $NR^{21}$ or $C(R^{21})_2$; and $R^2$ and $R^{21}$ represent the same as $R^2$ of the formula (2).

However, one of $R^2$ is a single bond to be bonded with $L^2$ in the formula (2). When Y is $C(R^{21})_2$, a plurality of $R^{21}$ are mutually the same or different.

r and s are an integer of 0 to 4.]

Among these groups, FA is more preferably represented by any one of the following formulae (2-1) to (2-4), particularly preferably by the formula (2-1) or (2-2).

[Formula 83]

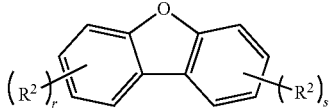

(2-1)

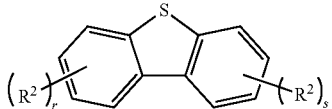

(2-2)

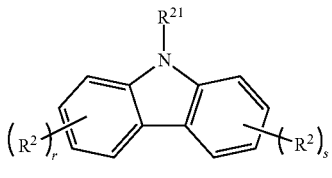

(2-3)

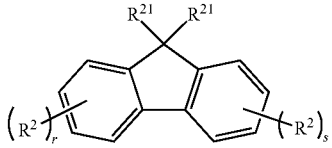

(2-4)

In the formulae (2-1) to (2-4), $R^2$ and $R^{21}$ represent the same as $R^2$ of the formula (2).

However, one of $R^2$ is a single bond to be bonded with $L^2$ in the formula (2).

r and s are an integer of 0 to 4.]

Examples of the fused aromatic cyclic group for FA are a naphthyl group, phenanthryl group, fluoranthenyl group, triphenylenyl group, phenanthrenyl group, fluorenyl group, spirofluorenyl group, 9,9-diphenyl fluorenyl group, 9,9'-spirobi[9H-fluorene]-2-yl group, 9,9-dimethylfluorenyl group, benzofluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, benzo[b]fluoranthenyl group, chrysenyl group and pyrenyl group.

The fused aromatic cyclic group for FA more preferably has 6 to 20 ring carbon atoms, and further preferably has 6 to 12 ring carbon atoms. Among the fused aromatic cyclic group, a naphthyl group, phenanthryl group, triphenylenyl group, fluorenyl group, 9,9-dimethylfluorenyl group, spirobifluorenyl group and fluoranthenyl group are particularly preferable. With respect to a fluorenyl group, a carbon atom at a position 9 is preferably substituted by a substituted or unsubstituted alkyl group having 1 to 30 carbon atoms.

Examples of the fused aromatic heterocyclic group for FA are groups formed from an isoindole ring, benzofuran ring, isobenzofuran ring, dibenzothiophene ring, isoquinoline ring, quinoxaline ring, phenanthridine ring, phenanthroline ring, indole ring, quinoline ring, acridine ring, carbazole ring, benzoxazole ring, benzothiazole ring, benzimidazole ring, dibenzofuran ring, benzo[c]dibenzofuran ring, phenazine ring, phenothiazine ring, phenoxazine ring, azacarbazole ring, imidazopyridine ring, azatriphenylene ring, azadibenzofuran ring and derivatives thereof, among which a dibenzofuran ring, carbazole ring, dibenzothiophene ring, quinoxaline ring and derivatives thereof are preferable. With respect to a carbazolyl group, a nitrogen atom at a position 9 is preferably substituted by a substituted or unsubstituted aryl group having 6 to 30 ring carbon atoms or a substituted or unsubstituted heterocyclic group having 5 to 30 ring atoms. The aryl group having 6 to 30 ring carbon atoms and the heterocyclic group having 5 to 30 ring atoms are the same as those described above in relation to the first host material.

In the formulae (2), (2-A) and (2-1) to (2-4), when $L^2$, $R^2$, $R^{21}$ and FA have one or more substituents, the substituent(s) is the same as those of the formula (1).

Examples of the compound represented by the formula (2) are as follows. Note that a bond without a formula (e.g., Ph, CN and a benzene ring) at an end represents a methyl group in the following structures.

[Formula 84]

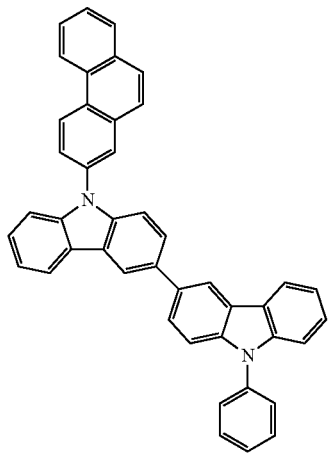

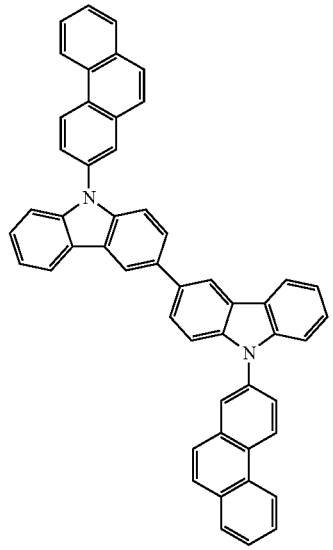

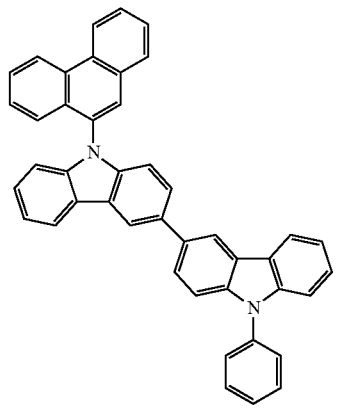

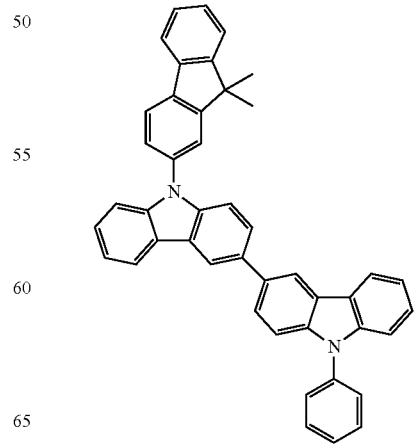

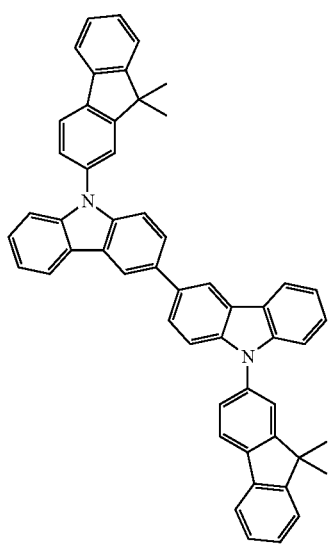
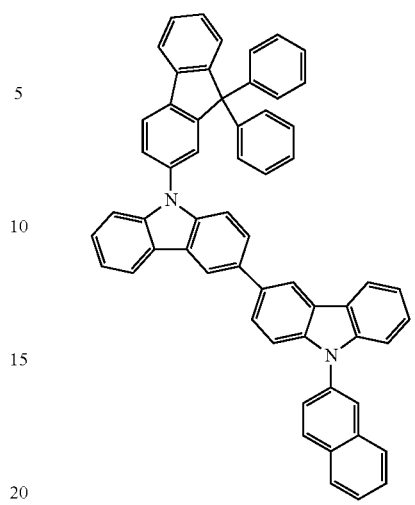
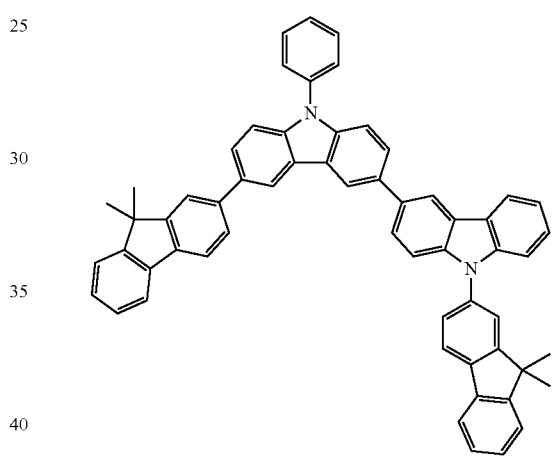
[Formula 85]
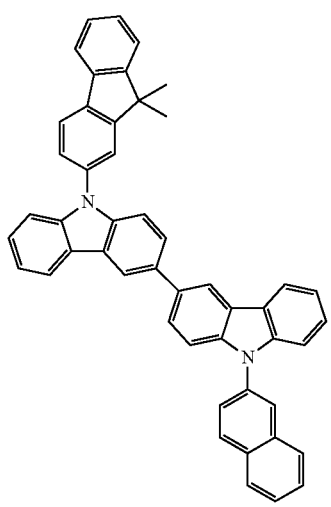
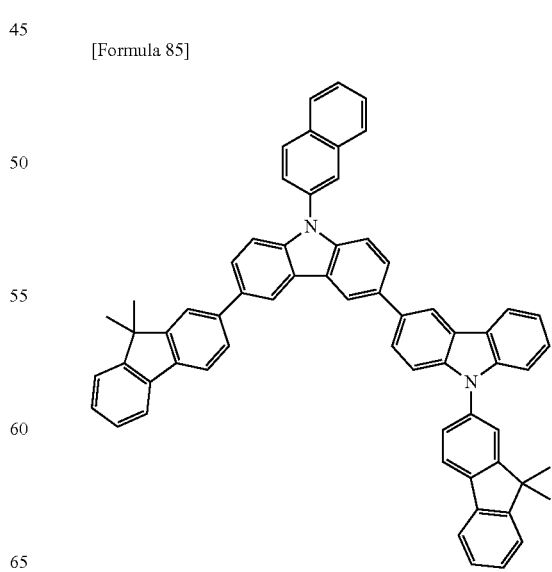

145
-continued
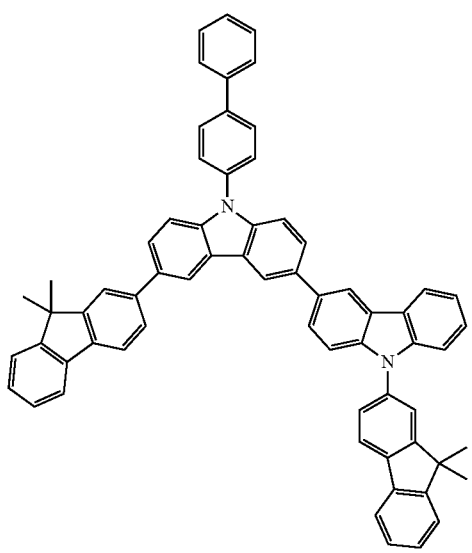
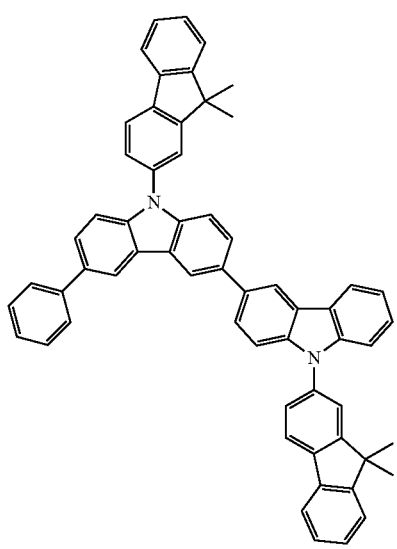
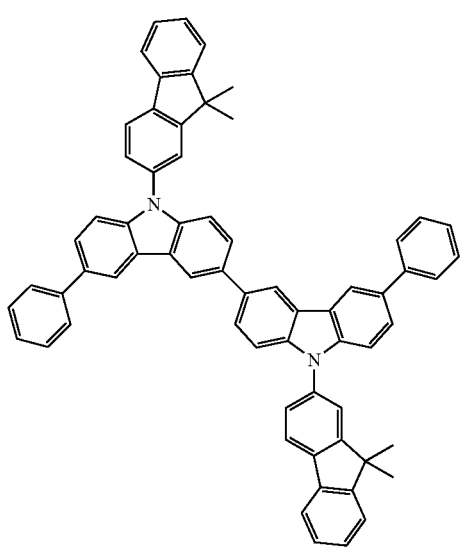
146
-continued
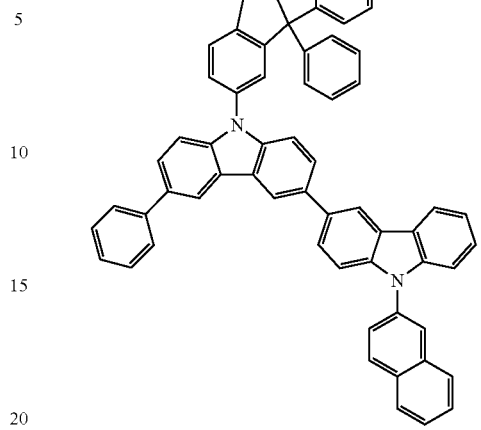
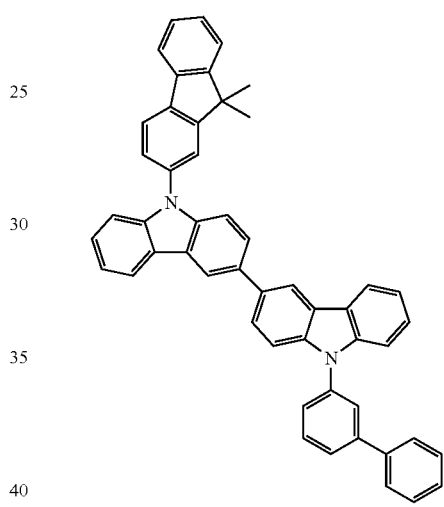
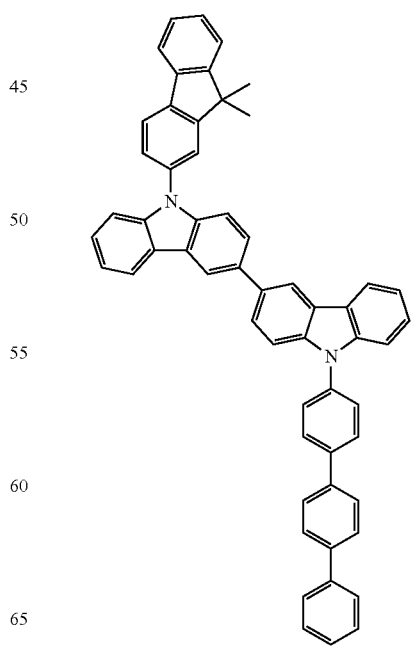

[Formula 86]
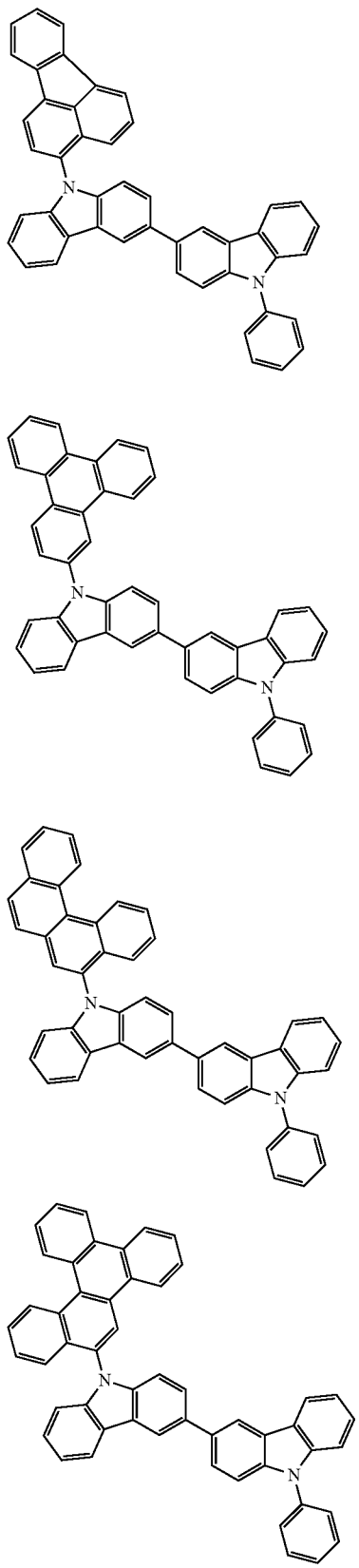
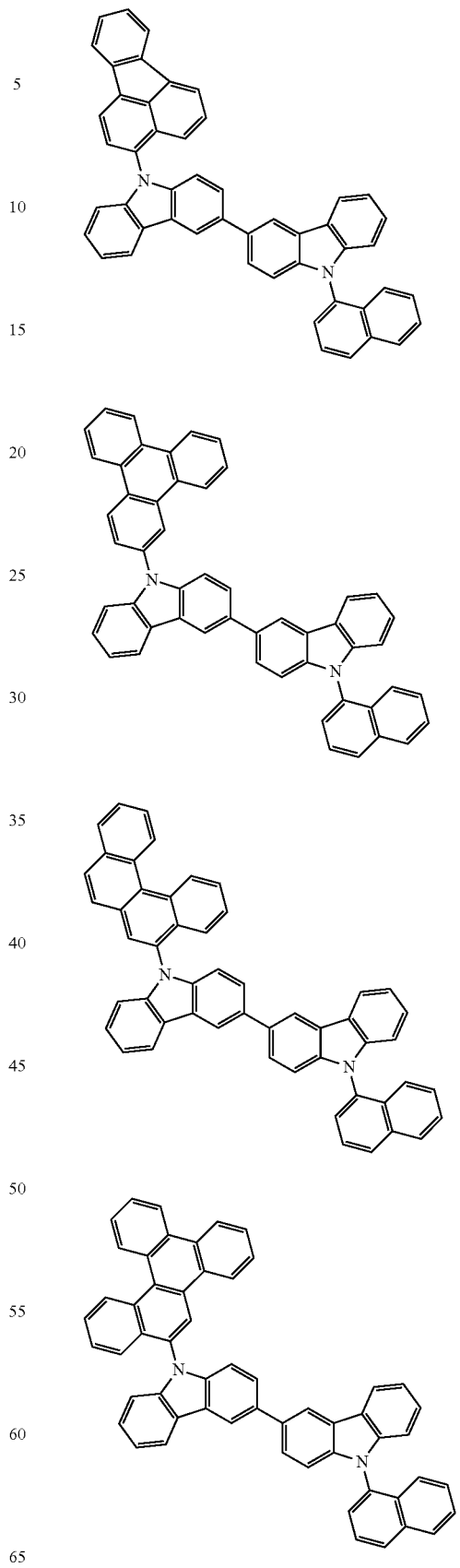

[Formula 87]
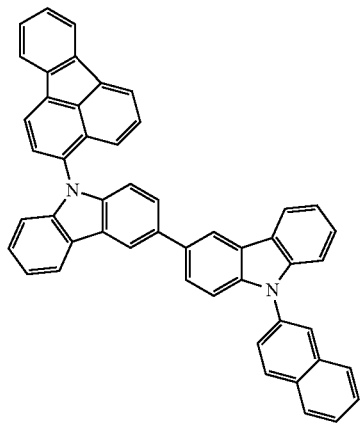
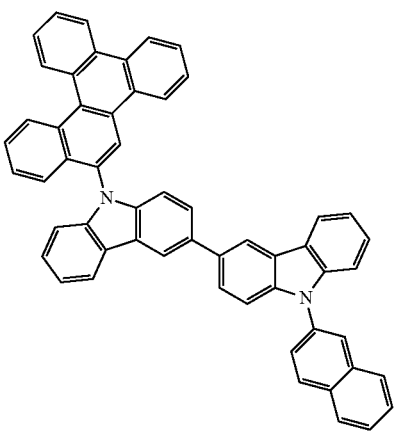
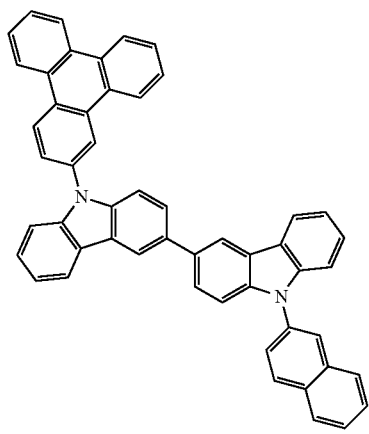
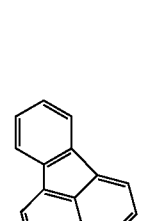
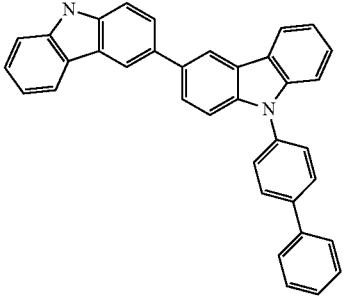
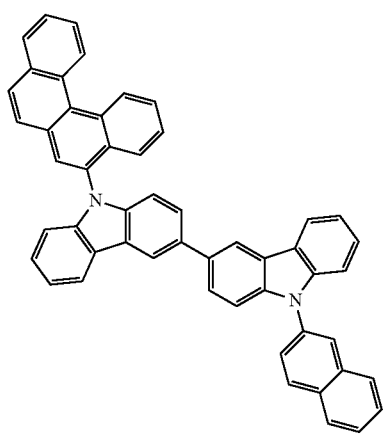
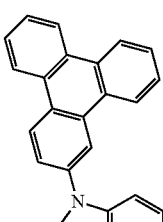

151
-continued
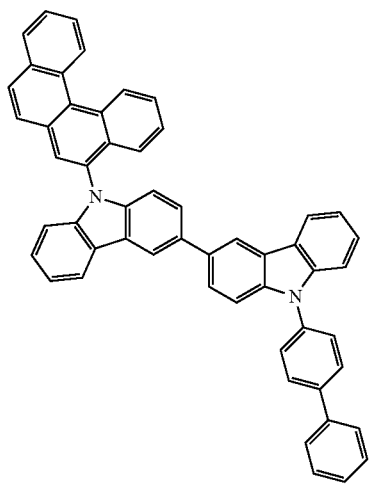
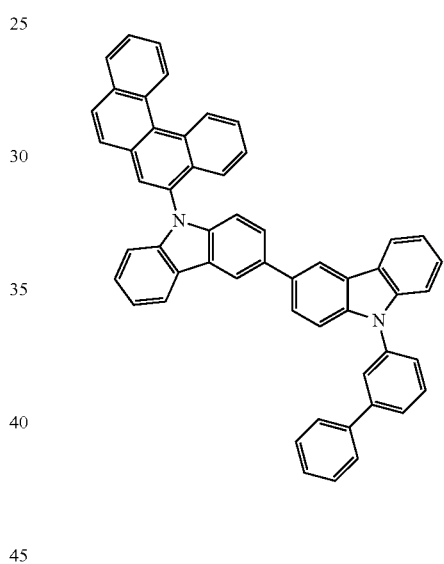
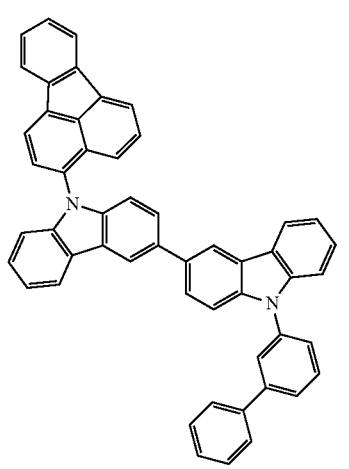
152
-continued
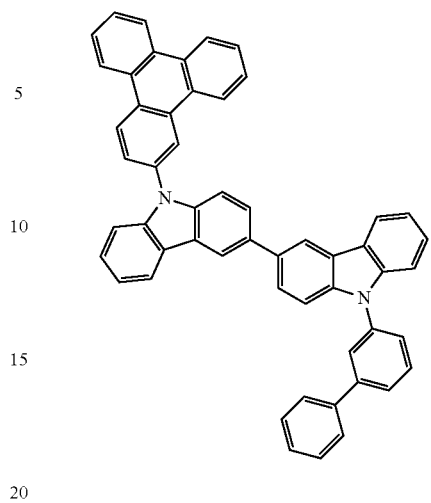
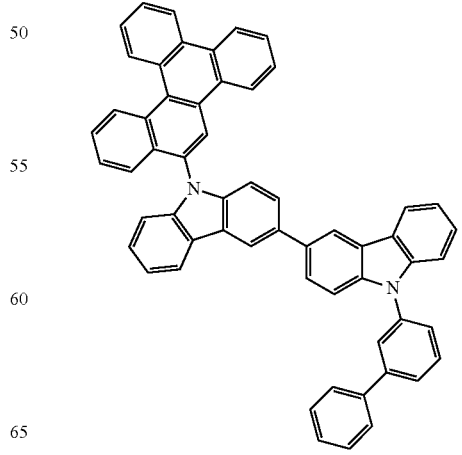

[Formula 88]
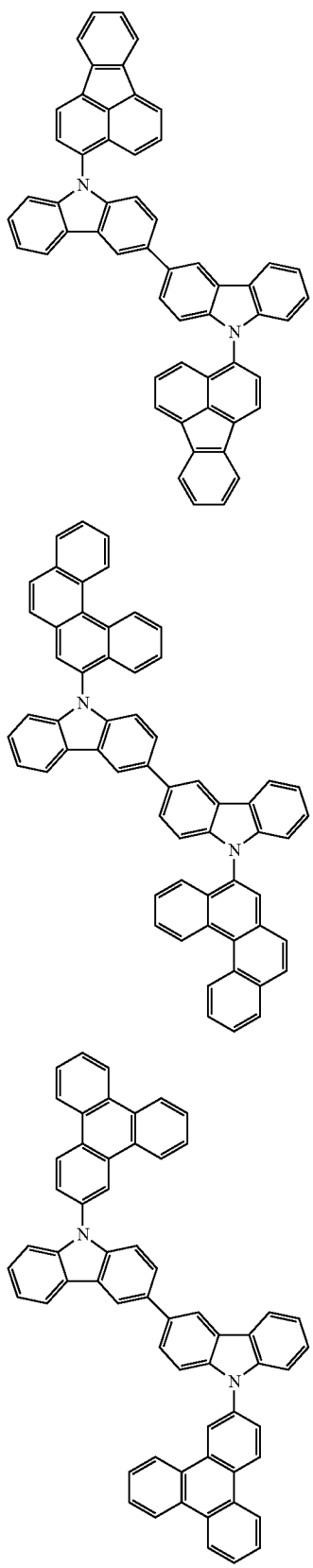
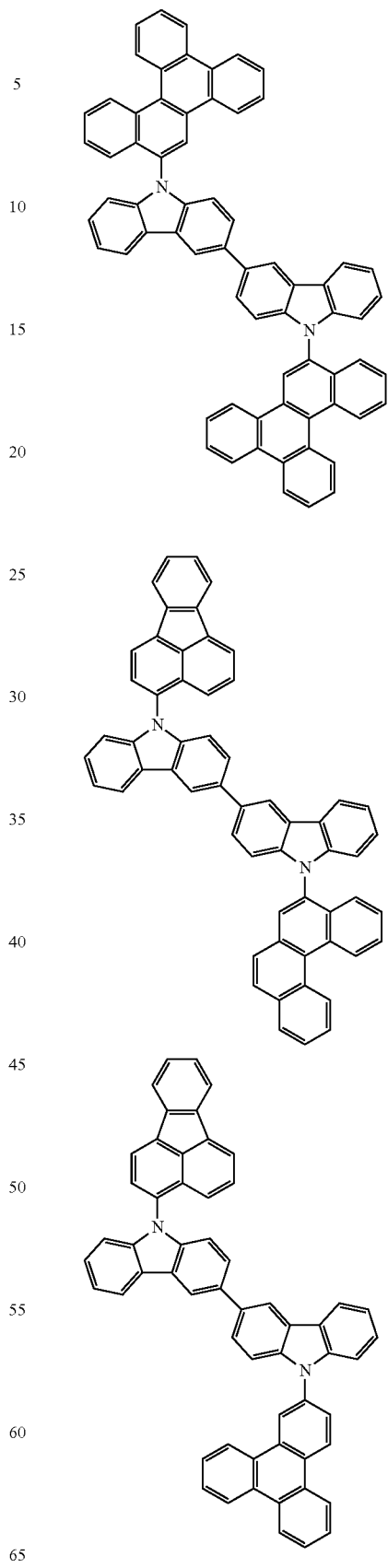

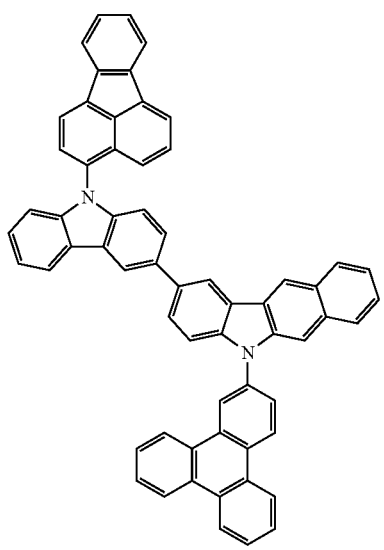
[Formula 89]
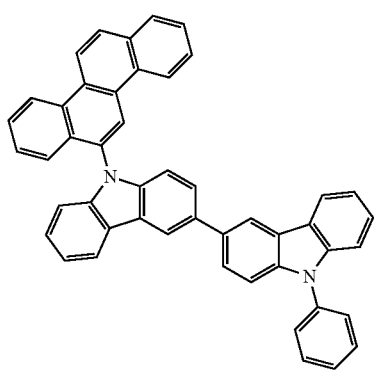
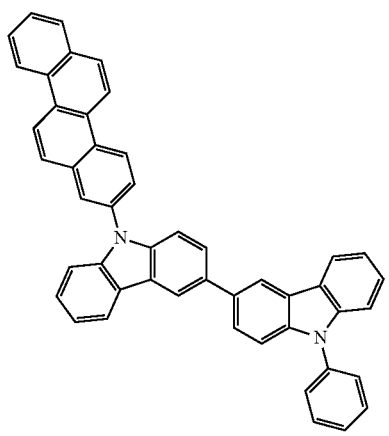
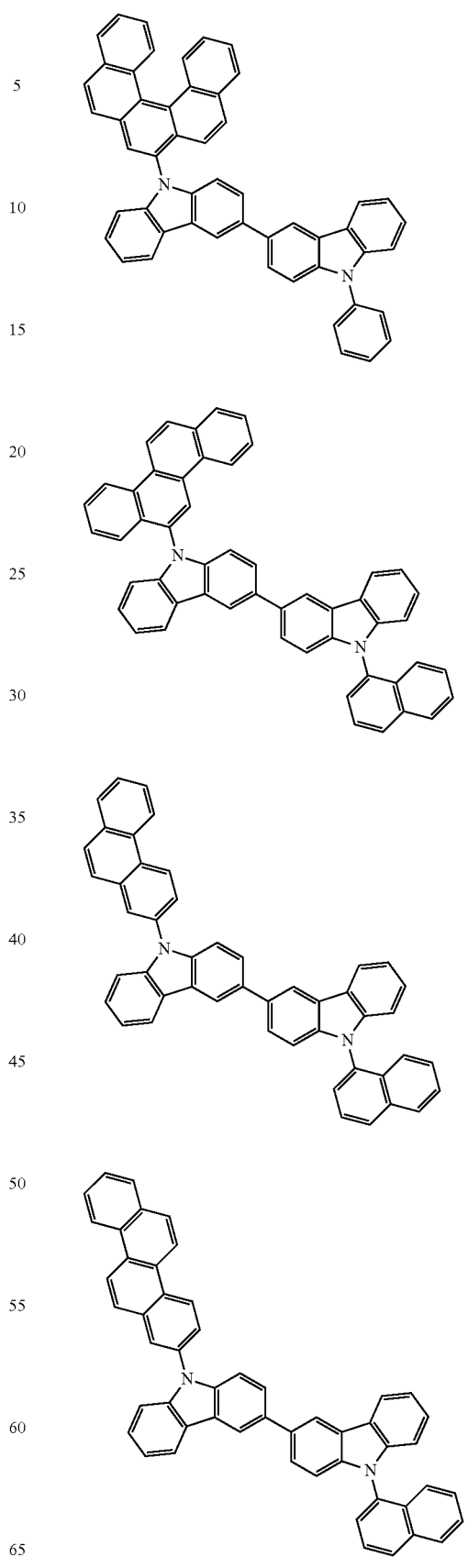

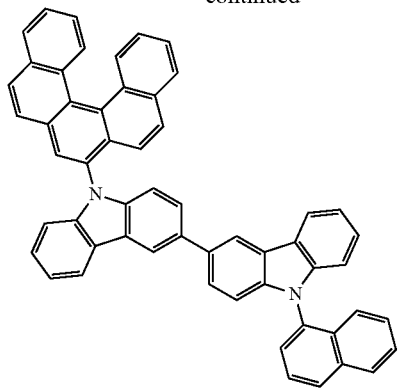
[Formula 90]
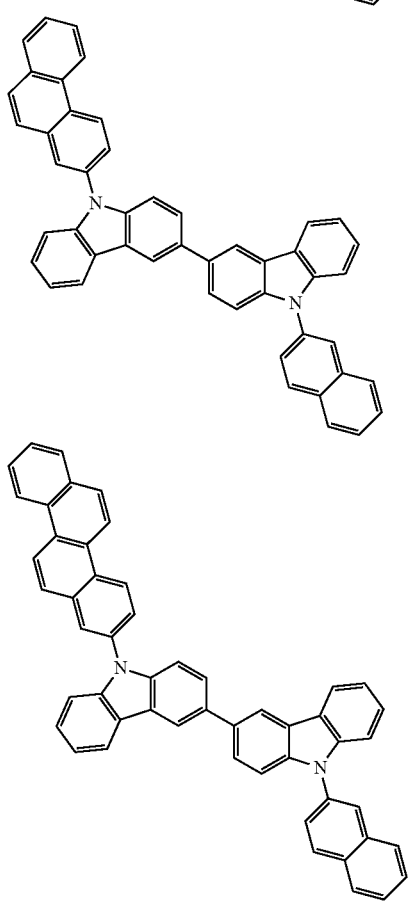
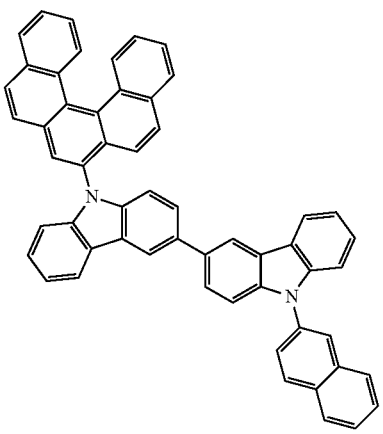

159
-continued
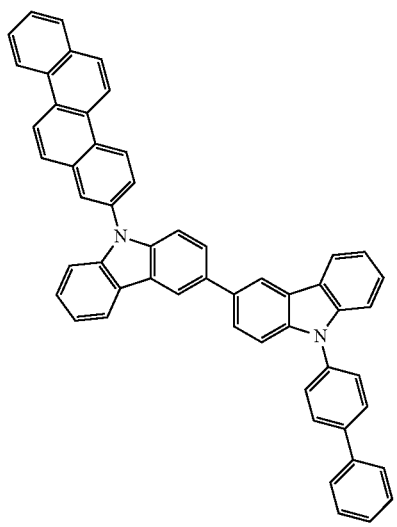
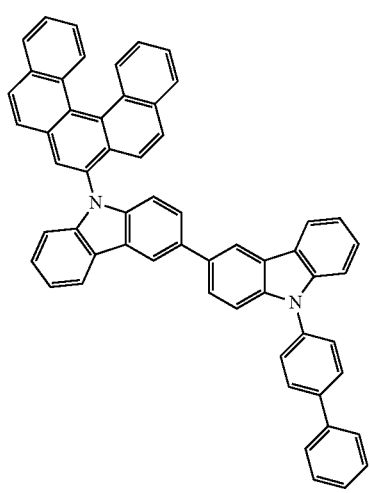
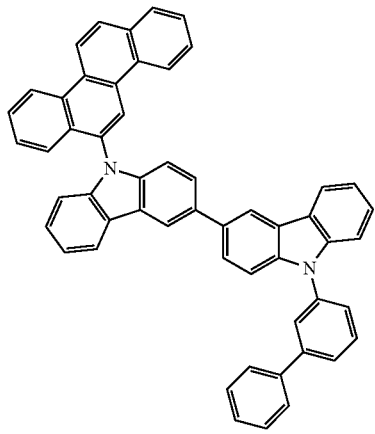
160
-continued
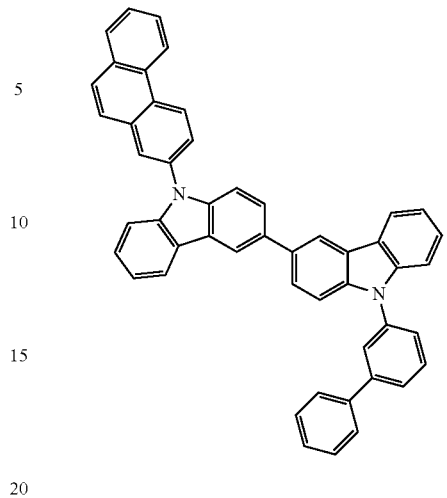
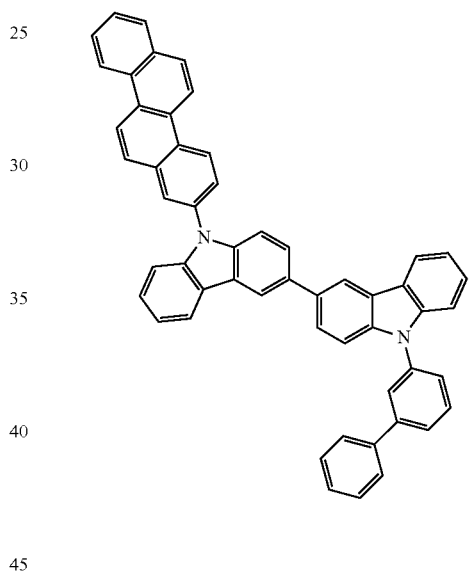
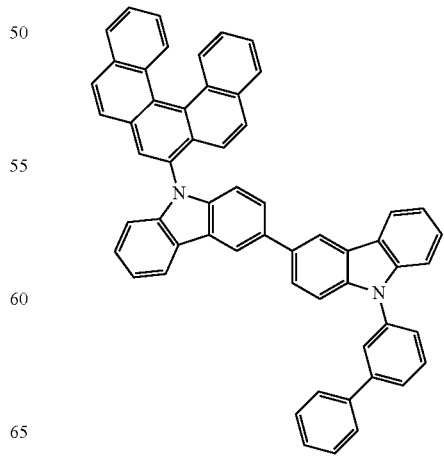

[Formula 91]
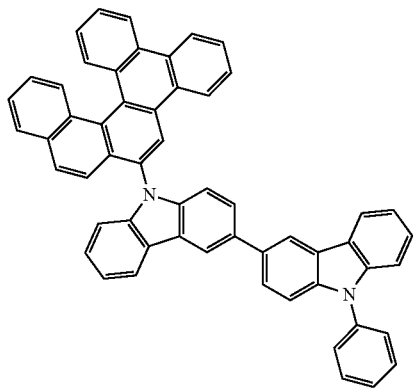
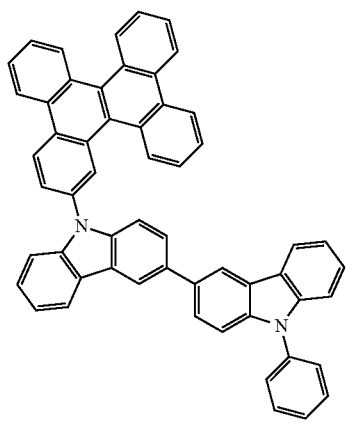
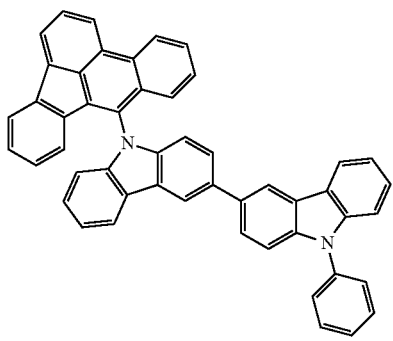
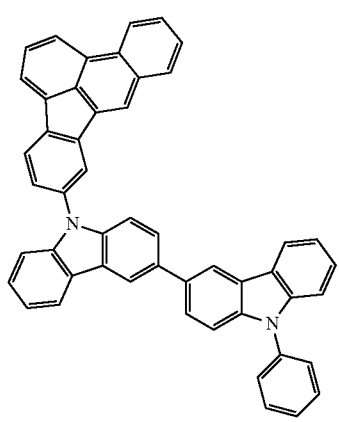
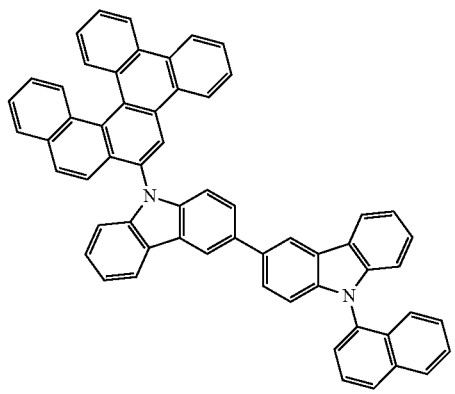
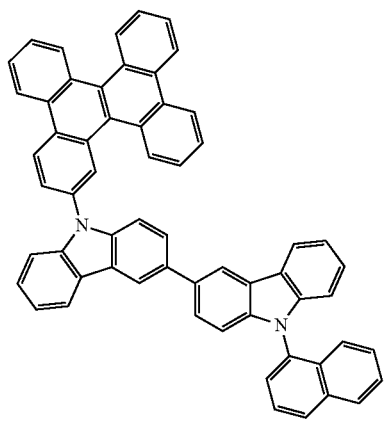
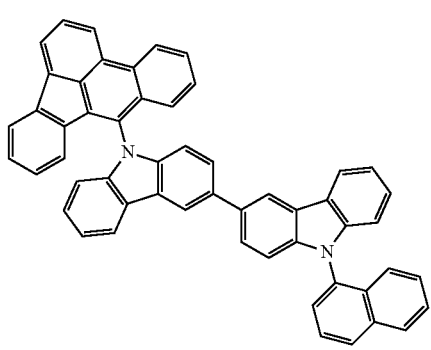
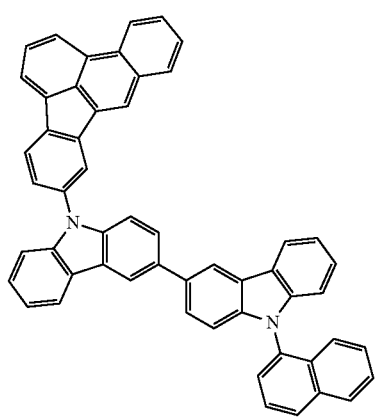

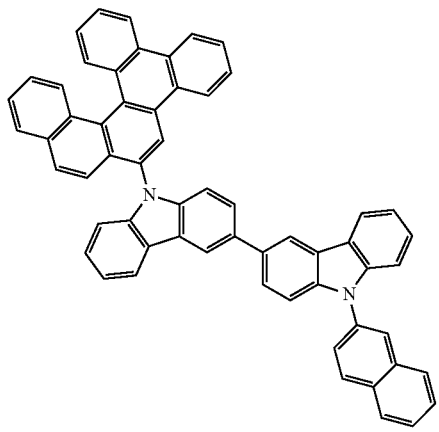
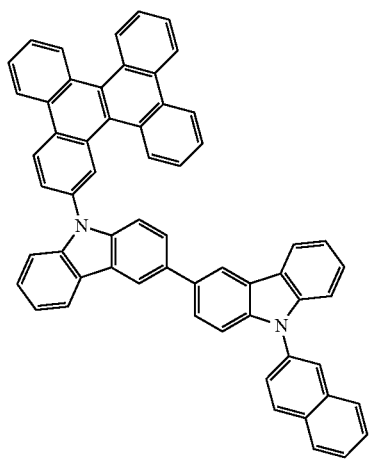
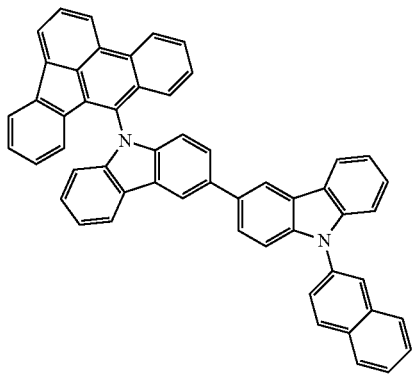
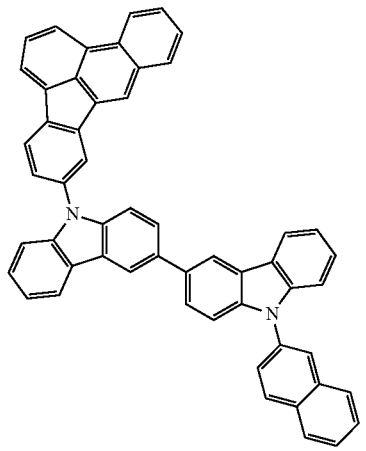
[Formula 92]
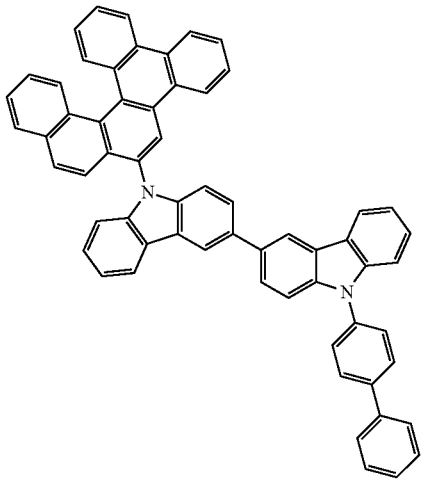
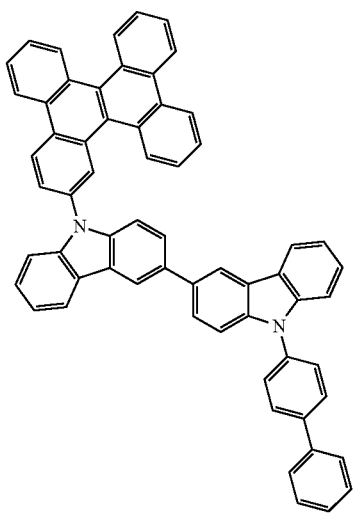
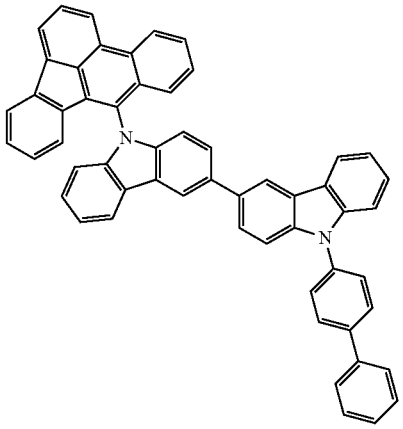

-continued
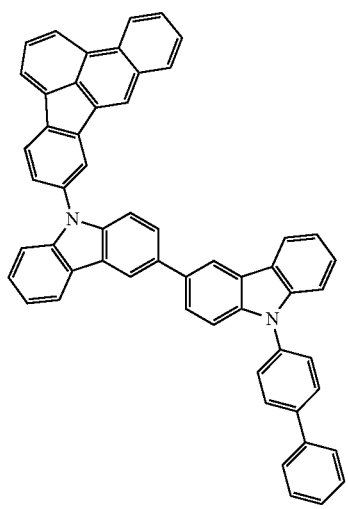
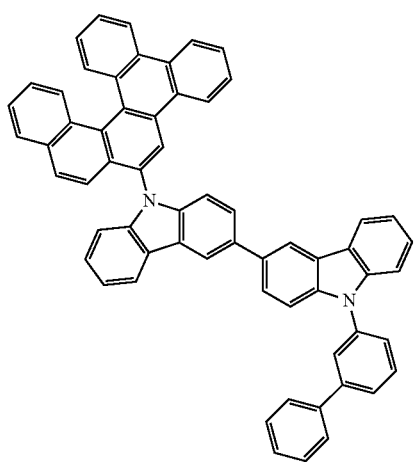
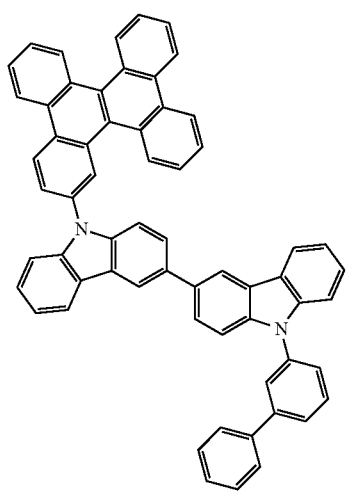
-continued
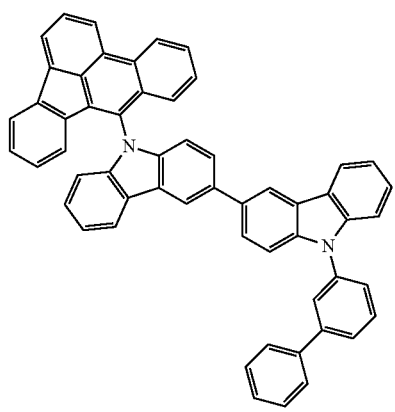
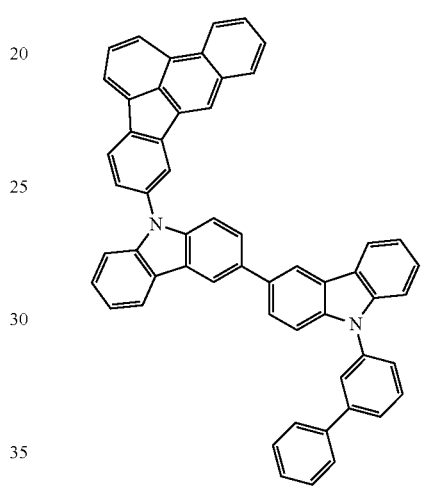
[Formula 93]
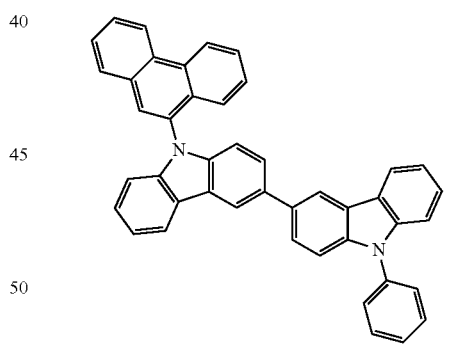
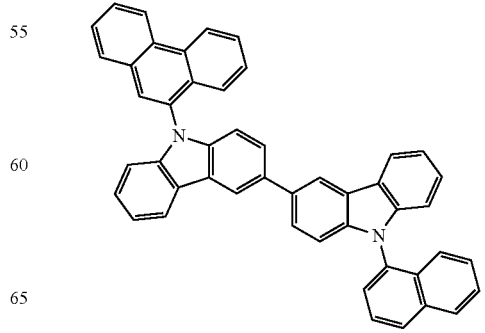

167
-continued
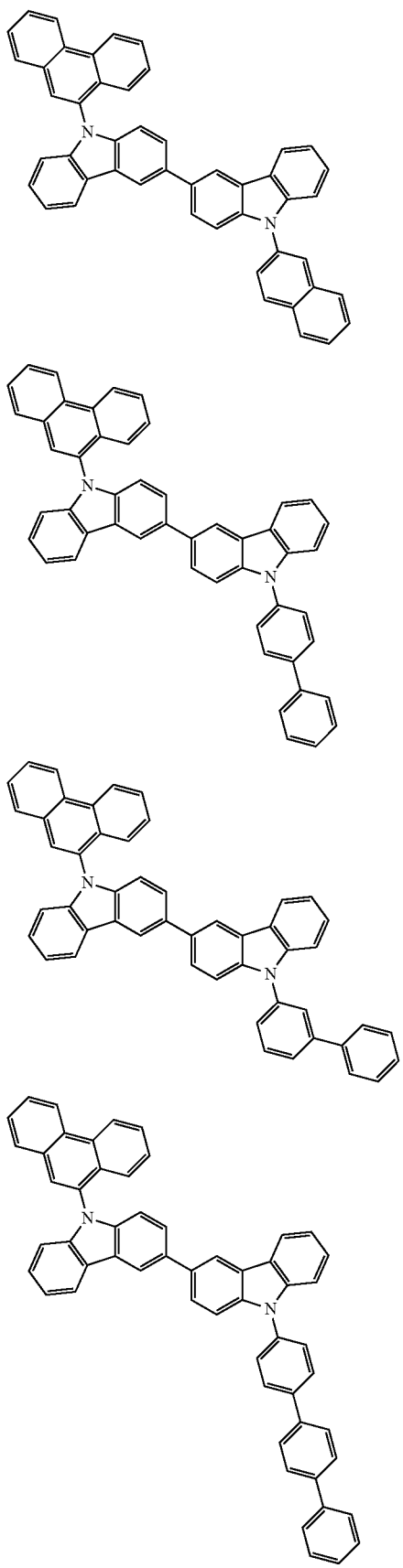
168
-continued
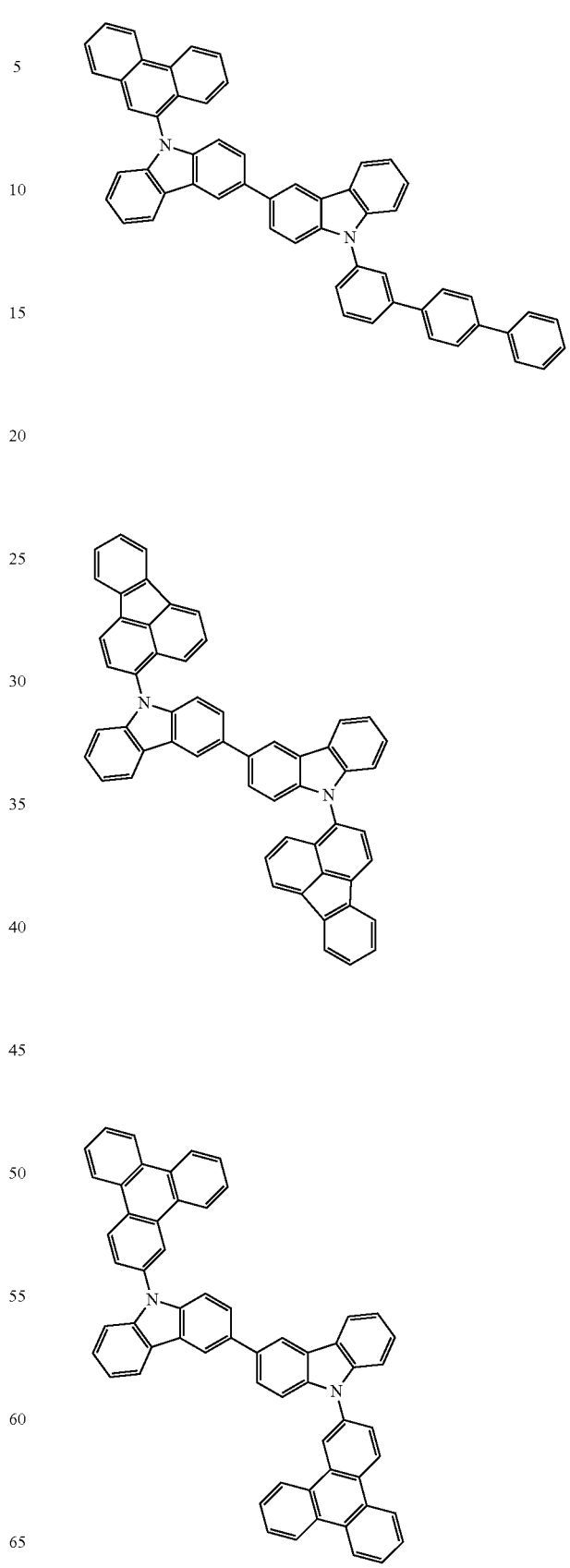

169
-continued
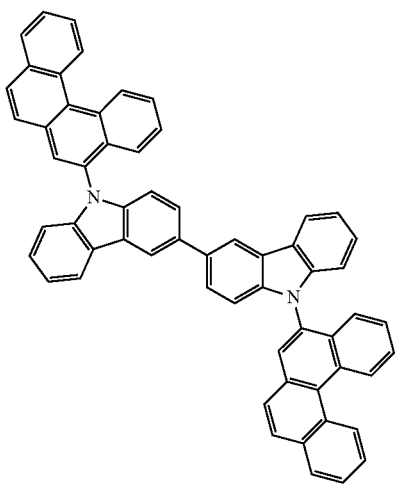
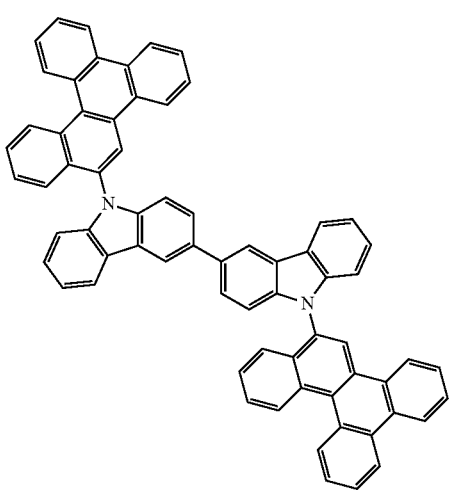
[Formula 94]
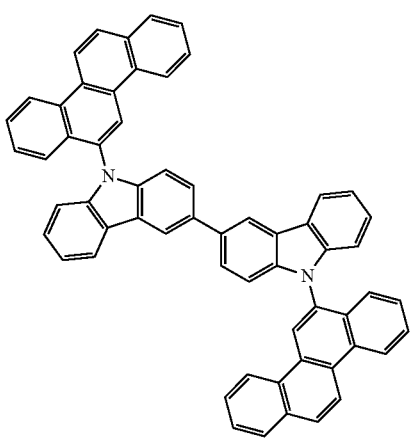
170
-continued
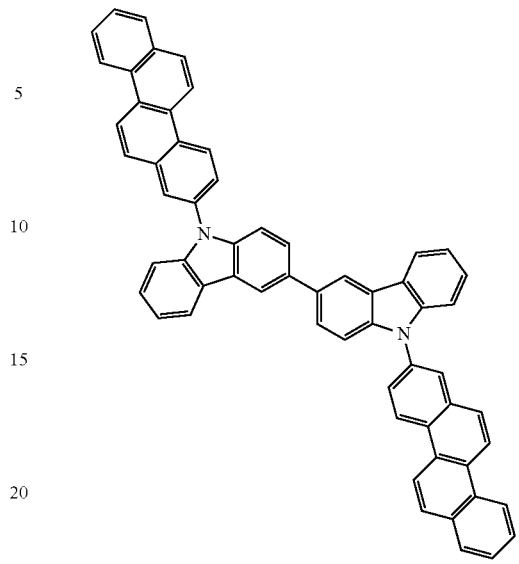
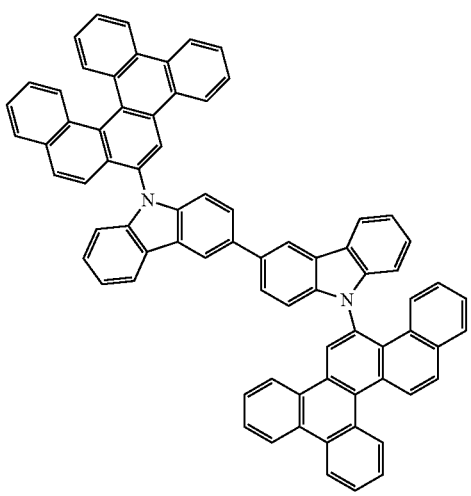

-continued
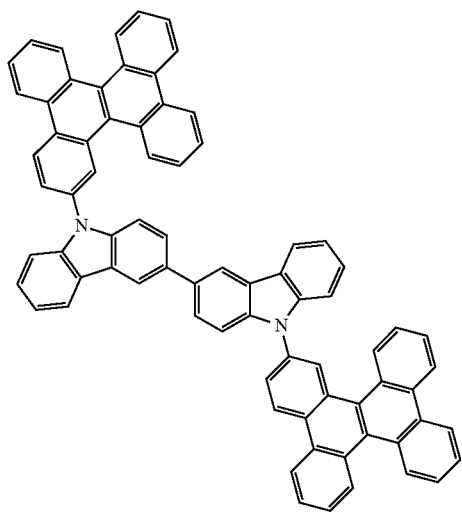
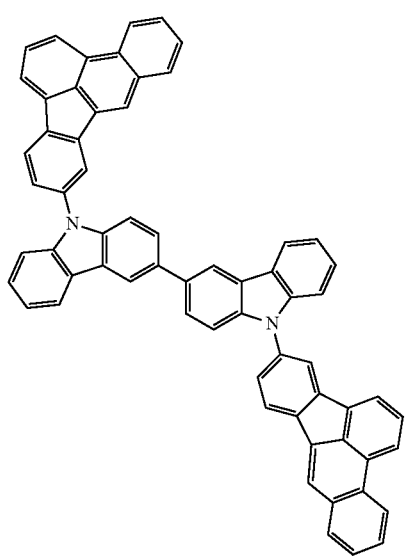 [SMILES: c1ccc2c(c1)cc1c3c(cccc32)-c2cc(-n3c4ccccc4c4cc(-c5ccc6c(c5)c5ccccc5n6-c5ccc6c(c5)-c5cc7ccccc7c7cccc-6c57)ccc43)ccc2-1]
[Formula 95]
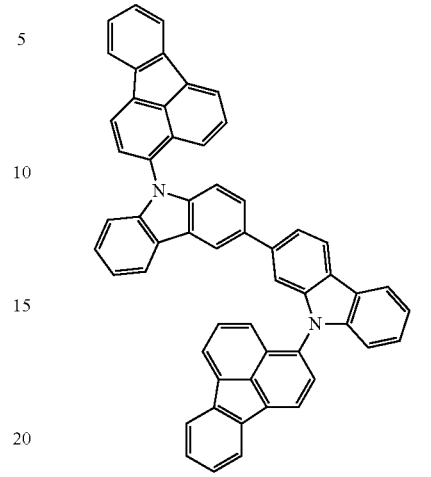
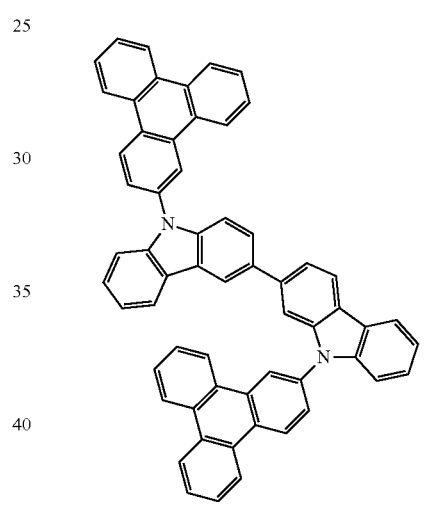
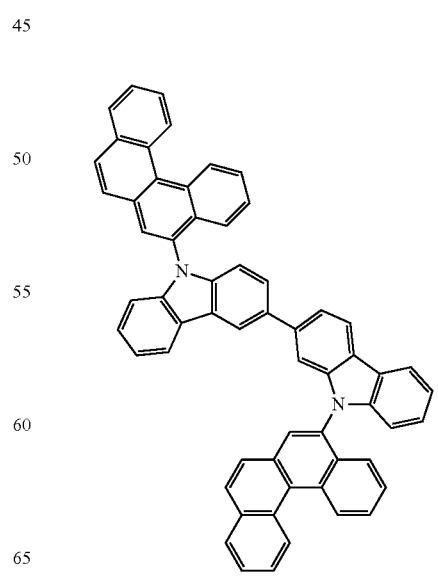

173
-continued
174
-continued
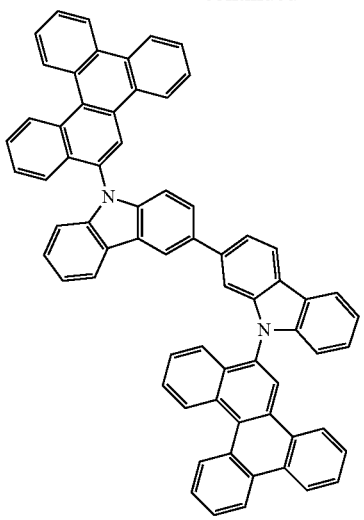
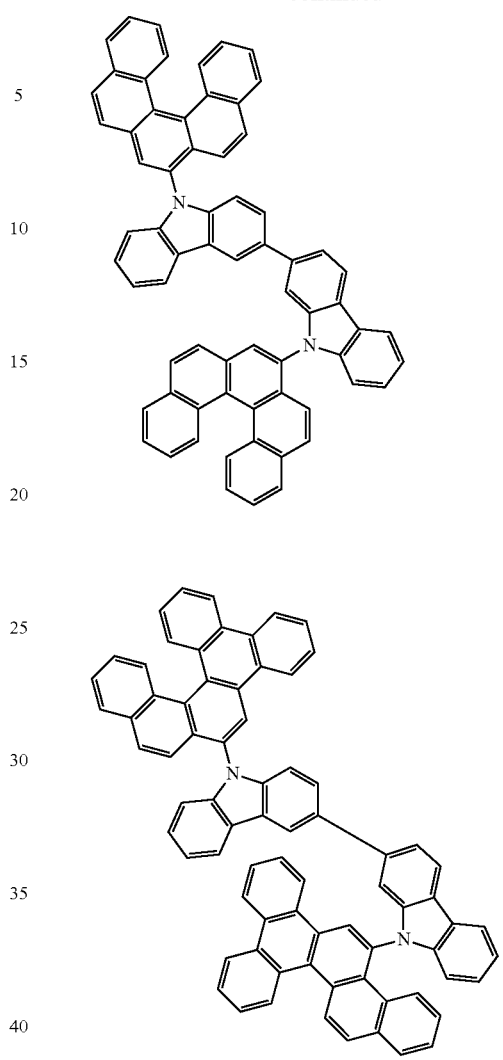
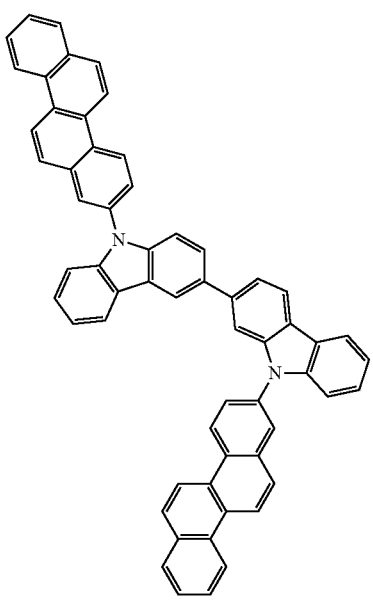
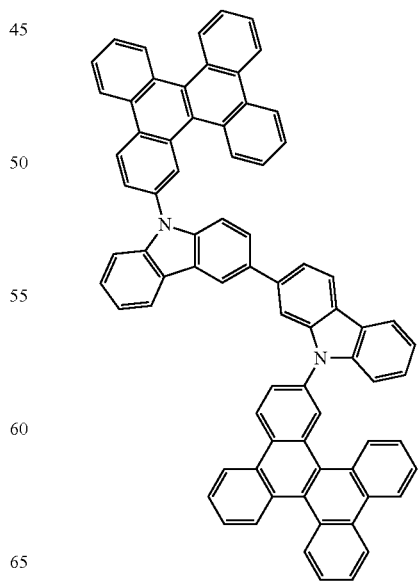

175
-continued
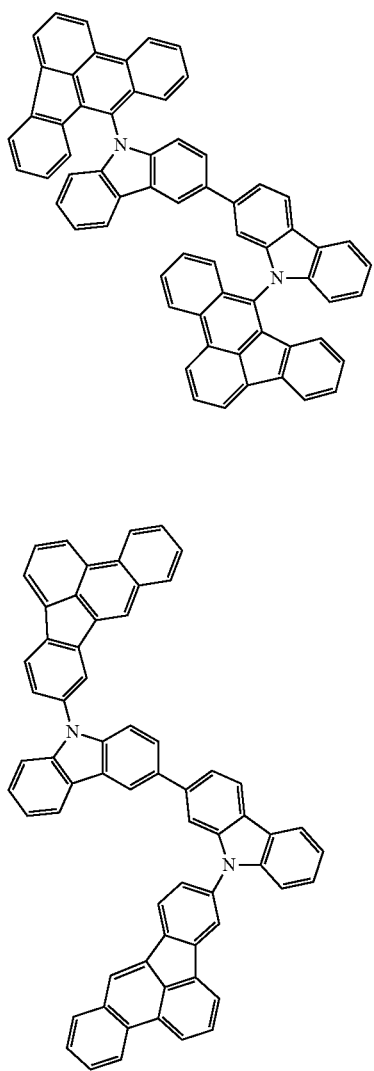
[Formula 96]
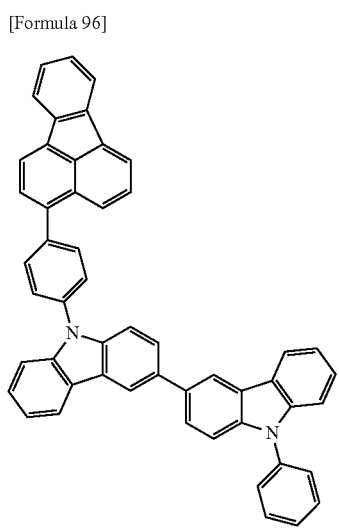
176
-continued
[Formula 96]
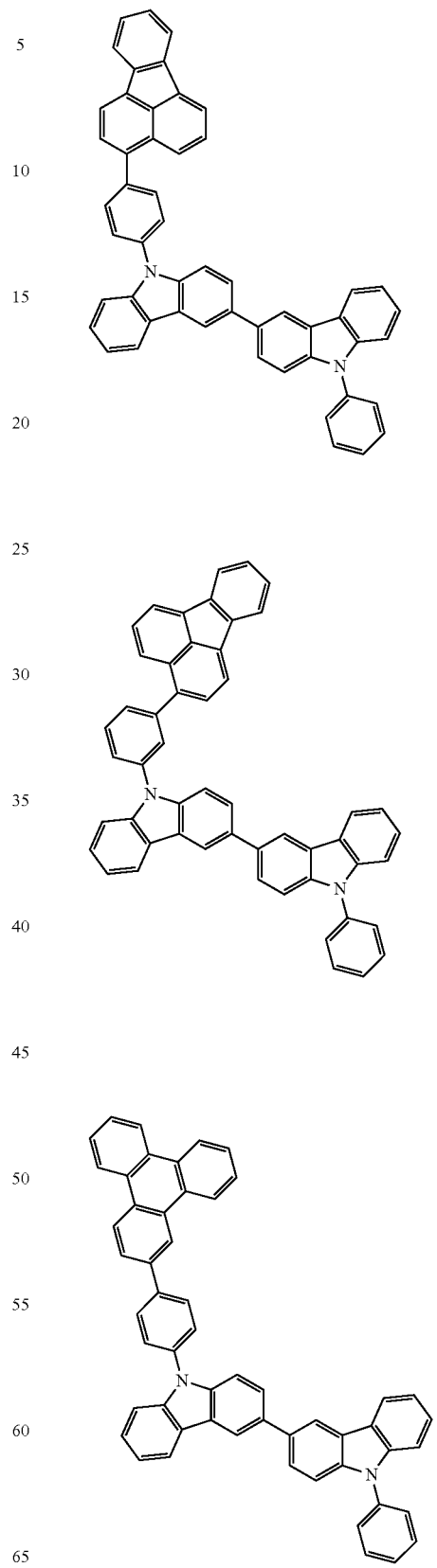

177
-continued
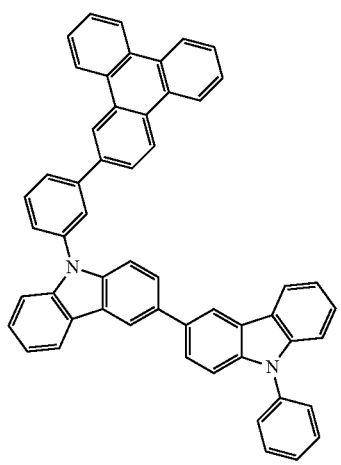
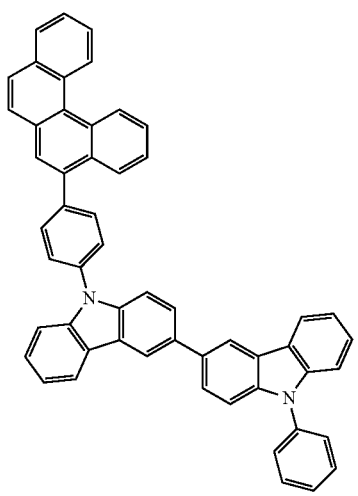
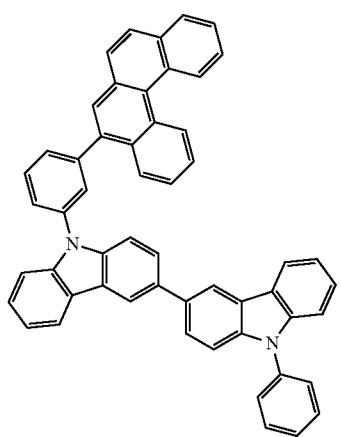
178
-continued
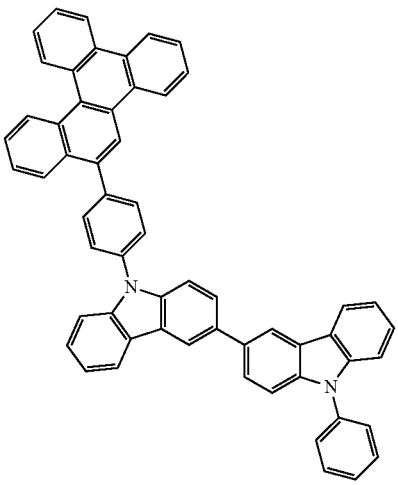
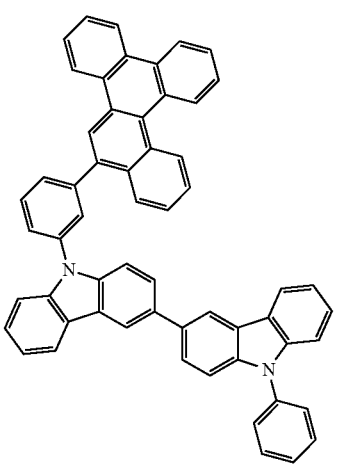
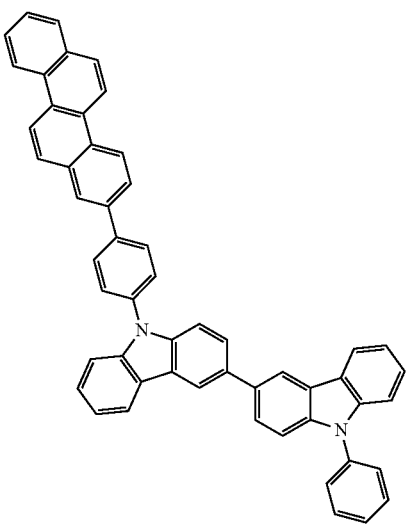

179
-continued
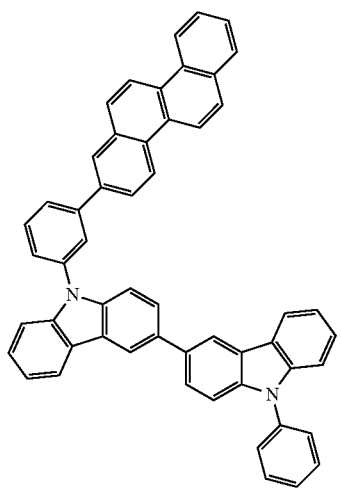
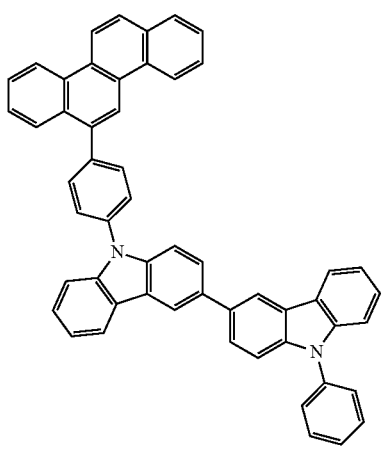
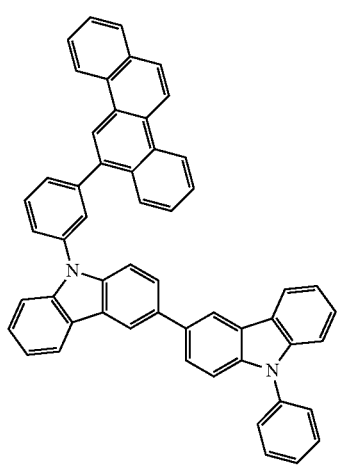
180
-continued
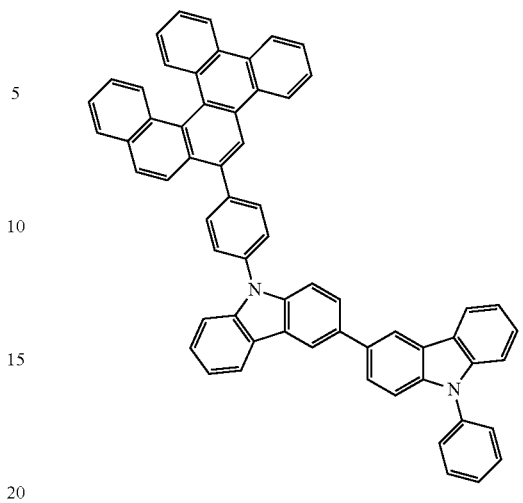
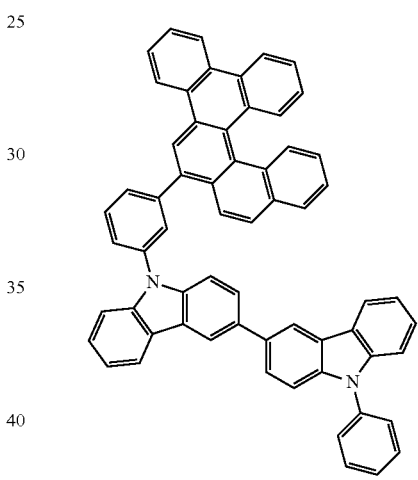
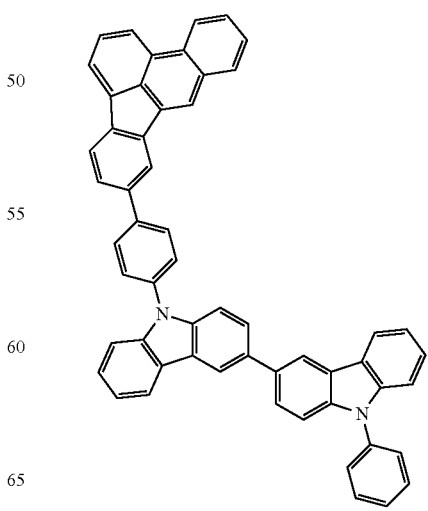

-continued
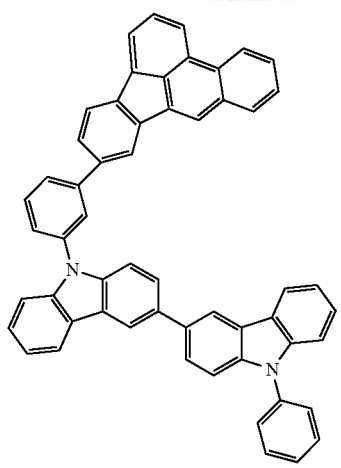
-continued
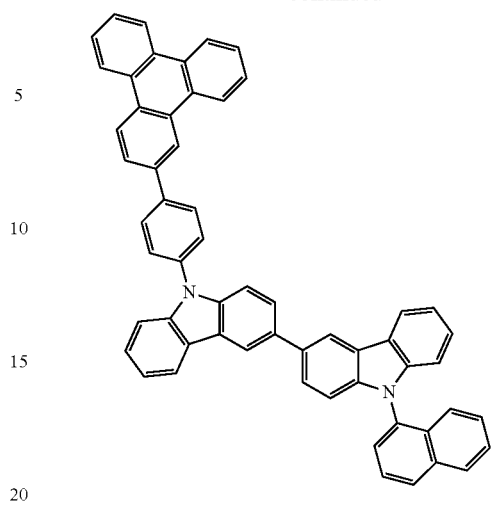
[Formula 98]
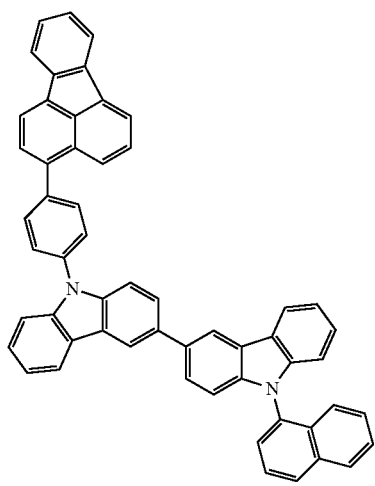
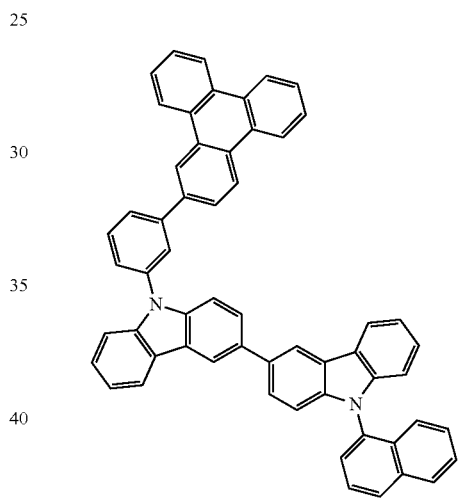
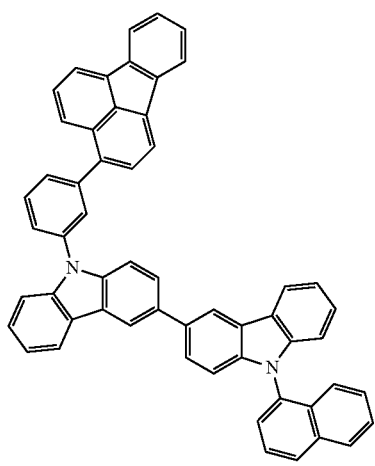
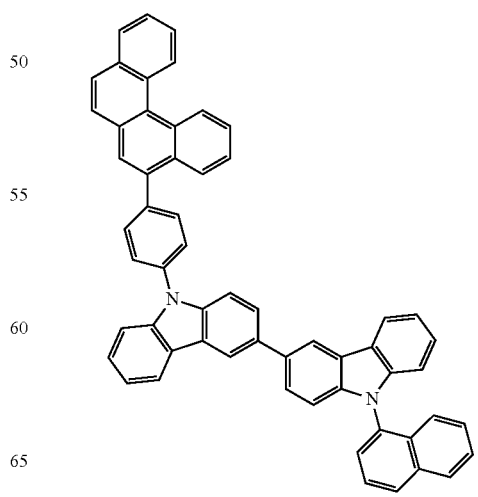

[Formula 99]
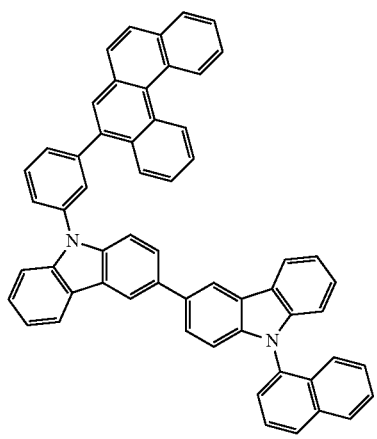
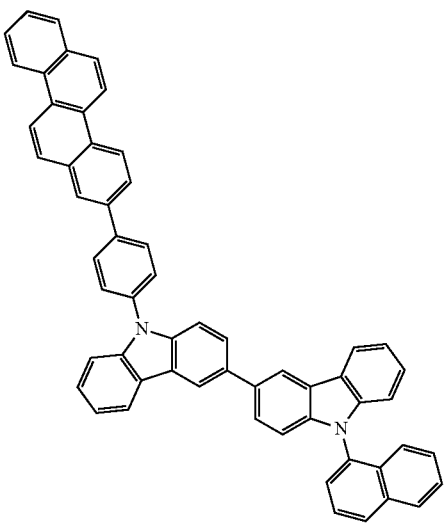
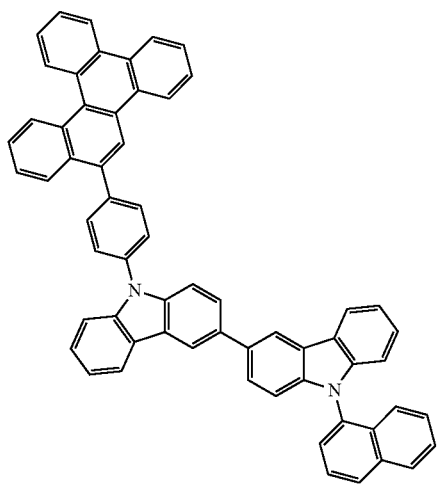
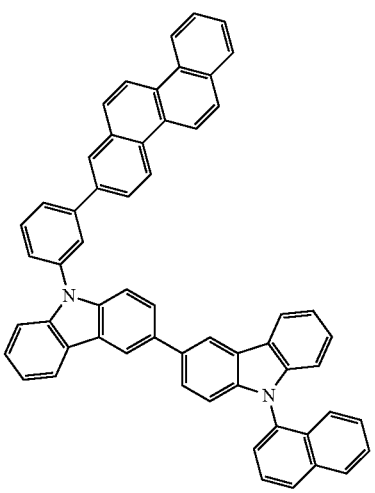
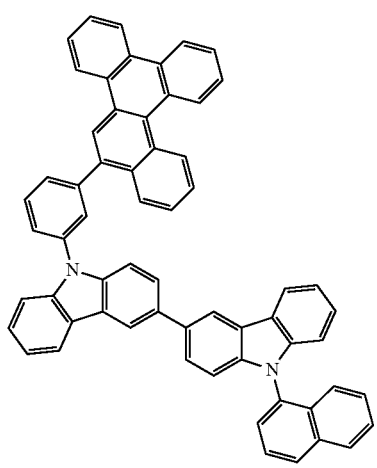
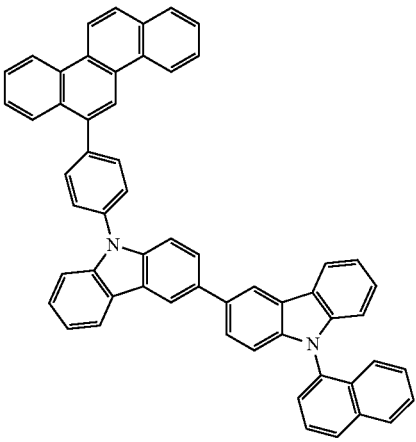

[Formula 100]
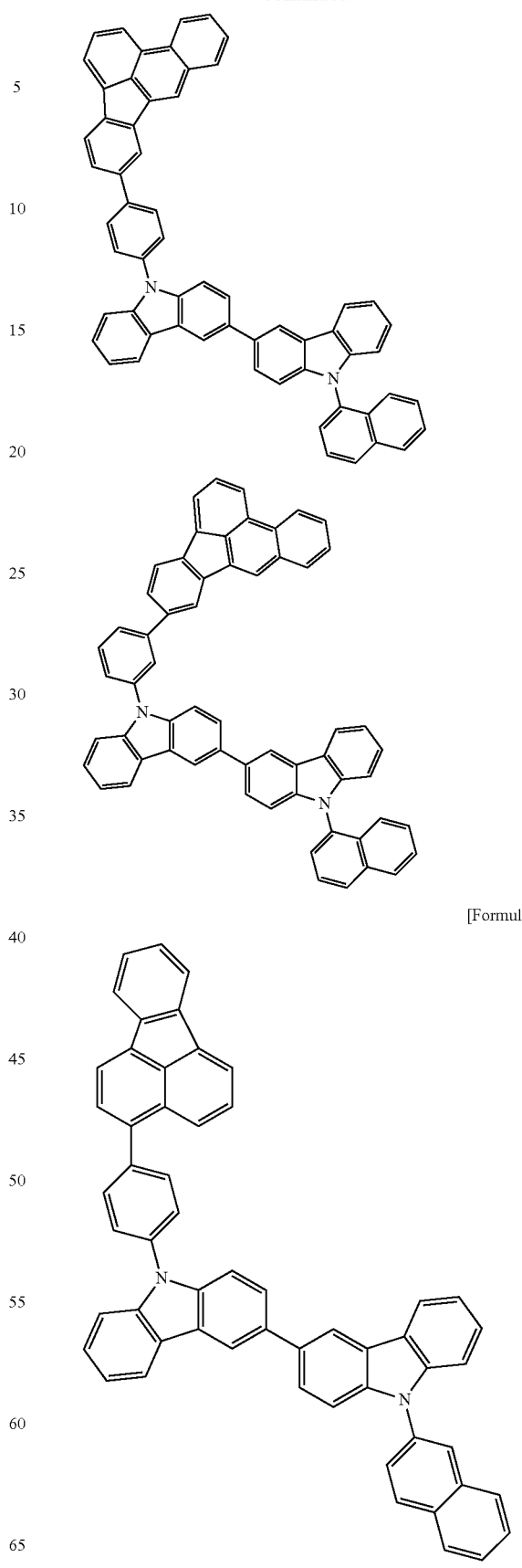

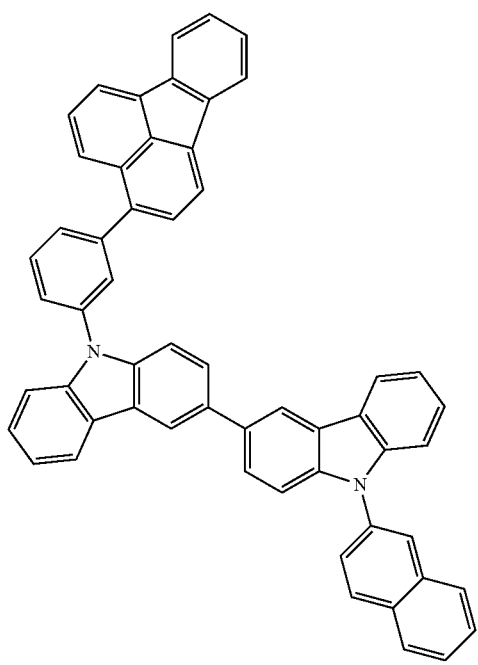
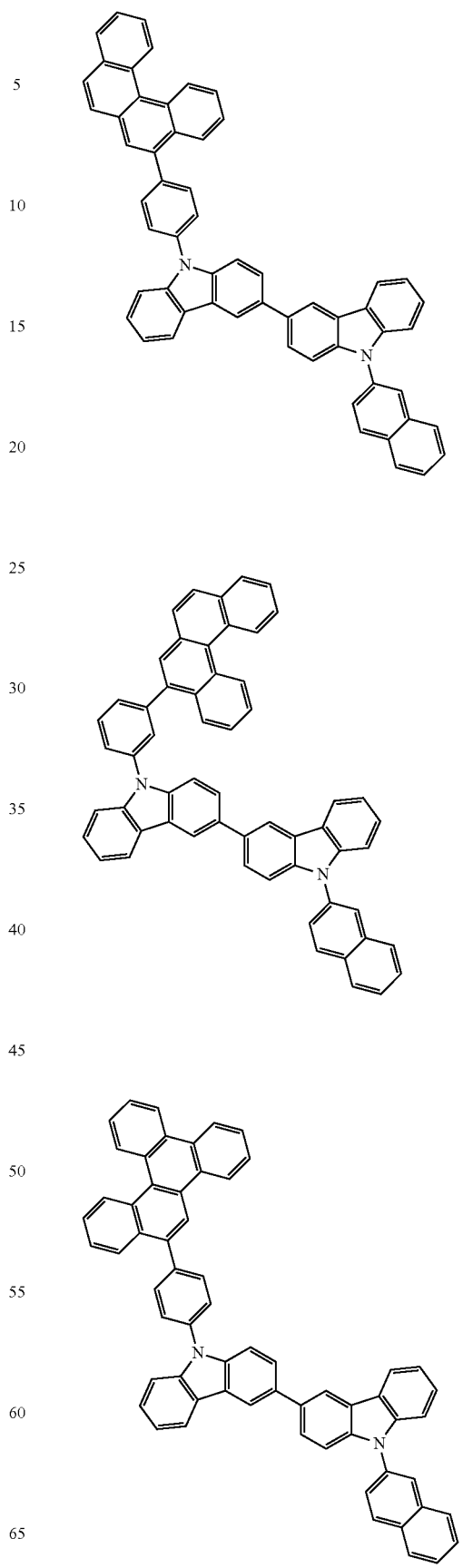

189
-continued
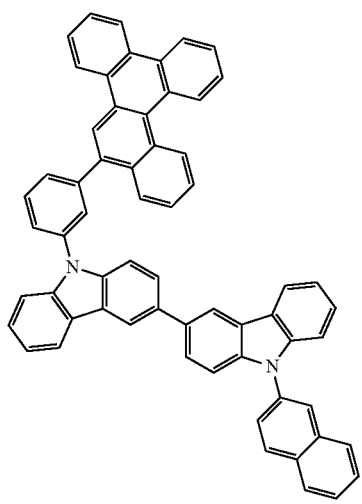
[Formula 101]
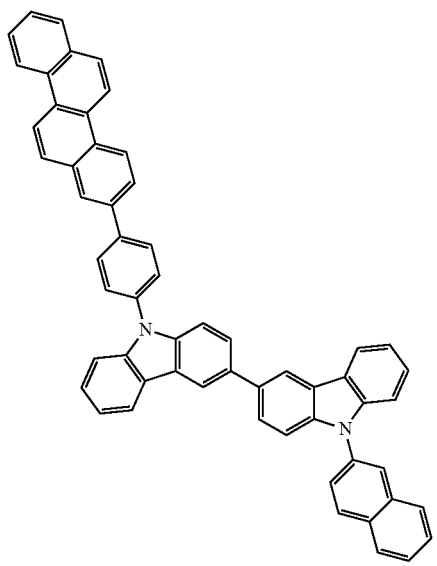
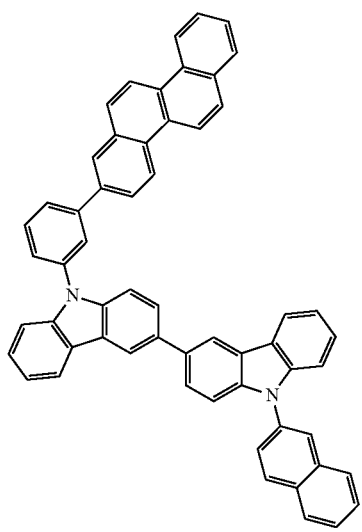
190
-continued
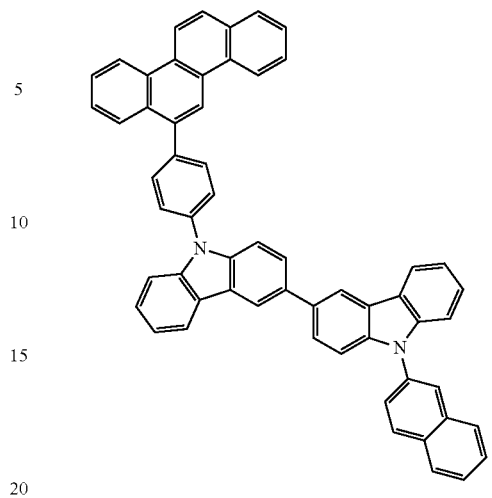
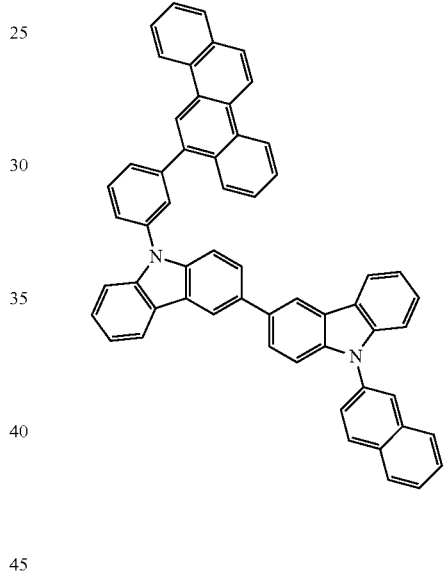
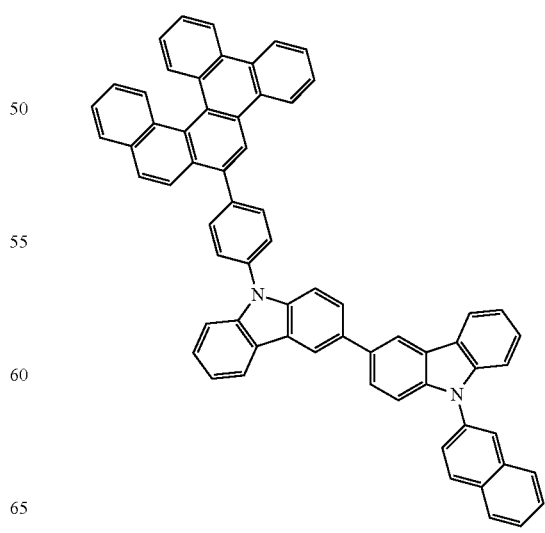

191
-continued
192
-continued
[Formula 102]
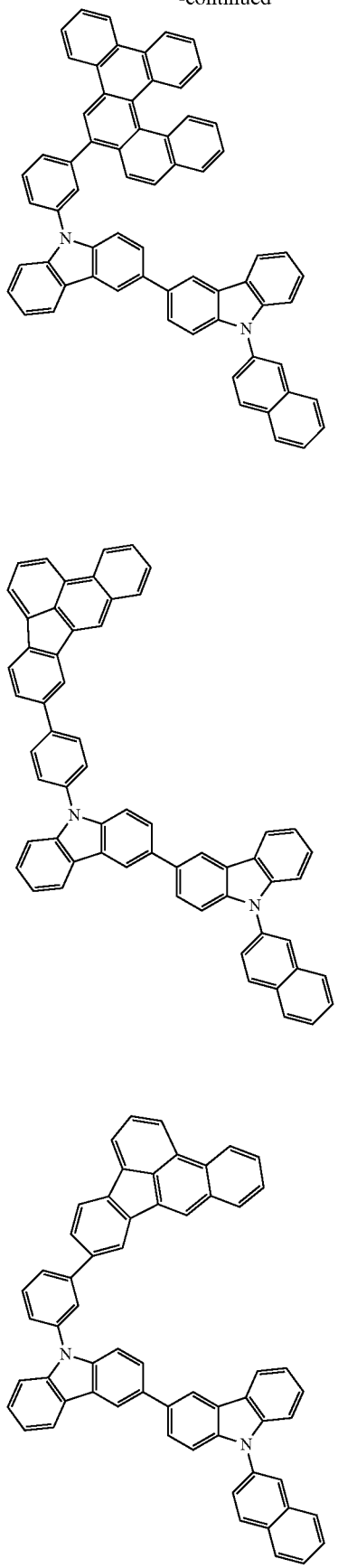
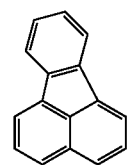
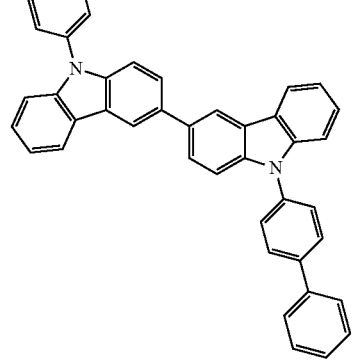
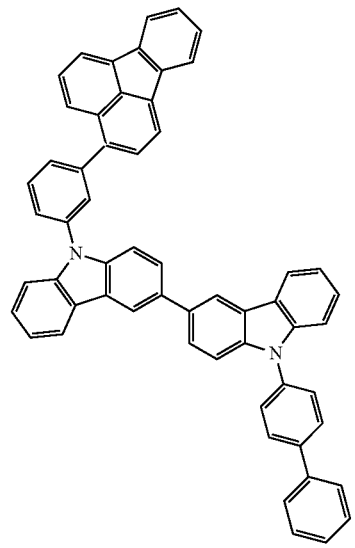

193
-continued
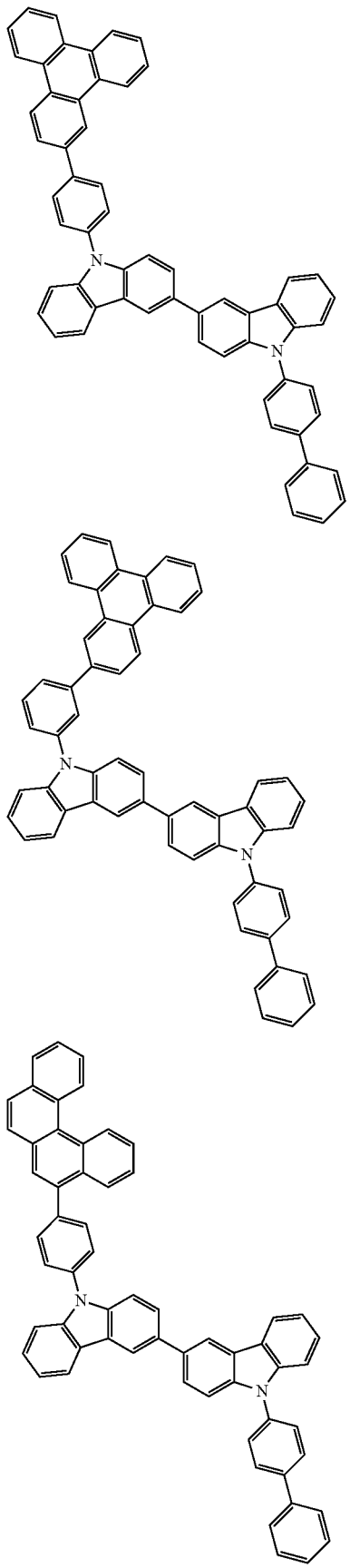
194
-continued
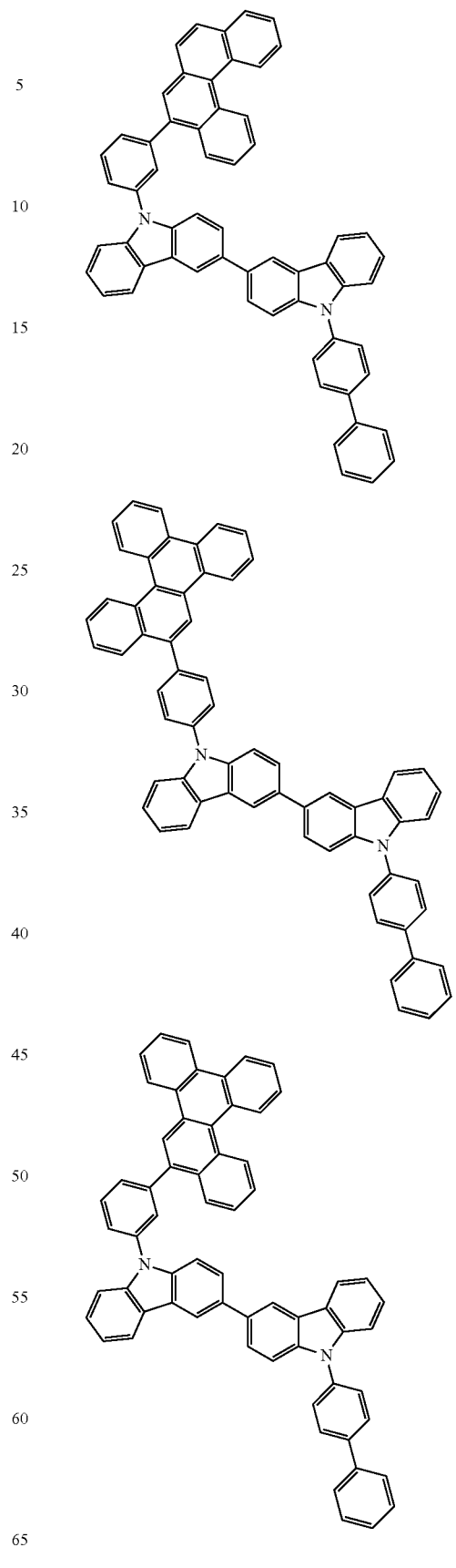

[Formula 103]
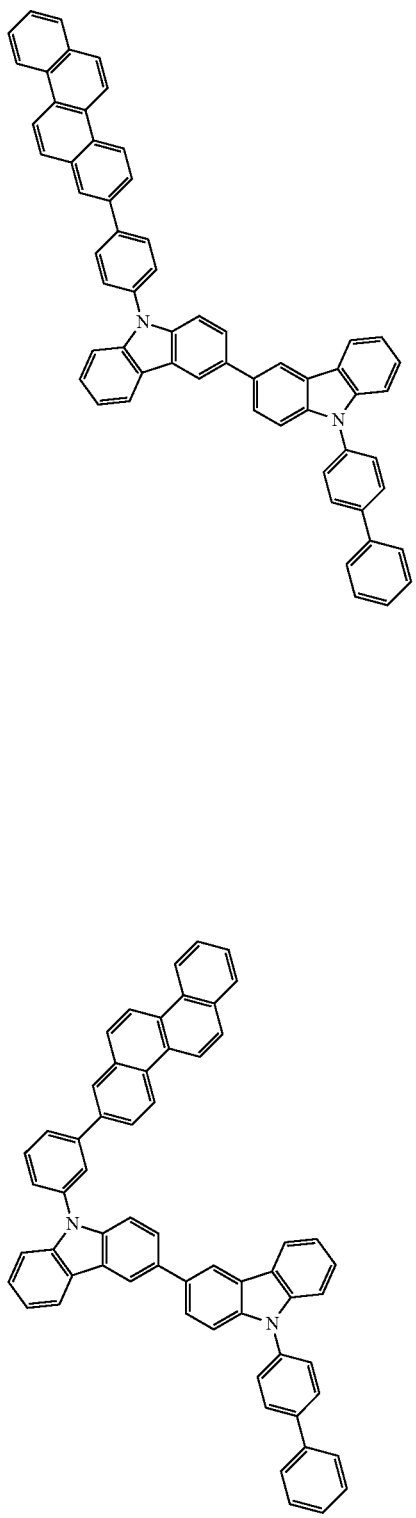
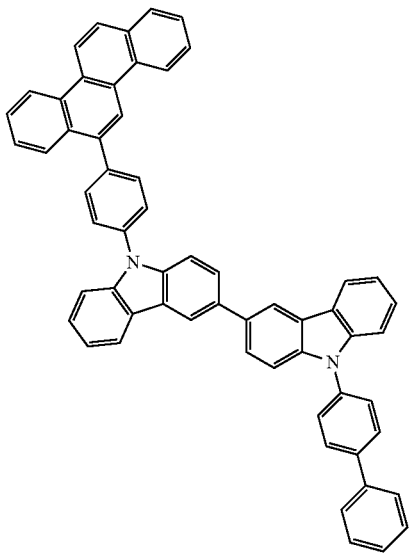
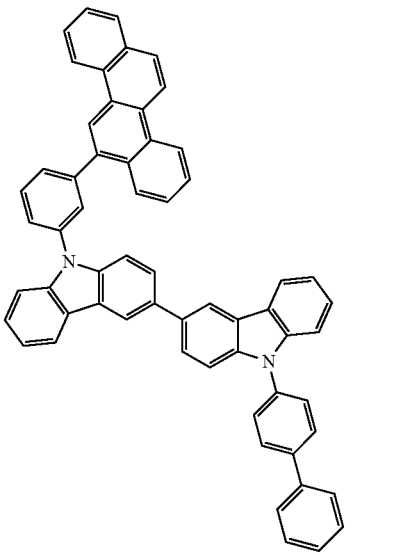
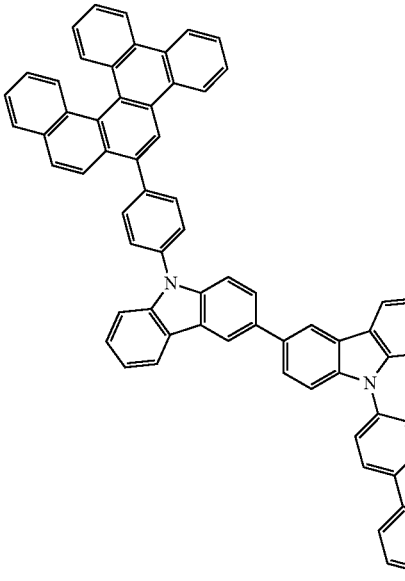

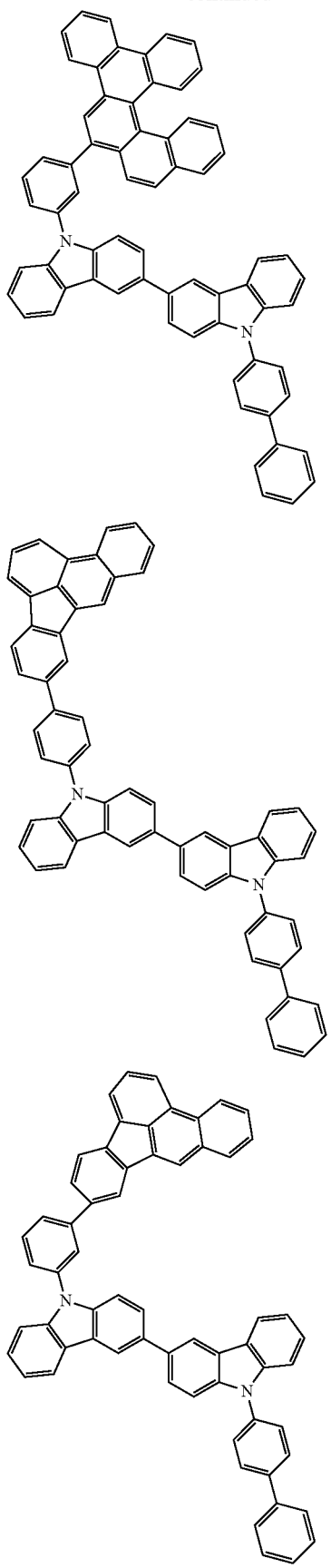
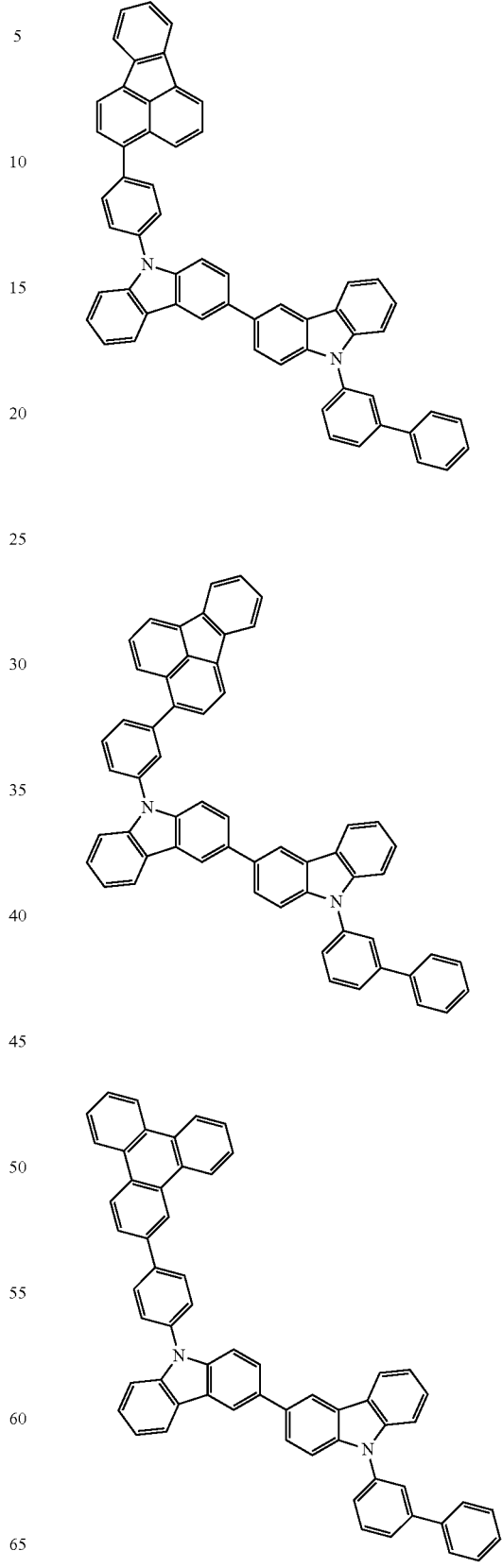
[Formula 104]

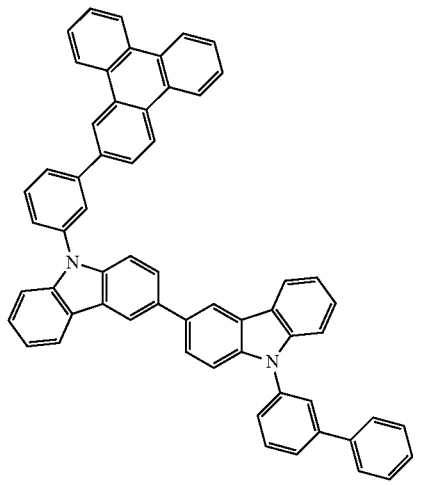
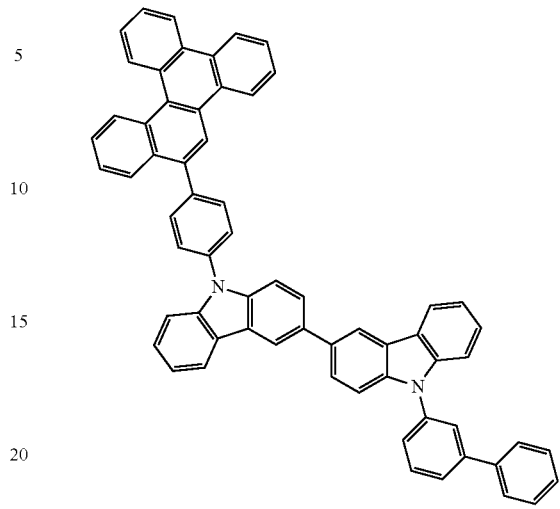
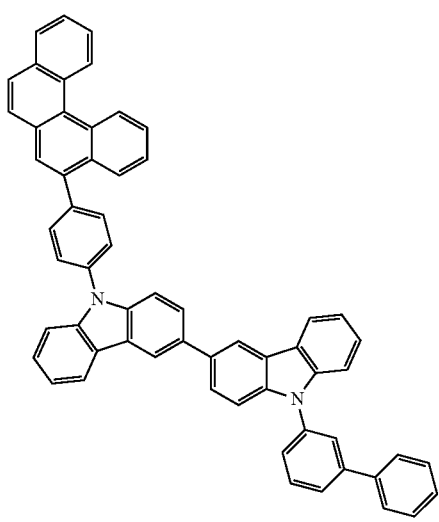
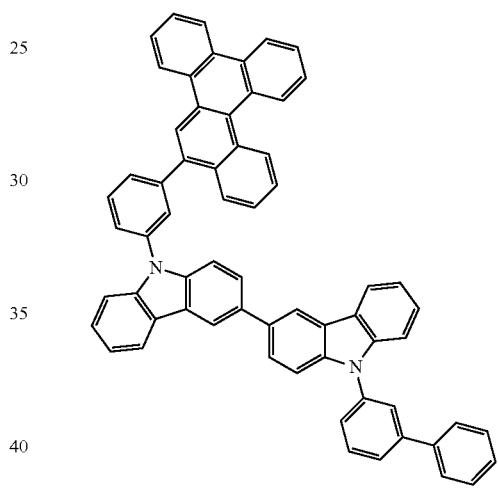
[Formula 105]
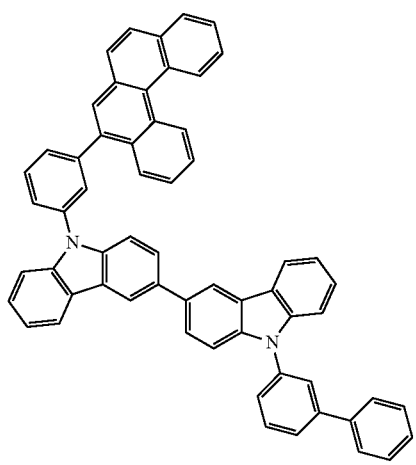
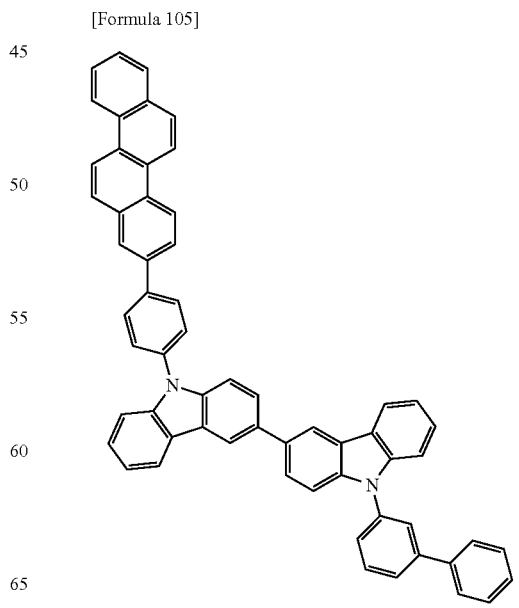

201
-continued
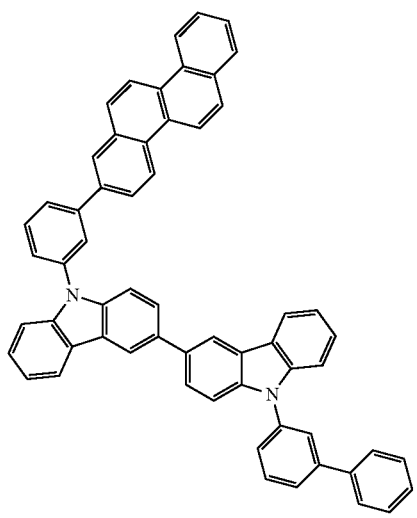
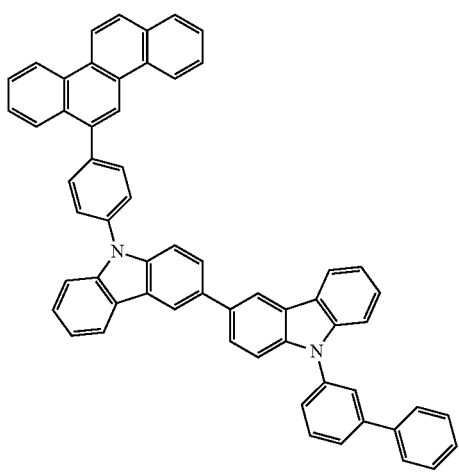
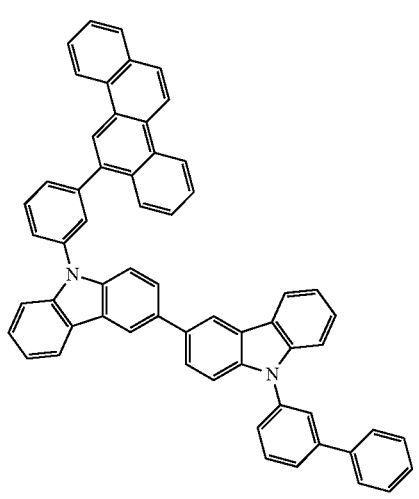
202
-continued
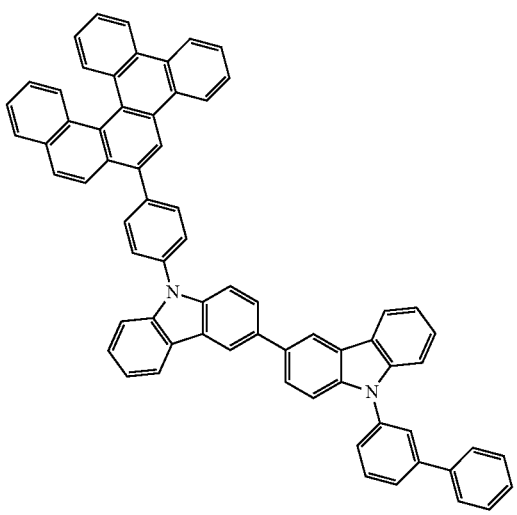
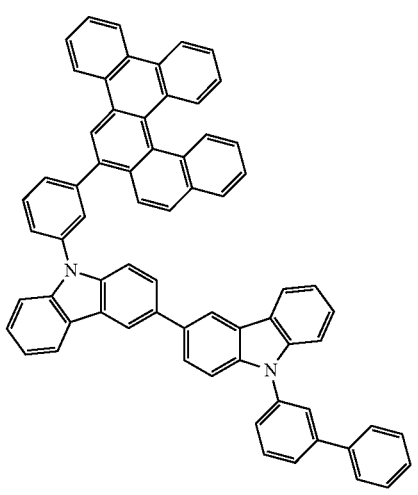
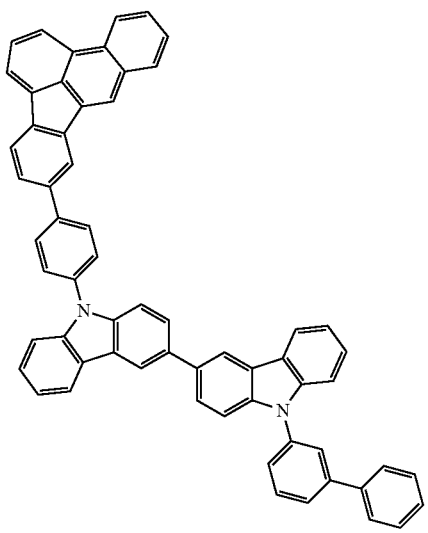

203
-continued
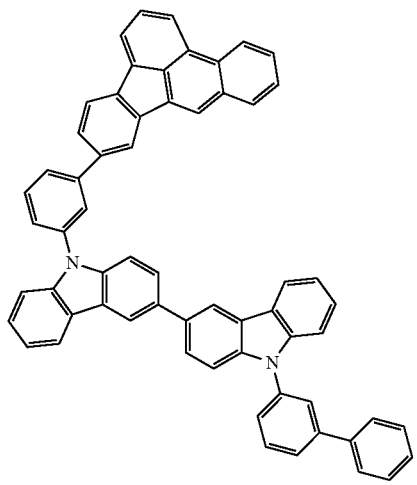
[Formula 106]
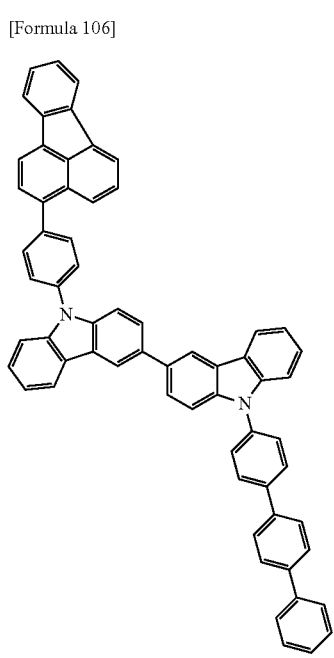
204
-continued
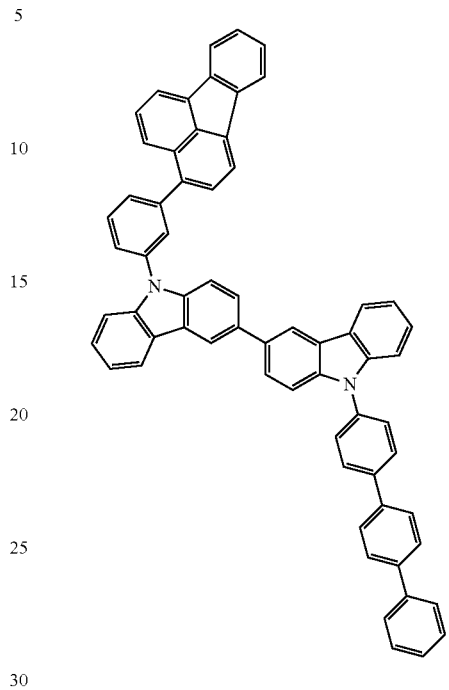
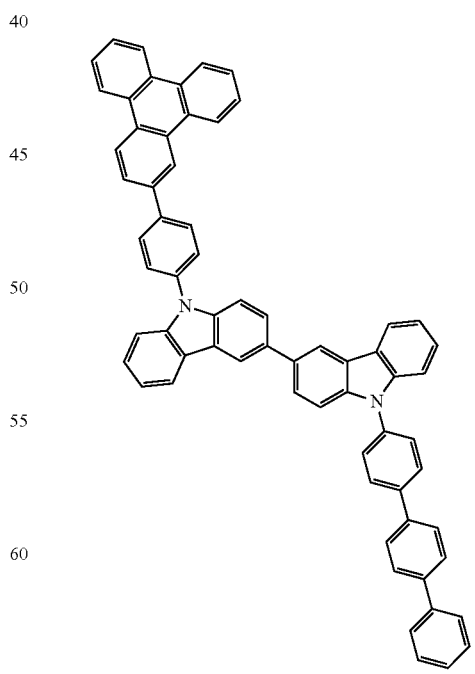

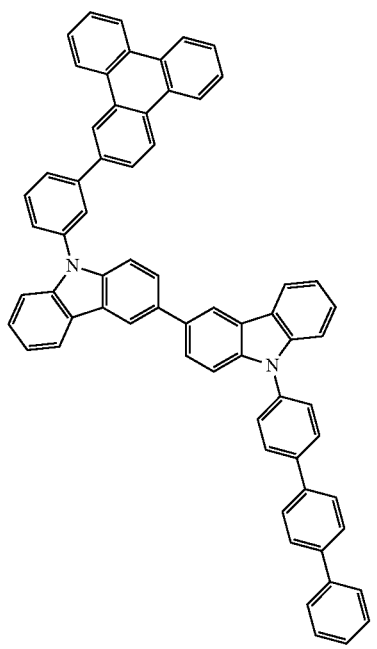
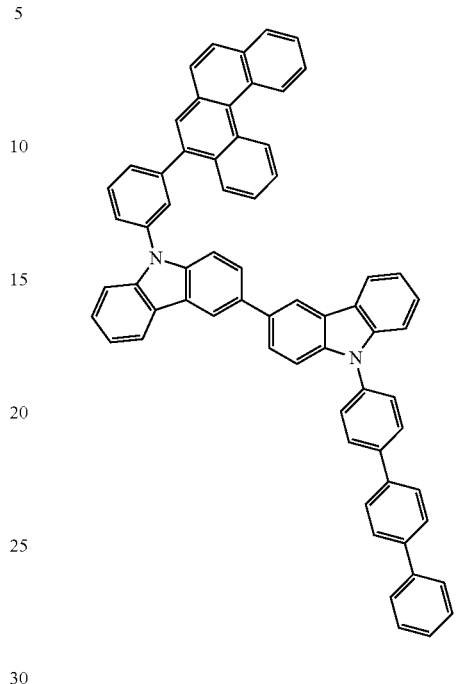
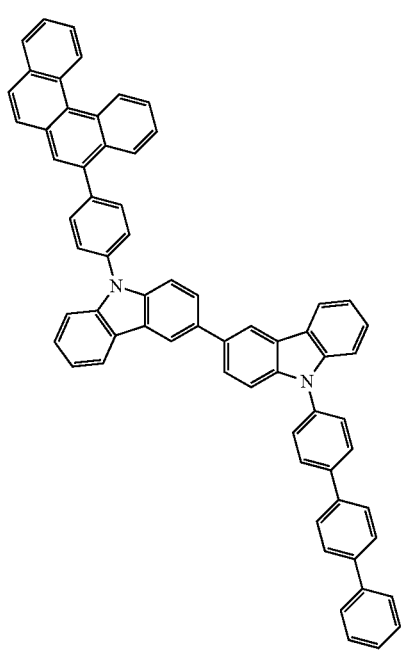
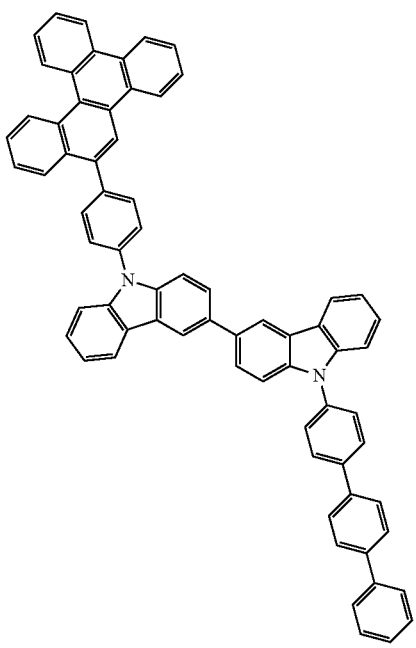

207
-continued
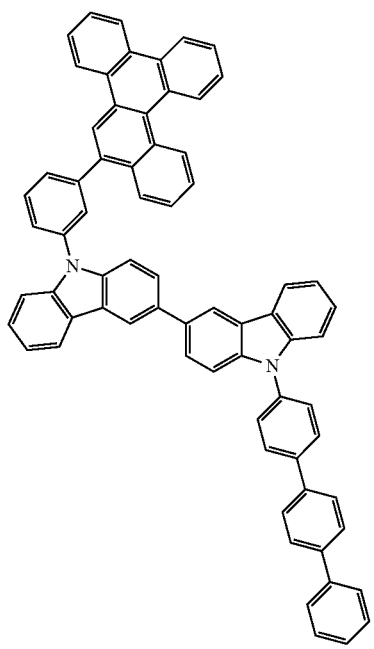
[Formula 107]
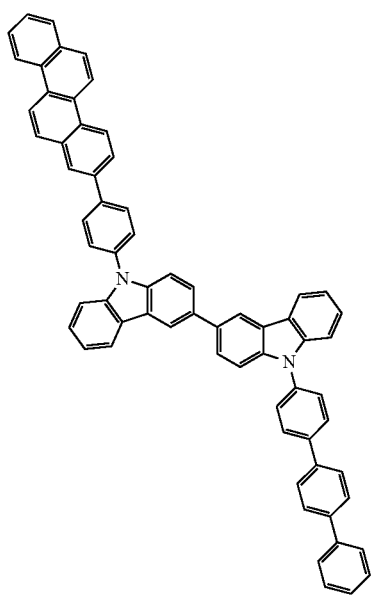
208
-continued
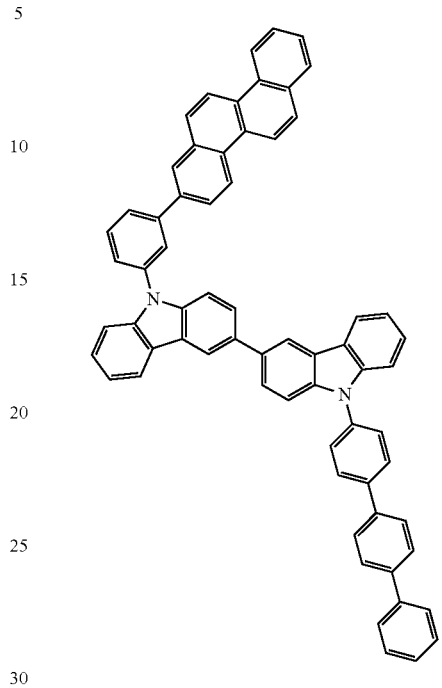
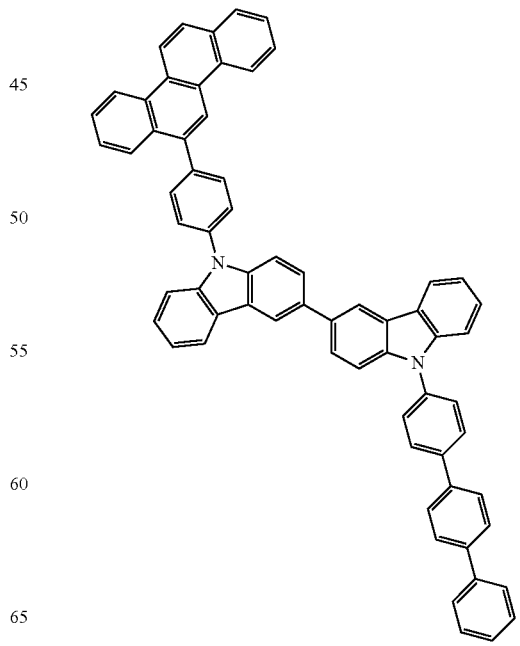

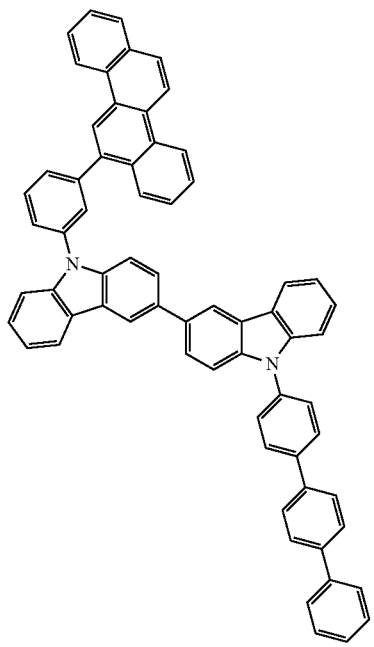

211
-continued
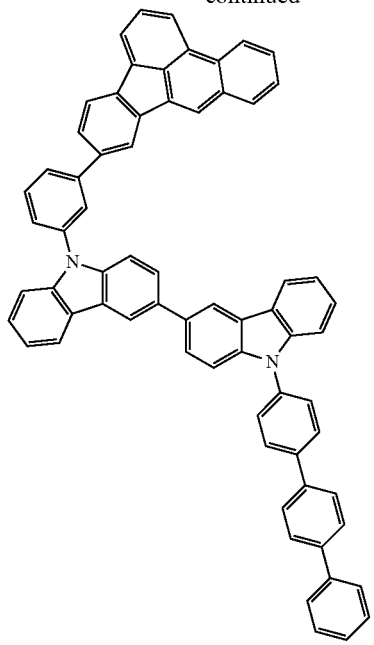
[Formula 108]
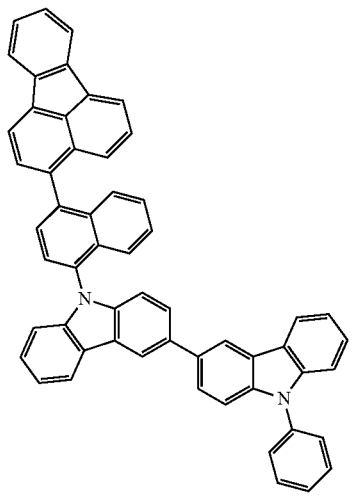
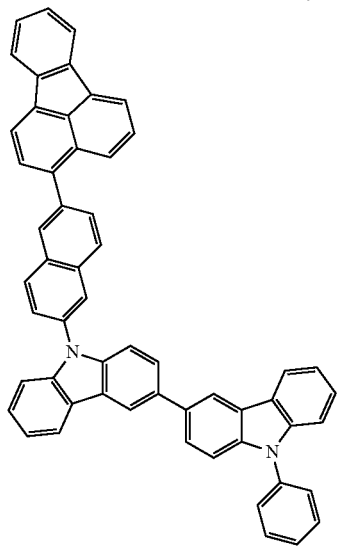
212
-continued
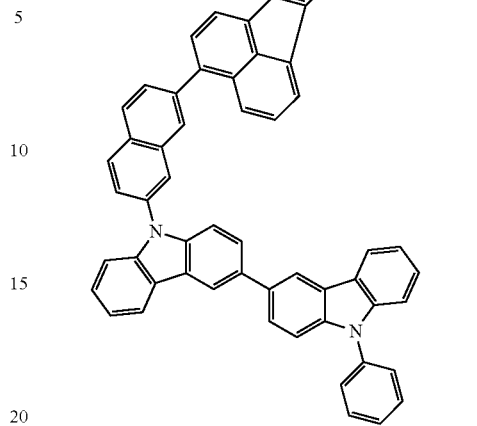
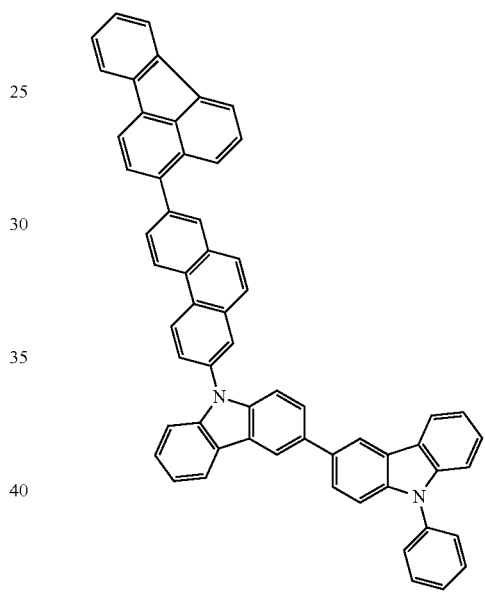
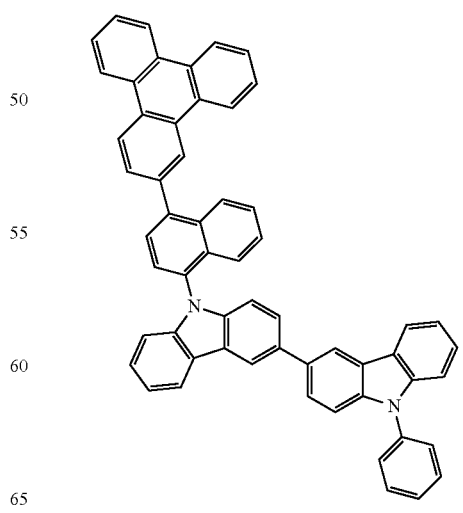

213
-continued
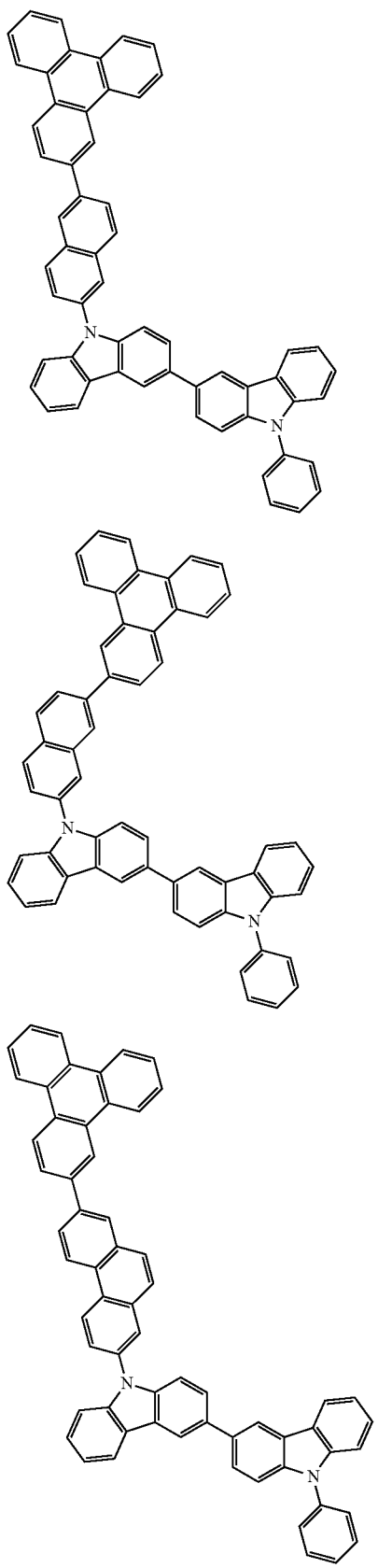
214
-continued
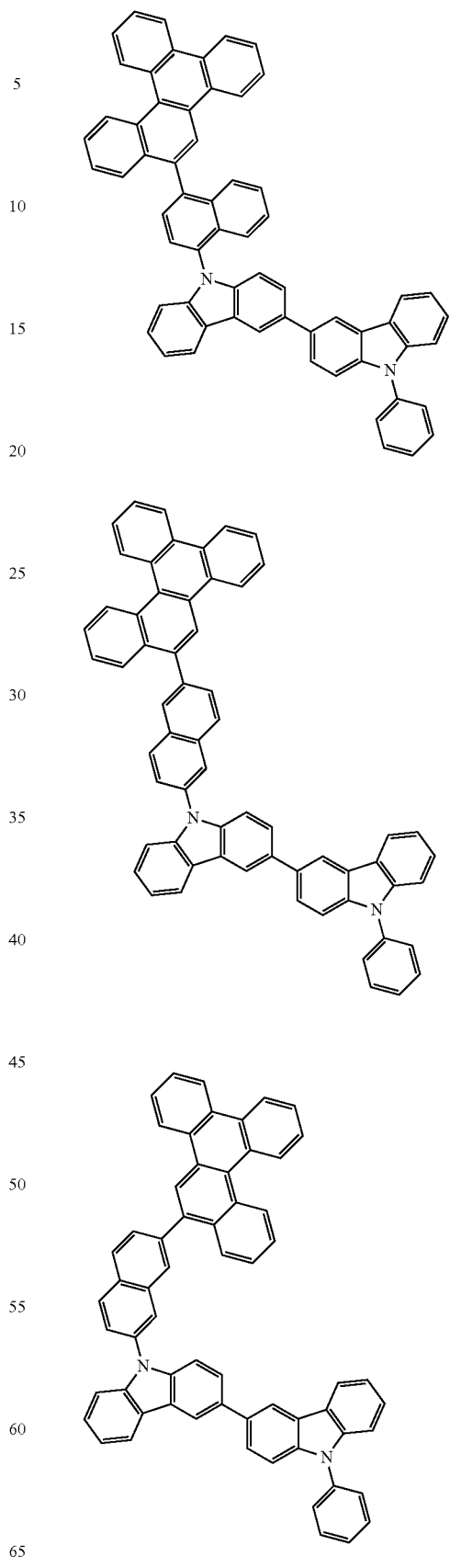

215
-continued
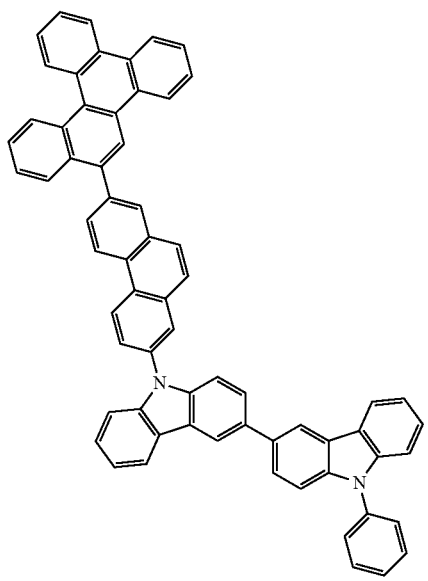
[Formula 109]
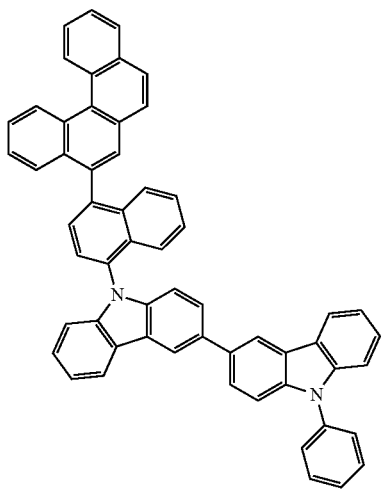
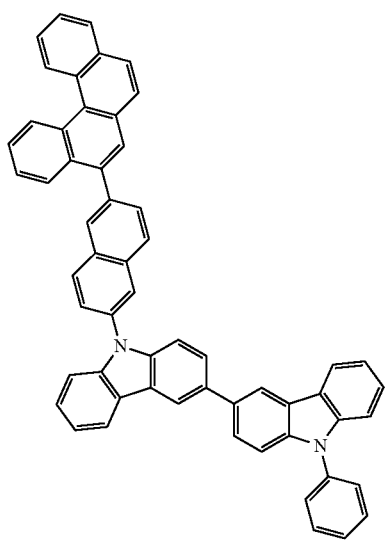
216
-continued
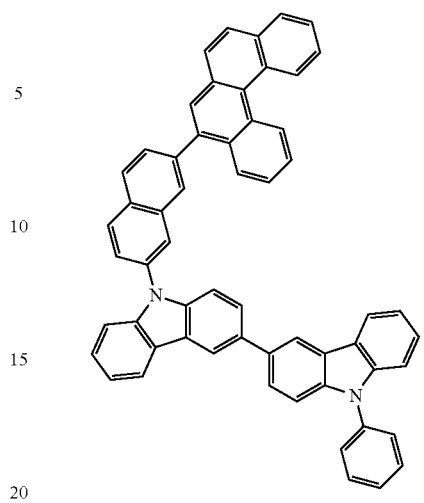
[Formula 110]
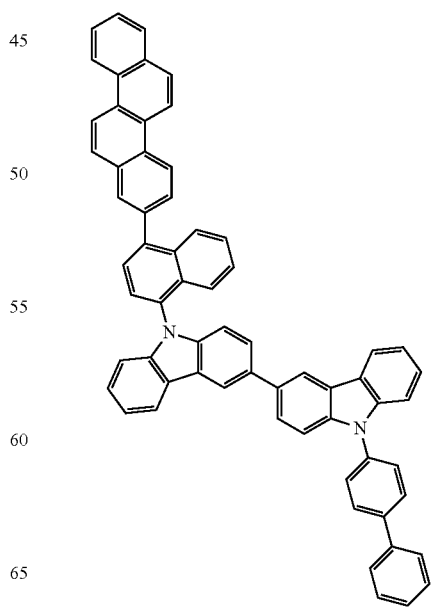

217
-continued
218
-continued
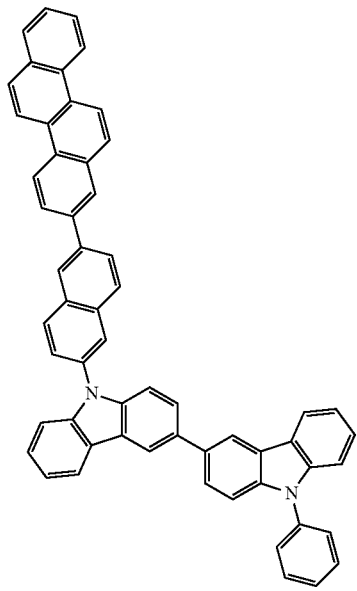
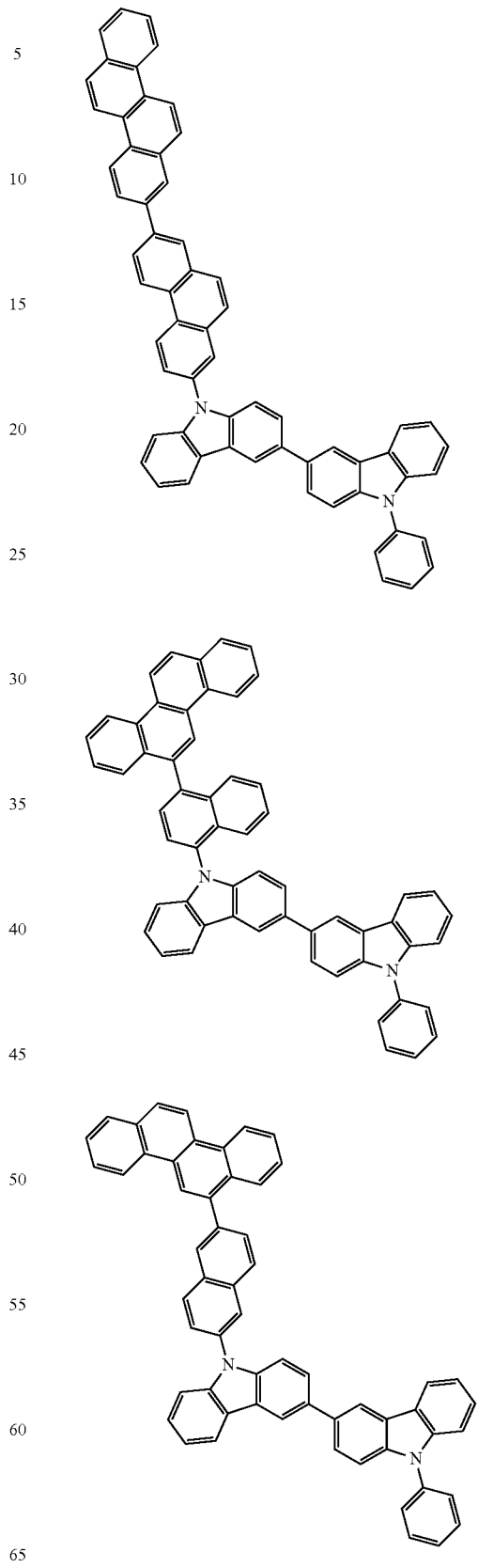

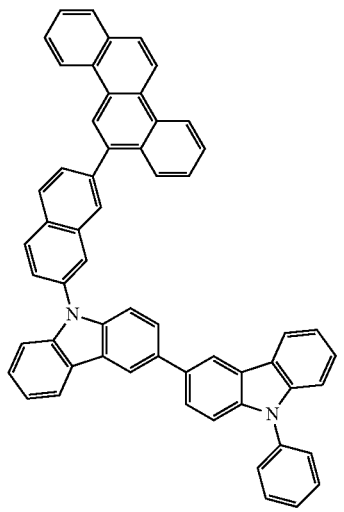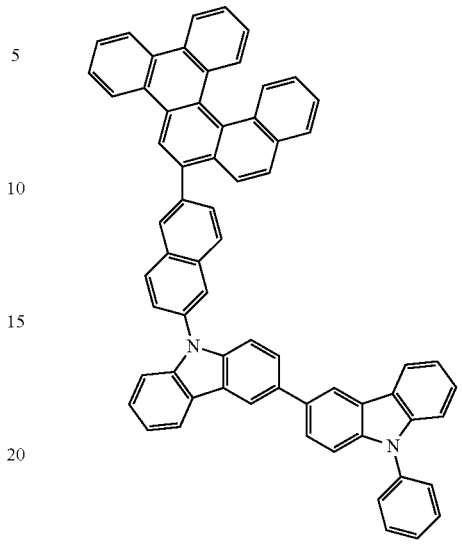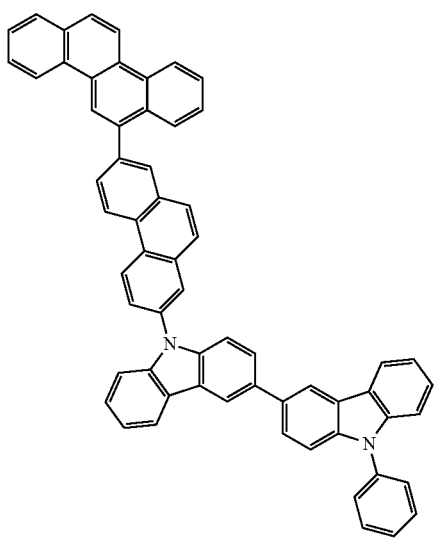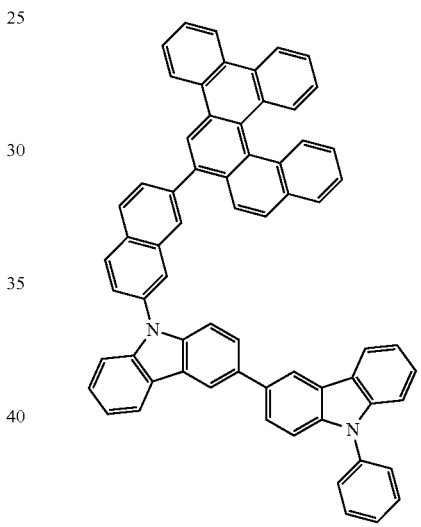
[Formula 111]
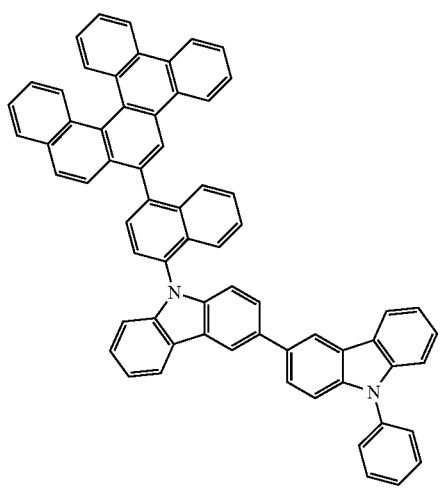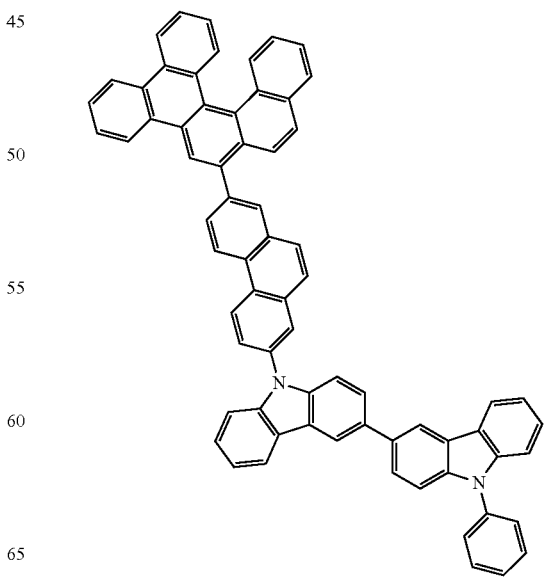

221
-continued
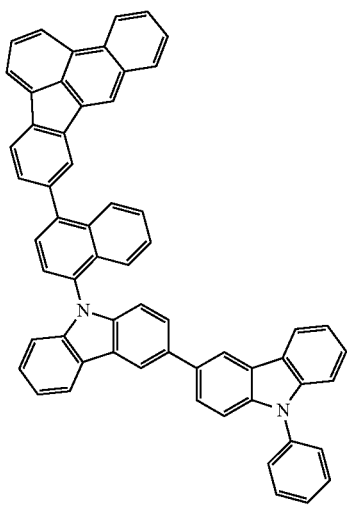
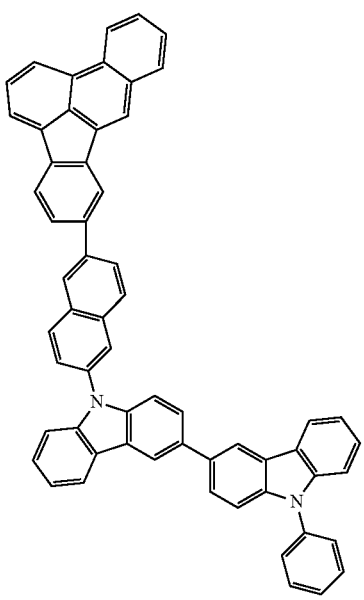
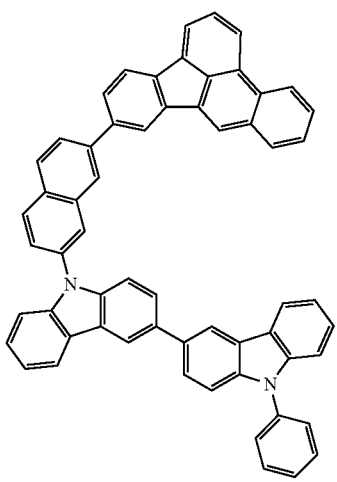
222
-continued
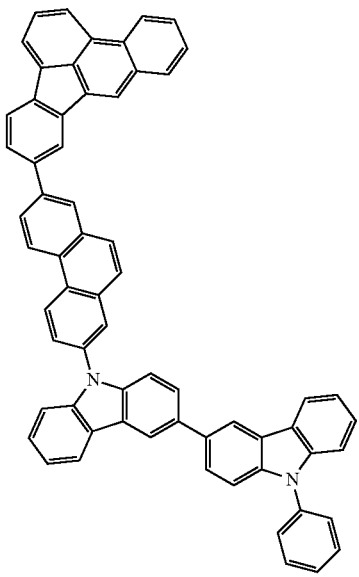
[Formula 112]
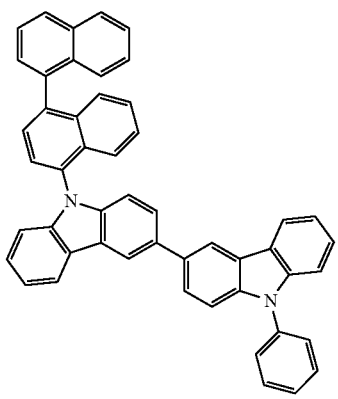
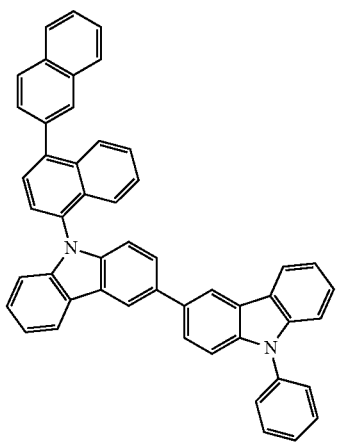

223
-continued
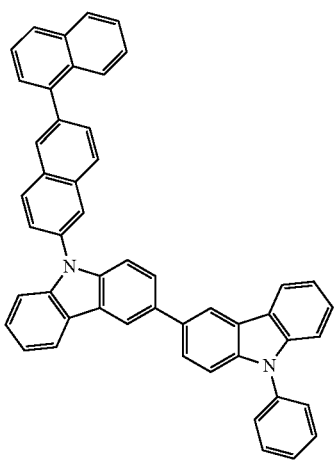
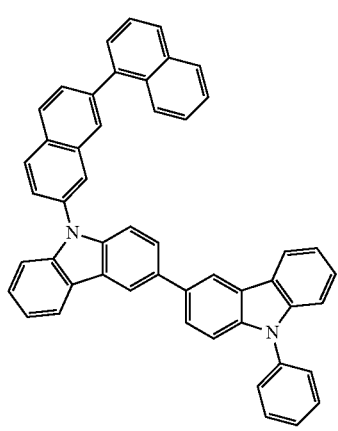
224
-continued
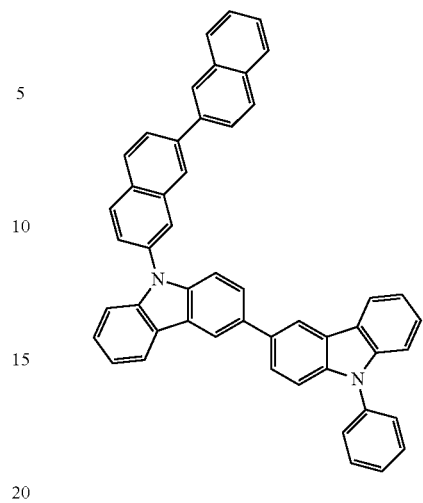
[Formula 113]
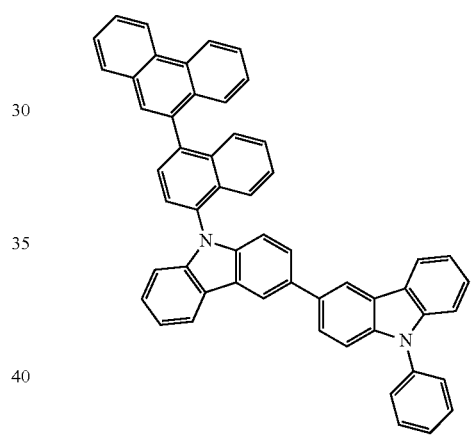
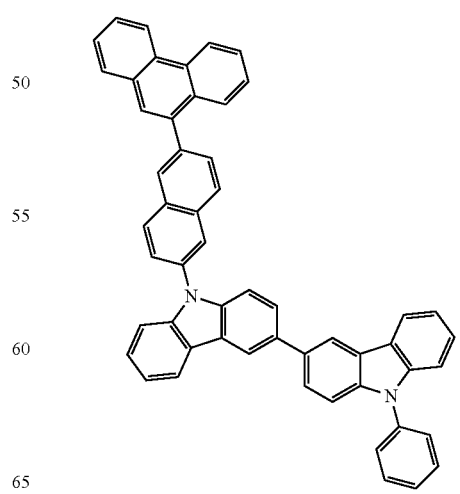

225
-continued
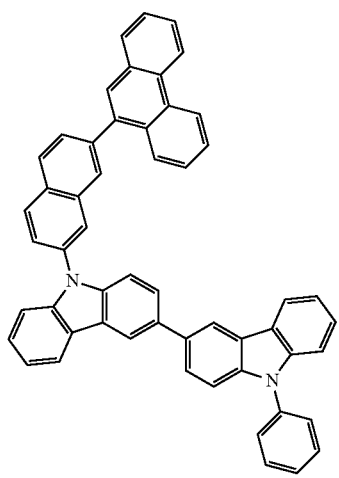
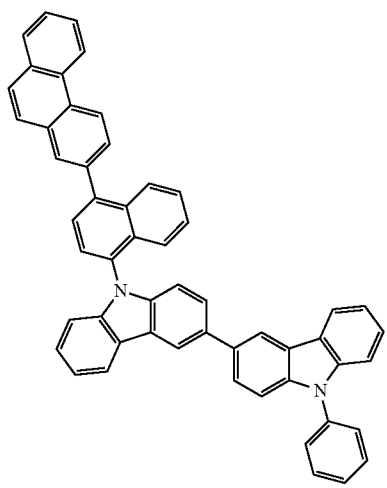
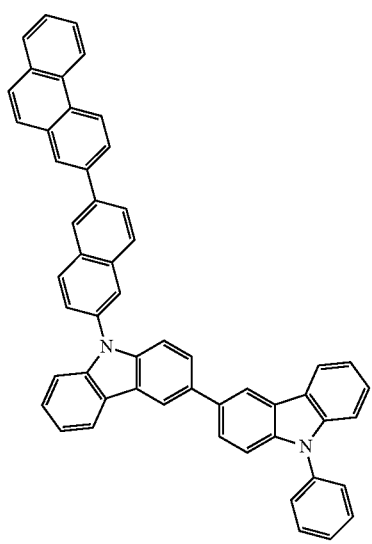
226
-continued
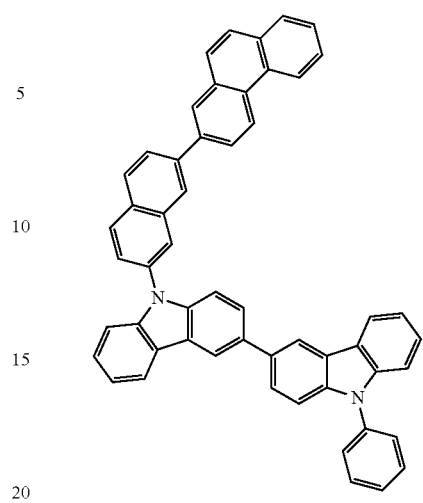
[Formula 114]
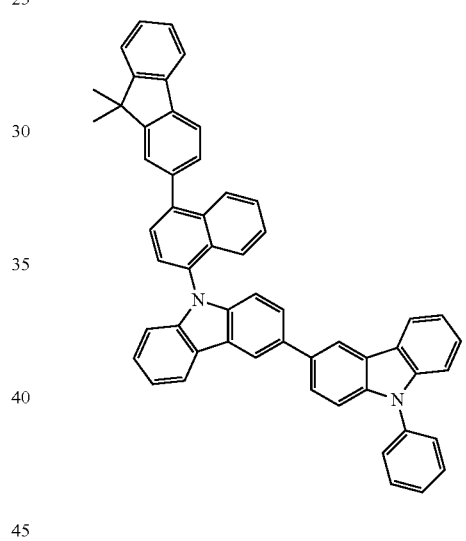
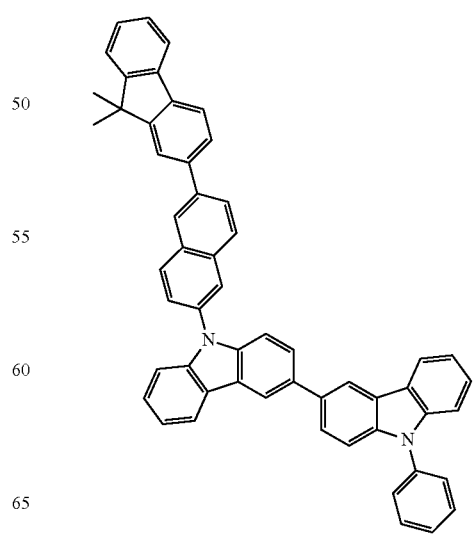

227
-continued
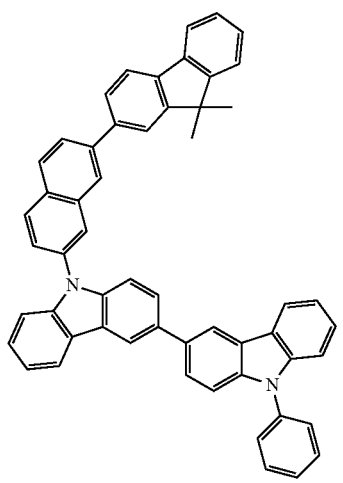
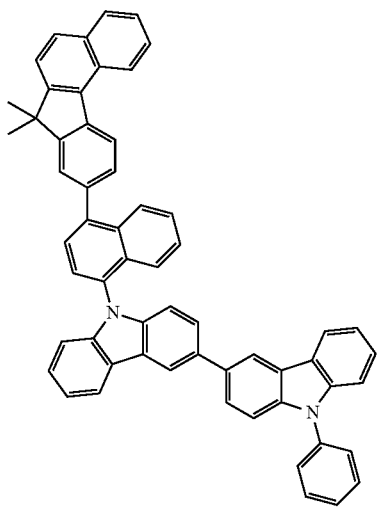
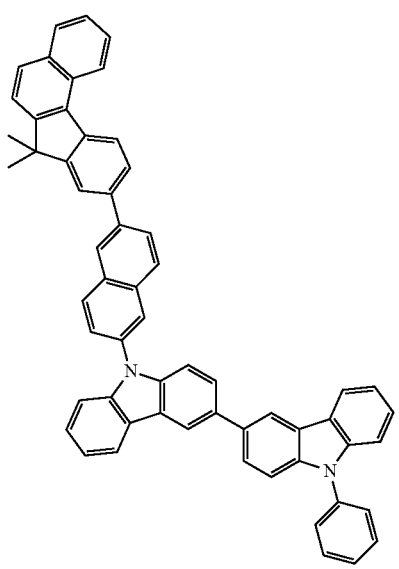
228
-continued
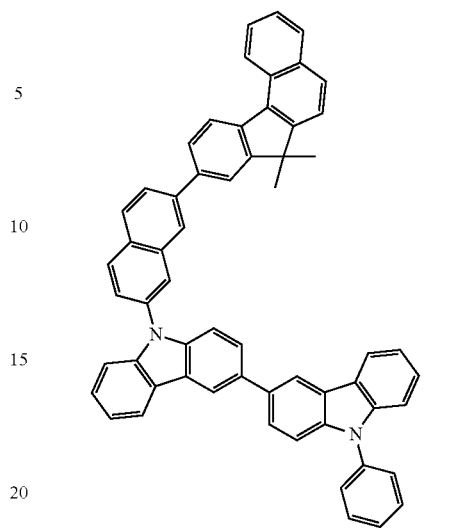
[Formula 115]

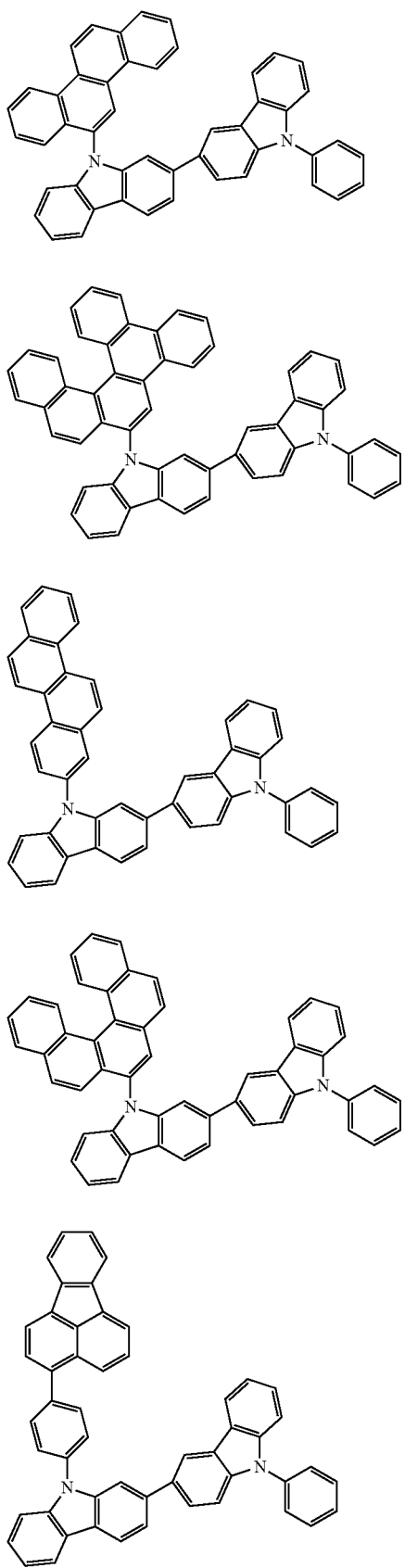
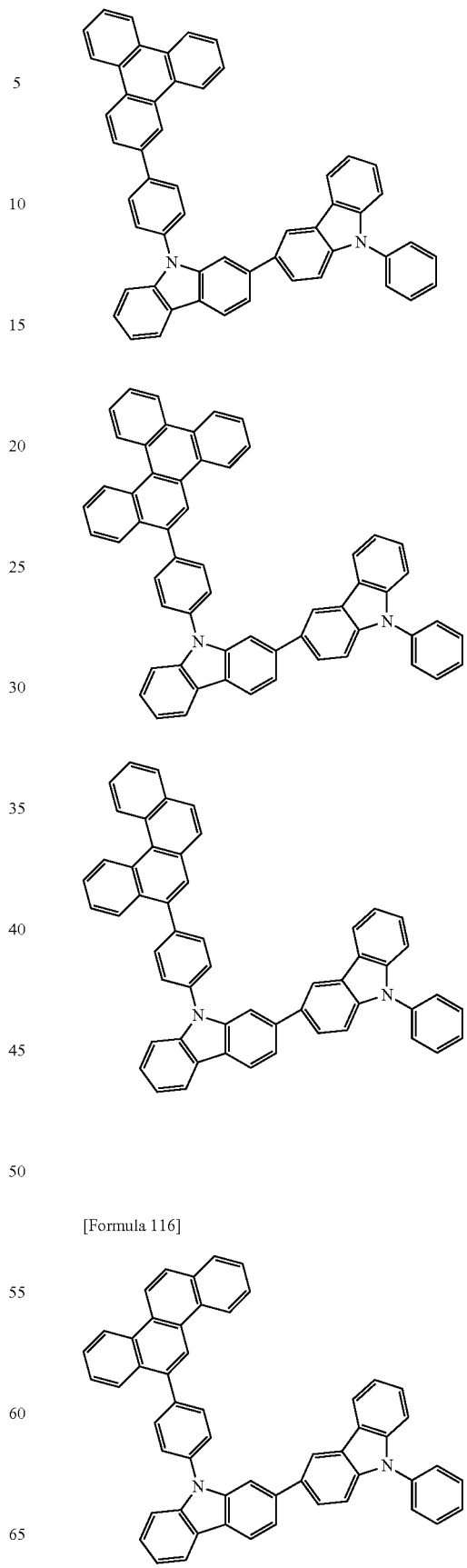
[Formula 116]

231
-continued
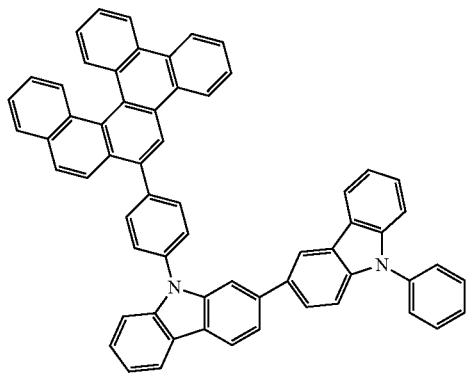
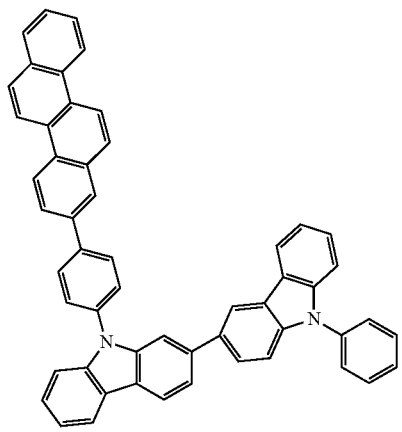
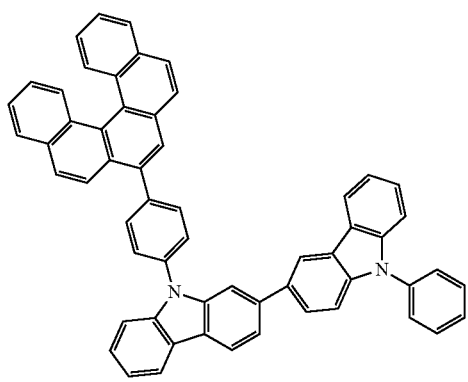
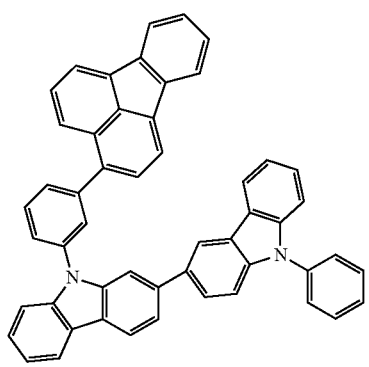
232
-continued
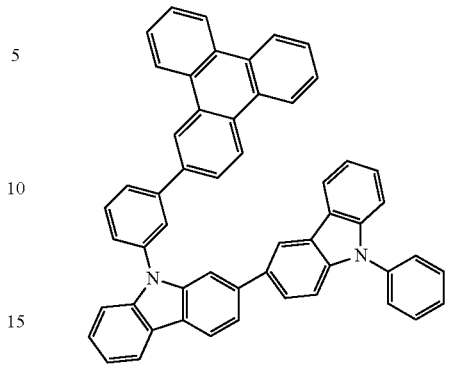
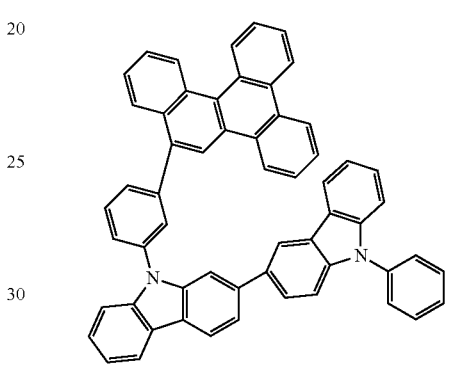
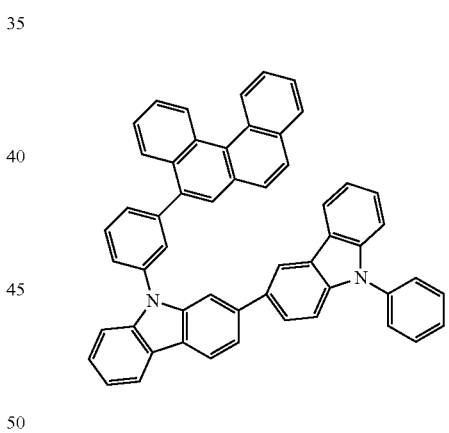
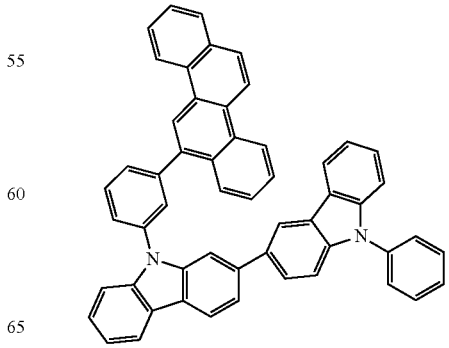

233
-continued
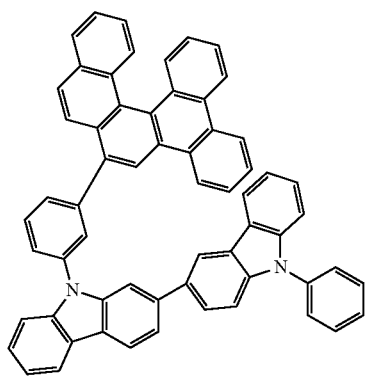
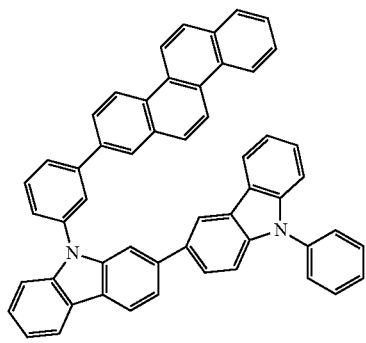
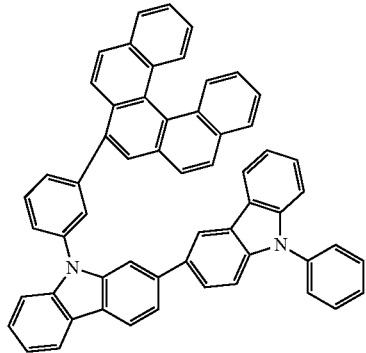
[Formula 117]
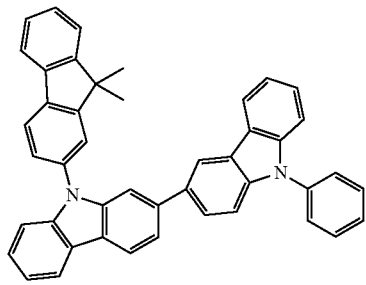
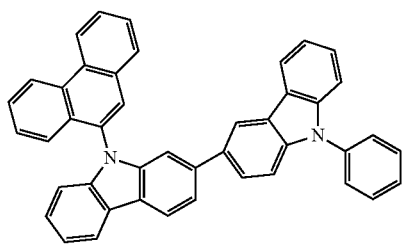
234
-continued
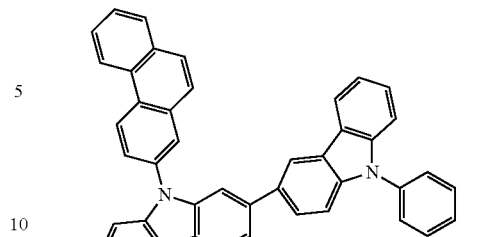
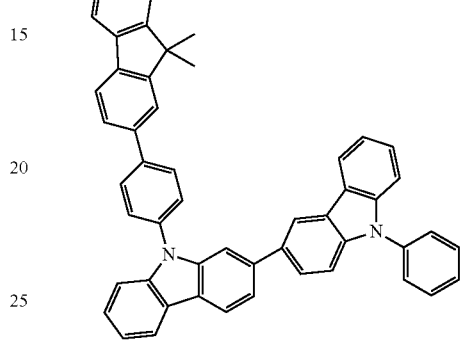
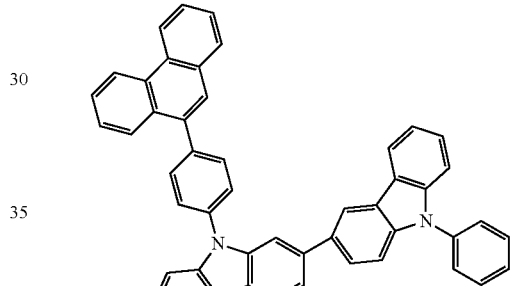
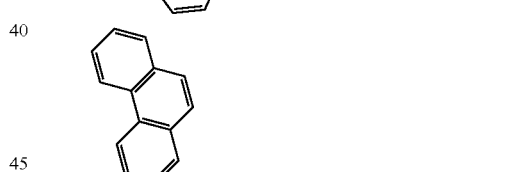
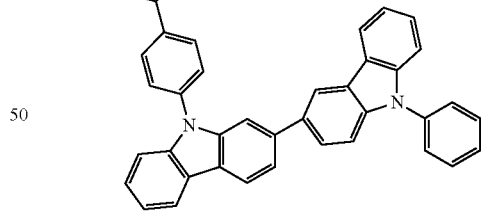
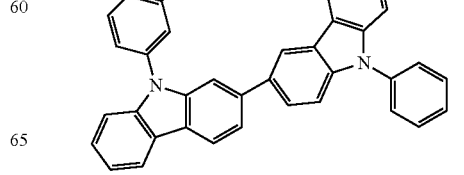

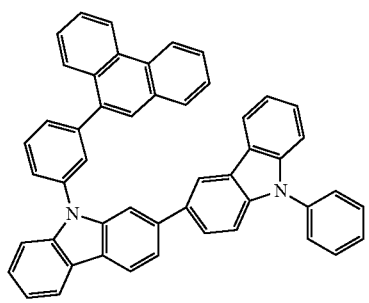
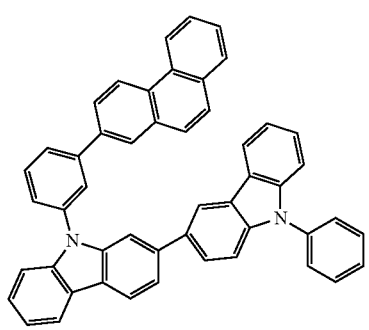
[Formula 118]
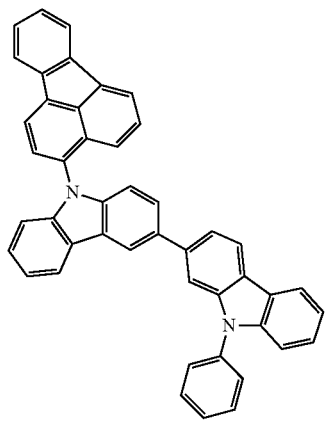
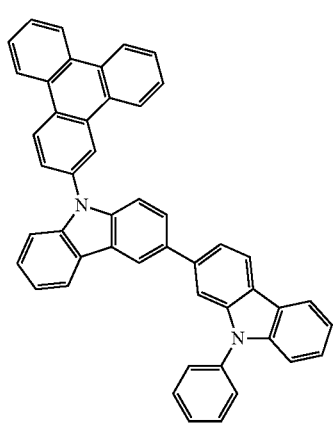
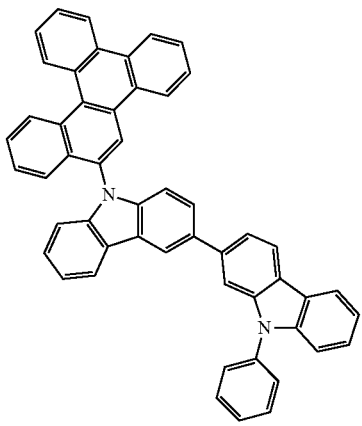
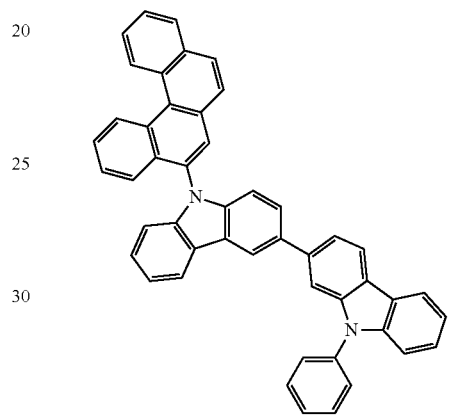
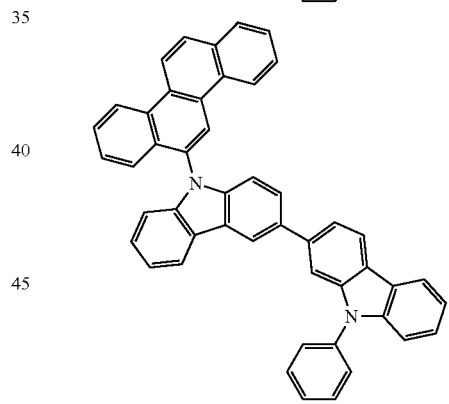
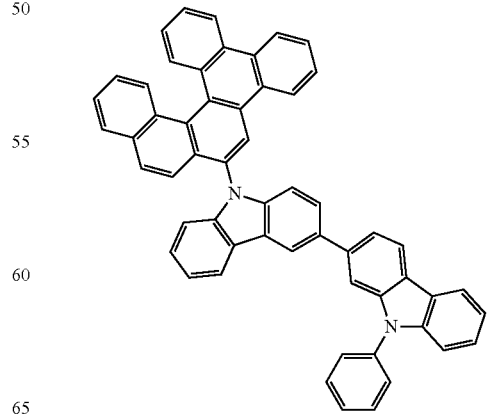

237
-continued
238
-continued
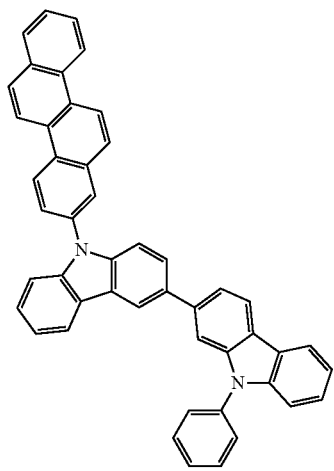
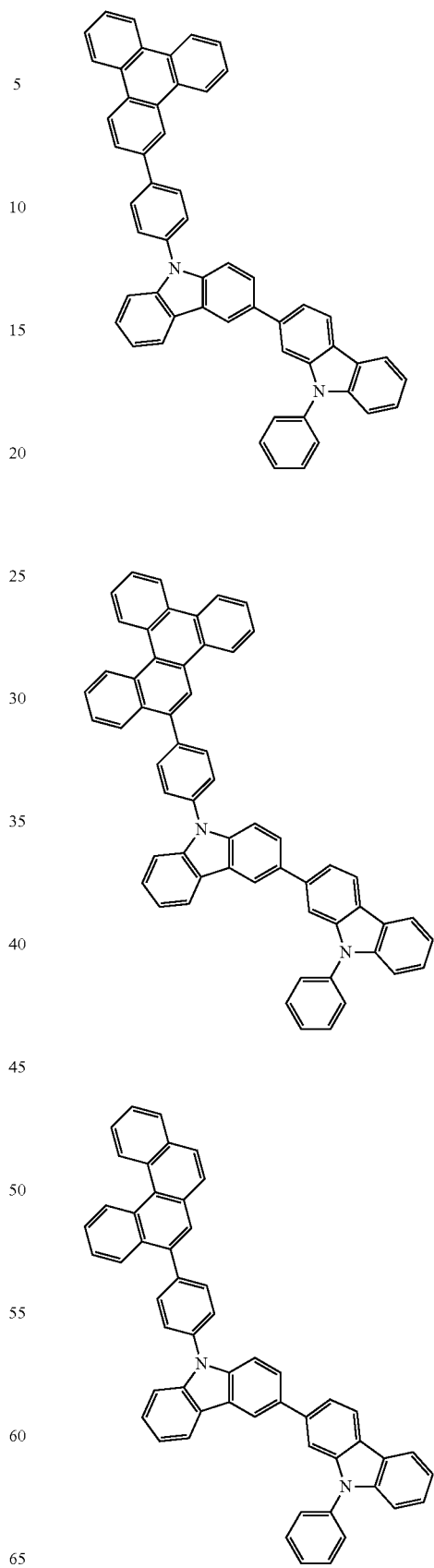

-continued
[Formula 119]
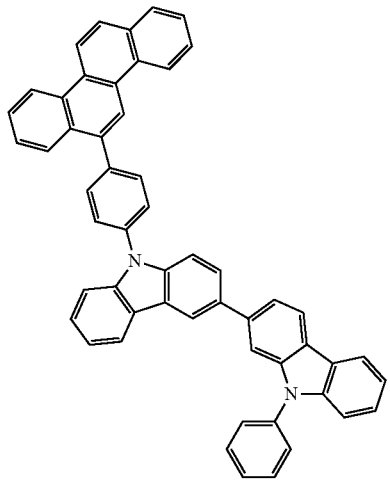
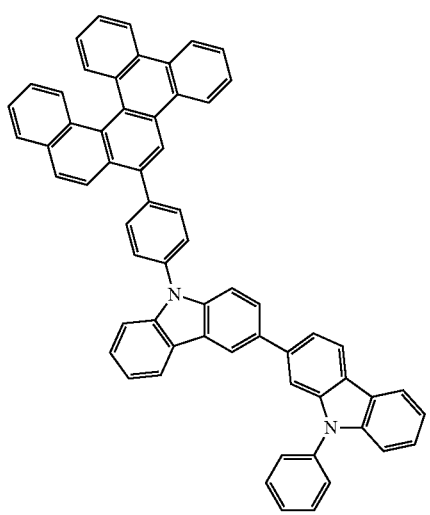
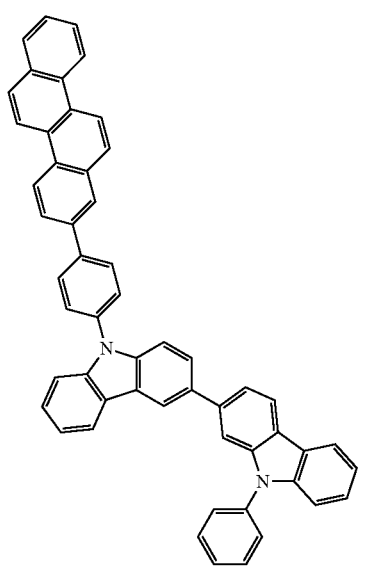
-continued
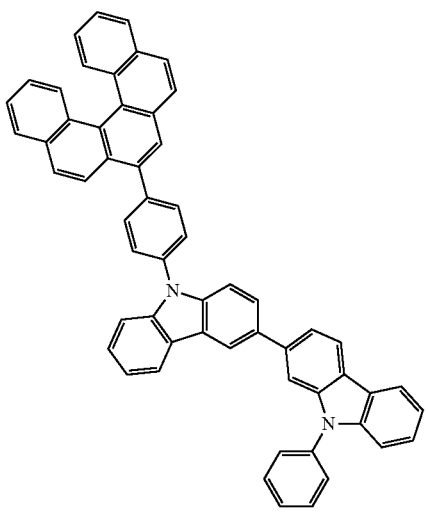
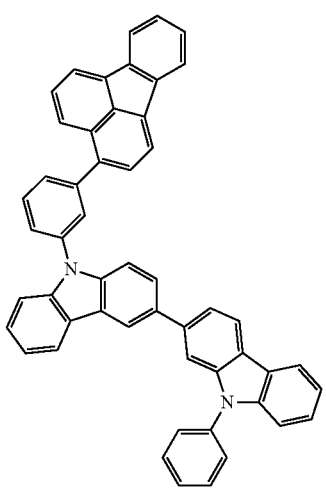
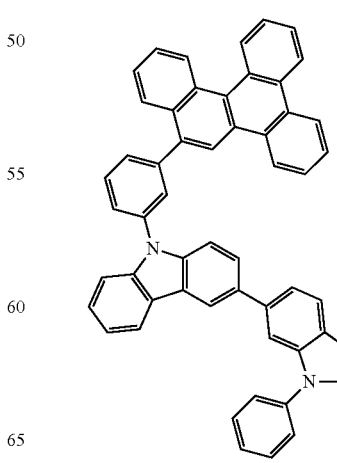

241
-continued
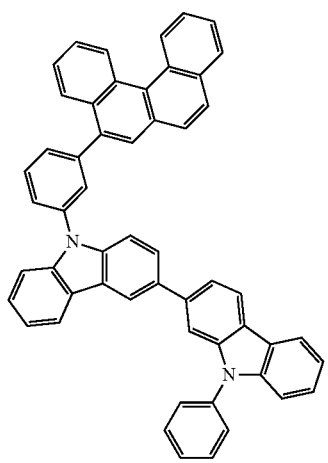
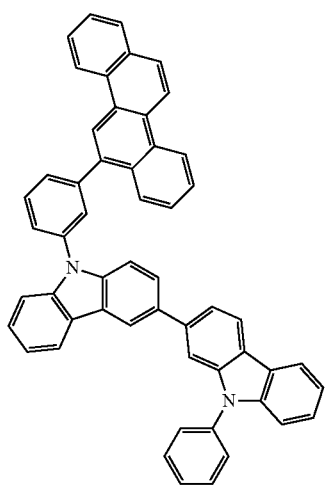
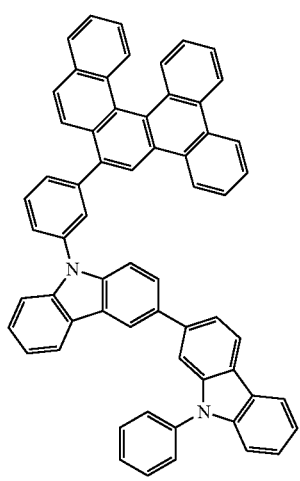
242
-continued
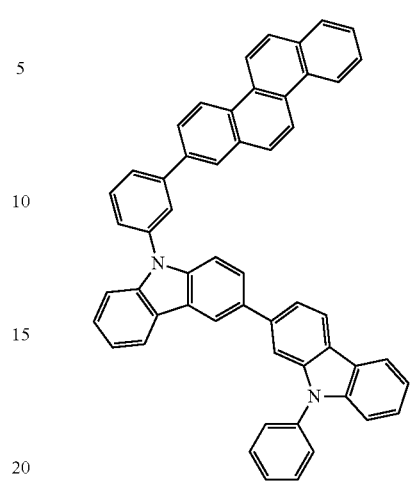
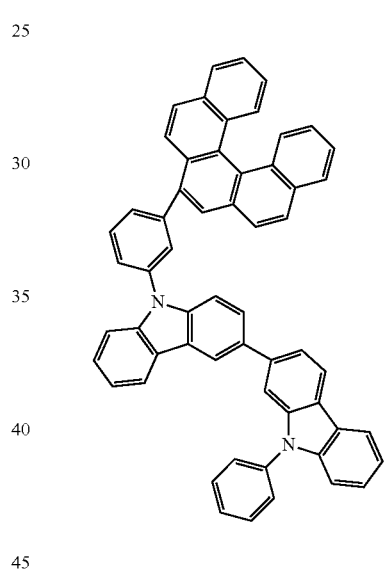
[Formula 120]
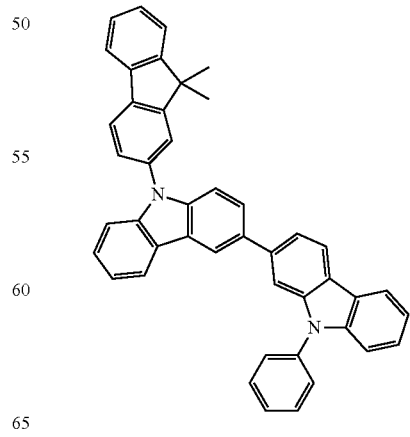

243
-continued
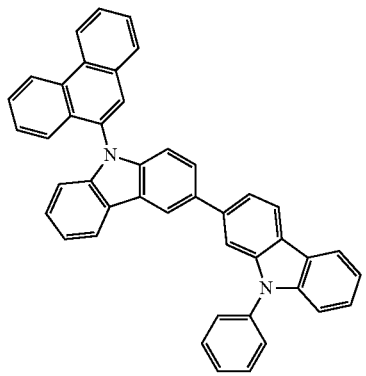
244
-continued
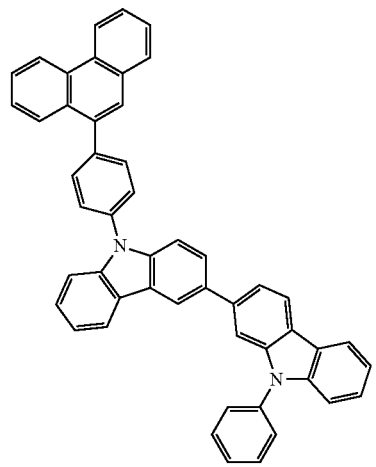
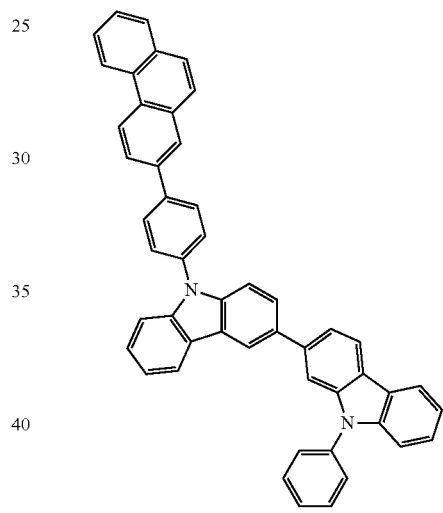
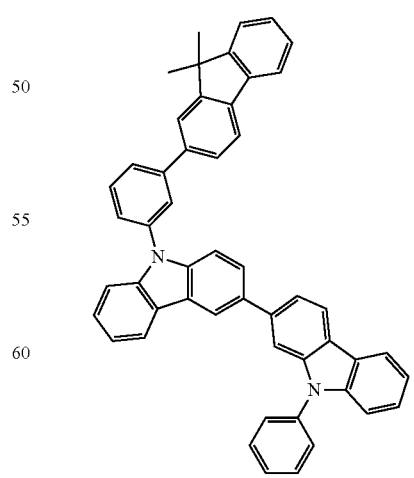

245
-continued
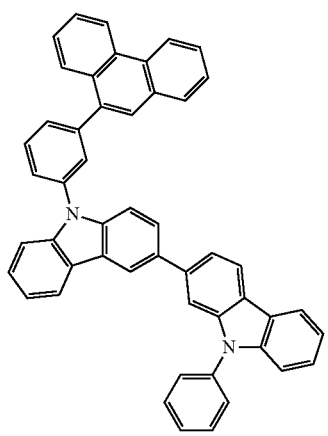
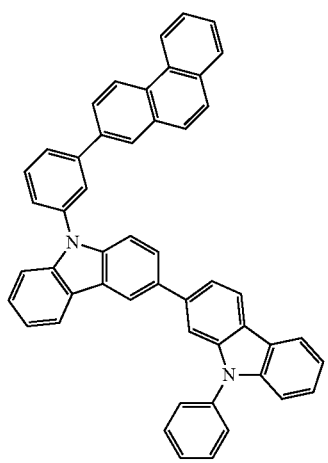
[Formula 121]
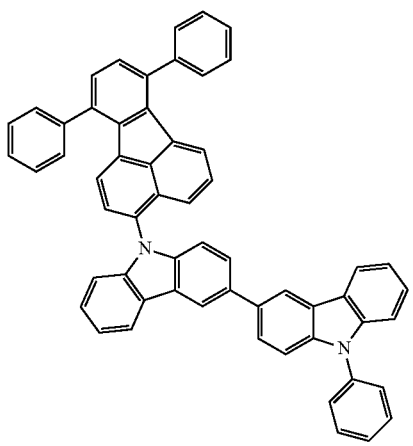
246
-continued
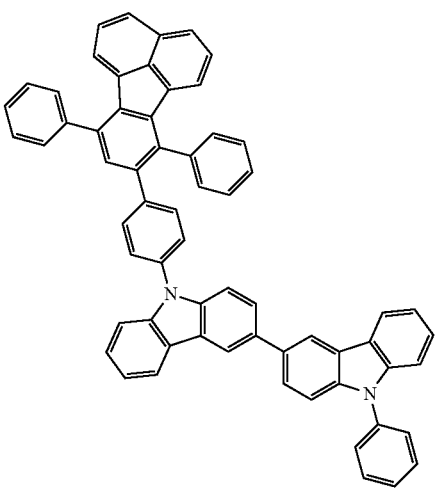
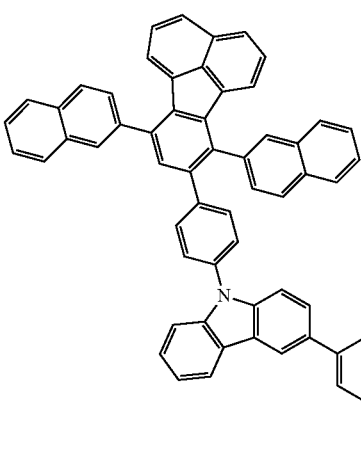
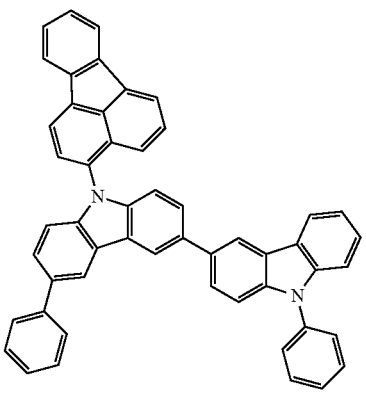

247
-continued
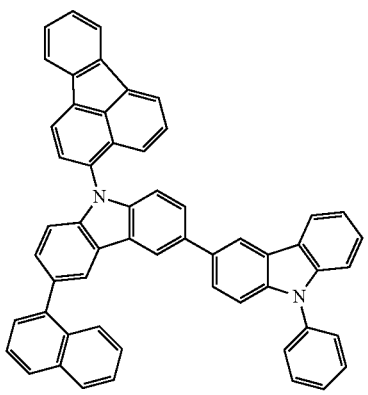
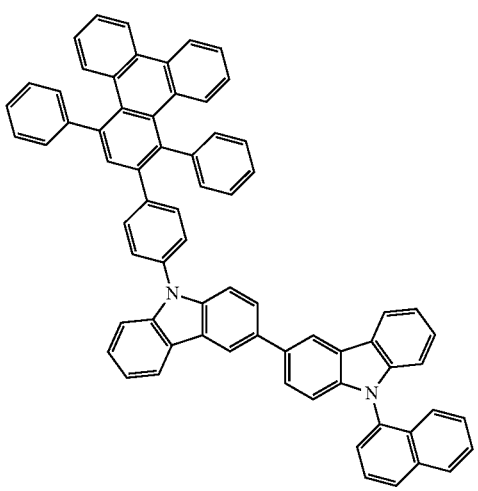
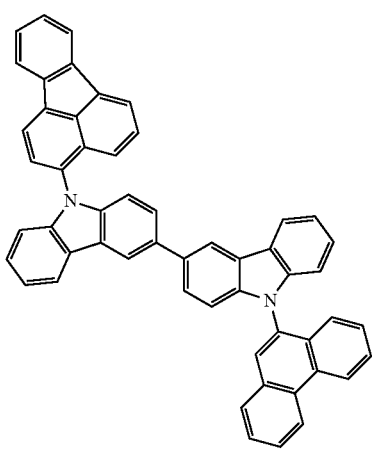
248
-continued
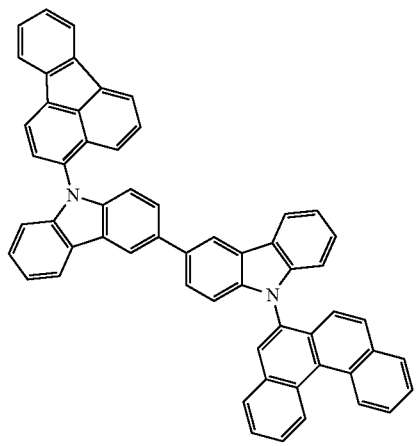
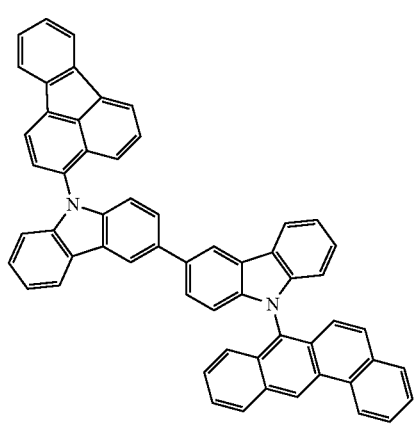
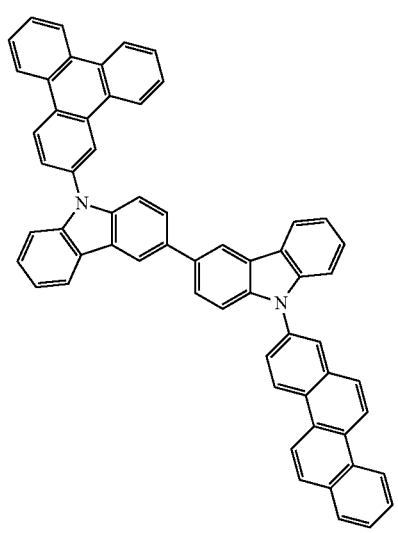

249
-continued
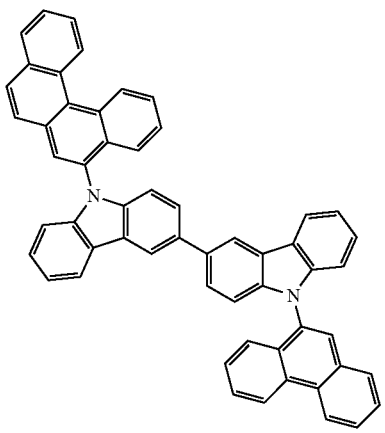
[Formula 122]
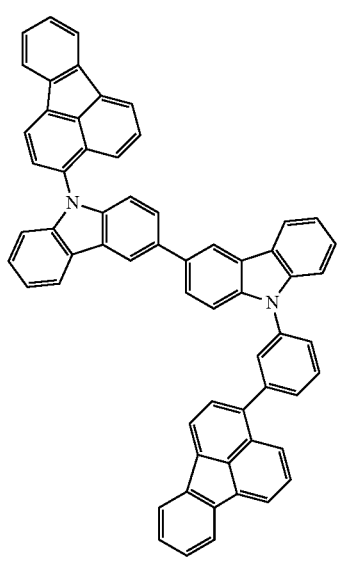
250
-continued
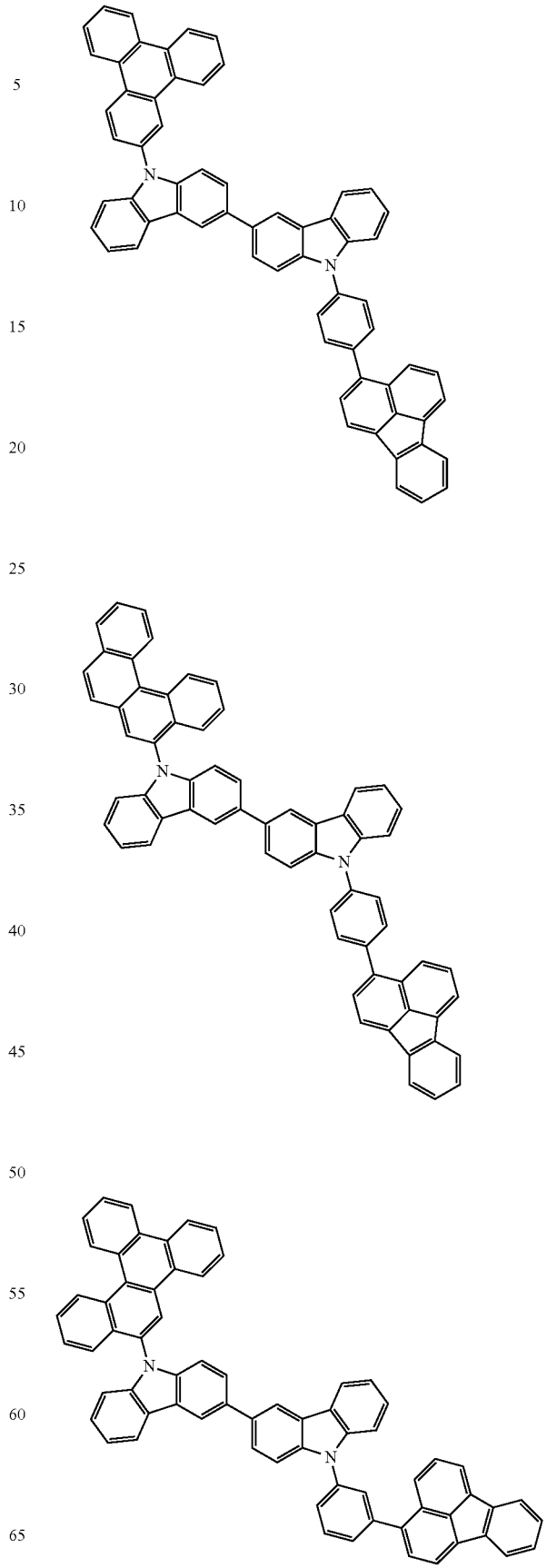

251
-continued
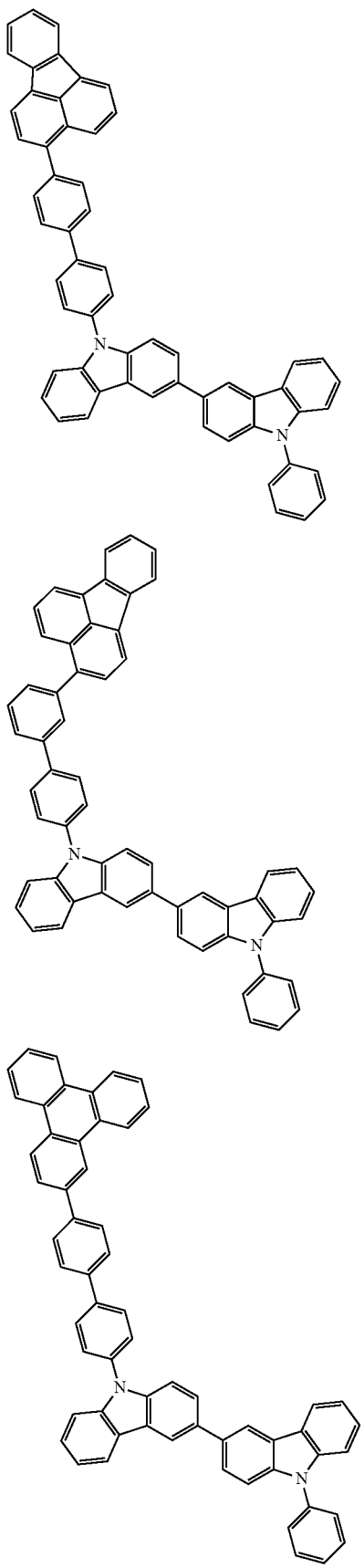
252
-continued
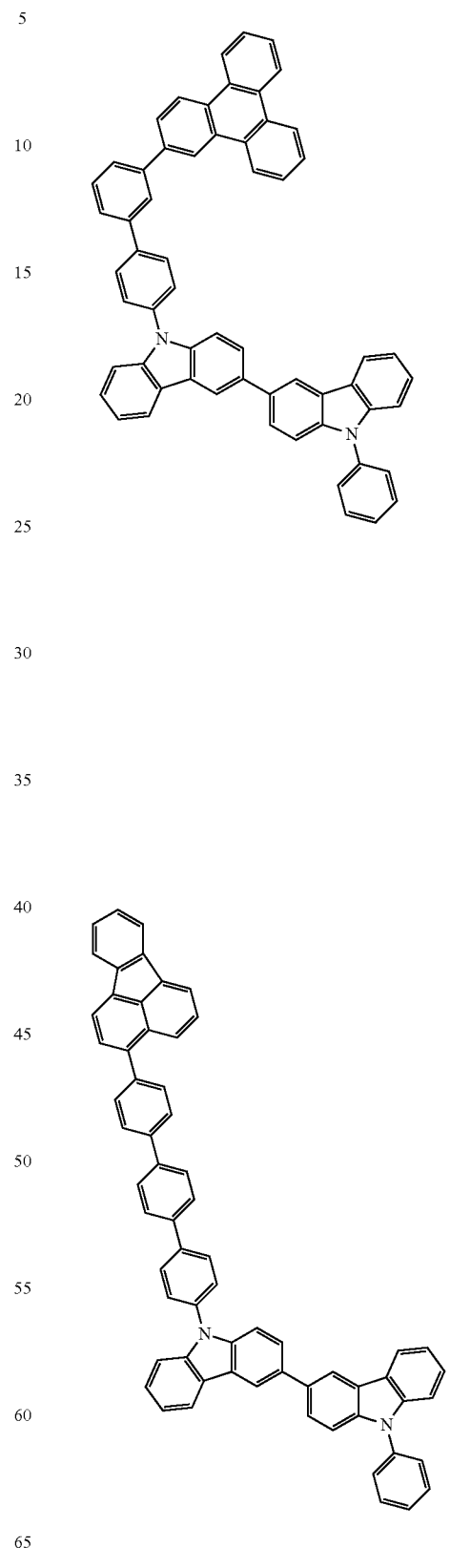

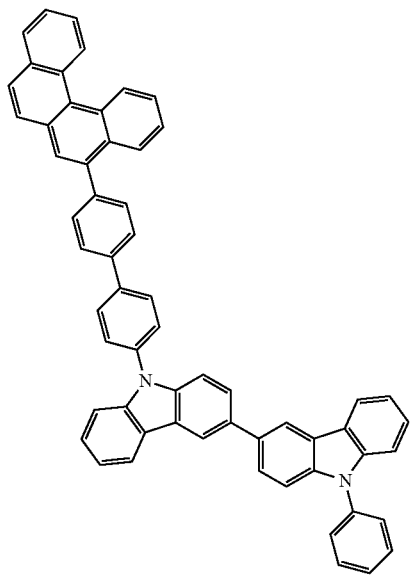

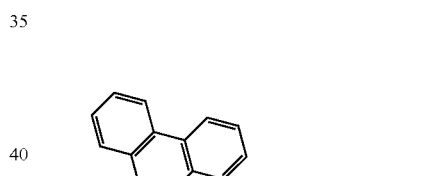
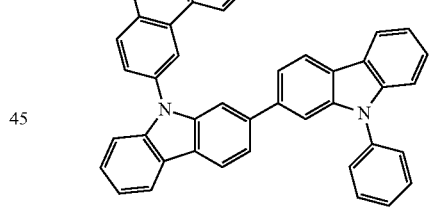
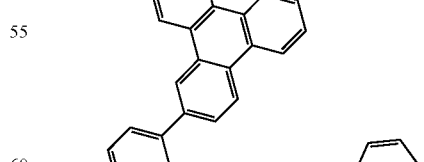
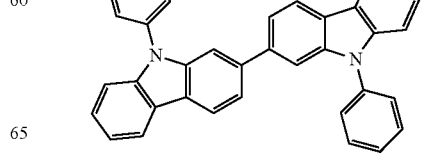
[Formula 123]
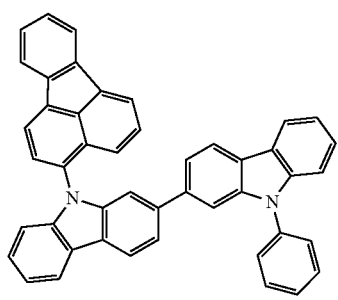

-continued
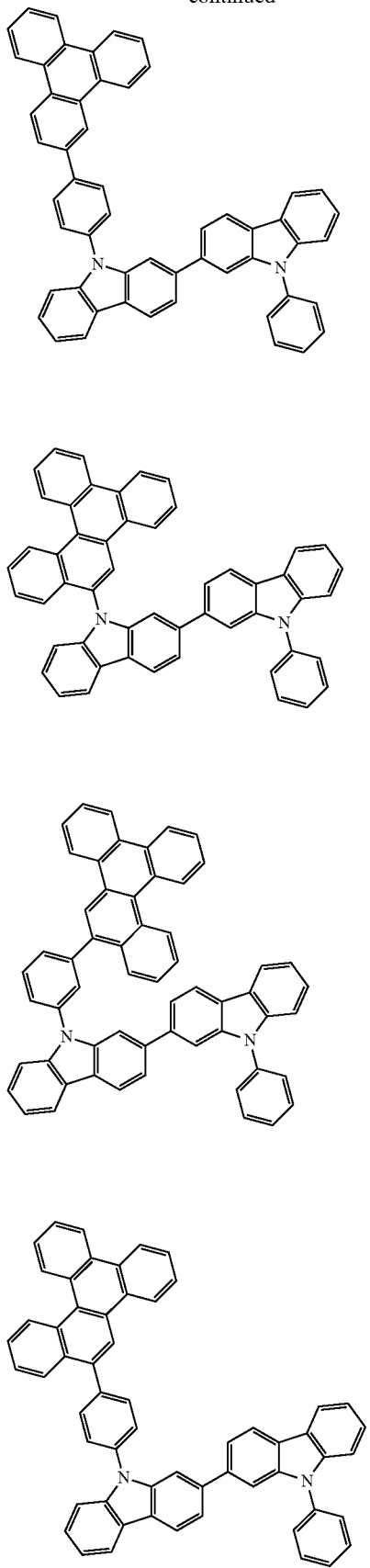
[Formula 124]
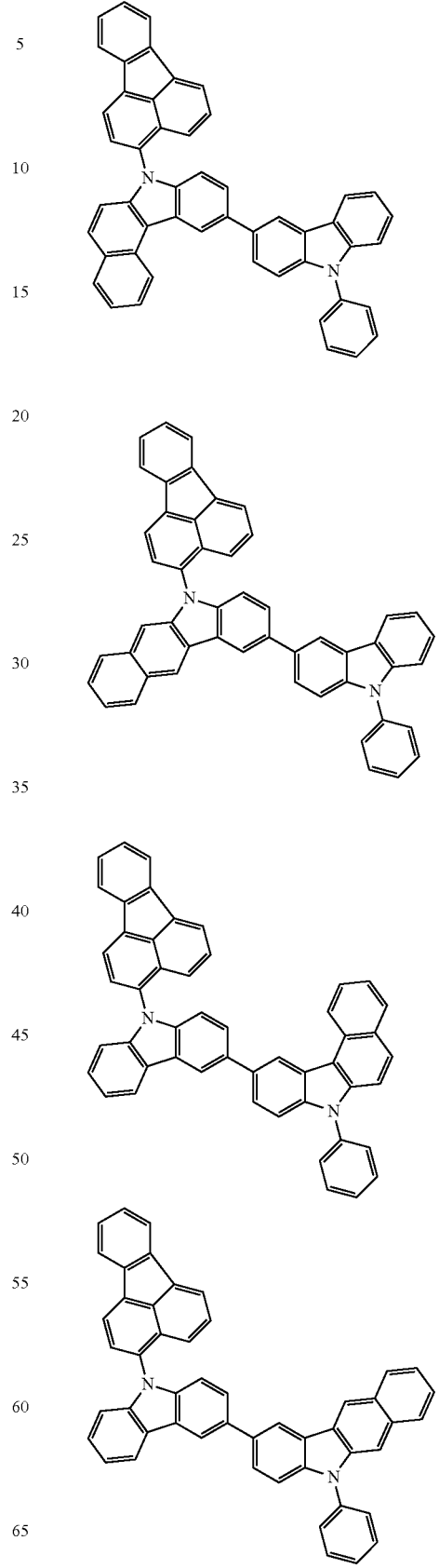

257
-continued
258
-continued
[Formula 125]
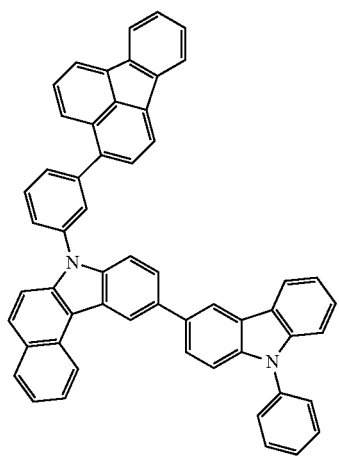
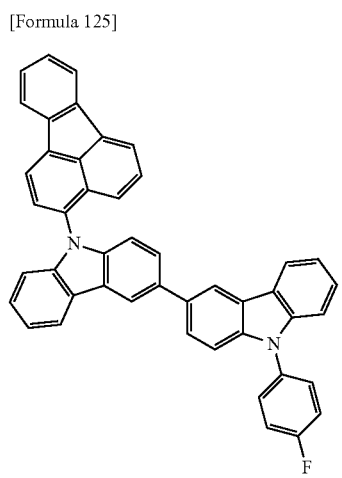
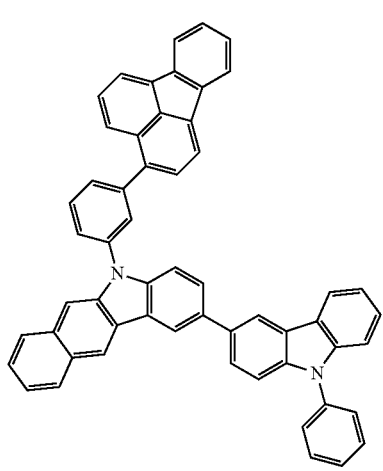
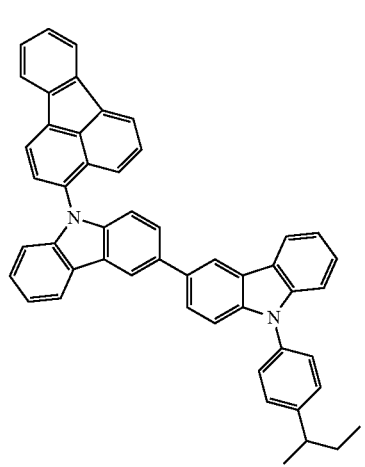

259
-continued
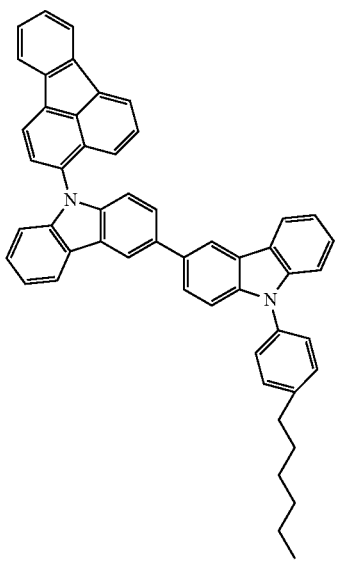
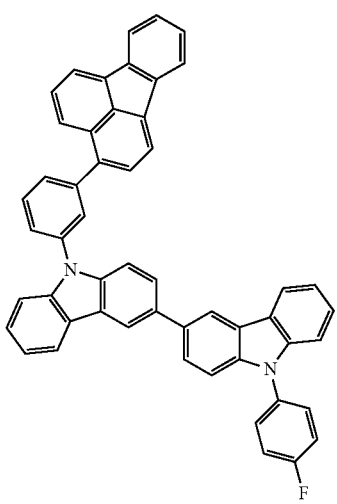
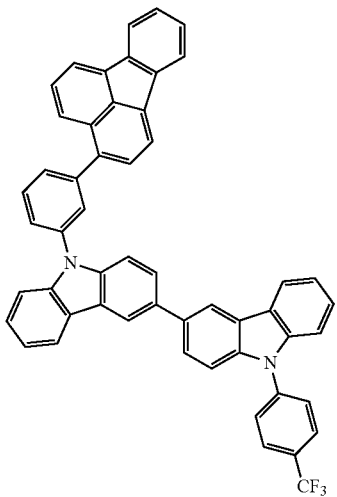
260
-continued
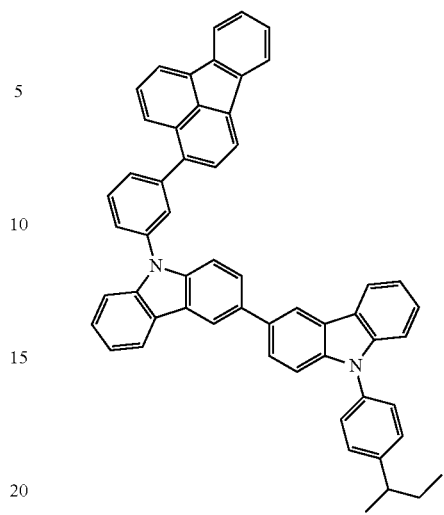
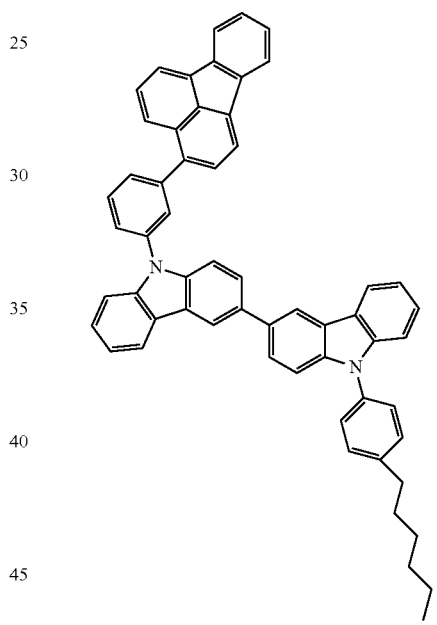
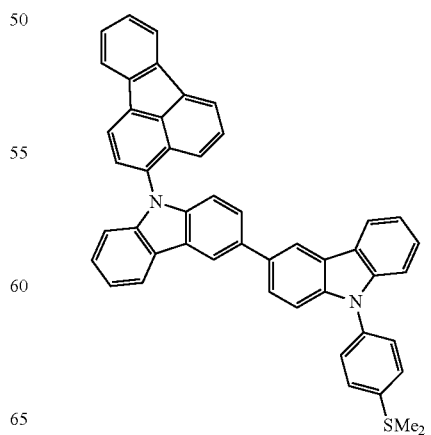

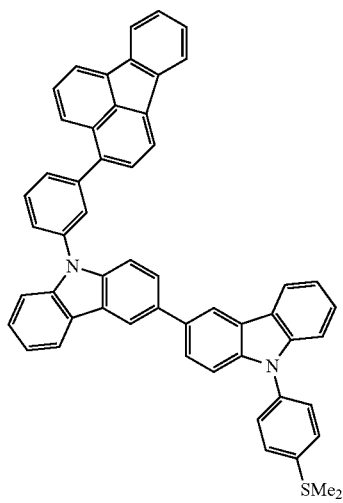
[Formula 126]
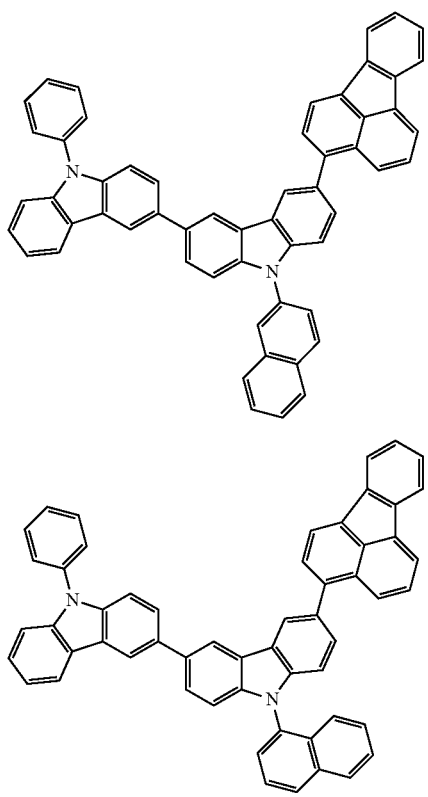
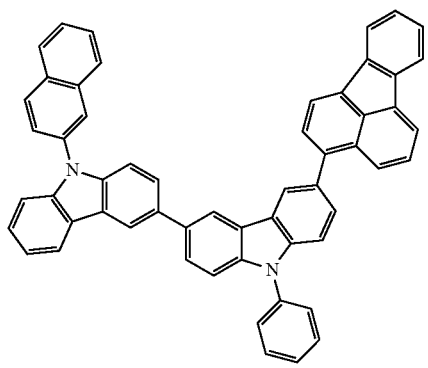
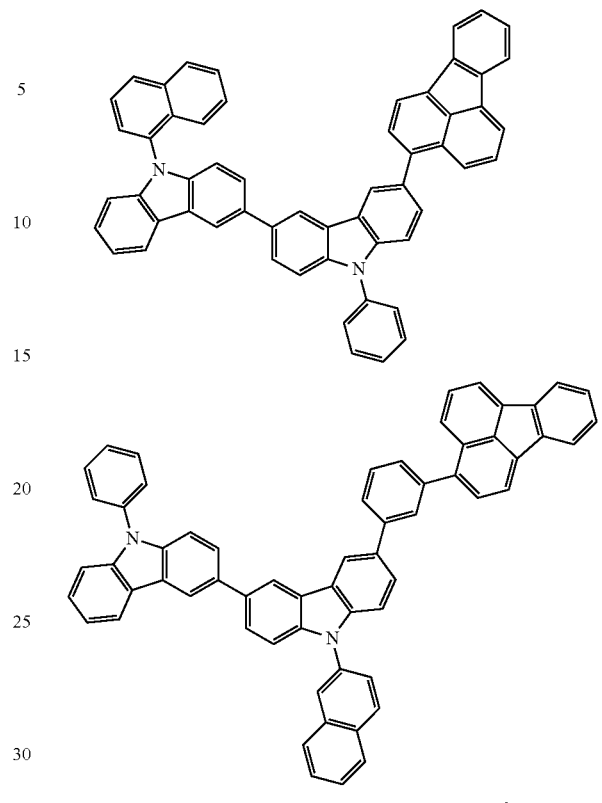
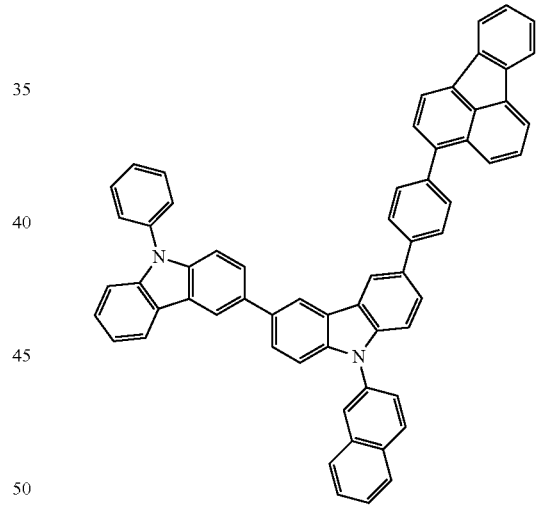
[Formula 127]
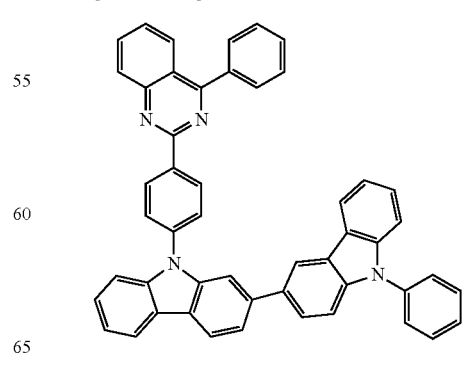

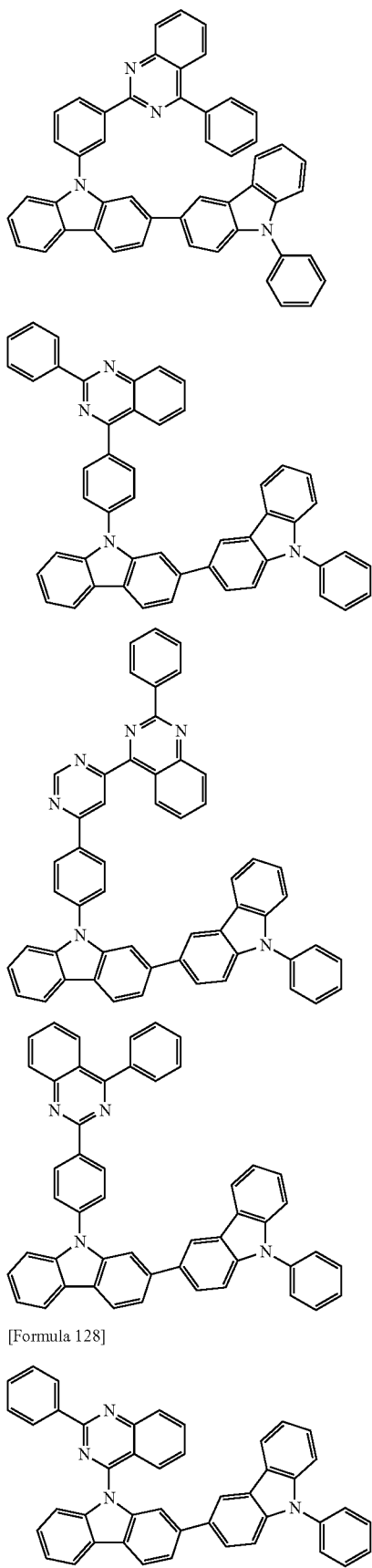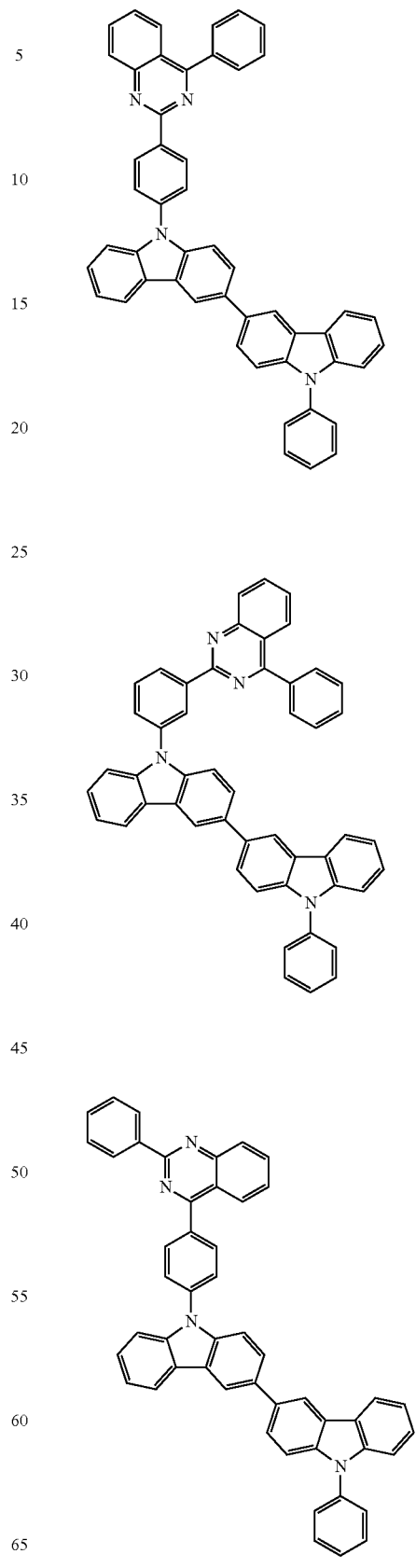
[Formula 128]

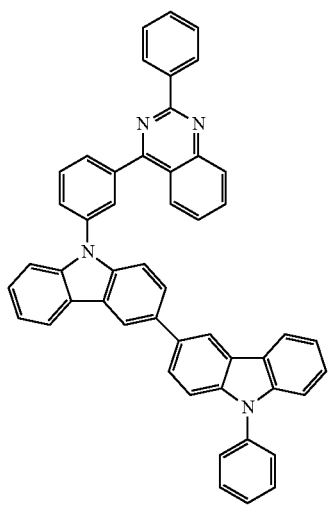
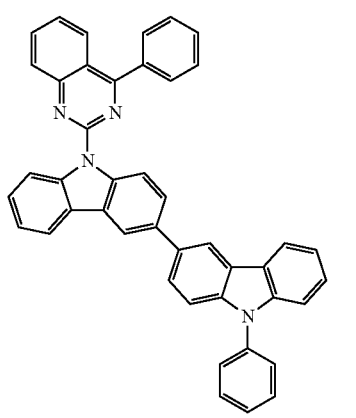
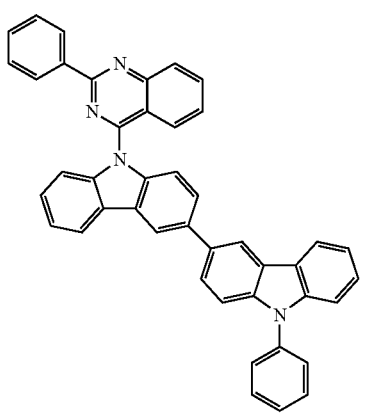
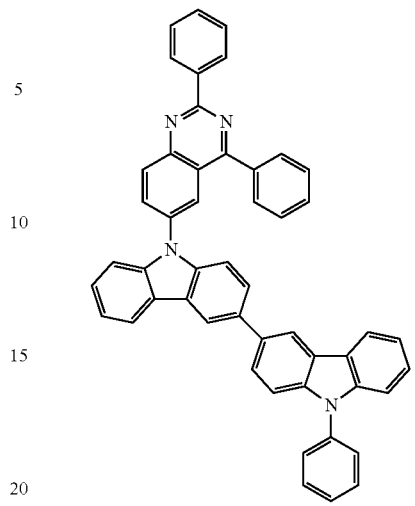
[Formula 129]
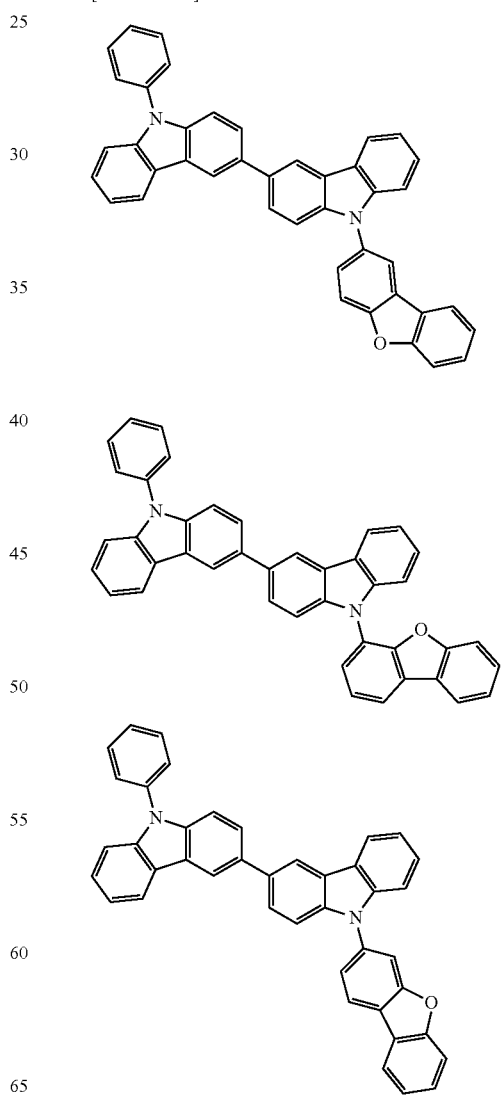

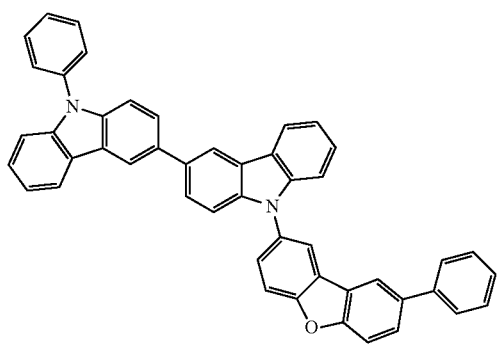
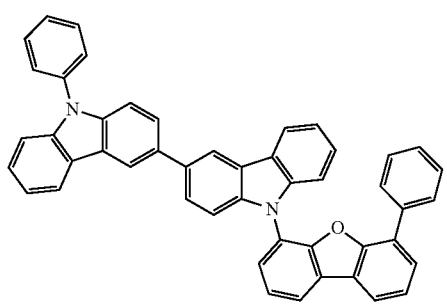
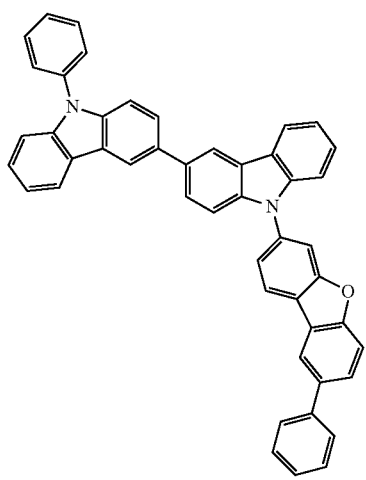
[Formula 130]
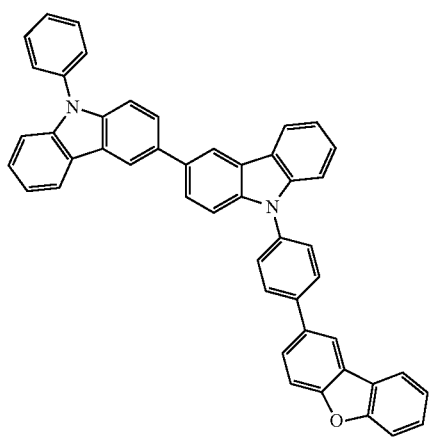
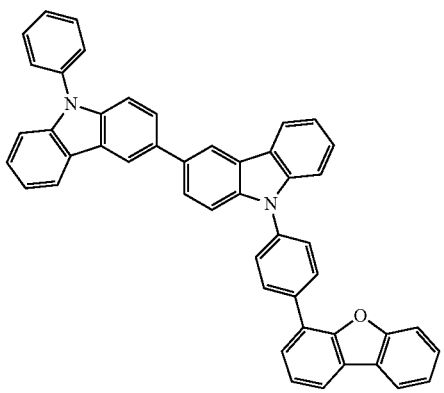
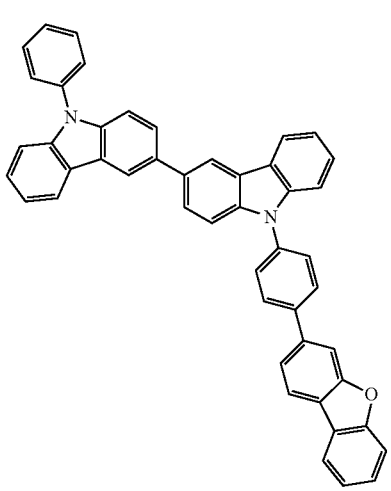
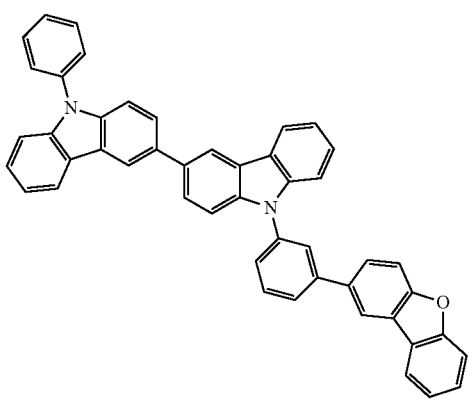
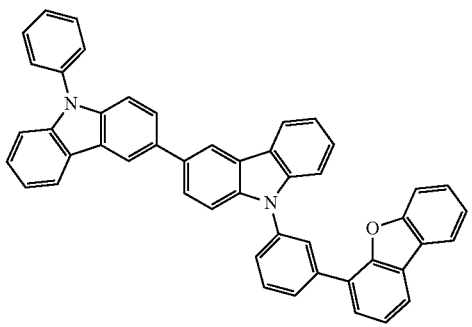

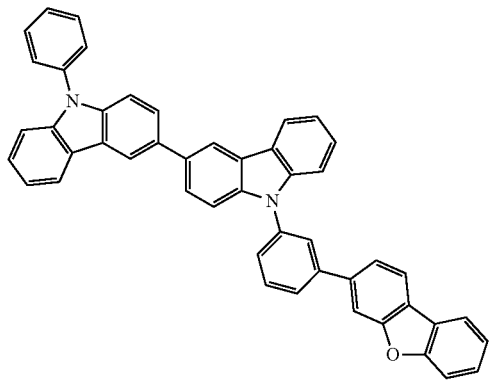
[Formula 131]
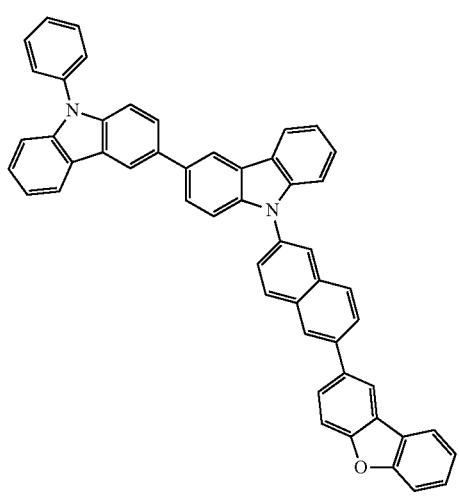
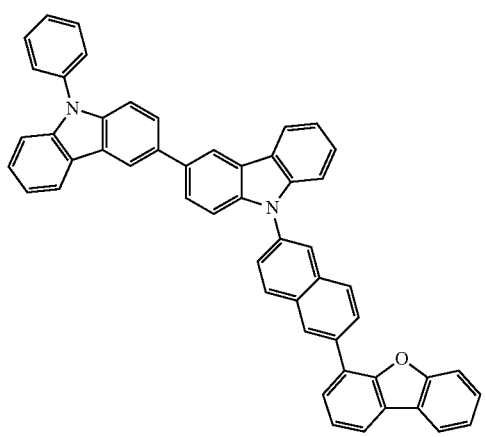
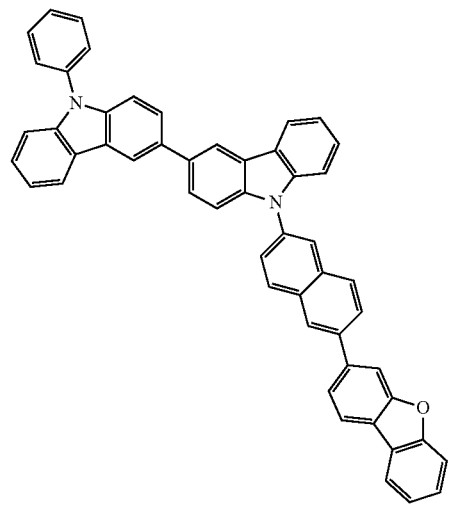
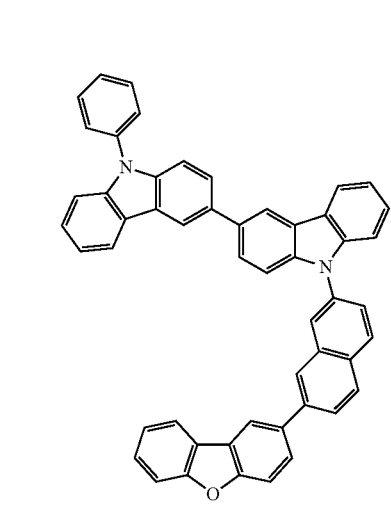
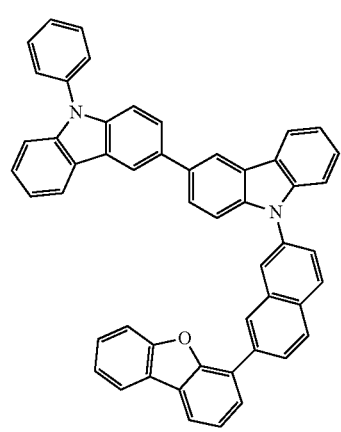

271
-continued
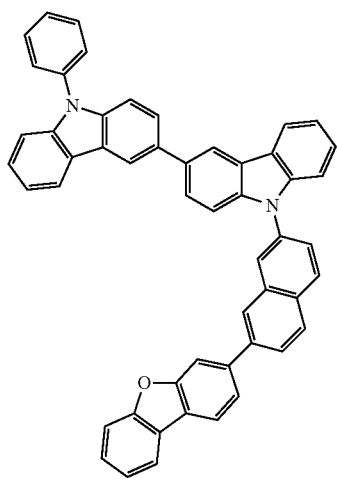
[Formula 132]
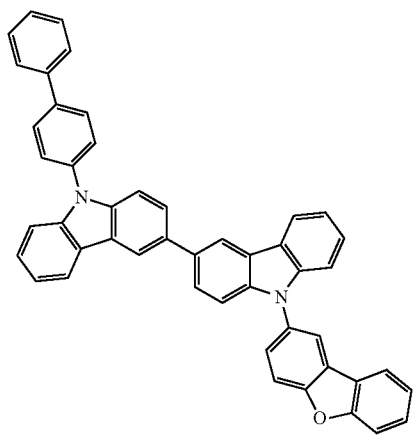
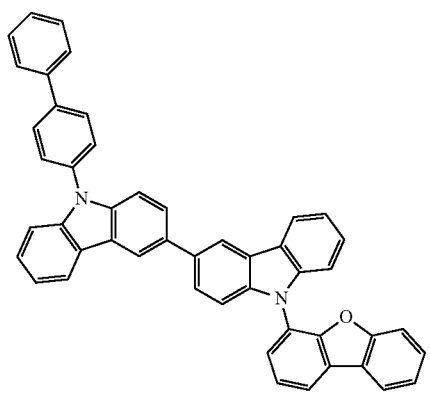
272
-continued
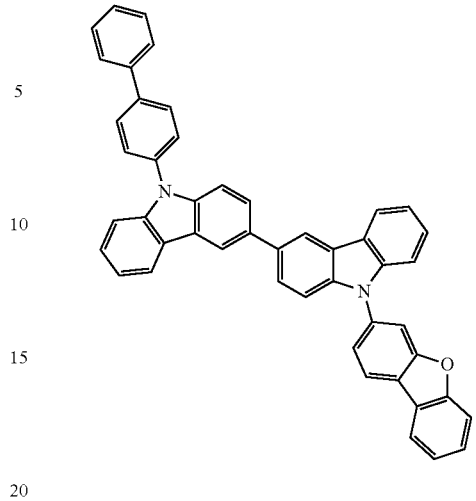
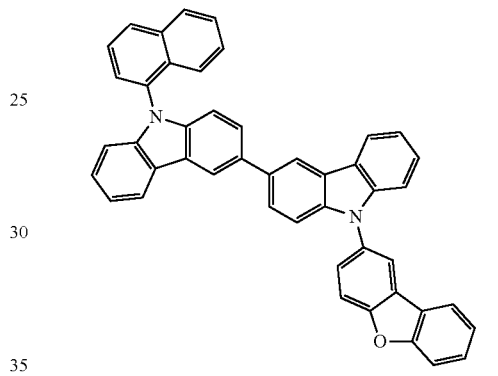
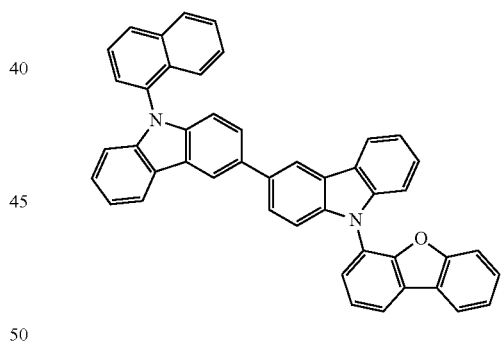

[Formula 133]
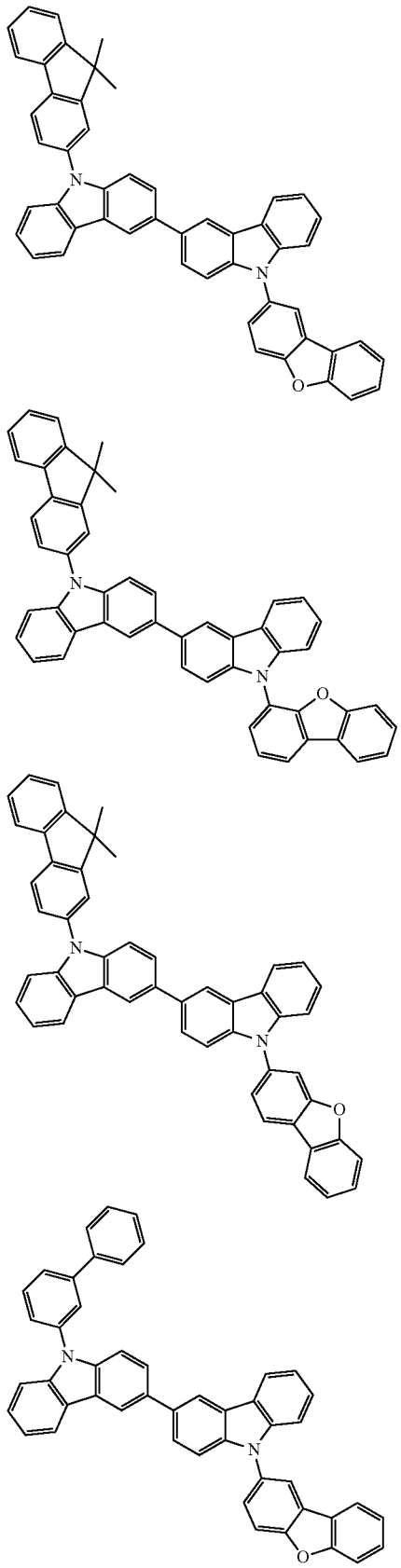
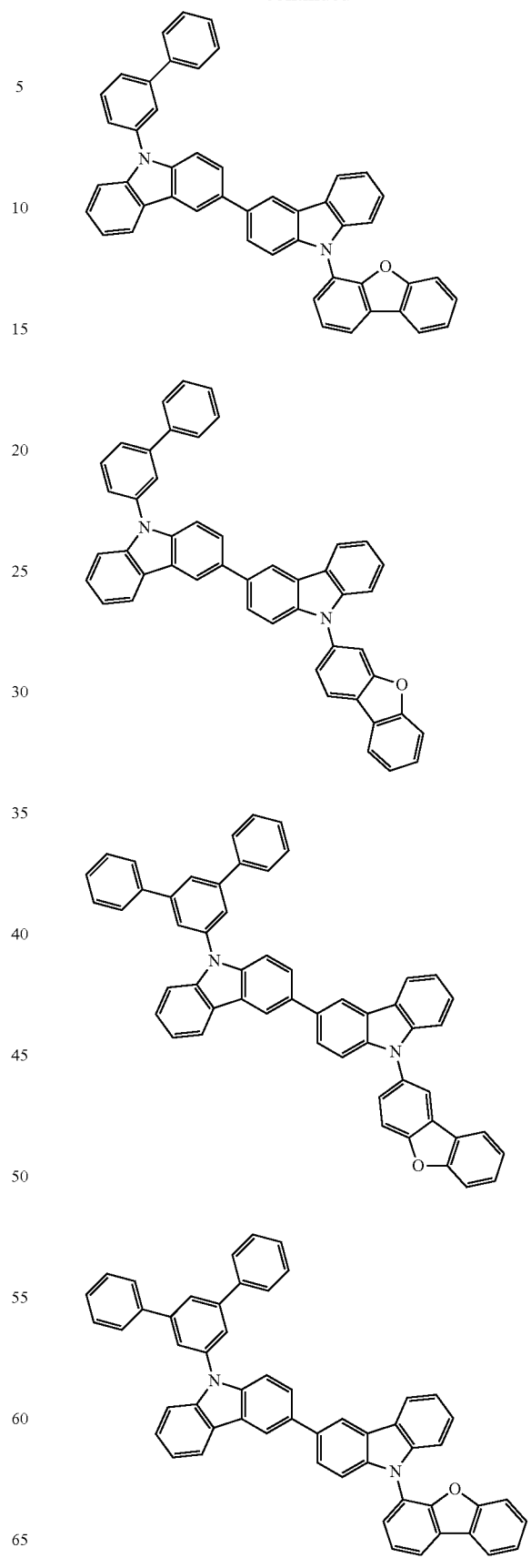

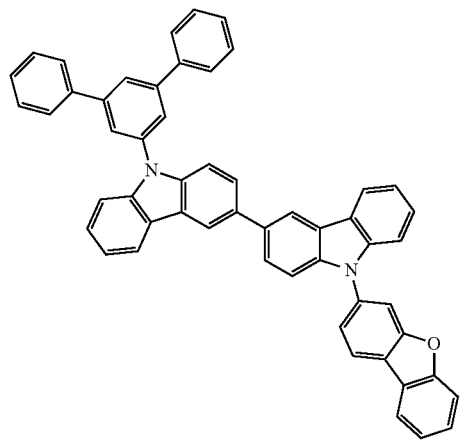
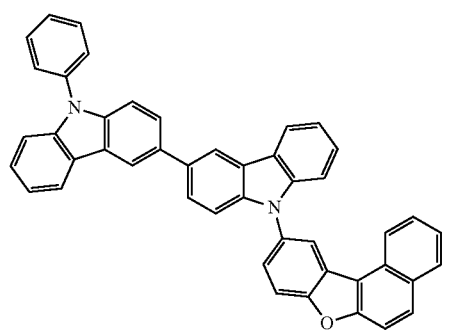
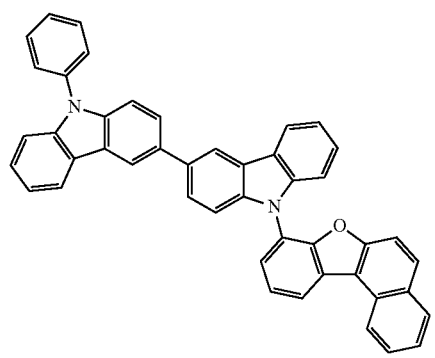
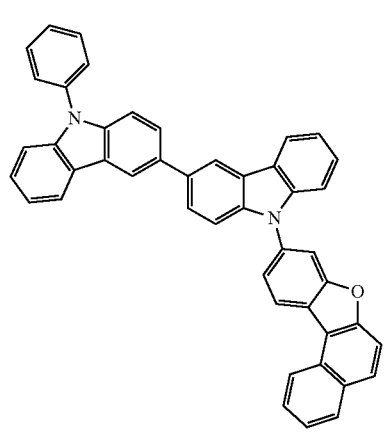
[Formula 134]
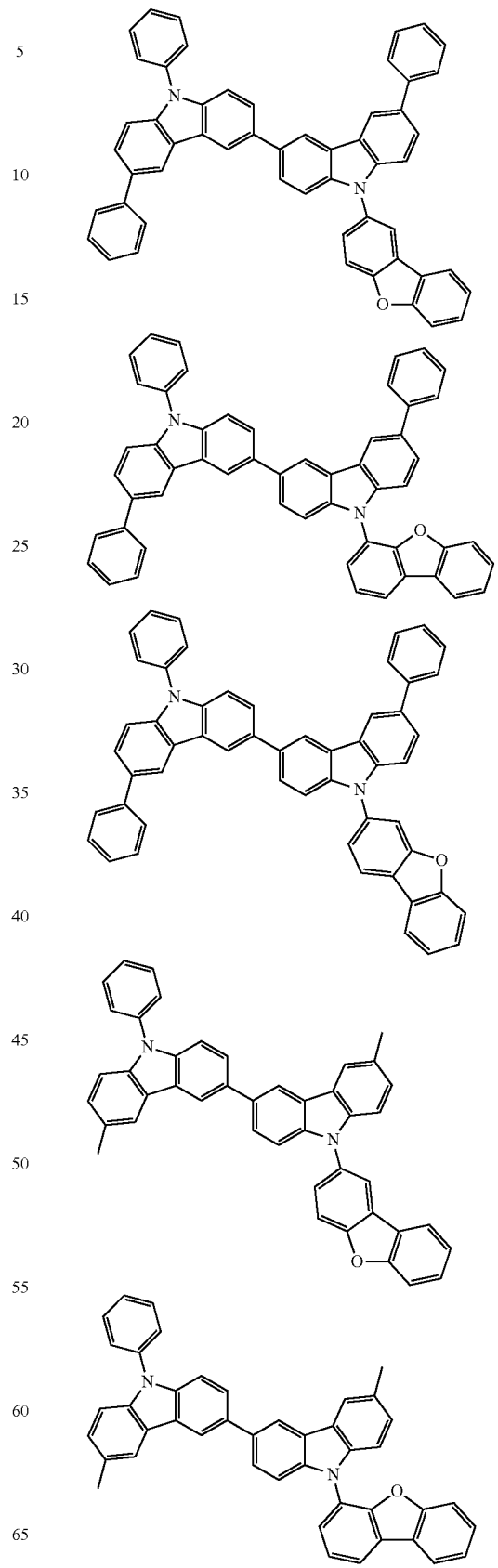

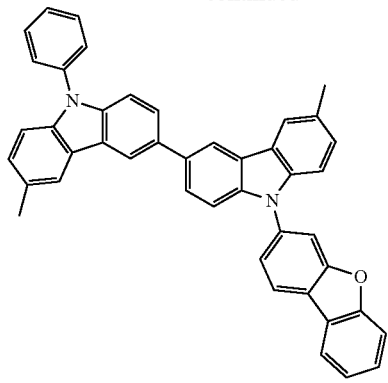
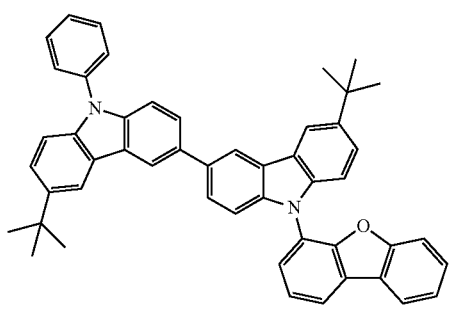
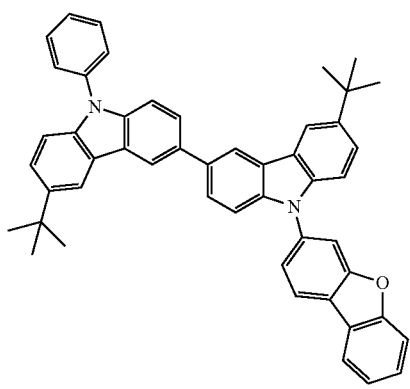
[Formula 135]
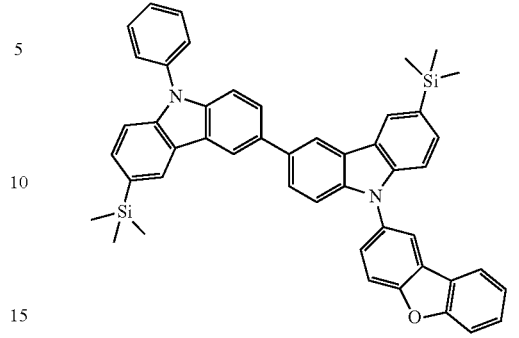
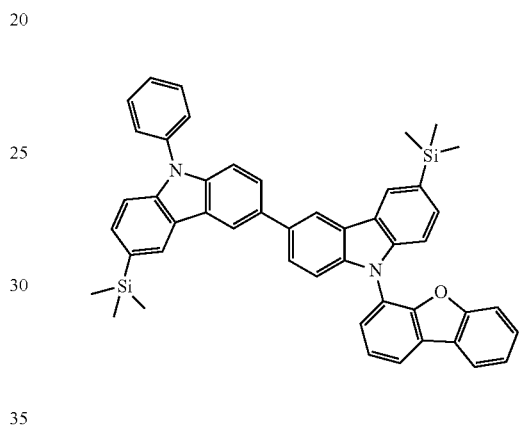
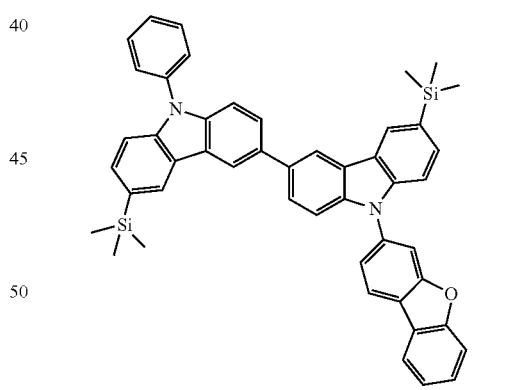
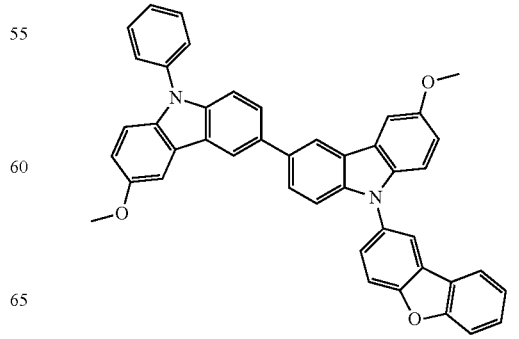

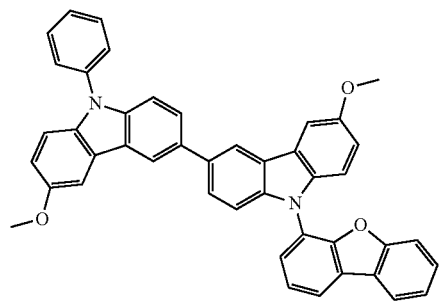
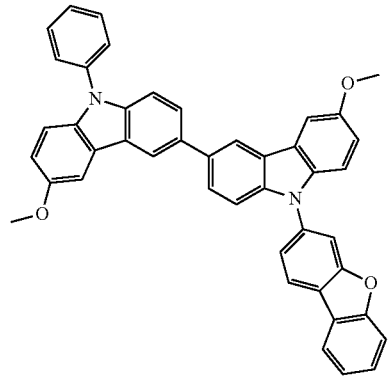
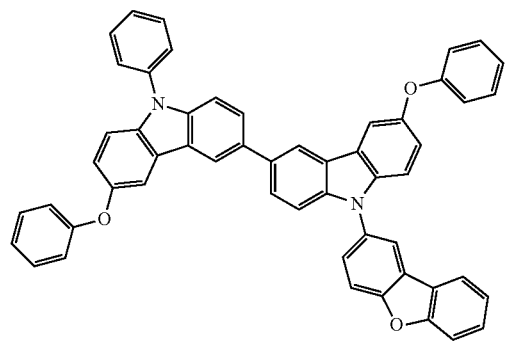
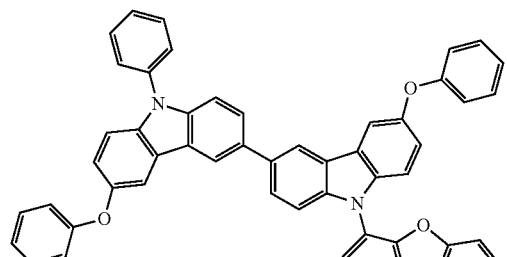
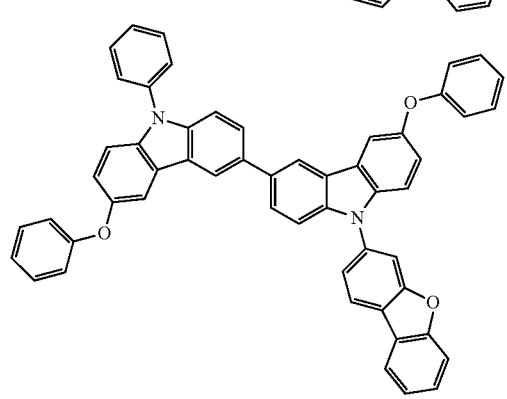
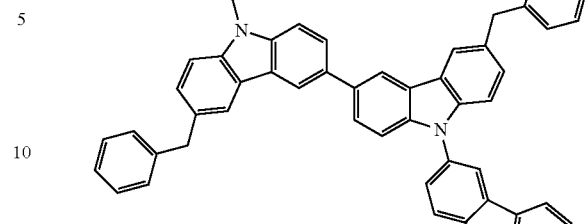
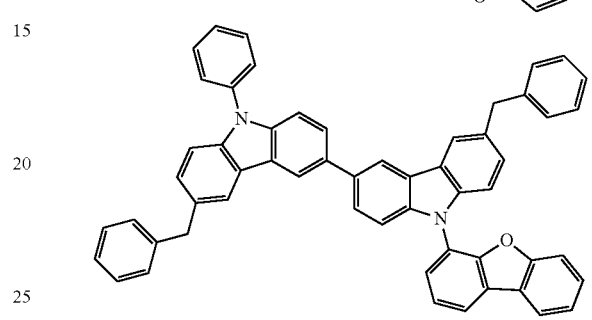
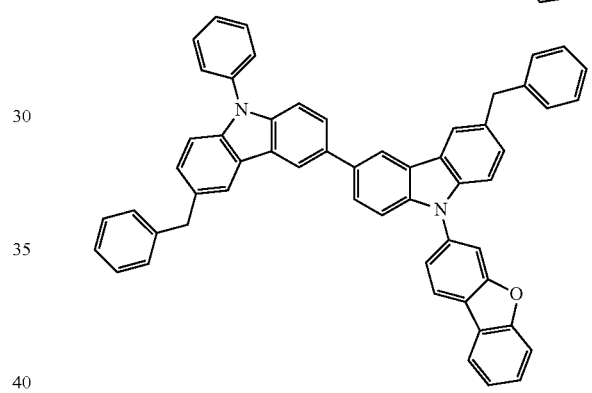
[Formula 136]
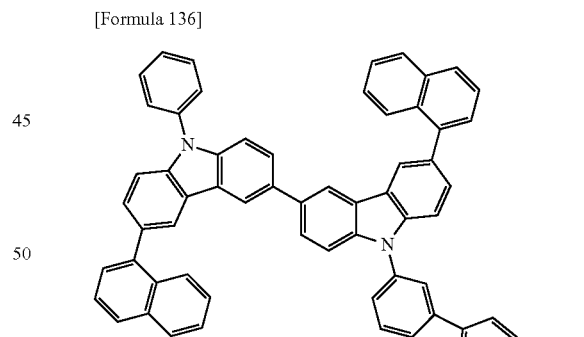
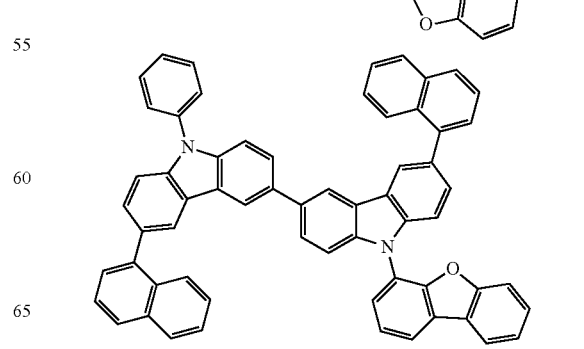

281
-continued
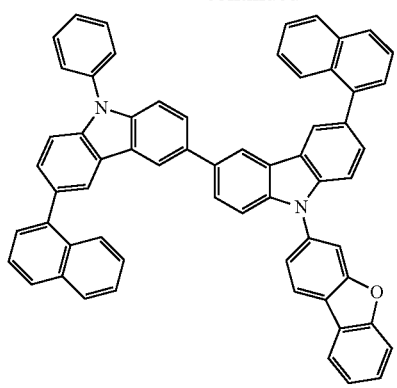
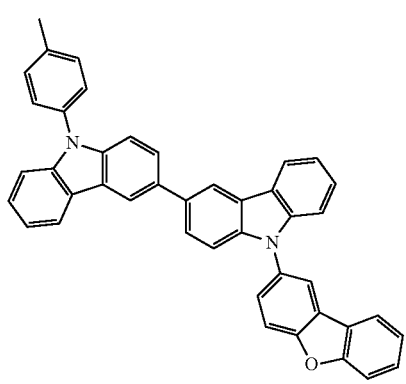
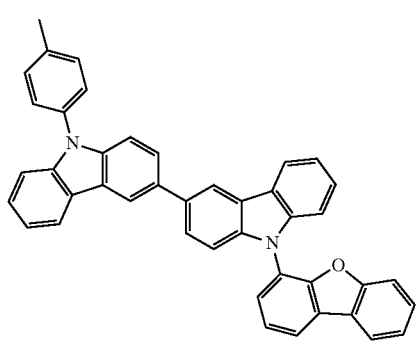
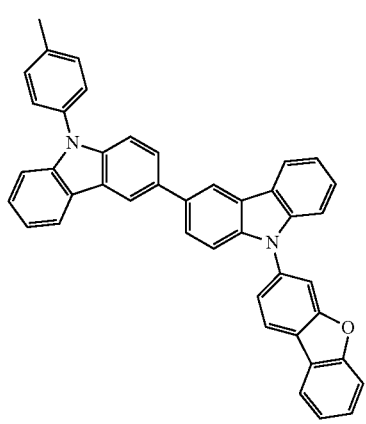
282
-continued
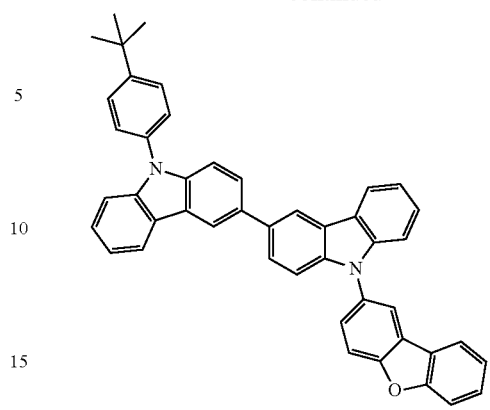
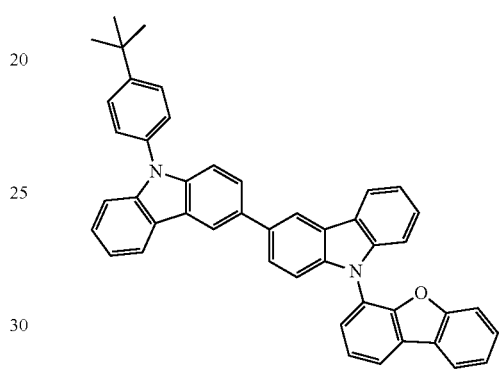
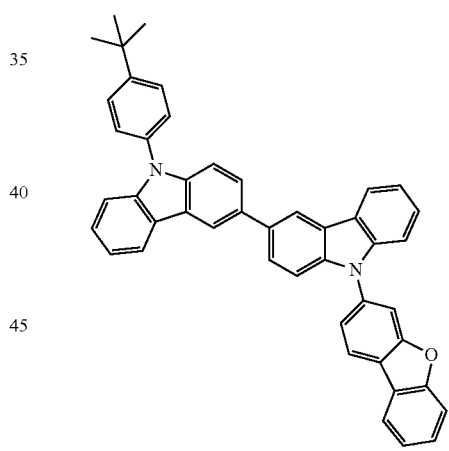
[Formula 137]
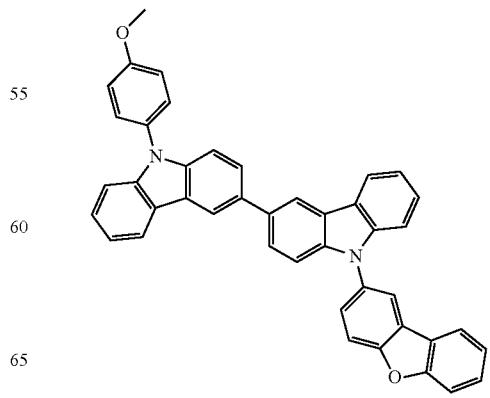

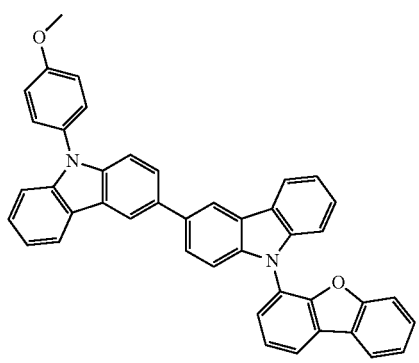
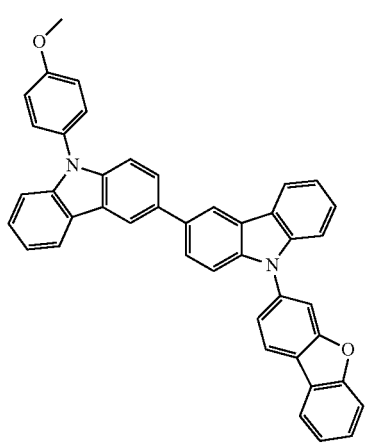
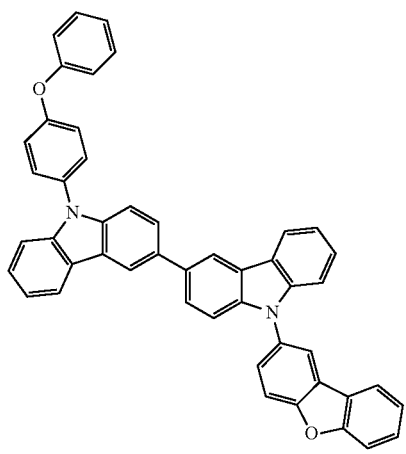
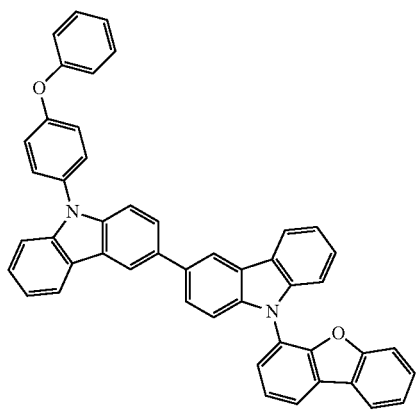
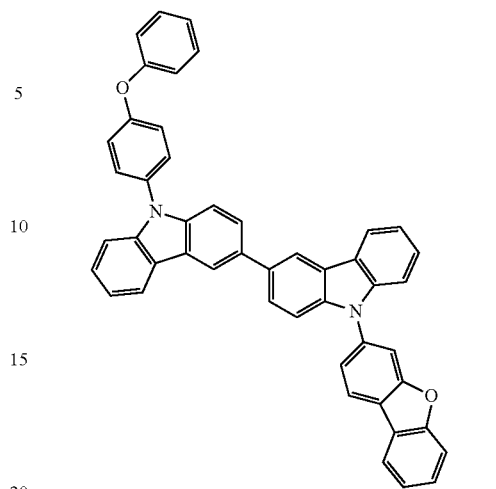
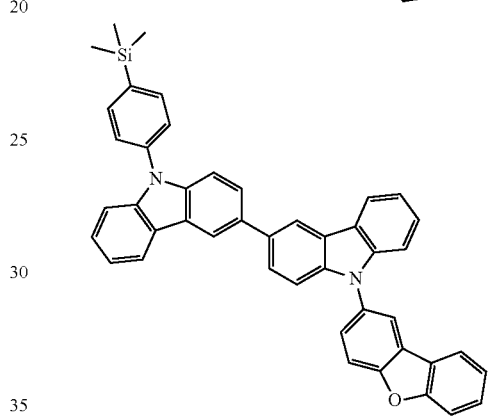
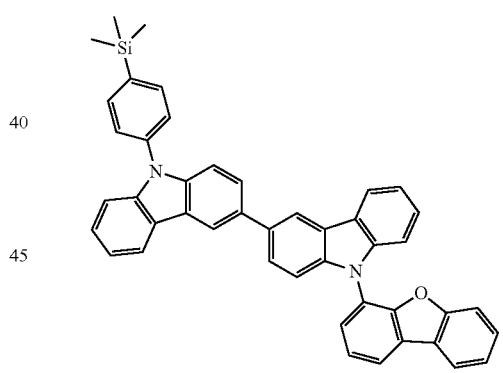
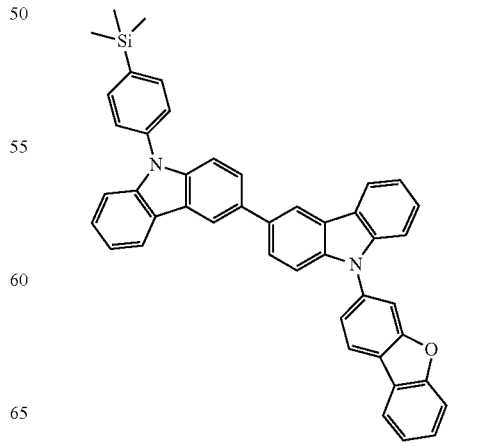

[Formula 138]
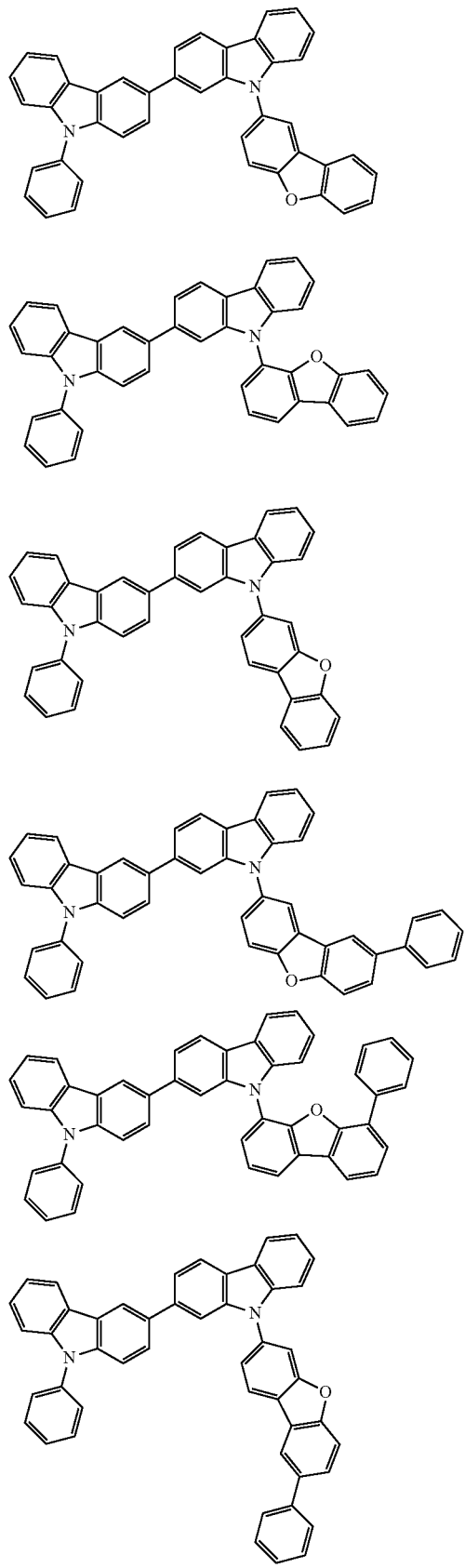
[Formula 139]
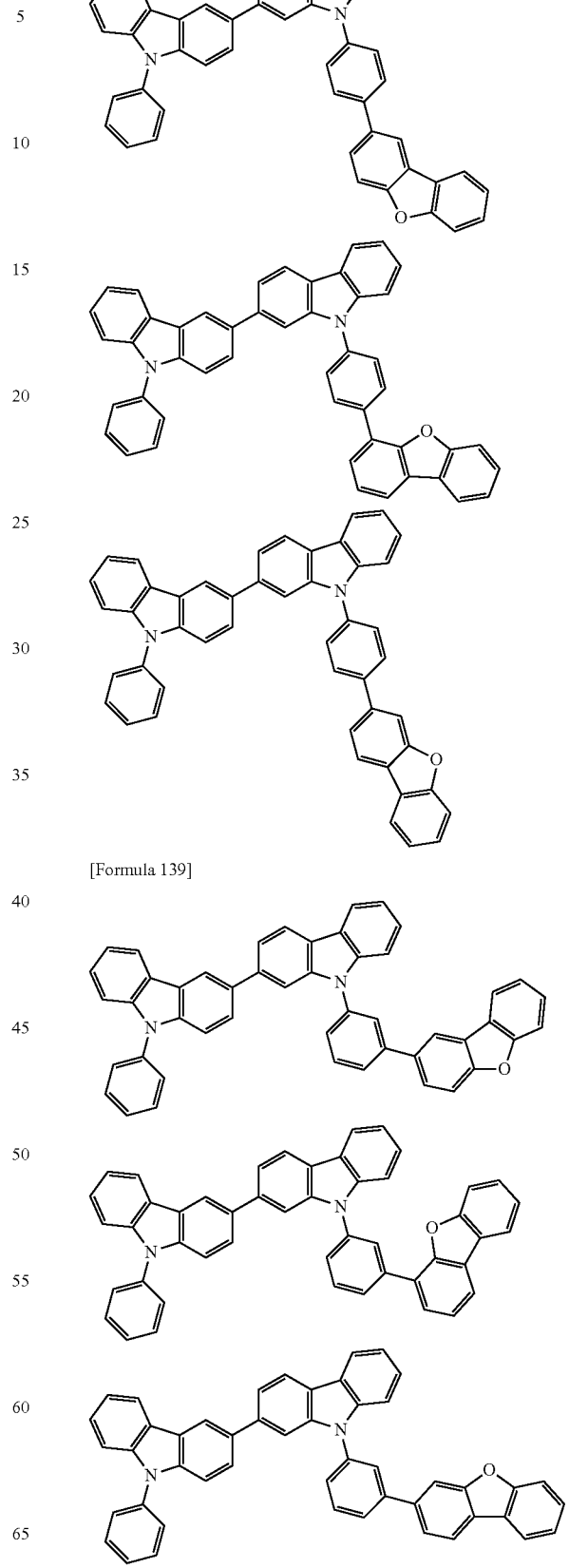

287
-continued
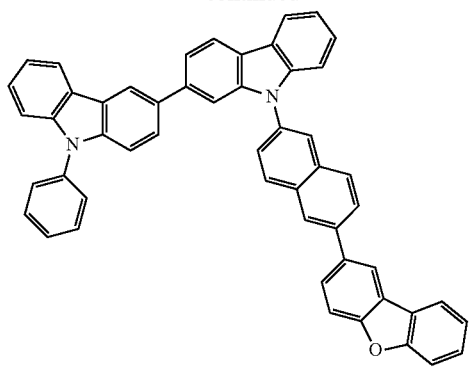
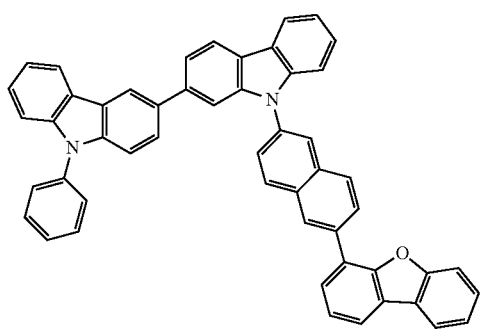
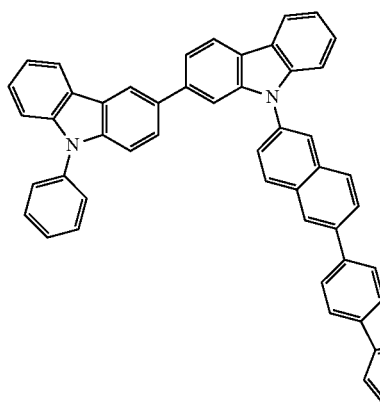
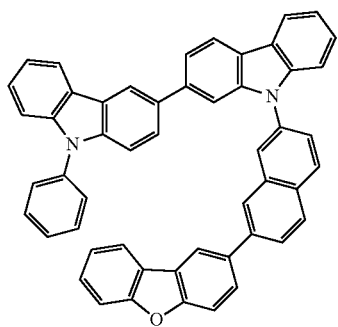
288
-continued
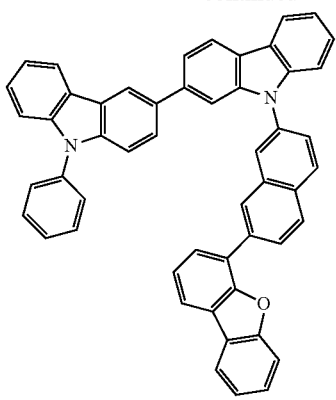
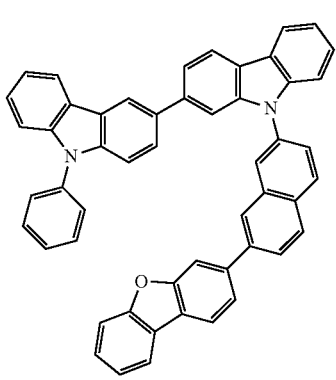
[Formula 140]
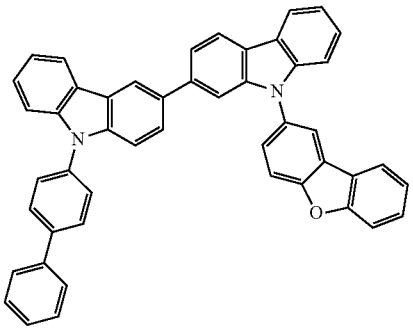
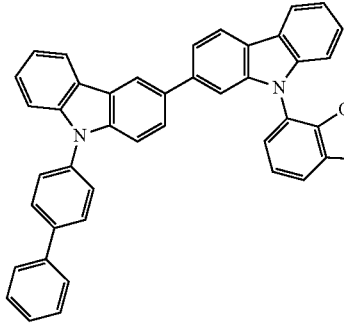

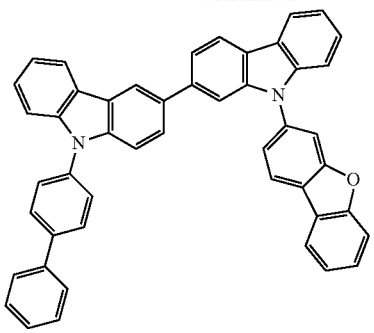
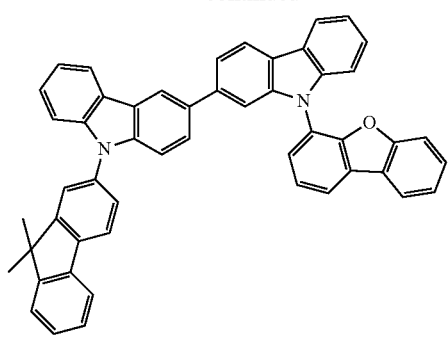
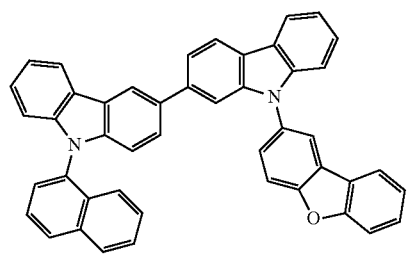
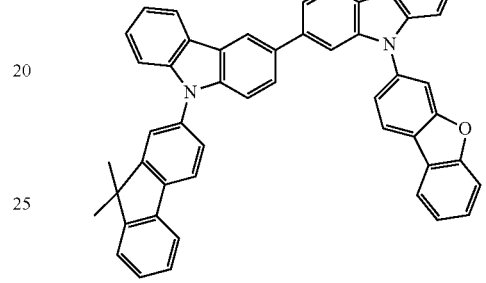
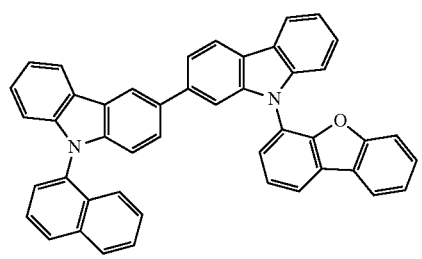
[Formula 141]
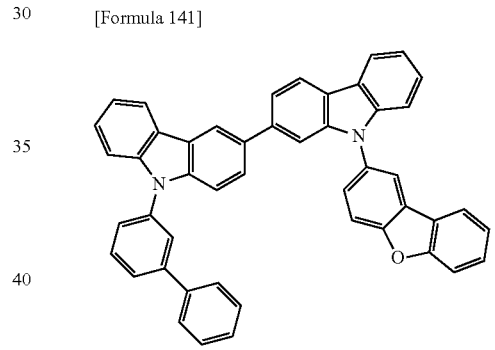
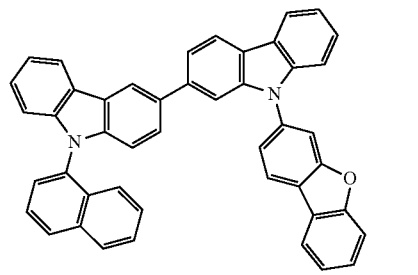
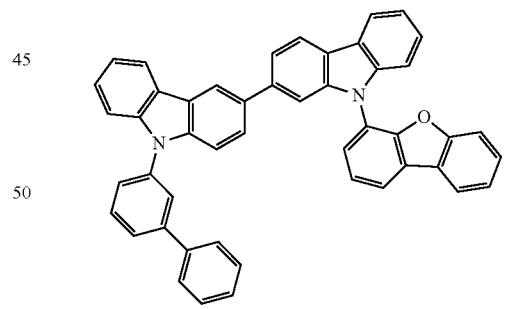
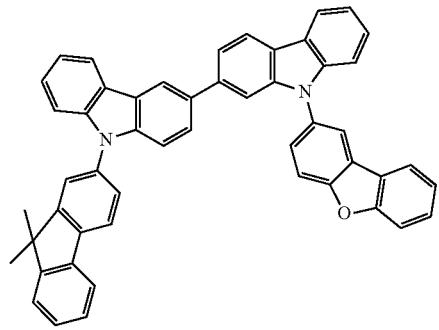
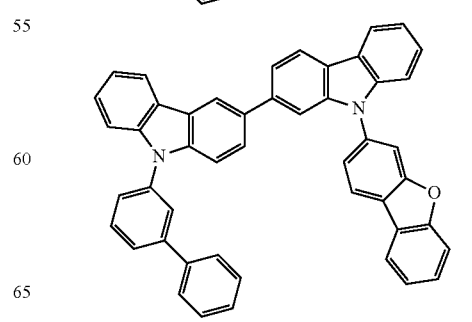

-continued
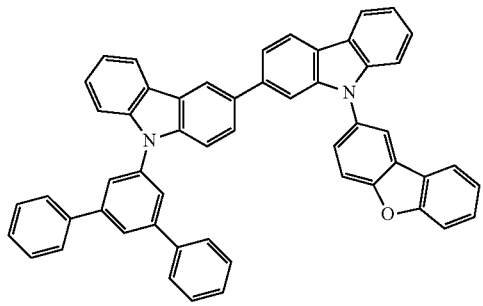
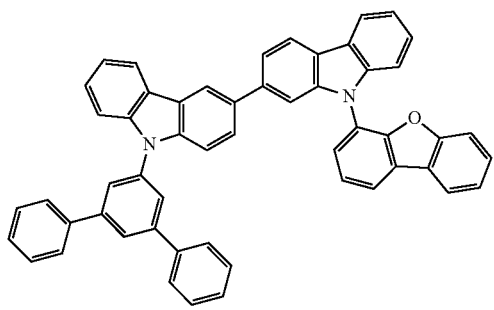
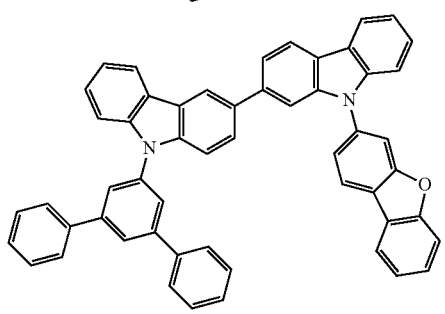
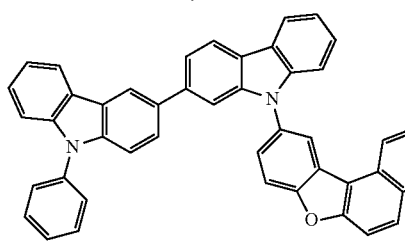
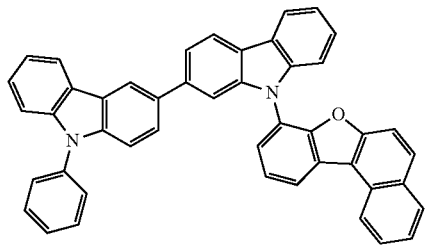
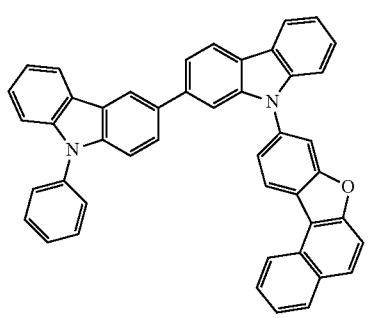
-continued
[Formula 142]
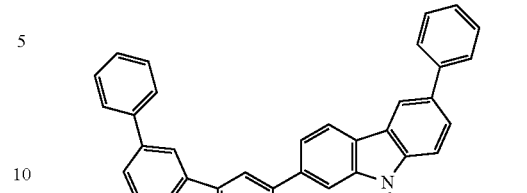
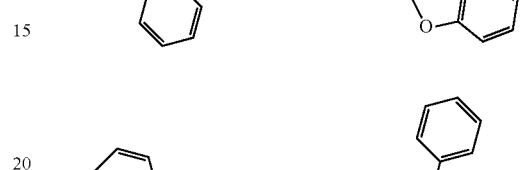
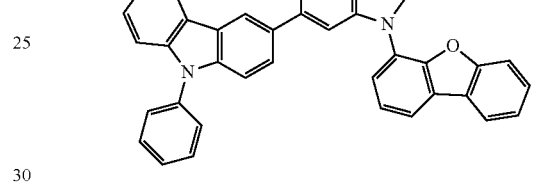
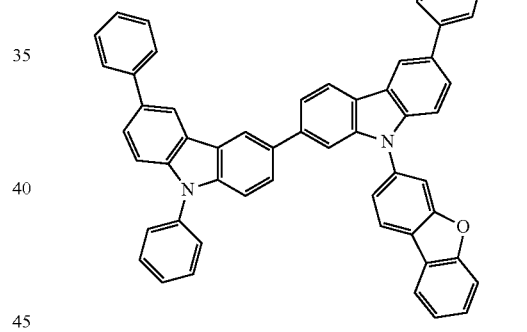
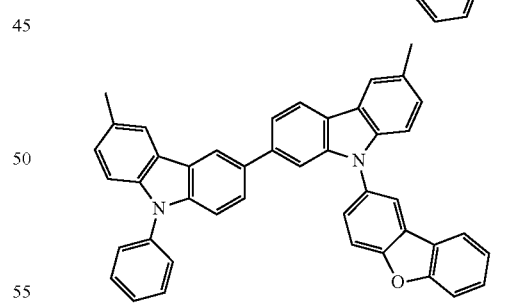
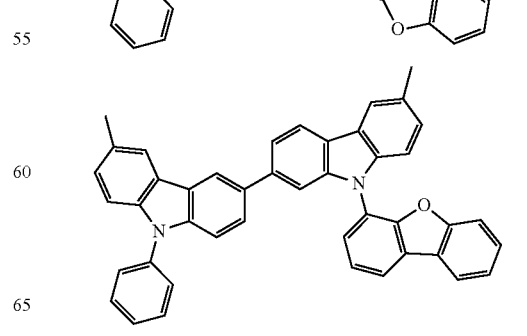

-continued
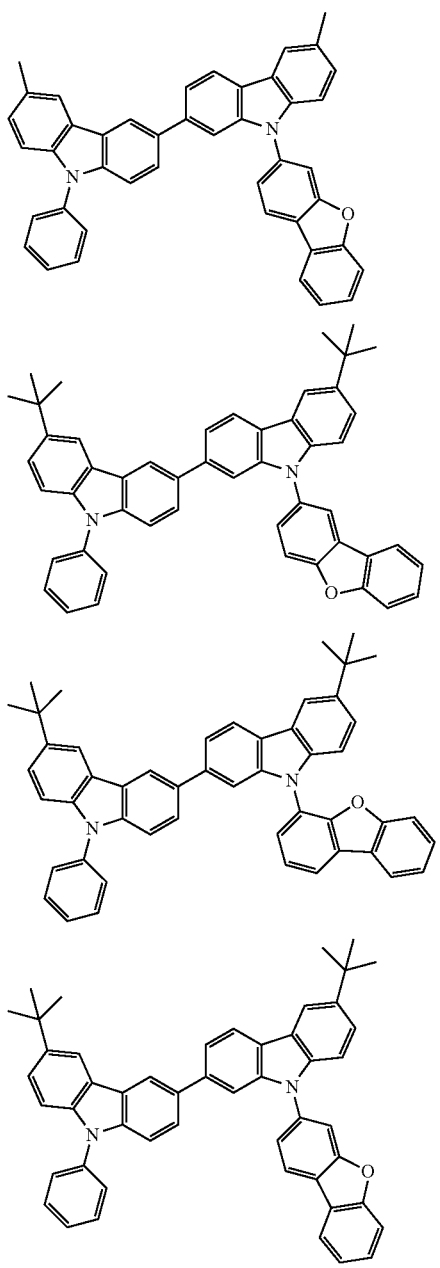
[Formula 143]
-continued
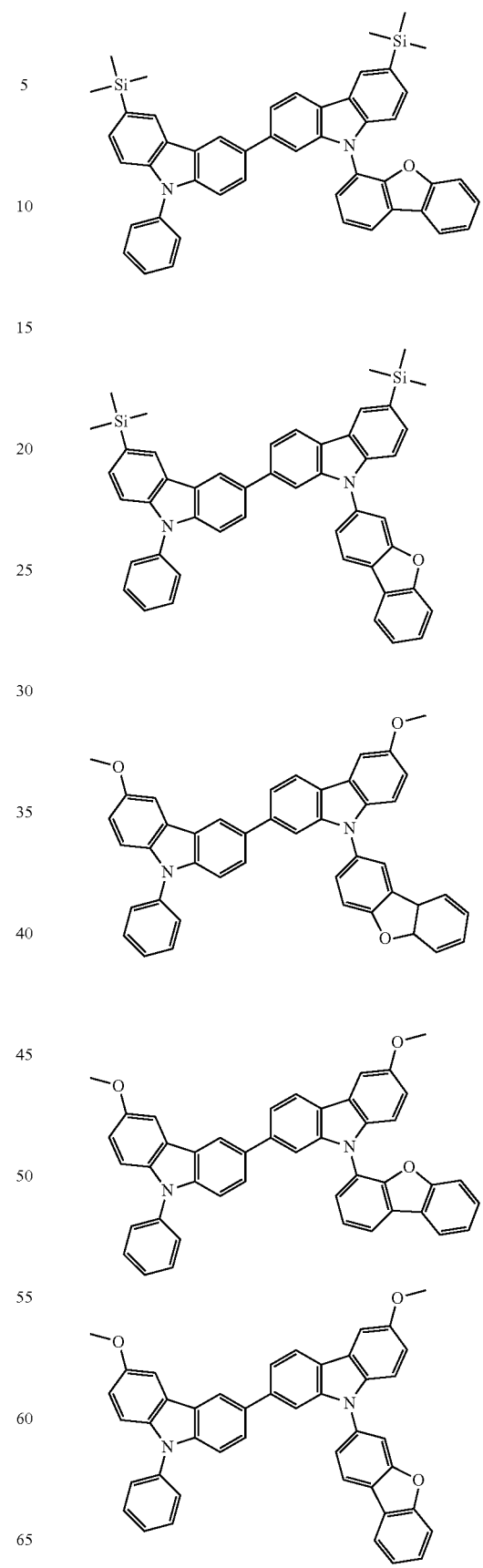

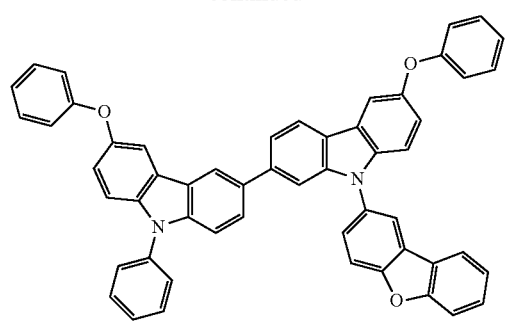
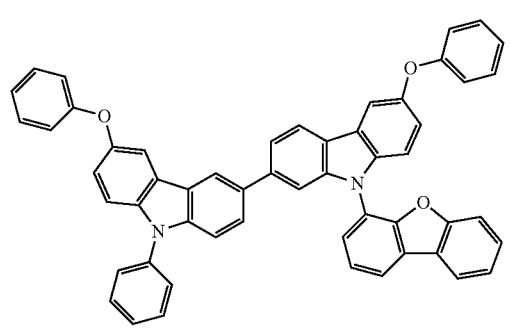
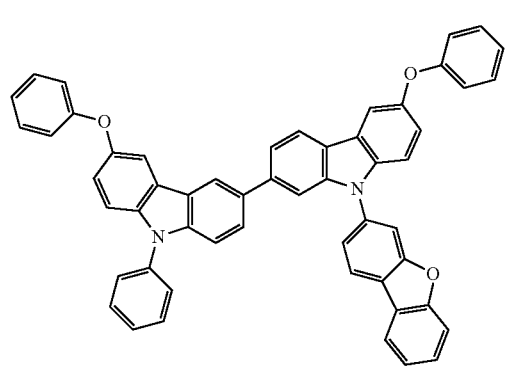
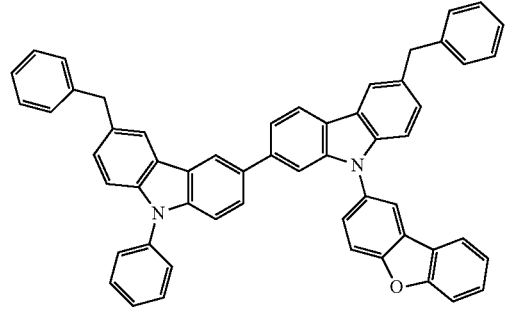
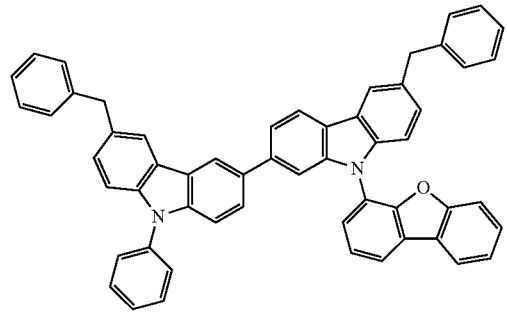
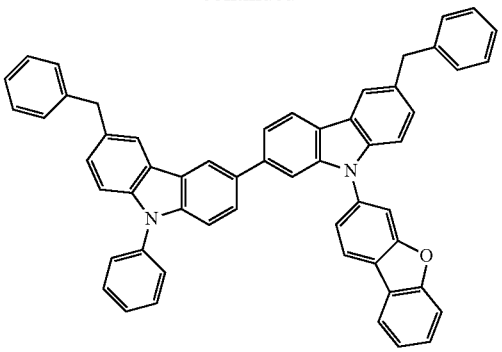
[Formula 144]
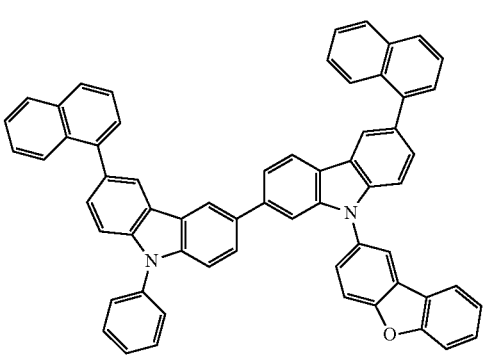
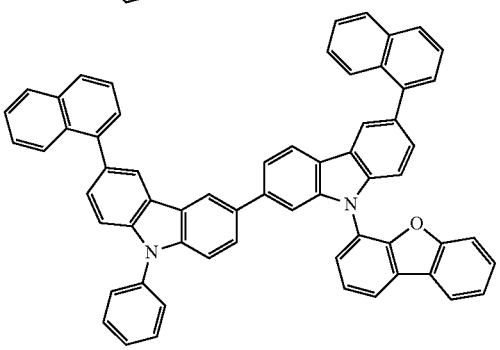
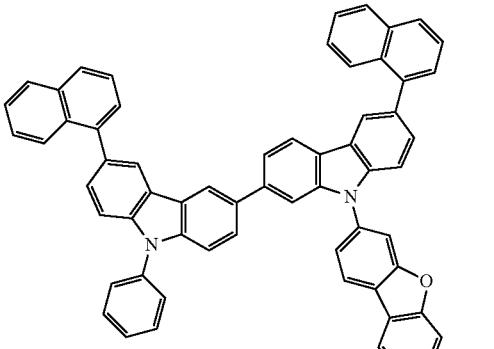
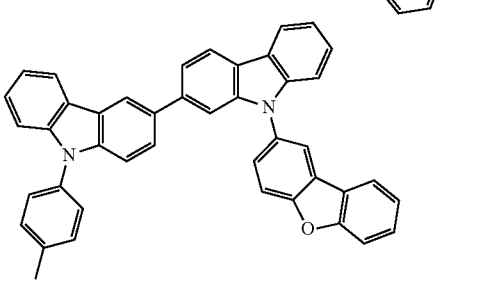

[Formula 145]
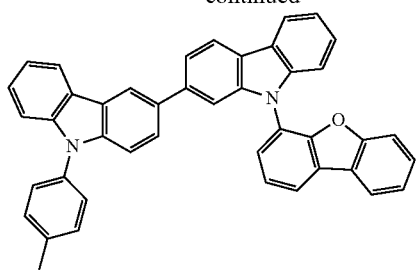
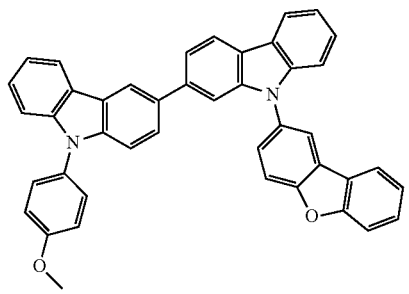
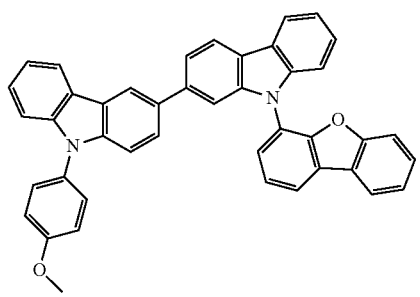
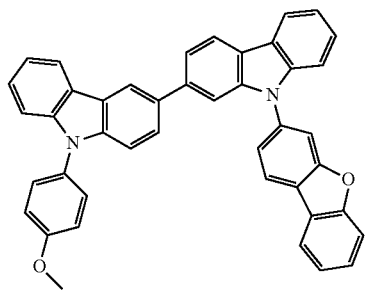
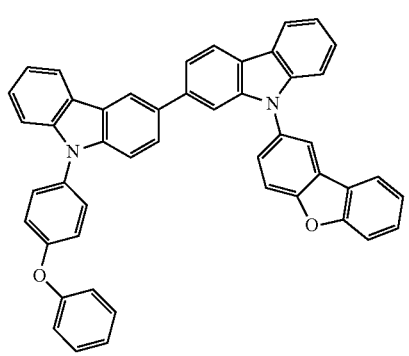
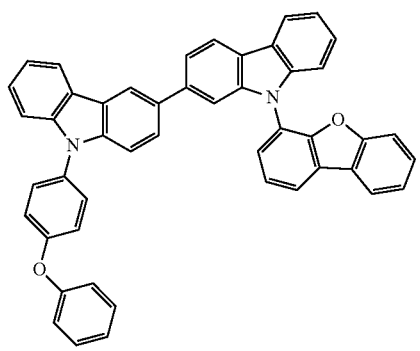

299
-continued
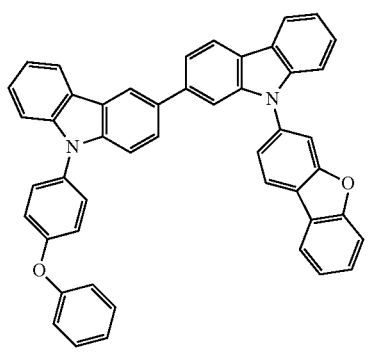
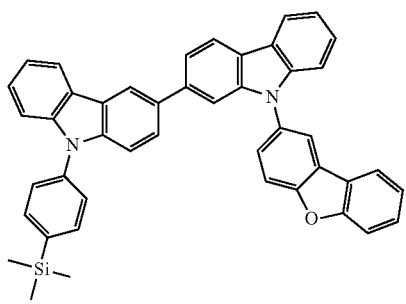
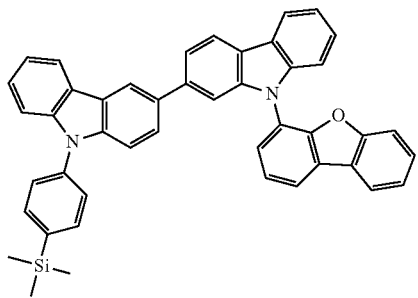
[Formula 146]
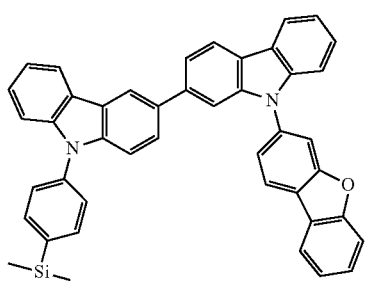
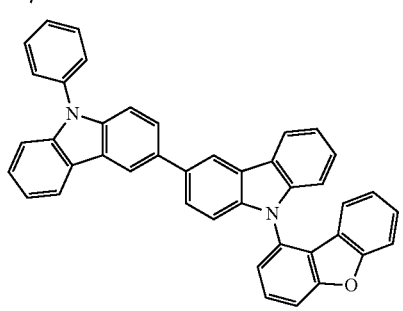
300
-continued
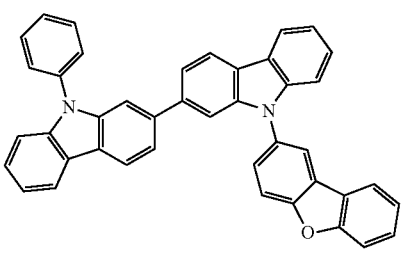
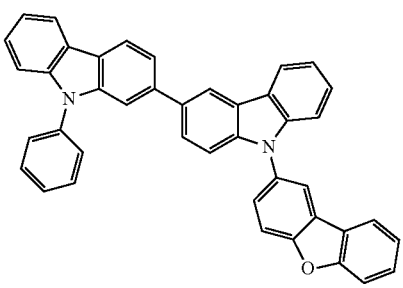
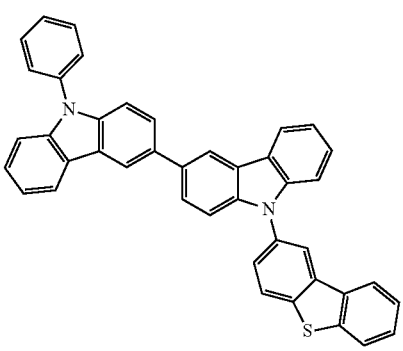
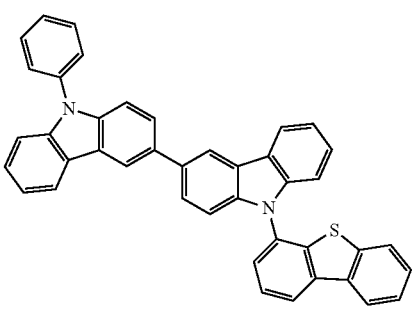
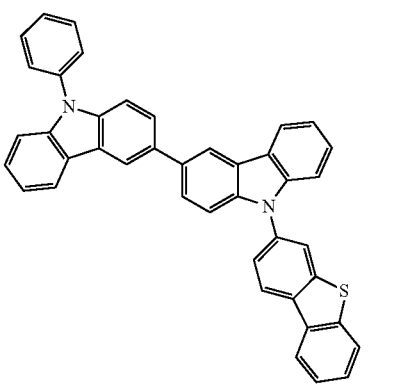

301
-continued
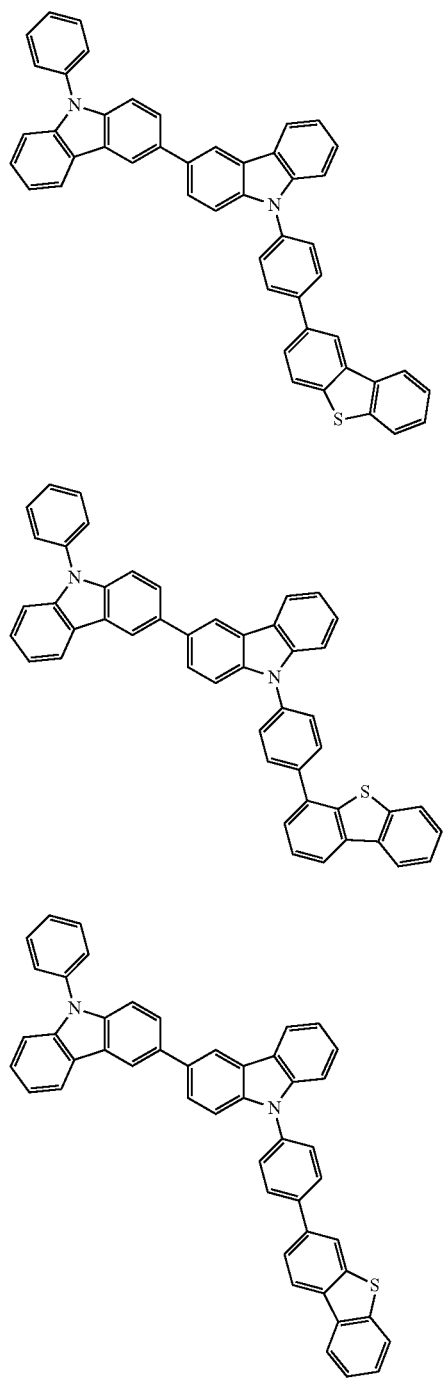
[Formula 147]
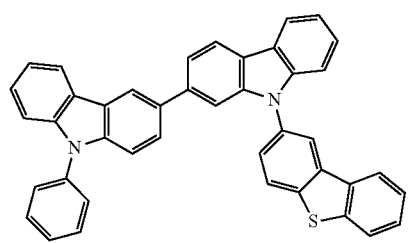
302
-continued
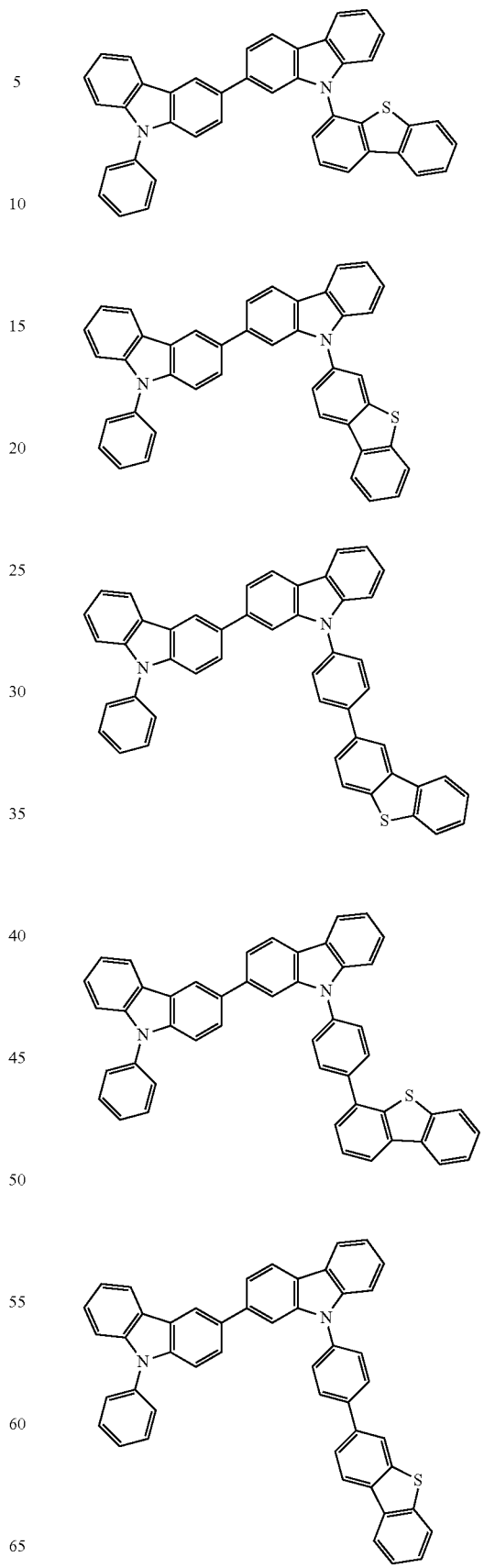

[Formula 148]
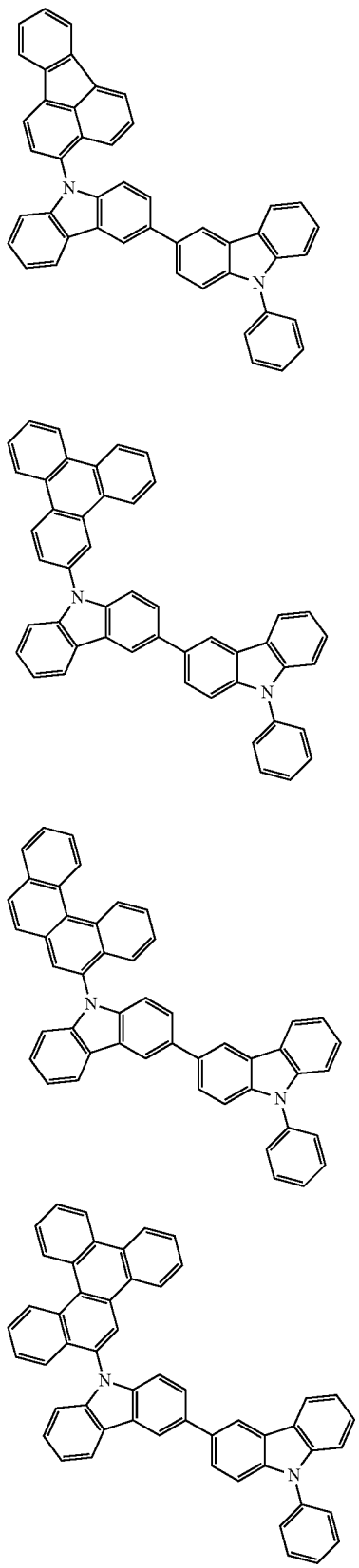
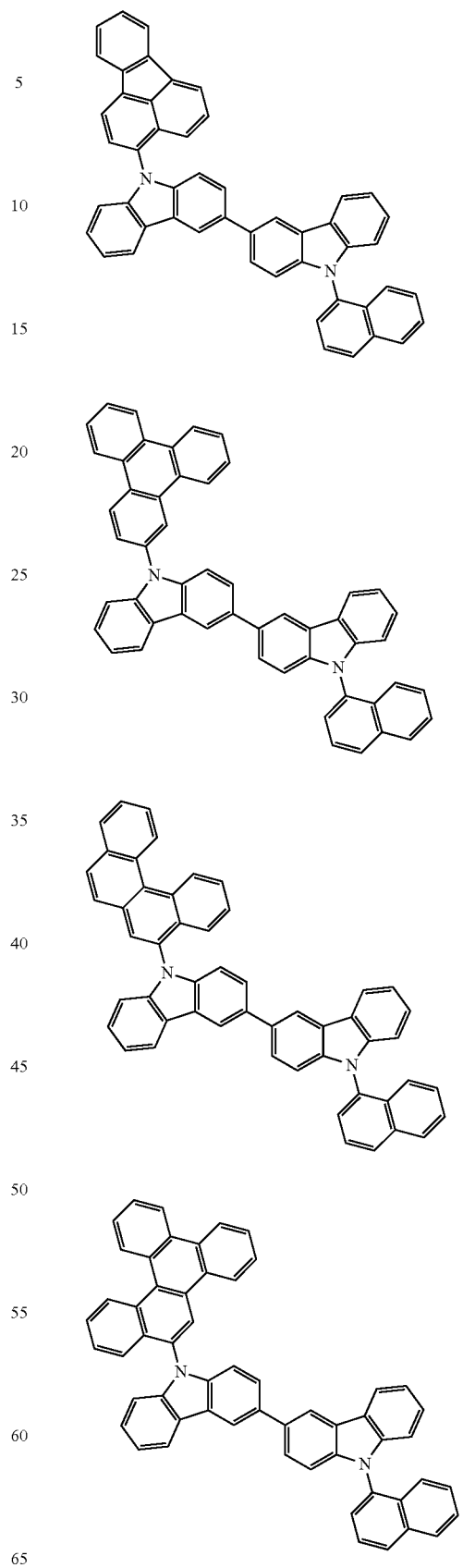

305
-continued
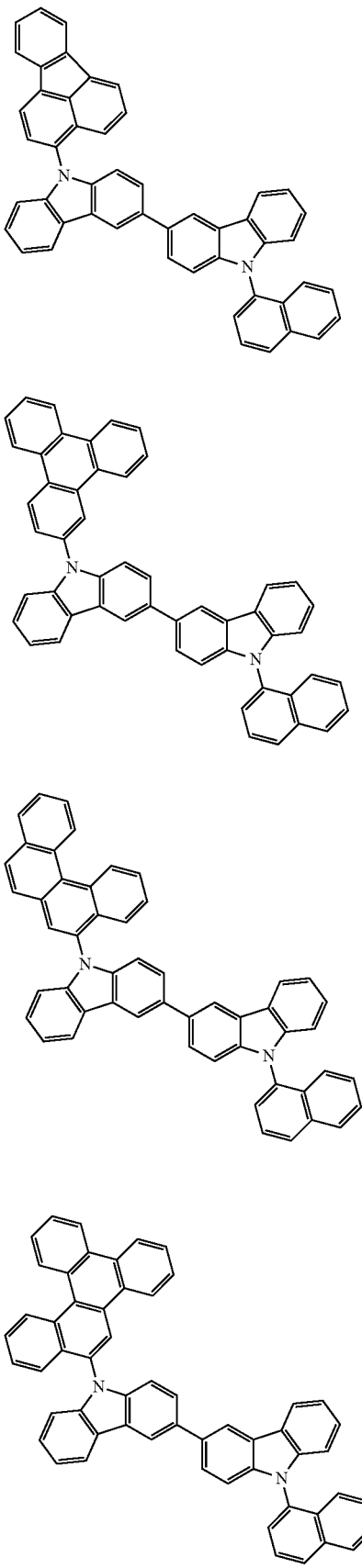
306
-continued
[Formula 149]
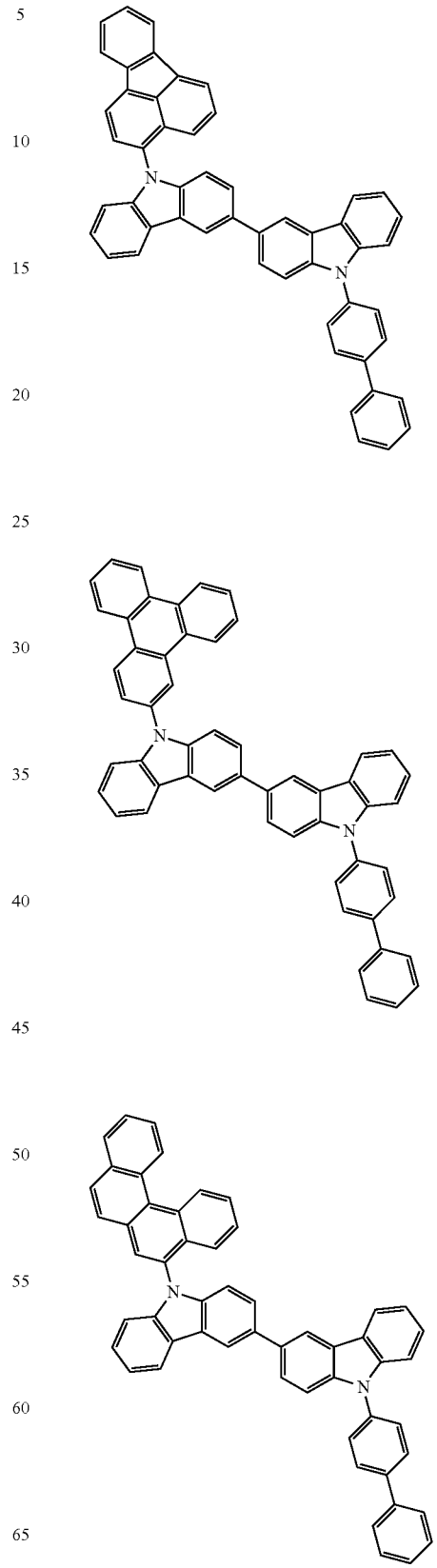

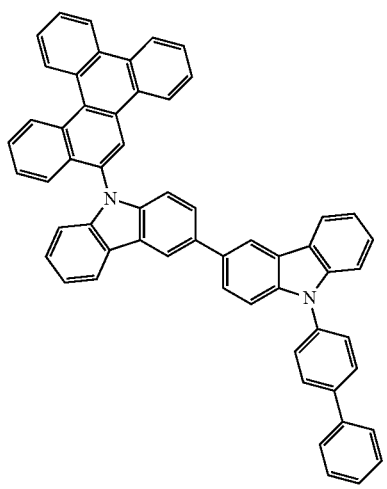
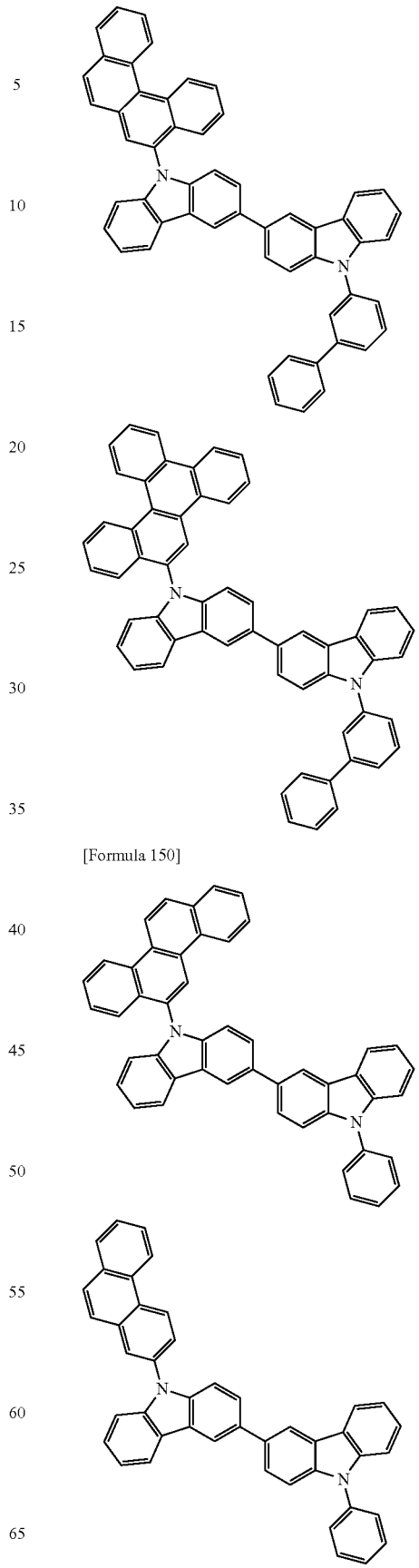
[Formula 150]

309
-continued
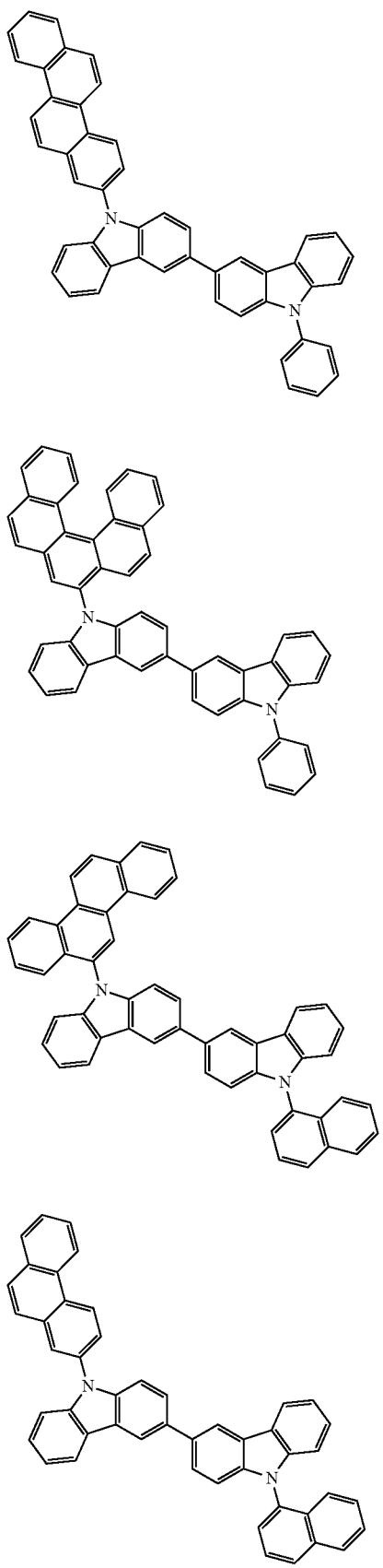
310
-continued
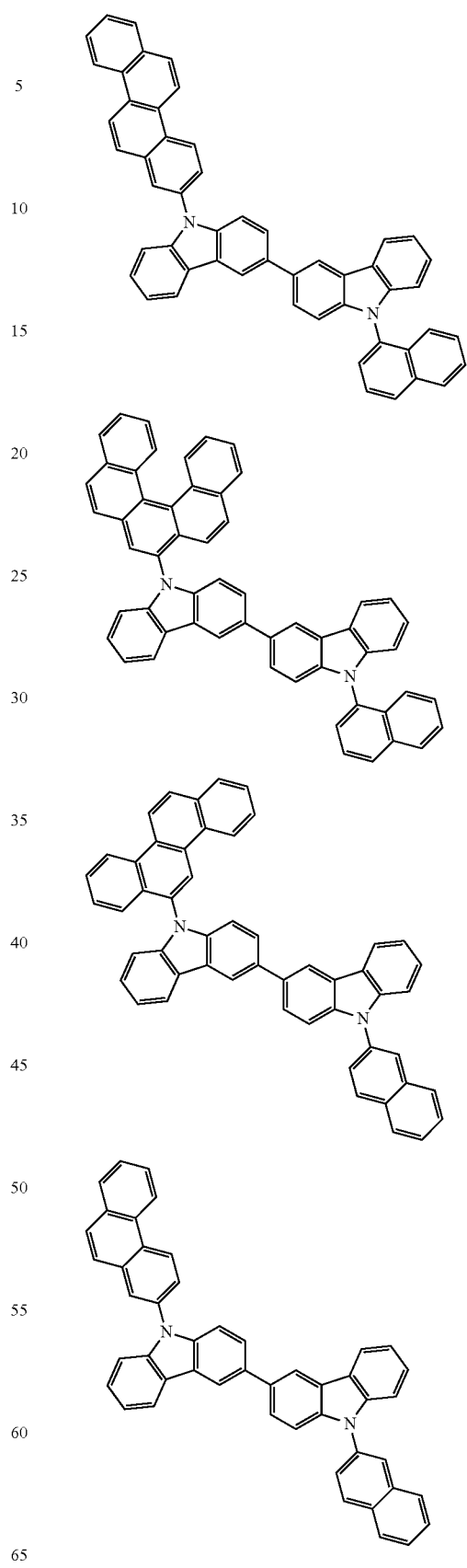

311
-continued
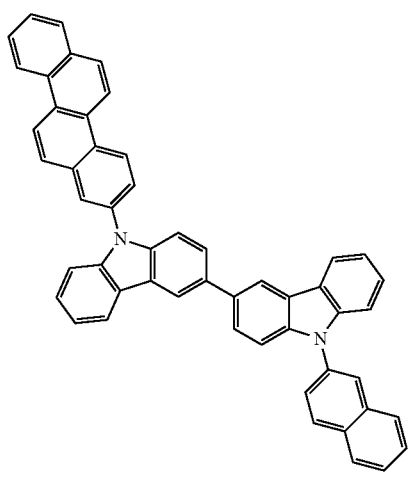
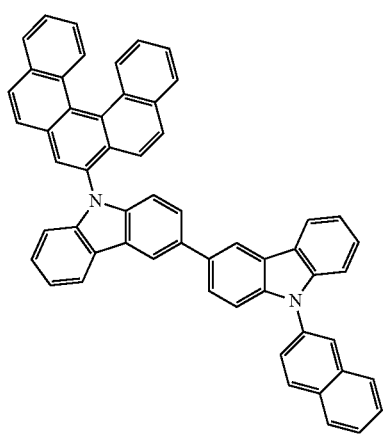
[Formula 151]
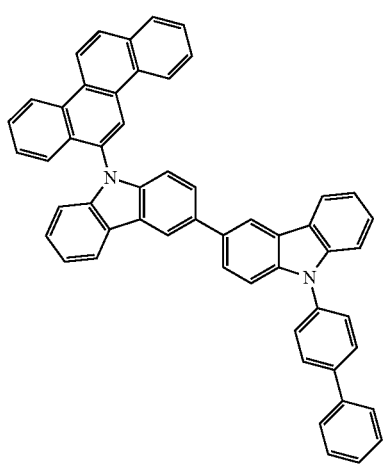
312
-continued
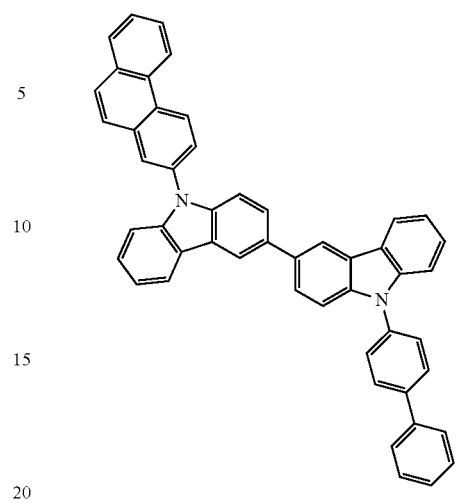
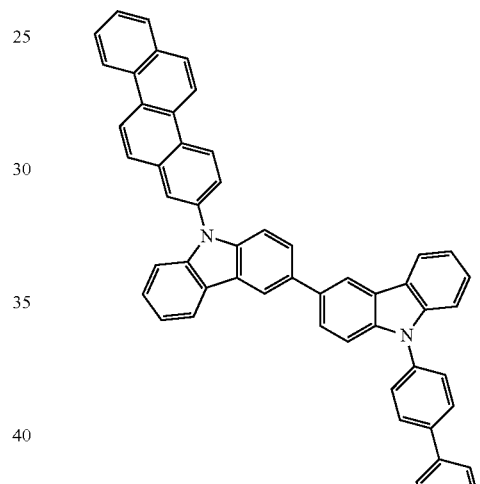
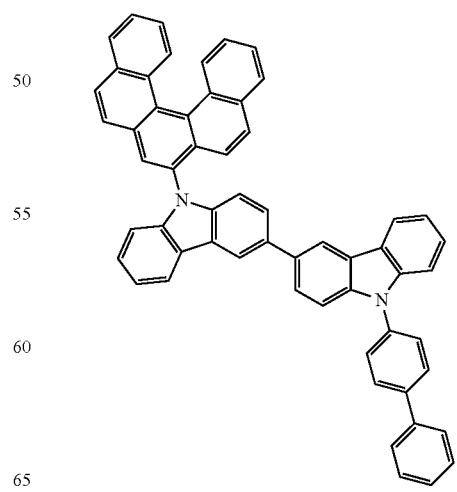

313
-continued
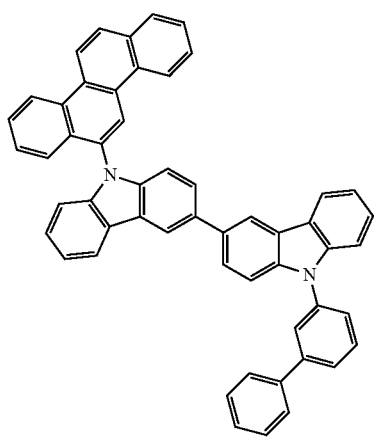
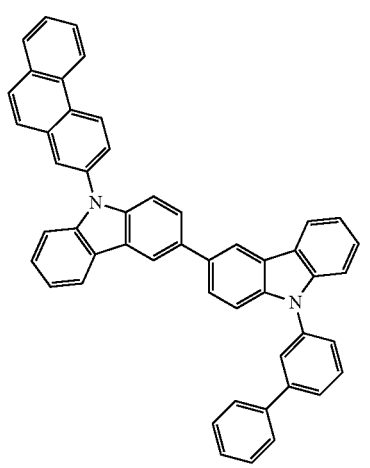
314
-continued
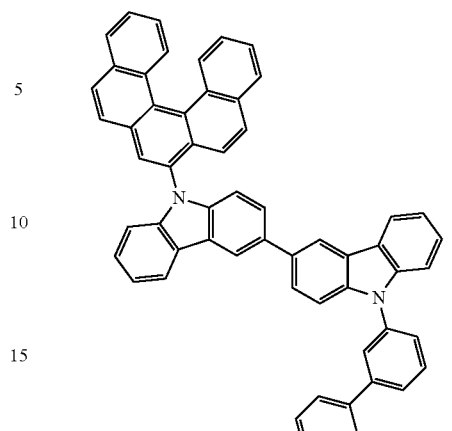
[Formula 152]
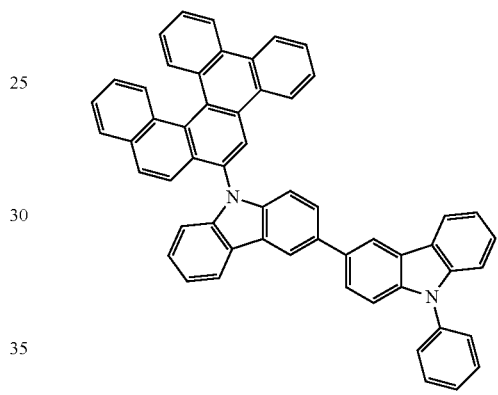
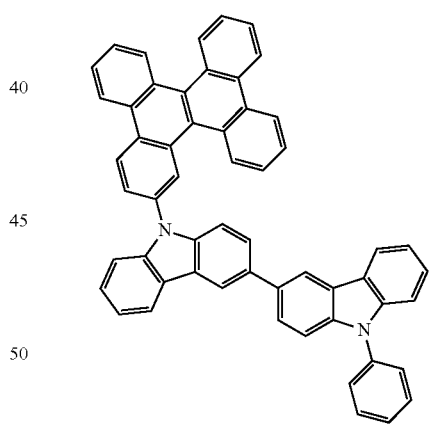
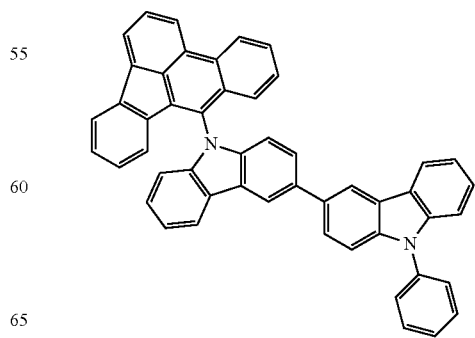

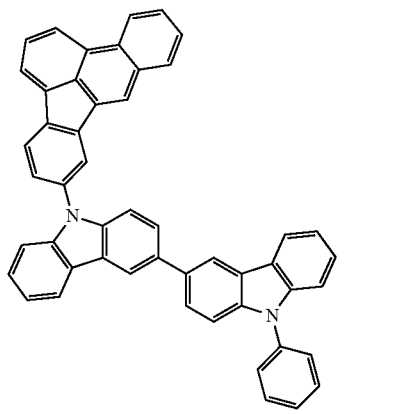
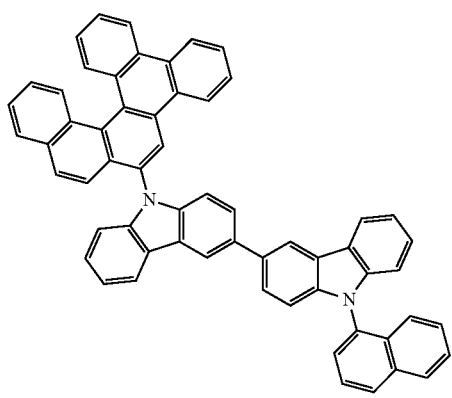
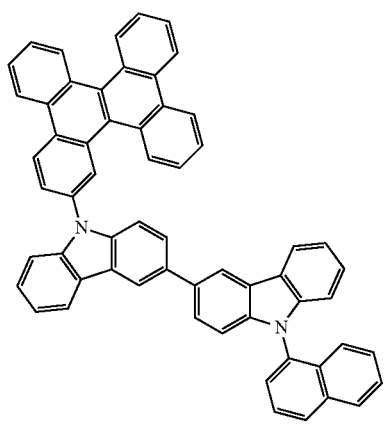
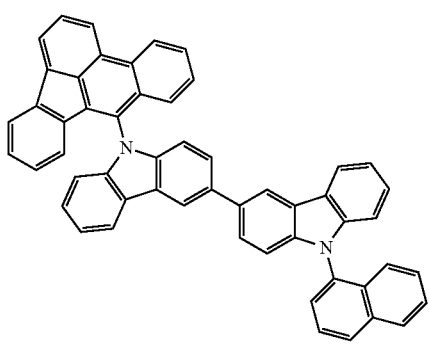
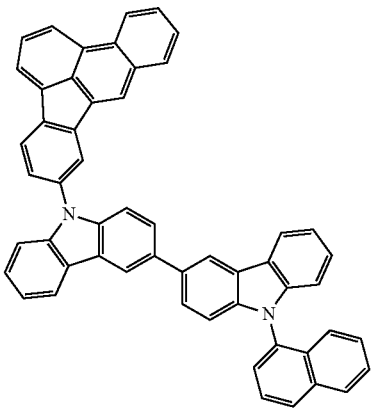
[Formula 153]
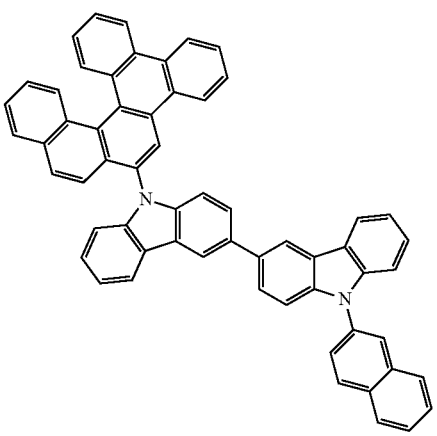
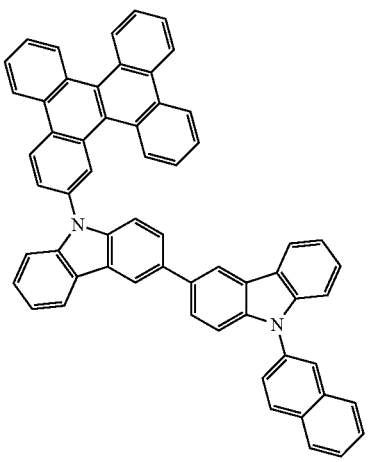
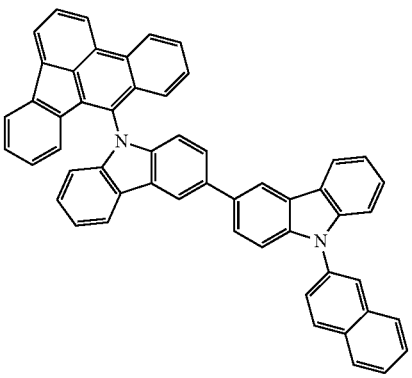

317
-continued
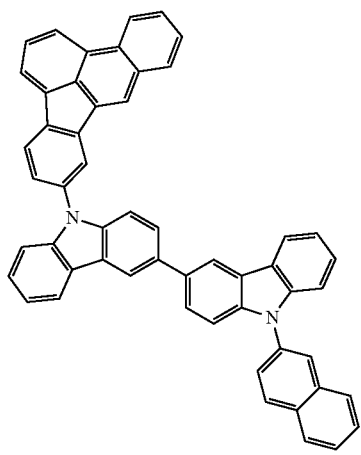
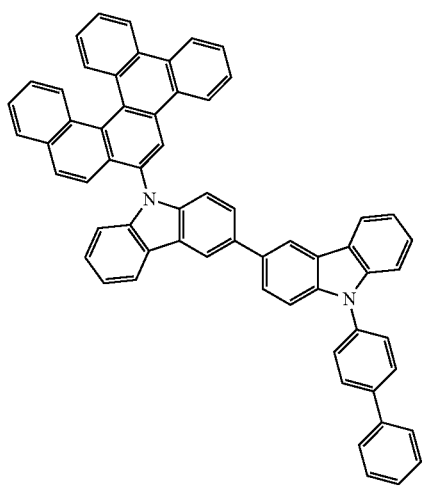
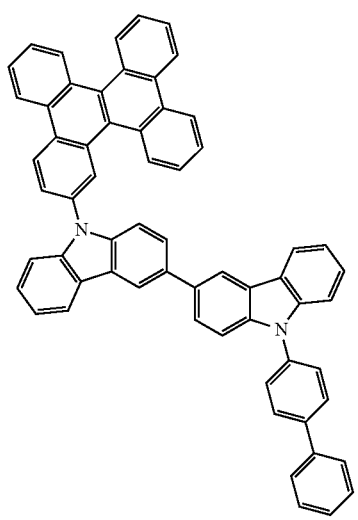
318
-continued
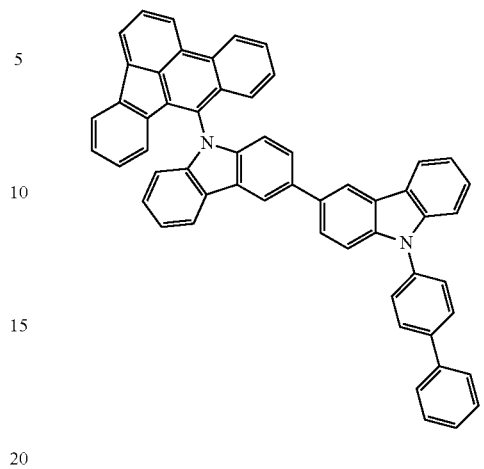
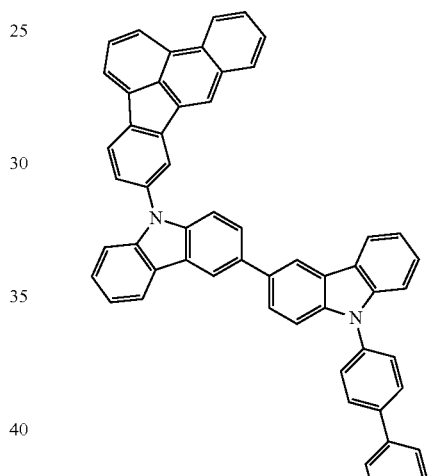
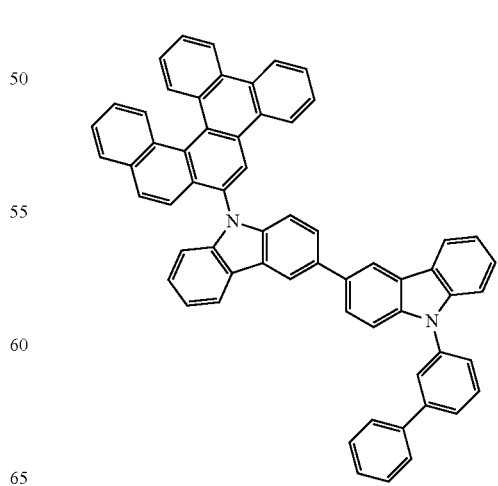

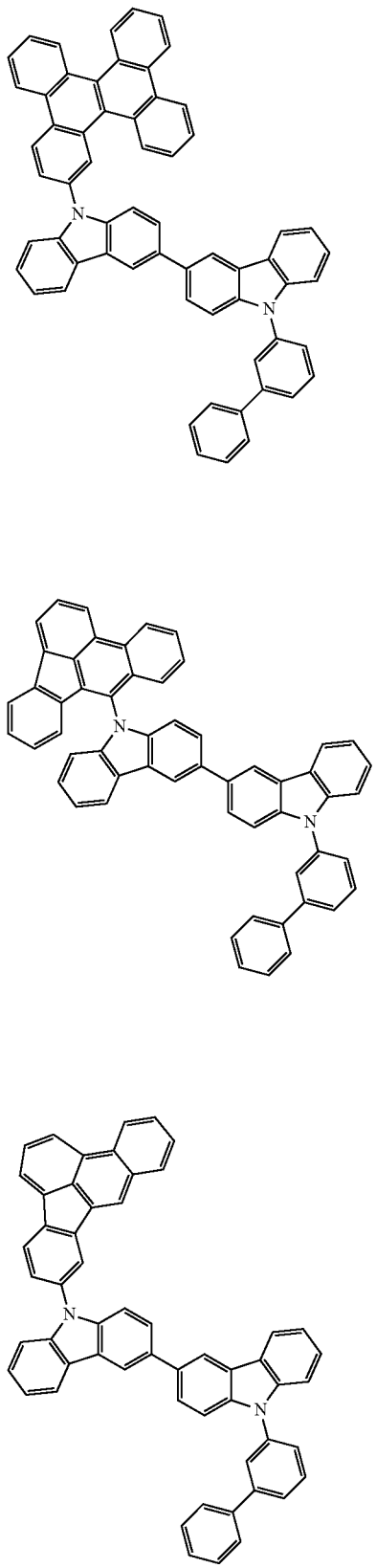
[Formula 154]
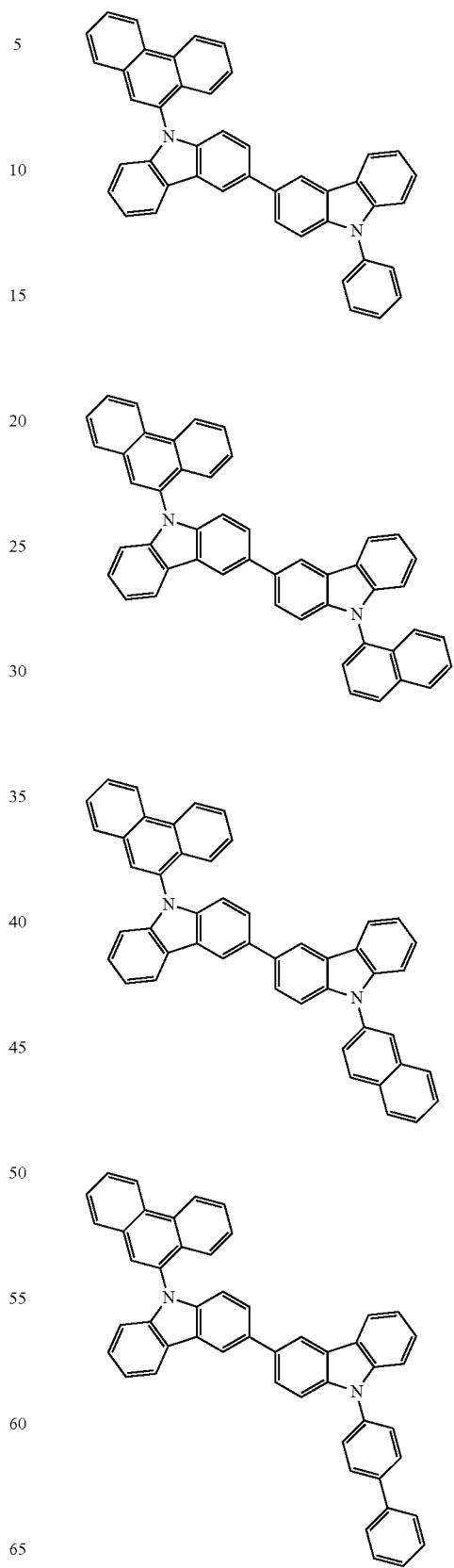

-continued
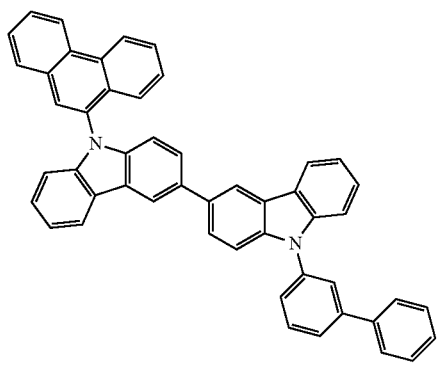
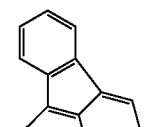
[Formula 155]
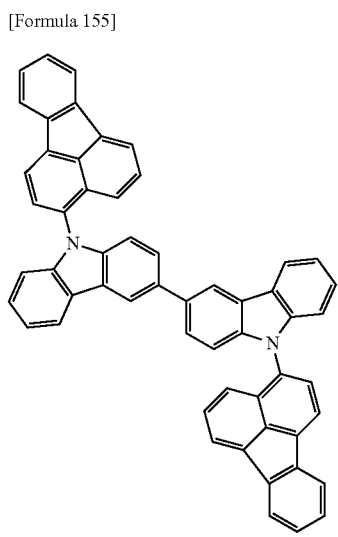
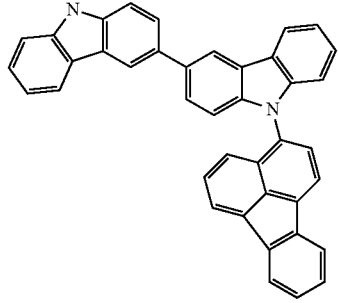
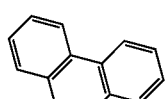
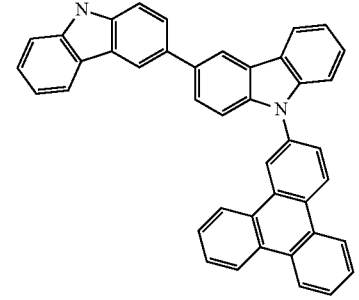
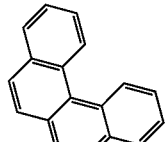
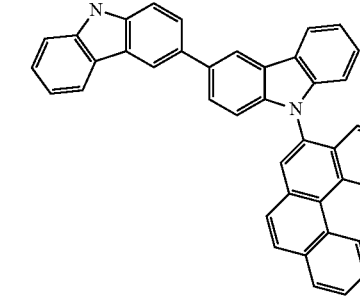

323
-continued
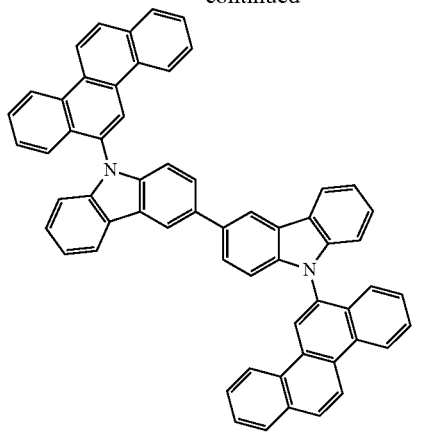
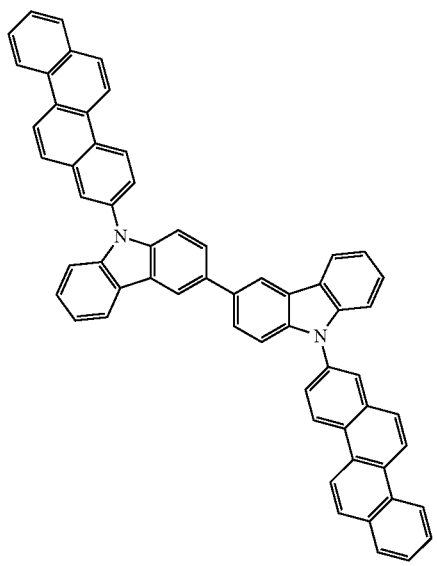
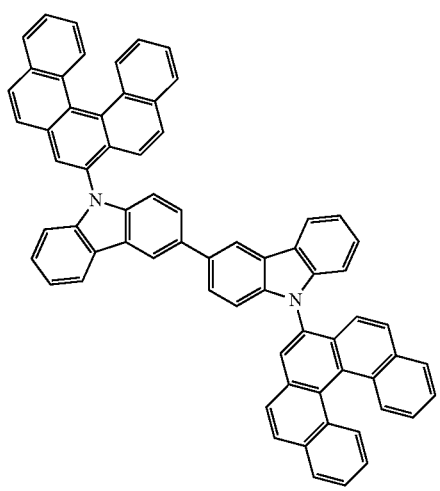
324
-continued
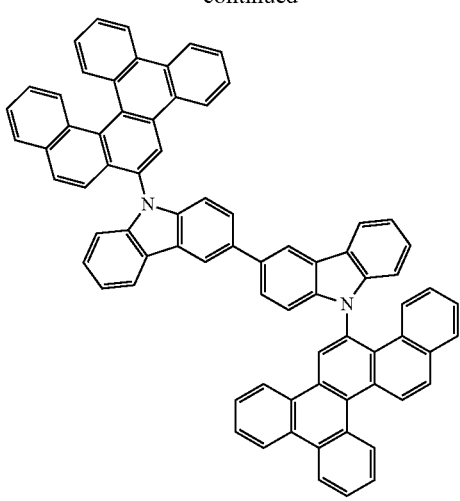
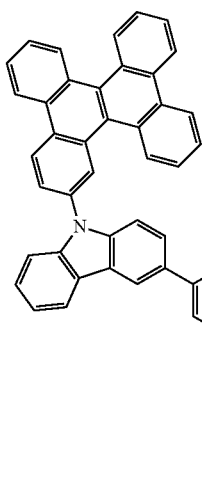
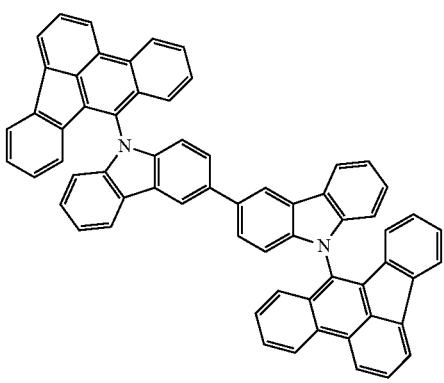

325
-continued
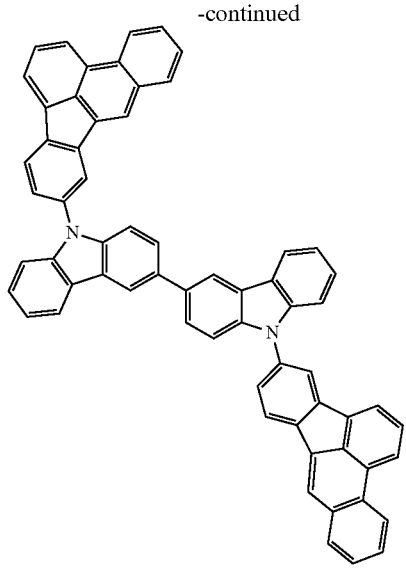
[Formula 156]
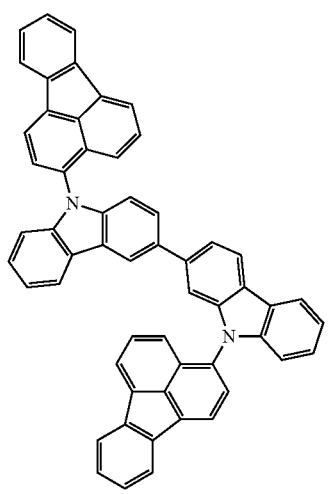
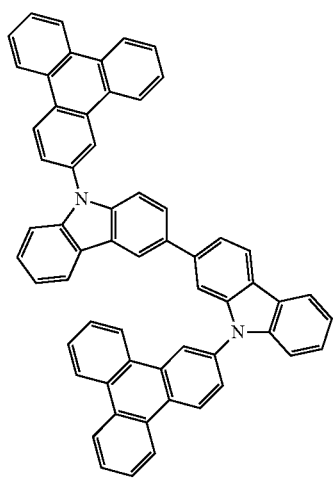
326
-continued
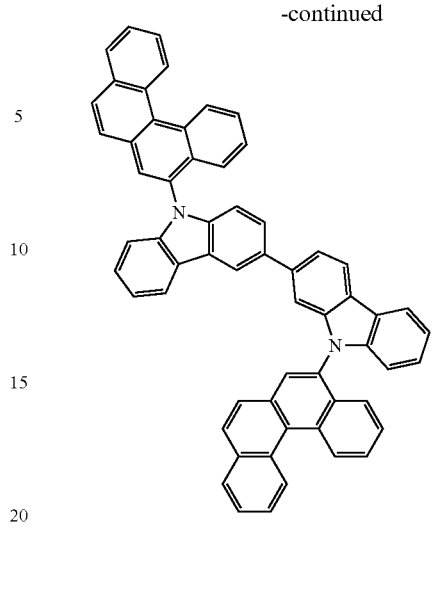
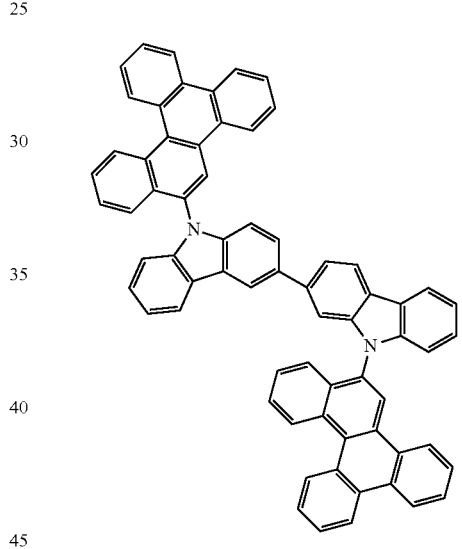
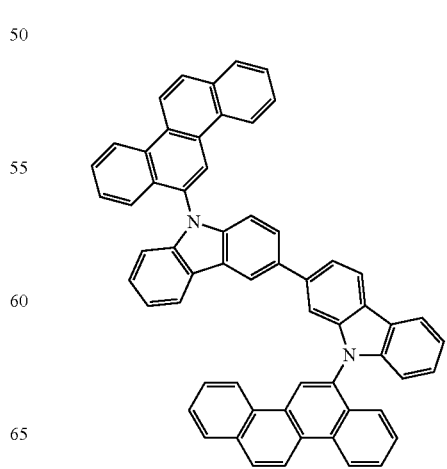

327
-continued
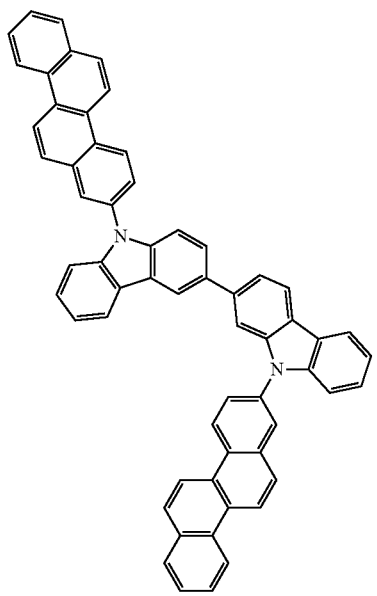
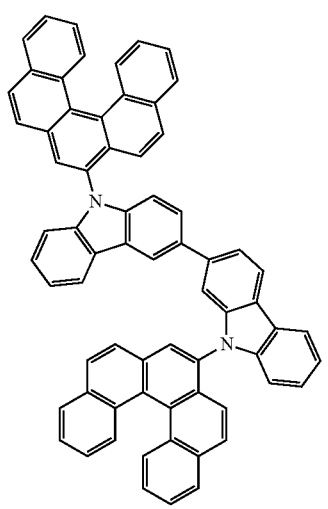
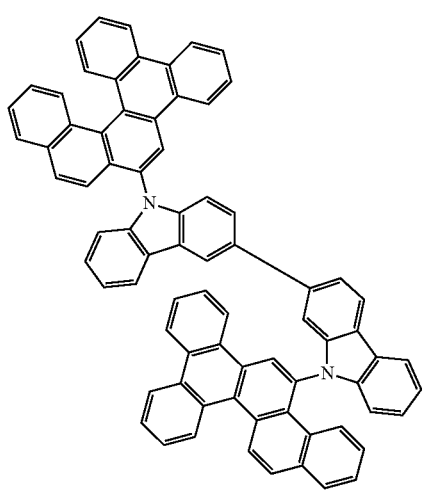
328
-continued
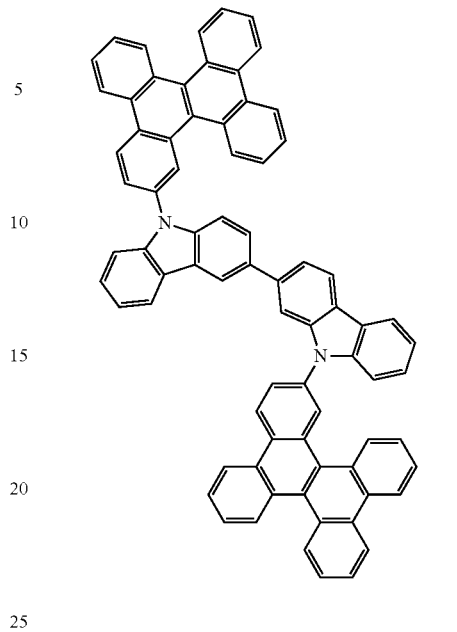
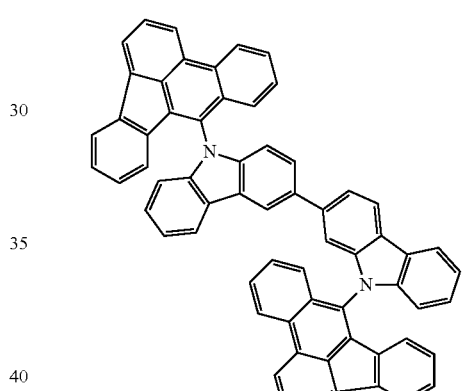
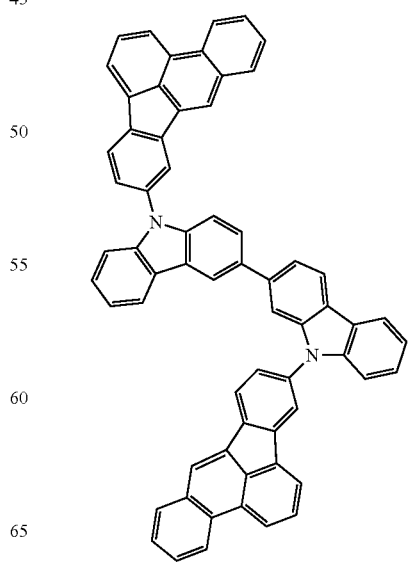

329
-continued
[Formula 157]
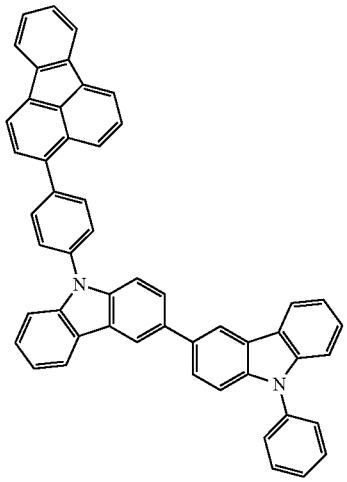
330
-continued
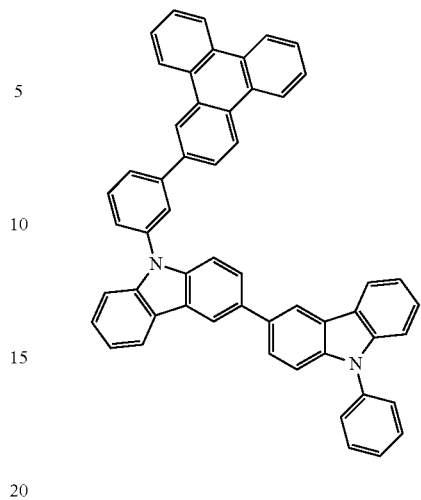
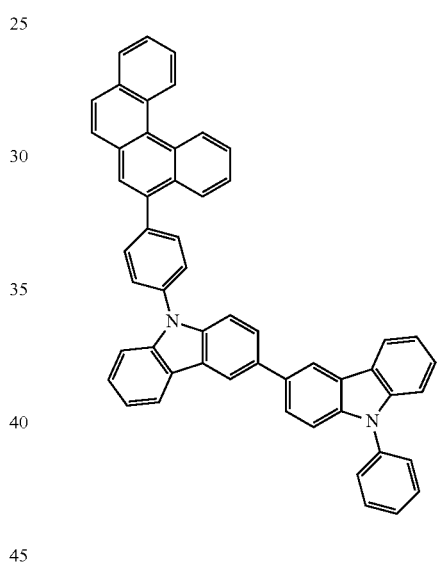
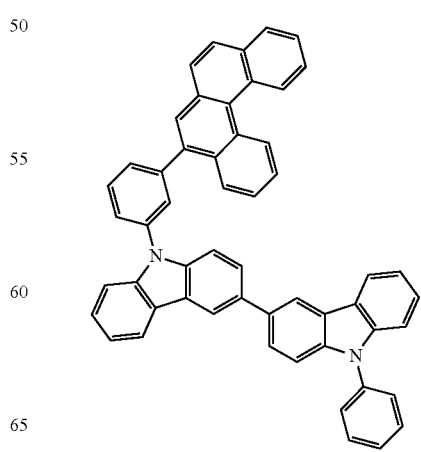

331
-continued
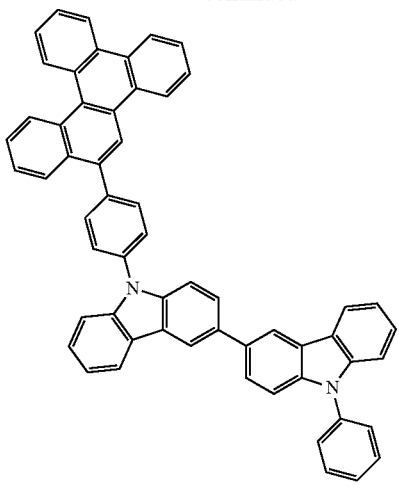
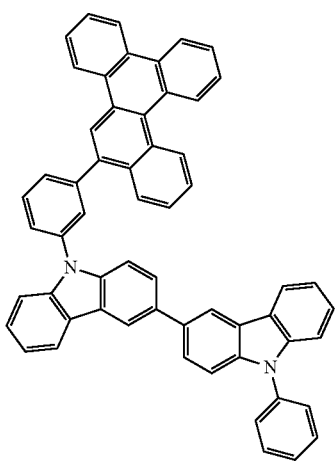
[Formula 158]
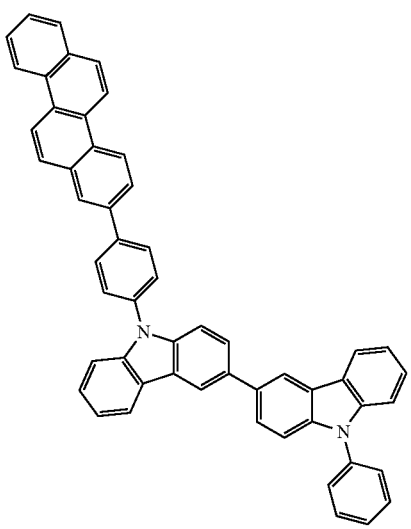
332
-continued
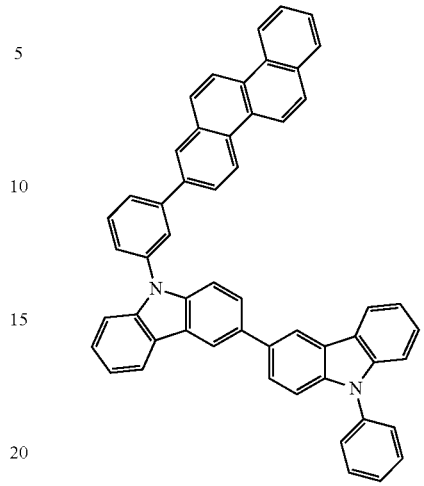
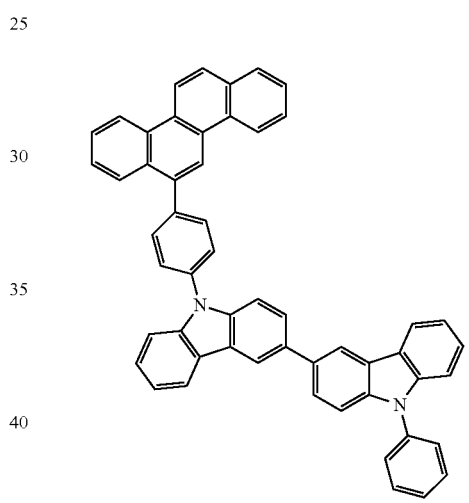
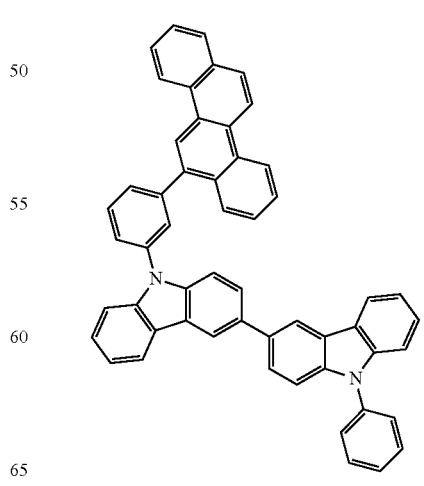

333
-continued
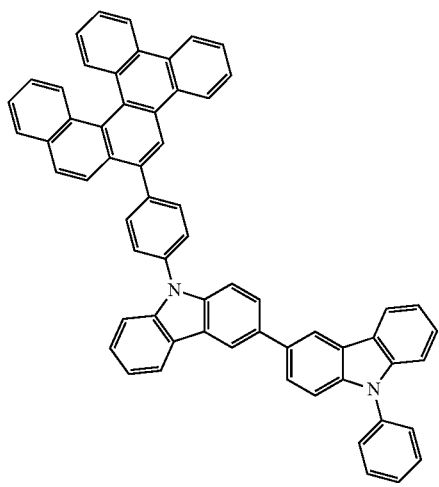
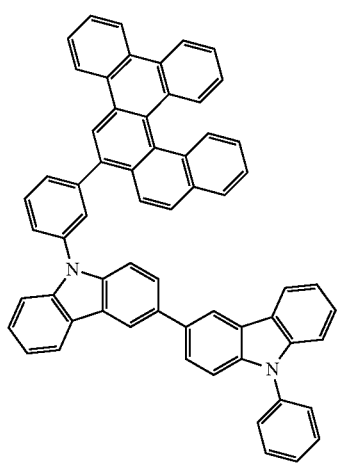
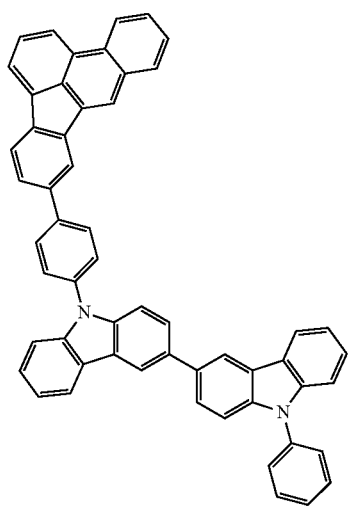
334
-continued
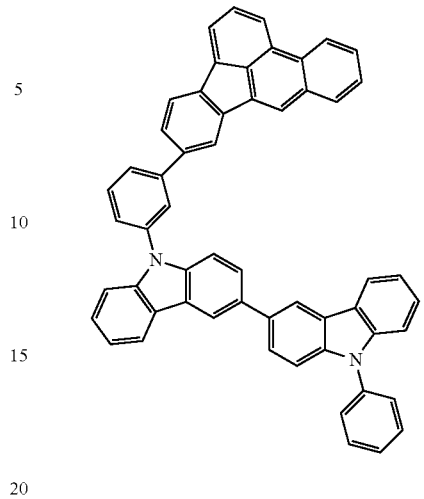
[Formula 159]
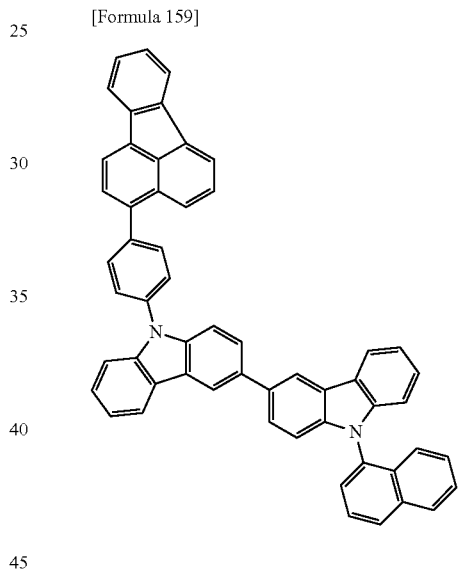
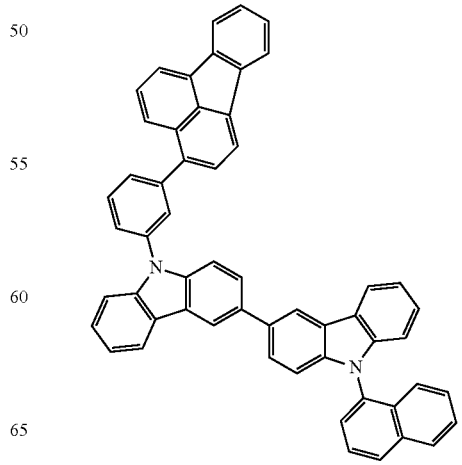

335
-continued
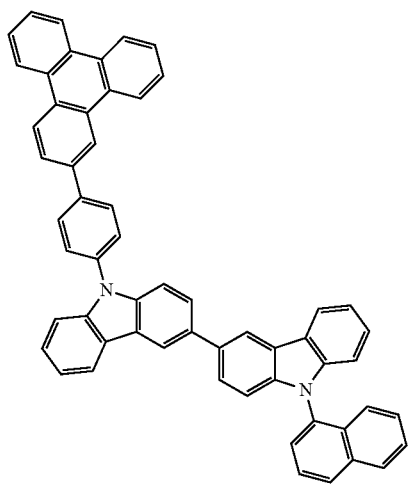
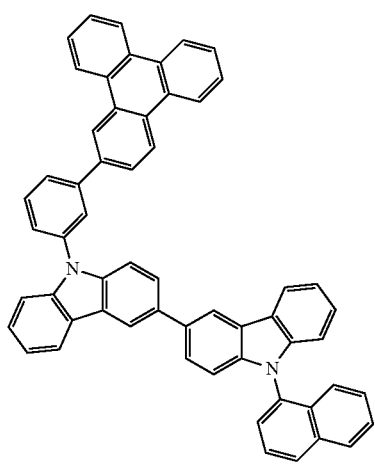
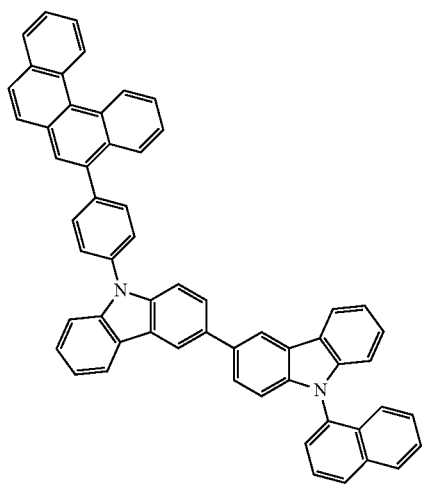
336
-continued
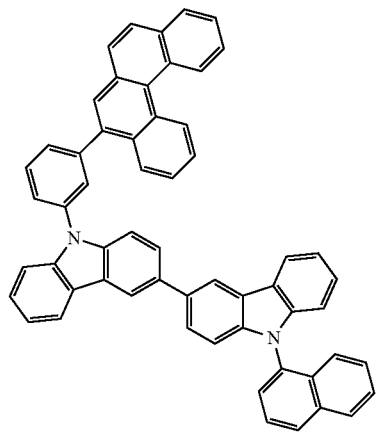

[Formula 160]
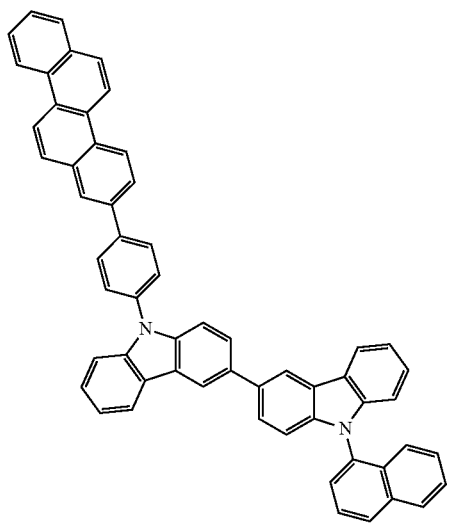
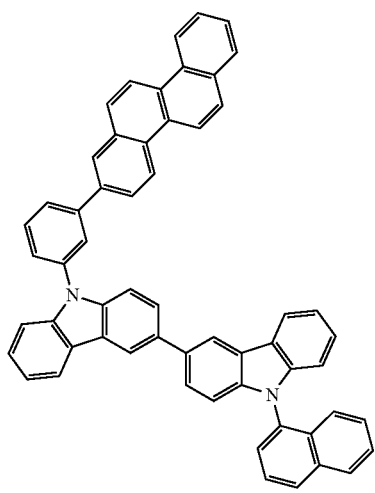
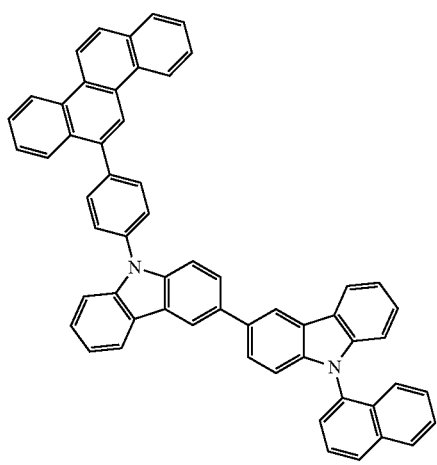
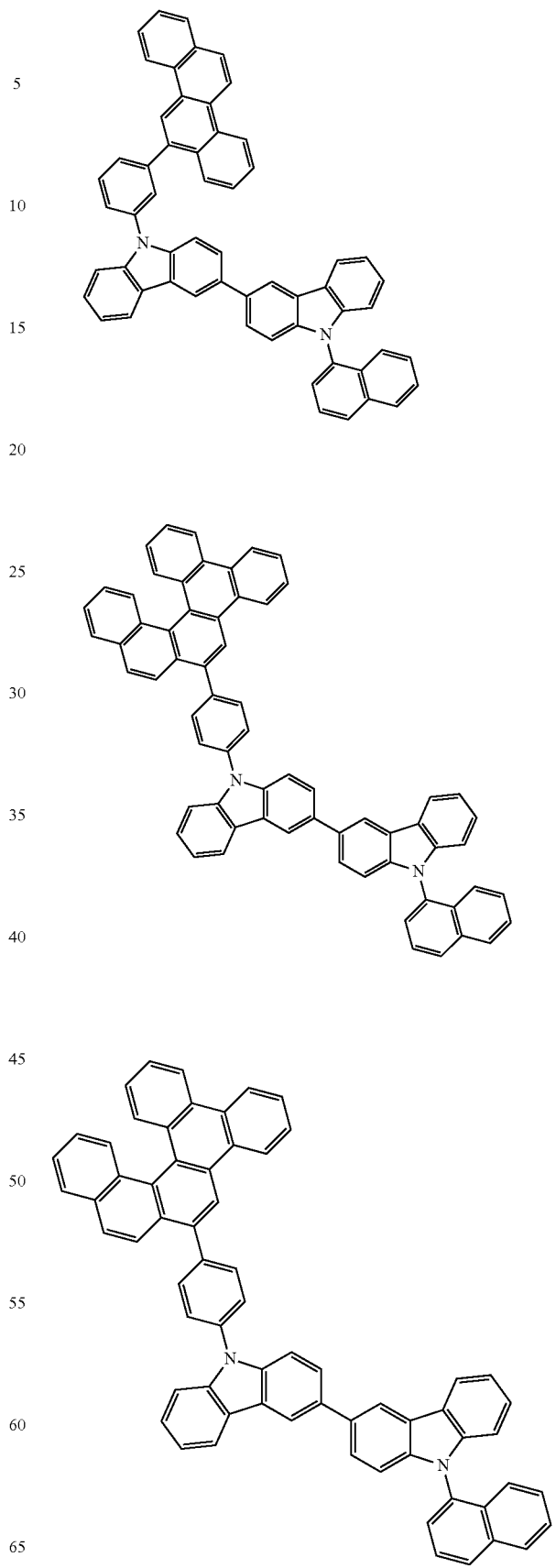

339
-continued
340
-continued
[Formula 161]
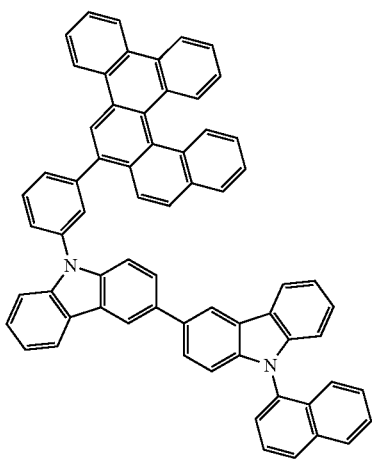
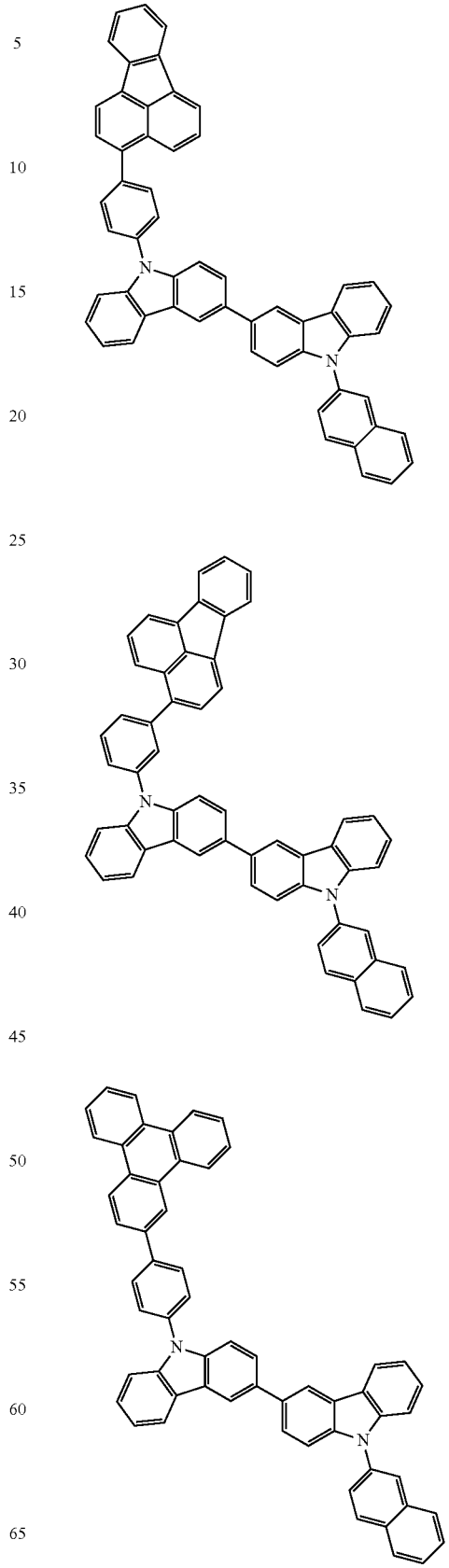

341
-continued
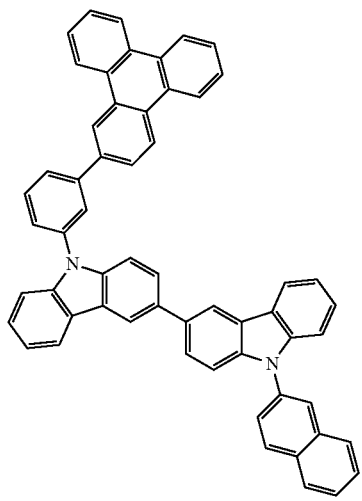
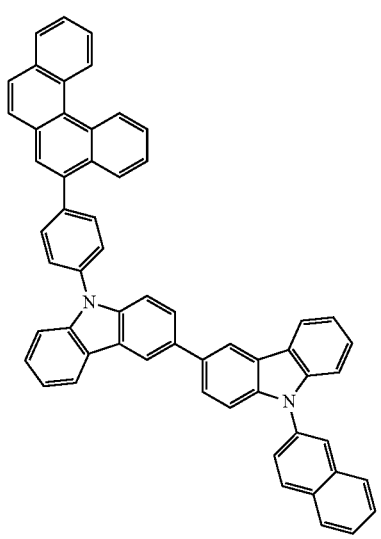
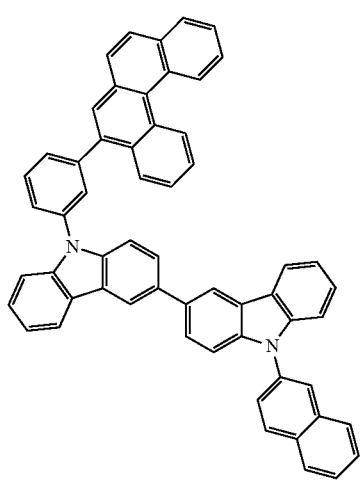
342
-continued
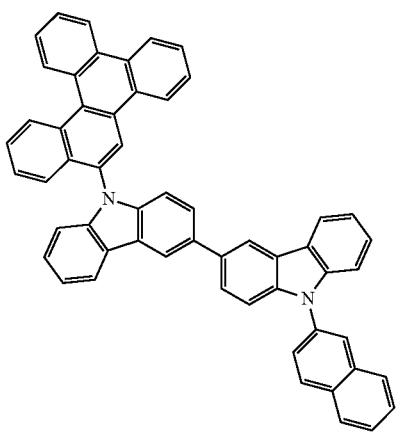
[Formula 162]
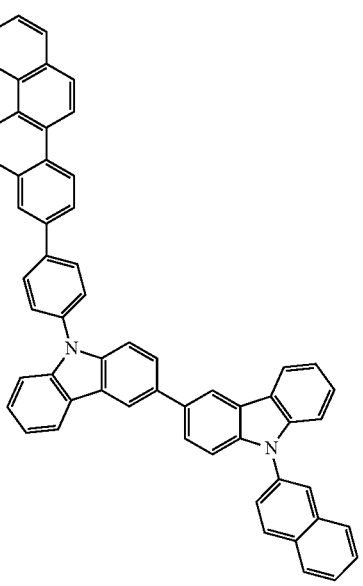

343
-continued
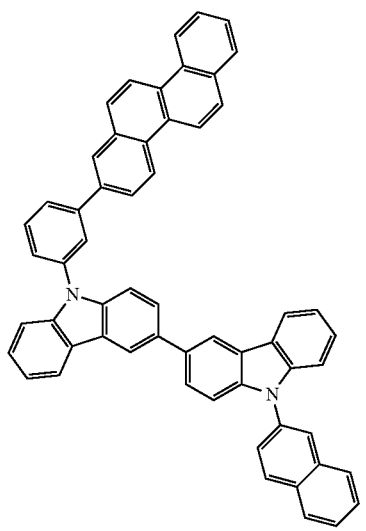
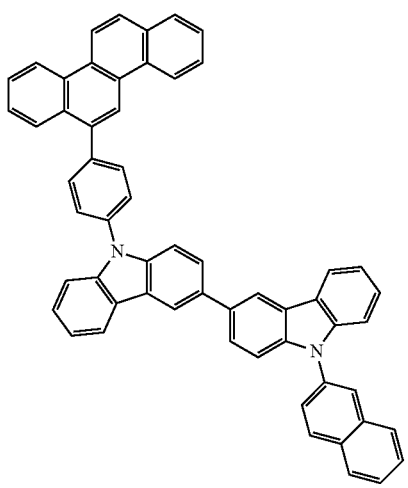
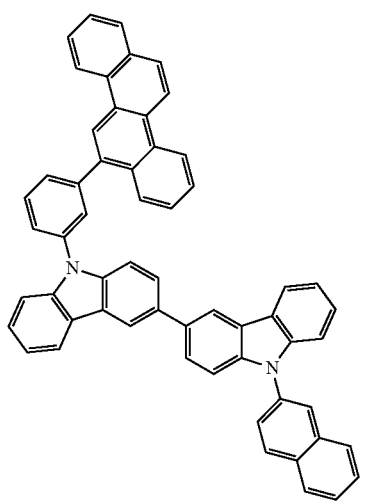
344
-continued
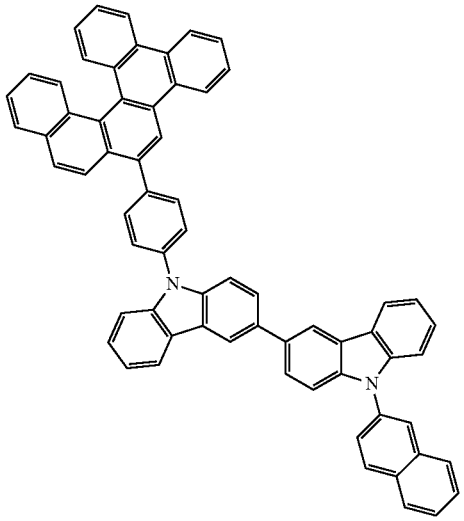
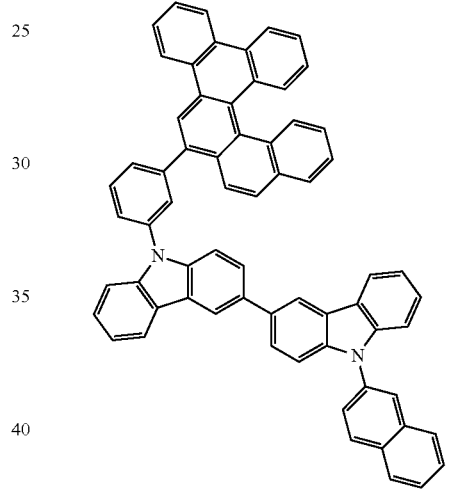
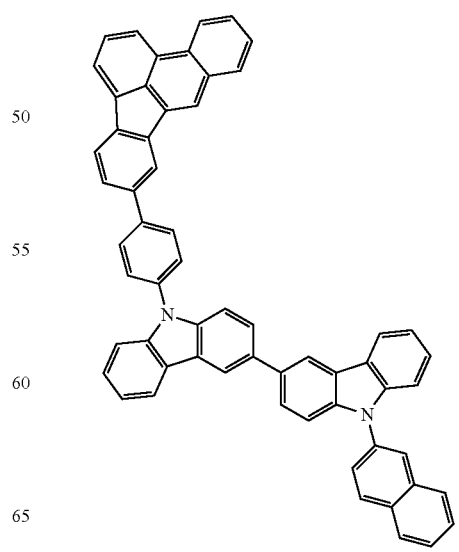

345
-continued
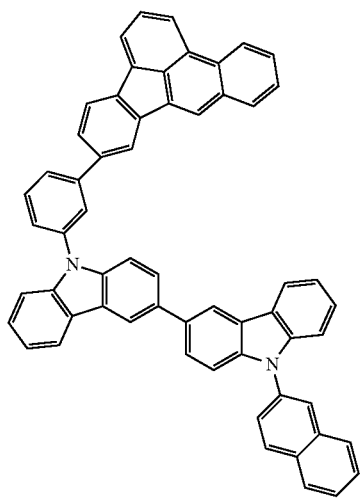
[Formula 163]
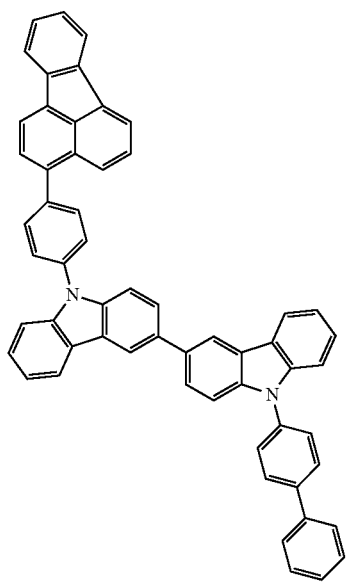
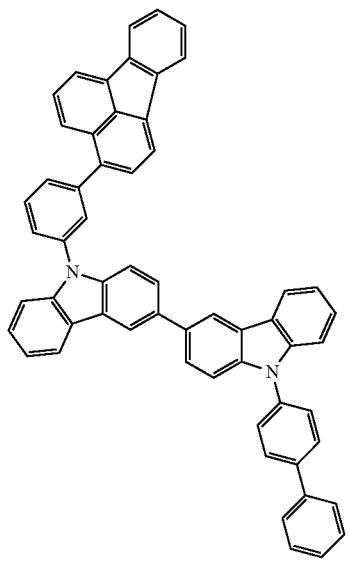
346
-continued
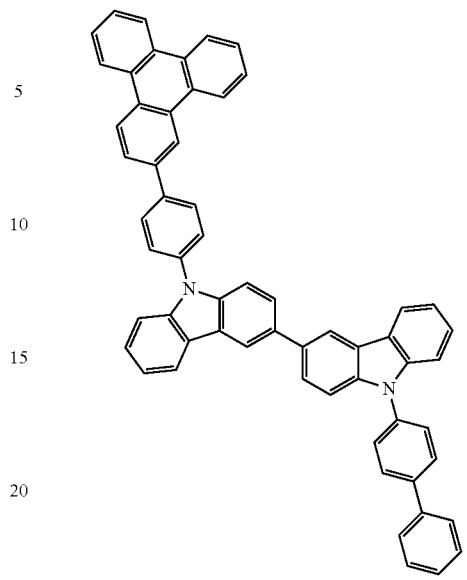
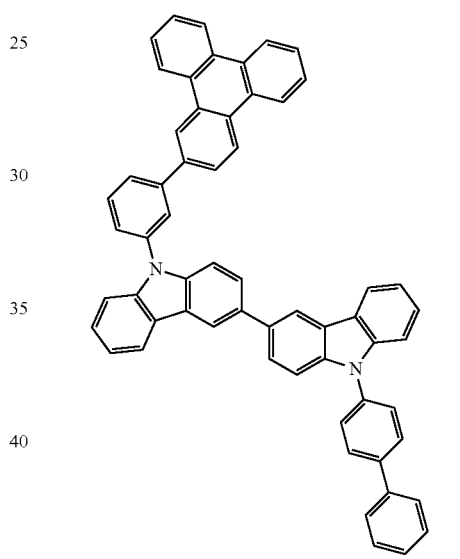
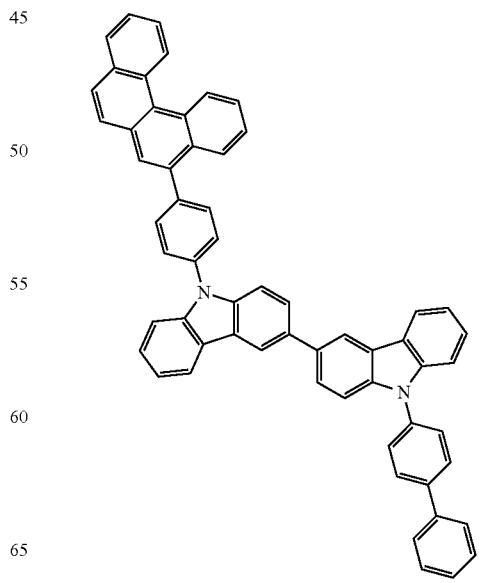

347
-continued
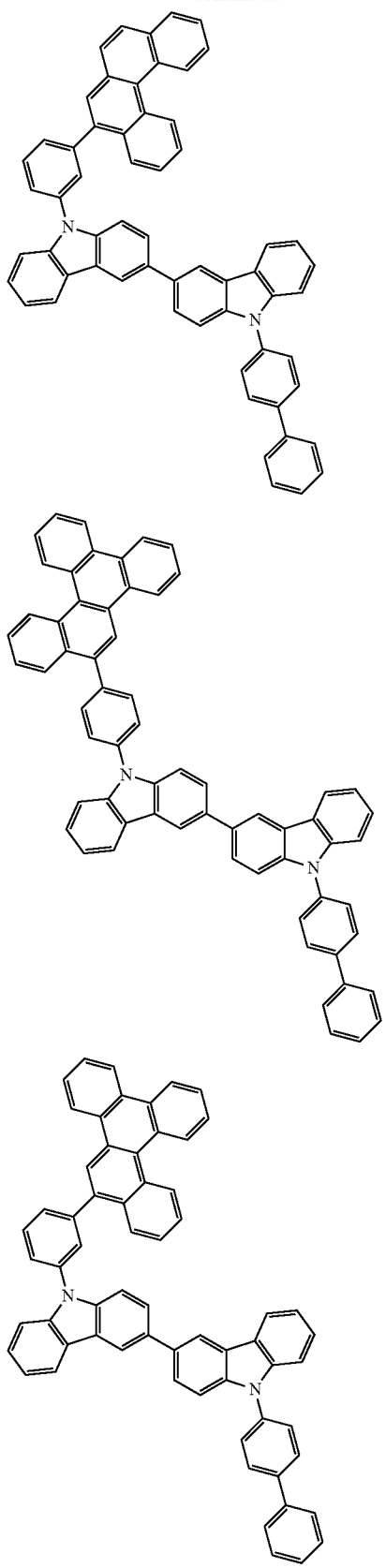
348
-continued
[Formula 164]

349
-continued
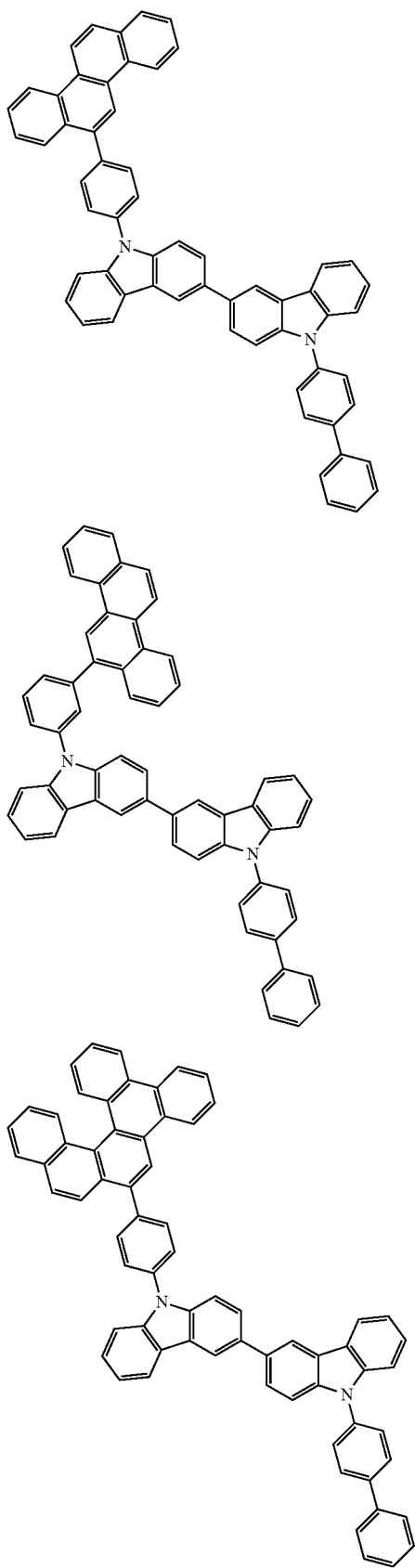
350
-continued
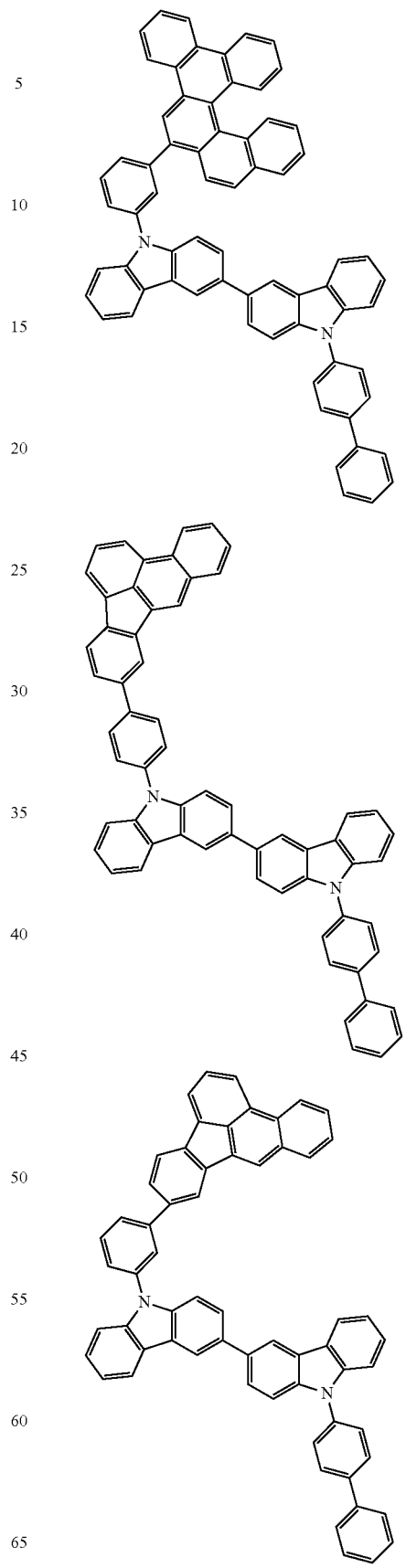

[Formula 165]
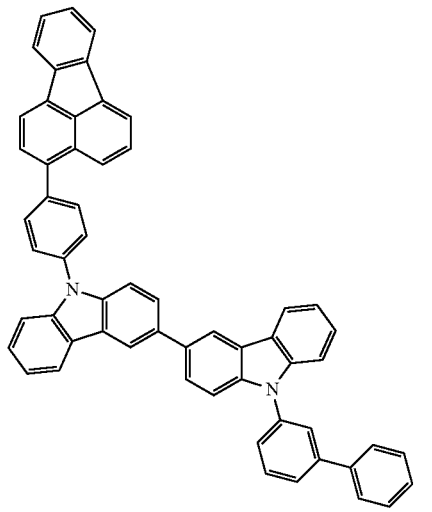
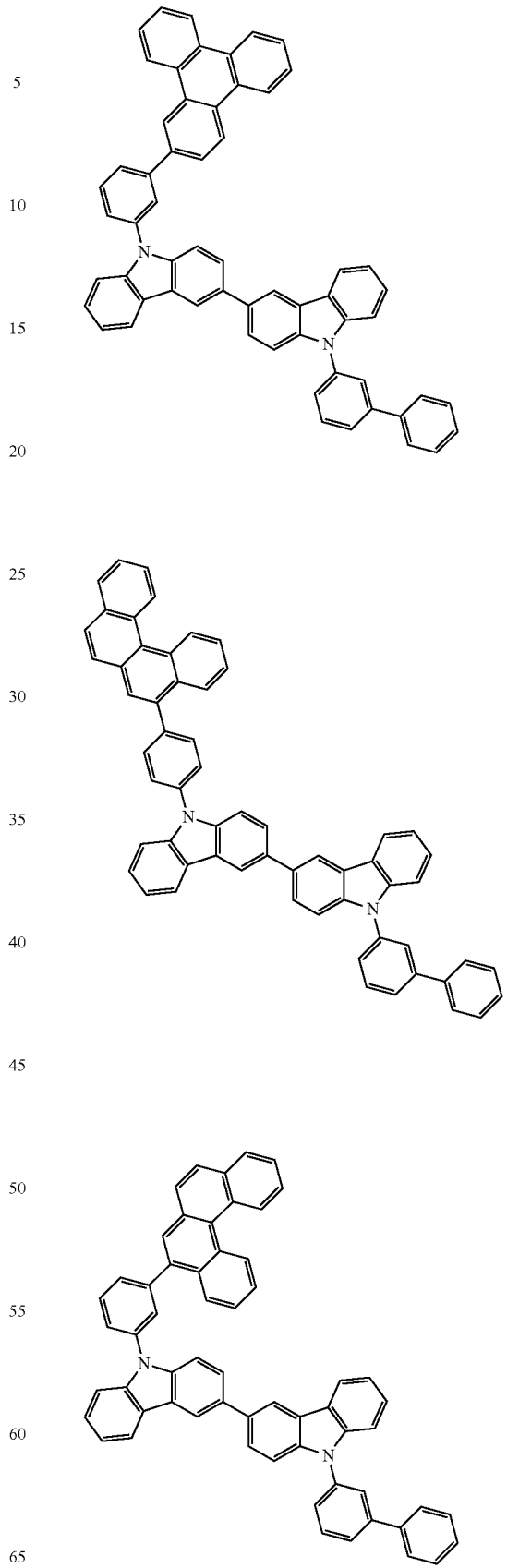

353
-continued
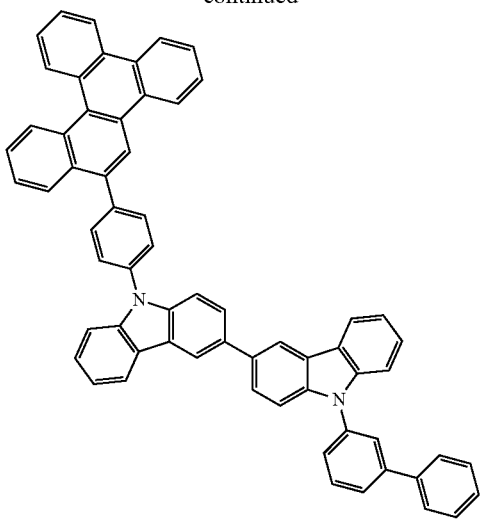
354
-continued
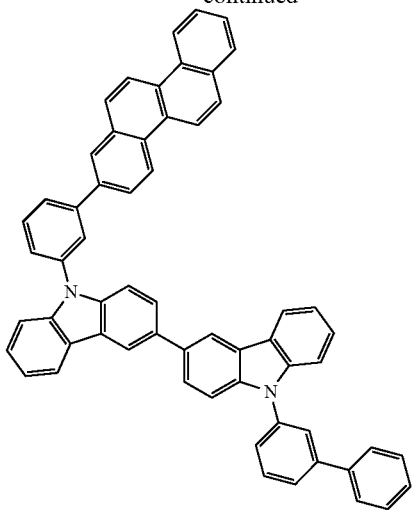
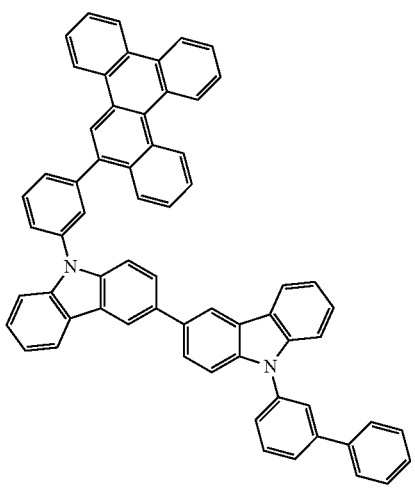
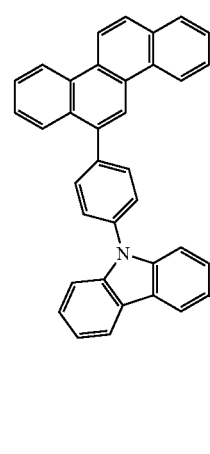
[Formula 166]
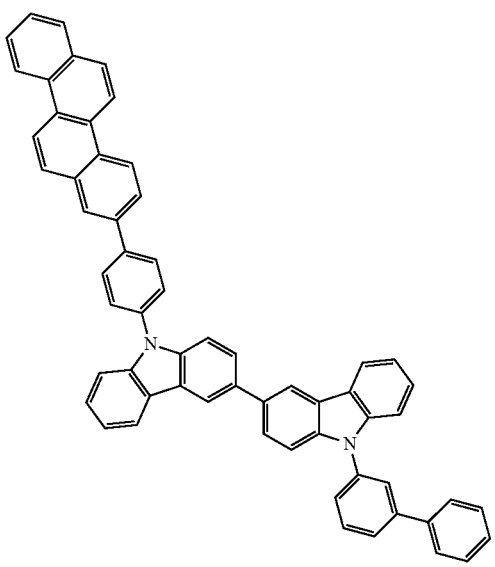
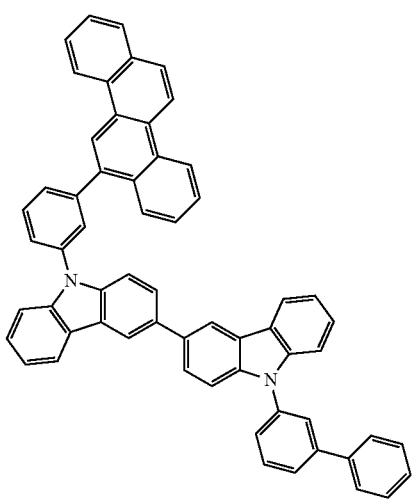

355
-continued
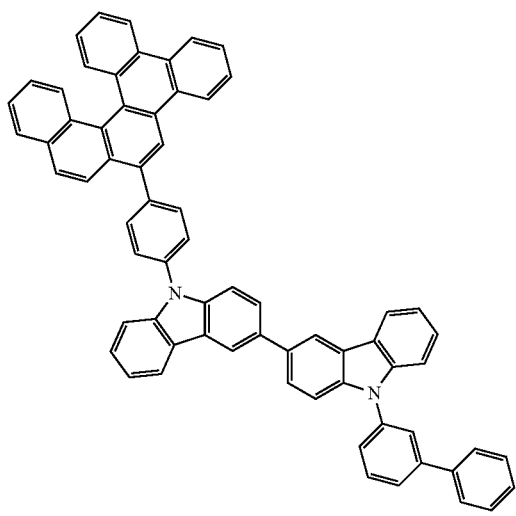
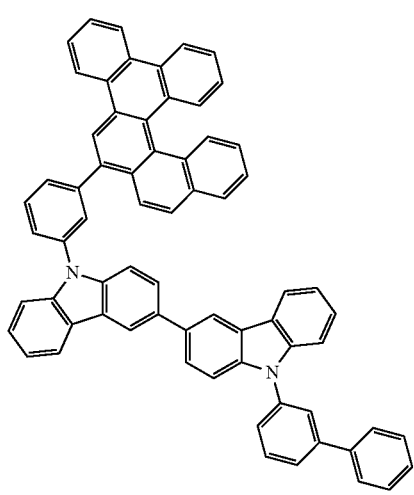
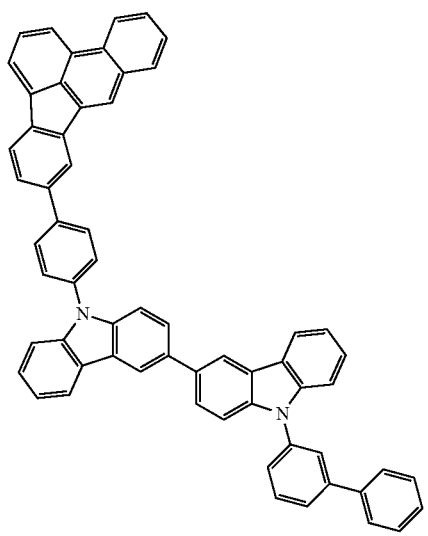
356
-continued
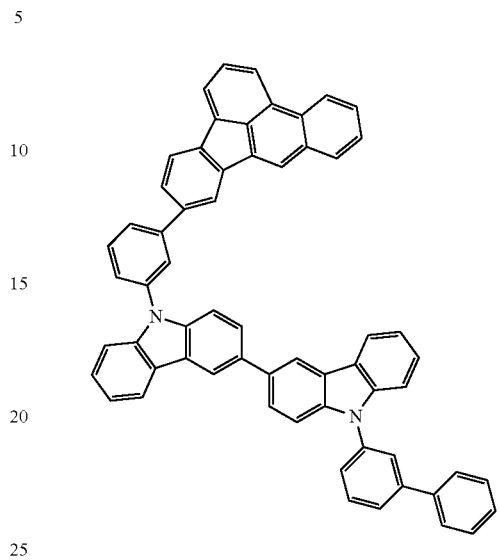
[Formula 167]
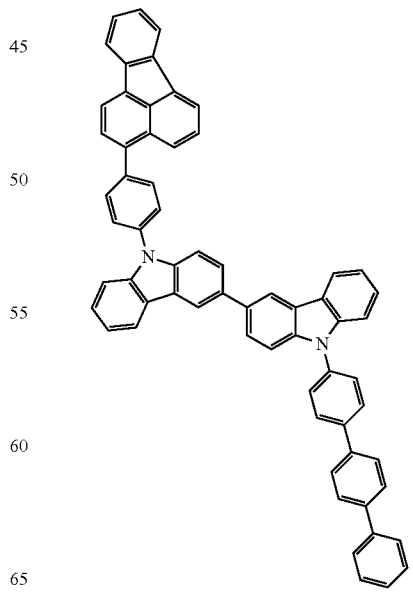

357
-continued
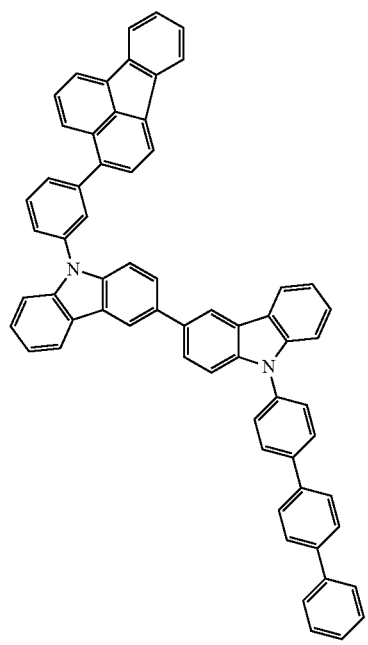
358
-continued
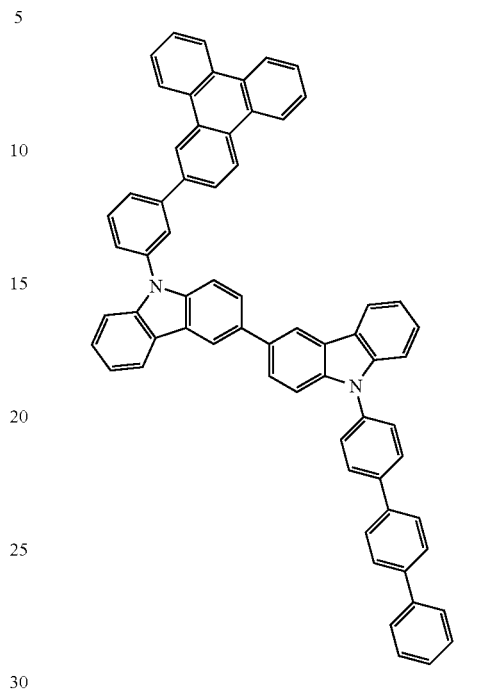
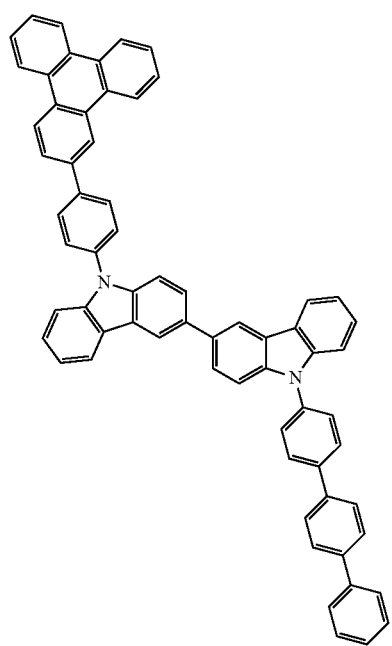
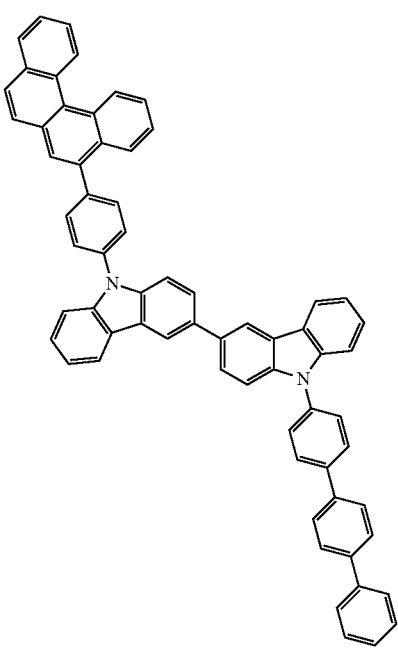

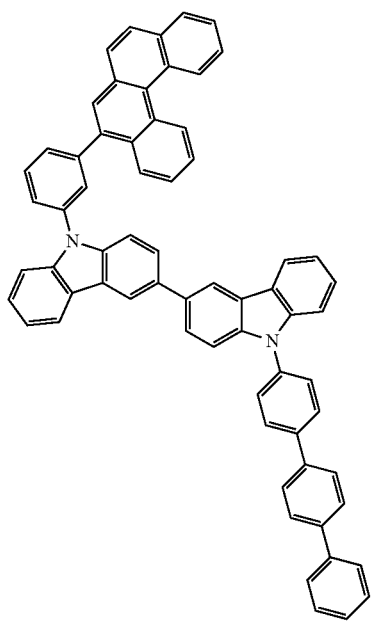
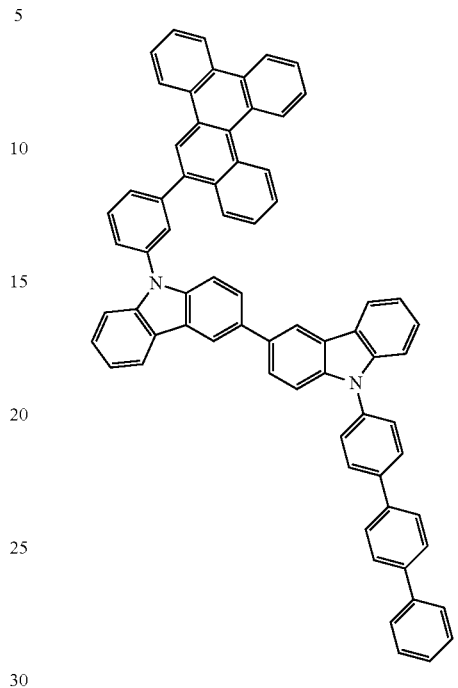
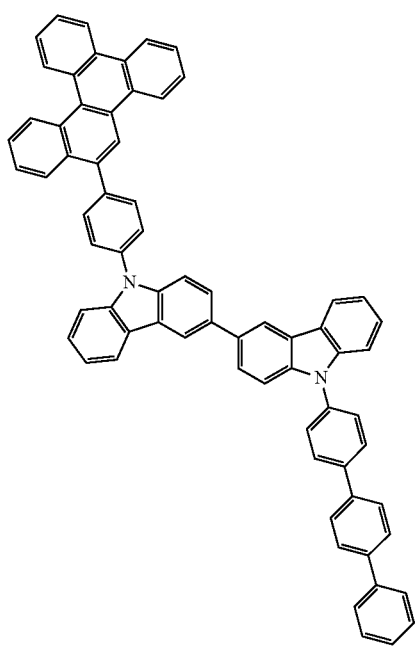
[Formula 168]
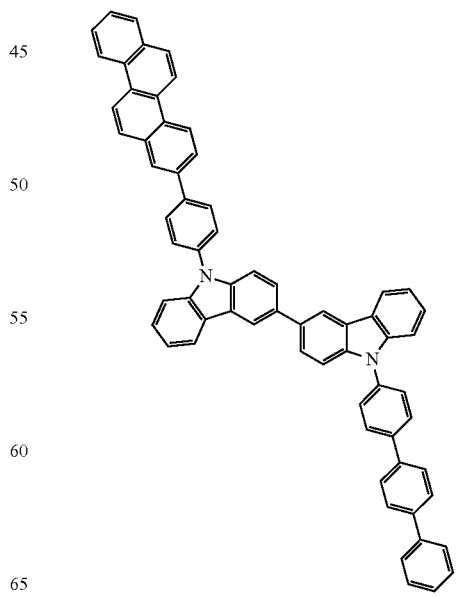

361
-continued
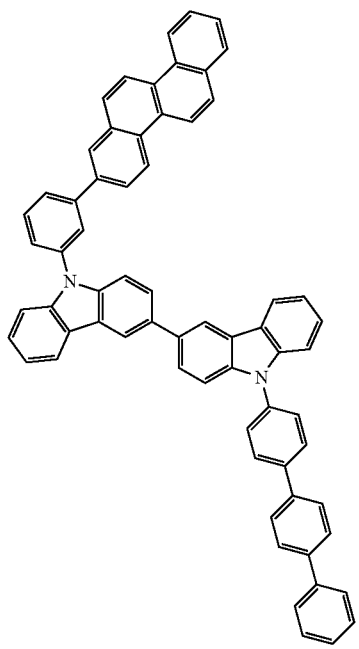
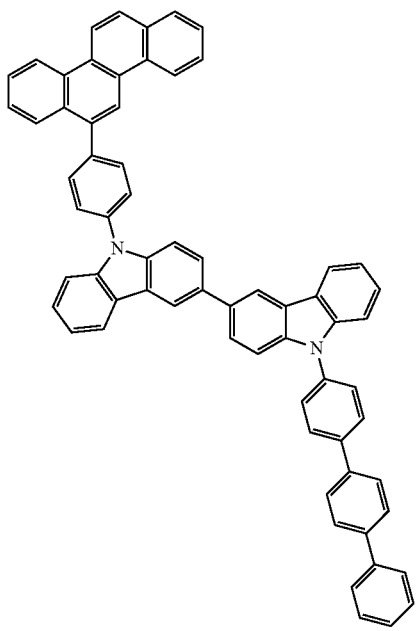
362
-continued
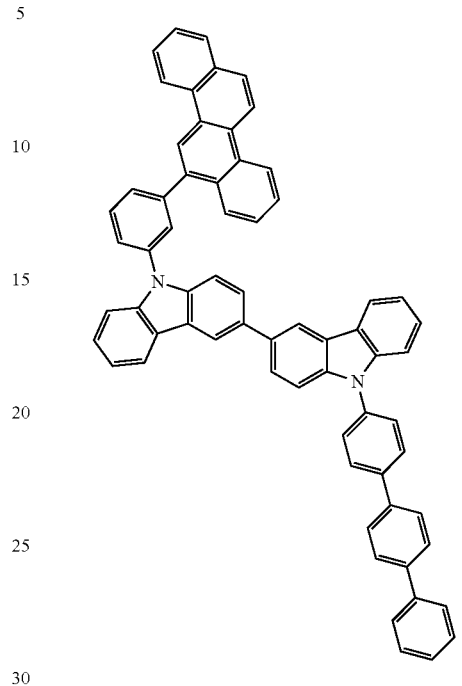
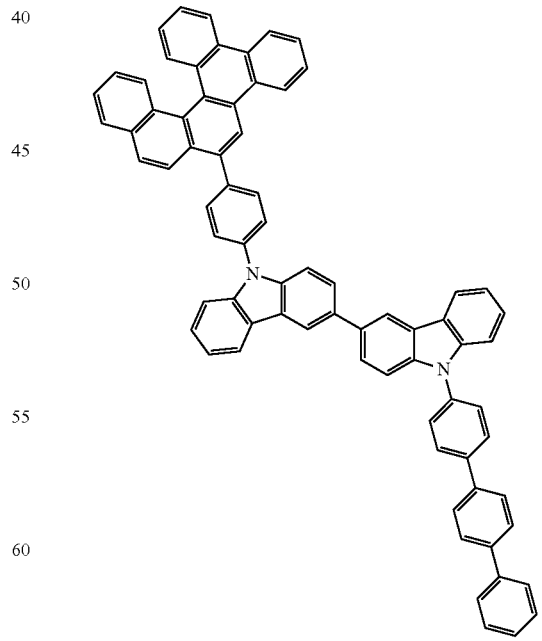

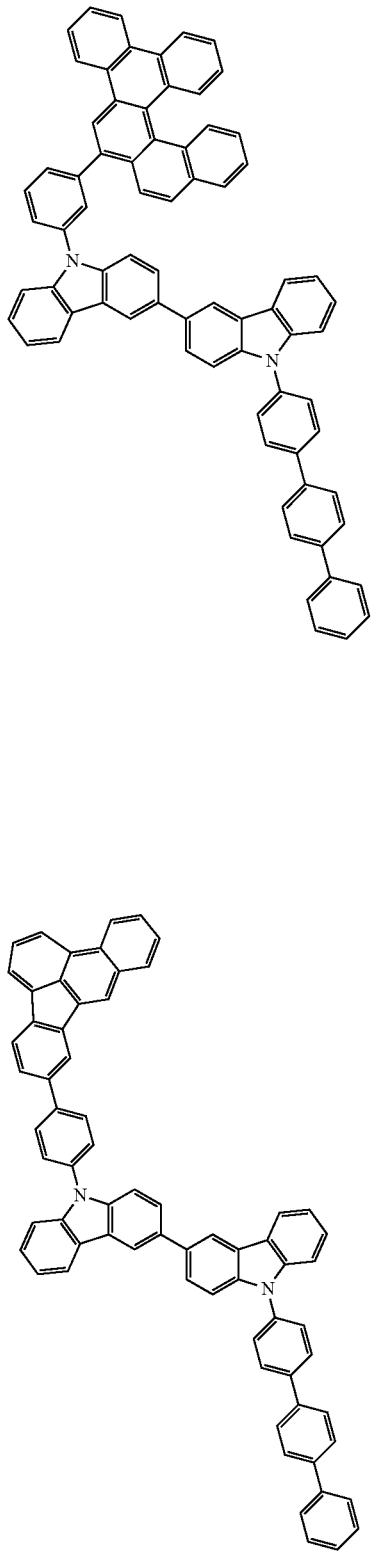
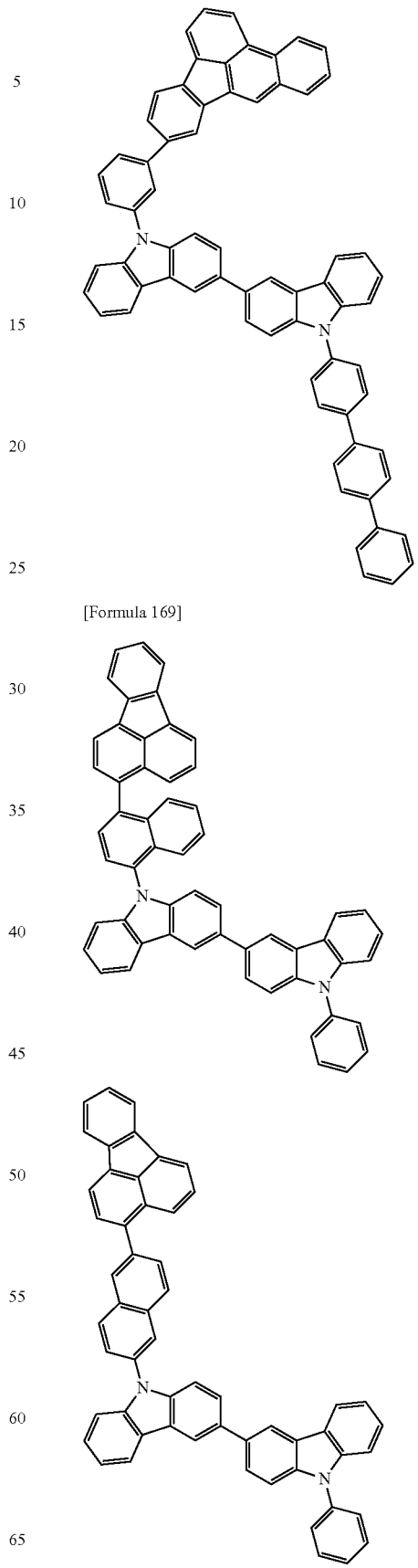
[Formula 169]

365
-continued
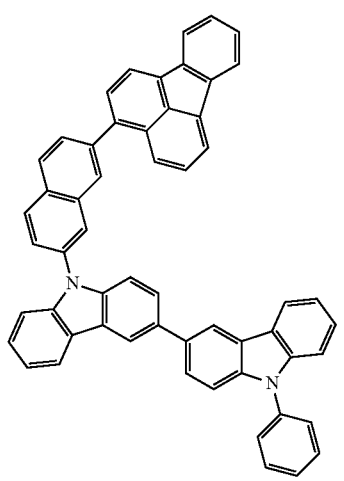
366
-continued
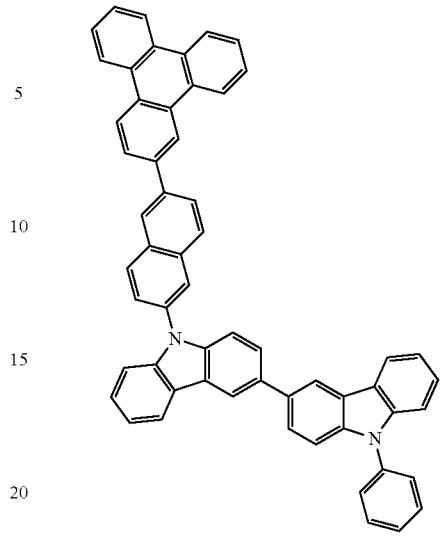
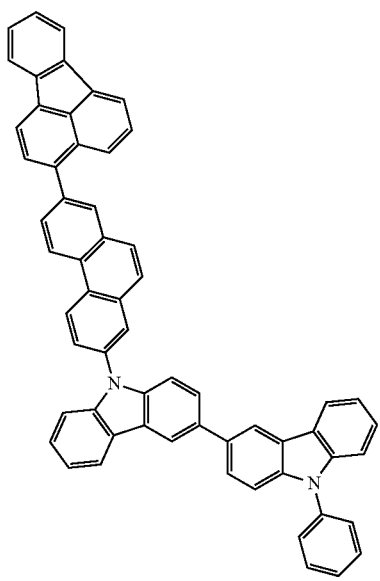
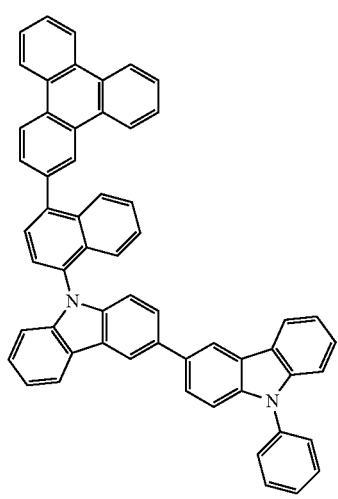
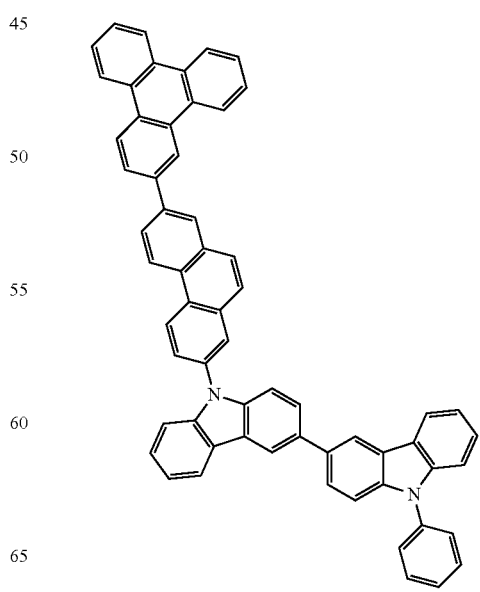

367
-continued
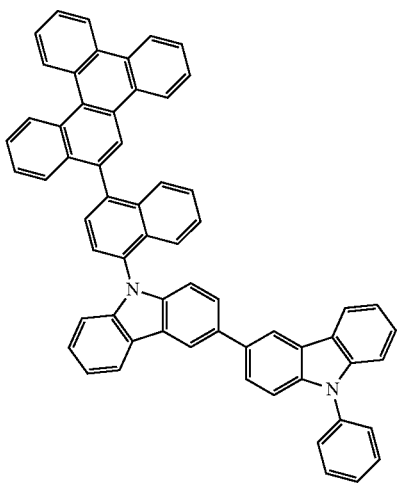
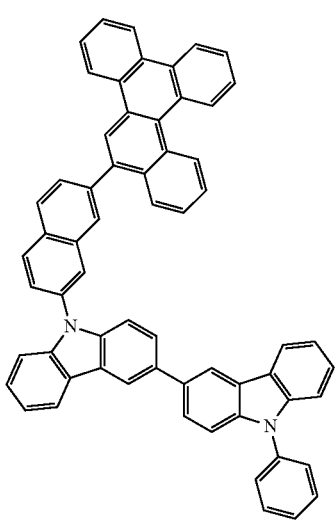
368
-continued
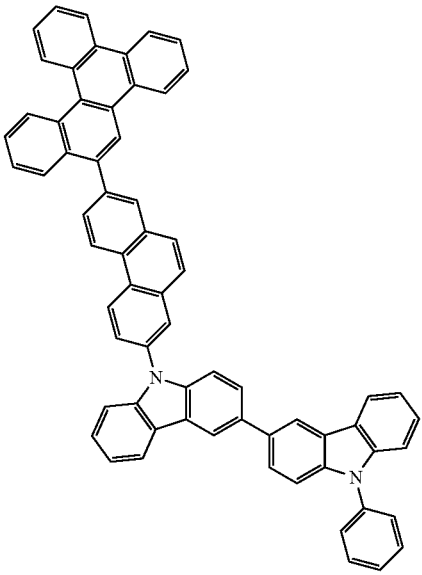
[Formula 170]
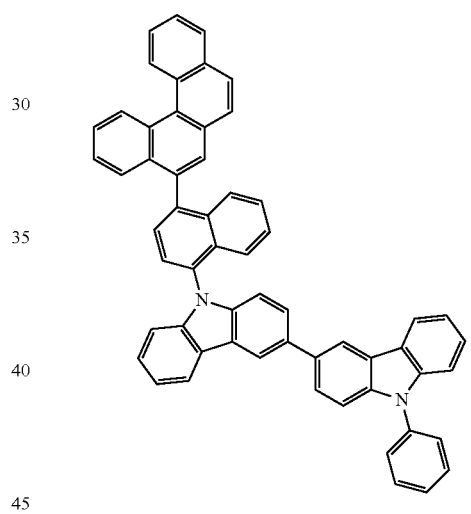
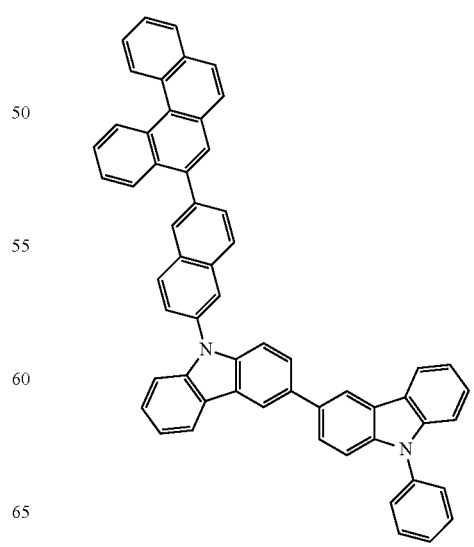

369
-continued
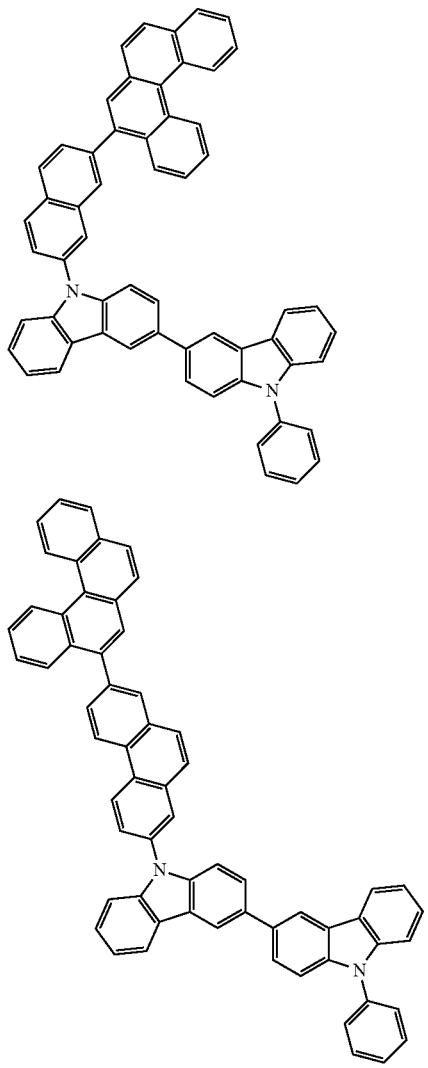
[Formula 171]
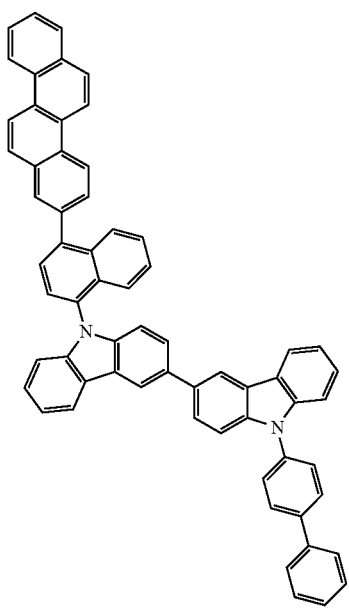
370
-continued
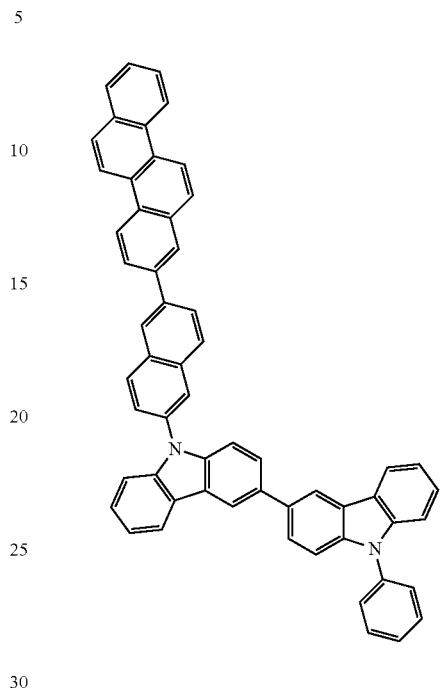
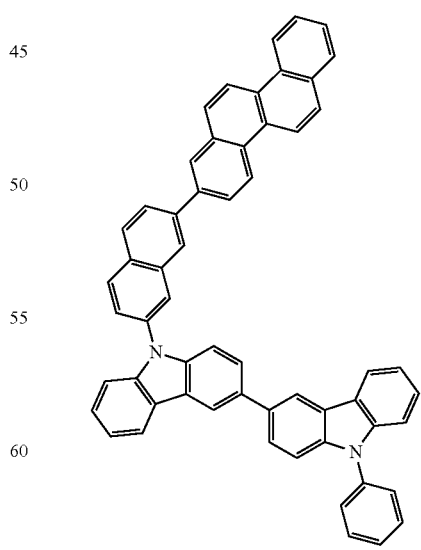

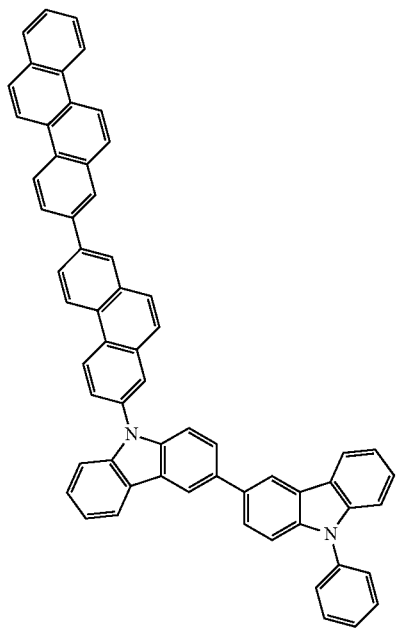
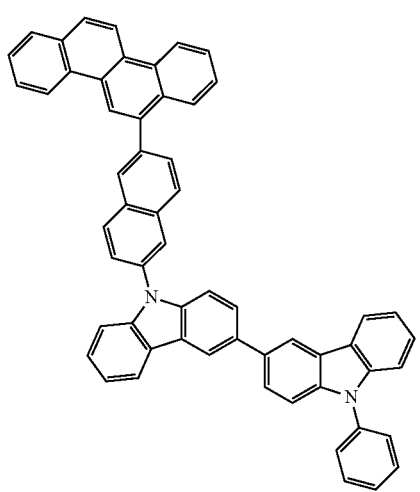
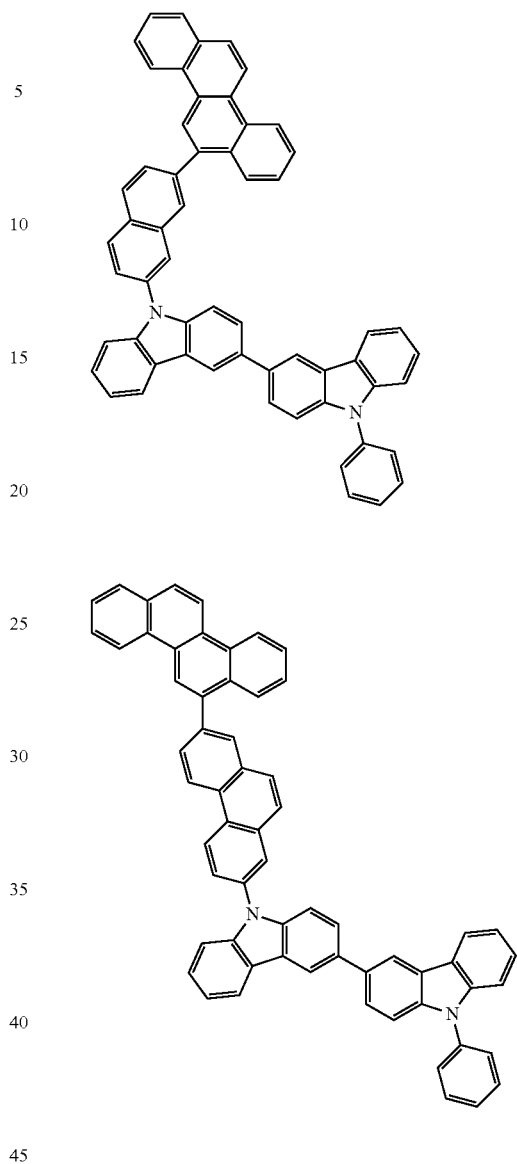
[Formula 172]
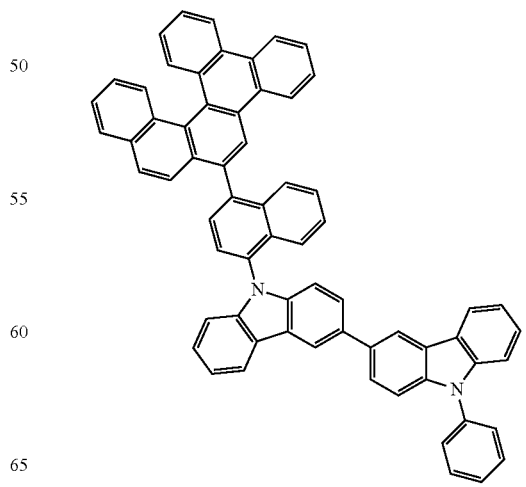

373
-continued
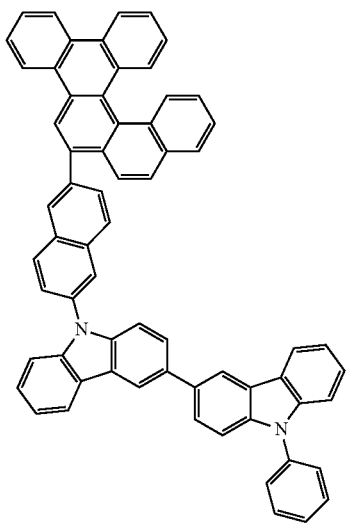
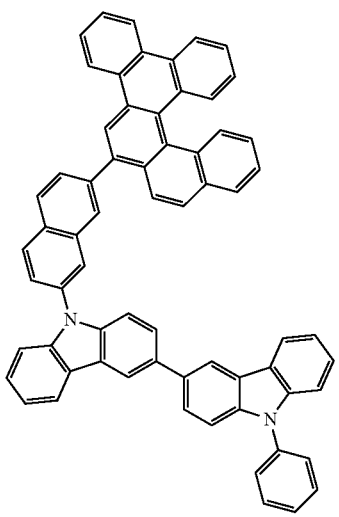
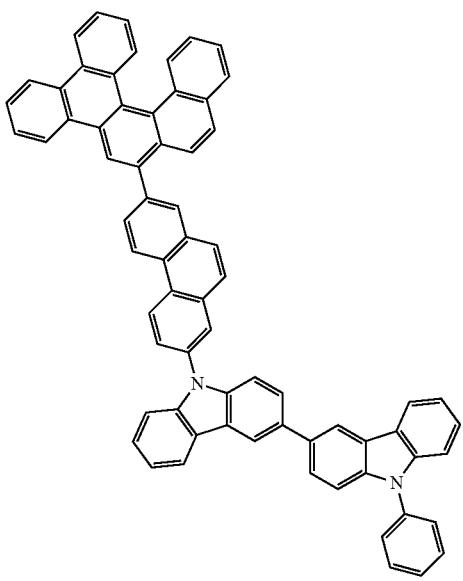
374
-continued
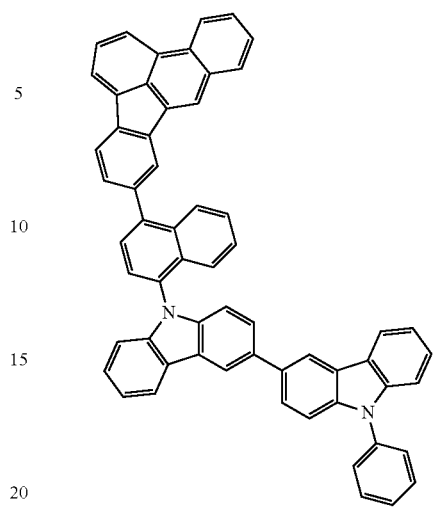
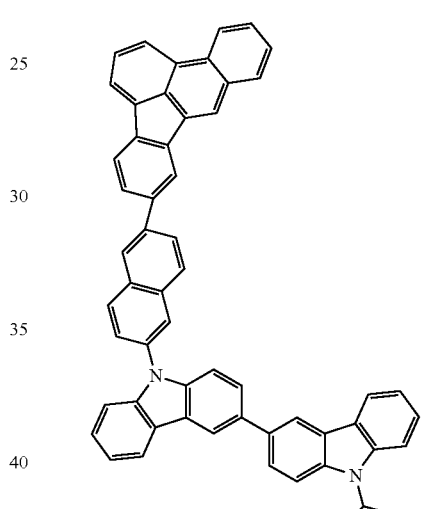
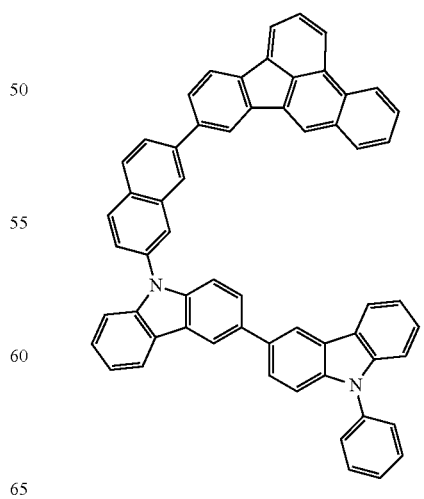

375
-continued
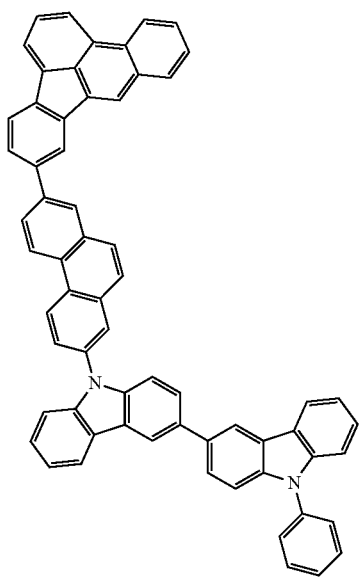
[Formula 173]
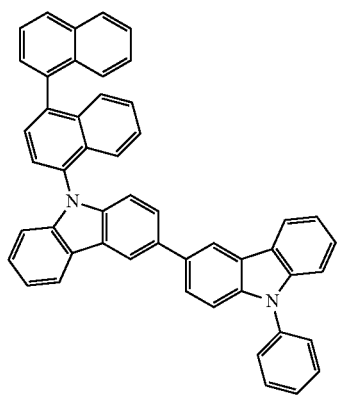
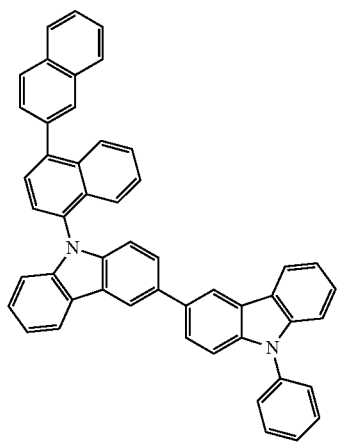
376
-continued
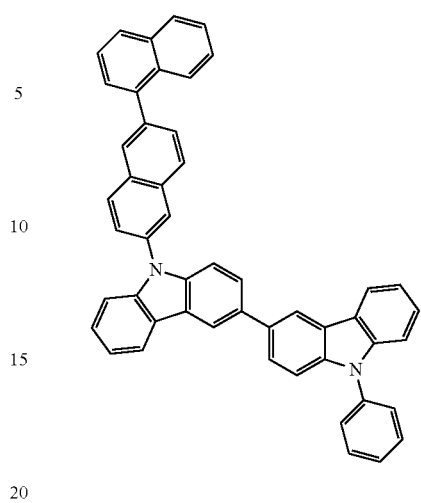
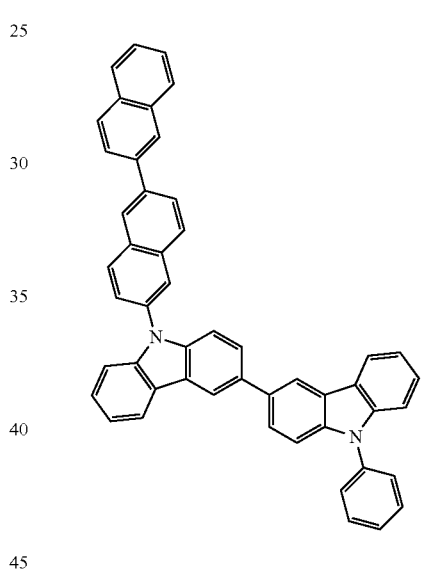
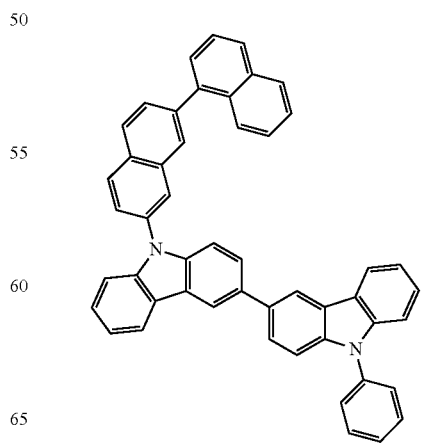

377
-continued
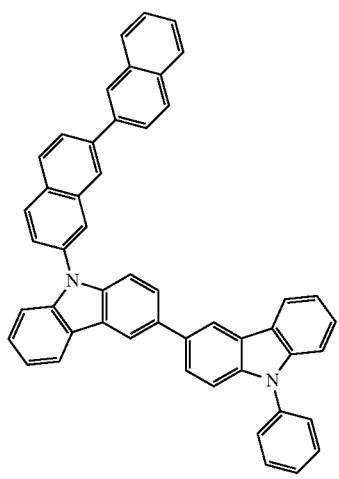
[Formula 174]
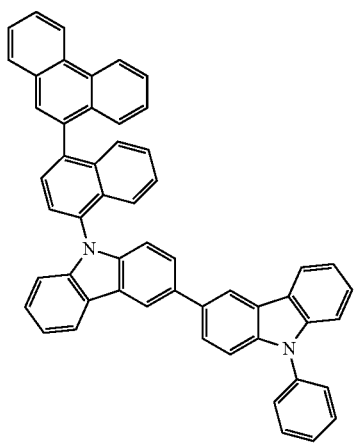
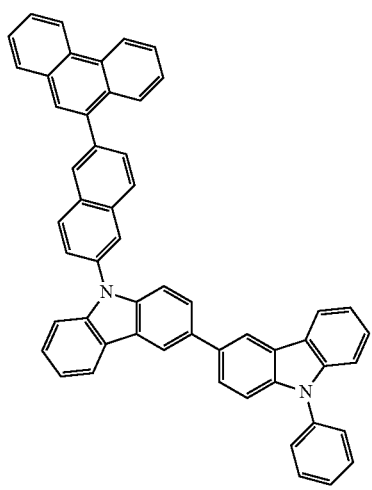
378
-continued
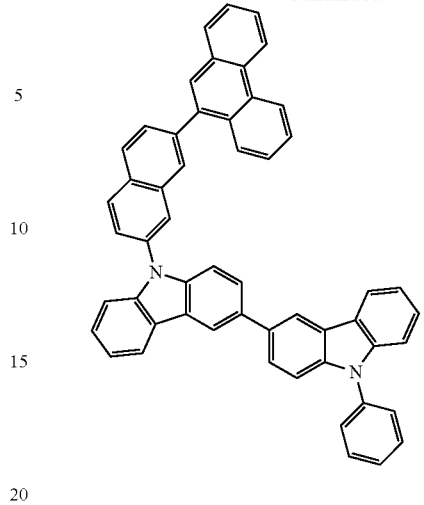
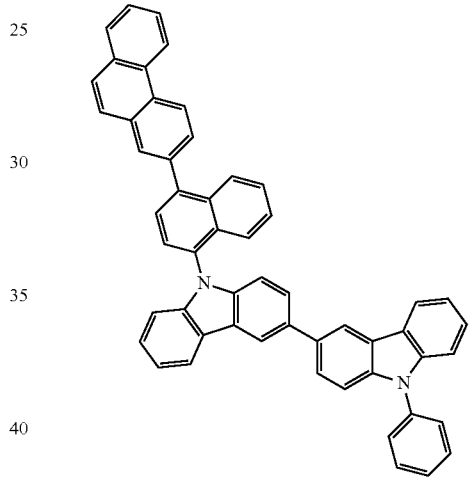
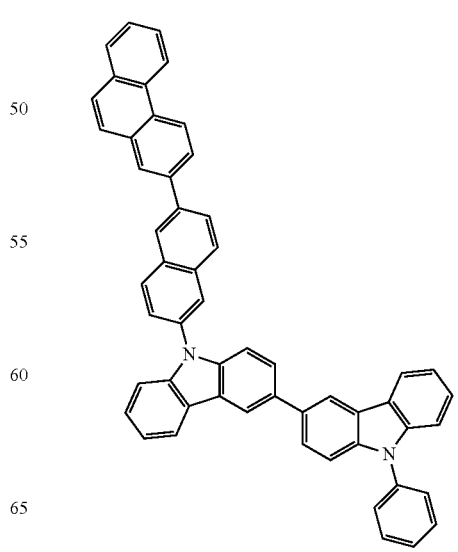

-continued
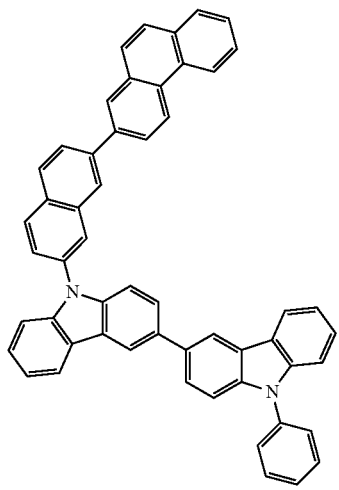
[Formula 175]
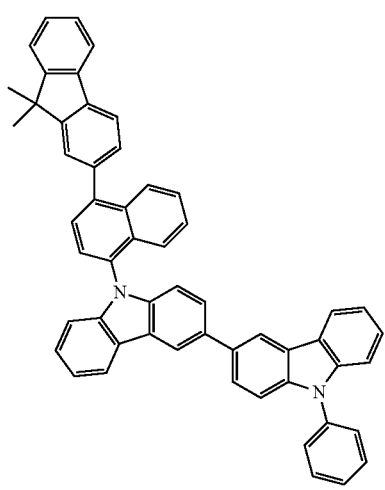
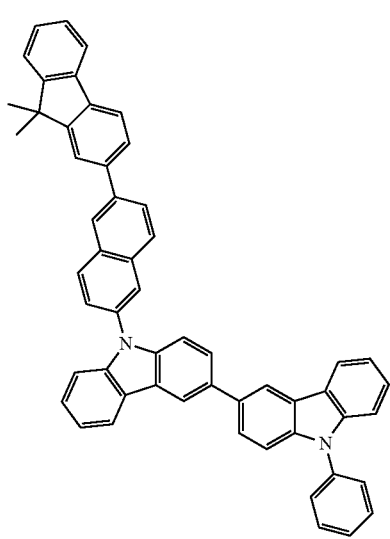
-continued
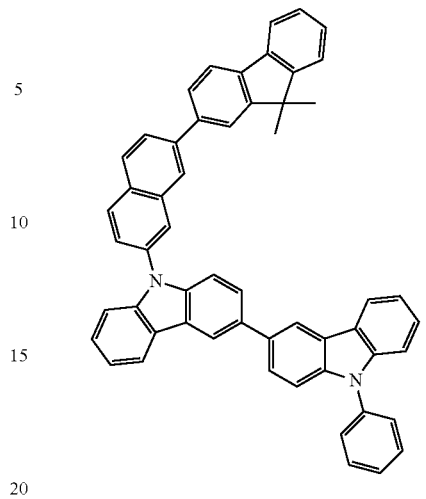
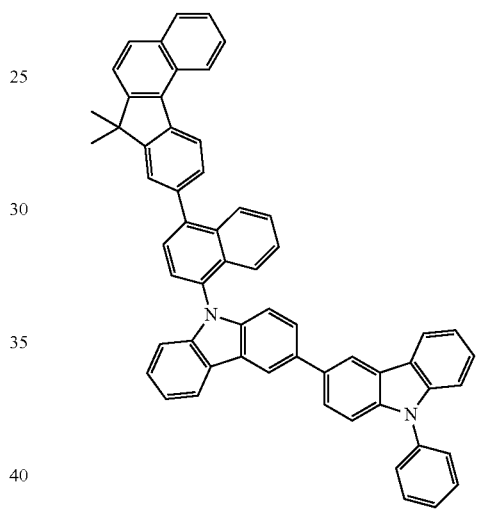
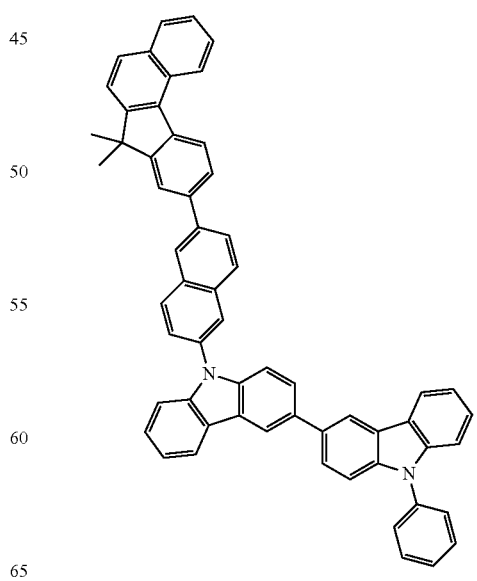

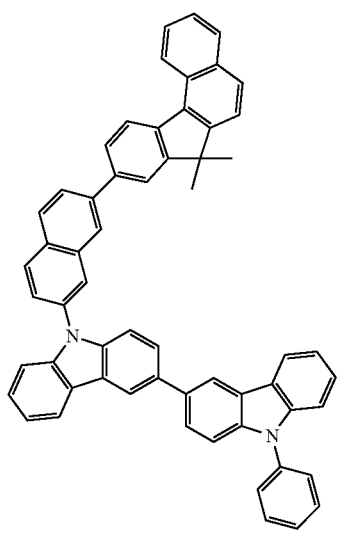
[Formula 176]
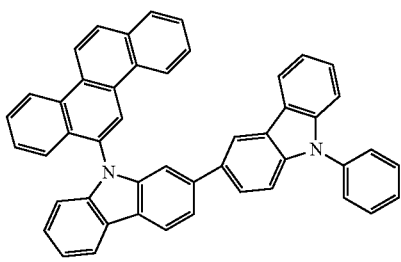
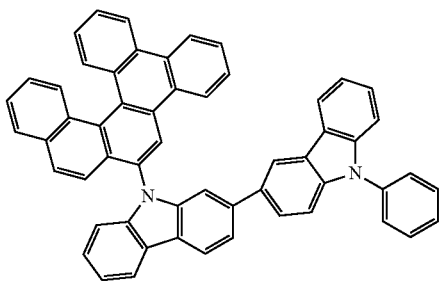
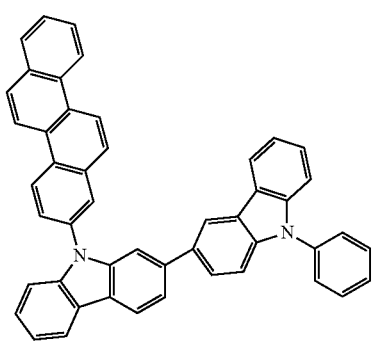
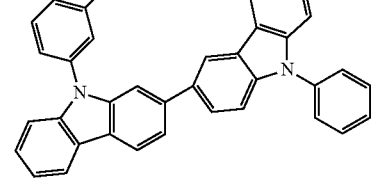
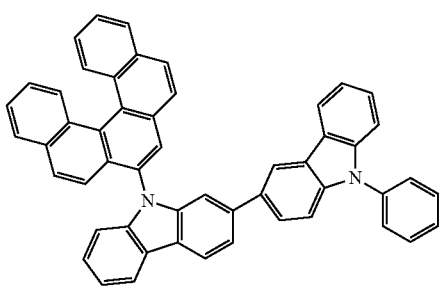
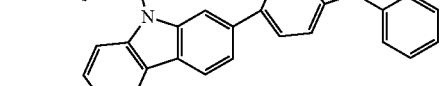
[Formula 177]
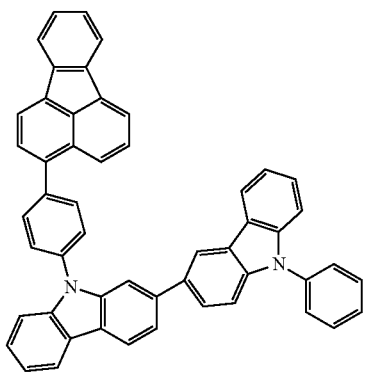

383
-continued
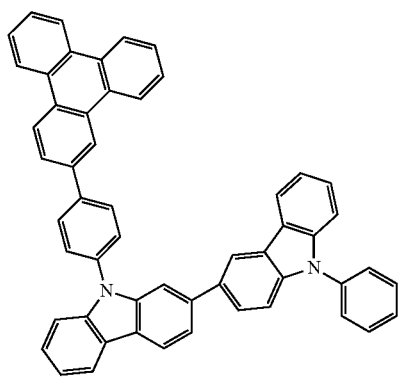
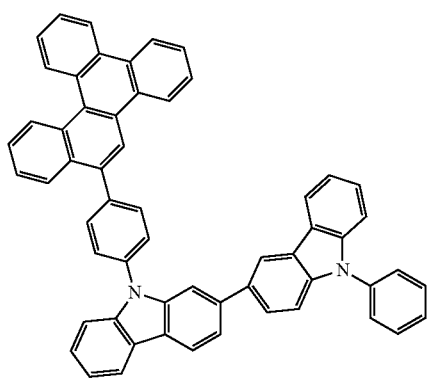
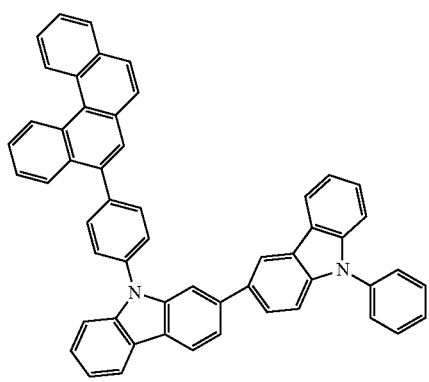
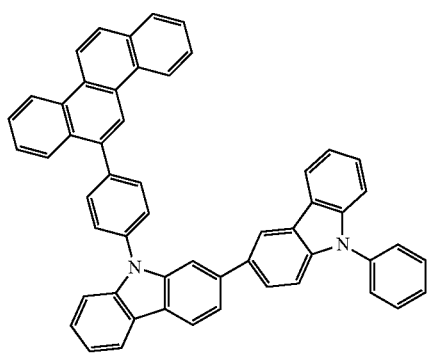
384
-continued
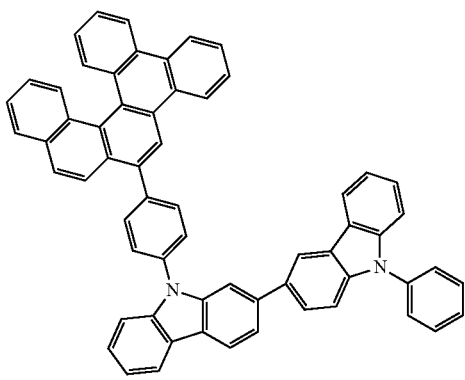
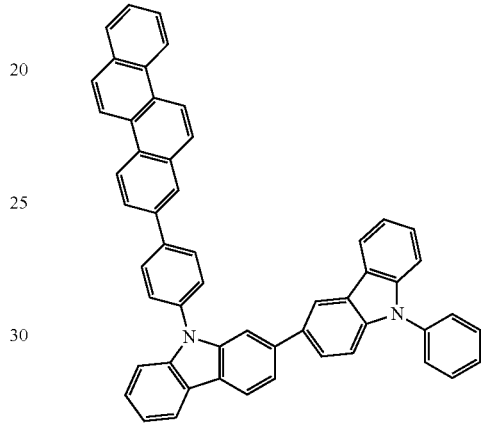
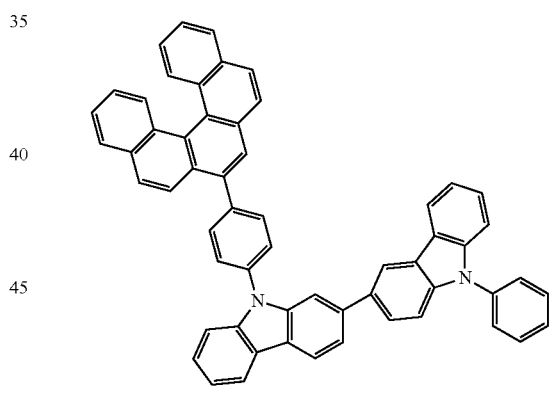
[Formula 178]
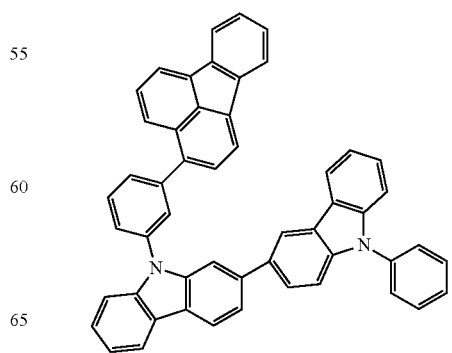

385
-continued
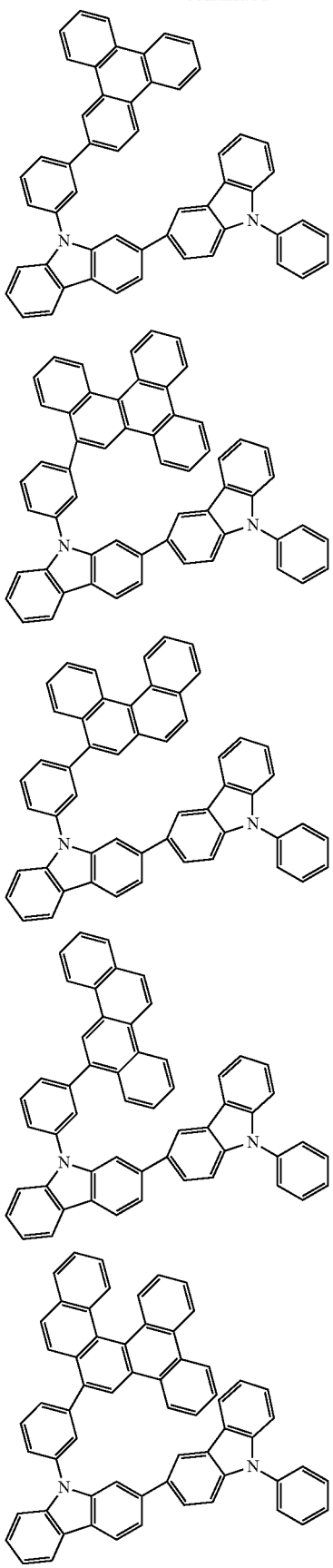
386
-continued
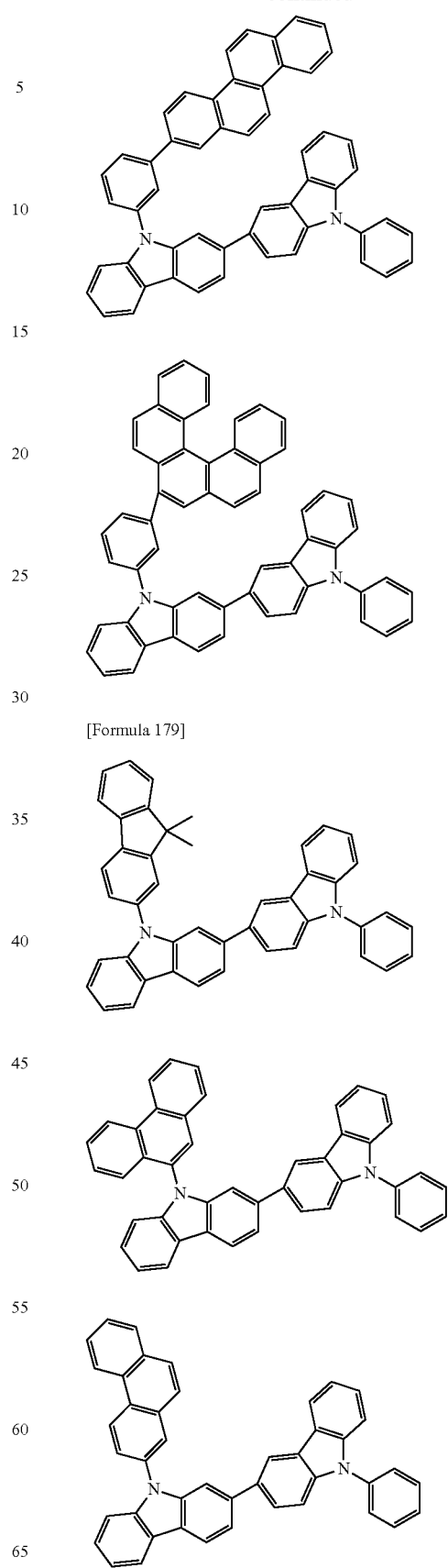
[Formula 179]

387
-continued
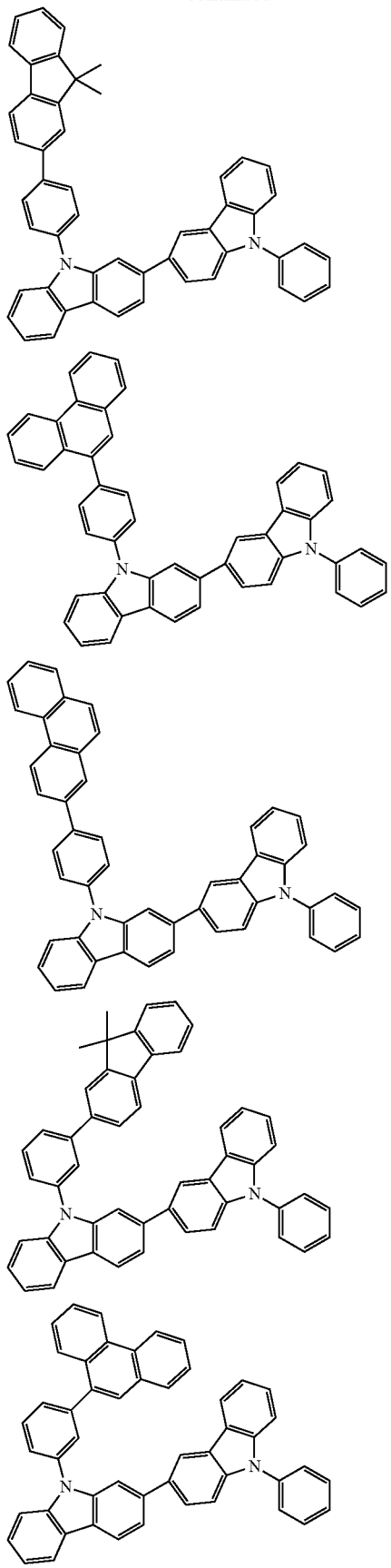
388
-continued
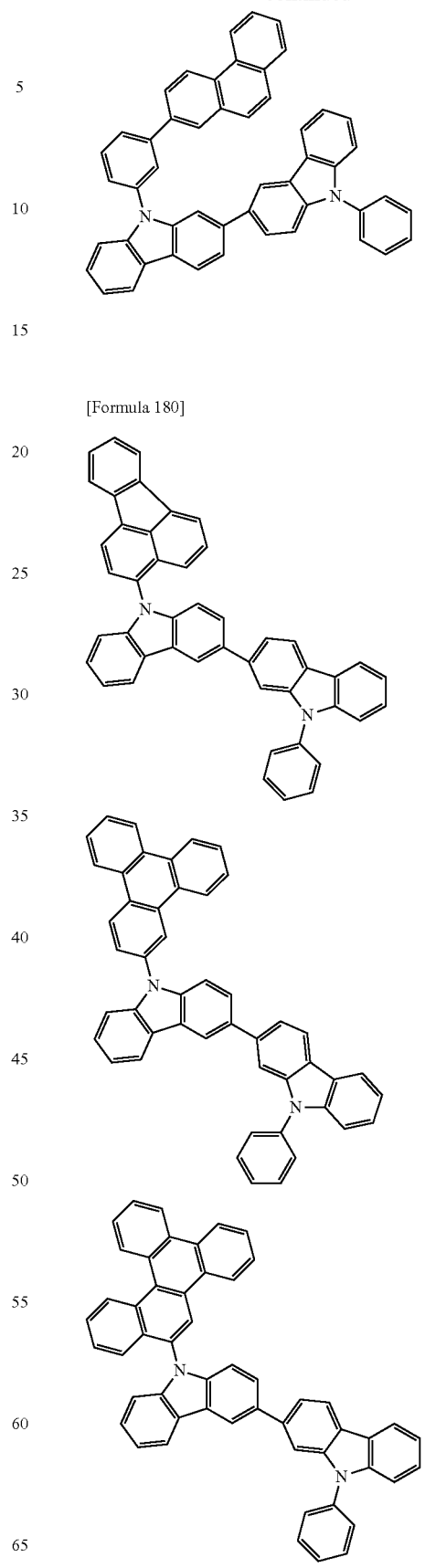
[Formula 180]

389
-continued
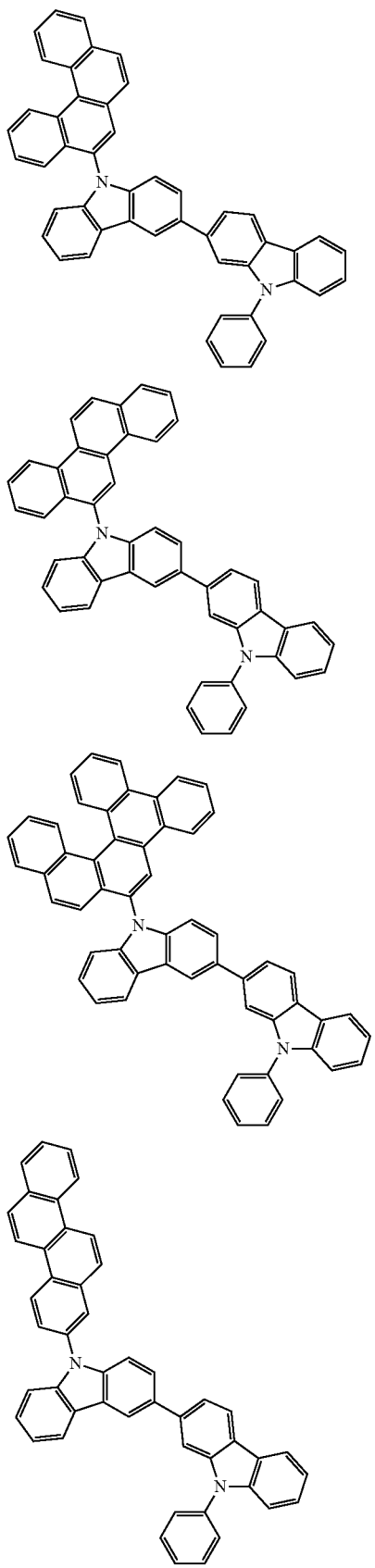
390
-continued
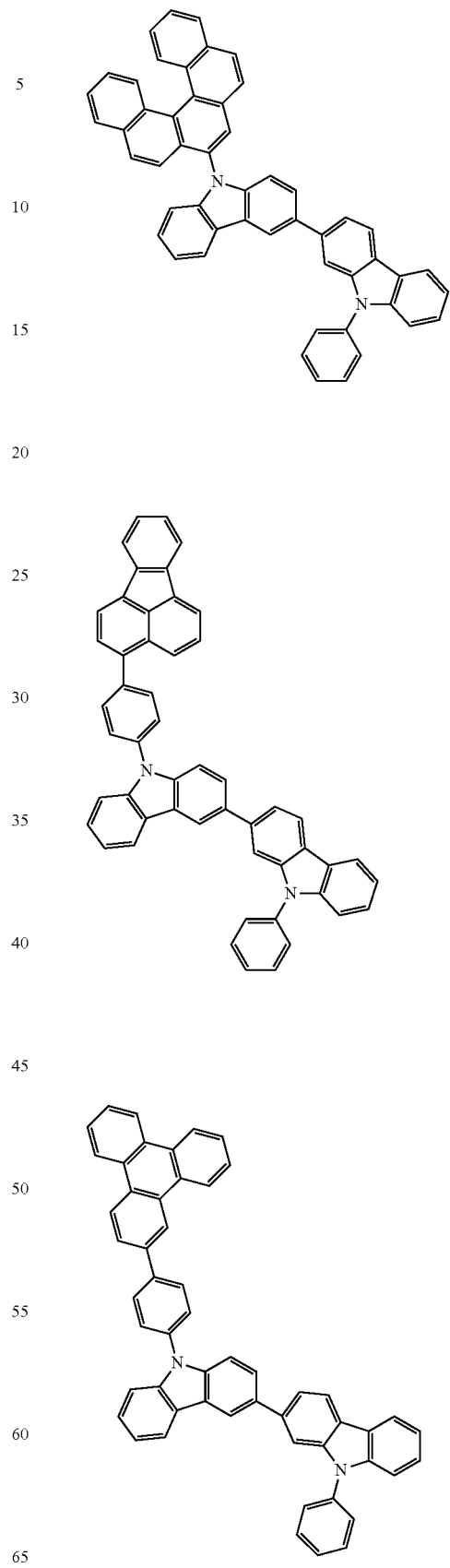

391
-continued
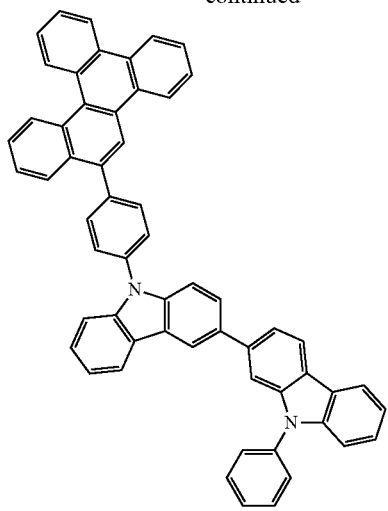
[Formula 181]
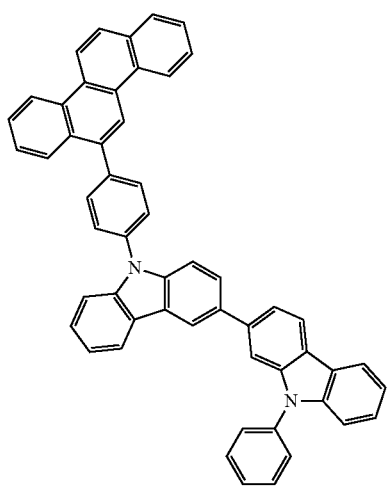
392
-continued
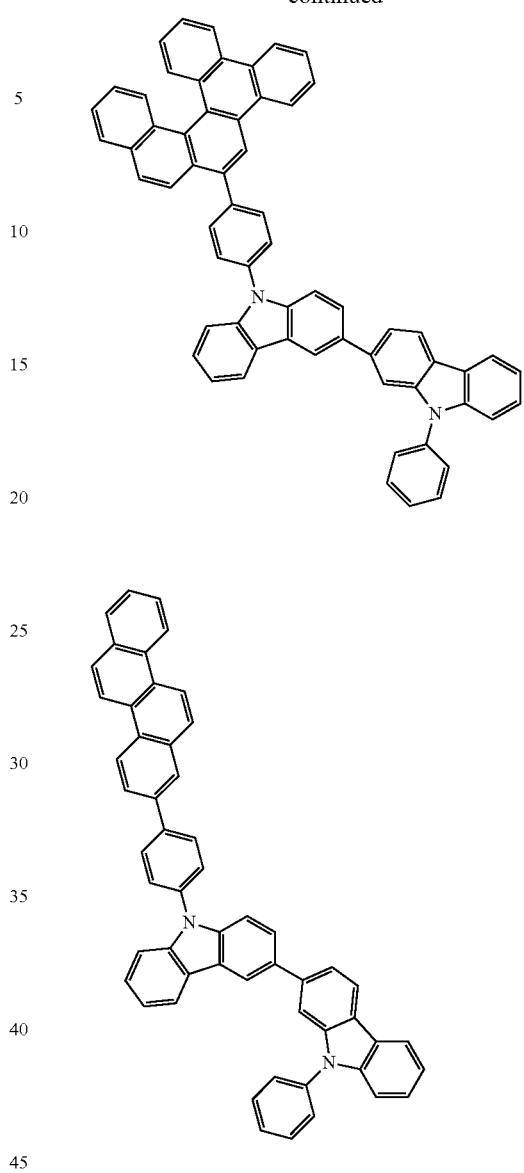

393
-continued
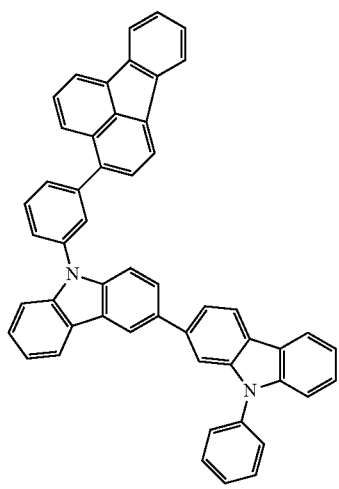
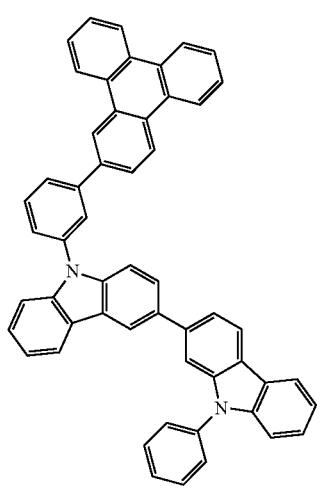
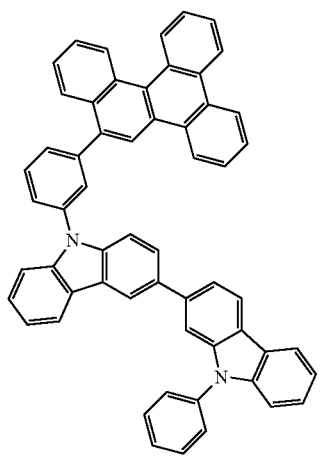
394
-continued
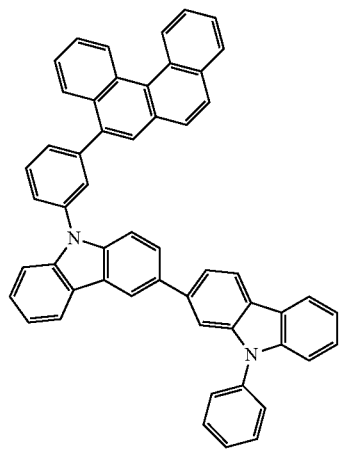
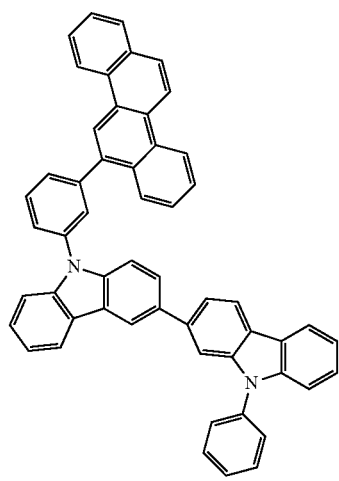
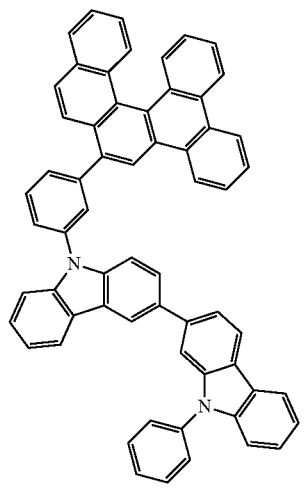

395
-continued
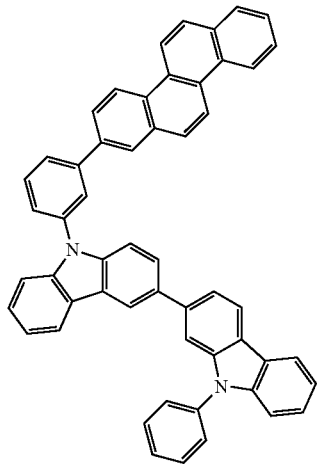
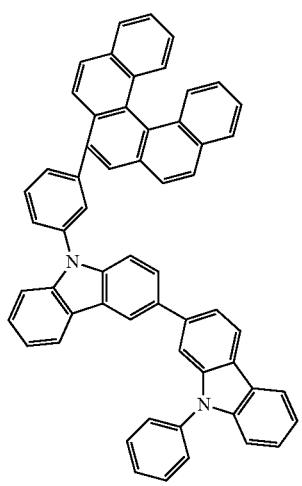
[Formula 182]
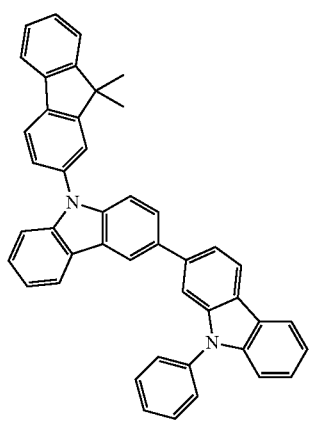
396
-continued
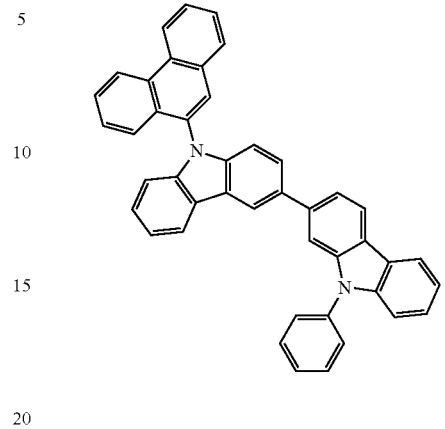
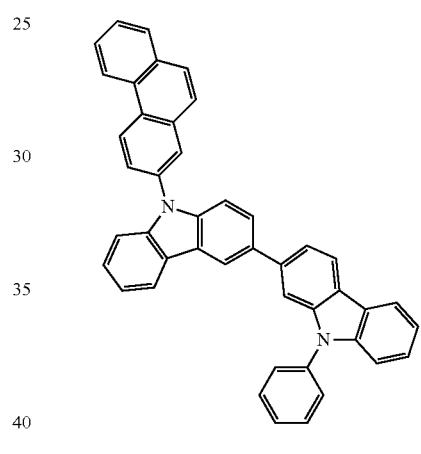
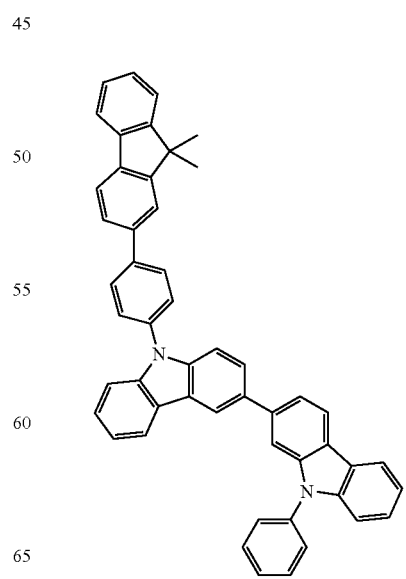

397
-continued
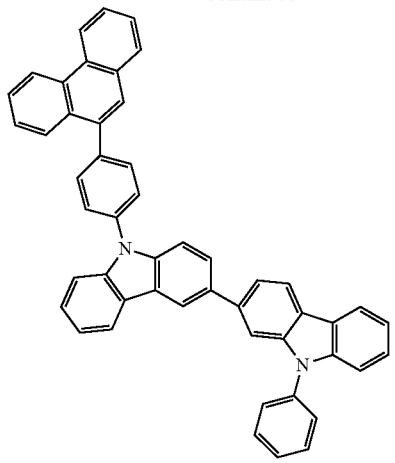
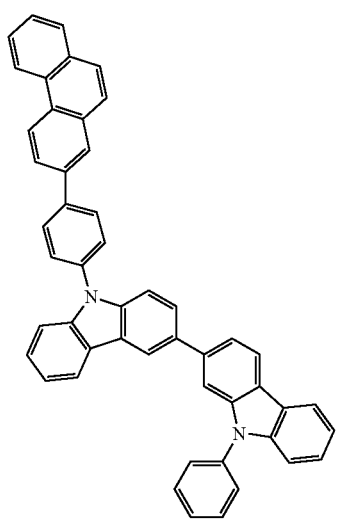
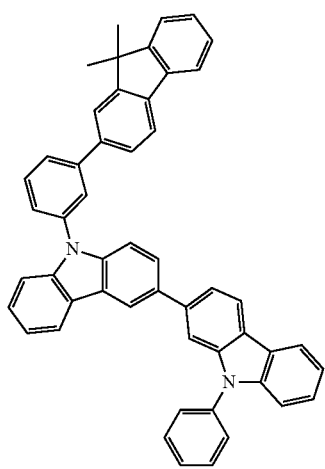
398
-continued
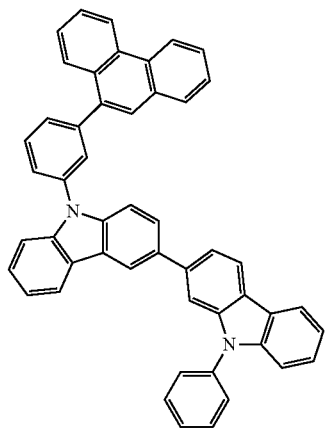
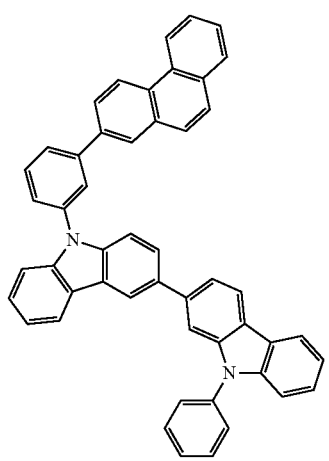
[Formula 183]
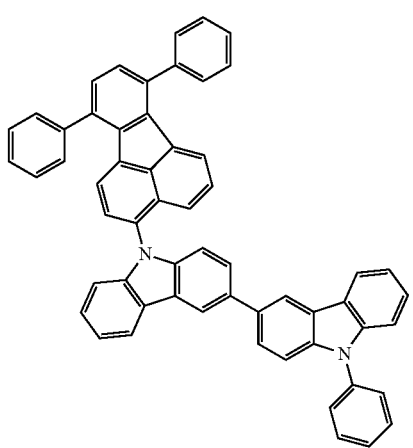

399
-continued
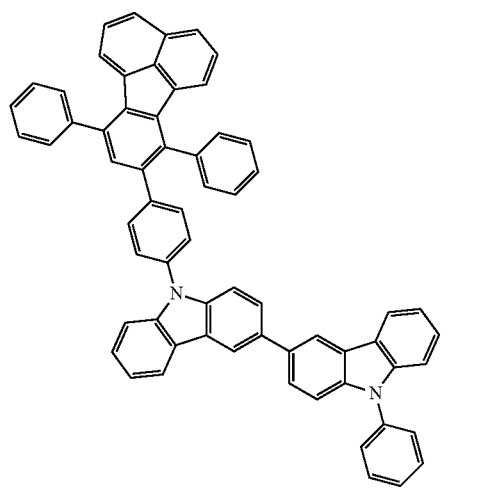
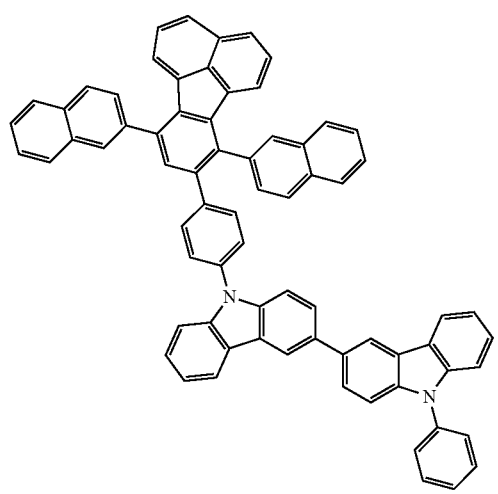
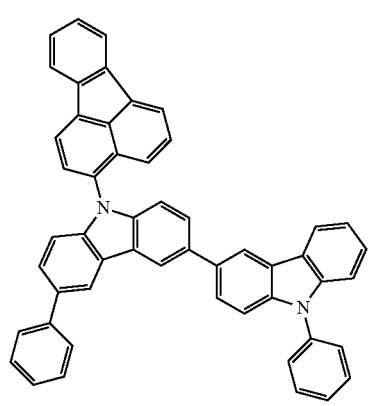
400
-continued
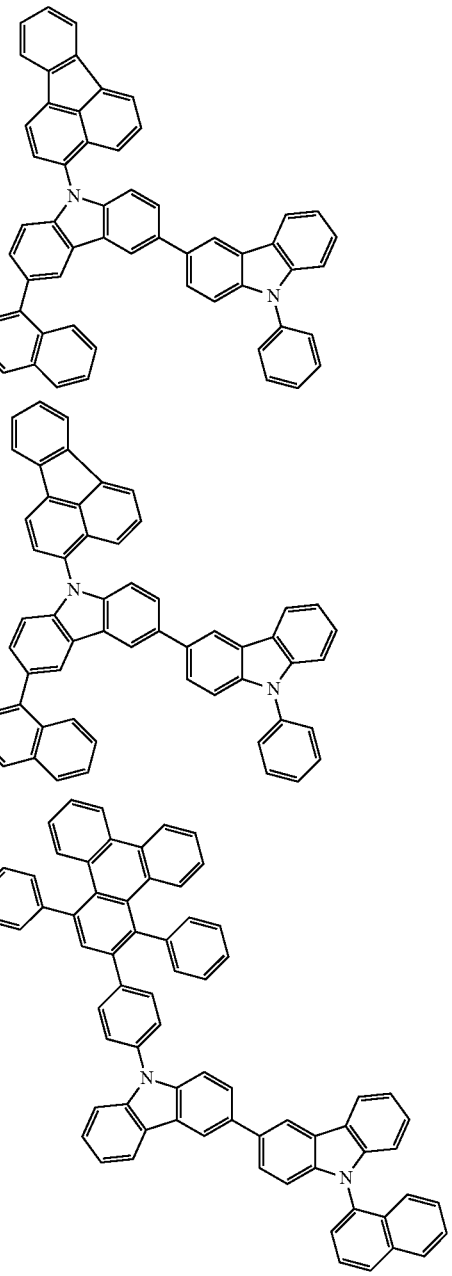
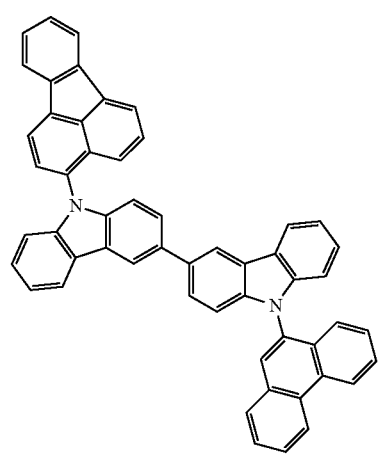

401
-continued
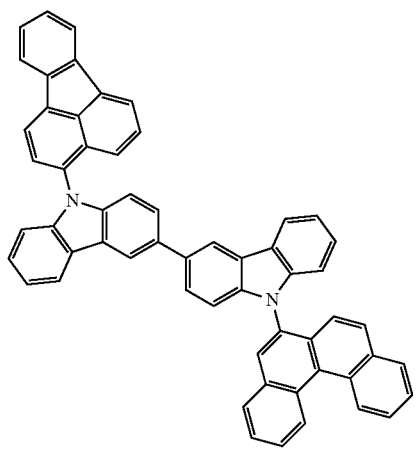
[Formula 184]
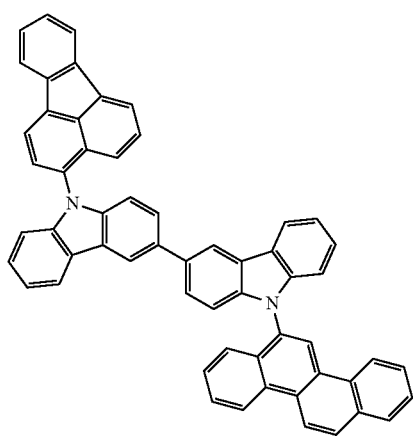
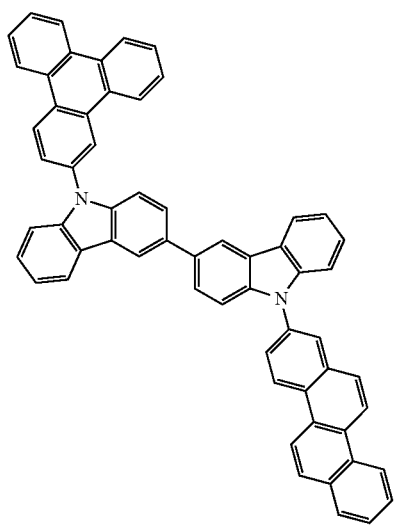
402
-continued
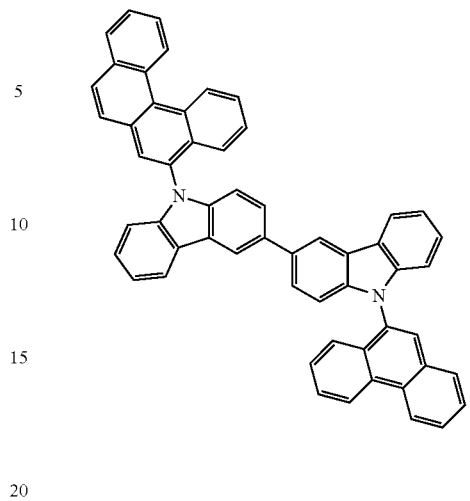
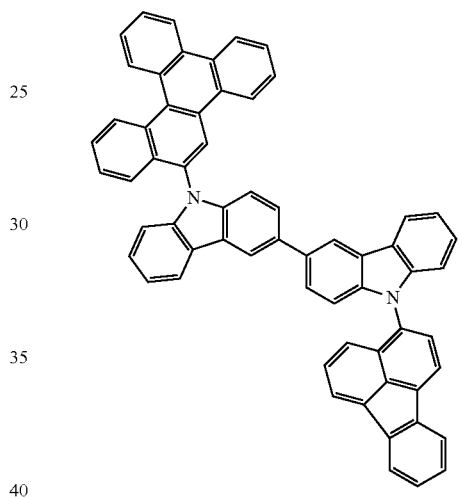
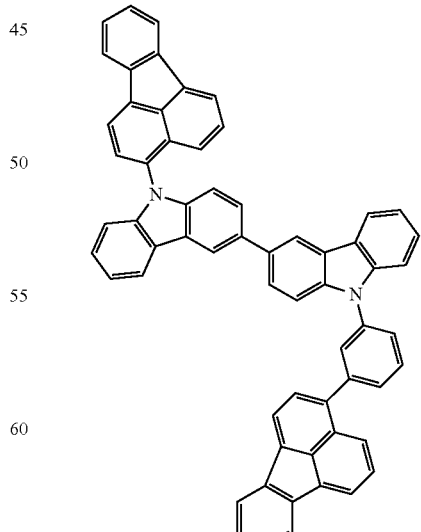

403
-continued
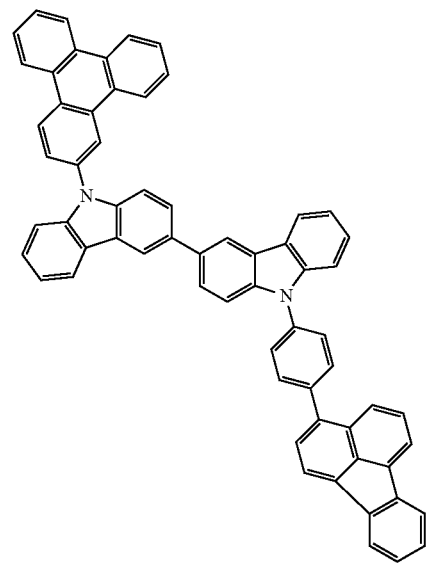
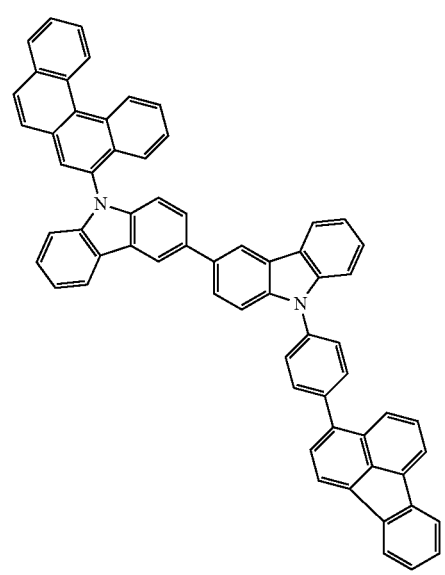
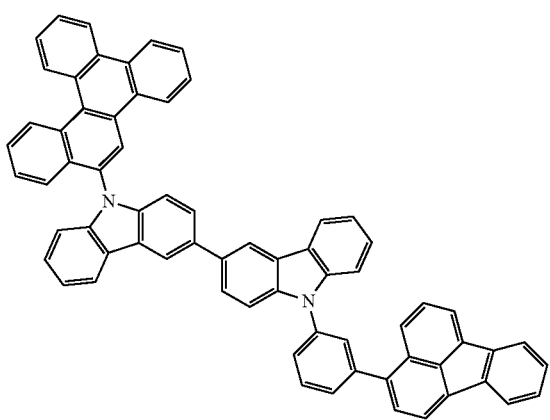
404
-continued
[Formula 185]
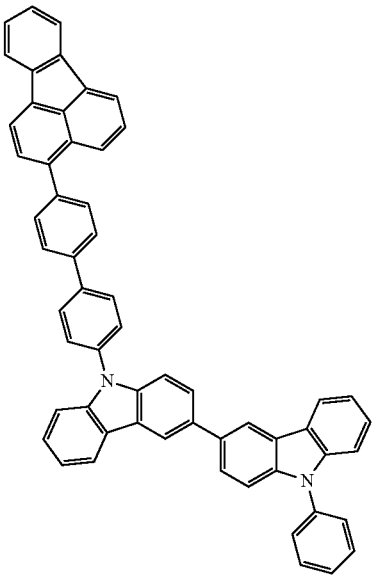
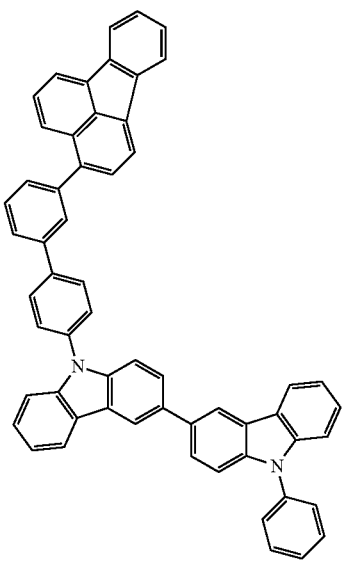

405
-continued
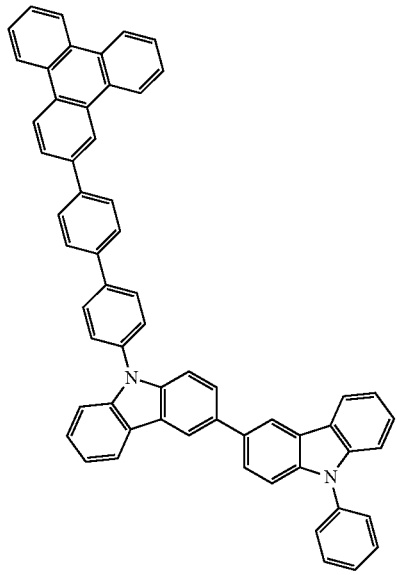
406
-continued
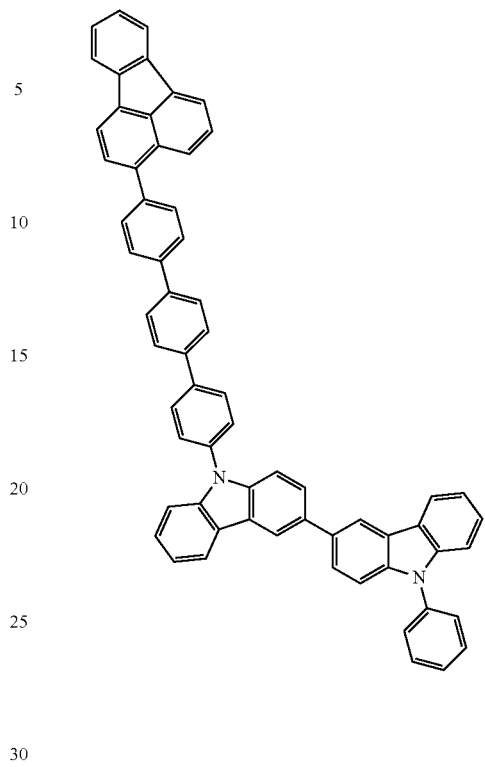
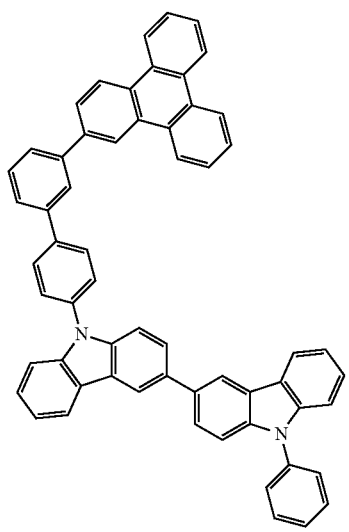
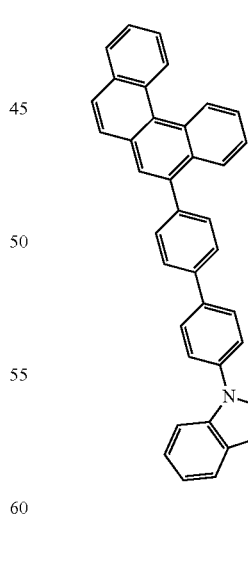

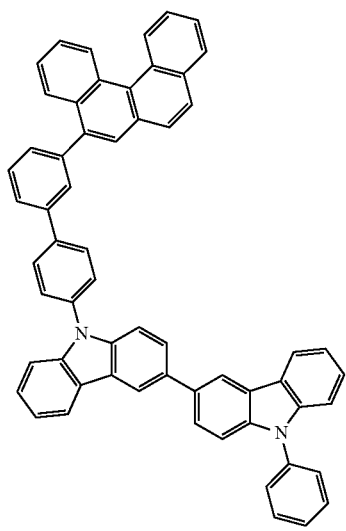
[Formula 186]
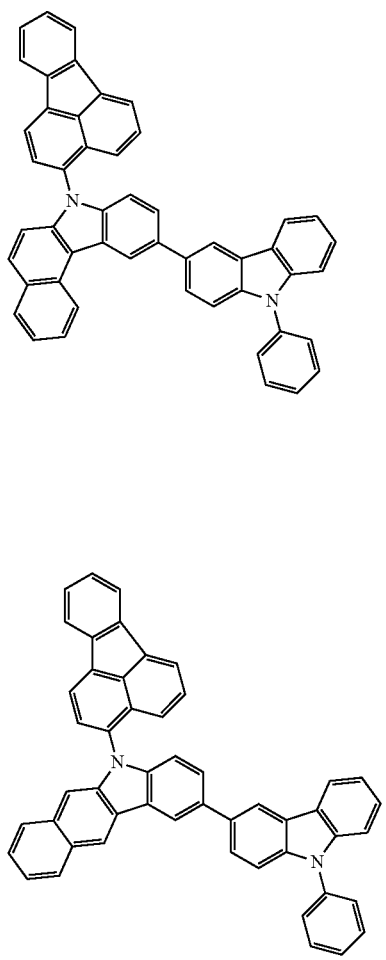
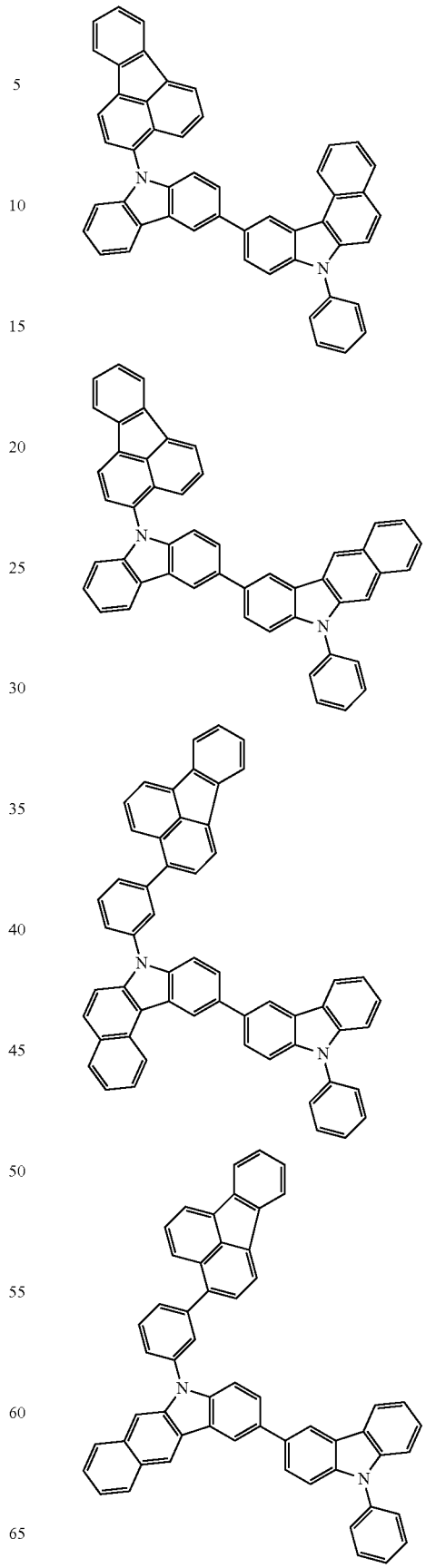

409
-continued
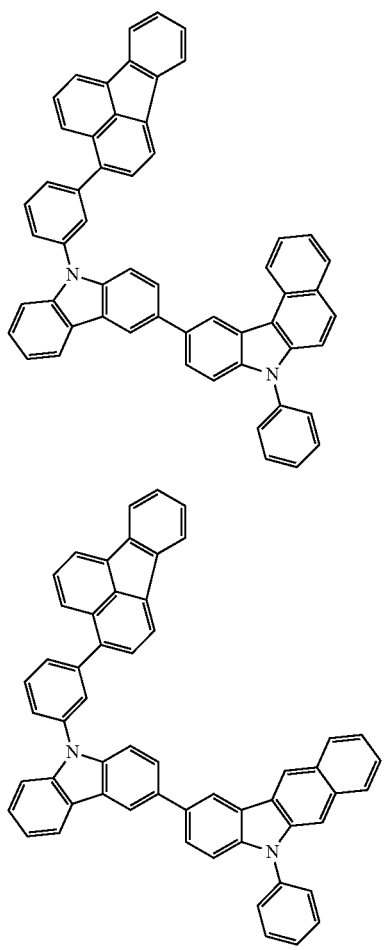
[Formula 187]
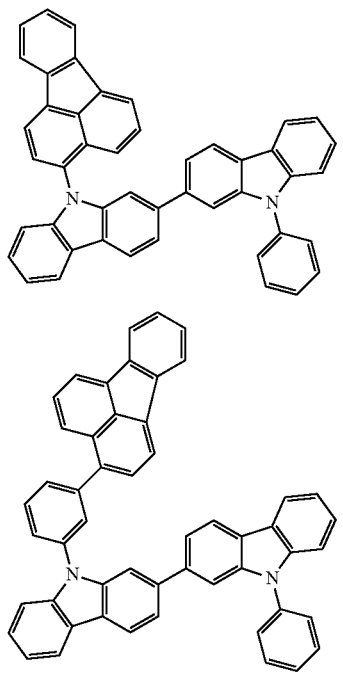
410
-continued
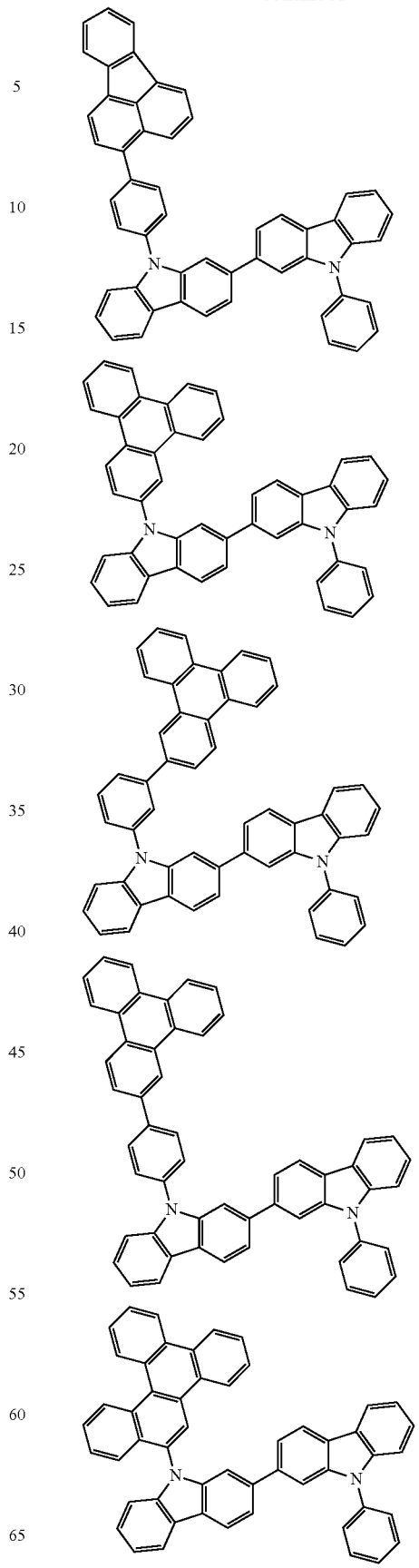

US 10,128,456 B2
411
-continued
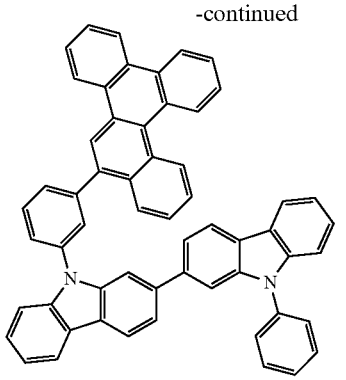
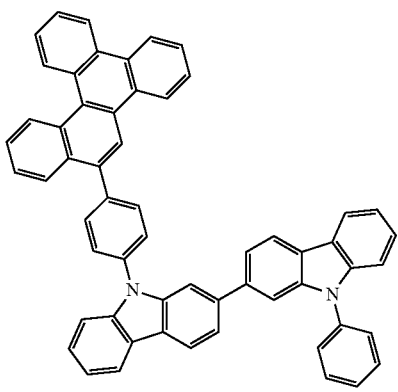 [SMILES: c1ccc(-n2c3ccccc3c3ccc(-c4ccc5c6ccccc6n(-c6ccc(-c7cc8c9ccccc9c9ccccc9c8c8ccccc78)cc6)c5c4)cc32)cc1]
[Formula 188]
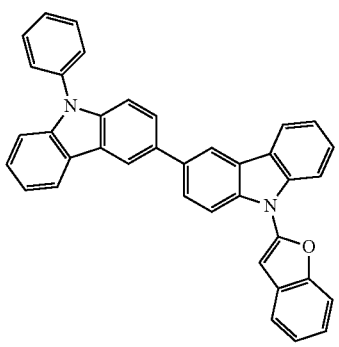
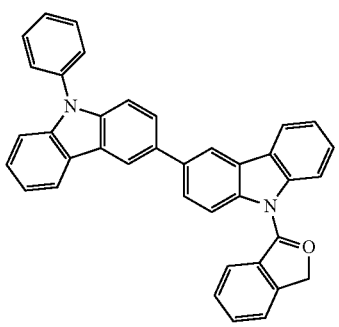
412
-continued
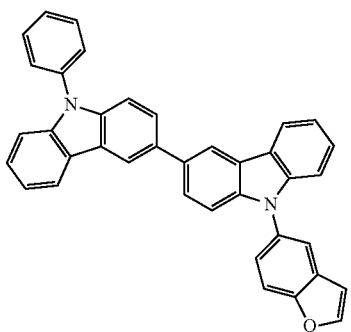
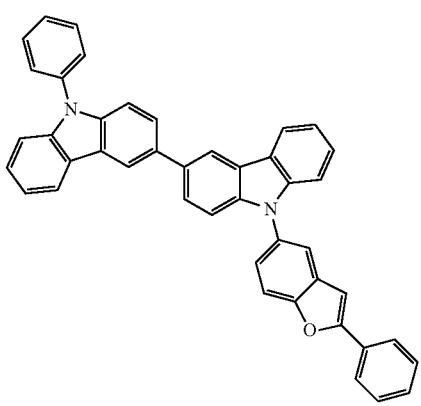
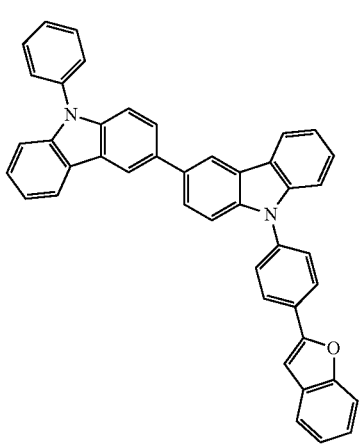
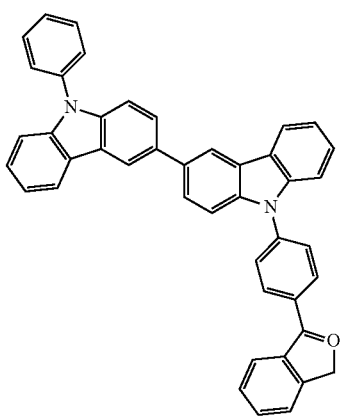

413
-continued
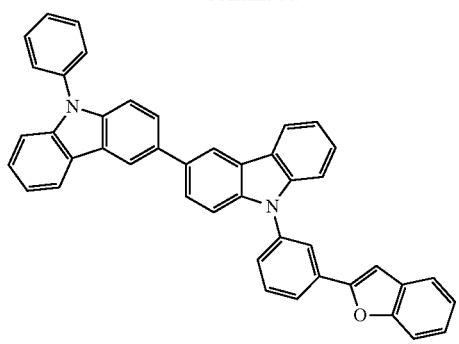
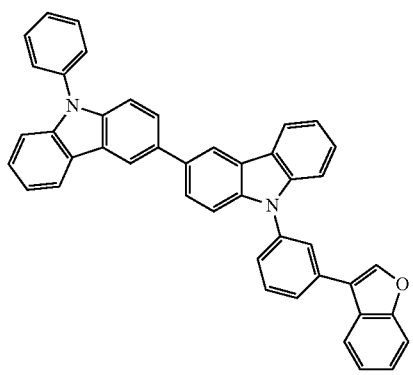
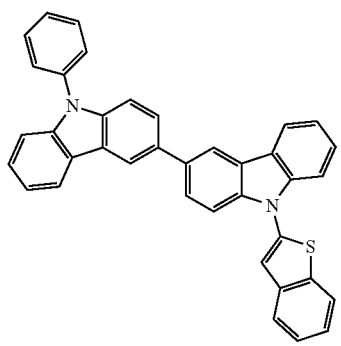
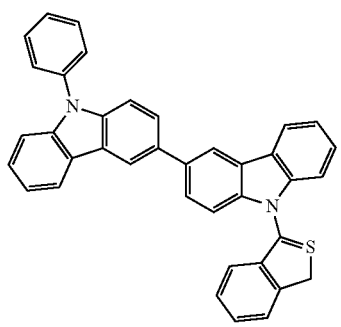
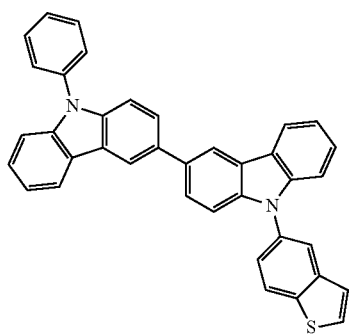
414
-continued
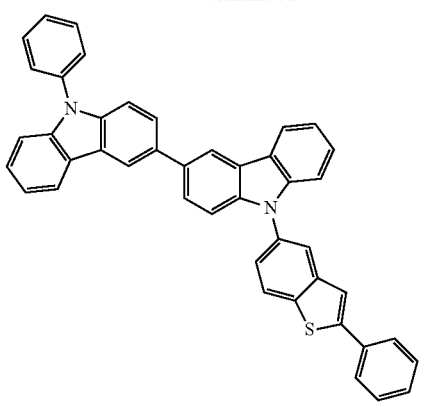
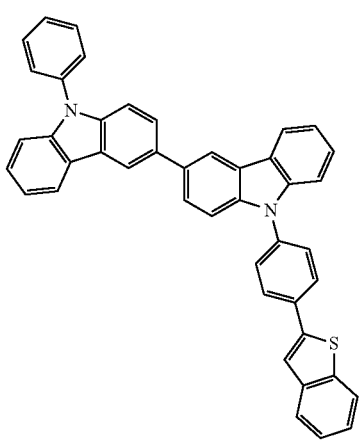
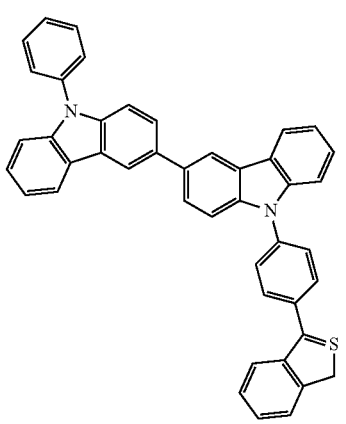
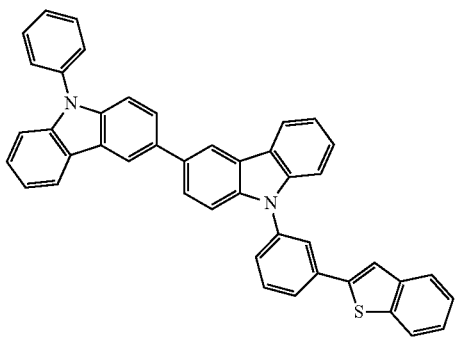

415
-continued
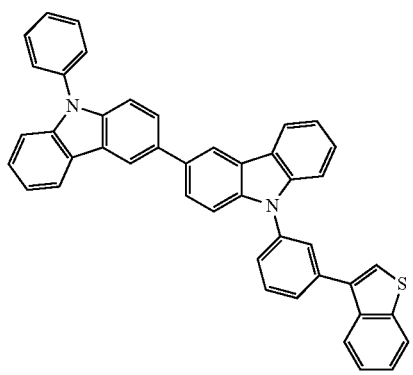
[Formula 189]
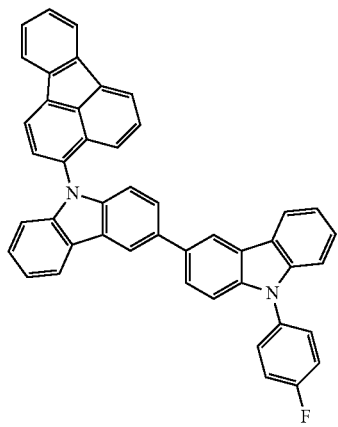
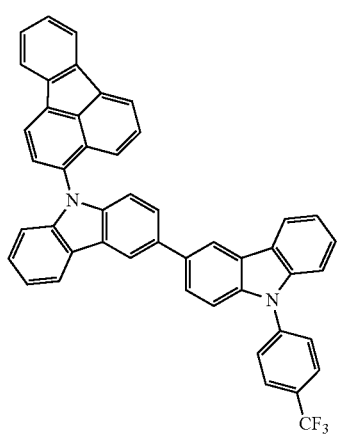
416
-continued
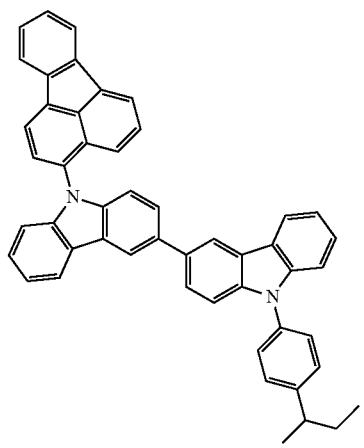
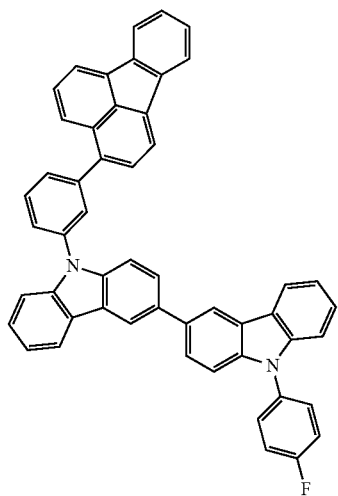

417
-continued
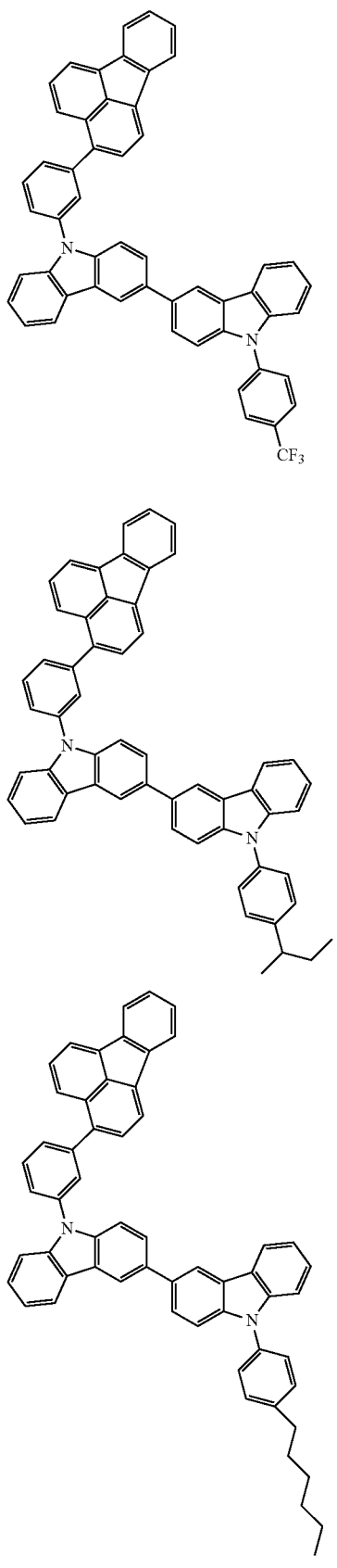
418
-continued
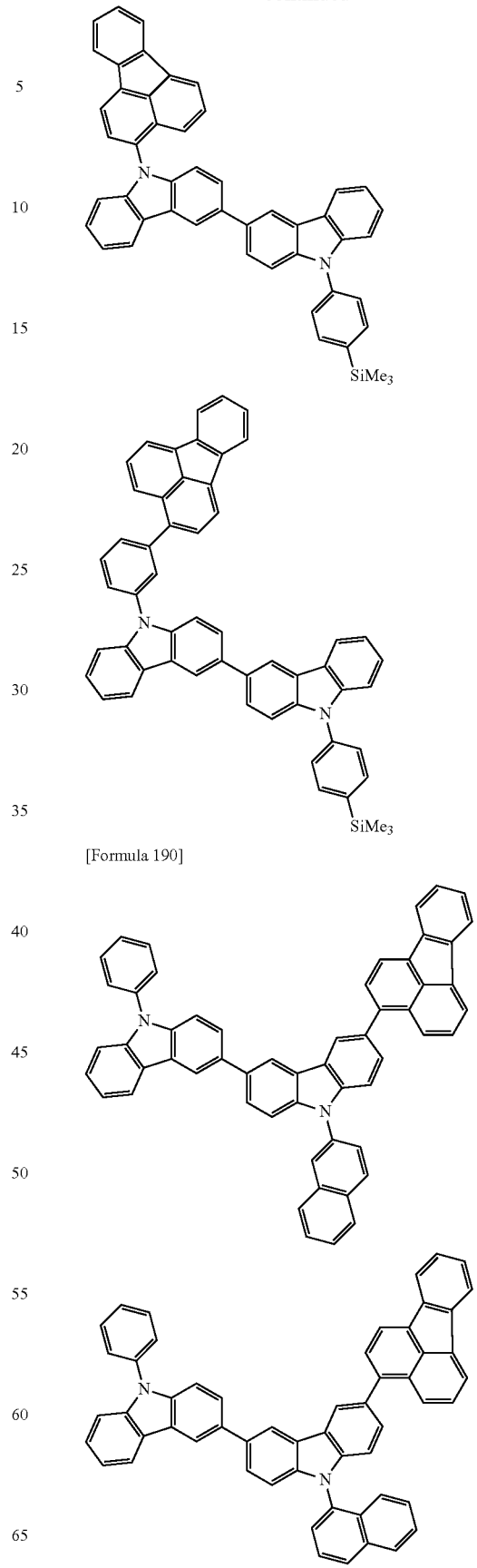
[Formula 190]

419
-continued
420
-continued
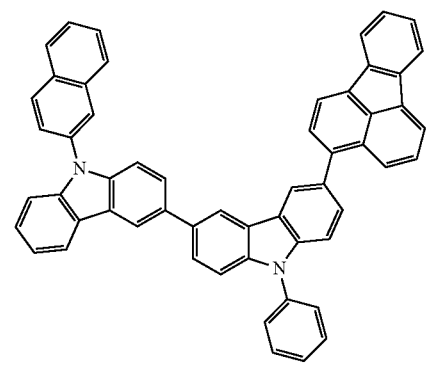
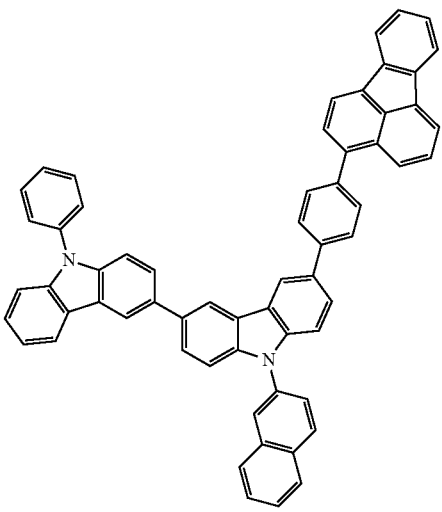
[Formula 191]
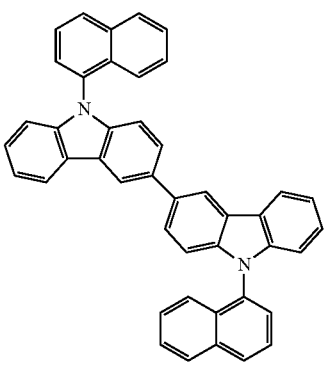
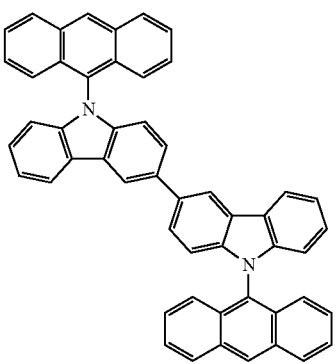

421
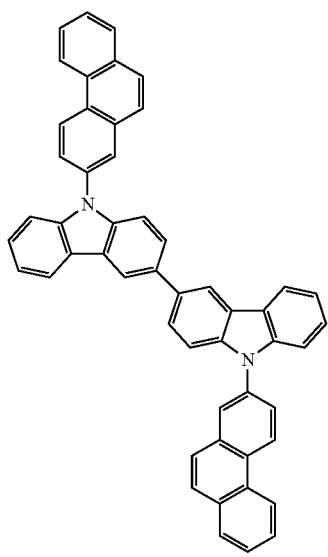
422
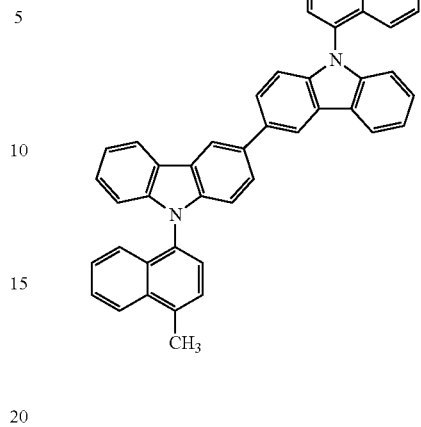
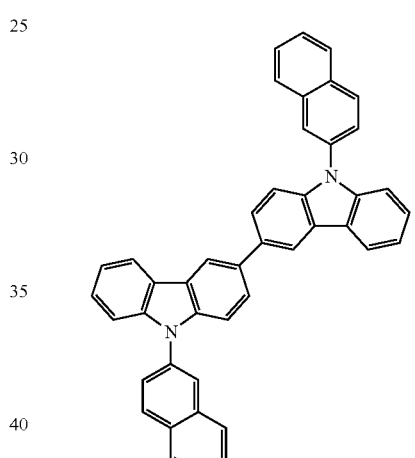
[Formula 192]
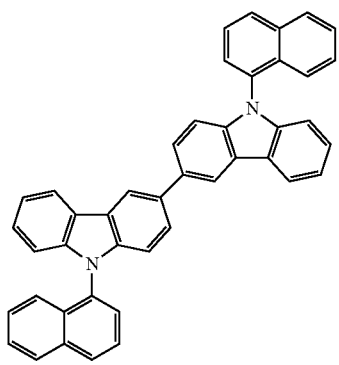
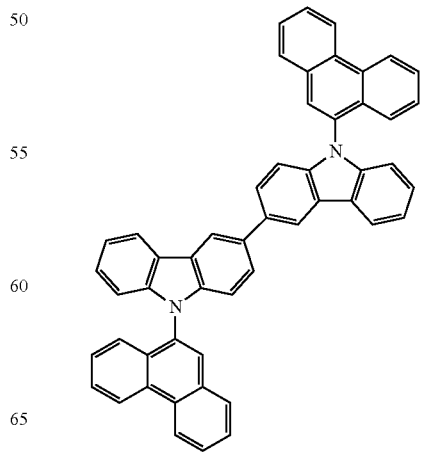

423
-continued
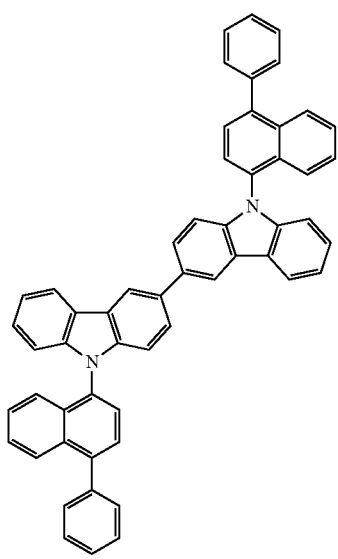
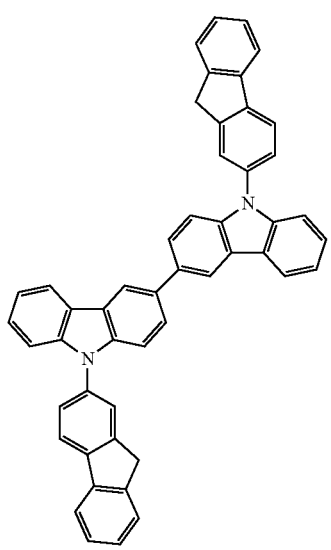
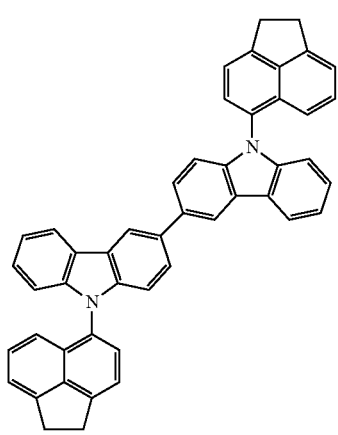
424
-continued
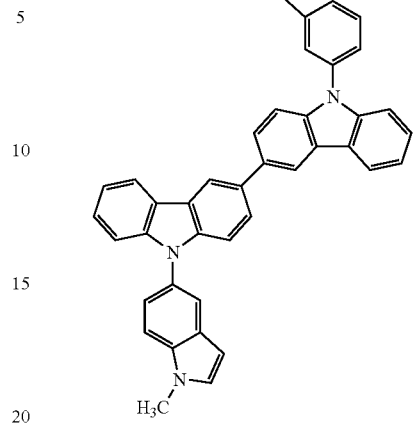
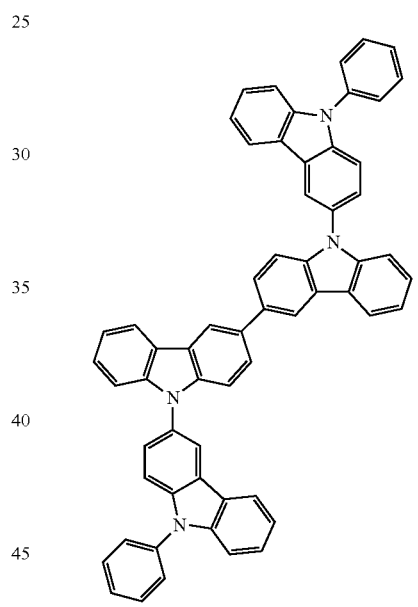
[Formula 193]
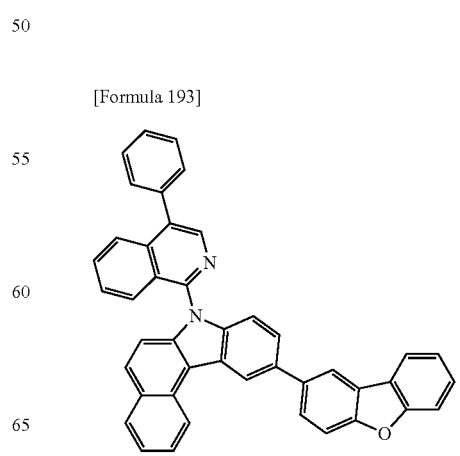

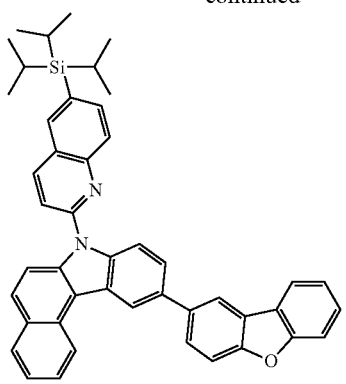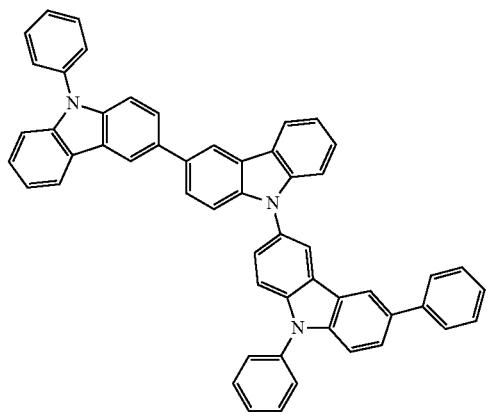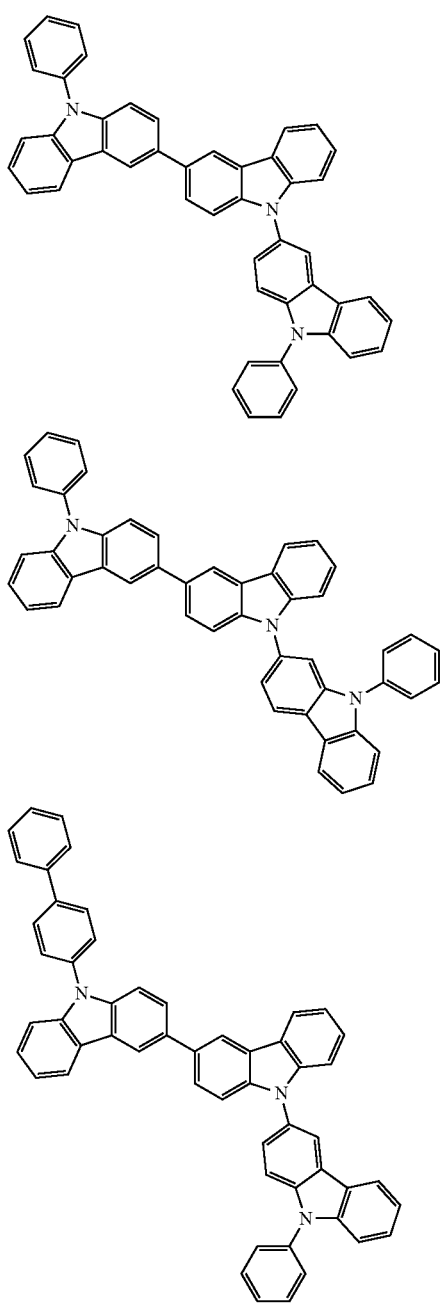

427
-continued
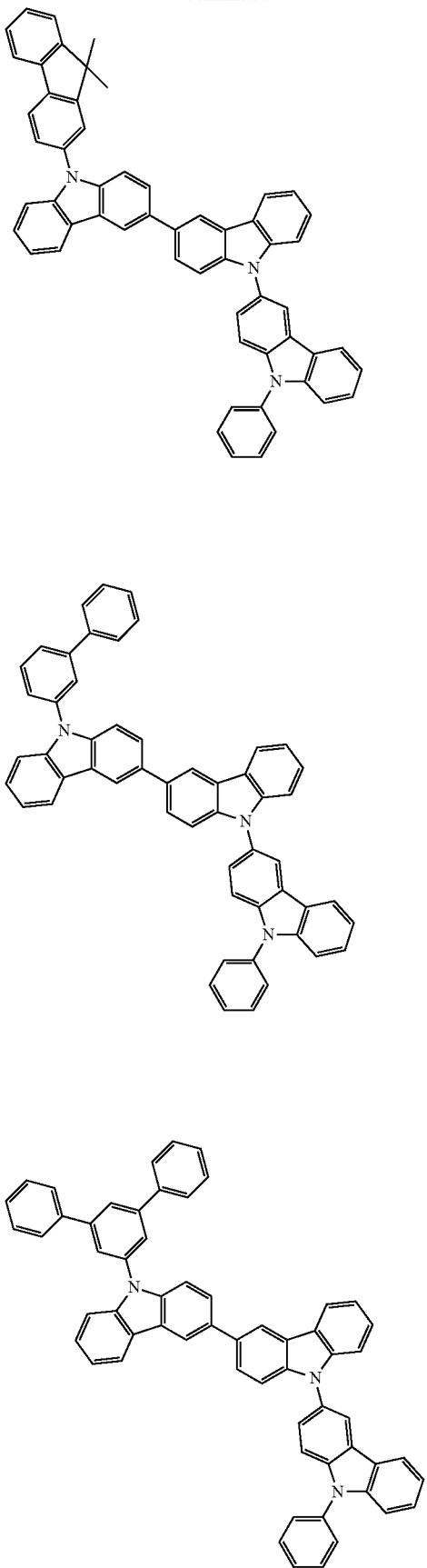
428
-continued
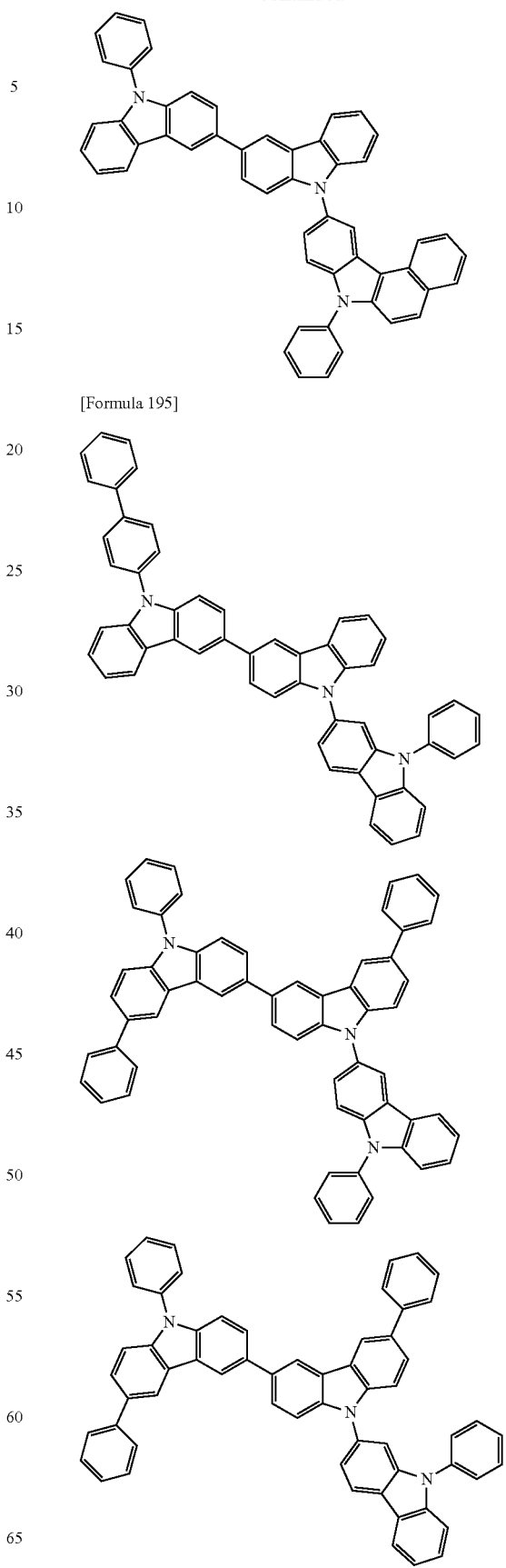
[Formula 195]

429
-continued
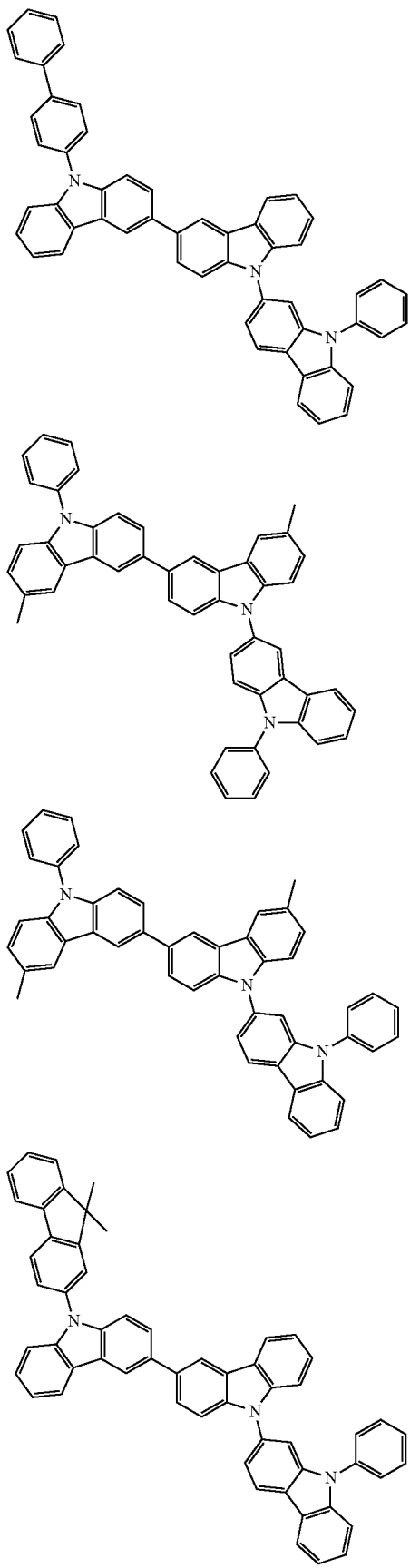
430
-continued
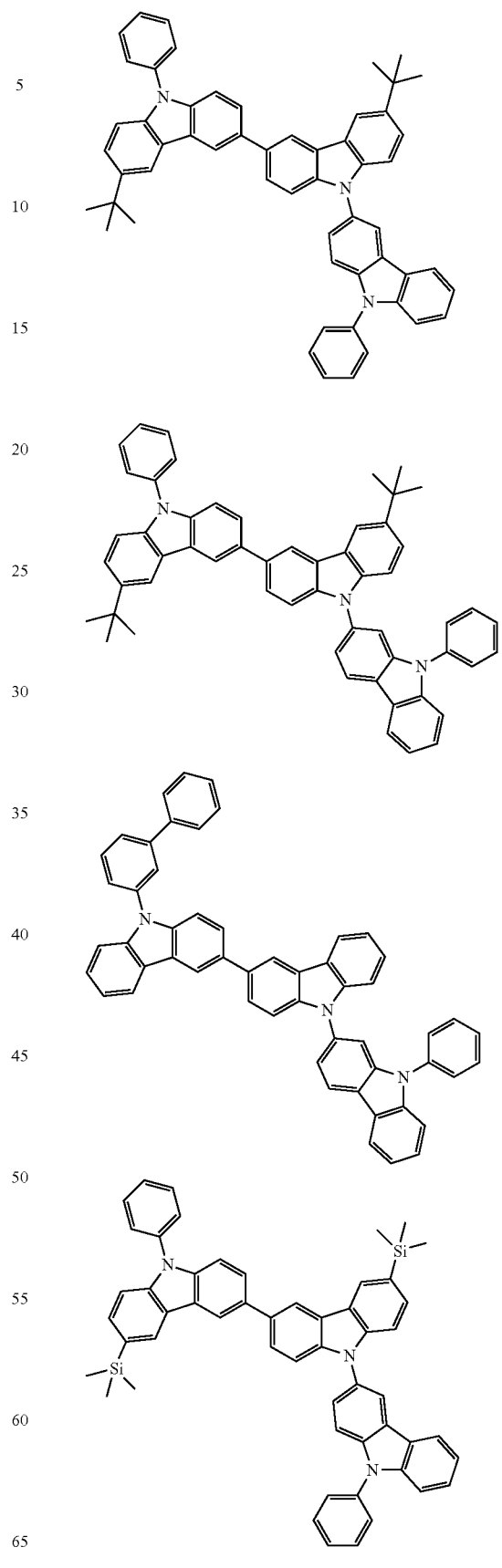

431
-continued
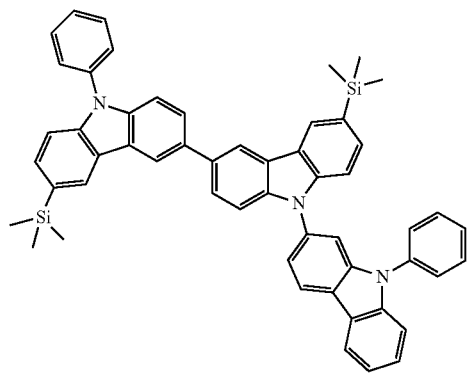
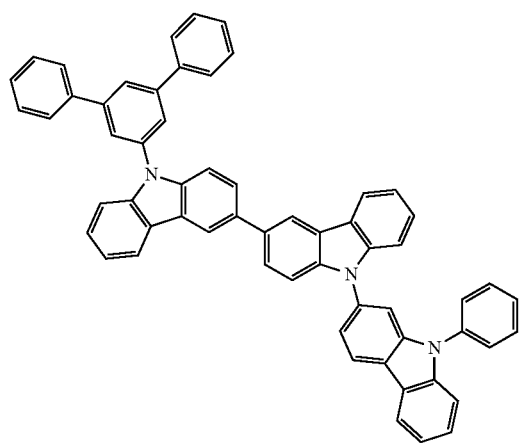
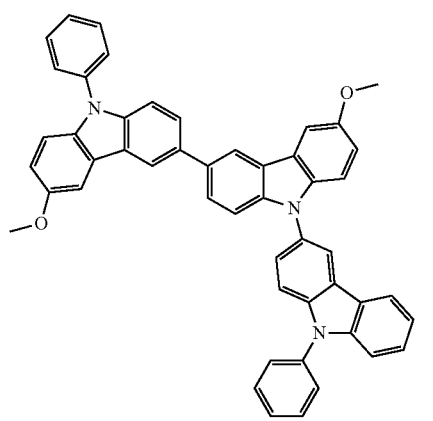
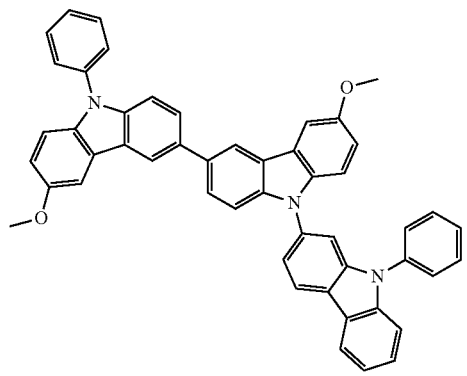
432
-continued
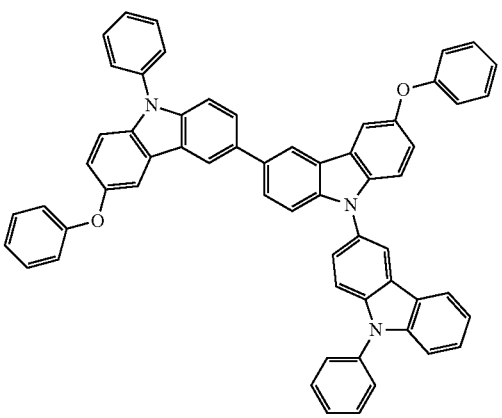
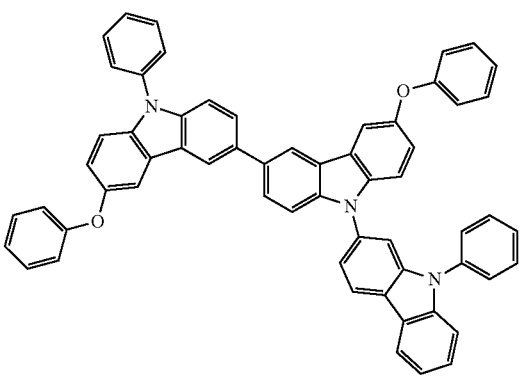 [SMILES: c1ccc(Cc2ccc3c(c2)c2cc(-c4ccc5c(c4)c4cc(Cc6ccccc6)ccc4n5-c4ccc5c6ccccc6n(-c6ccccc6)c5c4)ccc2n3-c2ccccc2)cc1]
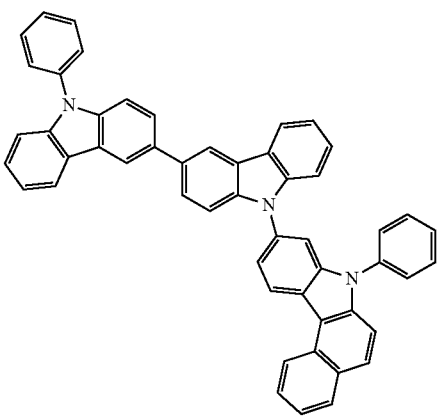
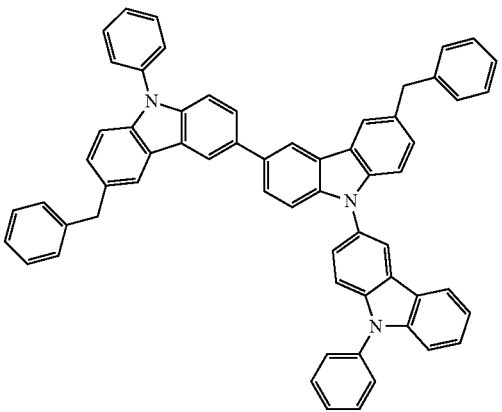

433
-continued
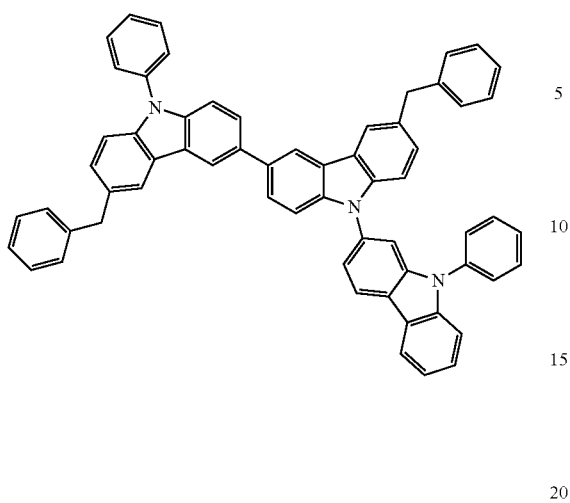
434
-continued
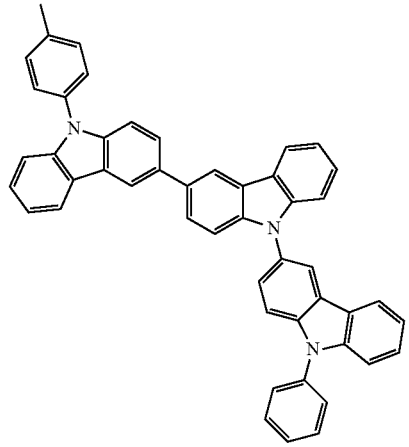
[Formula 196]
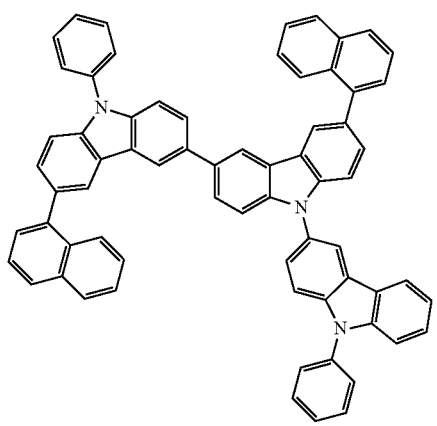
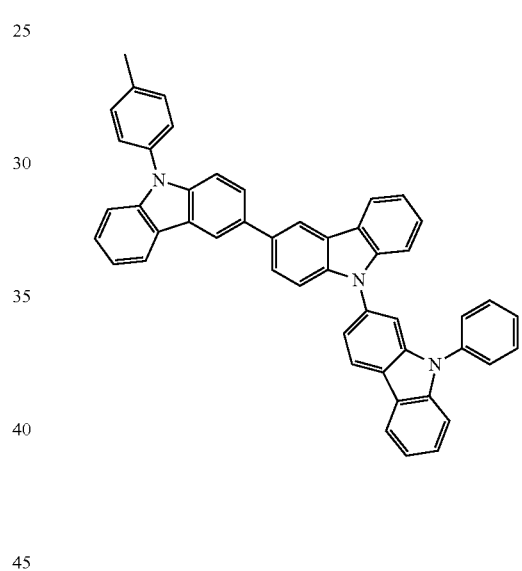
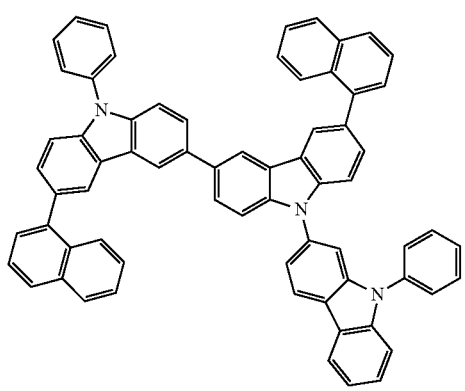
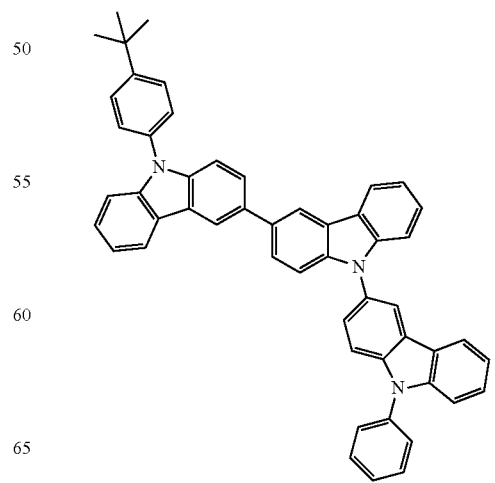

435
-continued
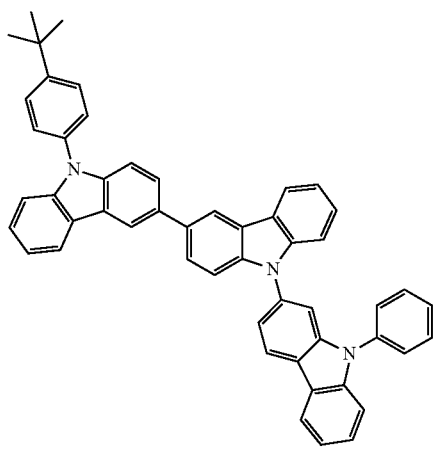
436
-continued
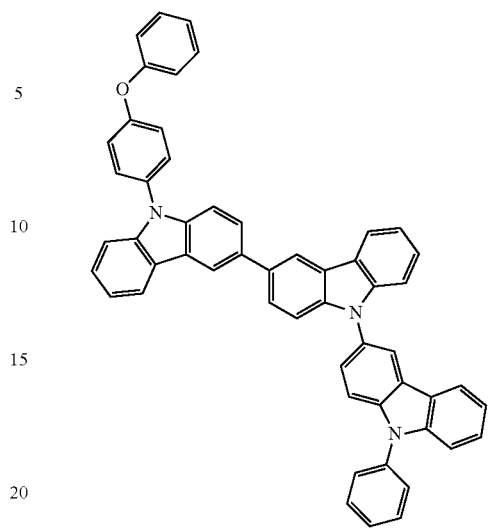
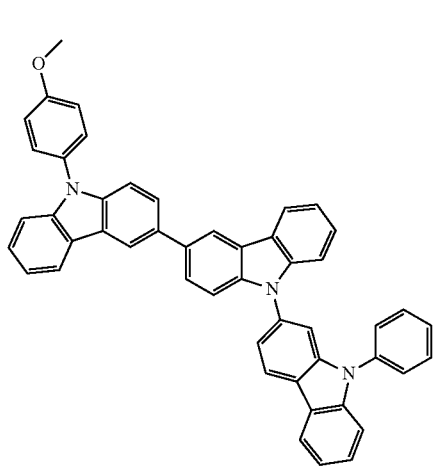
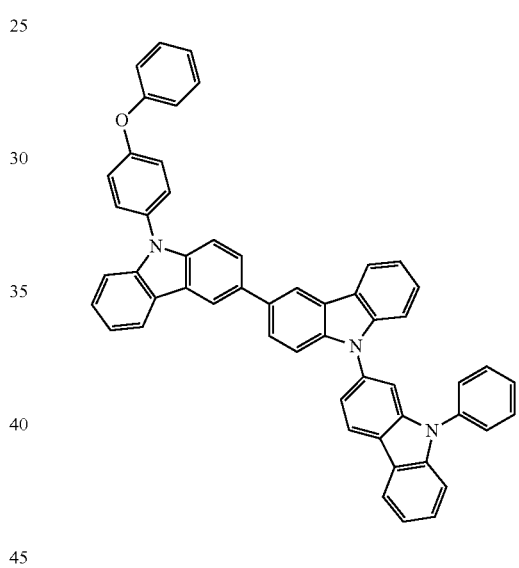

437
-continued
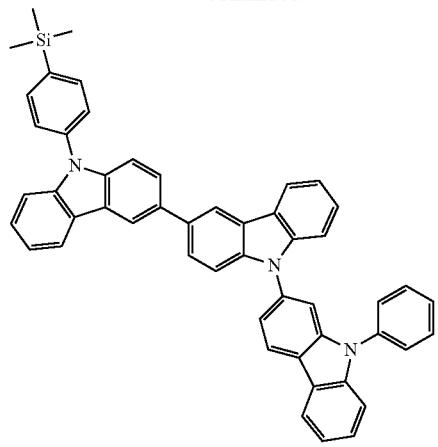
[Formula 197]
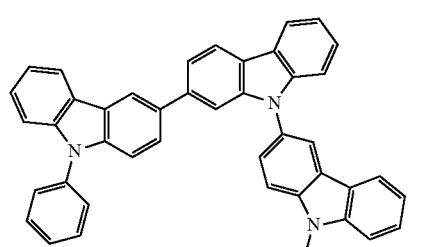
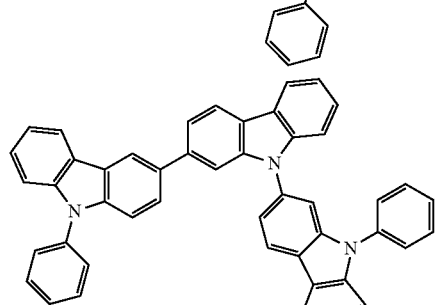
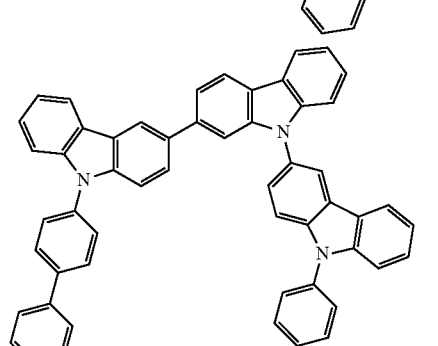
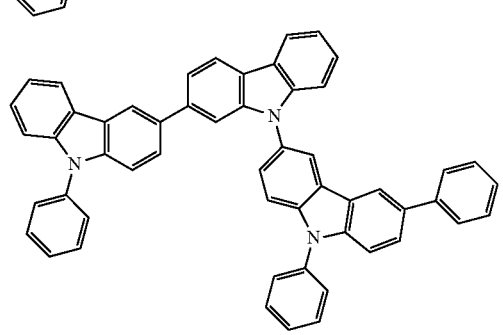
438
-continued
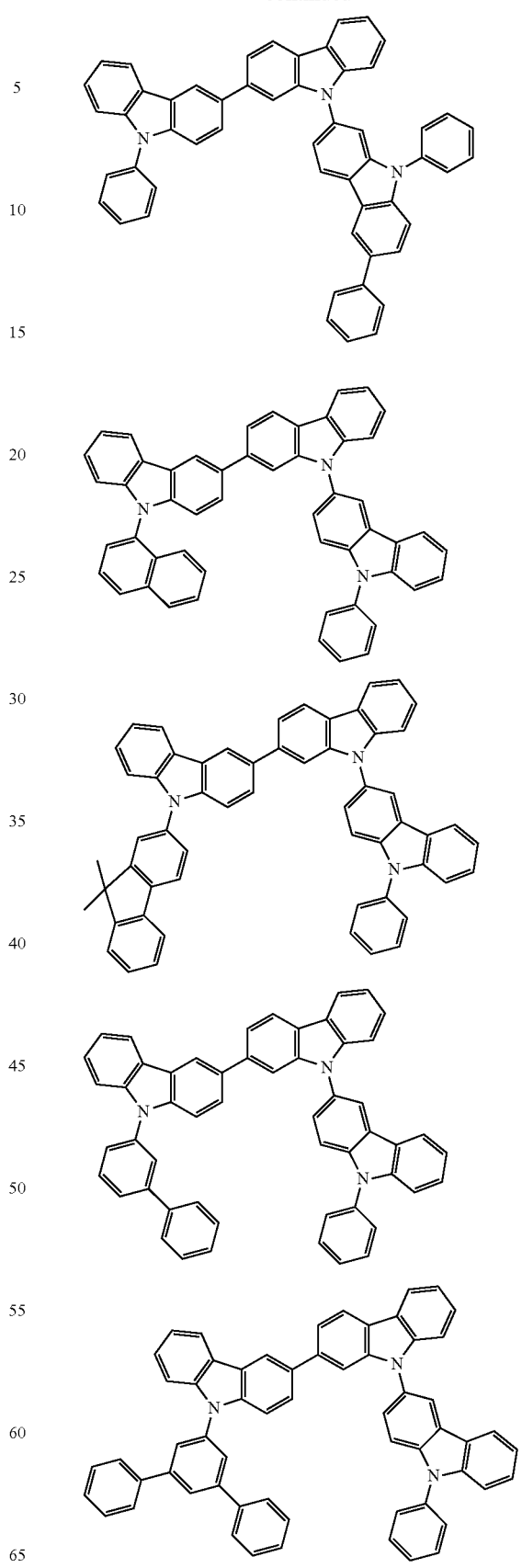

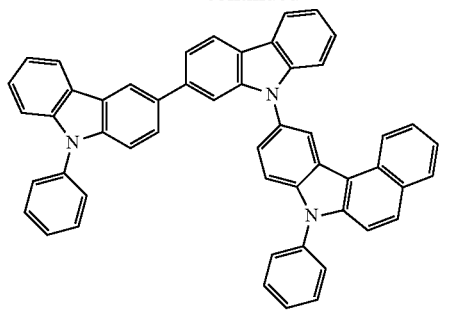
[Formula 198]
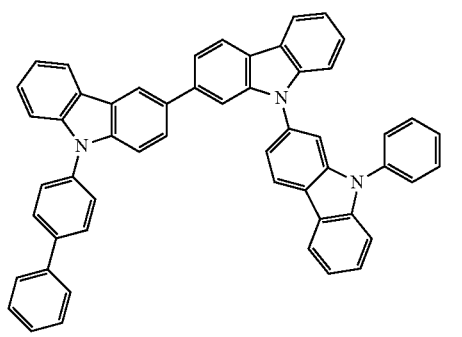
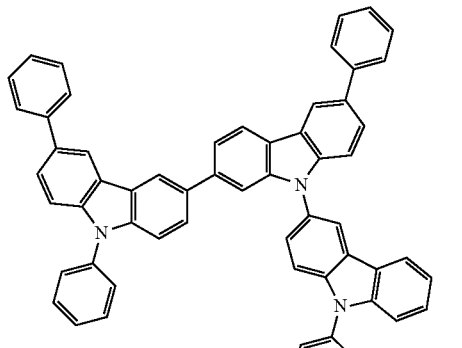
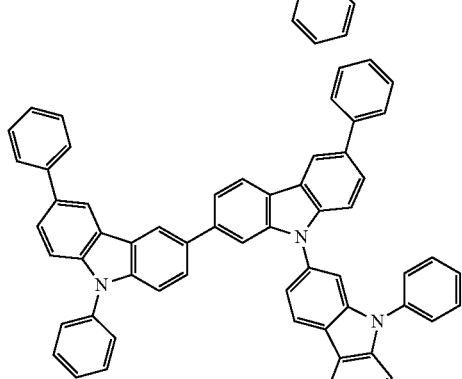
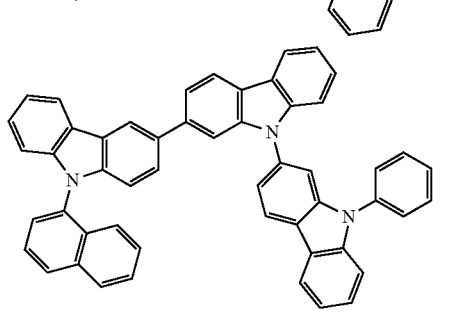
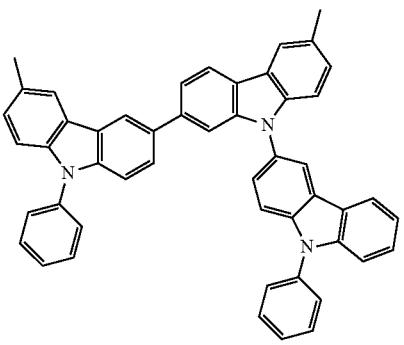
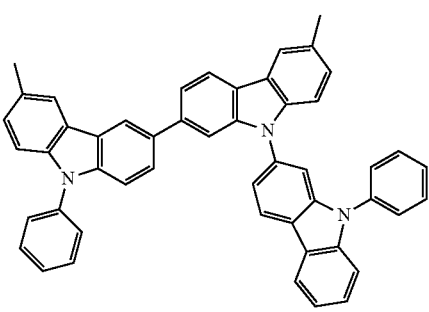
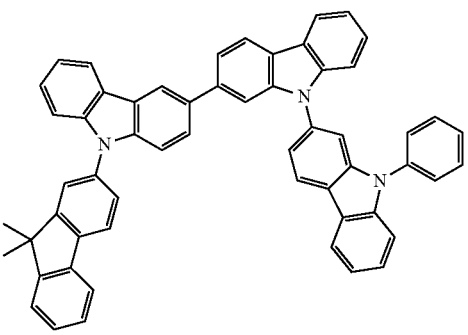
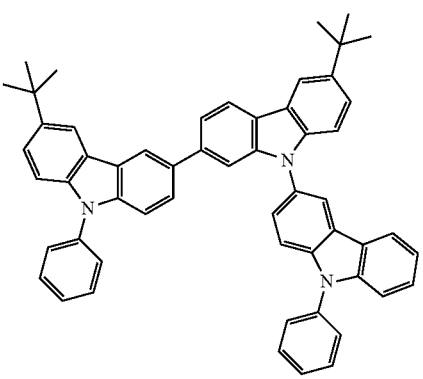
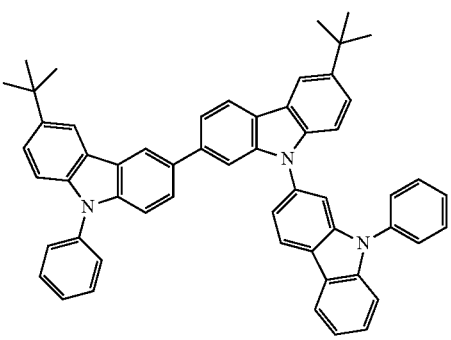

441
-continued
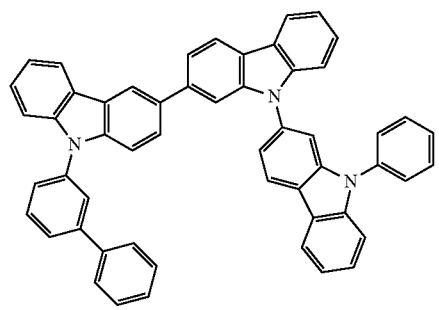
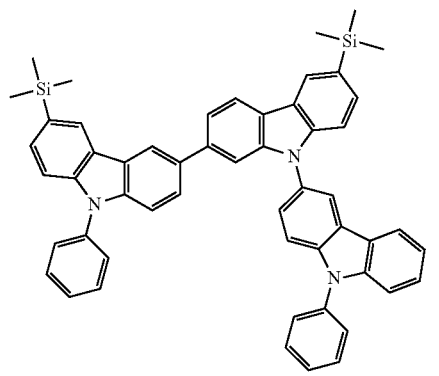
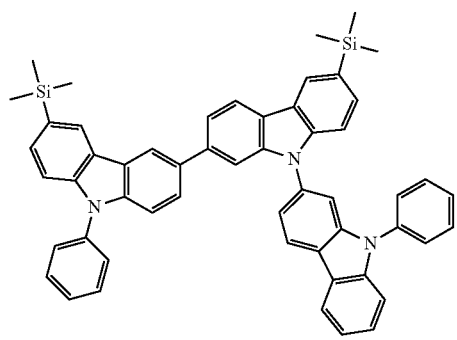
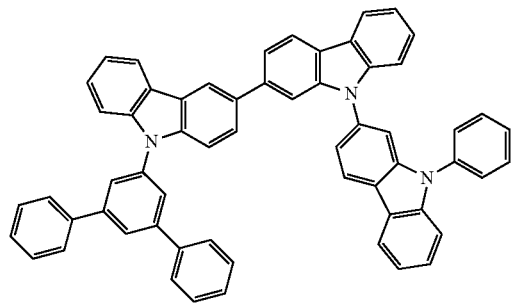
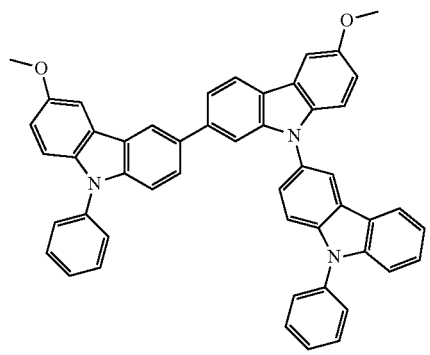
442
-continued
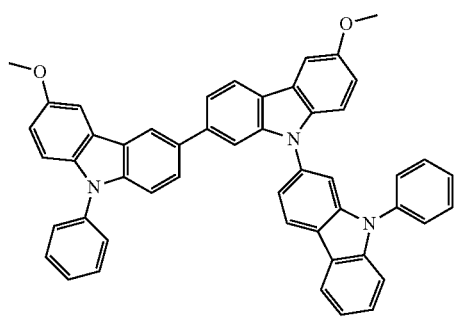
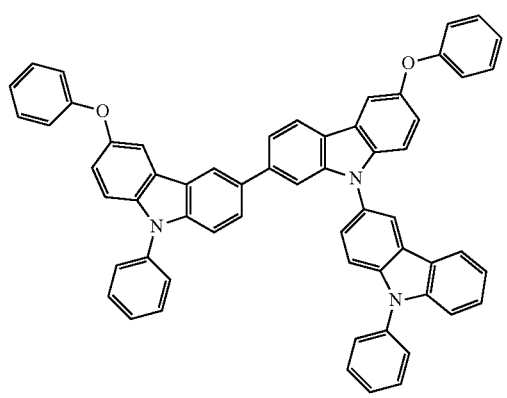
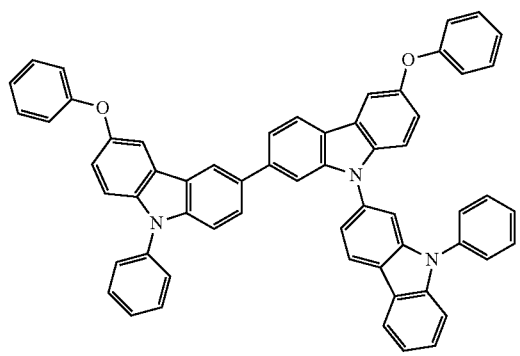
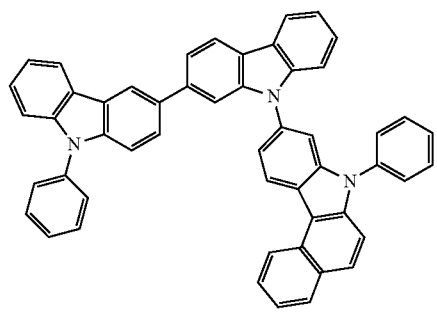

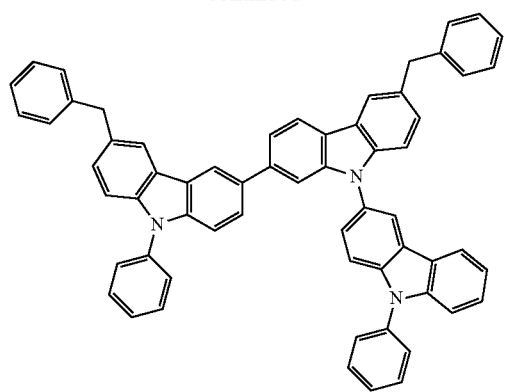
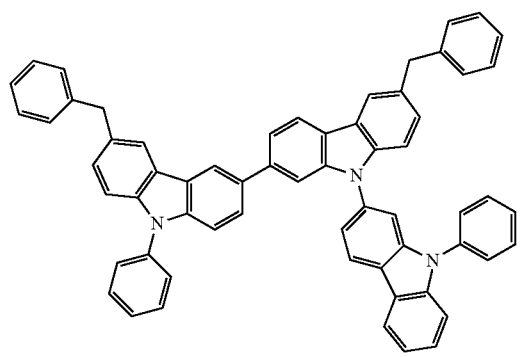
[Formula 199]
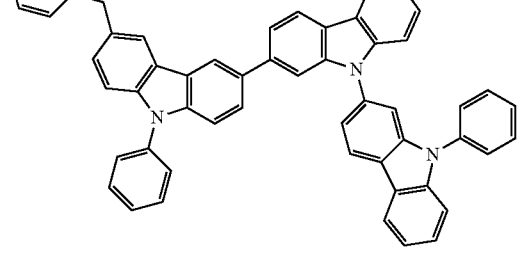
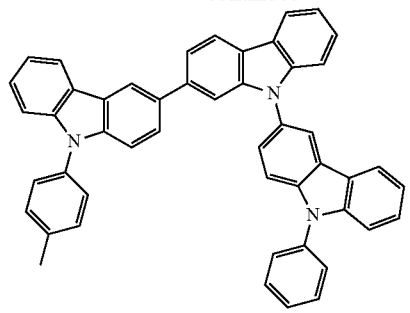
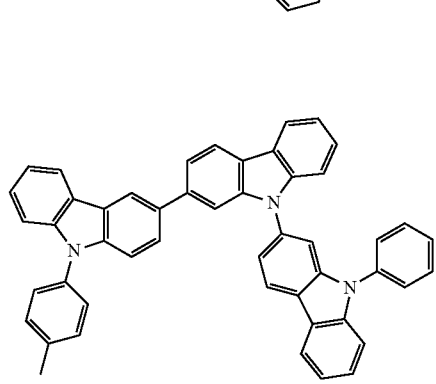
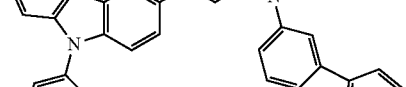
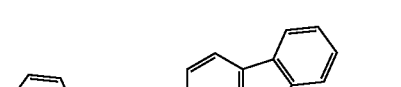
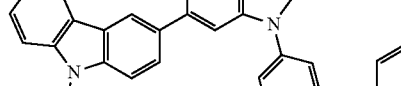
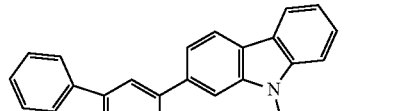
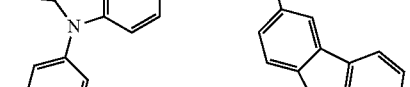

445
-continued
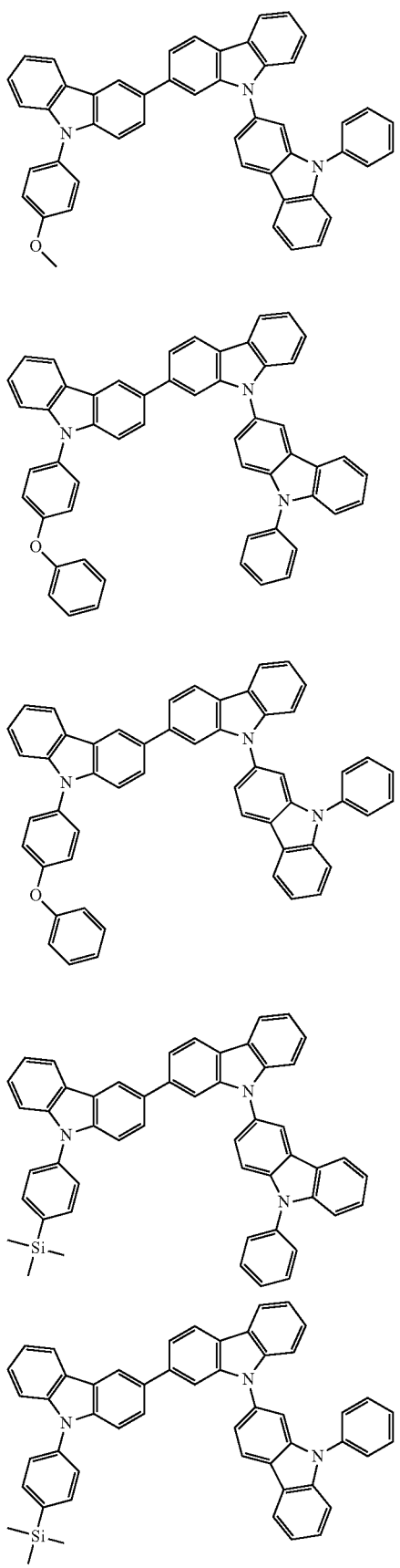
446
-continued
[Formula 200]
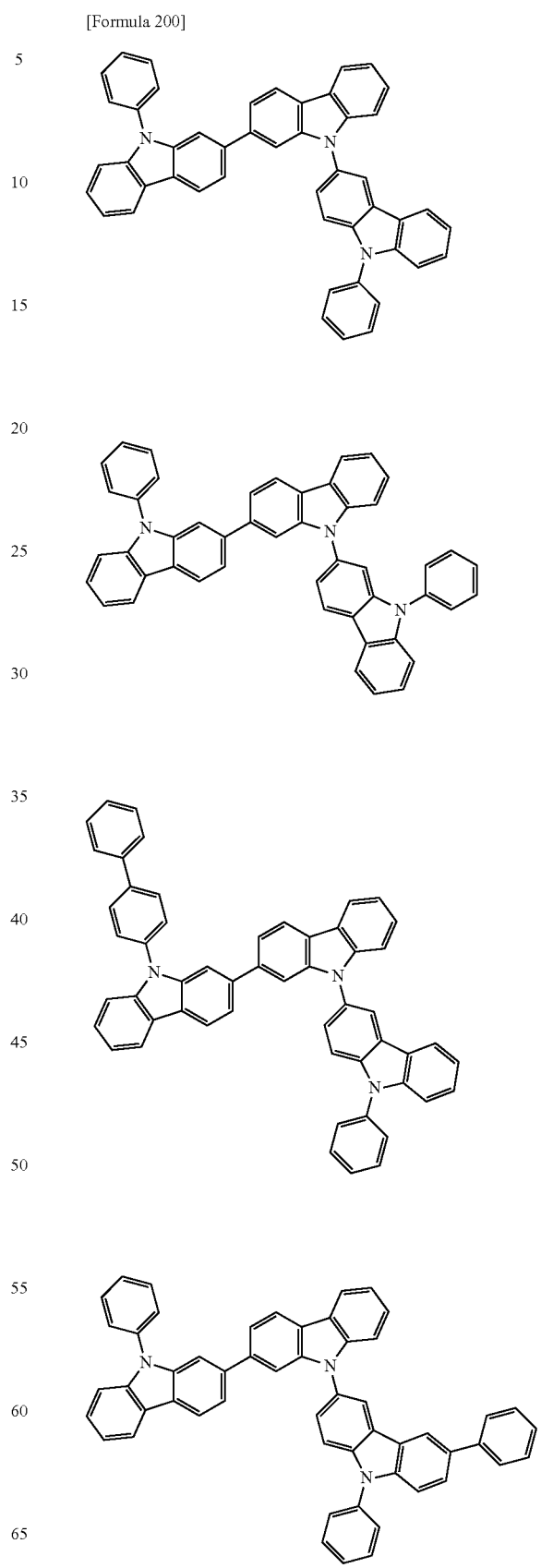

447
-continued
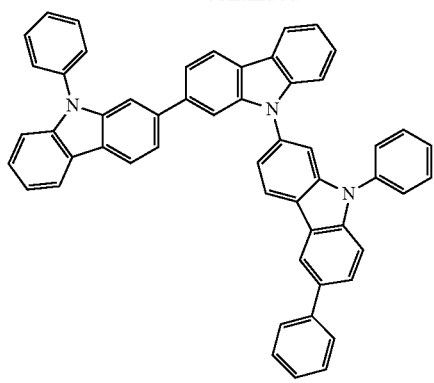
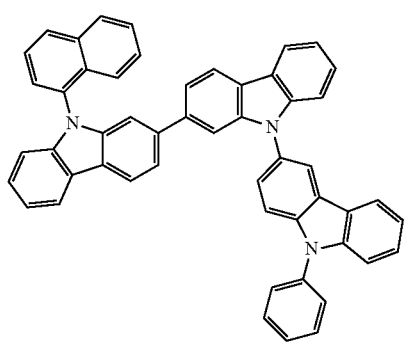
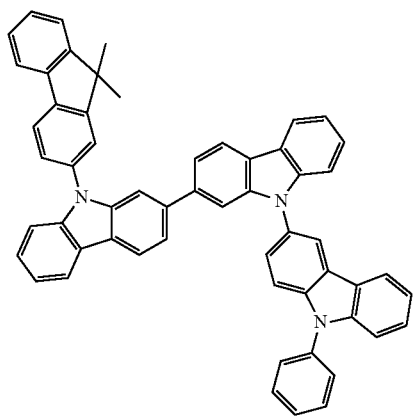
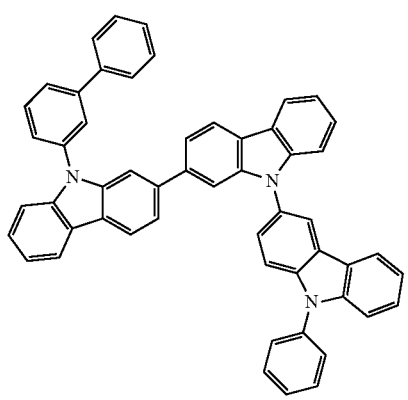
448
-continued
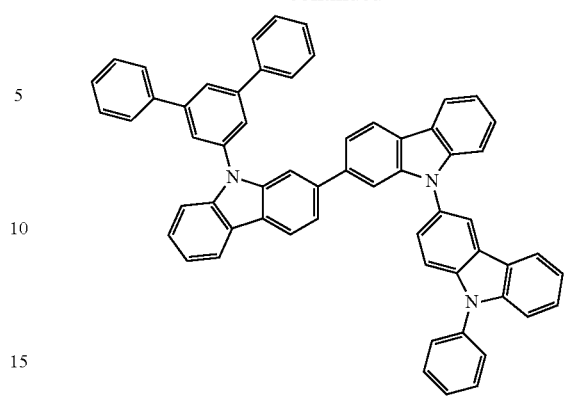
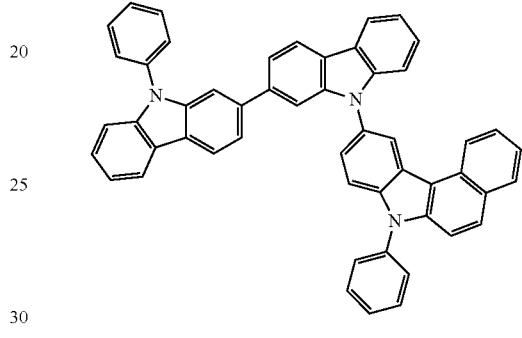
[Formula 201]
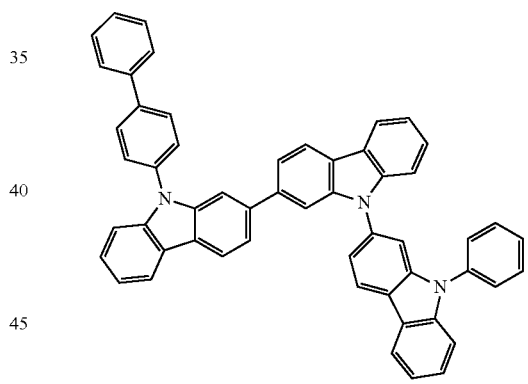
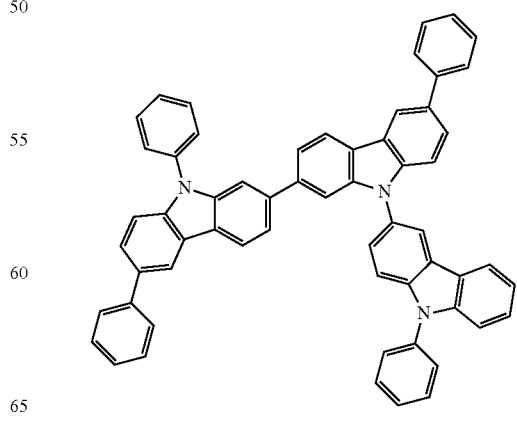

449
-continued
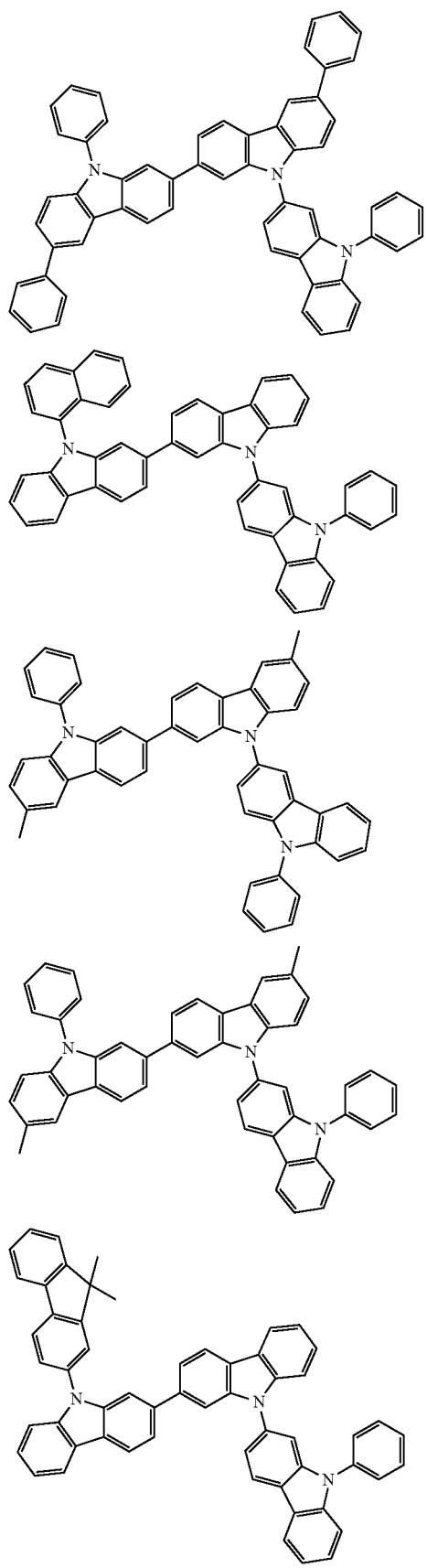
450
-continued
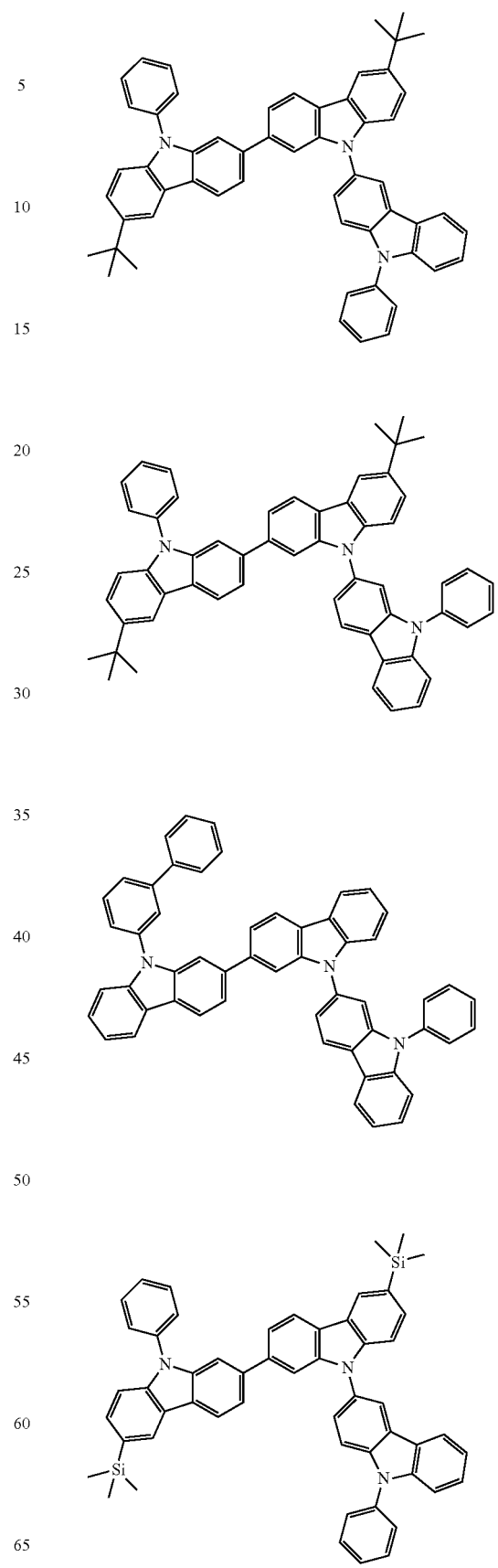

451
-continued
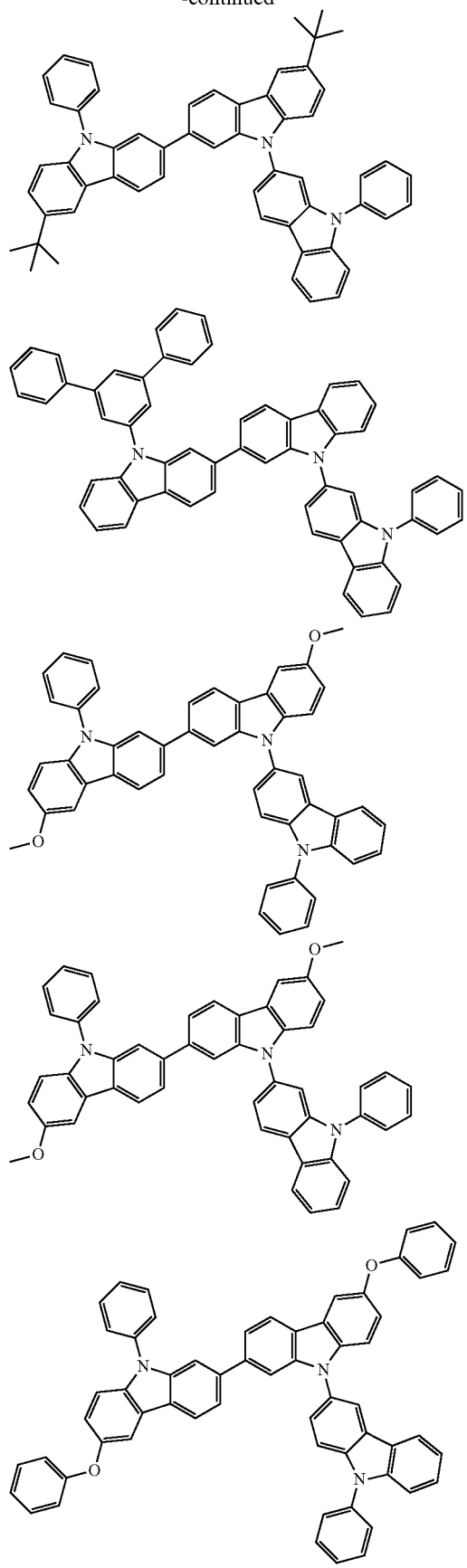
452
-continued
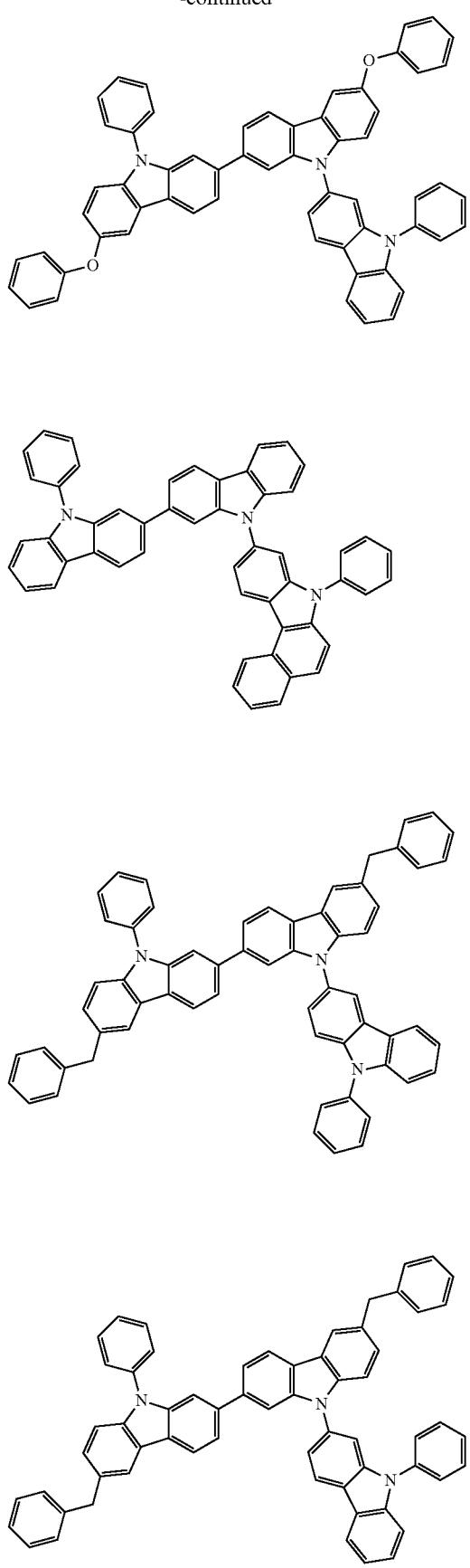

[Formula 202]
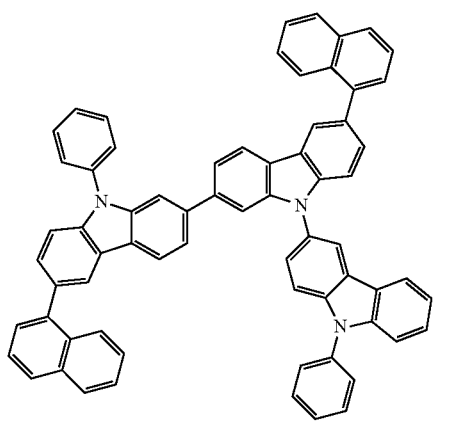
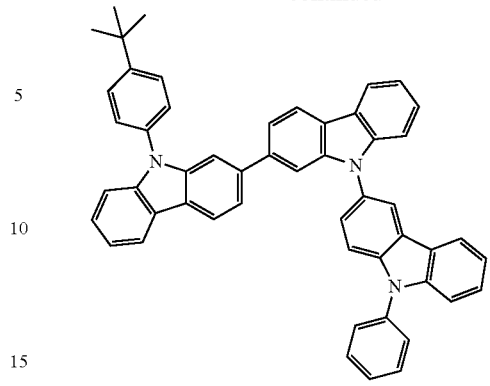
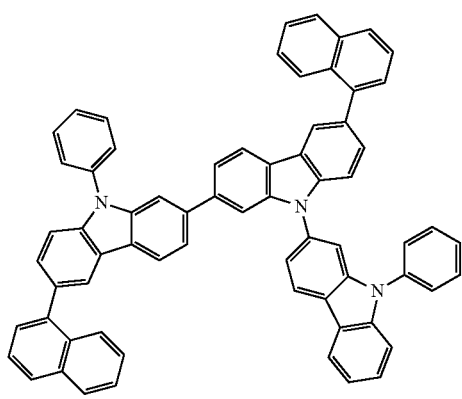
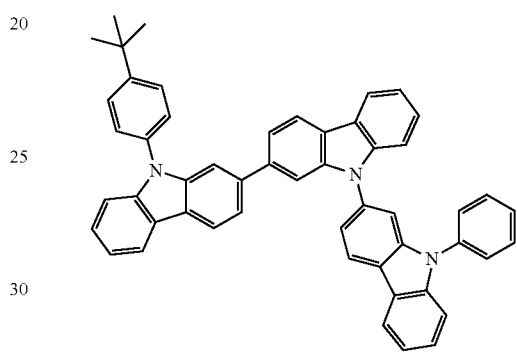
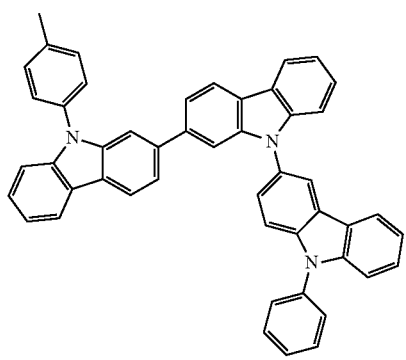
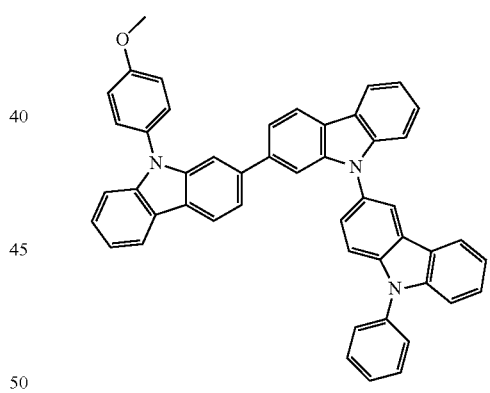
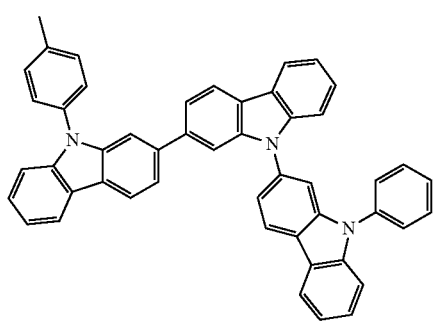
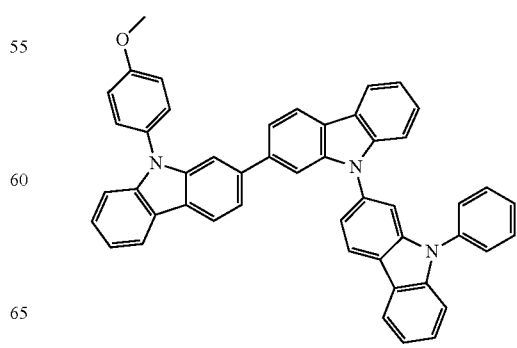

455
-continued
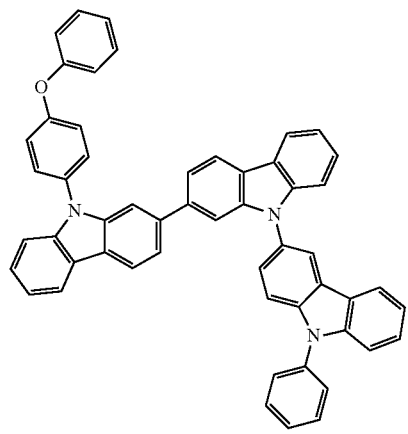
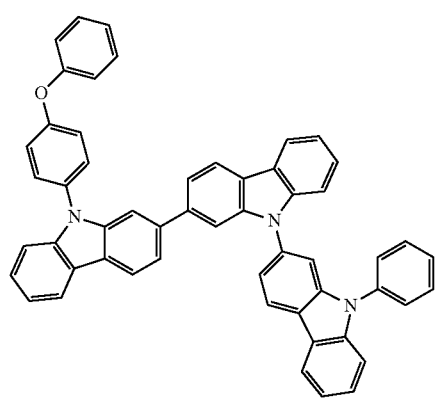
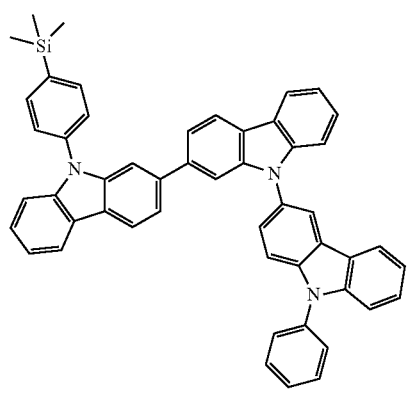
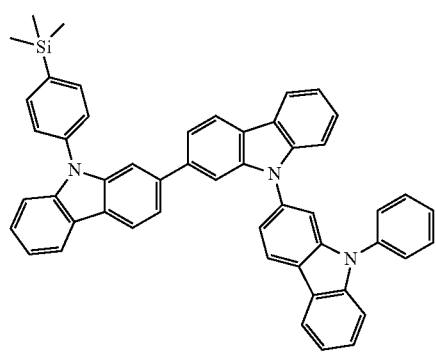
456
-continued
[Formula 203]
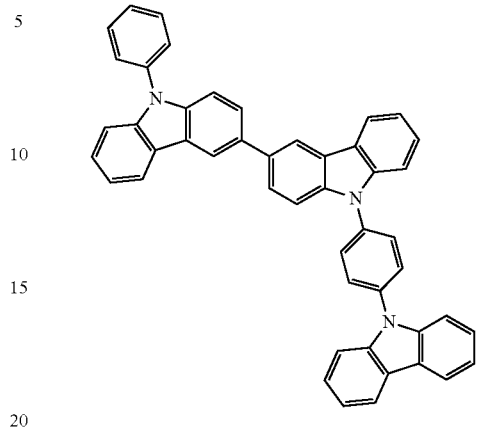
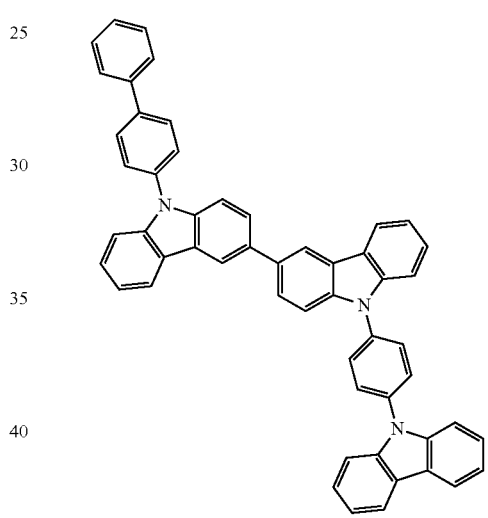
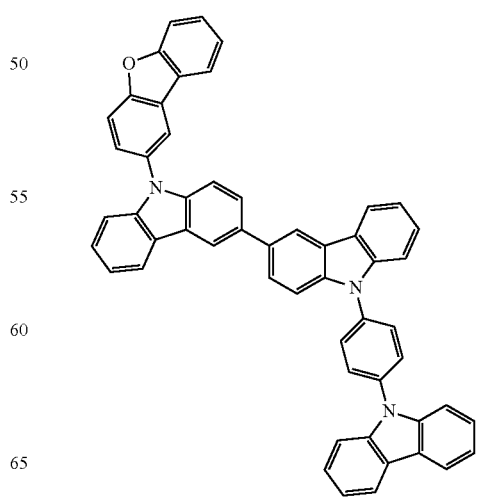

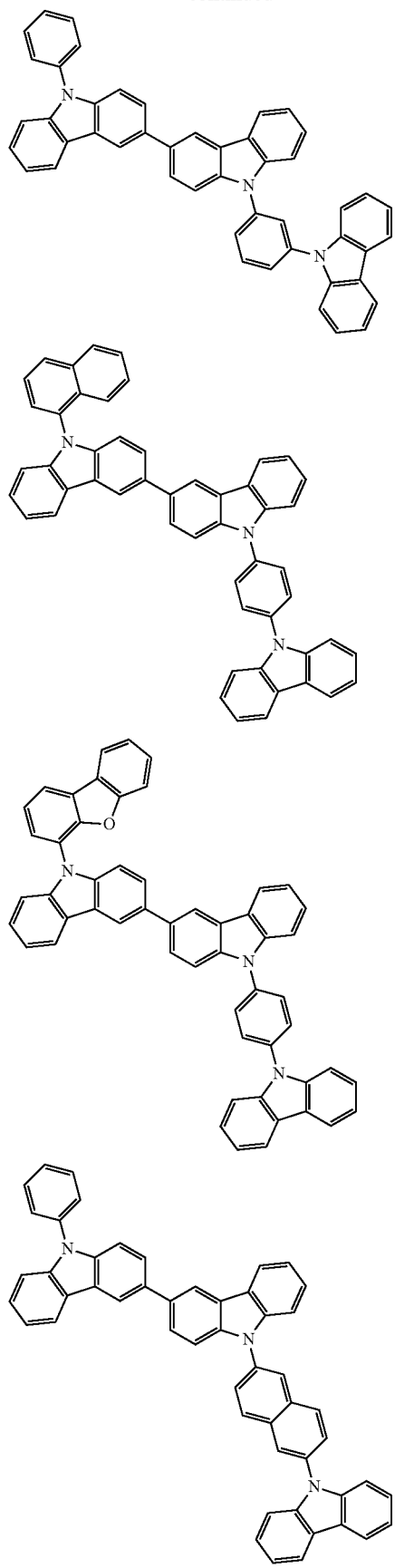
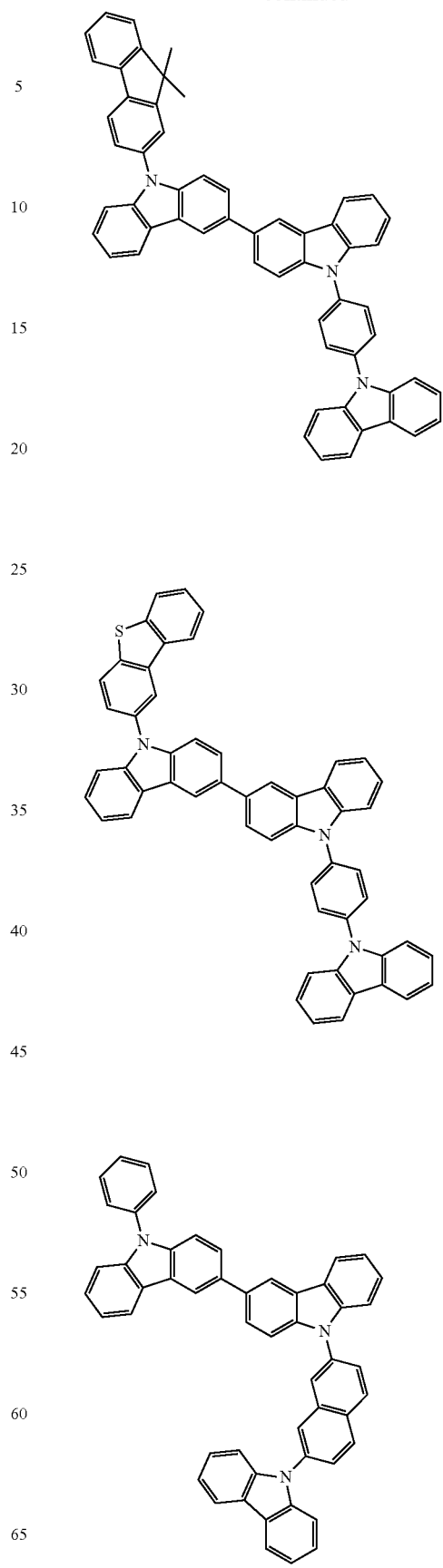

459
-continued
460
-continued
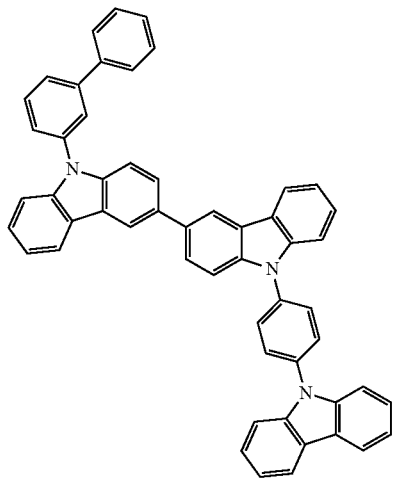
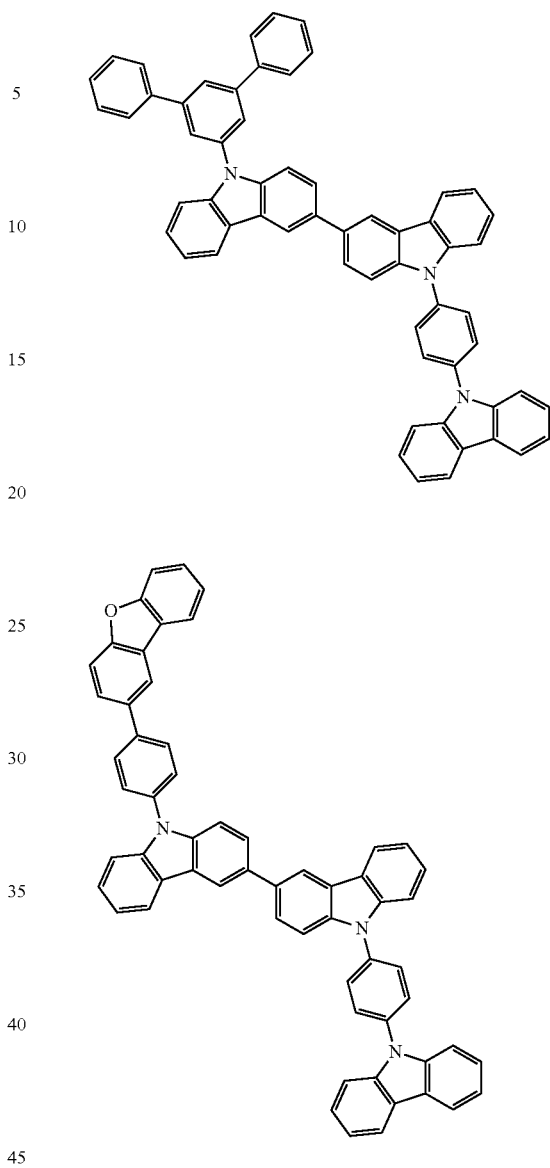
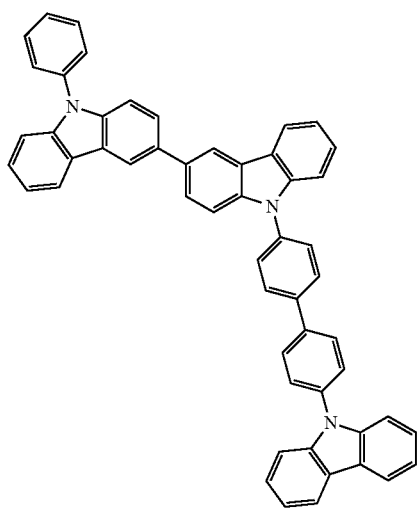
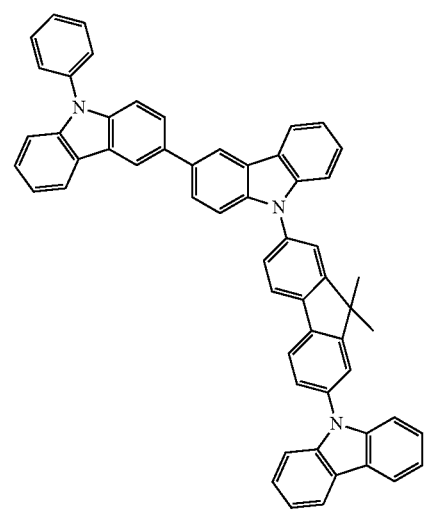

461
-continued
462
-continued
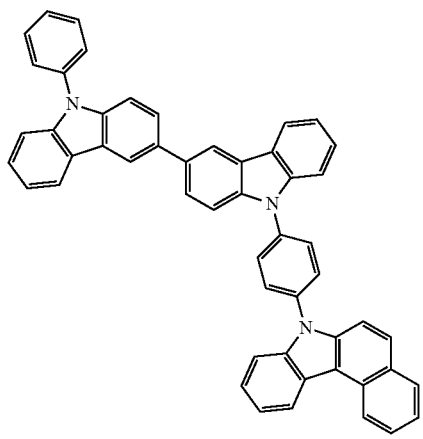
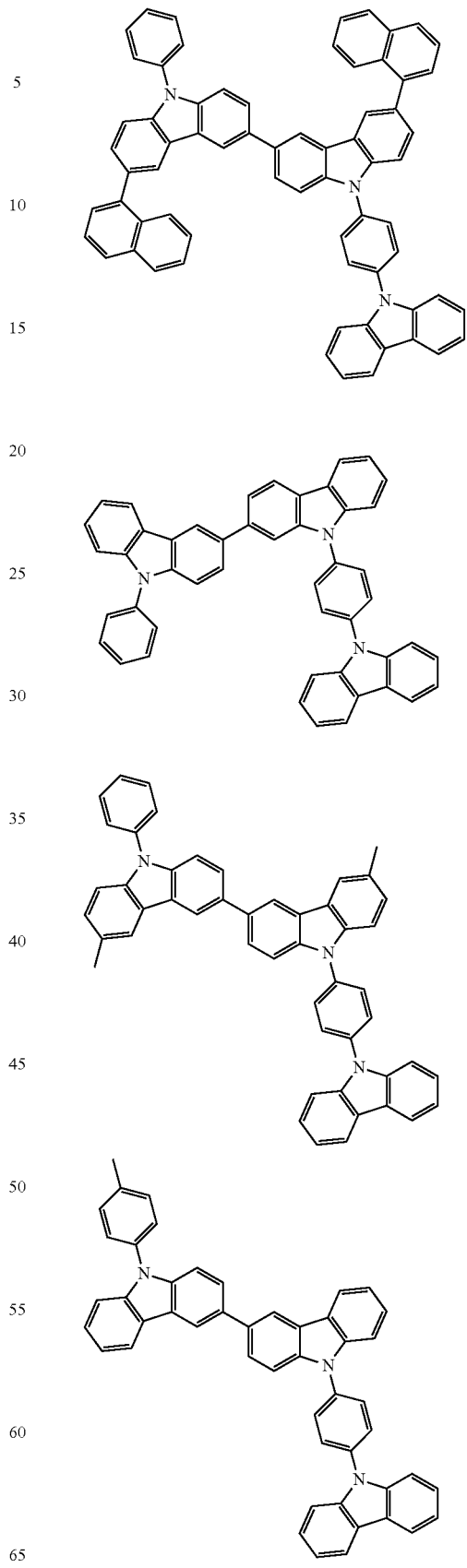
[Formula 204]
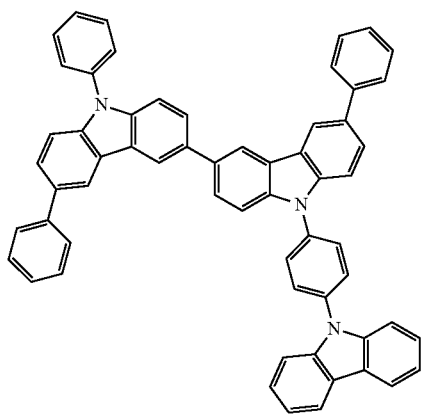

463
-continued
464
-continued
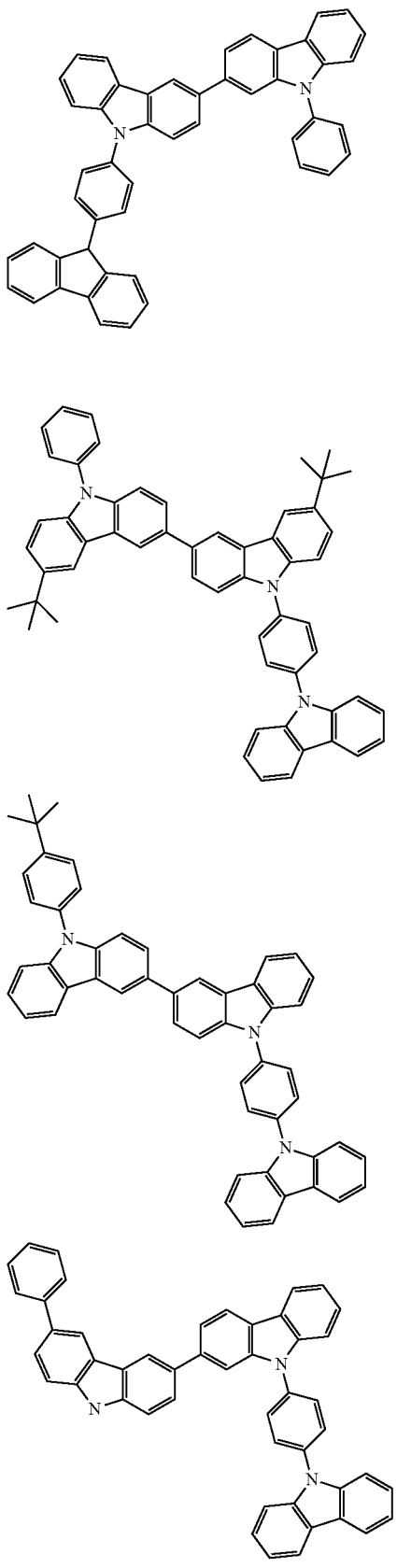
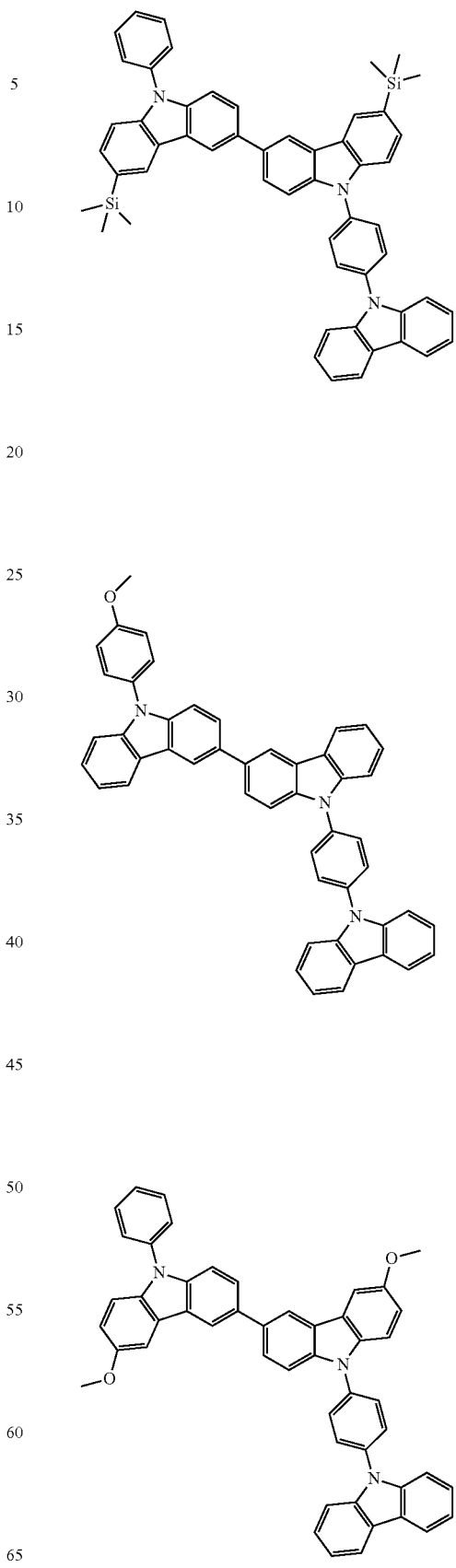

465
-continued
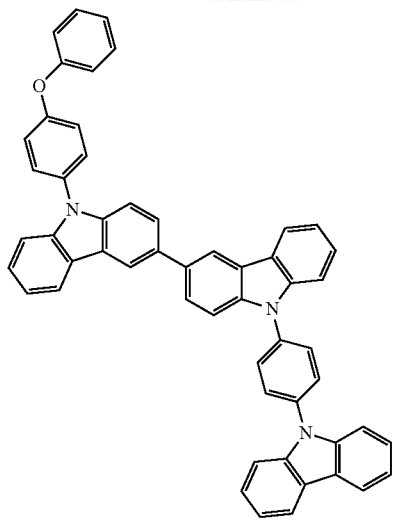
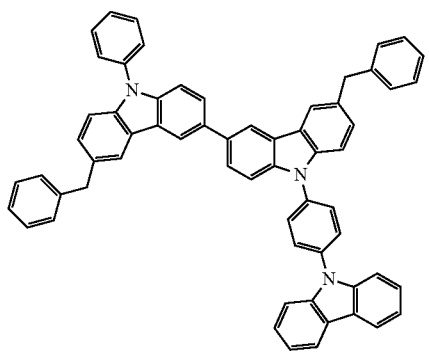
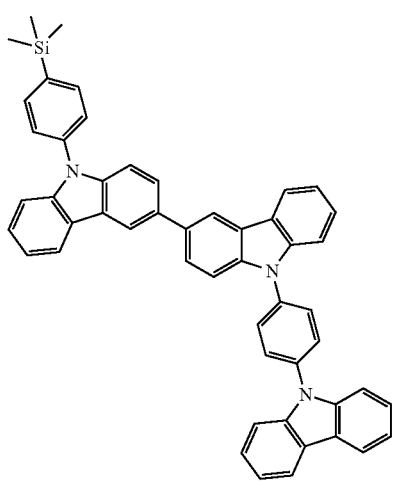
466
-continued
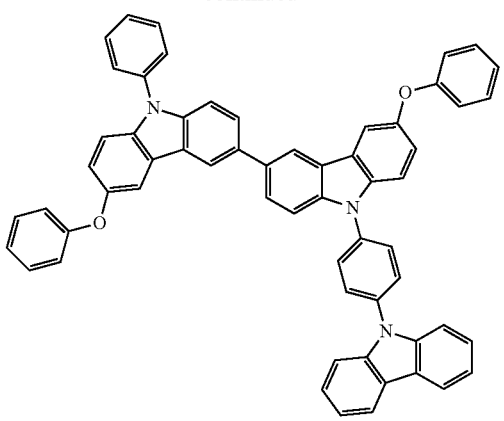
[Formula 205]
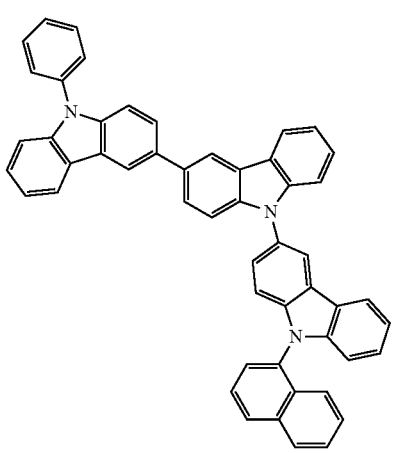
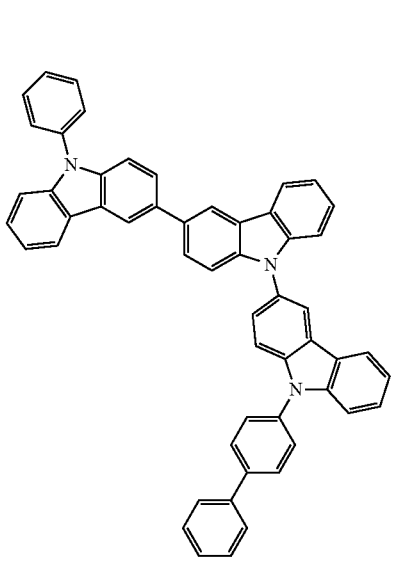

467
-continued
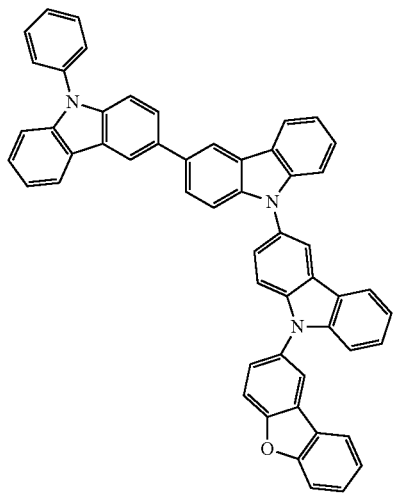
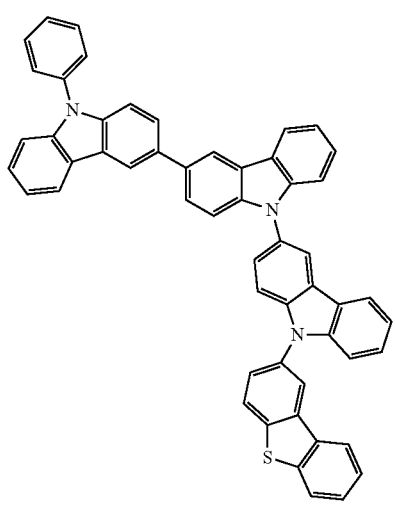
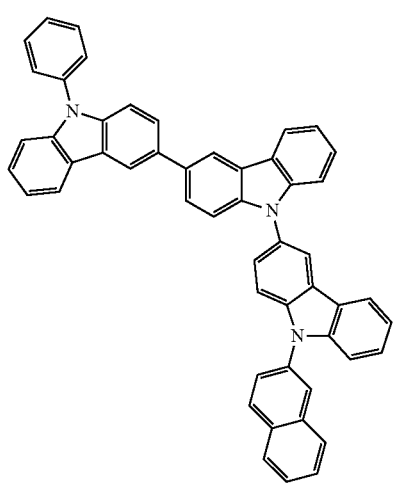
468
-continued
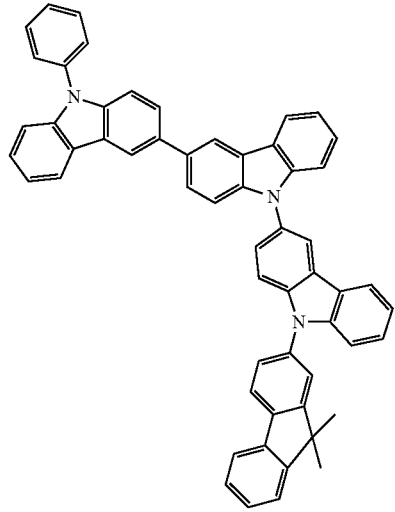
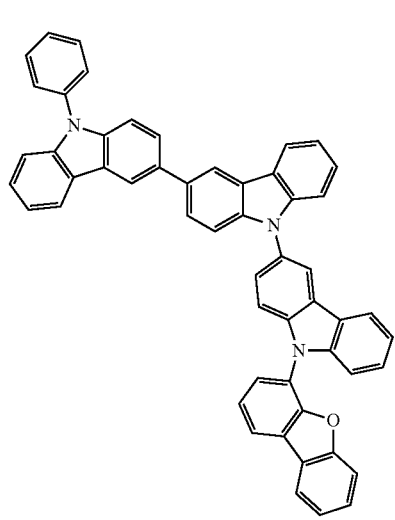
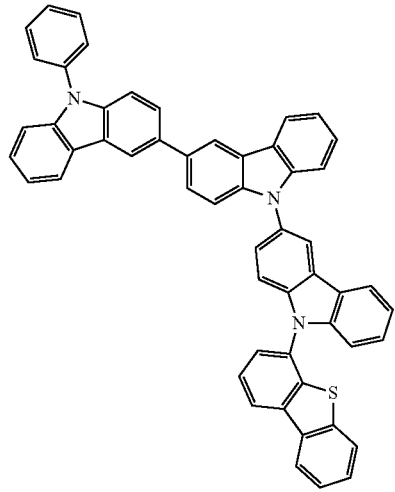

469
-continued
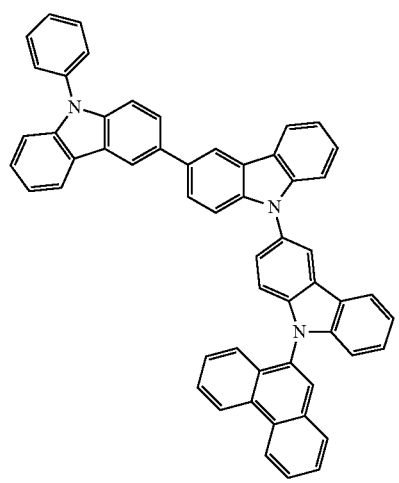
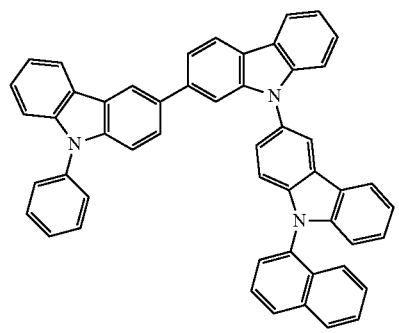
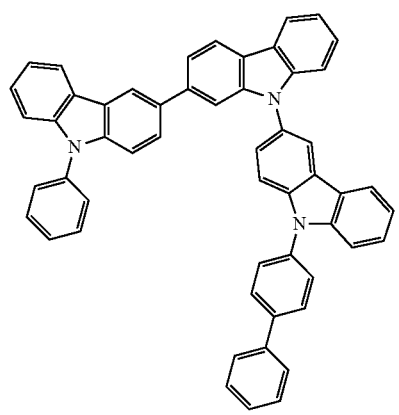
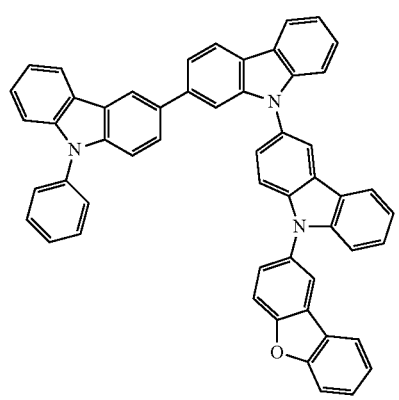
470
-continued
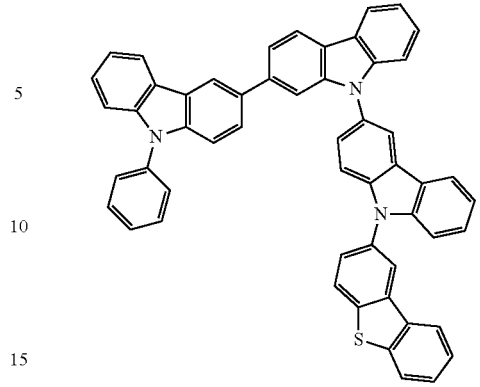
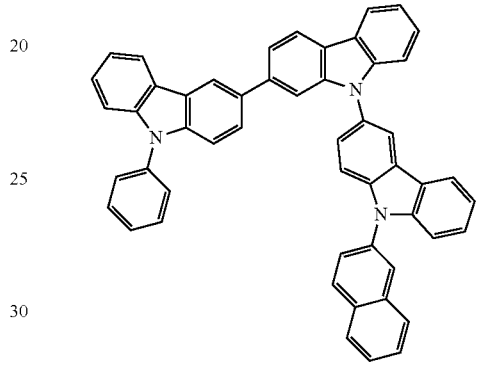
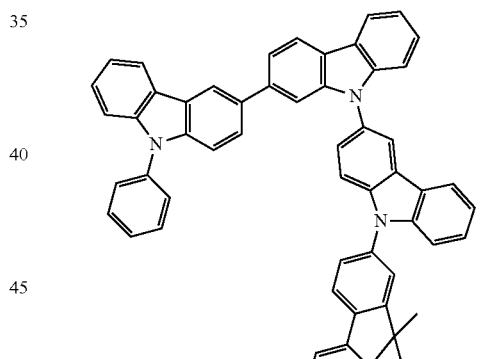
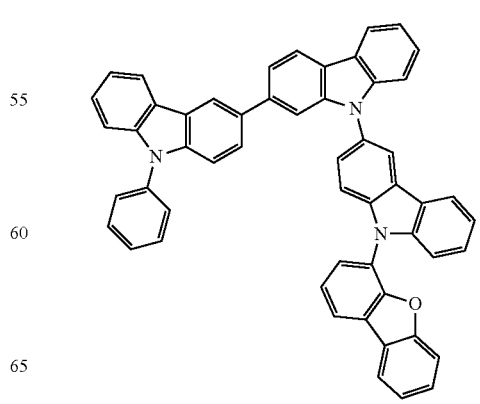

471
-continued
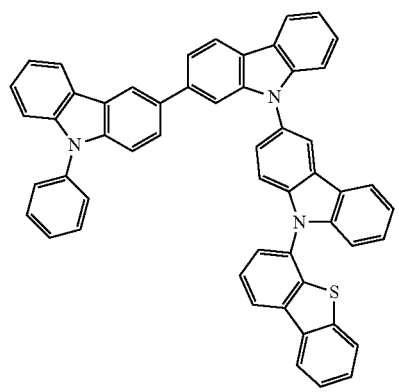
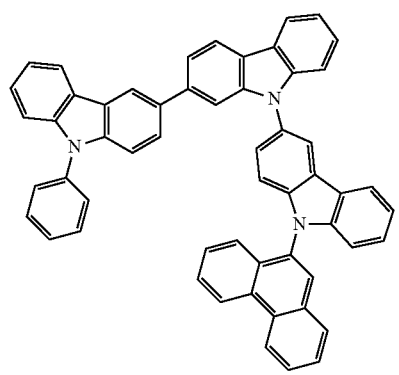
[Formula 206]
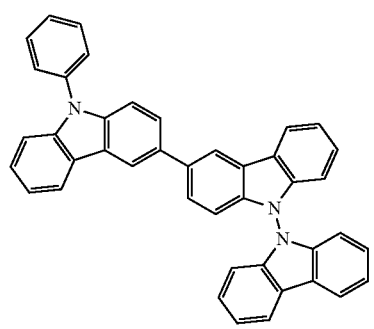
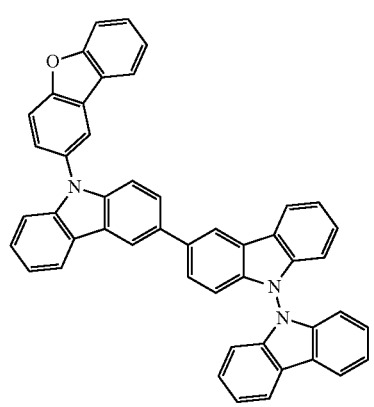
472
-continued
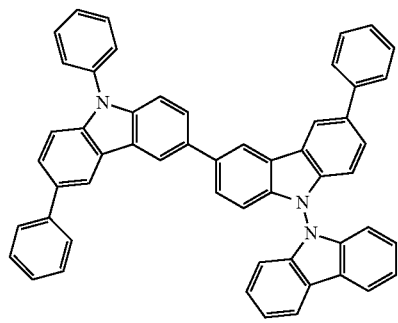
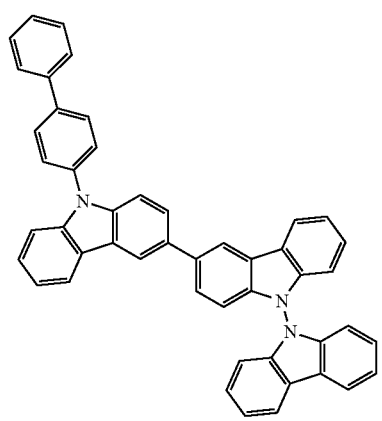
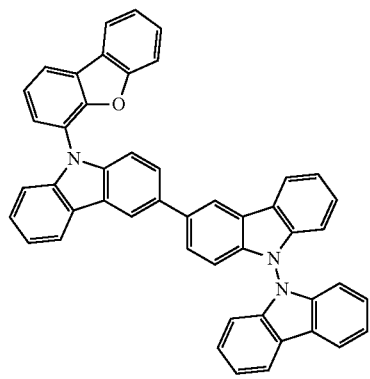
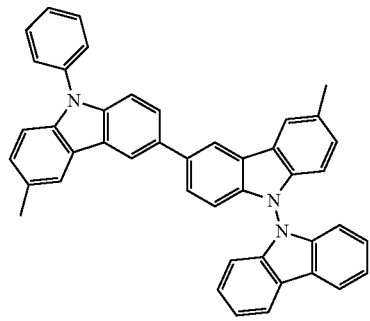

473
-continued
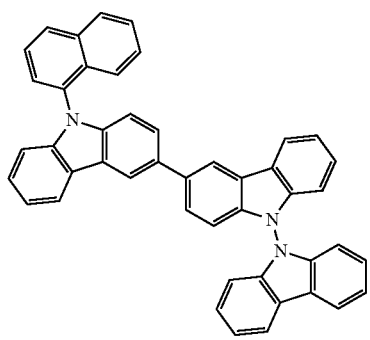
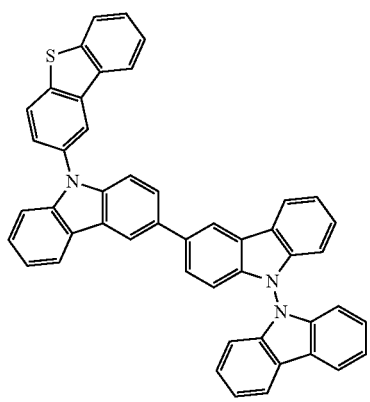
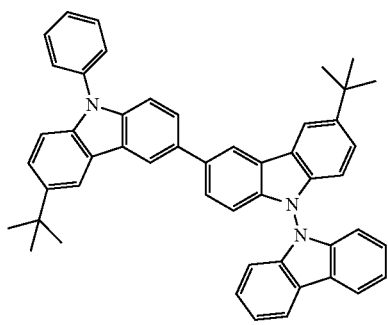
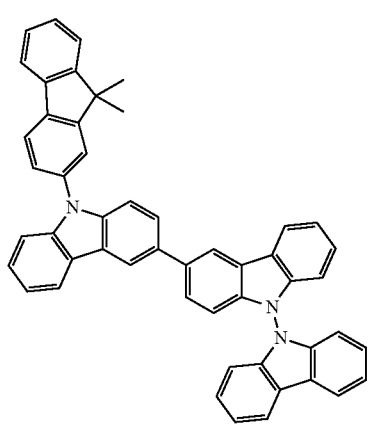
474
-continued
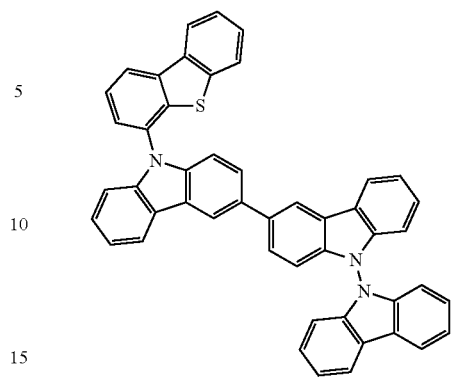
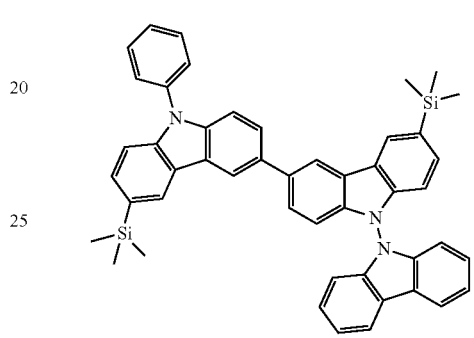
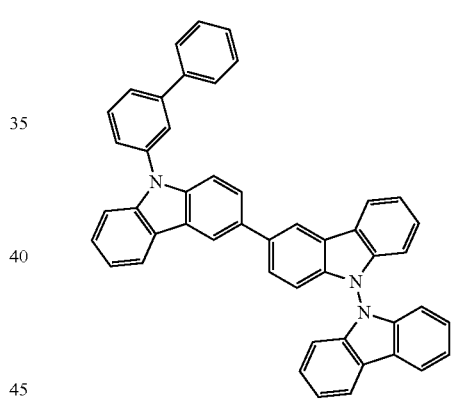
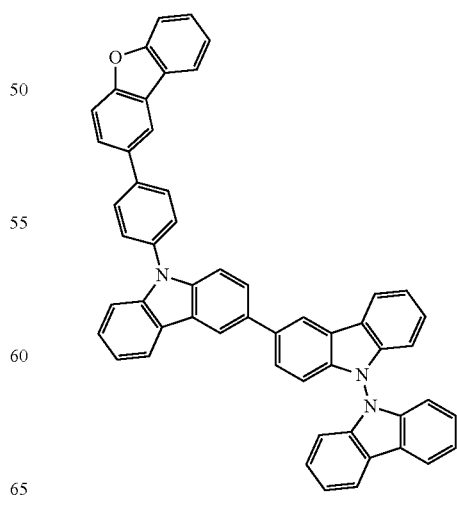

475
-continued
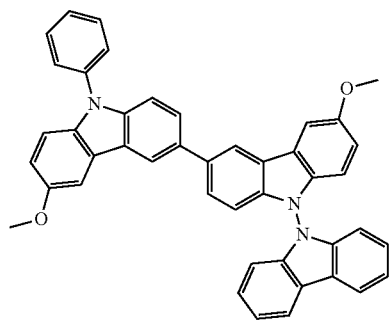
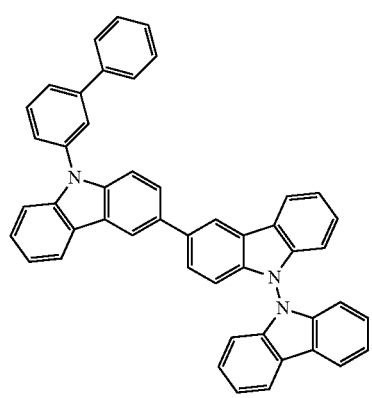
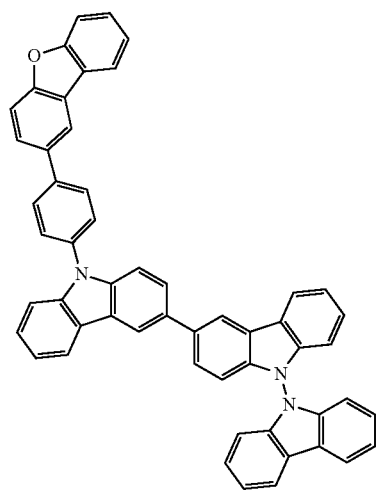
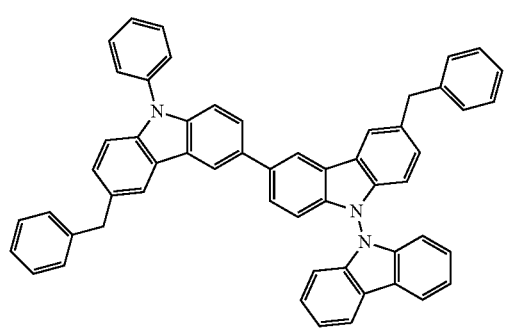
476
-continued
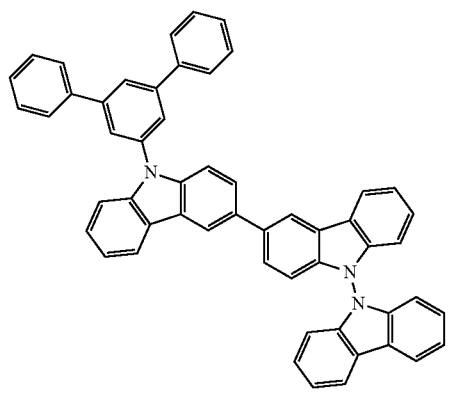
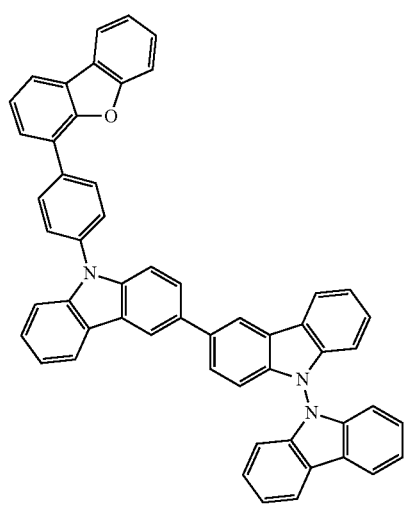
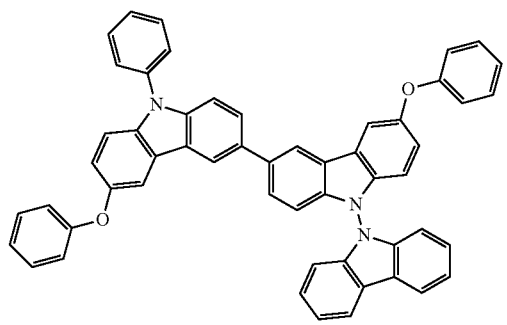
[Formula 207]
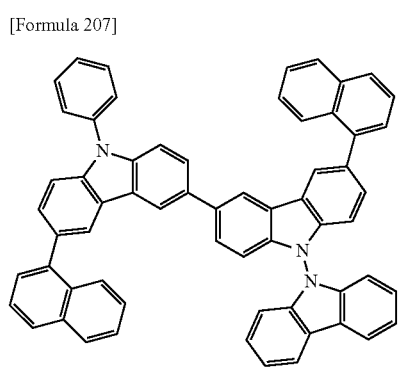

477
-continued
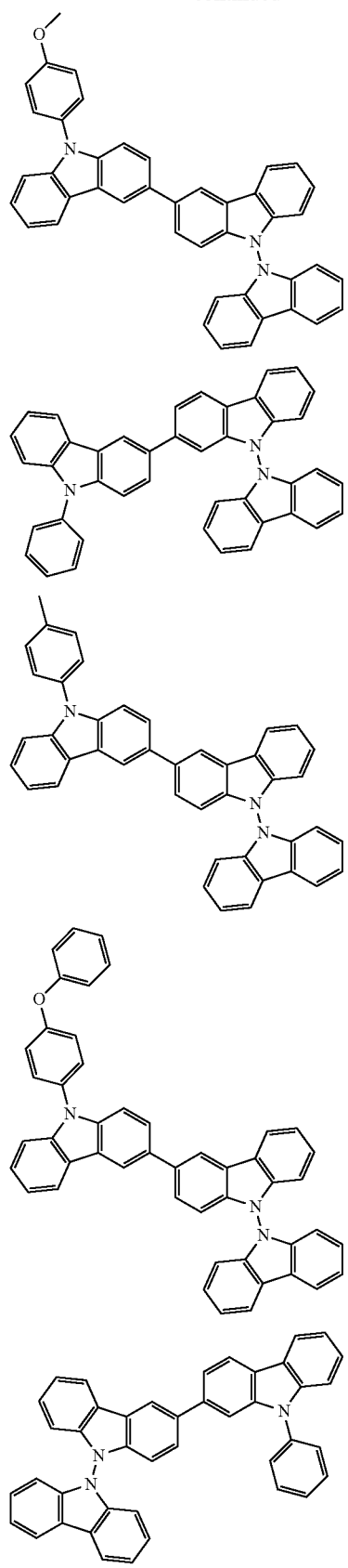
478
-continued
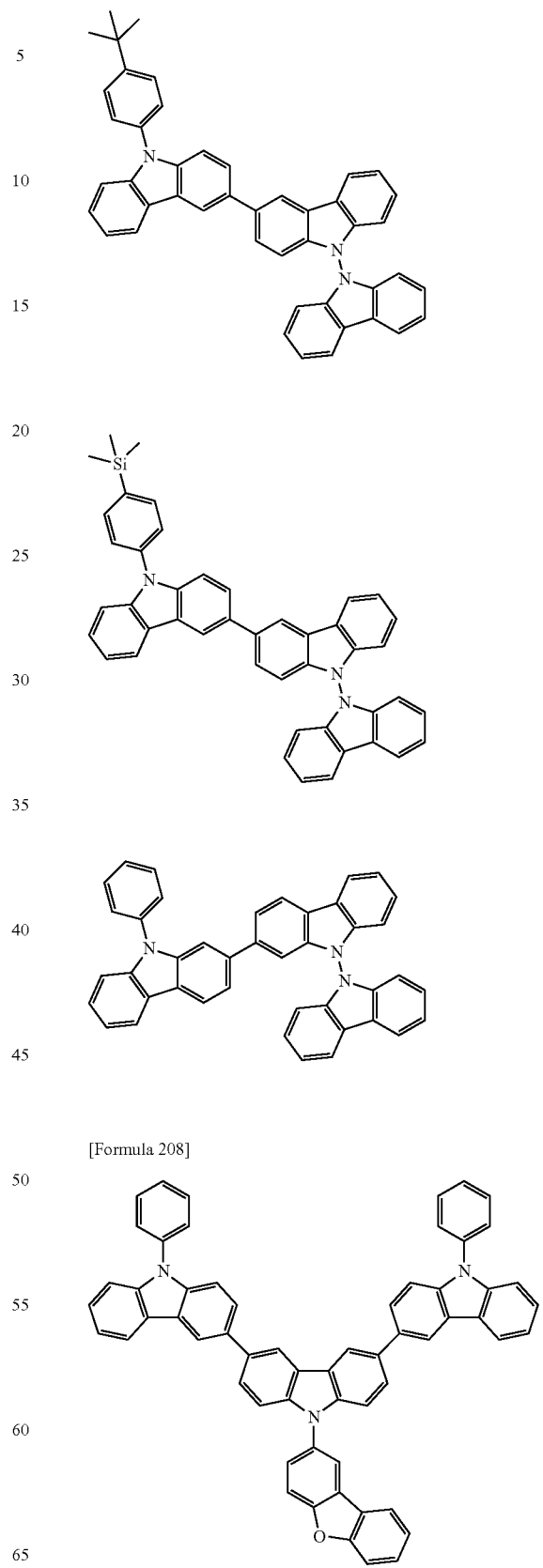
[Formula 208]

479
-continued
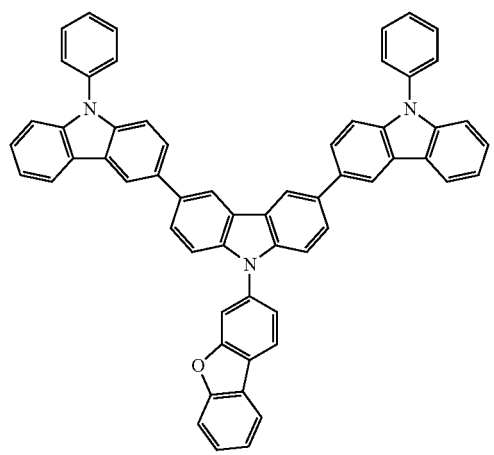
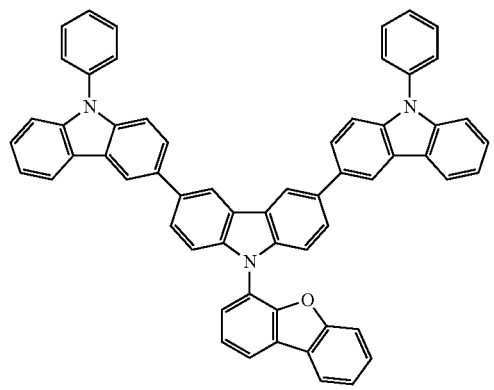
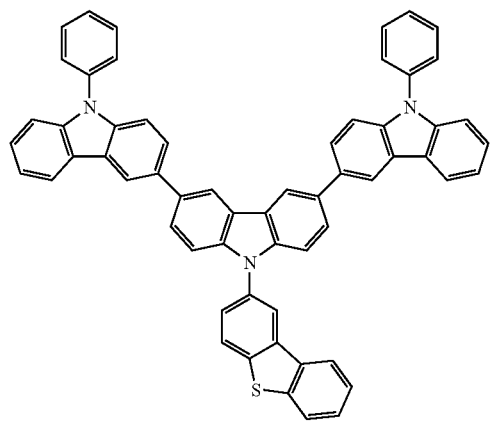
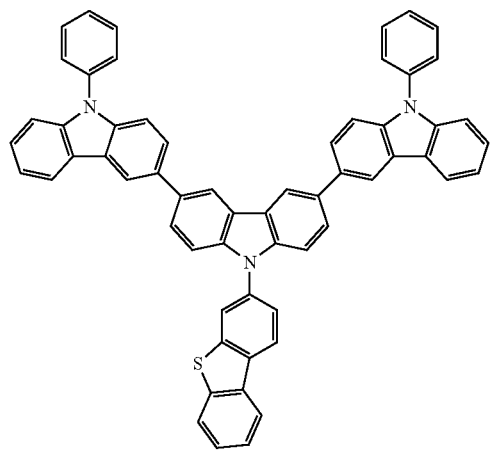
480
-continued
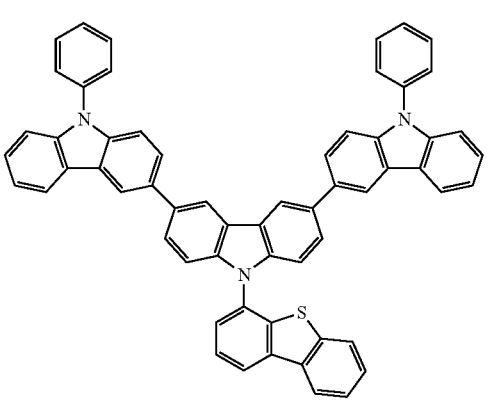
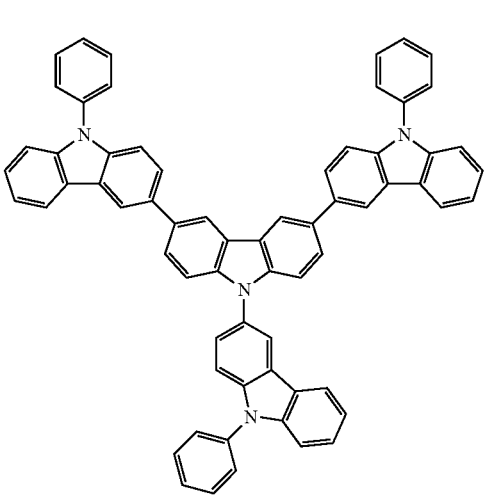
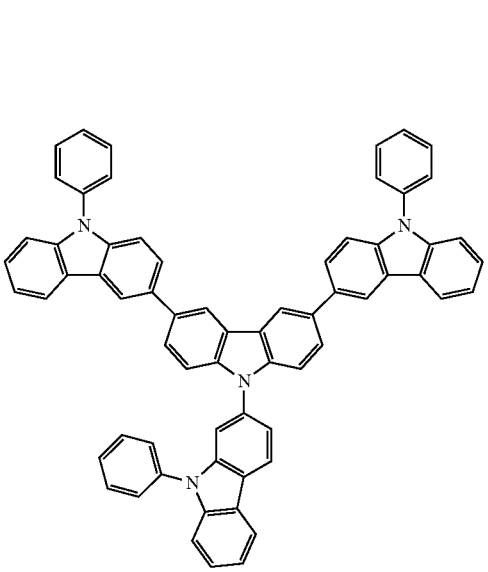

[Formula 209]
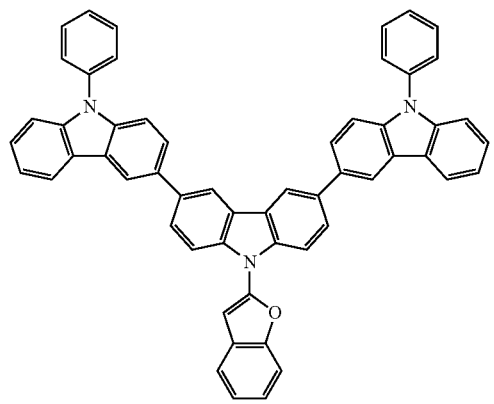
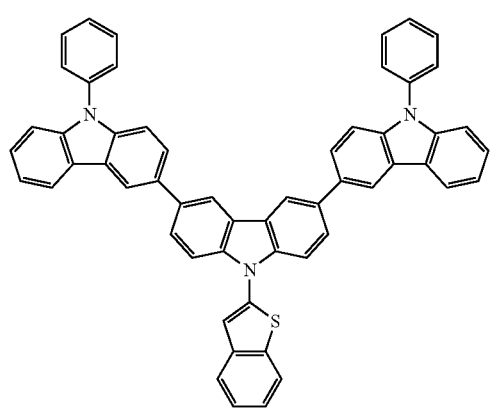
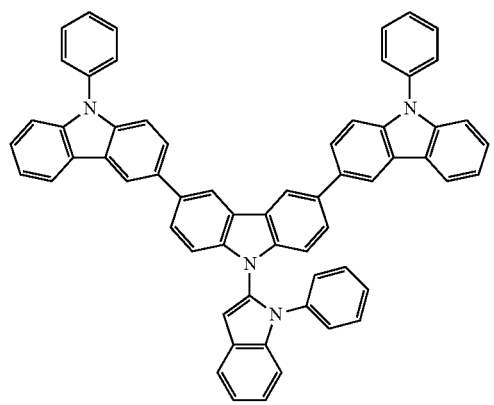
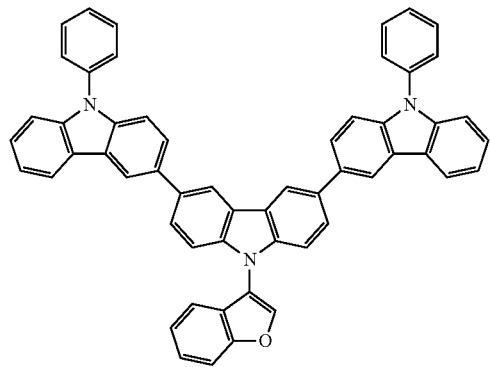
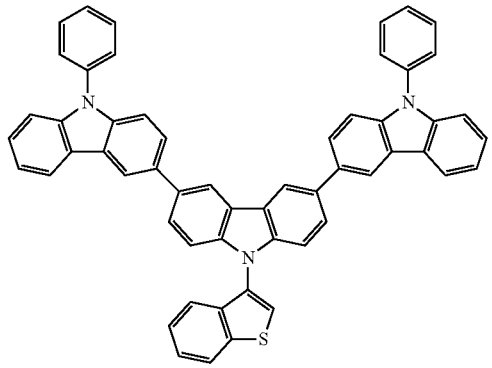
[Formula 210]
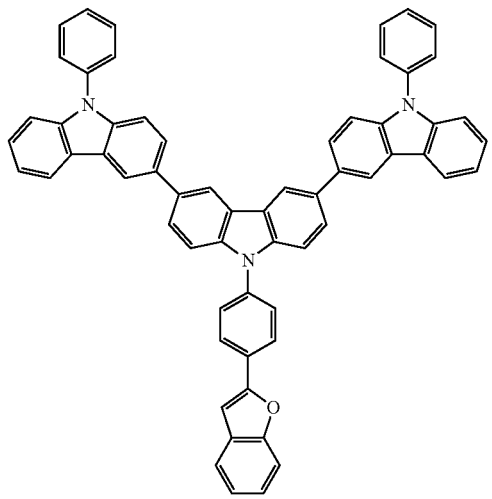

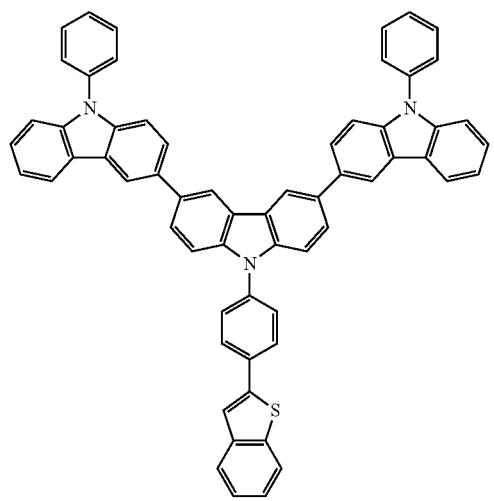
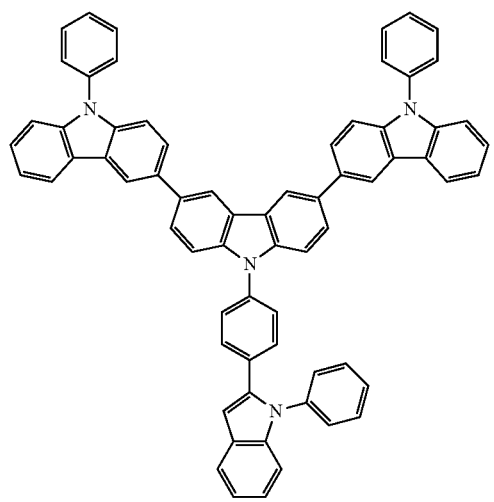
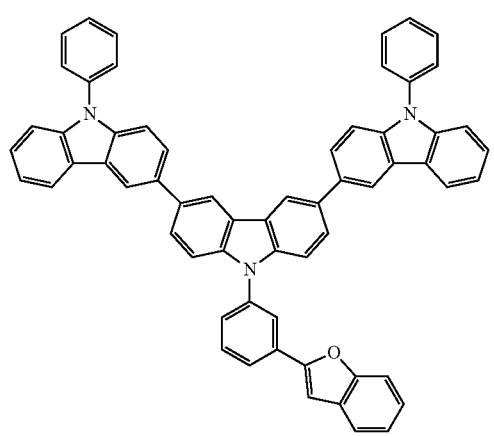
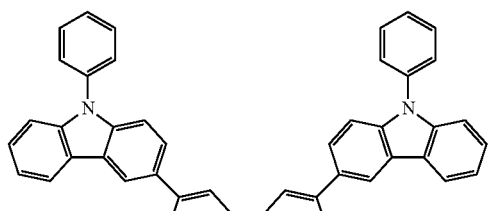
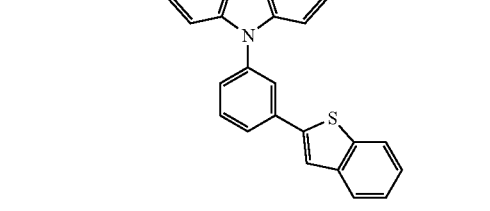
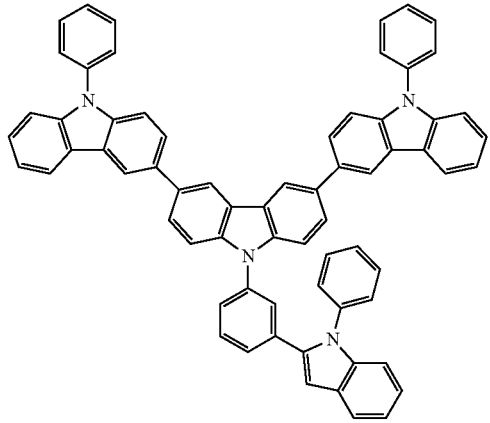
[Formula 211]
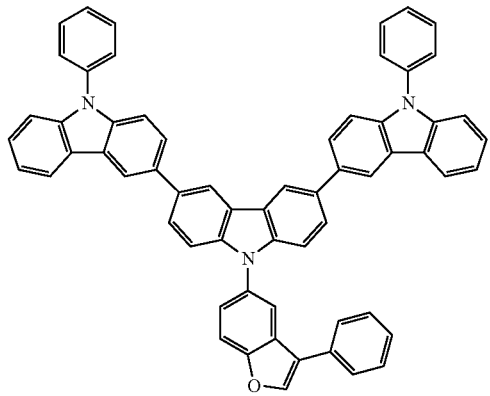
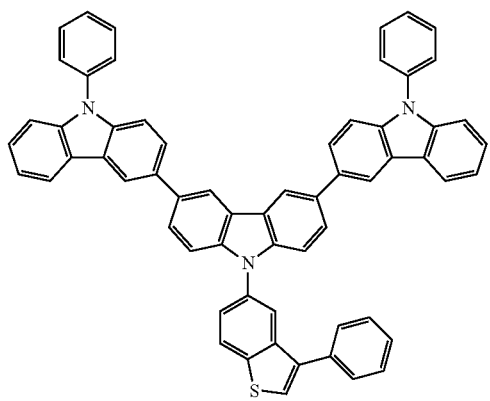

485
-continued
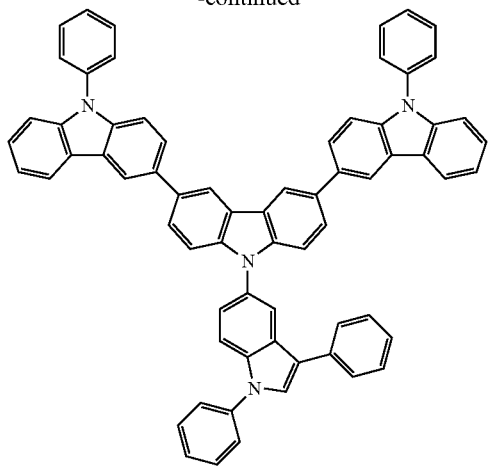
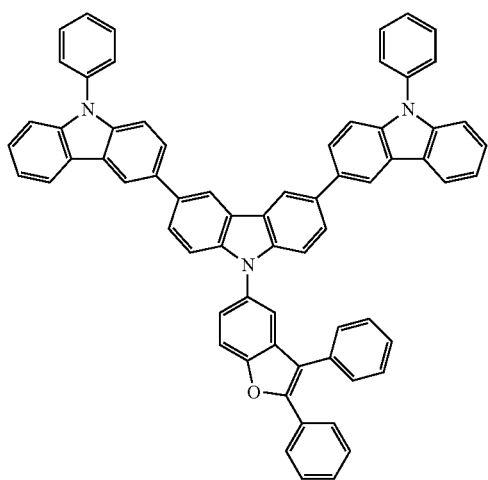
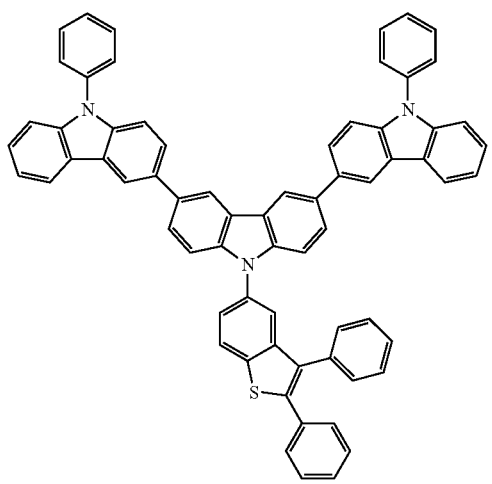
486
-continued
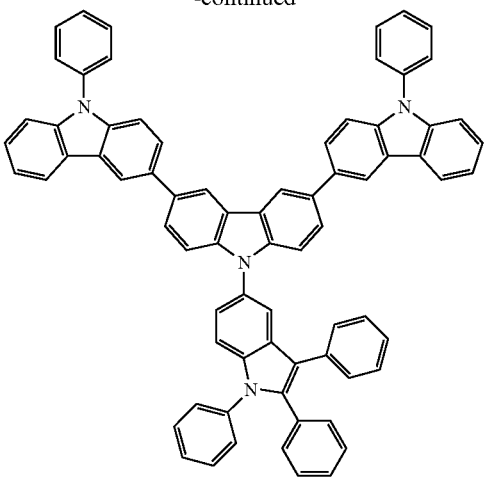
[Formula 212]
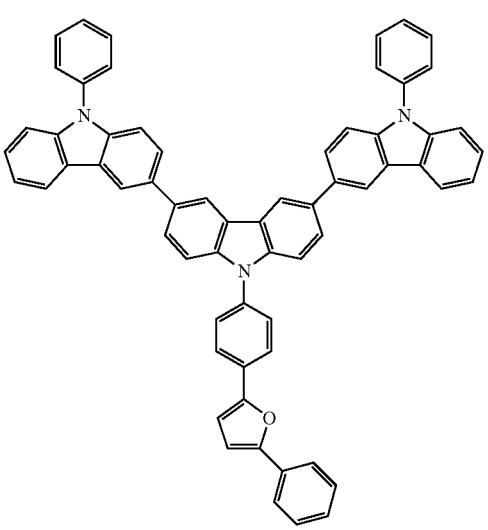
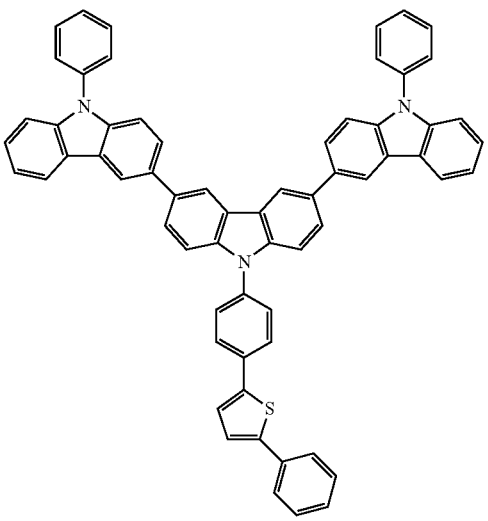

487
-continued
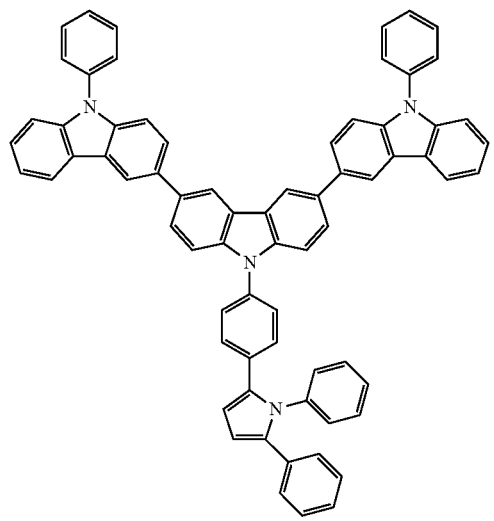
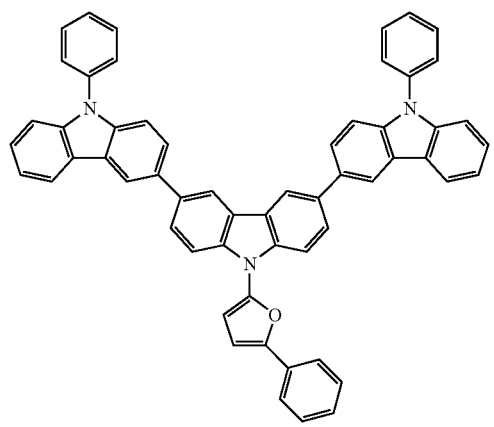
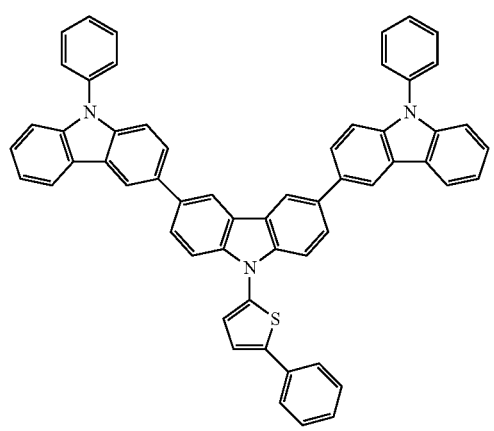
488
-continued
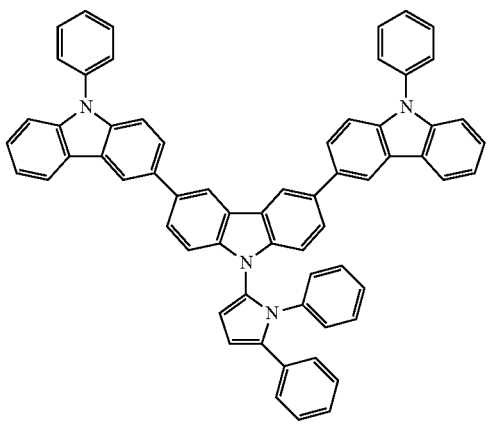
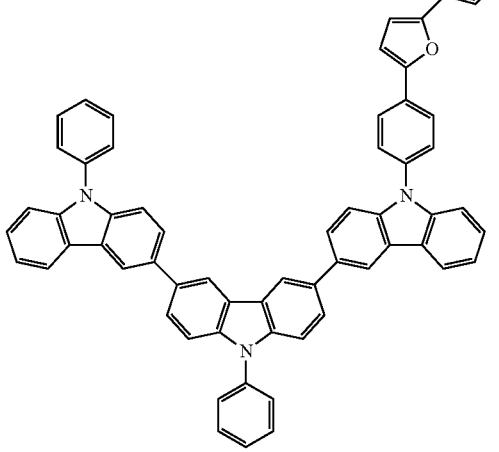
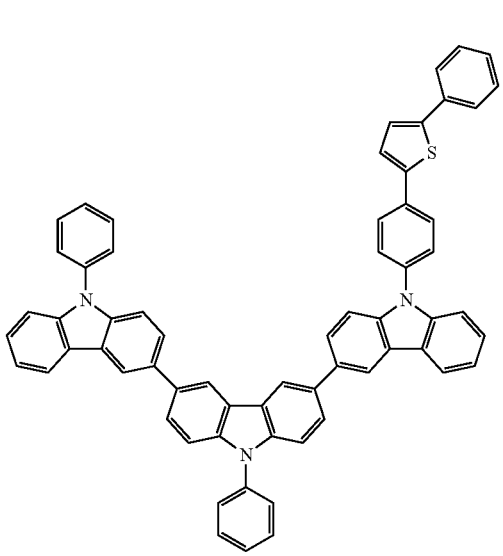

489
-continued
490
-continued
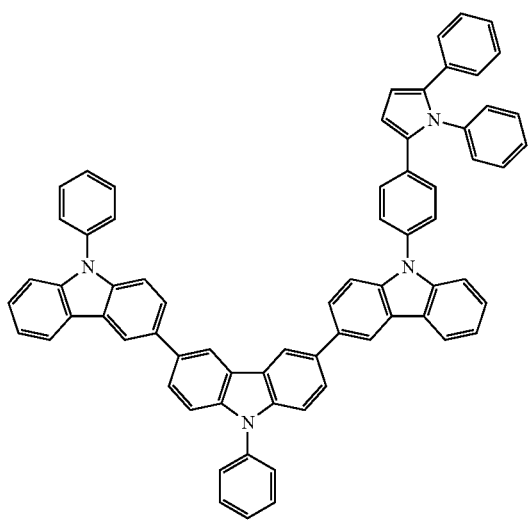
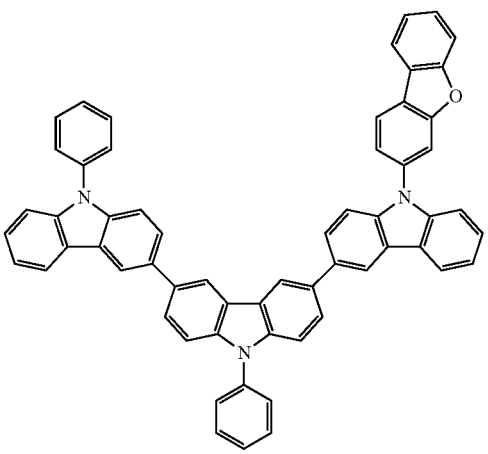
[Formula 213]
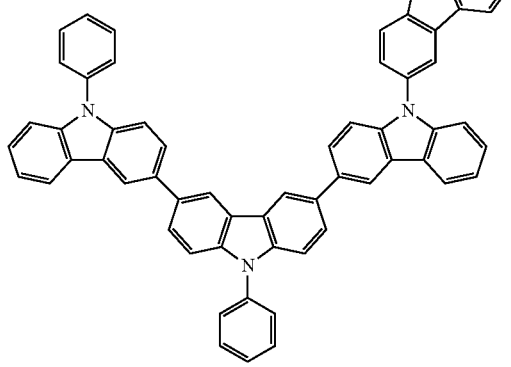
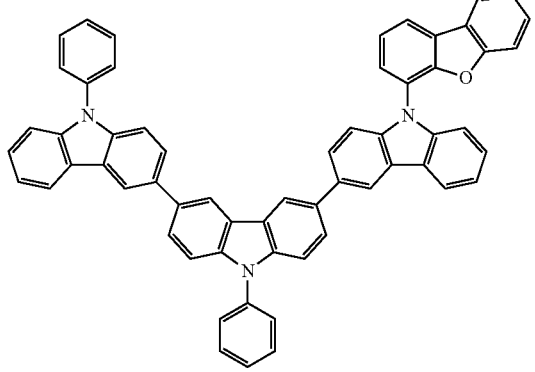

[Formula 214]
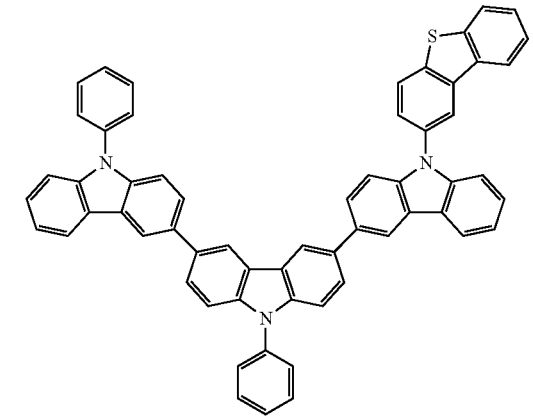
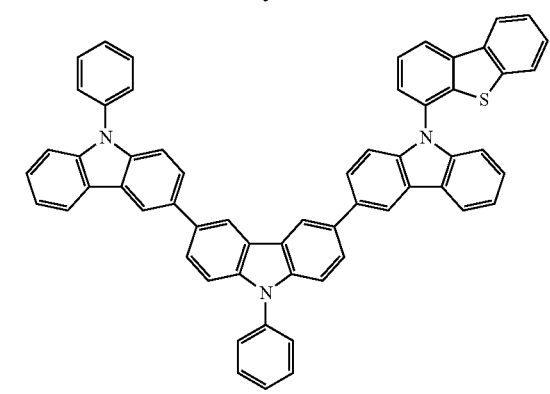
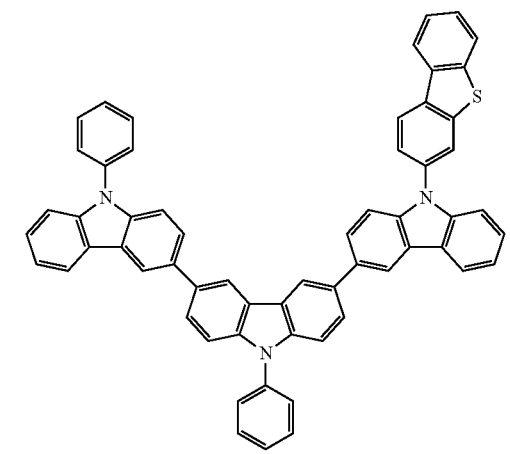
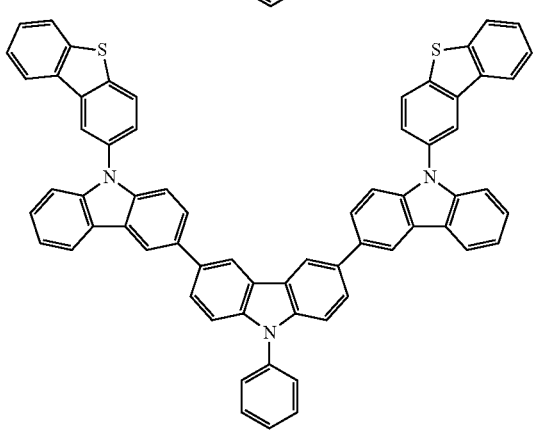
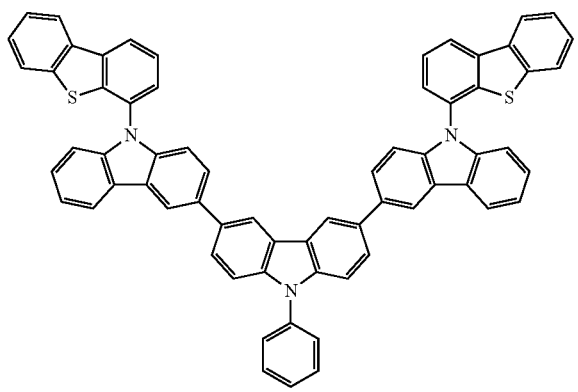
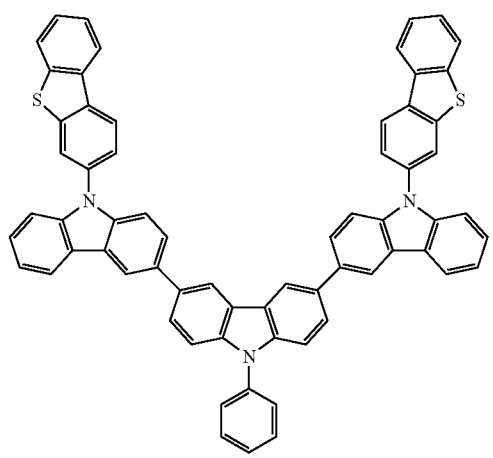
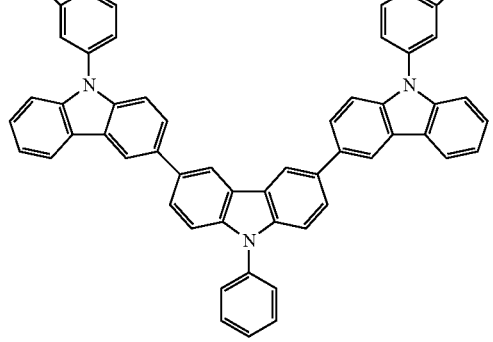
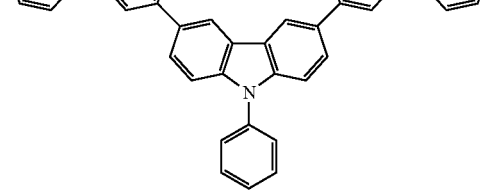
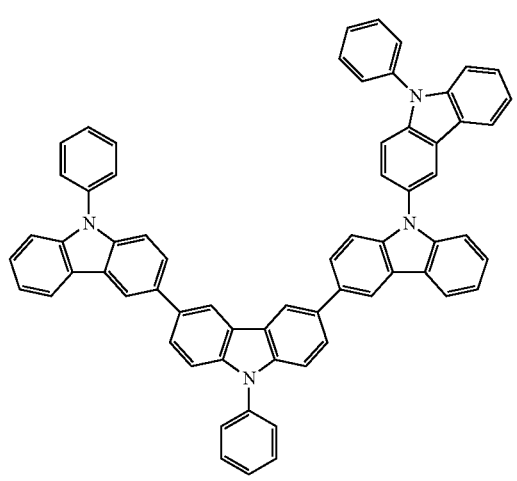

493
-continued
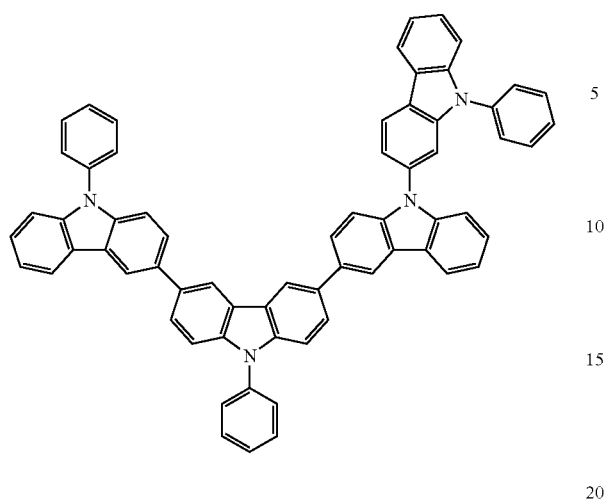
[Formula 215]
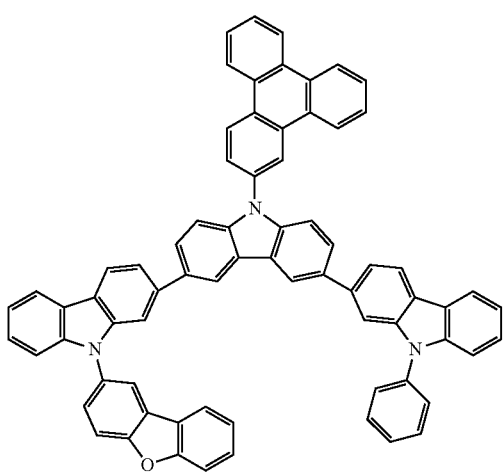
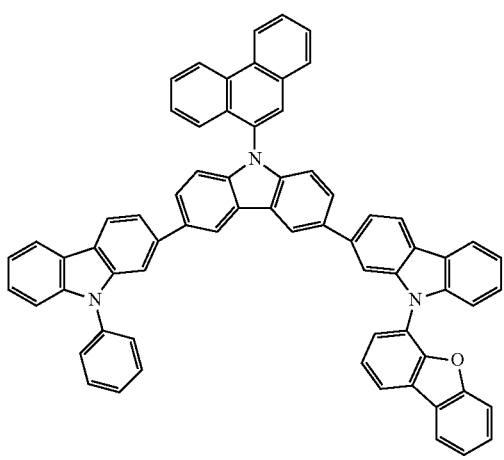
494
-continued
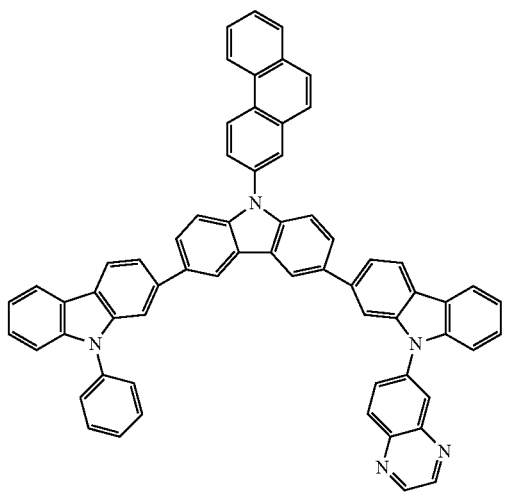
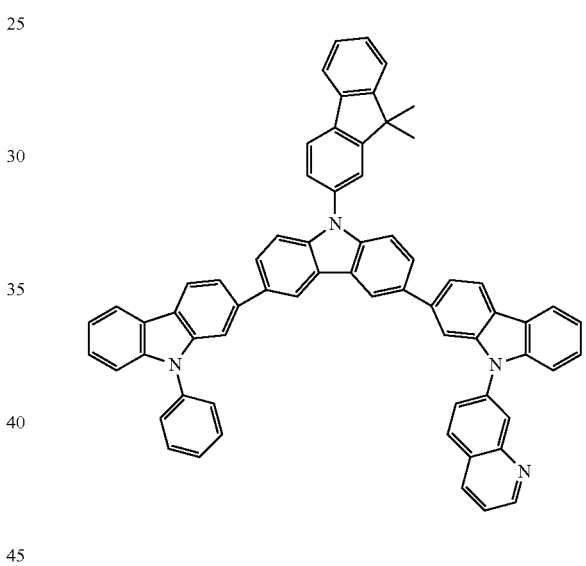
[Formula 216]
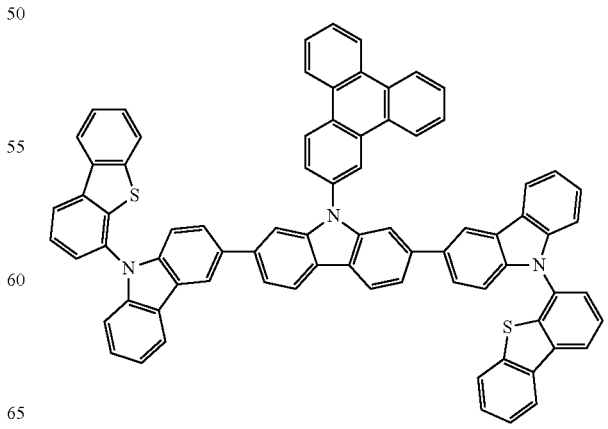

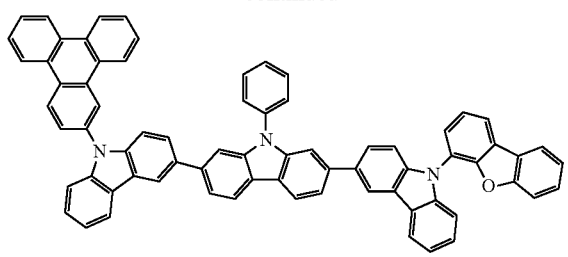
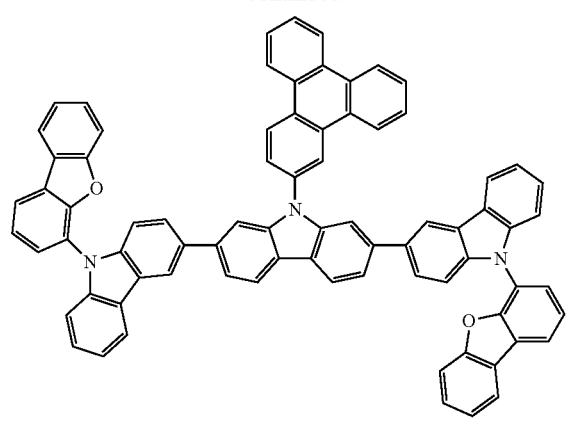
[Formula 217]
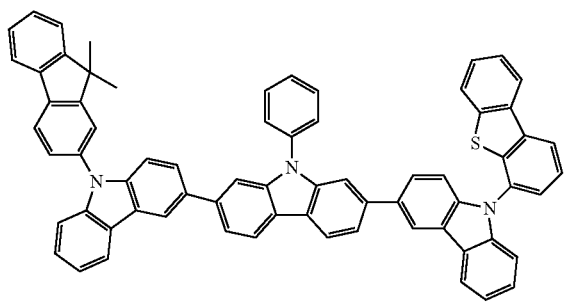
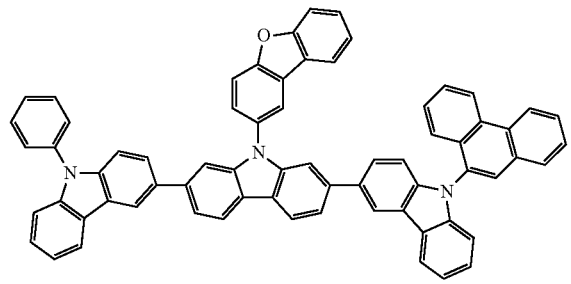
[Formula 218]
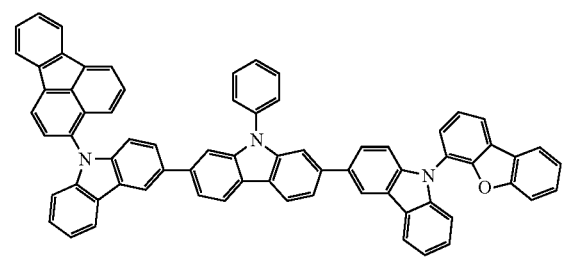
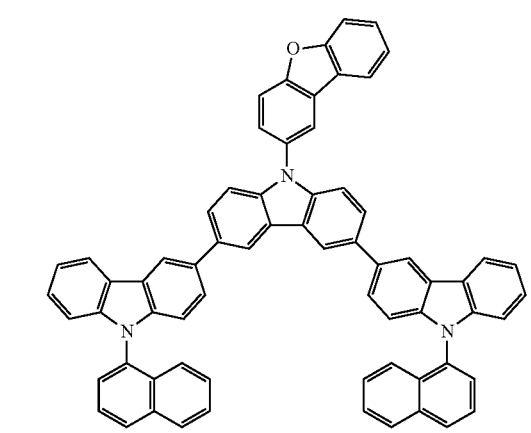
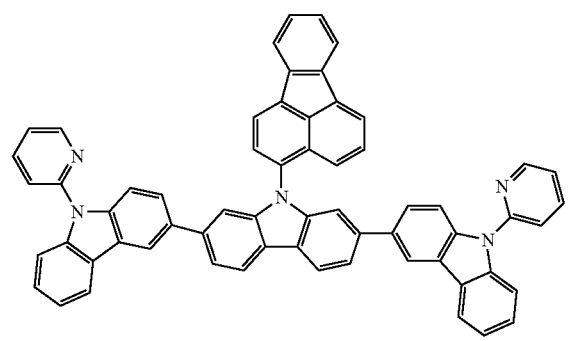
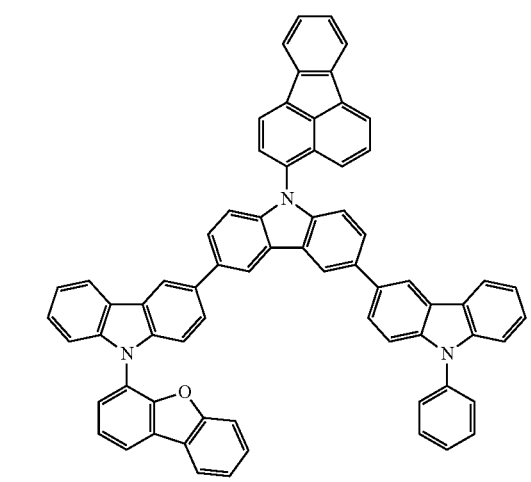
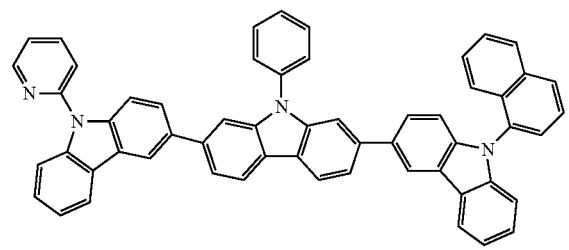

497
-continued
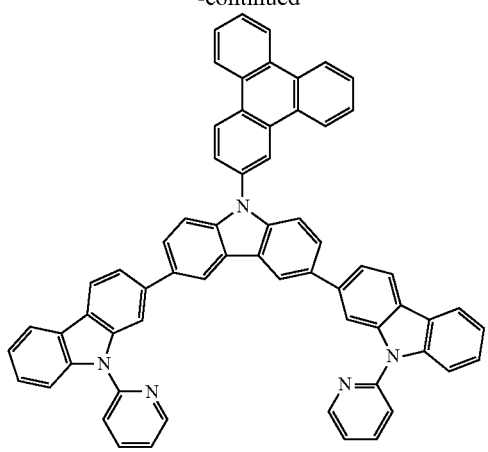
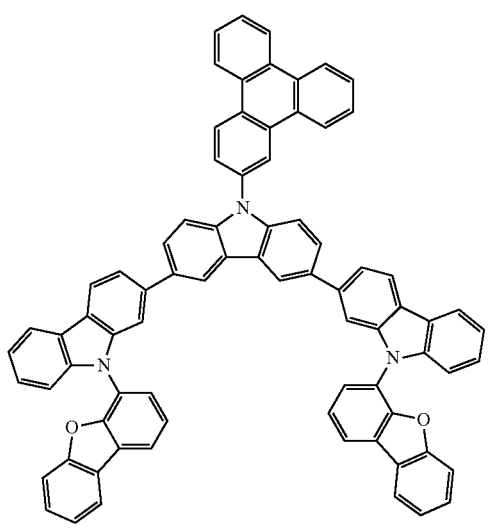
[Formula 219]
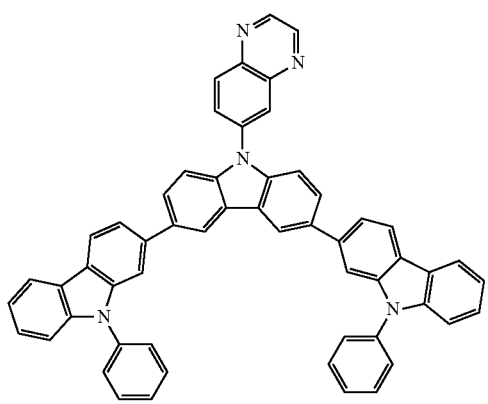
498
-continued
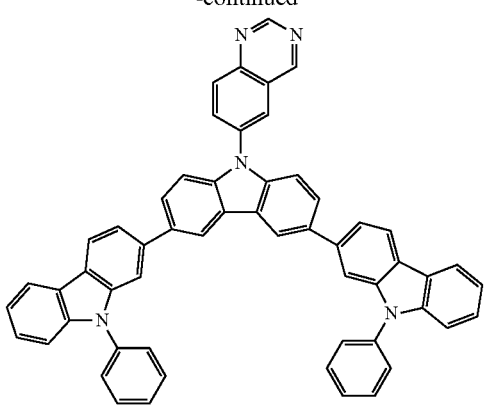
[Formula 220]
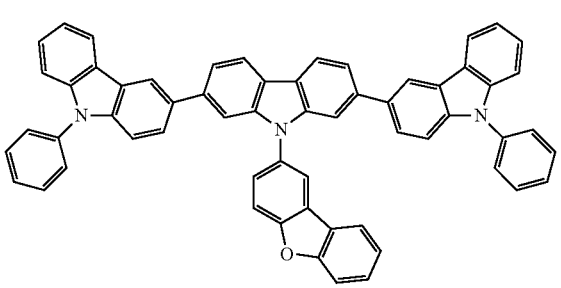
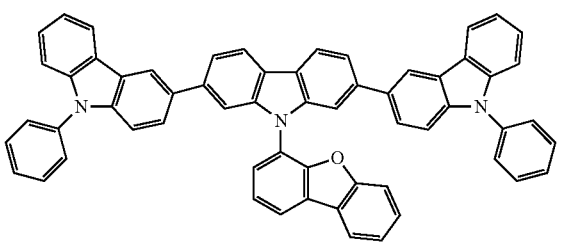
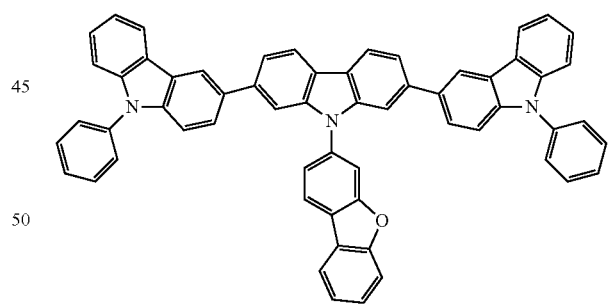

499
-continued
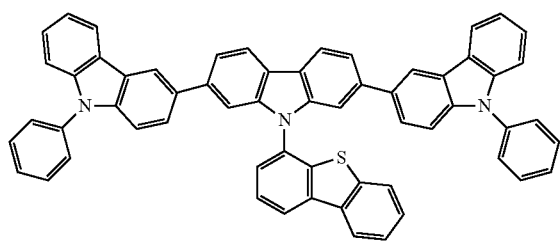
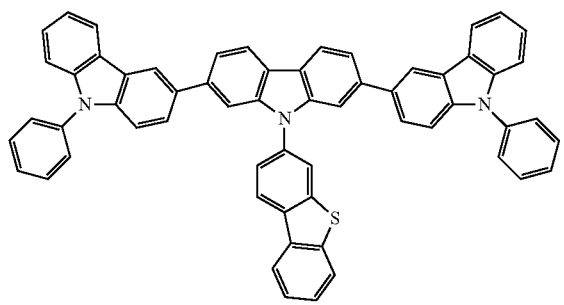
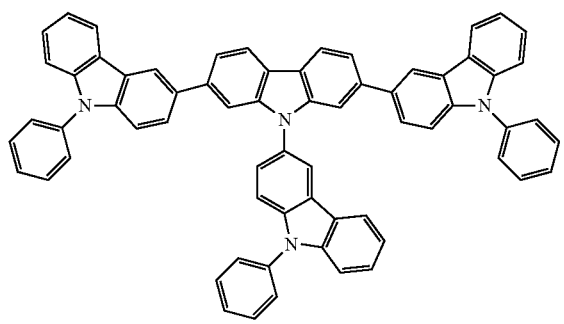
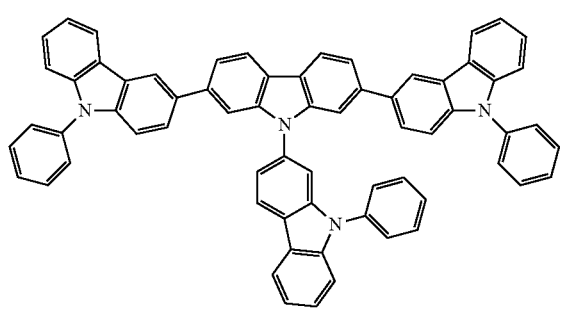
[Formula 221]
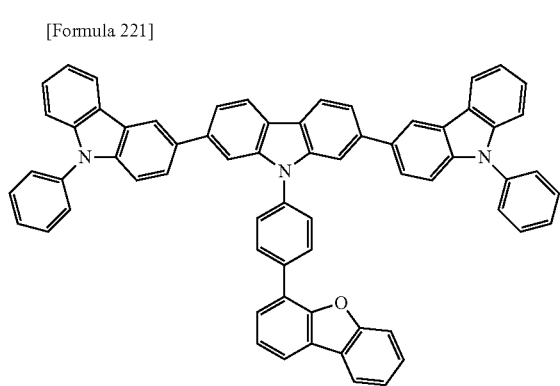
500
-continued
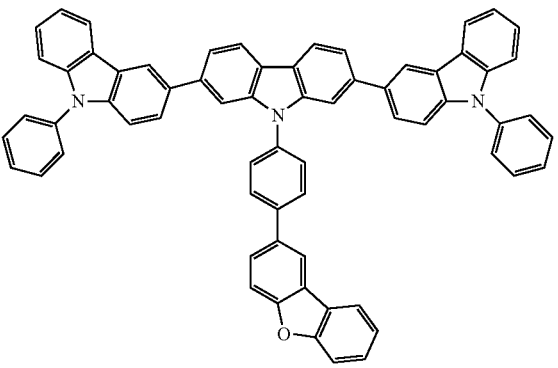
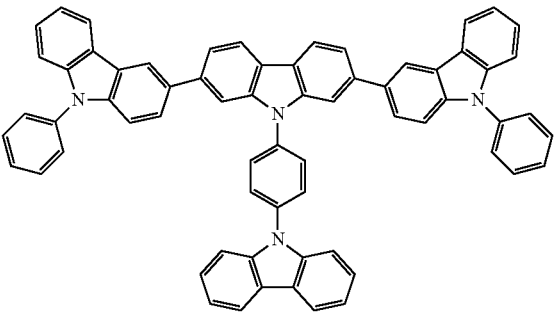
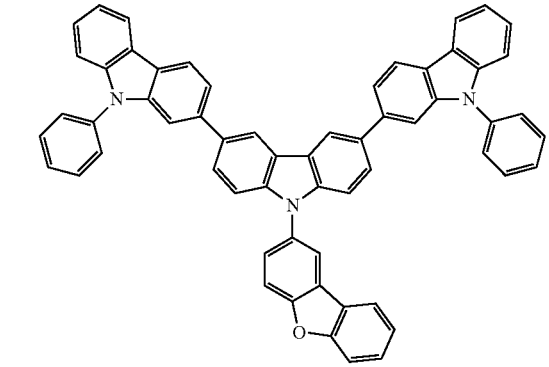
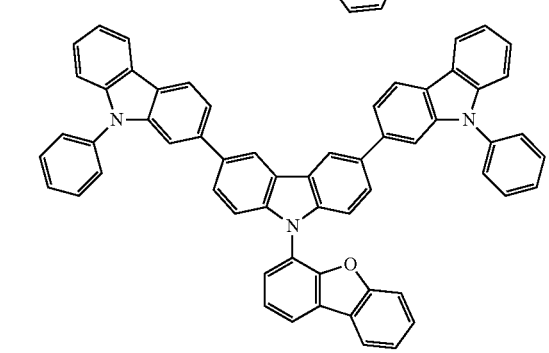
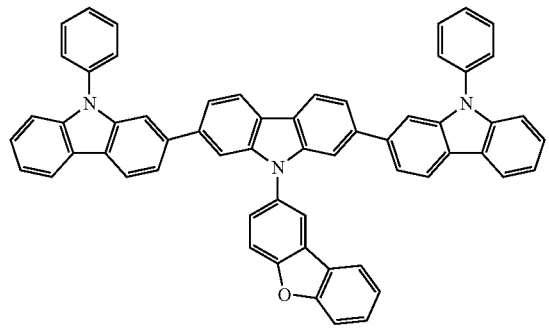

501
-continued
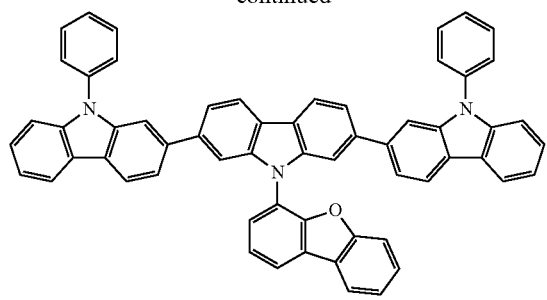
[Formula 222]
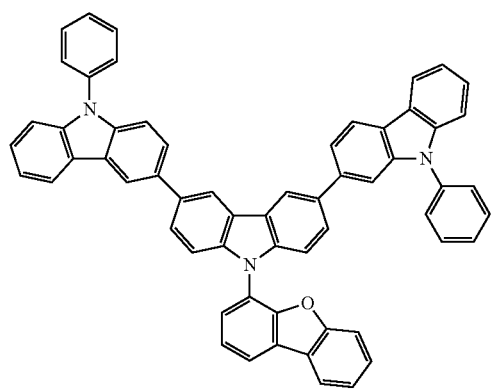
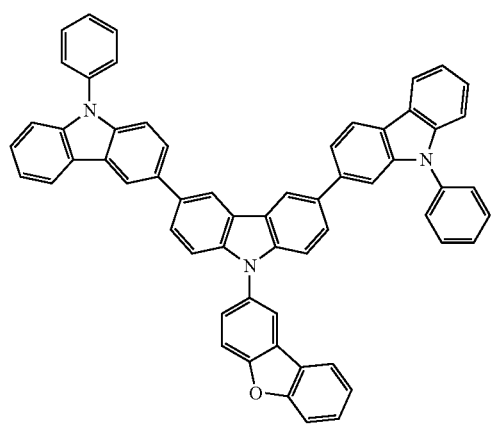
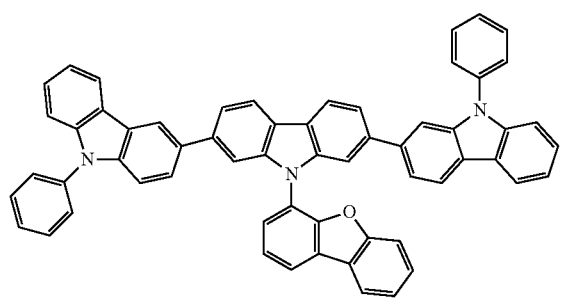
502
-continued
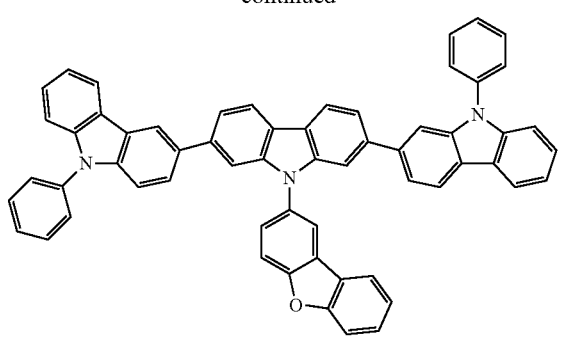
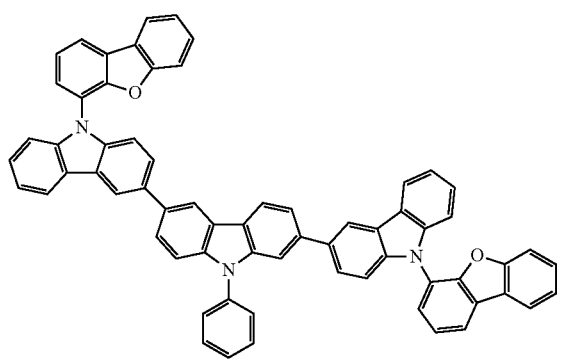
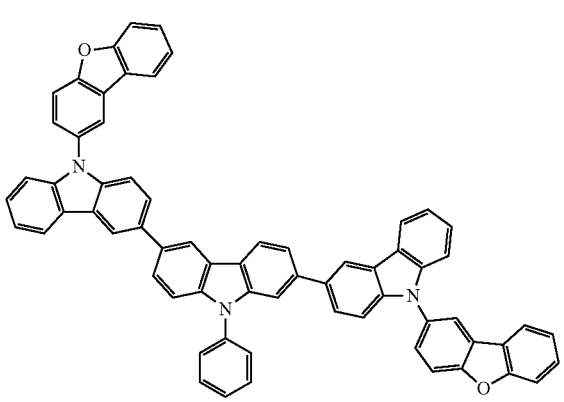
[Formula 223]
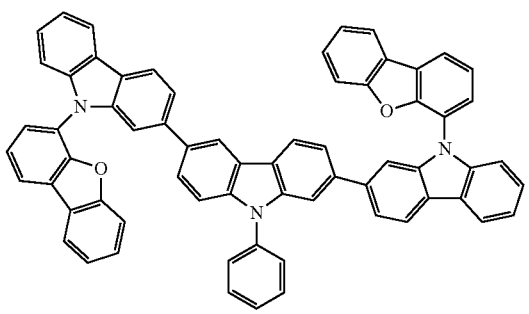

503
-continued
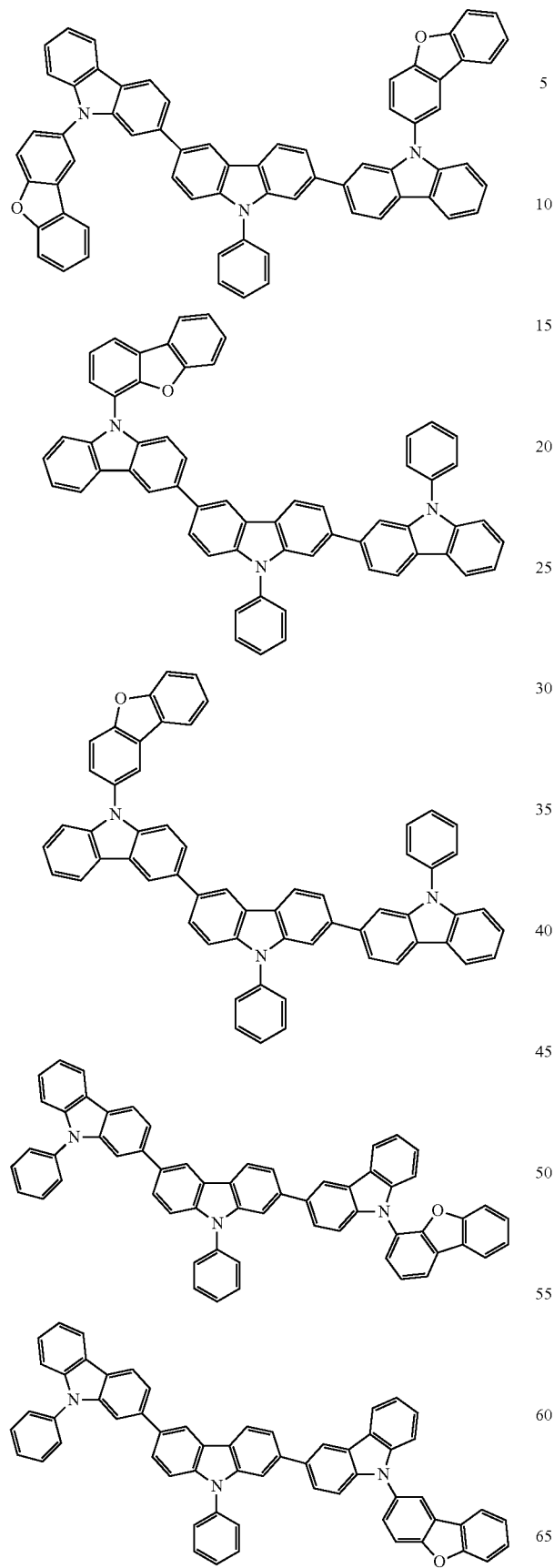
504
-continued
[Formula 224]
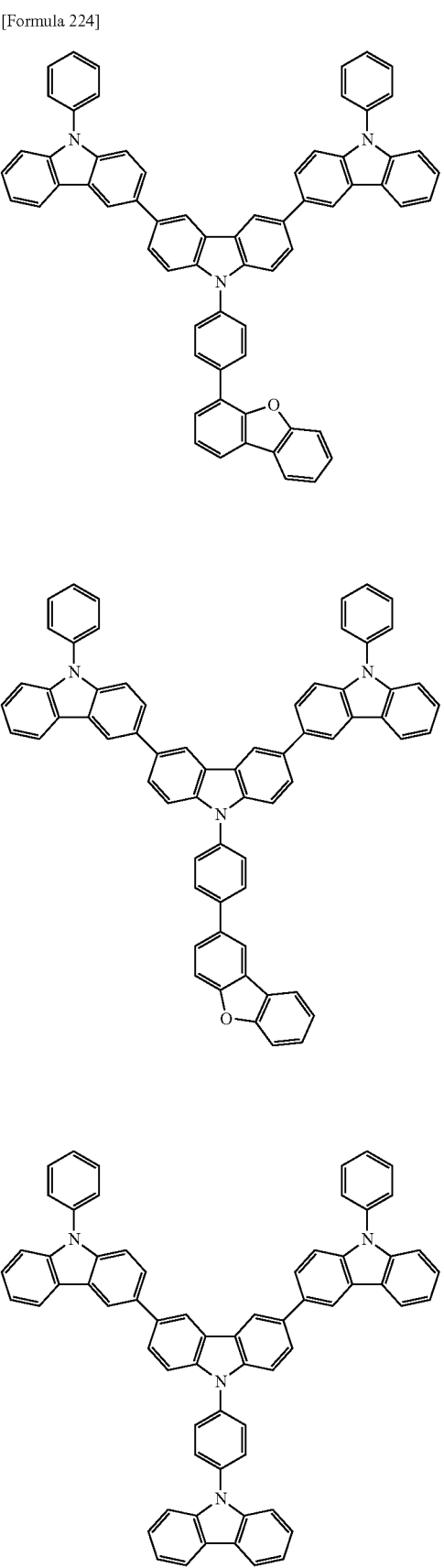

505
-continued
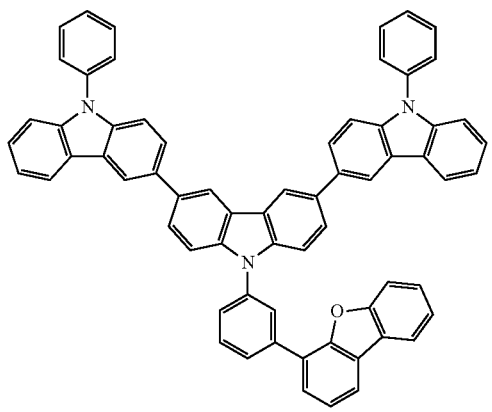
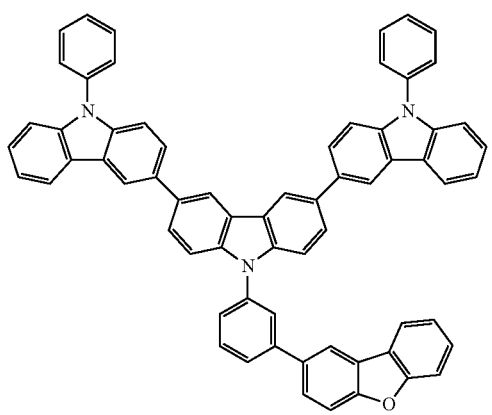
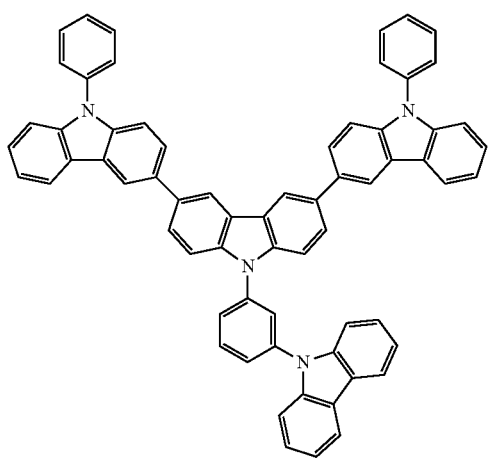
506
-continued
[Formula 225]
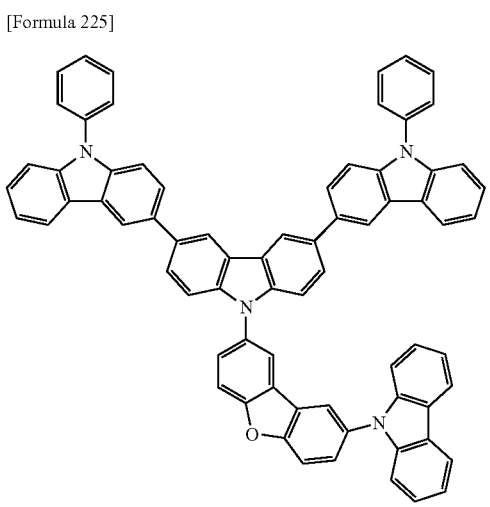
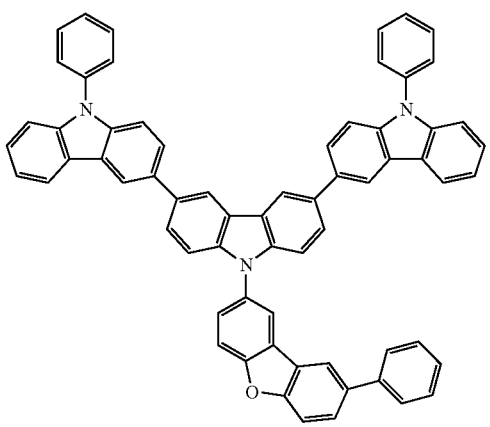
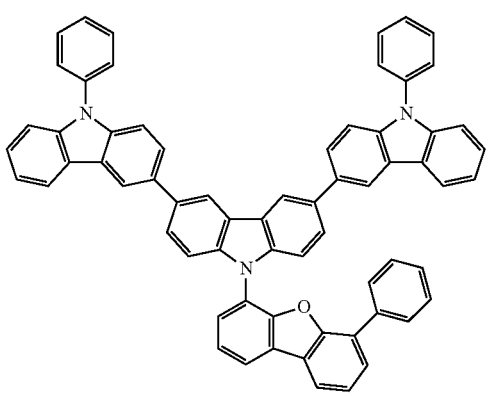

507
-continued
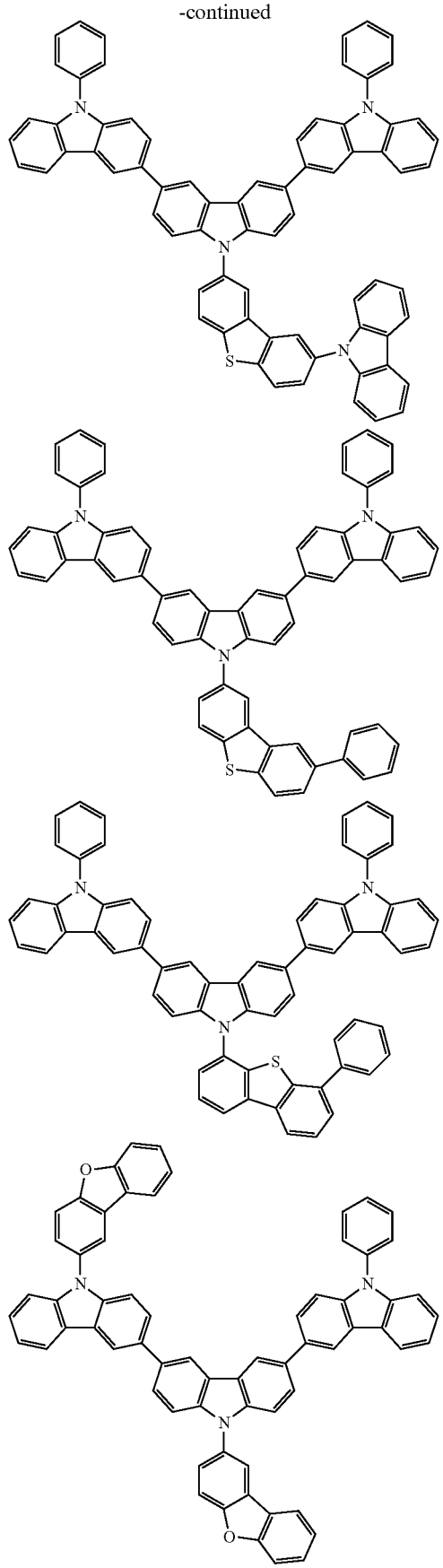
508
-continued
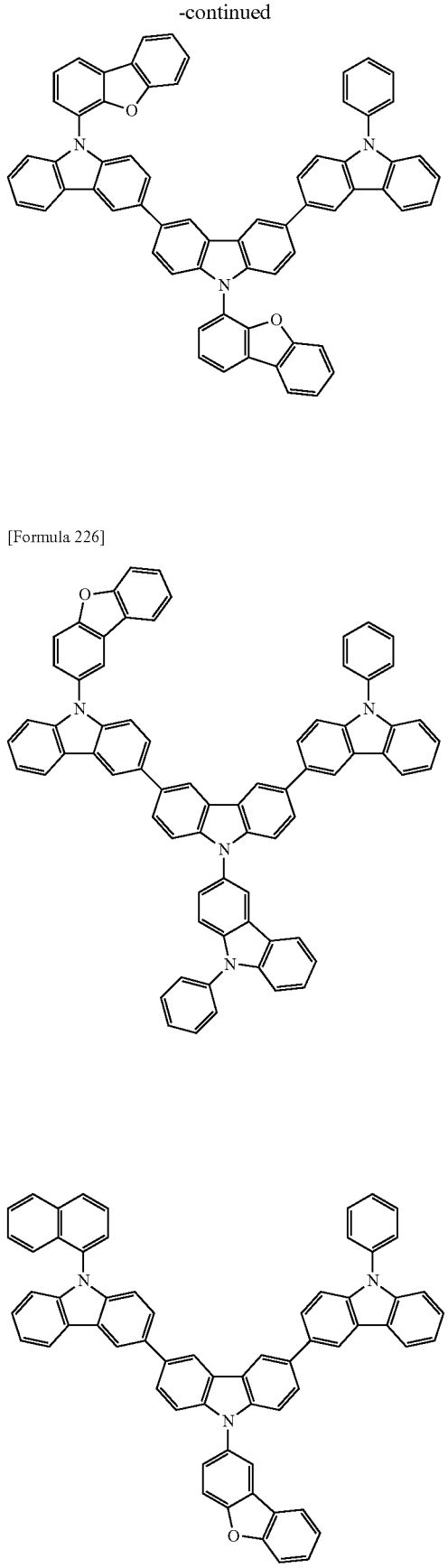
[Formula 226]

509
-continued
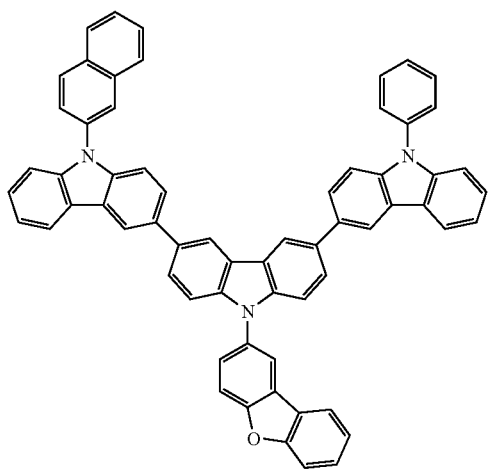
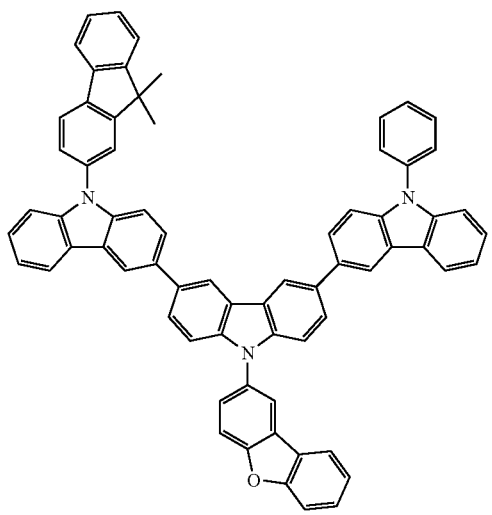
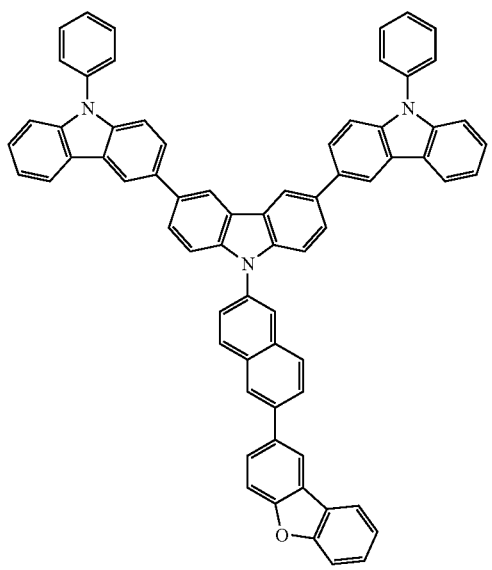
510
-continued
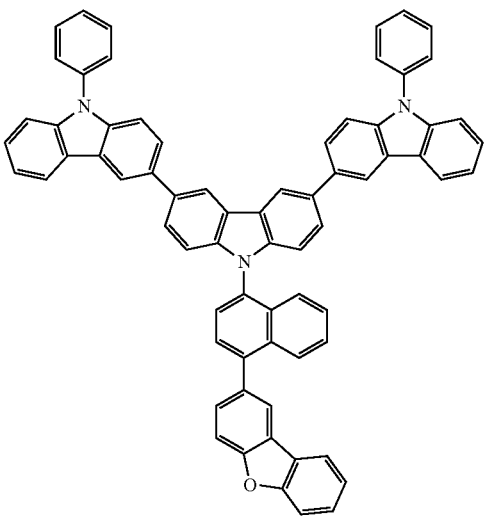
[Formula 227]
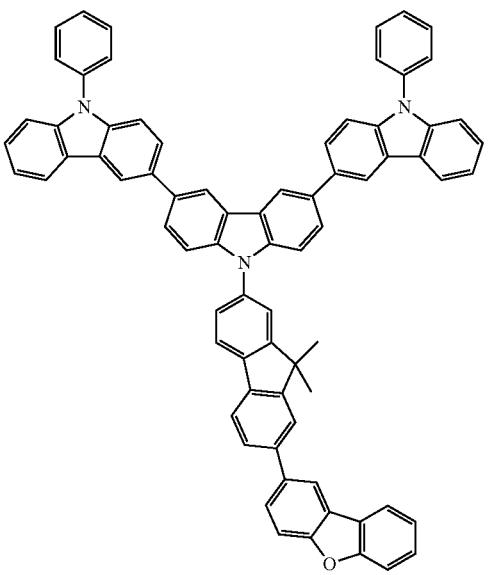
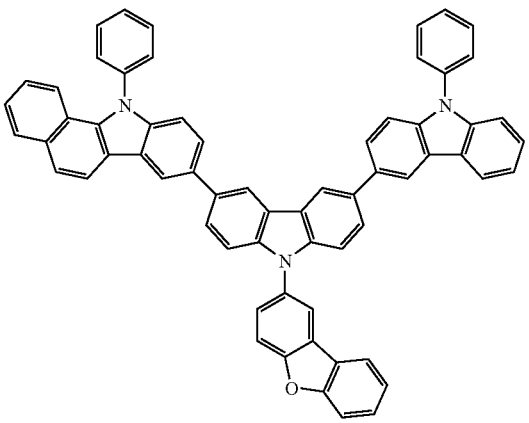

511
-continued
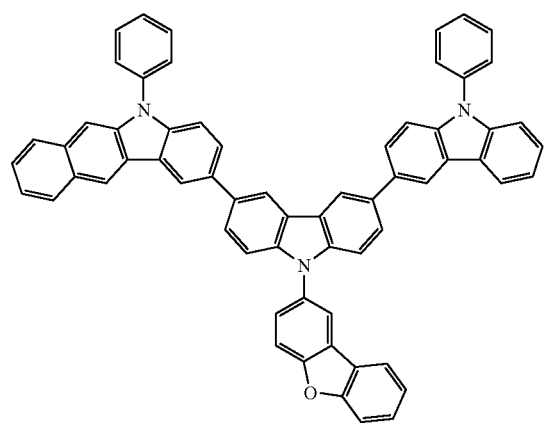
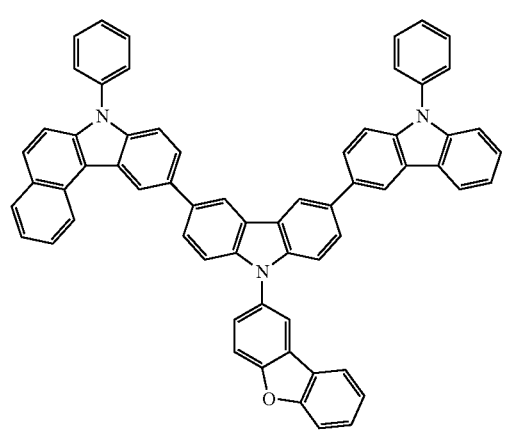
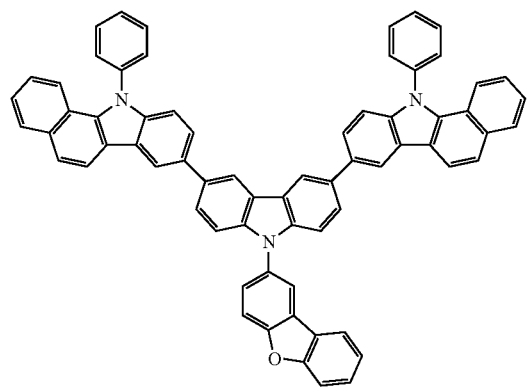
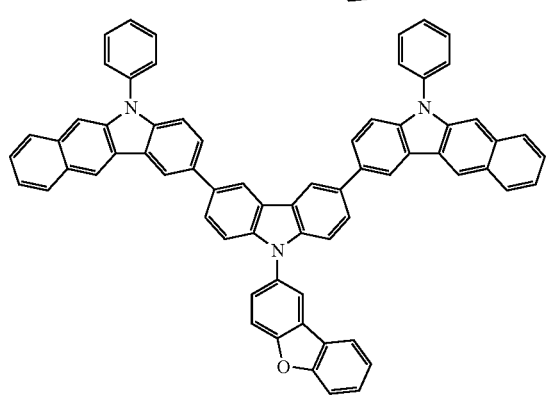
512
-continued
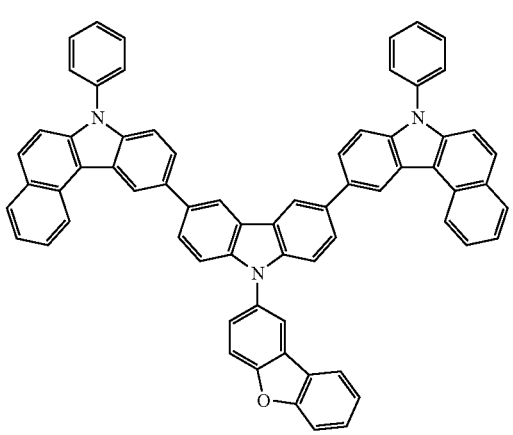
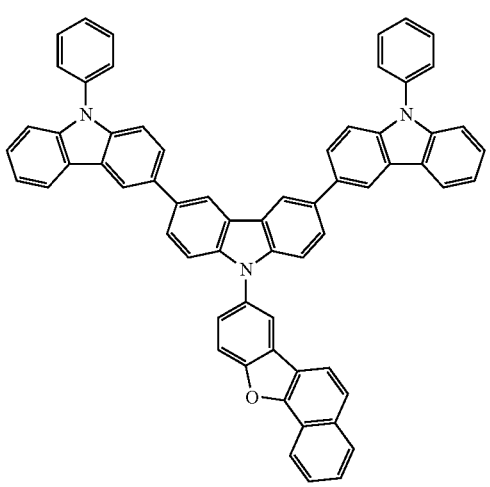
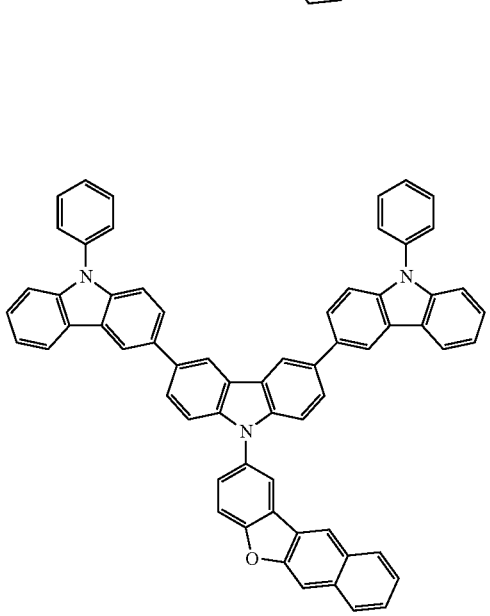

513
-continued
[Formula 228]
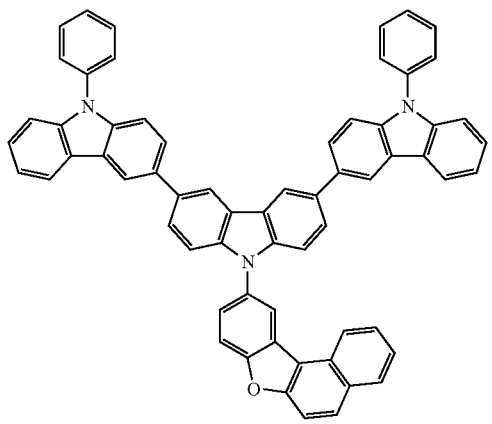
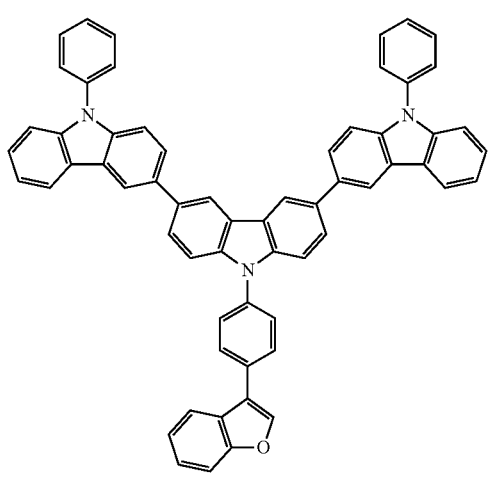
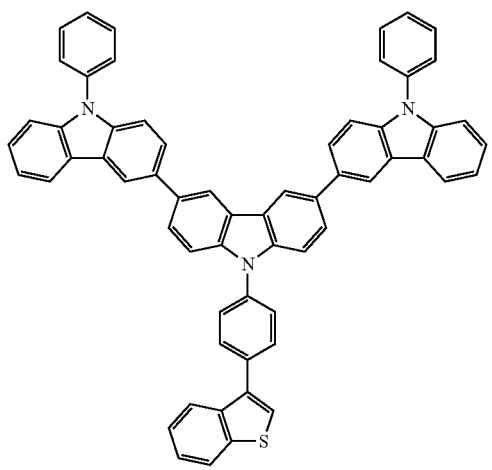
514
-continued
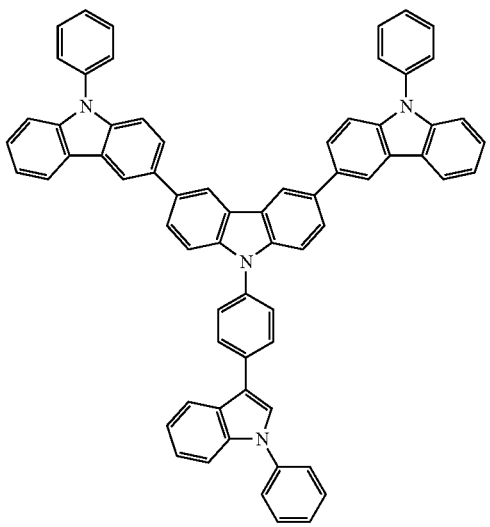
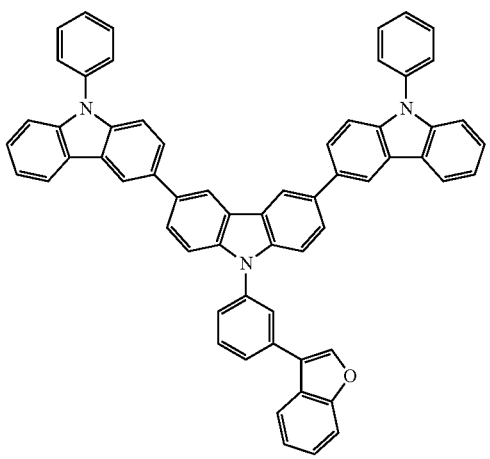
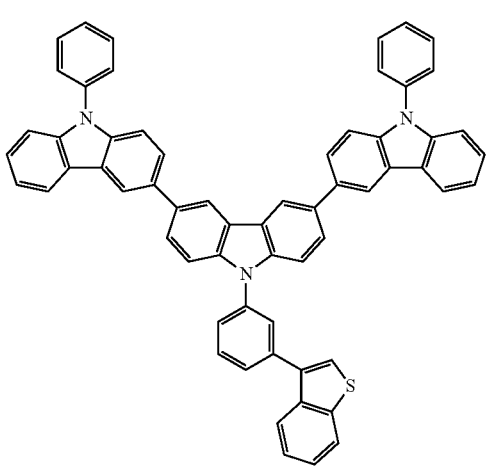

515
-continued
516
-continued
[Formula 229]
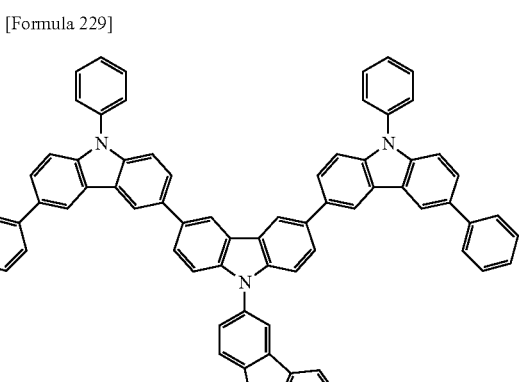
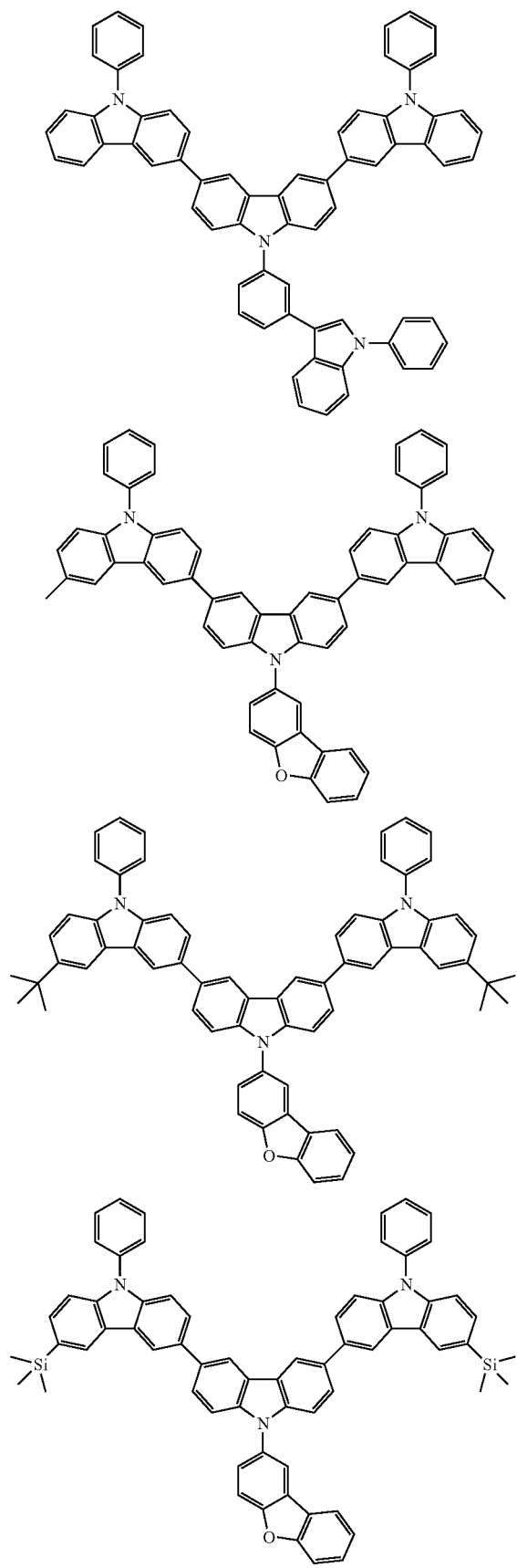

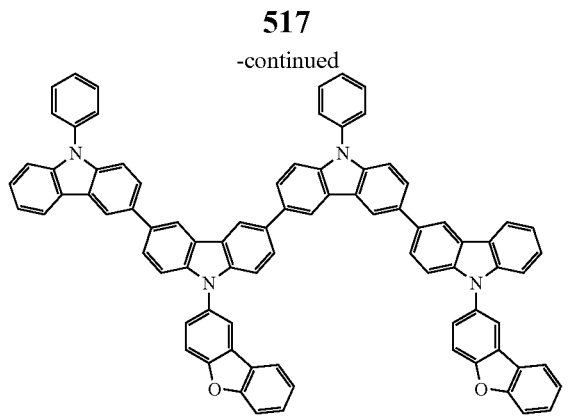

Phosphorescent Dopant Material

The phosphorescent material preferably contains a metal complex, and the metal complex preferably has a metal atom selected from Ir (iridium), Pt (platinum), Os (osmium), Au (gold), Cu (copper), Re (rhenium) and Ru (ruthenium), and a ligand. Particularly, the ligand preferably has an ortho-metal bond.

The phosphorescent material is preferably a compound containing a metal selected from Ir, Os and Pt because such a compound, which exhibits high phosphorescence quantum yield, can further enhance external quantum efficiency of the organic EL device. The phosphorescent material is more preferably a metal complex such as an iridium complex, osmium complex or platinum complex, among which an iridium complex and platinum complex are more preferable and ortho metalation of an iridium complex is the most preferable. The organic metal complex formed of the ligand selected from the group consisting of phenyl quinoline, phenyl isoquinoline, phenyl pyridine, phenyl pyrimidine, phenyl pyrazine, phenyl imidazole and benzoquinoline is preferable in terms of luminous efficiency and the like.

Examples of such a preferable metal complex are shown below.

[Formula 230]

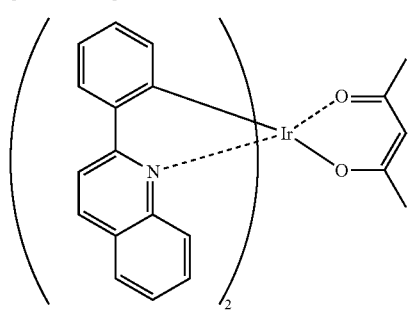

PQIr

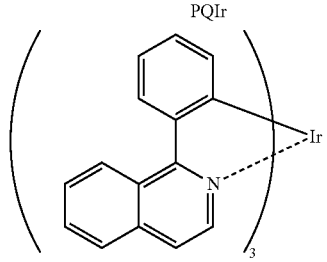

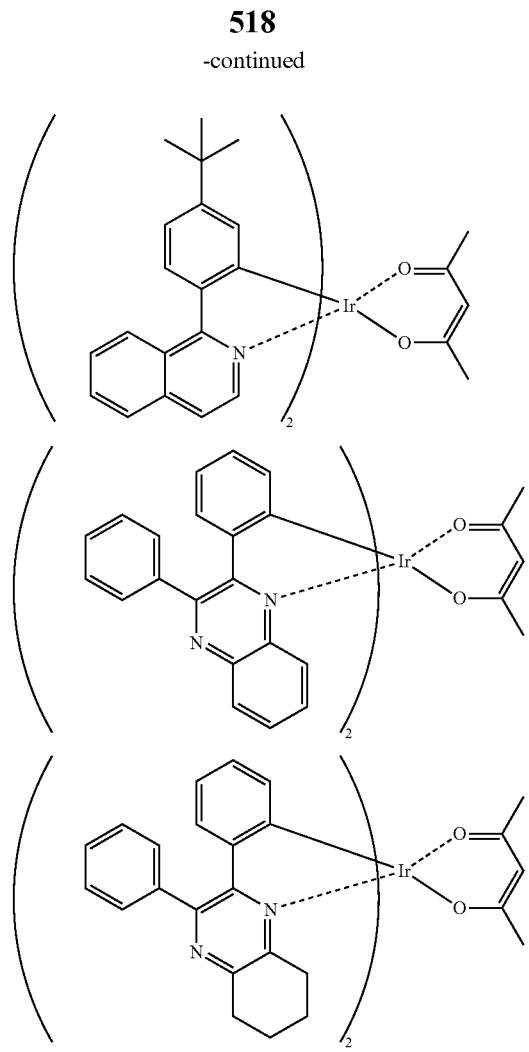

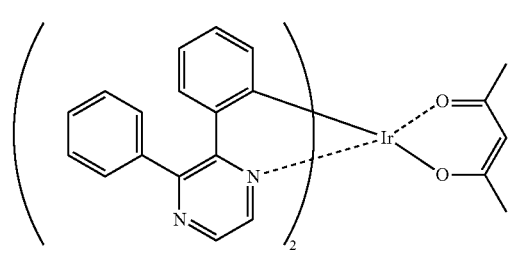

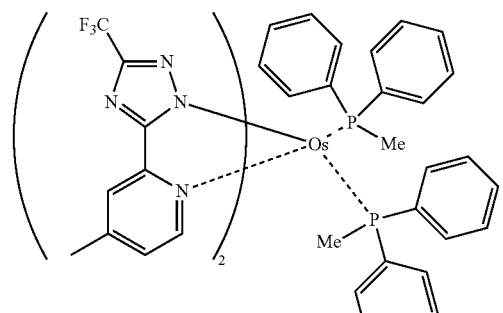

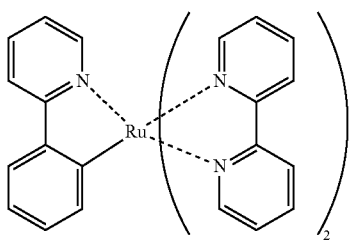
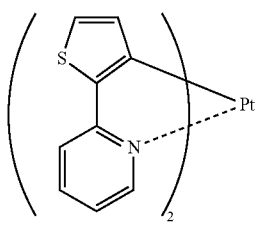
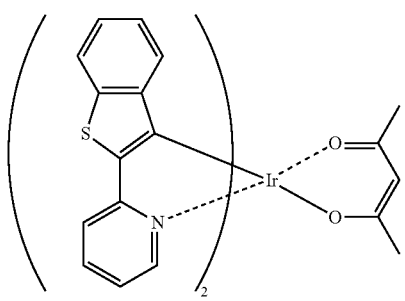
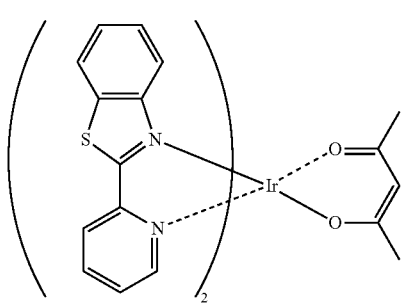
[Formula 231]
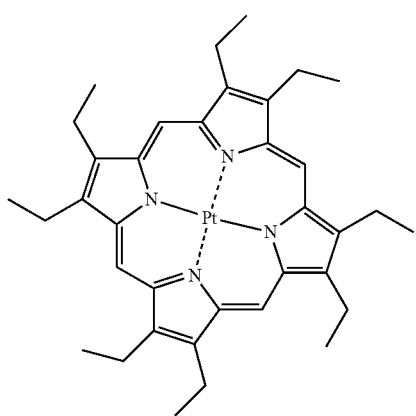
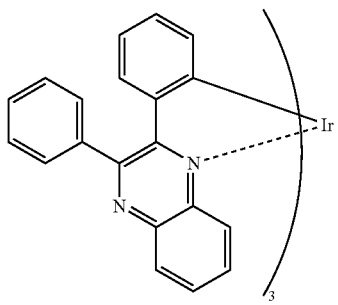
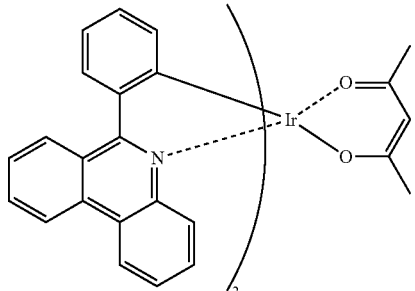
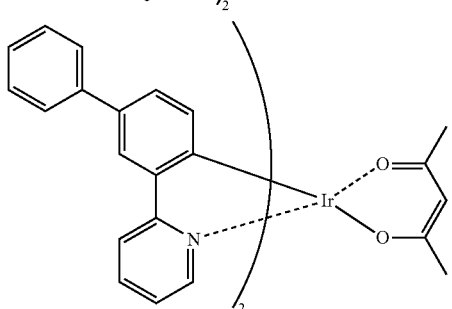
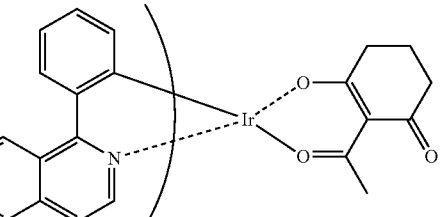
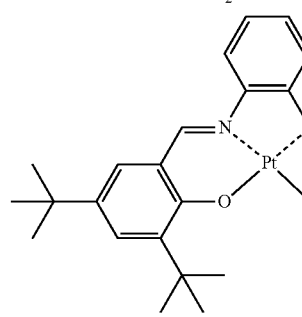
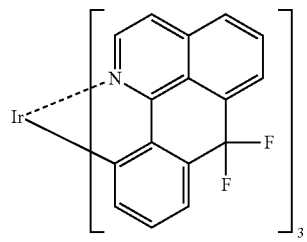

US 10,128,456 B2
[Formula 232]
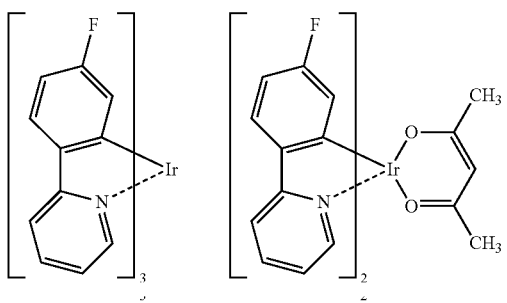
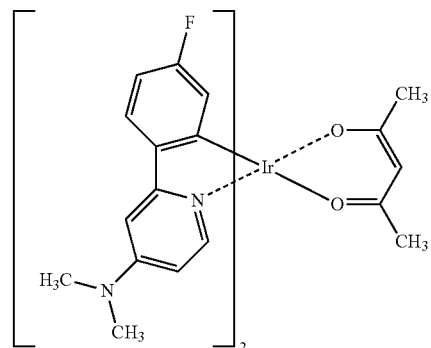
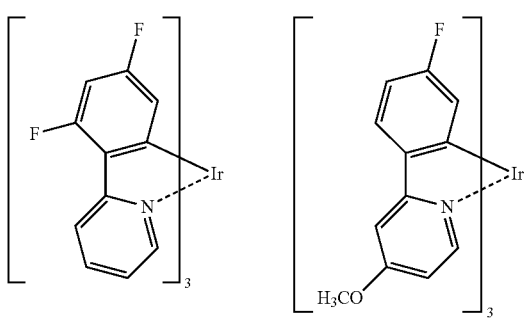
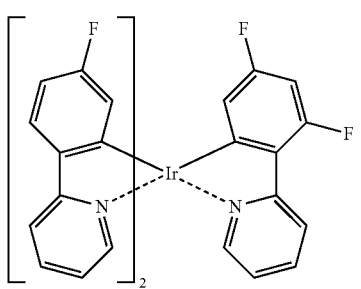
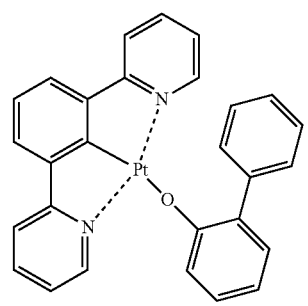
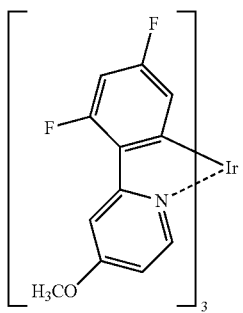
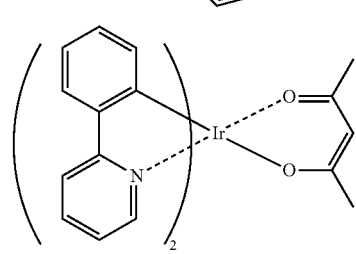
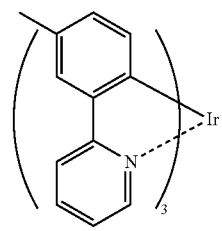
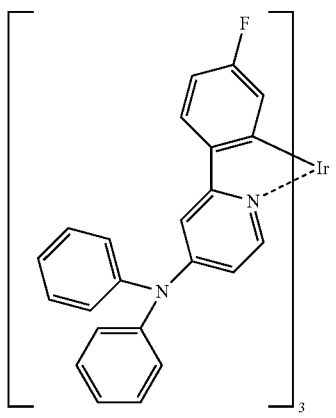
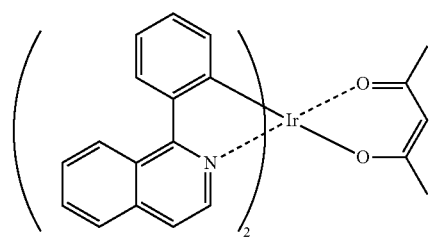

523
-continued
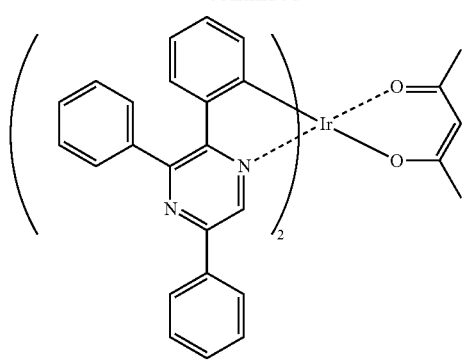
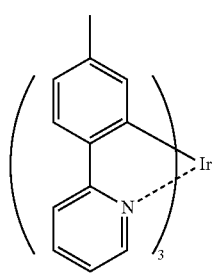
[Formula 233]
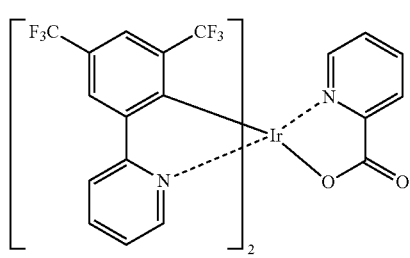
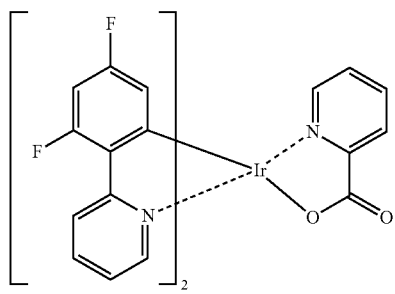
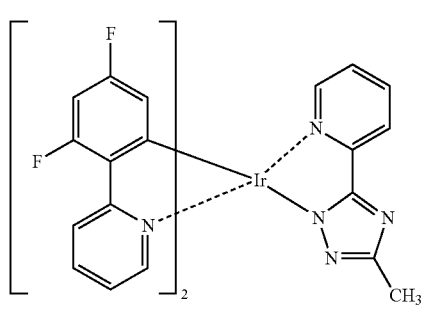
524
-continued
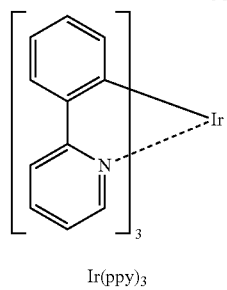
Ir(ppy)₃
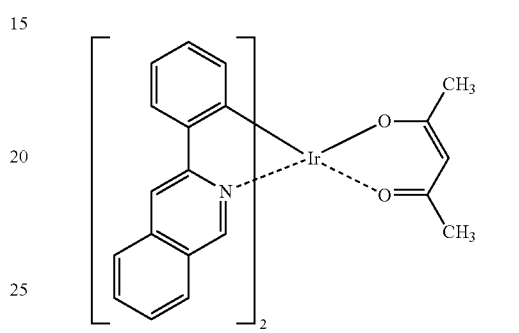
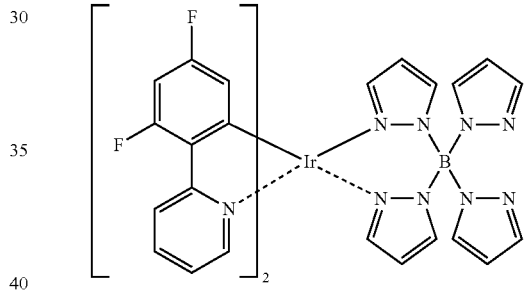
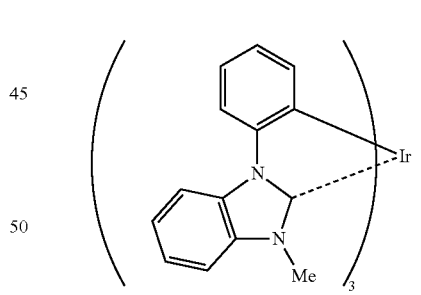
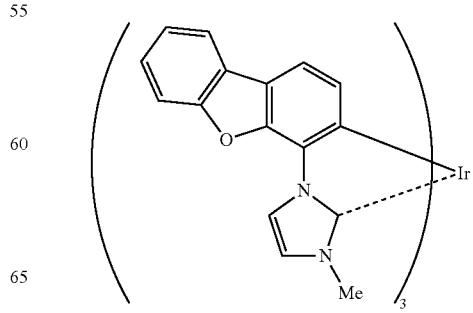

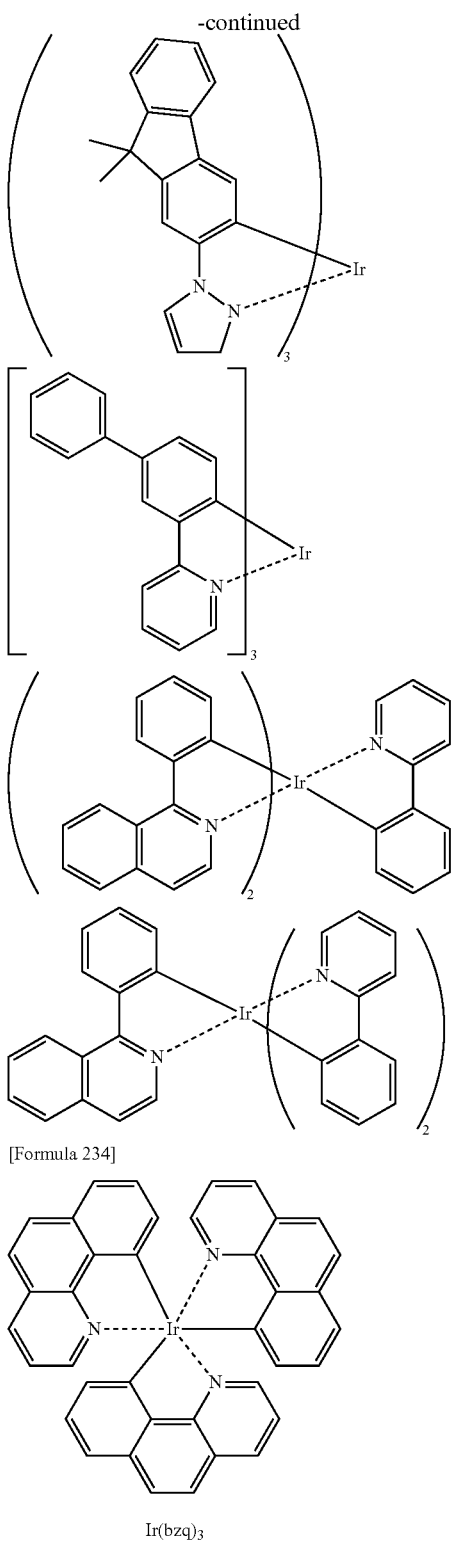

[Formula 234]

Ir(bzq)₃

One of the phosphorescent dopant materials may be used alone, or two or more thereof may be used in combination.

At least one phosphorescent material contained in the emitting layer 5 preferably has an emission wavelength peak in a range of 490 nm to 700 nm, more preferably in a range of 490 nm to 650 nm, further preferably in a range of 490 nm to 600 nm. An emission color of the emitting layer 5 in the exemplary embodiment is preferably yellow or green. Though an emission wavelength peak of yellow is typically in a range of 530 nm to 620 nm, the emission wavelength is particularly preferably in a range of 550 nm to 600 nm in the exemplary embodiment.

By doping the phosphorescent dopant material having such an emission wavelength to the aforementioned specific first and second host materials so as to form the emitting layer 5, the organic EL device can exhibit high efficiency.

Substrate

The organic EL device 1 is configured to include the anode 3, the emitting layer 5 and the cathode 4 laminated on the light-transmissive substrate. The substrate 2, which supports the anode 3 and the like, is preferably a flat and smooth substrate that transmits 50% or more of light in a visible region of 400 nm to 700 nm.

The light-transmissive plate is exemplarily a glass plate, a polymer plate or the like.

The glass plate is formed of soda-lime glass, barium/strontium-containing glass, lead glass, aluminosilicate glass, borosilicate glass, barium borosilicate glass, quartz, and the like.

The polymer plate is formed of polycarbonate, acryl, polyethylene terephthalate, polyether sulfide, polysulfone and the like.

Anode and Cathode

The anode 3 of the organic EL device 1 is used for injecting holes into the hole injecting layer, the hole transporting layer 6 or the emitting layer 5. It is effective that the anode 3 has a work function of 4.5 eV or more.

Specific examples of a material for the anode are alloys of indium-tin oxide (ITO), tin oxide (NESA), indium zinc oxide, gold, silver, platinum and copper.

The anode 3 is producible by forming a thin film of these anode materials through methods such as vapor deposition and sputtering, for instance, on the substrate 2.

When light from the emitting layer 5 is to be emitted through the anode 3, the anode 3 preferably transmits more than 10% of the light in the visible region. Sheet resistance of the anode 3 is preferably several hundreds Ω/sq. or lower. Although depending on the material of the anode 3, a thickness of the anode 3 is typically in a range of 10 nm to 1 μm preferably in a range of 10 nm to 200 nm.

The cathode is preferably formed of a material with smaller work function in order to inject electrons into the emitting layer.

Although the material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

Like the anode 3, the cathode 4 is also producible by forming a thin film through a method such as vapor deposition or sputtering, for instance, on the electron transporting layer 7. In addition, the light from the emitting layer 5 may be emitted through the cathode 4. When light from emitting layer 5 is to be emitted through the cathode 4, the cathode 4 preferably transmits more than 10% of the light in the visible region.

Sheet resistance of the cathode is preferably several hundreds Ω/sq. or lower.

Although depending on the material of the cathode, a thickness of the cathode is typically in a range of 10 nm to 1 μm, preferably in a range of 50 nm to 200 nm.

Other Layers

In order to improve current (luminous) efficiency, a hole injecting layer, a hole transporting layer, an electron injecting layer and the like may be provided. The organic El device 1 includes the hole transporting layer 6 and the electron transporting layer 7.

Hole Transporting Layer

The hole transporting layer 6 helps injection of holes to the emitting layer and transports the holes to an emitting region. The hole transporting layer 6 exhibits a large hole mobility and a small ionization potential.

A hole transporting material for forming the hole transporting layer 6 is preferably a material of transporting the holes to the emitting layer 5 at a lower electric field intensity. For instance, the second host material represented by the formula (2) in the exemplary embodiment is usable. In addition, an aromatic amine derivative represented by the following formula (A1) is preferably used as the material for the hole transporting layer 6.

[Formula 235]

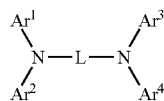
(A1)

In the formula (A1), $Ar^1$ to $Ar^4$ each represent: an aromatic hydrocarbon group having 6 to 50 ring carbon atoms, a fused aromatic hydrocarbon group having 6 to 50 ring carbon atoms, an aromatic heterocyclic group having 2 to 40 ring carbon atoms, a fused aromatic heterocyclic group having 2 to 40 ring carbon atoms, a group provided by bonding the aromatic hydrocarbon group and the aromatic heterocyclic group, a group provided by bonding the aromatic hydrocarbon group and the fused aromatic heterocyclic group, a group provided by bonding the fused aromatic hydrocarbon group and the aromatic heterocyclic group, and a group provided by bonding the fused aromatic hydrocarbon group and the fused aromatic heterocyclic group.

The aromatic hydrocarbon group, the fused aromatic hydrocarbon group, the aromatic heterocyclic group and the fused aromatic heterocyclic group described above may be substituted.

In the formula (A1), L is a linking group and represents a divalent aromatic hydrocarbon group having 6 to 50 ring carbon atoms, a divalent fused aromatic hydrocarbon group having 6 to 50 ring carbon atoms, a divalent aromatic heterocyclic group having 5 to 50 ring carbon atoms, a divalent fused aromatic heterocyclic group having 5 to 50 ring carbon atoms, or a divalent group including two or more of an aromatic hydrocarbon group or an aromatic heterocyclic group with a single bond, an ether bond, a thioether bond, an alkylene group having 1 to 20 carbon atoms, an alkenylene group having 2 to 20 carbon atoms, or an amino group.

The divalent aromatic hydrocarbon group, the divalent fused aromatic hydrocarbon group, the divalent aromatic heterocyclic group and the divalent fused aromatic heterocyclic group described above may be substituted.

Examples of the compound represented by the formula (A1) are shown below. However, the compound is not limited thereto.

[Formula 236]

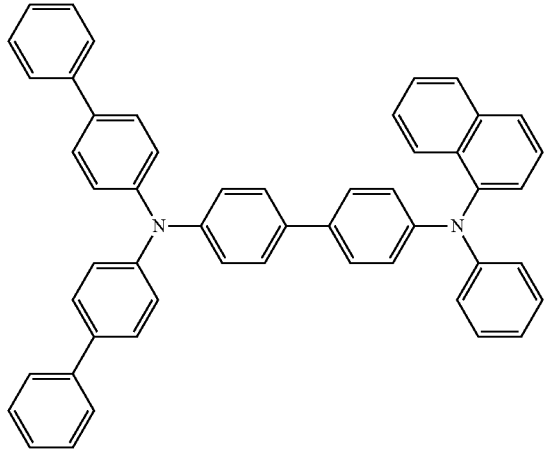

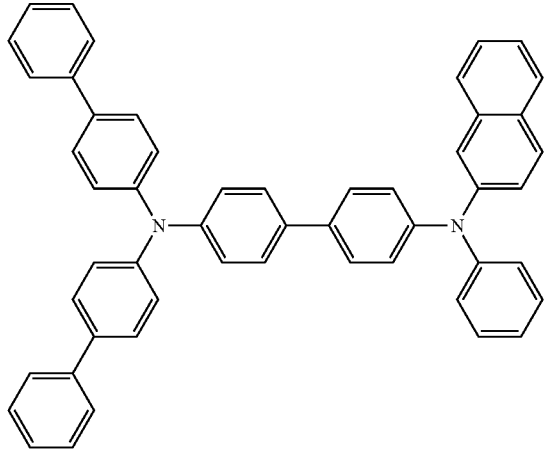

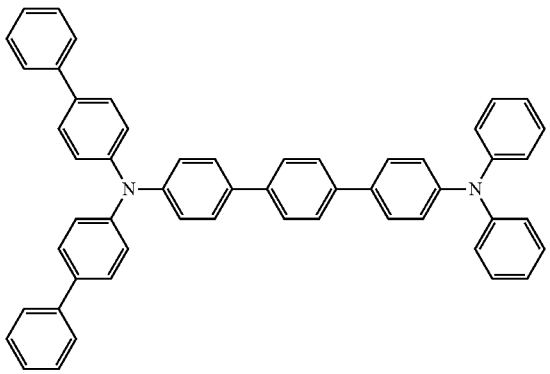

529
-continued
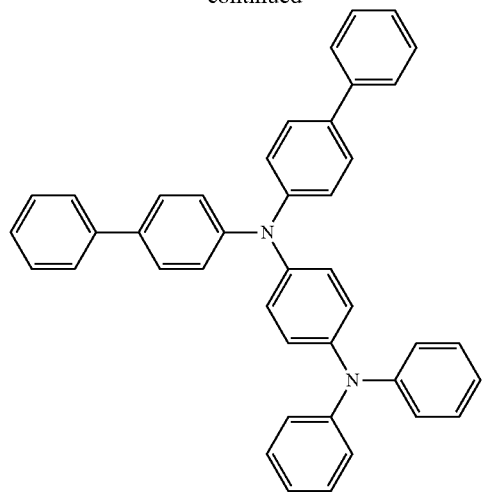
530
-continued
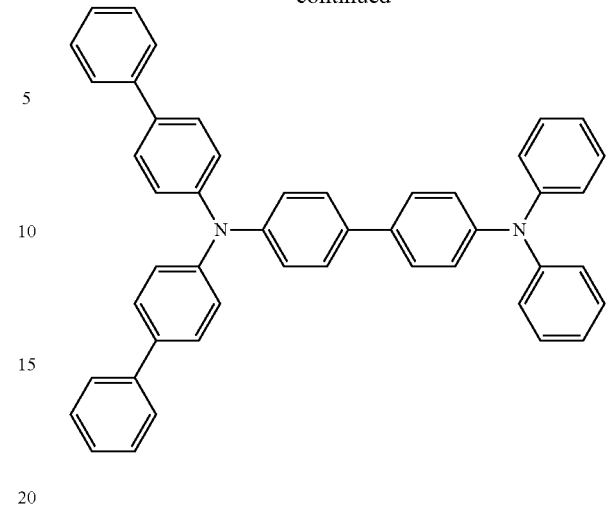
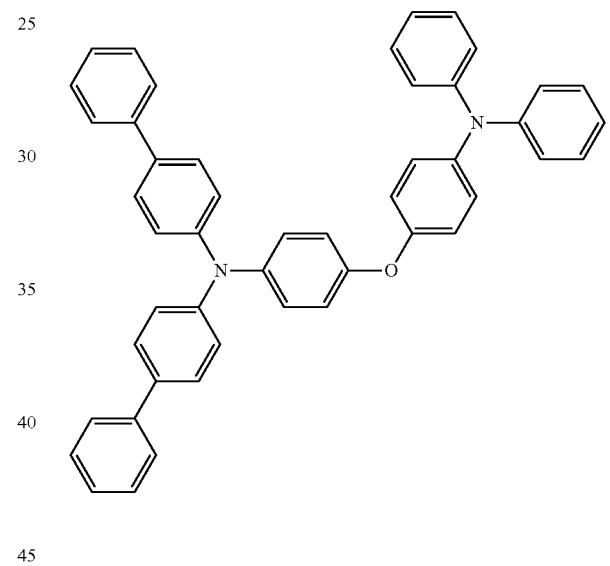
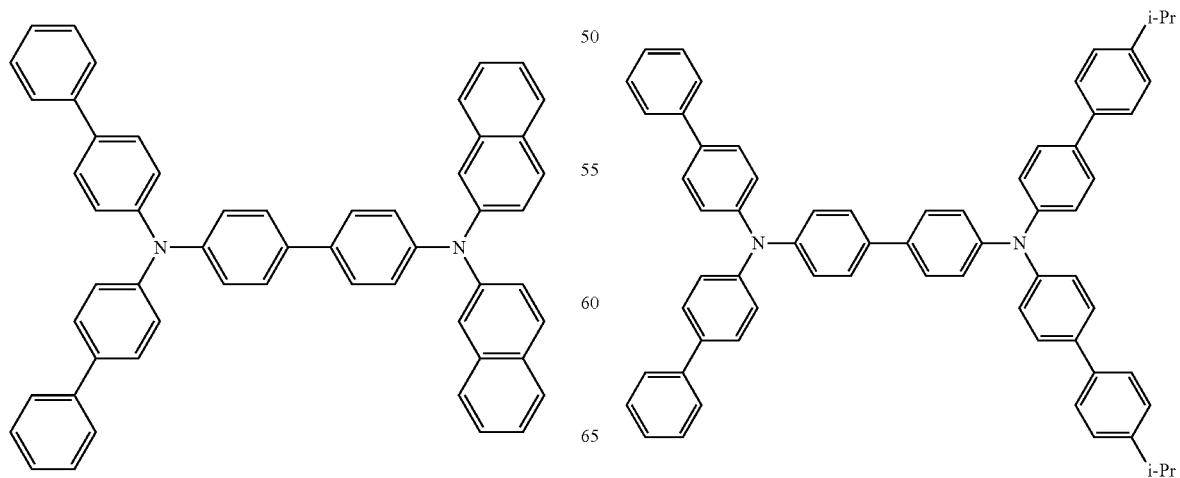

531
-continued
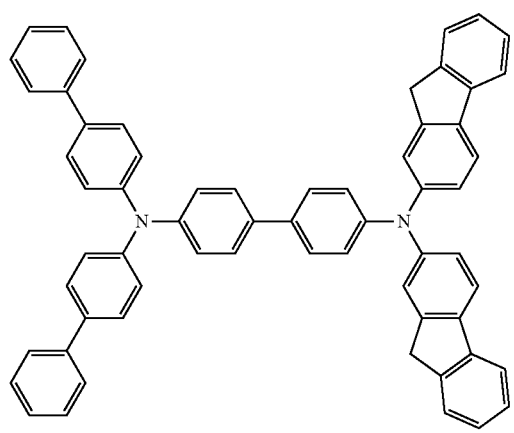
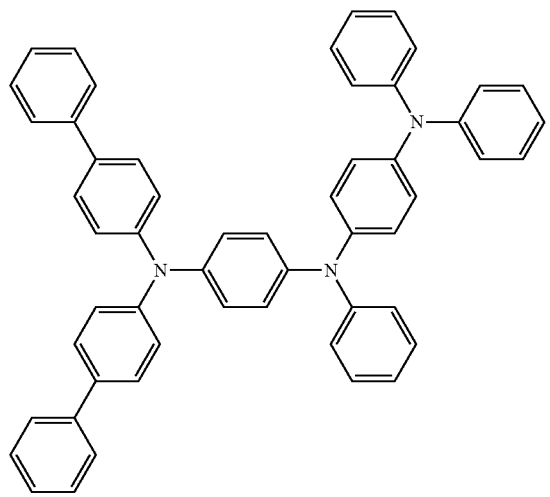
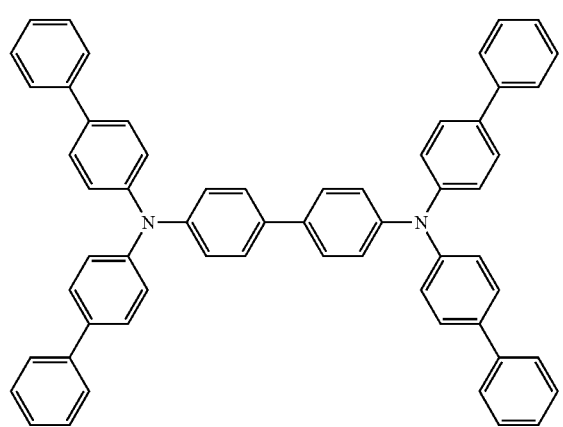
532
-continued
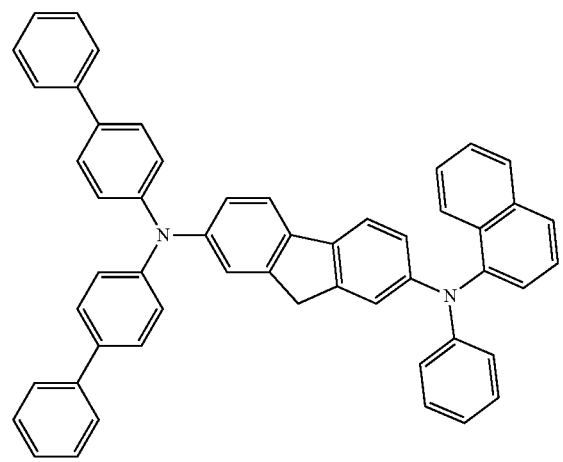
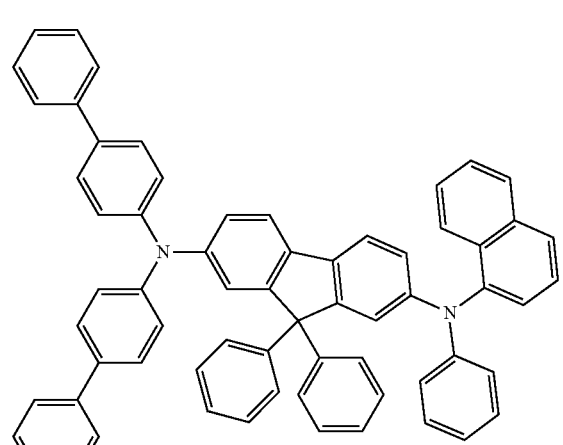
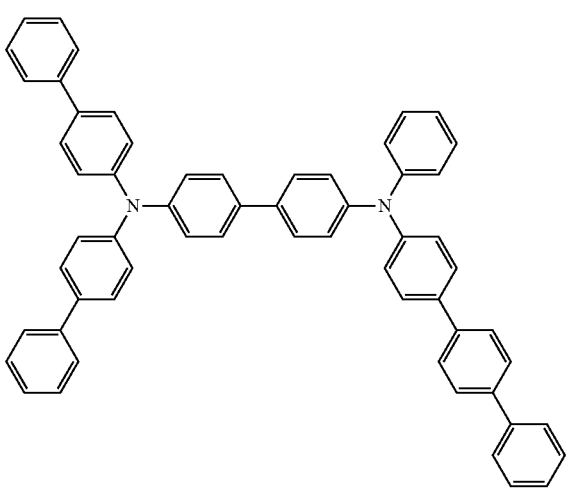

533
-continued
534
-continued
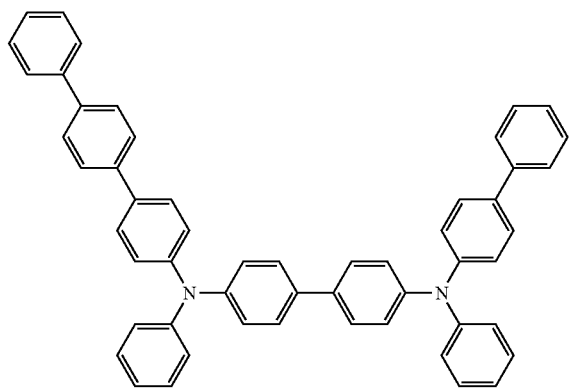
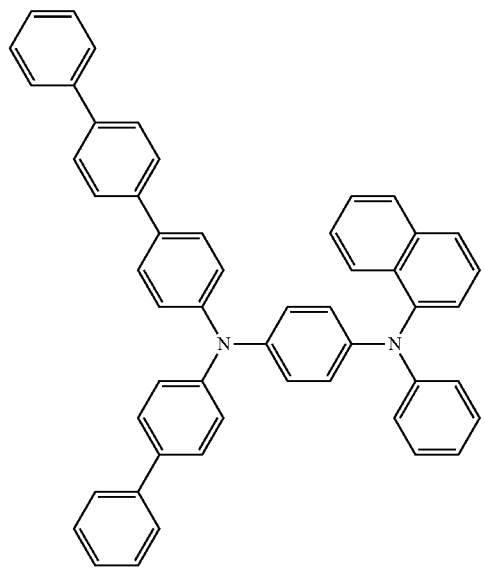
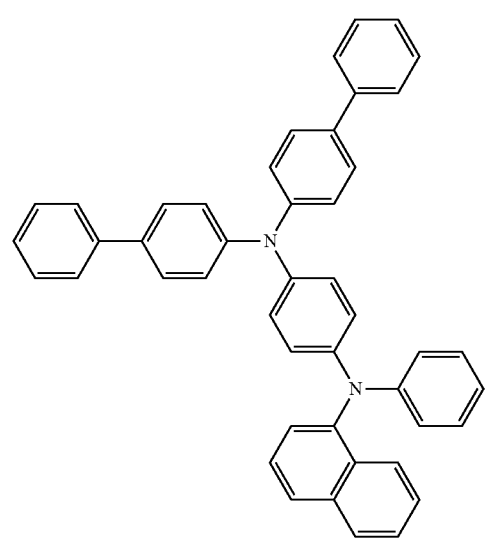
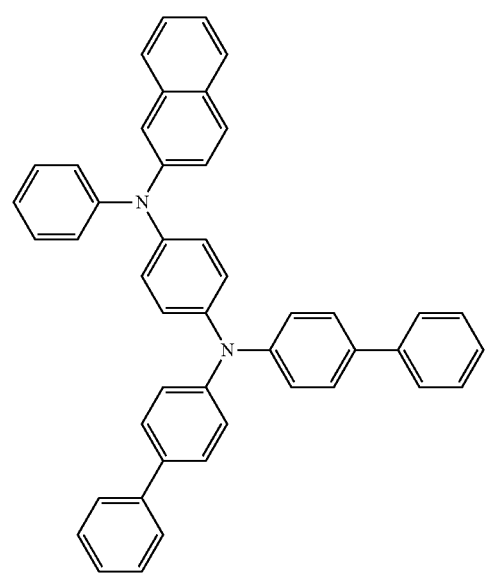

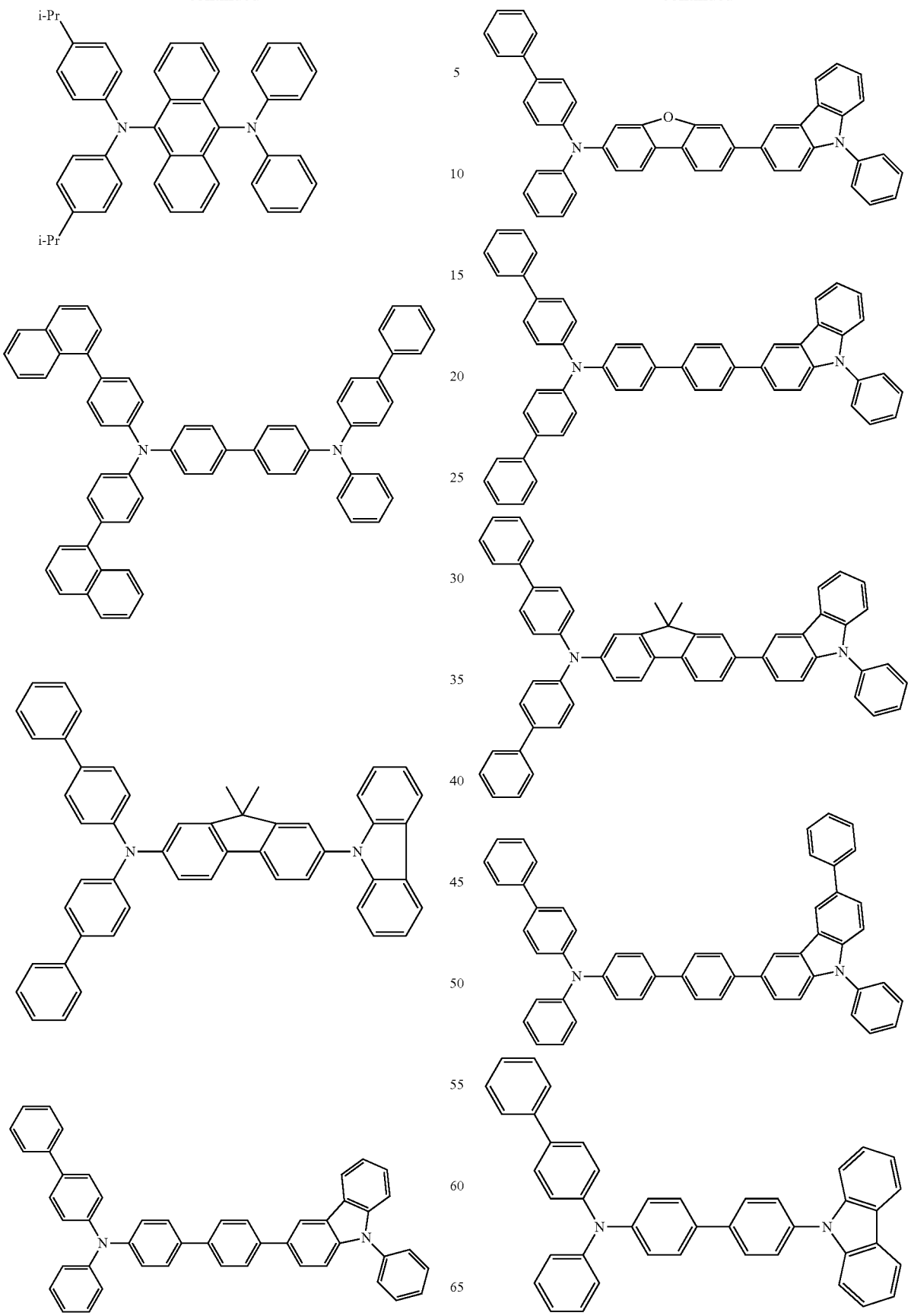

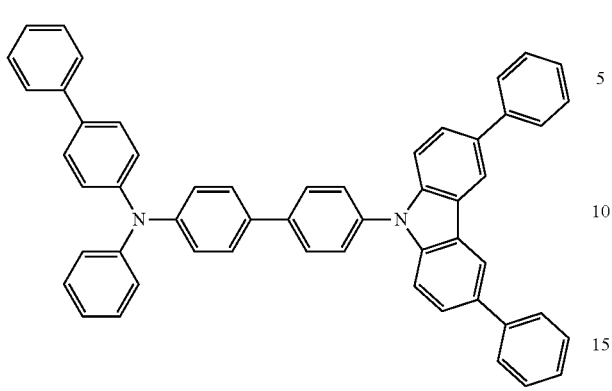

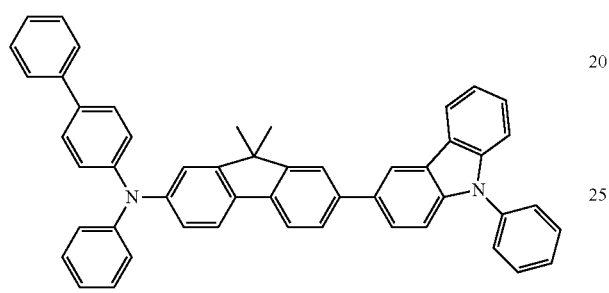

Aromatic amine represented by the following formula (A2) is also preferably usable for forming the hole transporting layer.

[Formula 237]

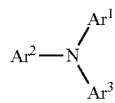
(A2)

In the formula (A2), $Ar^1$ to $Ar^3$ each represent the same as those represented by $Ar^1$ to $Ar^4$ of the above formula (A1). Examples of the compound of the formula (A2) are shown below. However, the compound of the formula (A2) is not limited thereto.

[Formula 238]

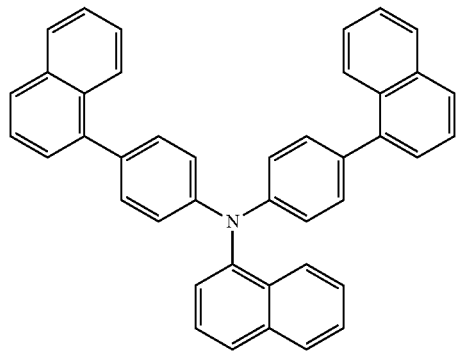

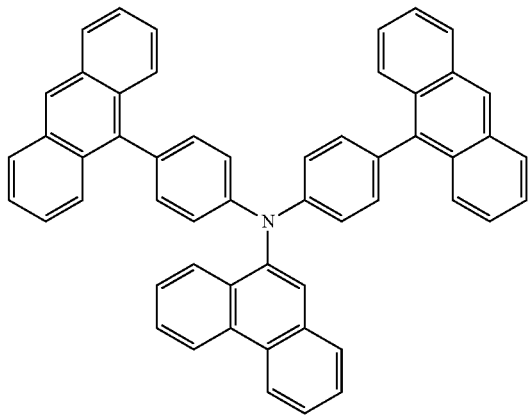

539
-continued
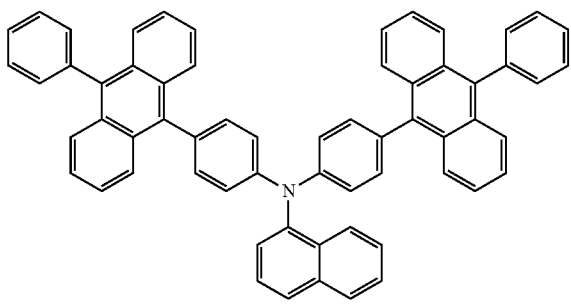
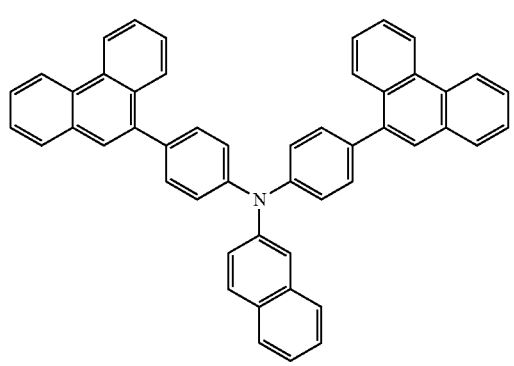
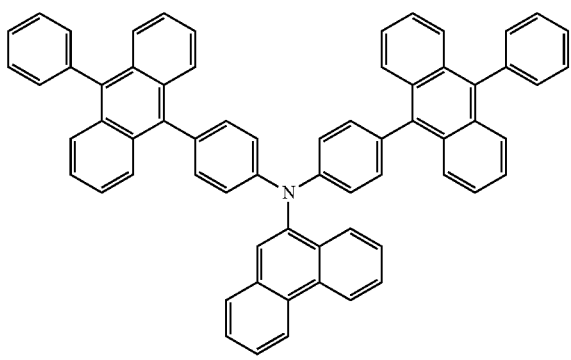
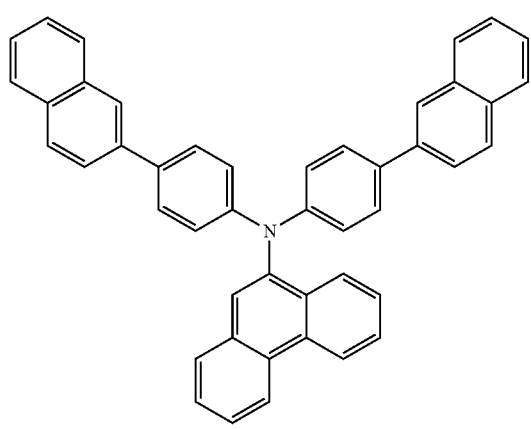
540
-continued
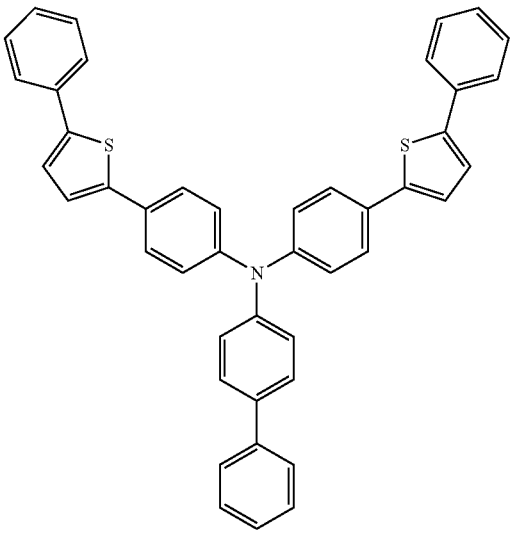
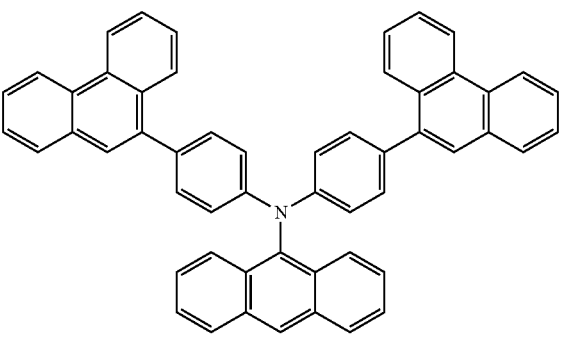
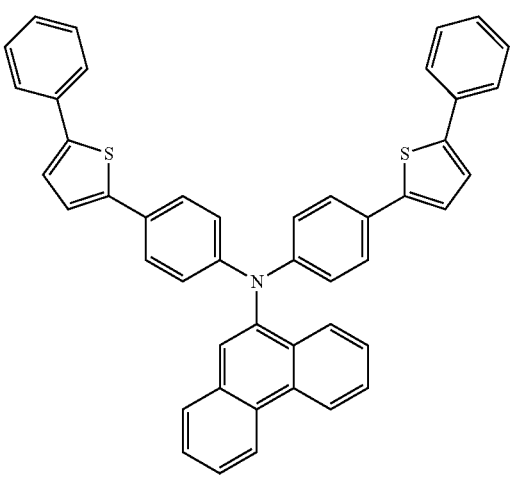

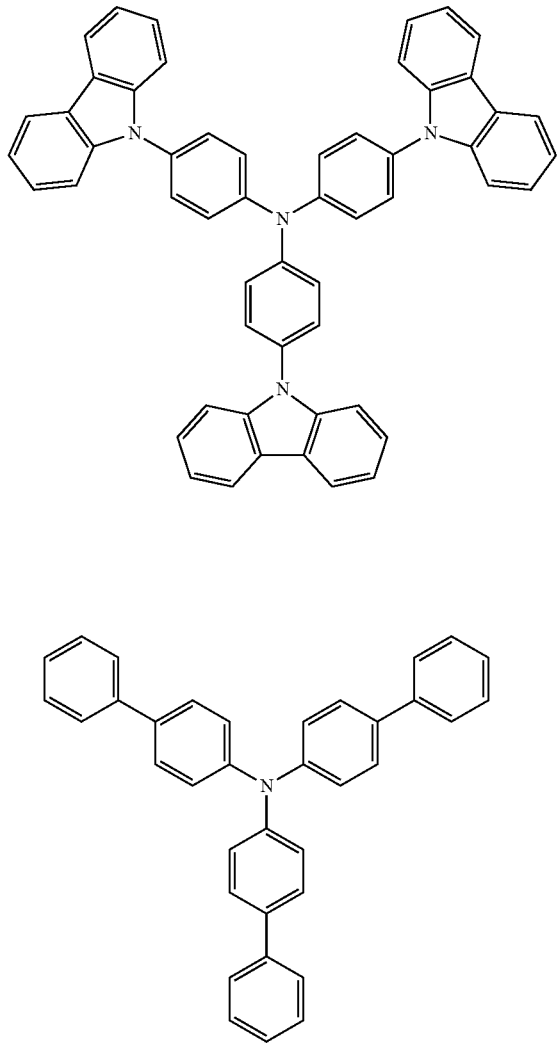

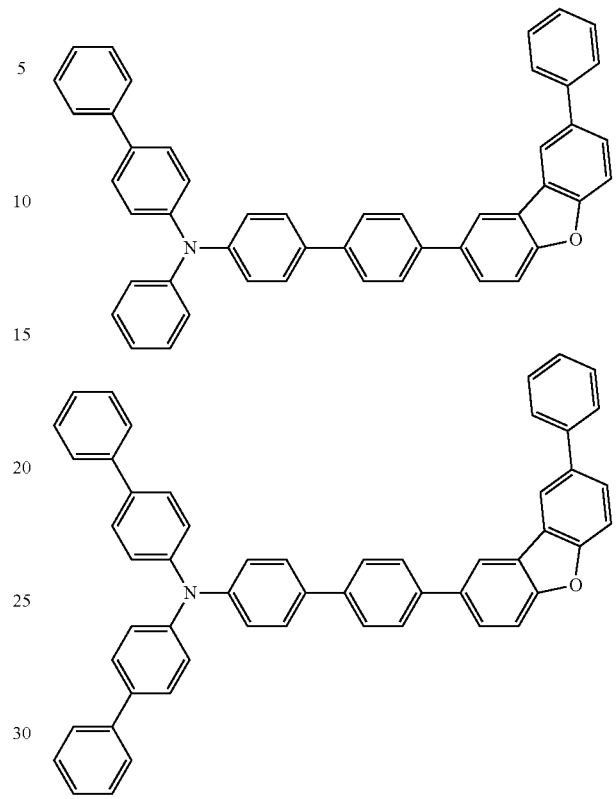

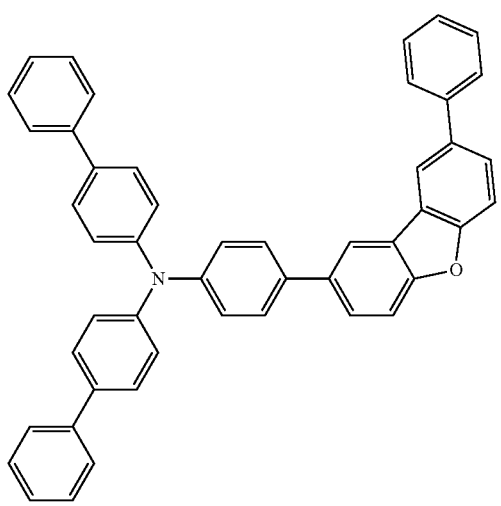

Although depending on a combination with the first host material, the second host material and the phosphorescent dopant material in the emitting layer 5, the hole transporting material preferably exhibits an ionization potential Ip(HT) in a range of 5.3 eV to 5.7 eV.

Electron Transporting Layer

The electron transporting layer 7, which helps injection of electrons to the emitting layer 5, has a high electron mobility.

In this exemplary embodiment, the electron transporting layer 7 is provided between the emitting layer 5 and the cathode, and the electron transporting layer 7 preferably contains a nitrogen-containing cyclic derivative as the main component. The electron injecting layer may serve as the electron transporting layer.

Note that "as the main component" means that the nitrogen-containing cyclic derivative is contained in the electron transporting layer 7 at a content of 50 mass % or more.

A preferable example of an electron transporting material for forming the electron transporting layer 7 is an aromatic heterocyclic compound having at least one heteroatom in a molecule. Particularly, a nitrogen-containing cyclic derivative is preferable. The nitrogen-containing cyclic derivative is preferably an aromatic ring having a nitrogen-containing six-membered or five-membered ring skeleton, or a condensed aromatic cyclic compound having a nitrogen-containing six-membered or five-membered ring skeleton.

A preferable example of the nitrogen-containing cyclic derivative is a nitrogen-containing cyclic metal chelate complex represented by the following formula (B1).

[Formula 239]

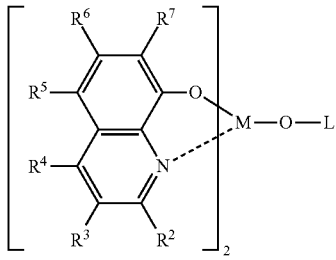
(B1)

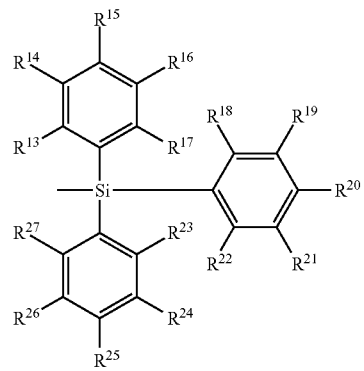
(B3)

In the formula (B1), $R^2$ to $R^7$ independently represent a hydrogen atom, a halogen atom, an oxy group, an amino group, a hydrocarbon group having 1 to 40 carbon atoms, an alkoxy group, an aryloxy group, an alkoxycarbonyl group, or an aromatic heterocyclic group, which may be substituted.

Examples of the halogen atom are fluorine, chlorine, bromine and iodine. Examples of a substituted or unsubstituted amino group are an alkylamino group, an arylamino group and an aralkylamino group.

The alkoxycarbonyl group is represented by —COOY'. Examples of Y' are the same as the examples of the alkyl group. The alkylamino group and the aralkylamino group are represented by —NQ$^1$Q$^2$. Examples for each of Q$^1$ and Q$^2$ are independently the same as the examples described in relation to the alkyl group and the aralkyl group, and preferable examples for each of Q$^1$ and Q$^2$ are also the same as those described in relation to the alkyl group and the aralkyl group. One of Q$^1$ and Q$^2$ may be a hydrogen atom. Note that the aralkyl group is provided by substituting a hydrogen atom of the alkyl group with the aryl group.

The arylamino group is represented by —NAr$^1$Ar$^2$. Examples for each of Ar$^1$ and Ar$^2$ are independently the same as the examples described in relation to the non-fused aromatic hydrocarbon group and the fused aromatic hydrocarbon group. One of Ar$^1$ and Ar$^2$ may be a hydrogen atom.

M represents aluminum (Al), gallium (Ga) or indium (In), among which In is preferable.

L in the formula (B1) represents a group represented by the following formula (B2) or (B3).

[Formula 240]

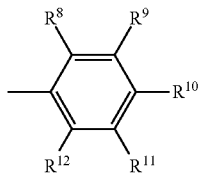
(B2)

In the formula (B2), $R^8$ to $R^{12}$ independently represent a hydrogen atom or a hydrocarbon group having 1 to 40 carbon atoms. Adjacent groups may form a cyclic structure. The hydrocarbon group may be substituted.

In the formula (B3), $R^{13}$ to $R^{27}$ independently represent a hydrogen atom or a hydrocarbon group having 1 to 40 carbon atoms. Adjacent groups may form a cyclic structure. The hydrocarbon group may be substituted.

Examples of the hydrocarbon group having 1 to 40 carbon atoms represented by each of $R^8$ to $R^{12}$ and $R^{13}$ to $R^{27}$ in the formulae (B2) and (B3) are the same as those of $R^2$ to $R^7$ in the formula (B1).

Examples of a divalent group for forming a cyclic structure between adjacent ones of groups $R^8$ to $R^{12}$ and $R^{13}$ to $R^{27}$ are a tetramethylene group, a pentamethylene group, a hexamethylene group, a diphenylmethane-2,2'-diyl group, a diphenylethane-3,3'-diyl group and a diphenylpropane-4,4'-diyl group.

The electron transporting layer preferably contains at least one of nitrogen-containing heterocyclic derivatives respectively represented by the following formulae (B4) to (B6).

[Formula 241]

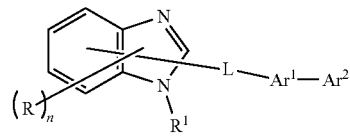
(B4)

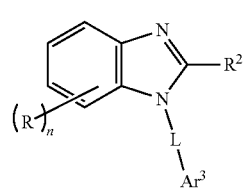
(B5)

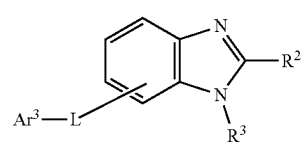
(B6)

In the formulae (B4) to (B6), R represents a hydrogen atom, an aromatic hydrocarbon group having 6 to 60 ring carbon atoms, a fused aromatic hydrocarbon group having 6 to 60 ring carbon atoms, a pyridyl group, a quinolyl group, an alkyl group having 1 to 20 carbon atoms or an alkoxy group having 1 to 20 carbon atoms.

n is an integer of 0 to 4.

In the formulae (B4) to (B6), $R^1$ represents an aromatic hydrocarbon group having 6 to 60 ring carbon atoms, a fused aromatic hydrocarbon group having 6 to 60 ring carbon atoms, a pyridyl group, a quinolyl group, an alkyl group having 1 to 20 carbon atoms or an alkoxy group having 1 to 20 carbon atoms.

In the formulae (B4) to (B6), $R^2$ and $R^3$ independently represent a hydrogen atom, an aromatic hydrocarbon group having 6 to 60 ring carbon atoms, a fused aromatic hydrocarbon group having 6 to 60 ring carbon atoms, a pyridyl group, a quinolyl group, an alkyl group having 1 to 20 carbon atoms or an alkoxy group having 1 to 20 carbon atoms.

In the formulae (B4) to (B6), L represents an aromatic hydrocarbon group having 6 to 60 ring carbon atoms, a fused aromatic hydrocarbon group having 6 to 60 ring carbon atoms, a pyridinylene group or a quinolinylene group or a fluorenylene group.

In the formulae (B4) to (B6), $Ar^1$ represents an aromatic hydrocarbon group having 6 to 60 ring carbon atoms, a fused aromatic hydrocarbon group having 6 to 60 ring carbon atoms, a pyridinylene group or a quinolinylene group.

In the formulae (B4) to (B6), $Ar^2$ represents an aromatic hydrocarbon group having 6 to 60 ring carbon atoms, a fused aromatic hydrocarbon group having 6 to 60 ring carbon atoms, a pyridyl group, a quinolyl group, an alkyl group having 1 to 20 carbon atoms or an alkoxy group having 1 to 20 carbon atoms.

In the formulae (B4) to (B6), $Ar^3$ represents an aromatic hydrocarbon group having 6 to 60 ring carbon atoms, a fused aromatic hydrocarbon group having 6 to 60 ring carbon atoms, a pyridyl group, a quinolyl group, an alkyl group having 1 to 20 carbon atoms, an alkoxy group having 1 to 20 carbon atoms or a group represented by —$Ar^1$—$Ar^2$ (in which $Ar^1$ and $Ar^2$ are the same as the above).

The aromatic hydrocarbon group, the fused aromatic hydrocarbon group, the pyridyl group, the quinolyl group, the alkyl group, the alkoxy group, the pyridinylene group, the quinolinylene group and the fluorenylene group described in relation to the R, $R^1$, $R^2$, $R^3$, L, $Ar^1$, $Ar^2$ and $Ar^3$ in the formulae (B4) to (B6) may be substituted.

As an electron transport compound used for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quino-linol or 8-hydroxyquinoline). For instance, tris(8-quinolinol) aluminum can be used. Examples of the oxadiazole derivative are as follows.

[Formula 242]

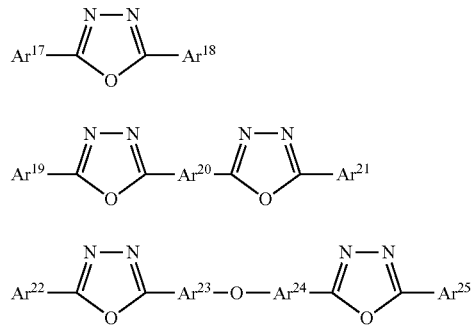

In the formulae representing the oxadiazole derivatives, $Ar^{17}$, $Ar^{18}$, $Ar^{19}$, $Ar^{21}$, $Ar^{22}$ and $Ar^{25}$ are an aromatic hydrocarbon group having 6 to 40 ring carbon atoms or a fused aromatic hydrocarbon group having 6 to 40 ring carbon atoms.

The aromatic hydrocarbon group and the fused aromatic hydrocarbon group may be substituted. $Ar^{17}$, $Ar^{19}$ and $Ar^{22}$ may be respectively the same as or different from $Ar^{18}$, $Ar^{21}$ and $Ar^{25}$.

Examples of the aromatic hydrocarbon group or the fused aromatic hydrocarbon group are a phenyl group, a naphthyl group, a biphenyl group, an anthranil group, a perylenyl group and a pyrenyl group. Examples of the substituent therefor are an alkyl group having 1 to 10 carbon atoms, an alkoxy group having 1 to 10 carbon atoms and a cyano group.

In the formulae representing the oxadiazole derivatives, $Ar^{20}$, $Ar^{23}$ and $Ar^{24}$ are a divalent aromatic hydrocarbon group having 6 to 40 ring carbon atoms or a divalent fused aromatic hydrocarbon group having 6 to 40 ring carbon atoms.

The aromatic hydrocarbon group and the fused aromatic hydrocarbon group may be substituted.

$Ar^{23}$ and $Ar^{24}$ may be mutually the same or different.

Examples of the divalent aromatic hydrocarbon group or the divalent fused aromatic hydrocarbon group are a phenylene group, a naphthylene group, a biphenylene group, an anthracylene group, a perylenylene group and a pyrenylene group. Examples of the substituent therefor are an alkyl group having 1 to 10 carbon atoms, an alkoxy group having 1 to 10 carbon atoms and a cyano group.

Such an electron transport compound is preferably an electron transport compound that can be favorably formed into a thin film(s). Examples of the electron transporting compounds are as follows.

[Formula 243]

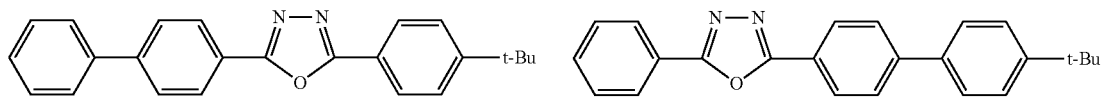

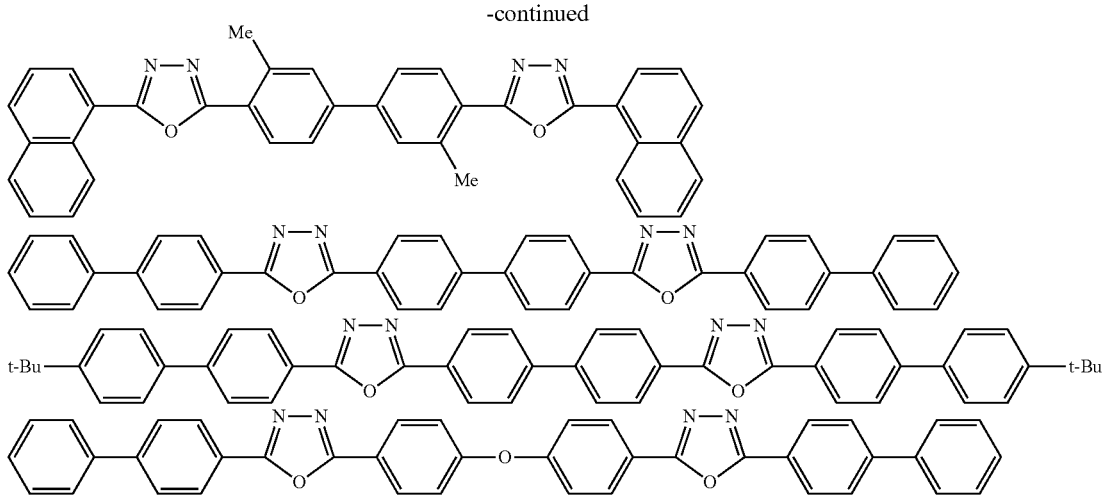

The nitrogen-containing heterocyclic derivative as the electron transport compound is exemplified by a nitrogen-containing heterocyclic derivative that is not a metal complex and is formed of an organic compound represented by one of the following formulae. Examples of the nitrogen-containing heterocyclic derivative are a five-membered ring or six-membered ring derivative having a skeleton represented by the following formula (B7) and a derivative having a structure represented by the following formula (B8).

[Formula 244]

 (B7)

 (B8)

In the formula (B8), X represents a carbon atom or a nitrogen atom. $Z_1$ and $Z_2$ each independently represent a group of atoms capable of forming a nitrogen-containing heterocycle.

More preferably, the nitrogen-containing heterocyclic derivative is an organic compound having a nitrogen-containing aromatic polycyclic group having a five-membered ring or six-membered ring. Further, when the nitrogen-containing heterocyclic derivative is such a nitrogen-containing aromatic polycyclic group that contains plural nitrogen atoms, the nitrogen-containing heterocyclic derivative is preferably a nitrogen-containing aromatic polycyclic organic compound having a skeleton formed by combining the skeletons respectively represented by the formulae (B7) and (B8), or by combining the skeletons respectively represented by the formulae (B7) and (B9).

[Formula 245]

 (B9)

A nitrogen-containing group of the nitrogen-containing aromatic polycyclic organic compound is selected from nitrogen-containing heterocyclic groups respectively represented by, for instance, the following formulae.

[Formula 246]

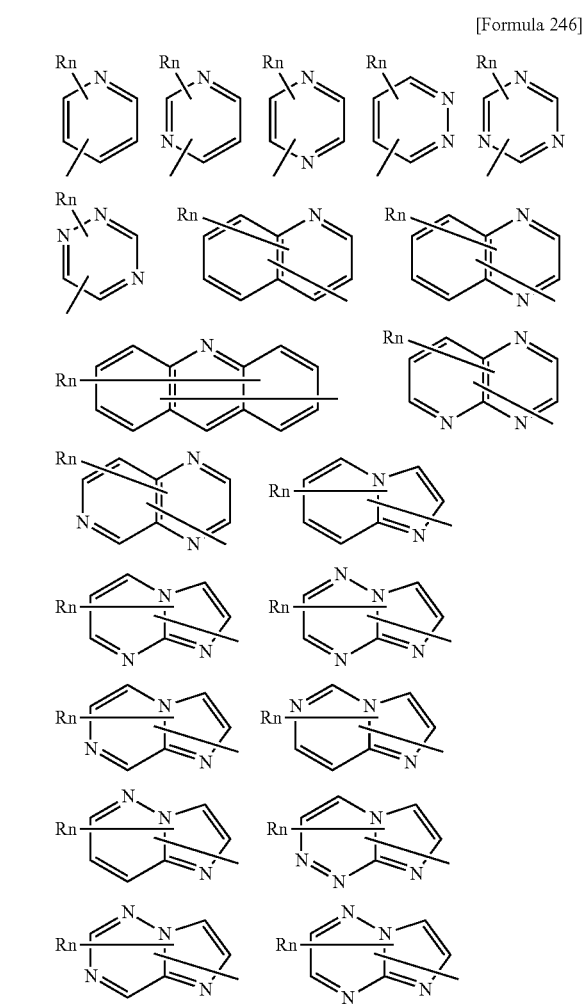

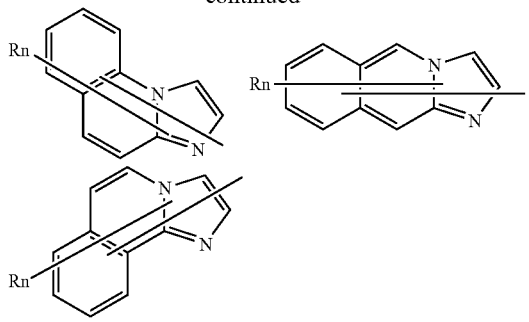

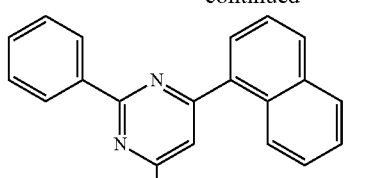

In the formulae representing the nitrogen-containing heterocyclic groups, R represents an aromatic hydrocarbon group having 6 to 40 ring carbon atoms, a fused aromatic hydrocarbon group having 6 to 40 ring carbon atoms, an aromatic heterocyclic group having 2 to 40 ring carbon atoms, a fused aromatic heterocyclic group having 2 to 40 ring carbon atoms, an alkyl group having 1 to 20 carbon atoms or an alkoxy group having 1 to 20 carbon atoms.

In the formulae representing the nitrogen-containing heterocyclic group, n is an integer of 0 to 5. When n is an integer of 2 or more, a plurality of R may be mutually the same or different.

A preferable specific compound is a nitrogen-containing heterocyclic derivative represented by the following formula (B 10).

$$\text{HAr-L}^1\text{-Ar}^1\text{—Ar}^2 \qquad (B10)$$

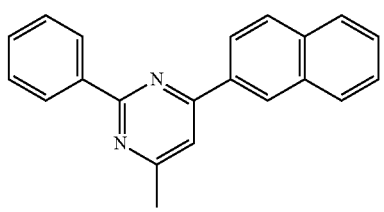

In the formula (B10), HAr represents:
In the formula (B10), HAr represents a nitrogen-containing heterocyclic group having 1 to 40 ring carbon atom.

In the formula (B10), $L^1$ represents a single bond, an aromatic hydrocarbon group having 6 to 40 ring carbon atoms, a fused aromatic hydrocarbon group having 6 to 40 ring carbon atoms, an aromatic heterocyclic group having 2 to 40 ring carbon atoms or a fused aromatic heterocyclic group having 2 to 40 ring carbon atoms.

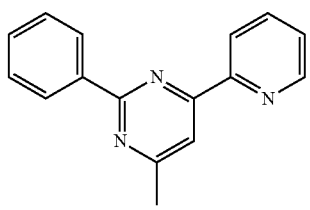

In the formula (B10), $Ar^1$ represents: a divalent aromatic hydrocarbon group having 6 to 40 ring carbon atom.

In the formula (B10), $Ar^2$ represents an aromatic hydrocarbon group having 6 to 40 ring carbon atoms, a fused aromatic hydrocarbon group having 6 to 40 ring carbon atoms, an aromatic heterocyclic group having 2 to 40 ring carbon atoms or a fused aromatic heterocyclic group having 2 to 40 ring carbon atoms.

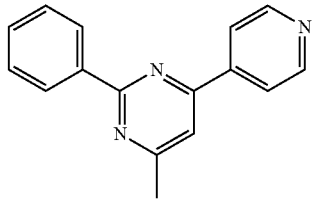

The nitrogen-containing heterocyclic group, the fused aromatic hydrocarbon group, the fused aromatic hydrocarbon group, the aromatic heterocyclic group and the fused aromatic heterocyclic group described in relation to HAr, $L^1$, $Ar^1$ and $Ar^2$ in the formula (B10) may be substituted.

HAr in the formula (B10) is exemplarily selected from the following group.

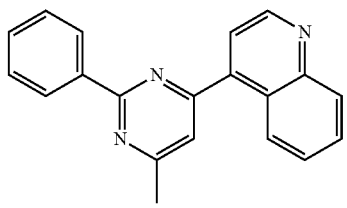

[Formula 247]

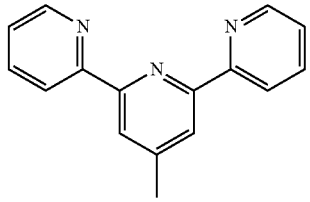

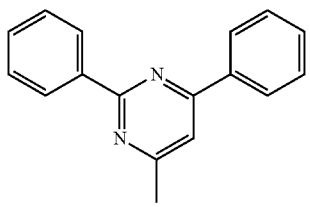

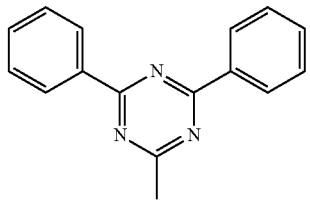

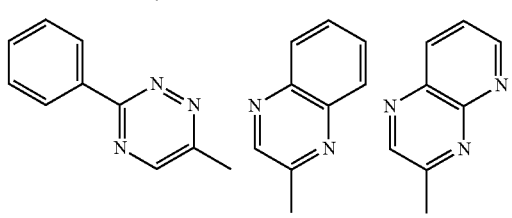

-continued

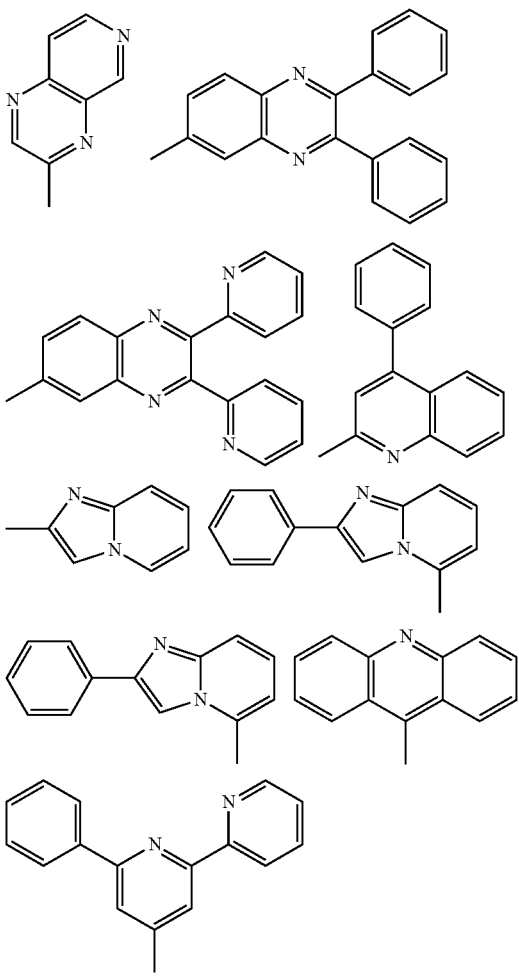

$L^1$ in the formula (B10) is exemplarily selected from the following group.

[Formula 248]

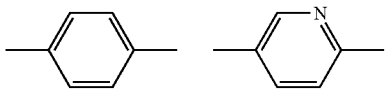

$Ar^1$ in the formula (B10) is exemplarily selected from the following arylanthranil group.

[Formula 249]

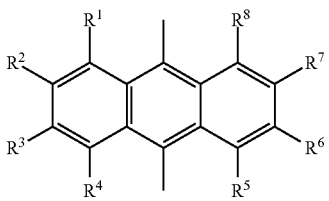

-continued

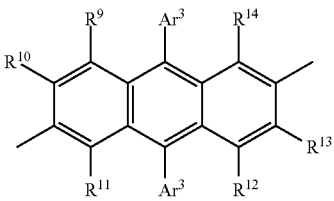

In the formulae representing the arylanthranil group, $R^1$ to $R^{14}$ independently represent a hydrogen atom, a halogen atom, an alkyl group having 1 to 20 carbon atoms, an alkoxy group having 1 to 20 carbon atoms, an aryloxy group having 6 to 40 ring carbon atoms, an aromatic hydrocarbon group having 6 to 40 ring carbon atoms, a fused aromatic hydrocarbon group having 6 to 40 ring carbon atoms, an aromatic heterocyclic group having 2 to 40 ring carbon atoms or a fused aromatic heterocyclic group having 2 to 40 ring carbon atoms.

In the formulae representing the arylanthranil group, $Ar^3$ represents an aromatic hydrocarbon group having 6 to 40 ring carbon atoms, a fused aromatic hydrocarbon group having 6 to 40 ring carbon atoms, an aromatic heterocyclic group having 2 to 40 ring carbon atoms or a fused aromatic heterocyclic group having 2 to 40 ring carbon atoms.

The aromatic hydrocarbon group, the fused aromatic hydrocarbon group, the aromatic heterocyclic group and the fuse aromatic heterocyclic group described in relation to $R^1$ to $R^{14}$ and $Ar^3$ in the formulae of the arylanthranil group may be substituted.

The nitrogen-containing heterocyclic derivative may be a nitrogen-containing heterocyclic derivative in which $R^1$ to $R^8$ each represent a hydrogen atom.

In the formulae of the arylanthranil group, $Ar^2$ is exemplarily selected from the following group.

[Formula 250]

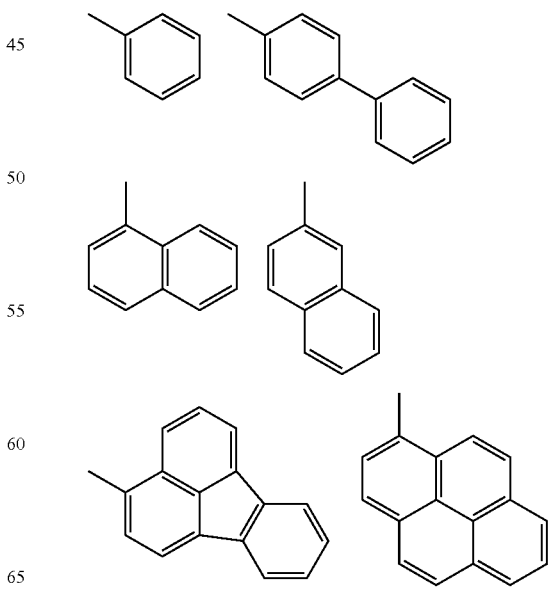

-continued

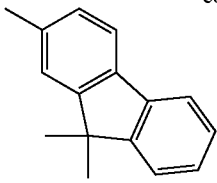

Other than the above, the following compound (see JP-A-9-3448) can be favorably used as the nitrogen-containing aromatic polycyclic organic compound (i.e., the electron transport compound).

[Formula 251]

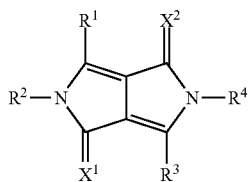

In the formula of the nitrogen-containing aromatic polycyclic organic compound, $R^1$ to $R^4$ independently represent a hydrogen atom, an aliphatic group, an alicyclic group, a carbocyclic aromatic cyclic group or a heterocyclic group. The aliphatic group, the alicyclic group, the carbocyclic aromatic cyclic group and the heterocyclic group may be substituted.

In the formula of the nitrogen-containing aromatic polycyclic organic compound, $X^1$ and $X^2$ independently represent an oxygen atom, a sulfur atom or a dicyanomethylene group.

Alternatively, the following compound (see JP-A-2000-173774) can also be favorably used for the electron transporting compound.

In the formula, $R^5$, $R^6$, $R^7$, $R^8$ and $R^9$ are mutually the same or different and each represent a hydrogen atom, a saturated or unsaturated alkoxyl group, alkyl group, amino group or alkylamino group. At least one of $R^5$, $R^6$, $R^7$, $R^8$ and $R^9$ represents a saturated or unsaturated alkoxyl group, alkyl group, amino group or alkylamino group.

The electron transport compound may be a polymer compound containing the nitrogen-containing heterocyclic group or the nitrogen-containing heterocyclic derivative.

The electron injecting layer preferably contains an insulator or a semiconductor as an inorganic compound in addition to the nitrogen-containing cyclic derivative. Such an insulator or a semiconductor, when contained in the electron injecting layer, can effectively prevent a current leak, thereby enhancing electron capability of the electron injecting layer.

It is also preferable that the electron injecting layer according to this exemplary embodiment contains a reduction-causing dopant.

Film Thickness

In the organic EL device of this exemplary embodiment, a thickness of each layer between the anode and the cathode is not particularly limited except for a thickness of each of the above-mentioned layers to be particularly defined. However, the thickness of each of the emitting layer and the like is typically preferably in a range from several nanometers to 1 μm because an excessively-thinned film is likely to entail defects such as a pin hole while an excessively-thickened film requires application of high voltage and deteriorates efficiency.

Manufacturing Method of Organic EL Device

A manufacturing method of the organic EL device of the invention is subject to no limitation. Any typical manufacturing method of the organic EL device is usable. Specifically, each layer is formable by vacuum deposition, a casting method, a coating method and a spin coating method. Moreover, in addition to the casting method, the coating method and the spin coating using a solution, in which the

[Formula 252]

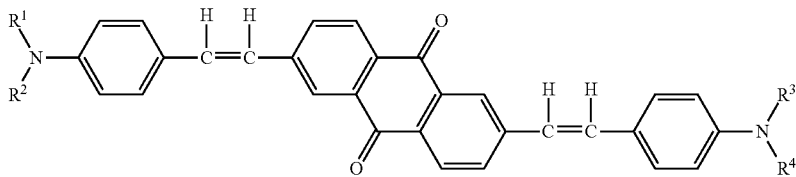

In the formula, $R^1$, $R^2$, $R^3$ and $R^4$ are mutually the same or different and each represent an aromatic hydrocarbon group or a fused aromatic hydrocarbon group represented by the following formula.

[Formula 253]

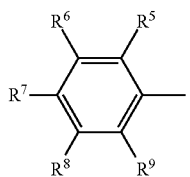

organic material of the layers are dispersed, on a transparent polymer such as polycarbonate, polyurethane, polystyrene, polyarylate and polyester, the respective layers can be formed by simultaneous deposition with the organic material and the transparent polymer.

Second Exemplary Embodiment

Next, a second exemplary embodiment is described below.

In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable.

Figure 2:
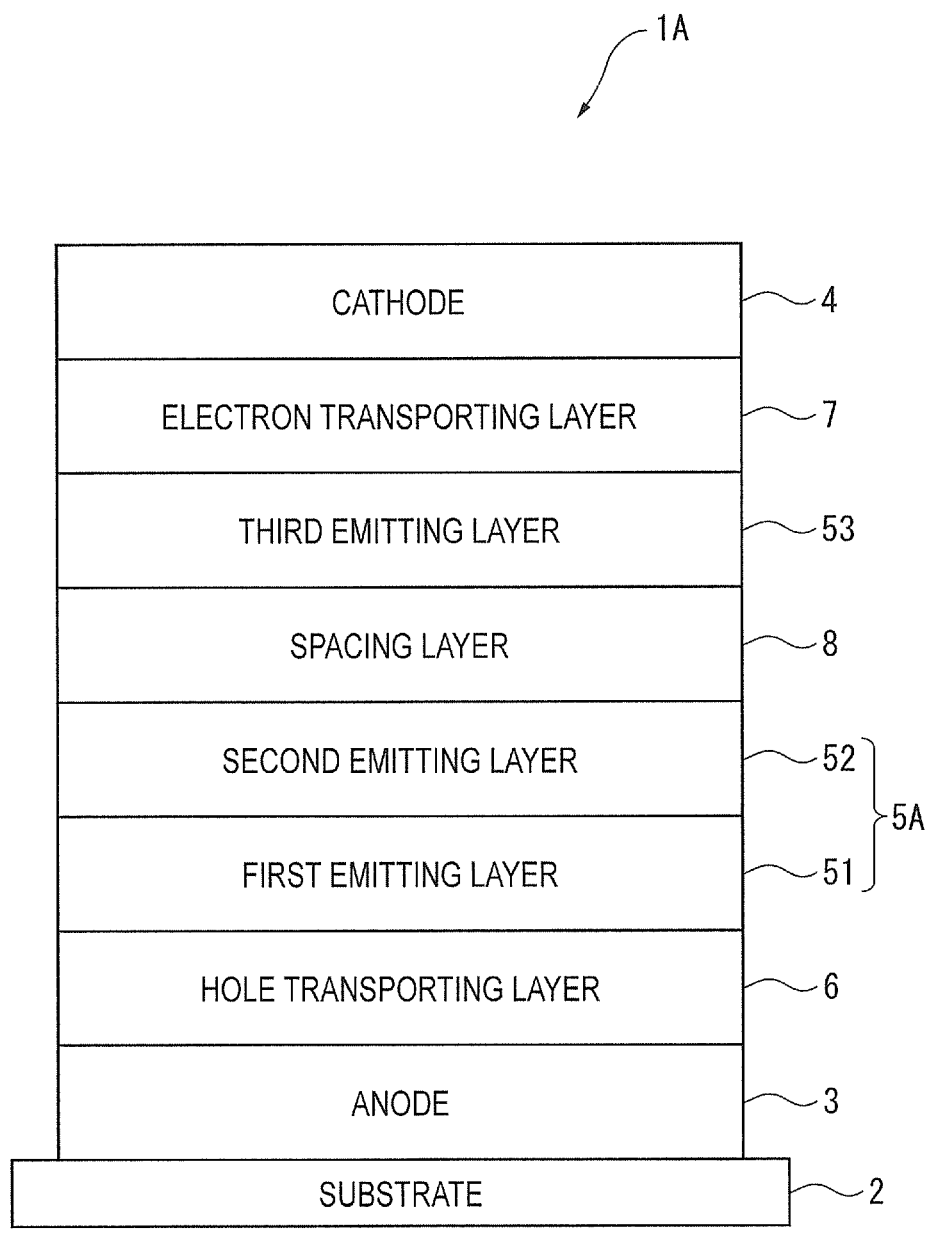
FIG. 2 schematically shows an exemplary arrangement of an organic EL device according to a second exemplary embodiment.

An organic EL device 1A according to the second exemplary embodiment is different from that of the first exemplary embodiment in that an emitting unit 5A, a third emitting layer 53 and a spacing layer 8 between the emitting unit 5A and the third emitting layer 53 are provided. As shown in FIG. 2, the anode, 3, the hole transporting layer 6, the emitting unit 5A, the spacing layer 8, the third emitting layer 53, the electron transporting layer 7 and the cathode 4 are sequentially laminated on the substrate 2.

The emitting unit 5A includes a first emitting layer 51 continuously formed to the hole transporting layer 6 and a second emitting layer 52 continuously formed between the first emitting layer 51 and the spacing layer 8.

The first emitting layer 51 contains a host material and a luminescent material. The host material is preferably an amine derivative such as a monoamine compound, a diamine compound, a triamine compound, a tetramine compound and an amine compound substituted by a carbazole group. The host material may be the same material as the first host material represented by the formula (1) and the second host material represented by the formula (2). The luminescent material preferably exhibits an emission peak of 570 nm or more. The emission peak of 570 nm or more is shown by, for instance, red emission.

The second emitting layer 52 is the emitting layer according to the invention. In other words, the second emitting layer 52 functions the same as the emitting layer 5 of the first exemplary embodiment.

Provided as an energy barrier of a HOMO level or a LUMO level between the second emitting layer 52 and the third emitting layer 53 adjacent thereto, the spacing layer 8 controls injection of charge (holes or electrons) into the second emitting layer 52 and the third emitting layer 53 and controls balance of charge injected thereinto. Moreover, the spacing layer 8 is provided as a barrier of triplet energy, thereby preventing diffusion of triplet energy generated in the second emitting layer 52 to the third emitting layer 53 and providing efficient emission within the second emitting layer 52.

The third emitting layer 53 is, for instance, a blue fluorescent emitting layer having a peak wavelength of 450 nm to 500 nm. The third emitting layer 53 contains the third host material and the third luminescent material.

Examples of the third host material are a compound having a central anthracene skeleton which is represented by the following formula (41).

[Formula 254]

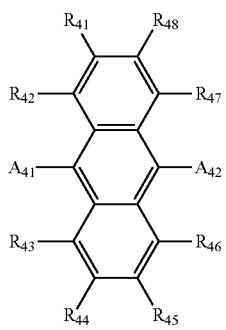

(41)

In the formula (41), $Ar_{41}$ and $Ar_{42}$ each are a group induced from a substituted or unsubstituted aromatic ring having 6 to 20 ring carbon atoms.

$R_{41}$ to $R_{48}$ each are a hydrogen atom, a substituted or unsubstituted aryl group having 6 to 50 ring carbon atoms, a substituted or unsubstituted heteroaryl group having 5 to 50 atoms for forming a ring (hereinafter referred to as ring atoms), a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of a substituent for the aromatic ring of each of $Ar_{41}$ and $Ar_{42}$ are a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of the third luminescent material are an arylamine compound, a styrylamine compound, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumaline, oxadiazole, aldazine, bisbenzoxazoline, bisstyryl, pyrazine, cyclopentadiene, a metal complex of quinoline, a metal complex of aminoquinoline, a metal complex of benzoquinoline, imine, diphenylethylene, vinylanthracene, diaminocarbazole, pyrane, thiopyrane, polymethine, mecocyanin, an imidazole chelated oxinoid compound, quinacridone, rubrene and a fluorescent dye.

The third emitting layer 53 is, for instance, a blue fluorescent emitting layer having a peak wavelength of 450 nm to 500 nm.

Since the organic EL device 1A includes the first emitting layer 51 exhibiting red emission, the second emitting layer 52 exhibiting green emission and the third emitting layer 53 exhibiting blue emission, the organic EL device 1A can exhibit white emission as a whole.

Accordingly, the organic EL device 1A is suitably applicable as a surface light source for lighting, a backlight and the like.

Third Exemplary Embodiment

Next, a third exemplary embodiment is described below.

In the description of the third exemplary embodiment, the same components as those in the first exemplary embodiment are denoted by the same reference signs and names to simplify or omit an explanation of the components. In the third exemplary embodiment, the same materials and compounds as described in the first exemplary embodiment are usable.

The organic EL device according to the third exemplary embodiment is a so-called tandem-type device including a charge generating layer and two or more emitting units. In addition to charges injected from a pair of electrodes, charges supplied from the charge generating layer are injected into the emitting unit. Accordingly, by providing the charge generating layer, luminous efficiency (current efficiency) relative to injected current is improved.

Figure 3:
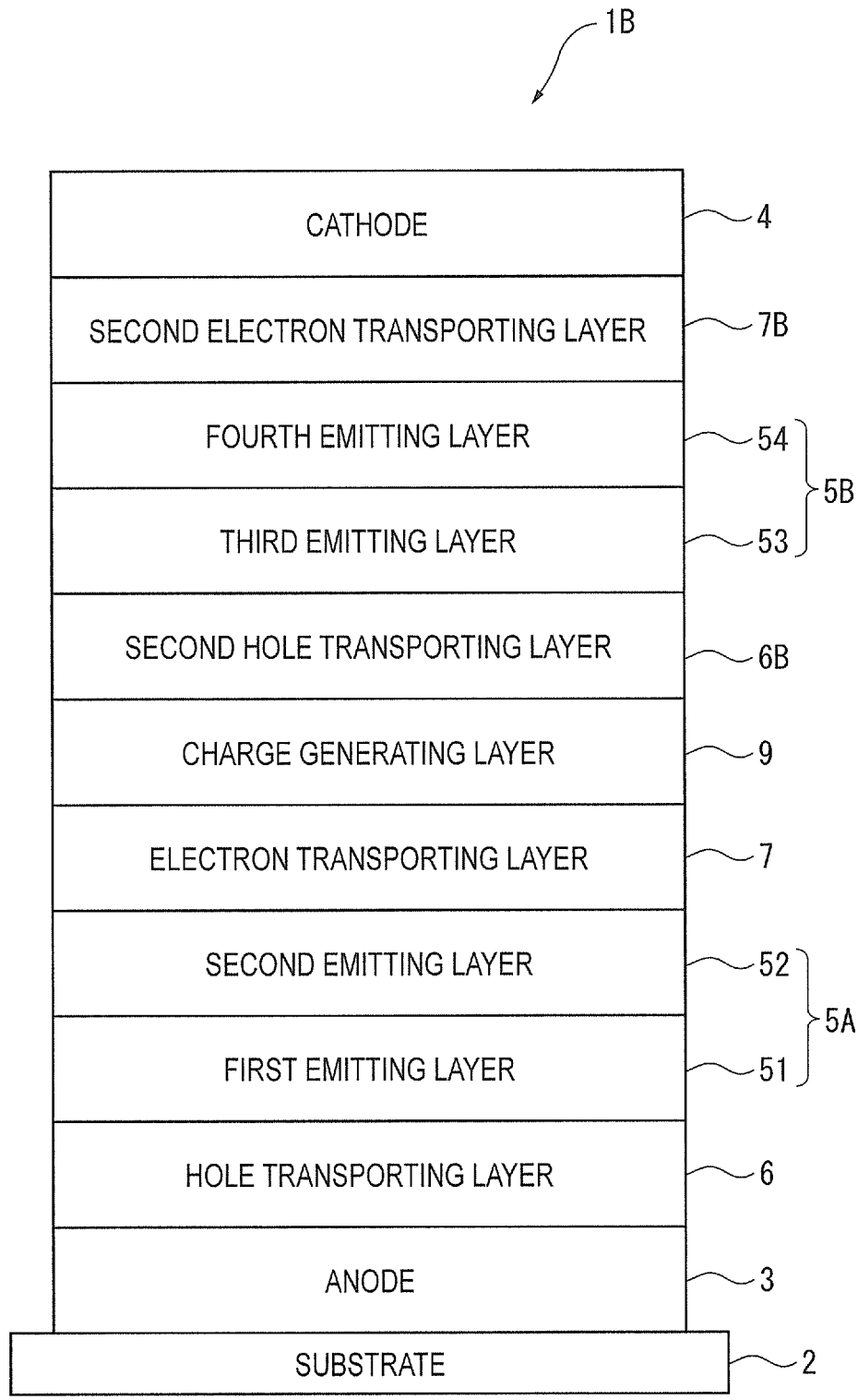
FIG. 3 schematically shows an exemplary arrangement of an organic EL device according to a third exemplary embodiment.

As shown in FIG. 3, an organic EL device 1B according to the third exemplary embodiment is configured to include the anode 3, the hole transporting layer 6, the first emitting unit 5A, the electron transporting layer 7, a charge generating layer 9, a second hole transporting layer 6B, a second emitting unit 5B, a second electron transporting layer 7B and the cathode 4 sequentially laminated on the substrate 2.

The first emitting unit 5A functions the same as the first emitting unit of the second exemplary embodiment. The second emitting layer 52 forming the first emitting unit 5A is the emitting layer of the invention. In other words, the first emitting unit 5A functions the same as the emitting layer 5 of the first exemplary embodiment and the second emitting layer of the second exemplary embodiment.

The second emitting unit 5B includes the third emitting layer 53 continuously formed to the second hole transporting layer 6B and the fourth emitting layer 54 continuously formed between the third emitting layer 53 and the second electron transporting layer 7B.

The third emitting layer 53 functions the same as the third emitting layer of the second exemplary embodiment.

The fourth emitting layer 54 is a green fluorescent emitting layer having a peak wavelength of about 500 nm to 570 nm. The fourth emitting layer 54 contains the fourth host material and the fourth luminescent material.

The charge generating layer 9 in which charges are generated when an electrical field is applied injects electrons into the electron transporting layer 7 and injects holes into the second hole transporting layer 6B.

As a material for the charge generating layer 9, known materials such as the materials described in the specification of U.S. Pat. No. 7,358,661 are usable. Specifically, examples of the material for the charge generating layer 9 are metal oxides, nitrides, iodides, borides and the like of In, Sn, Zn, Ti, Zr, Hf, V, Mo, Cu, Ga, Sr, La, Ru and the like. The electron transporting zone 7 near an interface with the charge generating layer is preferably doped with a donor (e.g., an alkali metal) in order that the third emitting layer 53 can easily accept electrons from the charge generating layer 9. As the donor, at least one of a donor metal, a donor metal compound and a donor metal complex can be used. Examples of the compounds usable for the donor metal, the donor metal compound and the donor metal complex are compounds disclosed in International Publication No. 2010/134352.

The second hole transporting layer 6B and the second electron transporting layer 7B function the same as the hole transporting layer and the electron transporting layer of the first exemplary embodiment.

Since the organic EL device 1B is a so-called tandem-type device, electrical current for driving can be reduced and durability can be improved.

Fourth Exemplary Embodiment

An organic EL device 1C according to a fourth exemplary embodiment is different from that of the second exemplary embodiment in that the first emitting layer 51 is not provided.

In the description of the fourth exemplary embodiment, the same components as those in the second exemplary embodiments are denoted by the same reference signs and names to simplify or omit an explanation of the components. In the fourth exemplary embodiment, the same materials and compounds as described in the second exemplary embodiments are usable.

Figure 4:
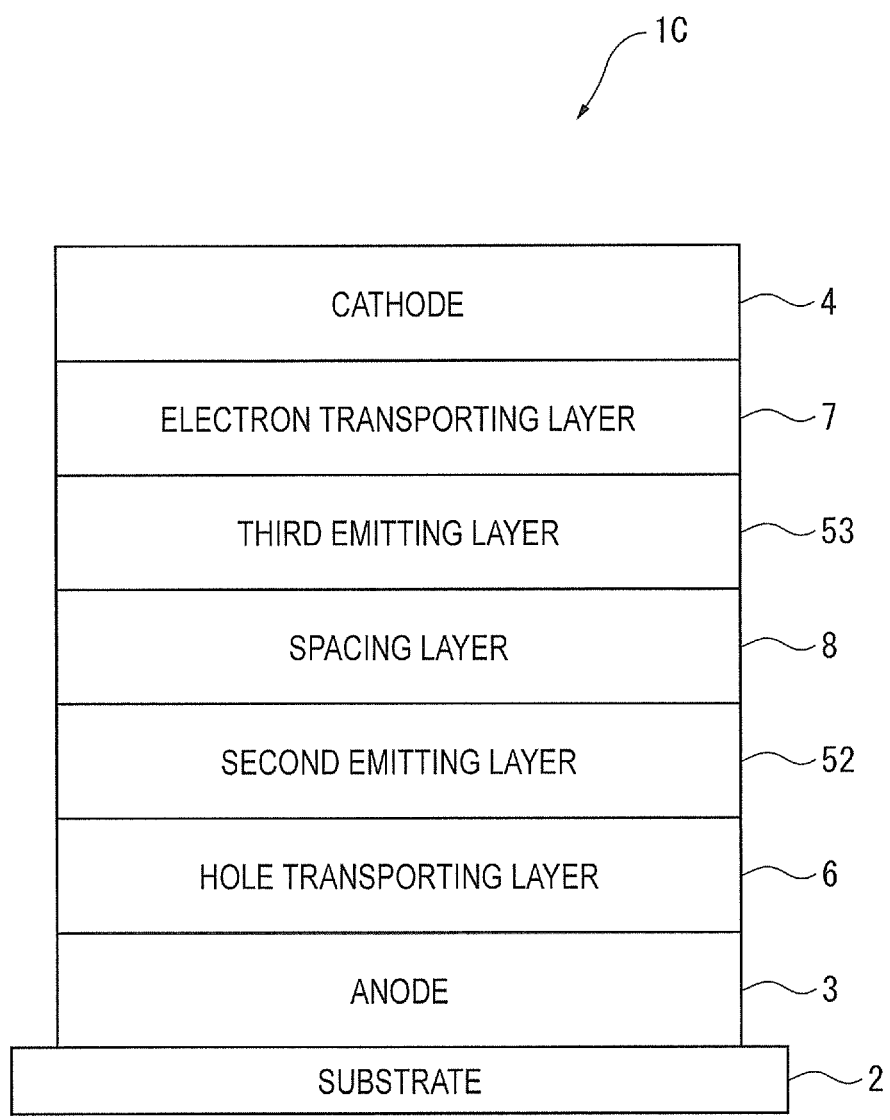
FIG. 4 schematically shows an exemplary arrangement of an organic EL device according to a fourth exemplary embodiment.

As shown in FIG. 4, the organic EL device 1C according to the fourth exemplary embodiment is configured to include the anode 3, the hole transporting layer 6, the second emitting layer 52, the spacing layer 8, the third emitting layer 53, the electron transporting layer 7 and the cathode 4 sequentially laminated on the substrate 2.

The second emitting layer 52 is the emitting layer according to the invention. In other words, the second emitting layer 52 functions the same as the emitting layer 5 of the first exemplary embodiment.

The third emitting layer 53 is, for instance, a blue fluorescent emitting layer having a peak wavelength of 450 nm to 500 nm. The third emitting layer 53 contains the third host material and the third luminescent material.

When a dopant material exhibiting yellow emission is used as the second emitting layer 52 in the organic EL device 1C, since the organic EL device 1C includes the second emitting layer 52 exhibiting yellow emission and the third emitting layer 53 exhibiting blue emission, the organic EL device 1C can exhibit white emission as a whole. Typically, white emission of the entire device requires three layers respectively exhibiting red emission, green emission and blue emission to exhibit emission in good balance. However, in this exemplary embodiment, the layers exhibiting red emission and green emission can be replaced by only the second emitting layer 52 exhibiting yellow emission. Accordingly, the organic EL device 1A is suitably applicable as a surface light source for lighting, a backlight and the like.

Fifth Exemplary Embodiment

An organic EL device 1D according to a fifth exemplary embodiment is different from that of the third exemplary embodiment in that the first emitting layer 51 is not provided.

In the description of the fifth exemplary embodiment, the same components as those in the third exemplary embodiments are denoted by the same reference signs and names to simplify or omit an explanation of the components. In the fifth exemplary embodiment, the same materials and compounds as described in the third exemplary embodiments are usable.

Figure 5:
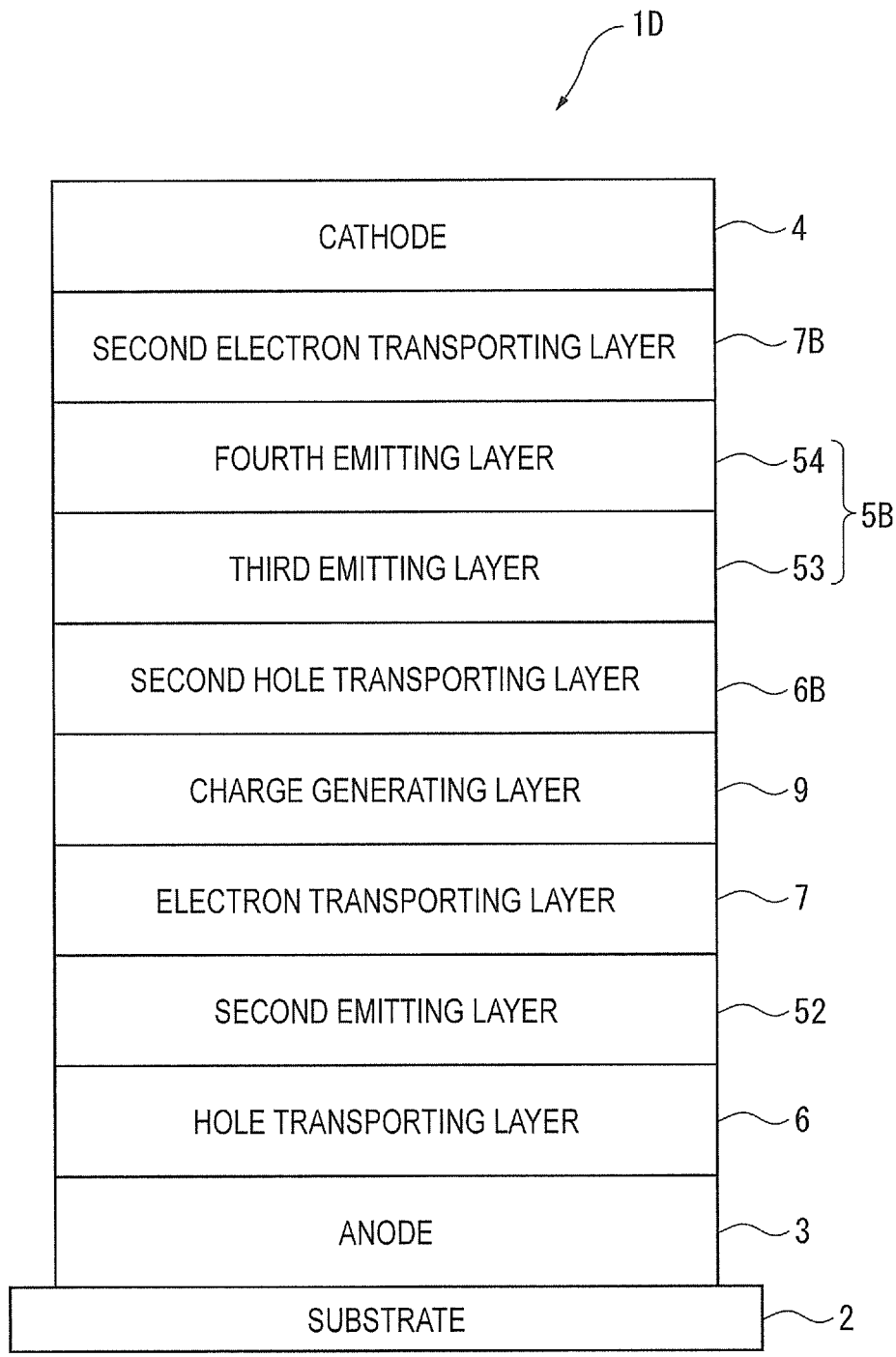
FIG. 5 schematically shows an exemplary arrangement of an organic EL device according to a fifth exemplary embodiment.

As shown in FIG. 5, the organic EL device 1D of the fifth exemplary embodiment is configured to include the anode 3, the hole transporting layer 6, the second emitting layer 52, the electron transporting layer 7, the charge generating layer 9, the second hole transporting layer 6B, the second emitting unit 5B, the second electron transporting layer 7B and the cathode 4 sequentially laminated on the substrate 2.

The second emitting layer 52 is the emitting layer of the invention. In other words, the second emitting layer 52 functions the same as the emitting layer 5 of the first exemplary embodiment and the second emitting layer of the third exemplary embodiment.

The second emitting unit 5B includes the third emitting layer 53 continuously formed to the second hole transporting layer 6B and the fourth emitting layer 54 continuously formed between the third emitting layer 53 and the second electron transporting layer 7B.

The third emitting layer 53 functions the same as the third emitting layer of the second exemplary embodiment.

The fourth emitting layer 54 is a green fluorescent emitting layer having a peak wavelength of about 500 nm to 570 nm. The fourth emitting layer 54 contains the fourth host material and the fourth luminescent material.

Since the organic EL device 1D is a so-called tandem-type device, electrical current for driving can be reduced and durability can be improved.

Sixth Exemplary Embodiment

Next, a sixth exemplary embodiment will be described below.

In the sixth exemplary embodiment, a material for an organic EL device (an organic-EL-device material) used for manufacturing the organic EL device according to the above exemplary embodiments will be described below.

The organic-EL-device material contains a compound represented by the formula (1) and a compound represented by the formula (2). It should not be excluded that the organic-EL-device material contains other material(s).

In the organic-EL-device material, the compound represented by the formula (1) is preferably a compound represented by the formula (3).

In the organic-EL-device material, the compound represented by the formula (1) is also preferably a compound represented by the formula (4) or (5).

Further, in the organic-EL-device material, the compound represented by the formula (2) in which FA is preferably a substituted or unsubstituted fused aromatic cyclic group having 2 to 5 fused rings, or a substituted or unsubstituted fused aromatic heterocyclic group having 2 to 5 fused rings.

Furthermore, FA is preferably represented by the formula (2-A), more preferably represented by any one of the formulae (2-1) to (2-4). Particularly preferably, FA is represented by the formula (2-1) or (2-2).

Herein, when a total mass percentage of the first and second host materials contained in the organic-EL-device material is 100 mass %, the first host material is preferably set in a range of 10 mass % to 90 mass % and the second host material is preferably set in a range of 10 mass % to 90 mass %. More preferably, the first host material is set in a range of 40 mass % to 60 mass % and the second host material is set in a range of 40 mass % to 60 mass %.

Since the organic-EL-device material according to the sixth exemplary embodiment contains the compound represented by the formula (1) (the first host material) and the compound represented by the formula (2) (the second host material), the organic-EL-device material is preferably used for forming the emitting layer of the organic EL devices according to the above exemplary embodiments. The organic-EL-device material may be used for a layer other than the emitting layer forming the organic EL device.

When the organic-EL-device material is used for the emitting layer, the organic-EL-device material may contain a phosphorescent dopant material in addition to the compound represented by the formula (1) and the compound represented by the formula (2).

When the organic-EL-device material according to the sixth exemplary embodiment is used for manufacturing an organic EL device, since the compound represented by the formula (1) and the compound represented by the formula (2) are mixed in advance, there is no need to mix those compounds while adjusting a mass ratio therebetween, which facilitates manufacturing the organic EL device. Moreover, for instance, when the organic-EL-device material is used for forming the emitting layer by vacuum deposition, with a proviso that deposition temperatures of the first and second host materials are approximate to each other, there is no need to prepare an evaporation boat for each of the first and second host materials, which simplifies a manufacturing device.

Modification(s) of Embodiment(s)

It should be noted that the invention is not limited to the above description but may include any modification as long as such modification stays within a scope and a spirit of the invention.

In the first and second exemplary embodiments, the anode and the hole transporting layer are continuously formed. However, the hole injecting layer may be further provided between the anode and the hole transporting layer.

Preferable examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

In the first to third exemplary embodiments, the cathode and the electron transporting layer are continuously formed to each other. However, the electron injecting layer may be further formed between the cathode and the electron transporting layer.

Although two emitting units are formed in the third exemplary embodiments, three or more emitting units may be formed.

EXAMPLES

The invention will be described in more detail below by exemplifying examples and comparatives. It should be noted that the invention is not limited to specific description of the examples and the like.

Synthesis Example 1 (Synthesis of Compound GH1-1)

[Formula 255]

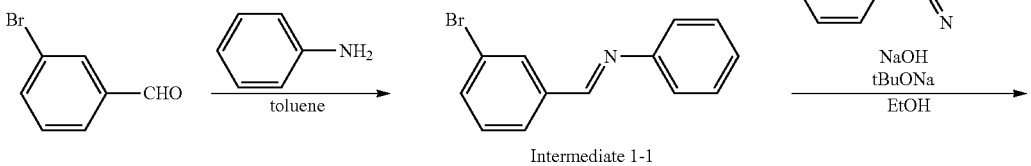

Intermediate 1-1

-continued

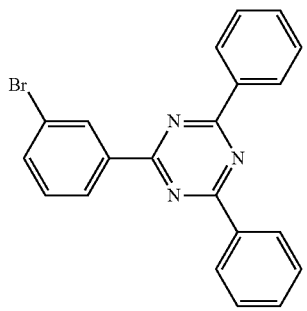

Intermediate 1-2

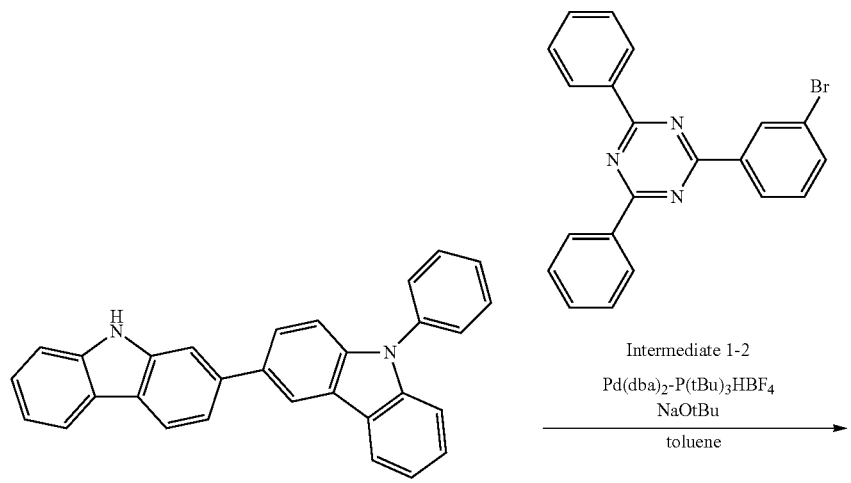

Intermediate 1-3

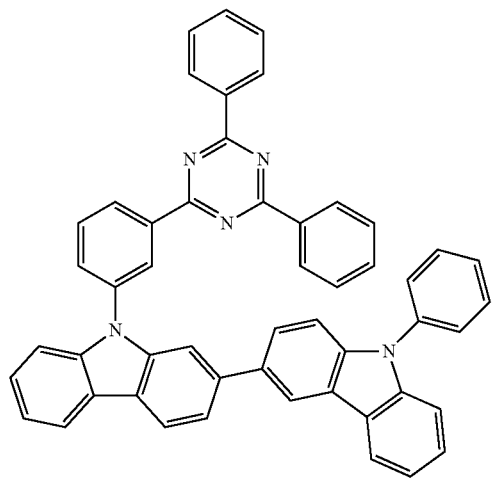

Compound GH-1

3-bromobenzaldehydro (100 g, 54 mmol) and aniline (50 g, 54 mmol) were added to toluene (1 L) and refluxed for 8 hours. After the reaction solution was cooled down, a solvent was concentrated under reduced pressure to obtain an intermediate 1-1 (130 g, a yield of 93%).

Subsequently, under an argon gas atmosphere, the intermediate body 1-1 (130 g, 50 mmol), benzamidine hydrochloride (152 g, 100 mmol), anhydrous ethanol (1 L), and sodium hydroxide (42 g) were added together in sequential order, and stirred at 80 degrees C. for 16 hours. Subsequently, sodium-t-butoxide (20 g, 208 mmol) were further added and heated at 80 degrees C. for 16 hours with stirring. After the reaction solution was cooled down to the room temperature, a solid was separated by filtration and washed with methanol to obtain an intermediate 1-2 (67 g, a yield of 37%).

Under an argon gas atmosphere, an intermediate 1-3 (1.6 g, 3.9 mmol), the intermediate 1-2 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and refluxed for 8 hours.

After the reaction solution was cooled down to the room temperature, an organic phase was removed and an organic solvent was distilled away under reduced pressure. The obtained residue was refined by silica-gel column chromatography, so that a compound GH-1 (2.3 g, a yield of 82%) was obtained.

As a result of FD-MS analysis, m/e was equal to 715 while a calculated molecular weight was 715.

Synthesis Example 2 (Synthesis of Compound GH2-1)

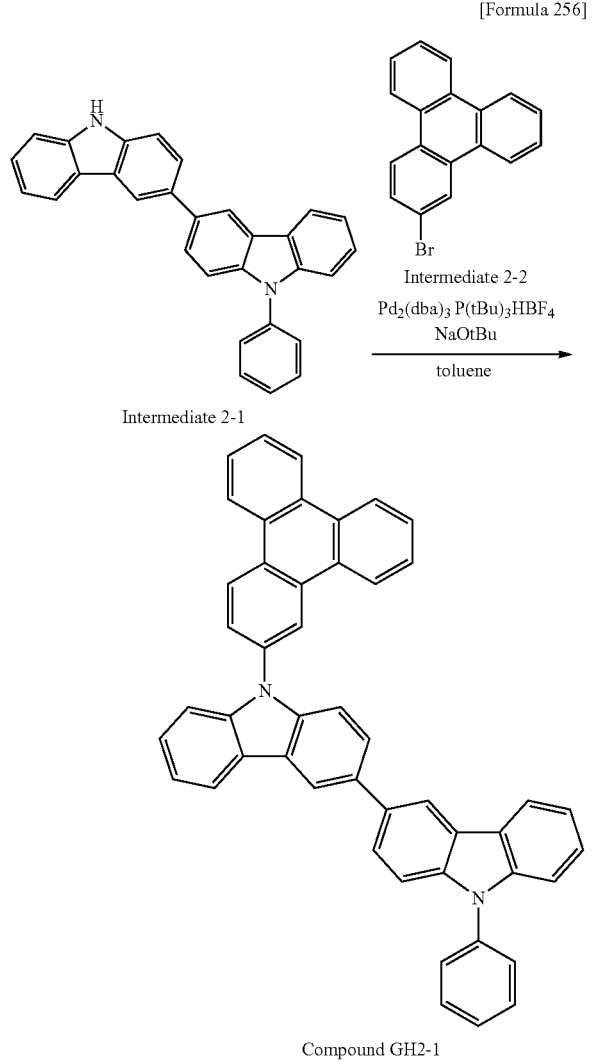

Compound GH2-1

Under an argon gas atmosphere, to a three-necked flask, an intermediate body 2-2 (2.5 g, 8.1 mmol), an intermediate 2-1 (3 g, 7.3 mmol), Pd$_2$(dba)$_3$ (0.14 g, 0.15 mmol), P(tBu)$_3$HBF4 (0.17 g, 0.6 mmol), sodium t-butoxide (1.1 g, 11 mmol), and anhydrous xylene (30 mL) were sequentially added, and refluxed for 8 hours.

Water was added to the reaction solution to precipitate solid. Then, the obtained solid was washed with hexane, followed by methanol. The obtained solid was then refined by silica-gel column chromatography, so that a compound GH2-1 (3.7 g, a yield of 80%) is obtained.

As a result of FD-MS analysis, m/e was equal to 634 while a calculated molecular weight was 634.

Synthesis Example 3 (Synthesis of Compound GH2-2)

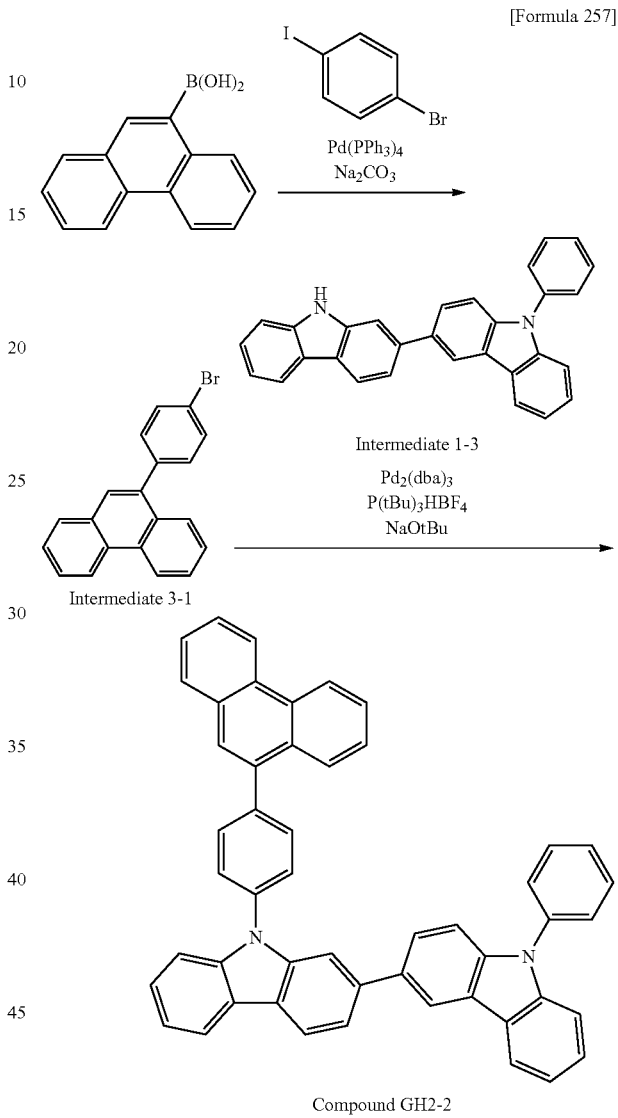

Compound GH2-2

Under an argon gas atmosphere, 9-phenanthreneboronic acid (2.7 g, 12.2 mmol), p-bromoiodobenzene (3.4 g, 12.2 mmol), tetrakis(triphenylphosphine)palladium (0.26 g, 0.24 mmol), and an aqueous solution of 2M sodium carbonate (20 mL) were added to toluene (40 mL), and heated at 80 degrees C. for 8 hours with stirring.

After the organic phase was separated and condensed with an evaporator, the obtained residue was refined by silica-gel column chromatography, whereby an intermediate 3-1 (3.0 g, a yield of 75%) was obtained.

Under an argon gas atmosphere, to a three-necked flask, an intermediate 1-3 (3.3 g, 8.1 mmol), an intermediate GH3-1 (2.4 g, 7.3 mmol), Pd$_2$(dba)$_3$ (0.14 g, 0.15 mmol), P(tBu)$_3$HBF4 (0.17 g, 0.6 mmol), sodium t-butoxide (1.1 g, 11 mmol), and anhydrous xylene (30 mL) were sequentially added, and refluxed for 8 hours.

Water was added to the reaction solution to precipitate solid. Then, the obtained solid was washed with hexane, followed by methanol. The obtained solid was then refined by silica-gel column chromatography, thereby obtaining a compound GH2-2 (3.3 g, a yield of 68%).

As a result of FD-MS analysis, m/e was equal to 660 while a calculated molecular weight was 660.

Synthesis Example 4 (Synthesis of Compound GH2-3)

[Formula 258]

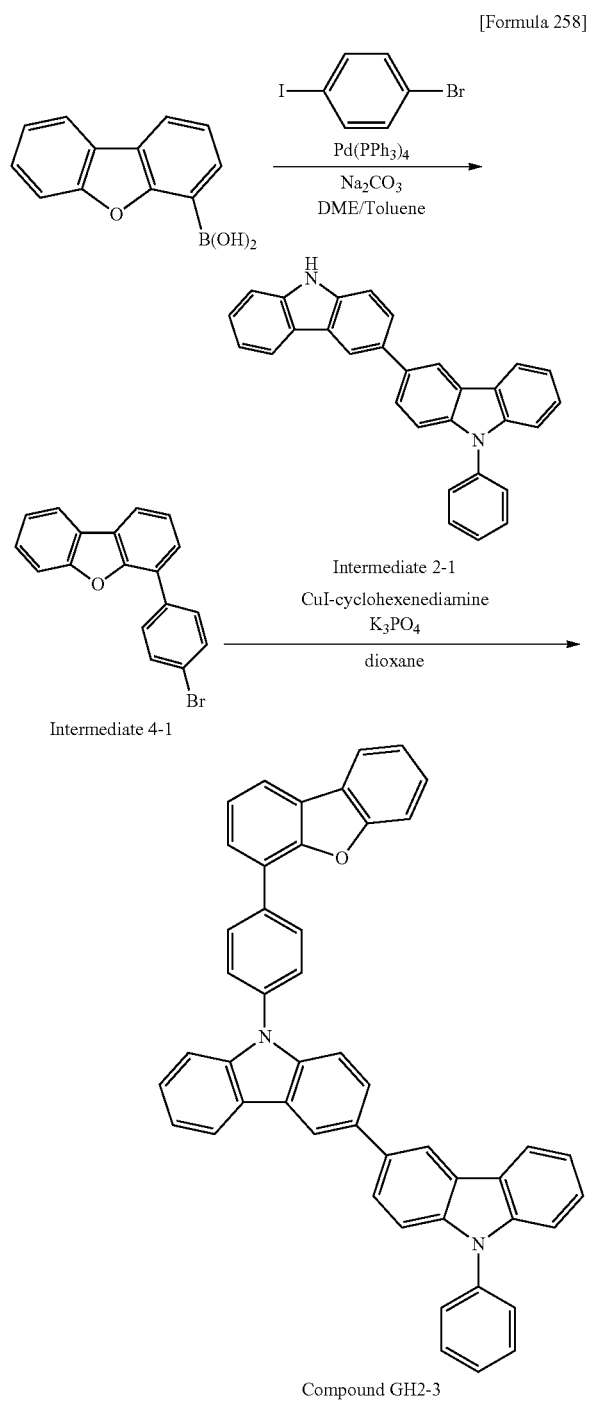

Compound GH2-3

Synthesis of Intermediate Body 4-1

Under an argon gas atmosphere, toluene (150 mL), dimethoxyethane (150 mL) and an aqueous solution of 2M sodium carbonate (150 mL) were added to 4-bromoiodobenzene (28.3 g, 100.0 mmol), dibenzofuran-4-boronic acid (22.3 g, 105 mmol), tetrakis(triphenylphosphine)palladium (0) (2.31 g, 2.00 mmol), and were refluxed for 10 hours.

After the reaction was over, the mixture was separated by filtration. The obtained aqueous phase thereof was removed. After an organic phase thereof was dried with sodium sulfate, the mixture was condensed. Residue thereof was refined by silica-gel column chromatography, so that an intermediate 4-1 (26.2 g, a yield of 81%) was obtained.

As a result of FD-MS analysis, m/e was equal to 322 while a calculated molecular weight was 322.

Synthesis of GH2-3

Under an argon gas atmosphere, to a three-necked flask, the intermediate 4-1 (2.36 g, 7.3 mmol), the intermediate 2-1 (3.0 g, 7.3 mmol), CuI (1.4 g, 7.3 mmol), tripotassium phosphate (2.3 g, 11 mmol), anhydrous dioxane (30 mL) and cyclohexane diamine (0.84 g, 7.3 mmol) were added together in sequential order, and stirred at 100 degrees C. for 8 hours.

Water was added to the reaction solution to precipitate solid. Then, the obtained solid was washed with hexane, followed by methanol. The obtained solid was then refined by silica-gel column chromatography, thereby obtaining a compound GH2-3 (2.9 g, a yield of 60%).

As a result of FD-MS analysis, m/e was equal to 650 while a calculated molecular weight was 650.

Synthesis Example 5 (Synthesis of Compound GH2-4)

[Formula 259]

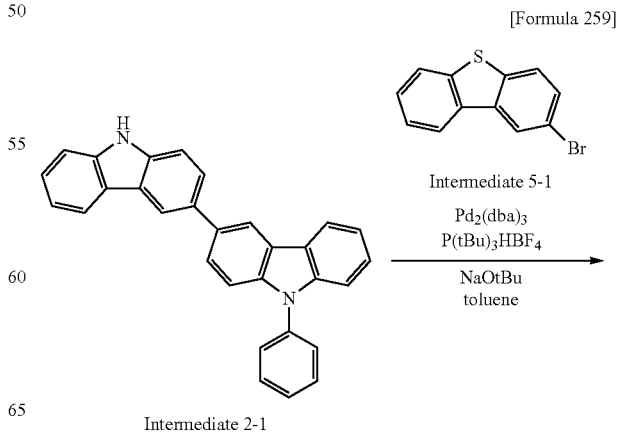

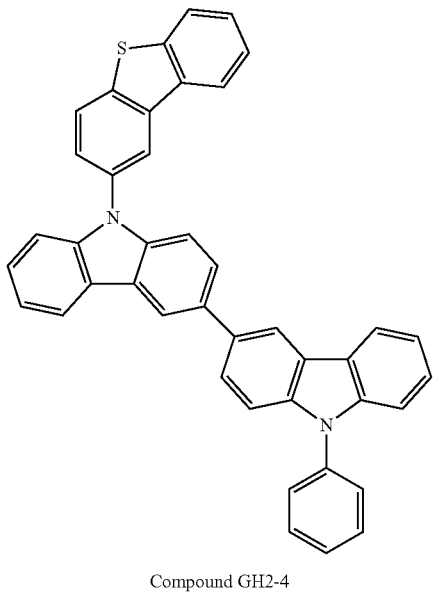

Compound GH2-4

Under an argon gas atmosphere, to a three-necked flask, an intermediate 5-1 (2.1 g, 8.1 mmol), the intermediate 2-1 (3 g, 7.3 mmol), $Pd_2(dba)_3$ (0.14 g, 0.15 mmol), $P(tBu)_3$ HBF4 (0.17 g, 0.6 mmol), sodium t-butoxide (1.1 g, 11 mmol), and anhydrous xylene (30 mL) were sequentially added, and refluxed for 8 hours.

Water was added to the reaction solution to precipitate solid. Then, the obtained solid was washed with hexane, followed by methanol. The obtained solid was then refined by silica-gel column chromatography, so that a compound GH2-4 (2.8 g, a yield of 65%) is obtained.

As a result of FD-MS analysis, m/e was equal to 590 while a calculated molecular weight was 590.

Example 1

In Example 1, an organic EL device was manufactured as follows.

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum deposition apparatus. A compound HA-1 was deposited on a surface of the glass substrate where the transparent electrode line was provided in a manner to cover the transparent electrode, thereby forming a 5-nm thick HA-1 film. The HA-1 film serves as a hole injecting layer.

A compound HT-1 was deposited on the HA-1 film to form a 65-nm thick HT-1 film. The FIT-1 film serves as the first hole transporting layer.

Next, a compound HT-2 was deposited on the HT-1 film to form a 10-nm thick HT-2 film. The HT-2 film serves as the second hole transporting layer.

The compound GH1-1 (the first host material), the compound GH2-1 (the second host material) and $Ir(bzq)_3$ (the phosphorescent dopant material) were co-deposited on the second hole transporting layer. Thus, a 25-nm thick emitting layer exhibiting yellow emission was formed. The concentration of each of the second host material and the phosphorescent dopant material was set at 10 mass %. The first host material accounted for the rest.

A compound ET-1 was deposited on the hole blocking layer to form a 35-nm thick first electron transporting layer.

A compound ET-2 was deposited on the first electron transporting layer to form a 30-nm thick second electron transporting layer. LiF was deposited at a rate of 1 Å/min on the electron transporting layer to form a 1-nm electron injecting cathode. A metal Al was deposited on the electron injecting cathode to form an 80-nm thick cathode.

Comparative 1

An organic EL device was manufactured in the same manner as Example 1, except that the compound GH2-1 (the second host material) was not used.

Table 1 shows the device arrangement of Example 1 and Comparative Example 1. The numerals without unit in parentheses in Table 1 indicate a thickness of each layer (unit: nm). The numerals with % indicate a mass % concentration of the compounds. With respect to the emitting layer, the mass % concentration of each of the second host material and the phosphorescent dopant material is indicated, but description of the concentration of the first host material is omitted.

Evaluation of Organic EL Device

The prepared organic EL devices were evaluated in terms of drive voltage, external quantum efficiency EQE and lifetime. The current density was set at 10.00 $mA/cm^2$ on each evaluation item. The results are shown in Table 2.

Drive Voltage

Voltage was applied between ITO and Al such that a current density was 1.00 $mA/cm^2$ or 10.00 $mA/cm^2$, where the voltage (unit: V) was measured. External Quantum Efficiency EQE The external quantum efficiency EQE (unit: %) was calculated from the obtained spectral-radiance spectrum, assuming that Lambertian radiation was carried out.

Lifetime

Time (LT90) elapsed before the luminance intensity was decreased to 90% was obtained based on the initial luminance intensity 10,000 nit ($cd/m^2$).

Examples 2 to 7

In Examples 2 to 7, the organic EL devices were formed in the same manner as in Example 1 except that the materials used in Example 1 were replaced as shown in Table 2.

Compounds used in Examples 1 to 7 and Comparative Example 1 are shown below. In Examples 1 to 7, the compounds GH1-1, GH1-2 and GH1-3 contained in the emitting layer are the first host material of the invention and the compounds GH2-1, GH2-2, GH2-3 and GH2-4 are the second host material of the invention.

These organic EL devices were evaluated in the same manner as in Example 1 and Comparative Example 1. The results are shown in Table 2.

[Formula 260]
GH1-1
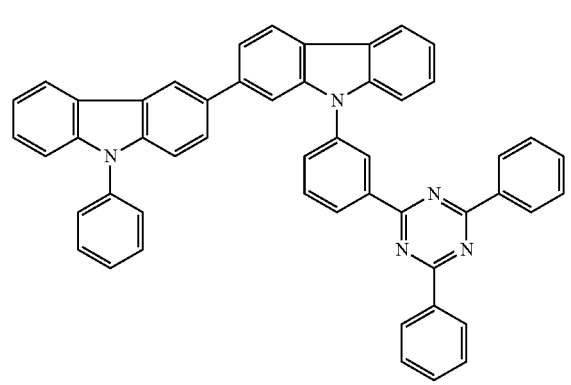
GH1-2
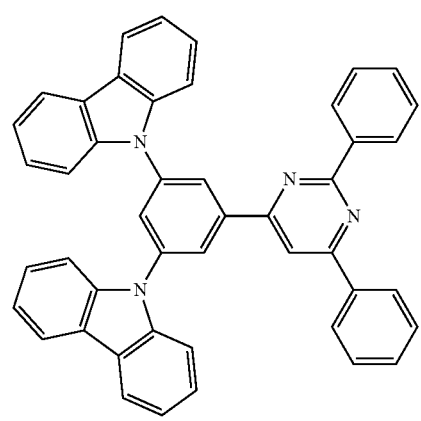
GH1-3
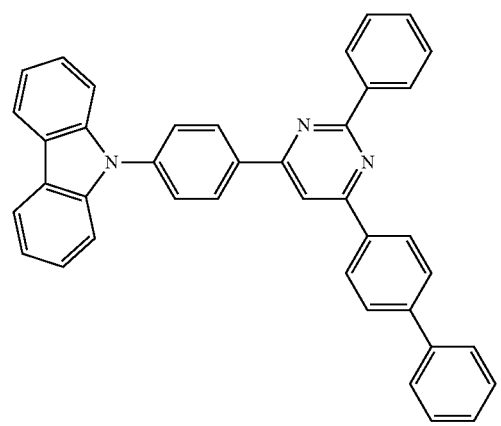
[Formula 261]
GH2-1
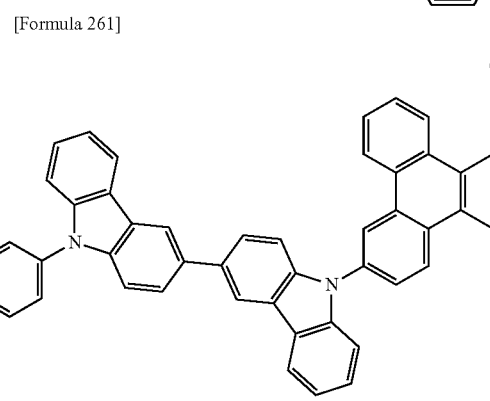
GH2-2
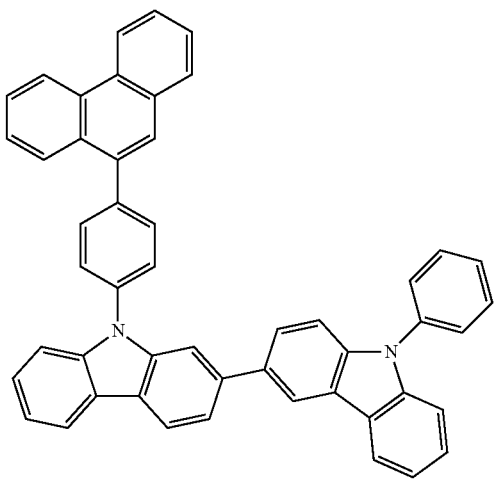
GH2-3
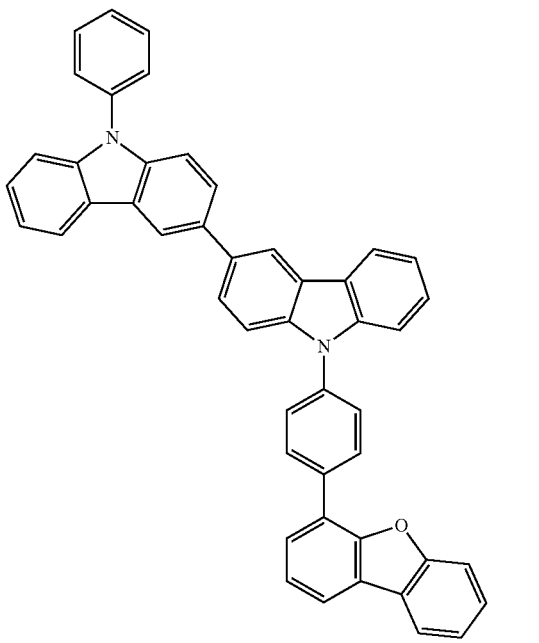
GH2-4
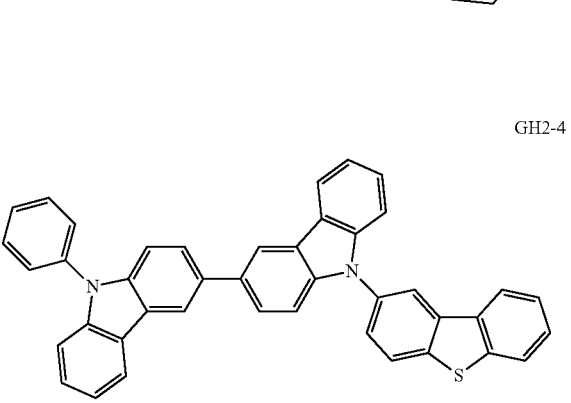

[Formula 262]

HA-1

HT-1

HT-2

ET-1

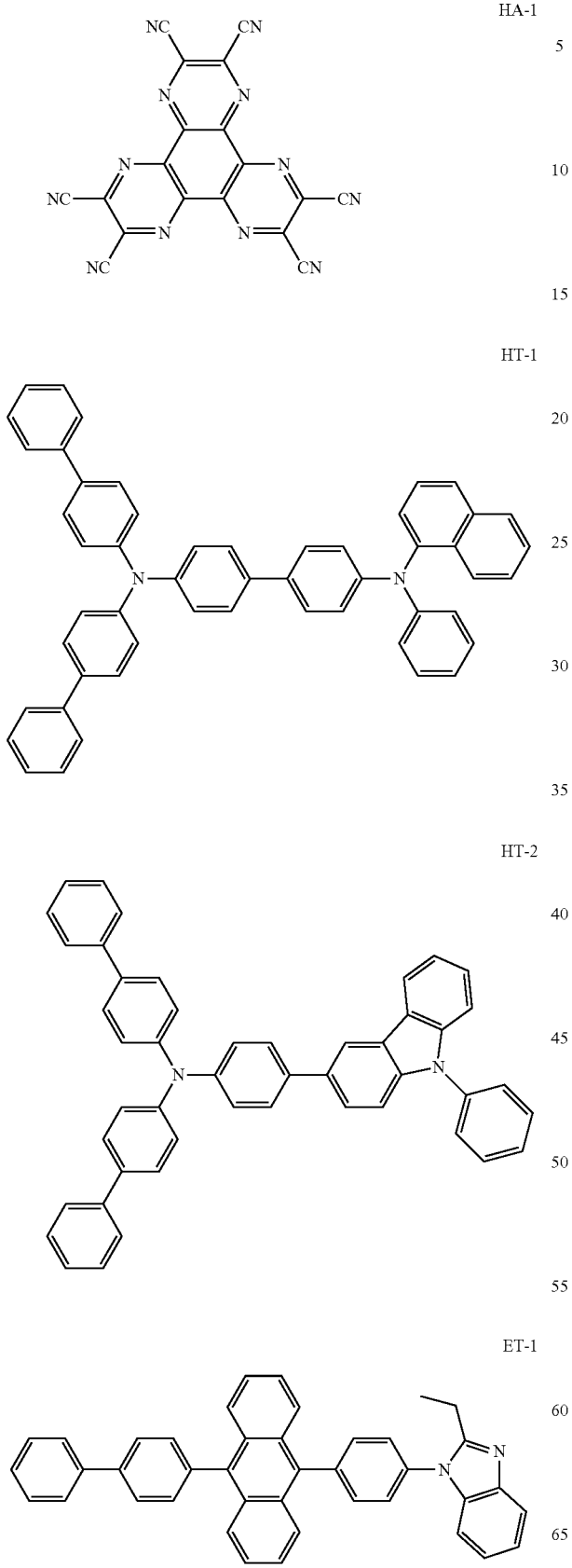

ET-2

[Formula 263]

Ir(bzq)₃

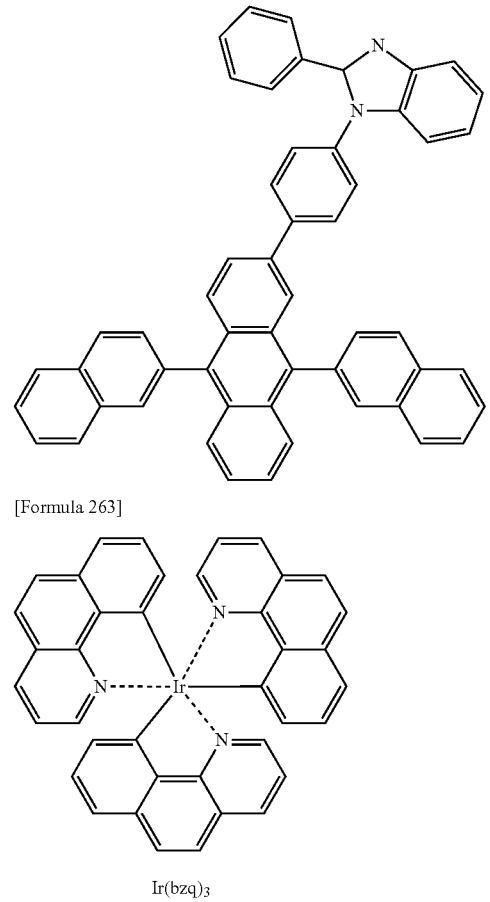

TABLE 1

| | Device Arrangement |
|---|---|
| Example 1 | ITO(75)/HA-1(5)/HT-1(65)/HT-2(10)/<br>GH1-1:GH2-1:Ir(bzq)3(25.10%:10%)/ET-1(35)/ET-2(30)/<br>LiF(1)/Al(80) |
| Comp. 1 | ITO(75)/HA-1(5)/HT-1(65)/HT-2(10)/<br>GH1-1:Ir(bzq)3(25.10%)/ET-1(35)/ET-2(30)/LiF(1)/<br>Al(80) |

TABLE 2

| | First Host Material | Second Host Material | Currnet Density (mA/cm²) | Drive Voltage (V) | EQE (%) | LT90 @10000nit (hrs) |
|---|---|---|---|---|---|---|
| Example 1 | GH1-1 | GH2-1 | 10 | 3.45 | 20.8 | 1200 |
| Example 2 | GH1-1 | GH2-2 | 10 | 3.64 | 20.8 | 500 |
| Example 3 | GH1-1 | GH2-3 | 10 | 3.23 | 21.8 | 900 |
| Example 4 | GH1-1 | GH2-4 | 10 | 3.27 | 23.1 | 800 |
| Example 5 | GH1-2 | GH2-3 | 10 | 3.34 | 20.9 | 200 |
| Example 6 | GH1-3 | GH2-3 | 10 | 3.29 | 22.0 | 200 |
| Example 7 | GH1-3 | GH2-4 | 10 | 3.32 | 21.8 | 150 |
| Comp. 1 | GH1-1 | — | 10 | 3.40 | 20.5 | 100 |

It is understood from Table 2 that the organic EL device of each of Examples has a longer lifetime than a lifetime of the organic EL device of Comparative Example while keeping a high efficiency.

The invention claimed is:
1. An organic electroluminescence device, comprising:
an anode;
a cathode; and
at least an emitting layer between the anode and the cathode, the emitting layer comprising:
a first host material;
a second host material; and
a phosphorescent dopant material,
wherein:
the first host material is a compound represented by formula (3):

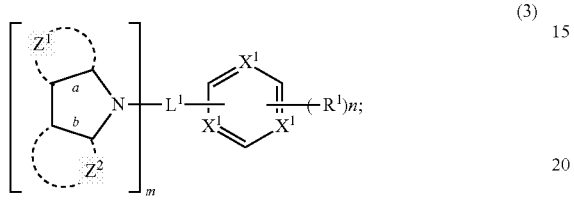

the second host material is a compound represented by formula (2):

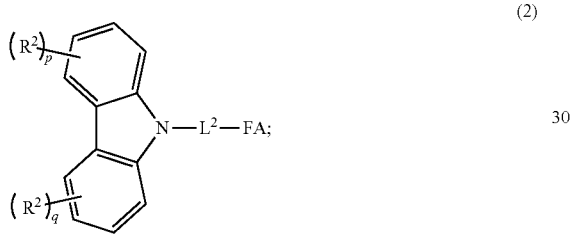

$Z^1$ represents a cyclic structure fused at a of the formula (3) and is represented by formula (1-1) or (1-2):

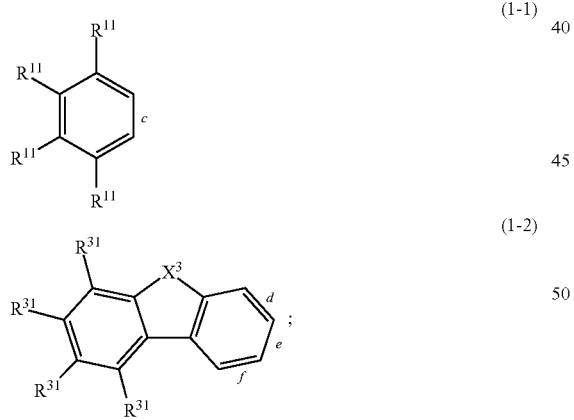

$Z^2$ represents a cyclic structure fused at b of the formula (3) and is represented by the formula (1-1) or (1-2);
at least one of $Z^1$ and $Z^2$ is represented by the formula (1-1);
$L^1$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms;
m is 1 or 2;
n is 2;
c, d, e, f are fused at a or b in the formula (3);
$R^{11}$ and $R^{31}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkenyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
a plurality of $R^{11}$ are mutually the same or different;
a plurality of $R^{31}$ are mutually the same or different;
adjacent groups of $R^{11}$ are optionally bonded with each other to form a ring;
$X^1$ is a nitrogen atom or C—$R^{10}$ and at least one of a plurality of $X^1$ is a nitrogen atom:
$R^1$ each independently represent a hydrogen atom, a halogen atom, a cyano group, a substituted or unsubstituted aryl group having 6 to 30 ring carbon atoms, a substituted or unsubstituted alkyl group having 1 to 30 carbon atoms, a substituted or unsubstituted alkenyl group having 2 to 30 carbon atoms, a substituted or unsubstituted alkenyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
a plurality of $R^1$ are mutually the same or different;
adjacent groups of $R^1$ are optionally bonded with each other to form a ring;
$R^{10}$ represent the same as $R^{11}$ of the formula (1-1);
$X^3$ is a sulfur atom, an oxygen atom, N—$R^{32}$ or C($R^{32}$)$_2$;
$R^{32}$ represents the same as $R^{11}$ and $R^{31}$; $R^2$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
at least one of $R^2$ at 2-position, 3-position, 4-position, 5-position, 6-position, and 7-position represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group; $R^2$ at 1-position and 8-position do not represent a substituted or unsubstituted carbazolyl group;

p and q are 4;

a plurality of $R^2$ are mutually the same or different;

adjacent groups of $R^2$ are optionally bonded with each other to form a ring;

$L^2$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms; and FA represents a substituted or unsubstituted fused aromatic cyclic group having 14 to 30 ring carbon atoms, or a substituted or unsubstituted fused aromatic heterocyclic group having 9 to 30 ring atoms except for a substituted or unsubstituted carbazolyl group.

2. The organic electroluminescence device according to claim 1, wherein the first host material is represented by formula (4):

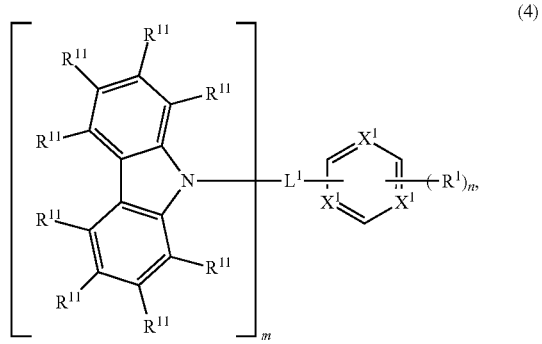

(4)

wherein:

$L^1$ represents the same as $L^1$ of the formula (3);

$X^1$ is a nitrogen atom or C—$R^{10}$ and at least one of a plurality of $X^1$ is a nitrogen atom;

$R^1$ represents the same as $R^1$ of the formula (3);

$R^{10}$ and $R^{11}$ represent the same as $R^{11}$ of the formula (1-1);

m is 1 or 2; and n is 2.

3. The organic electroluminescence device according to claim 1, wherein:

the first host material is represented by formula (5):

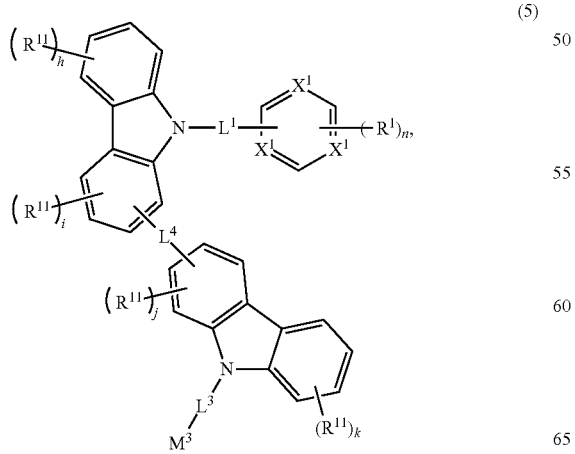

(5)

wherein:

$L^1$ and $R^1$ respectively represent the same as $L^1$ and $R^1$ of the formula (3);

$R^{11}$ represents the same as $R^{11}$ of the formula (1-1);

$L^3$ and $L^4$ represent the same as $L^1$ of the formula (3);

$X^1$ is a nitrogen atom or C—$R^{10}$ and at least one of a plurality of $X^1$ is a nitrogen atom:

$R^{10}$ represents the same as $R^{11}$ of the formula (1-1);

n is 2;

$M^3$ represents a substituted or unsubstituted aryl group having 6 to 30 ring carbon atoms, or a substituted or unsubstituted heterocyclic group having 5 to 30 ring atoms;

h and k are 4; and i and j are 3.

4. The organic electroluminescence device according to claim 1, wherein the second host material is represented by the formula (2) in which FA is a substituted or unsubstituted fused aromatic cyclic group having 2 to 5 fused rings, or a substituted or unsubstituted fused aromatic heterocyclic group having 2 to 5 fused rings.

5. The organic electroluminescence device according to claim 1 wherein:

the second host material is represented by the formula (2) which FA is represented by formula (2-A):

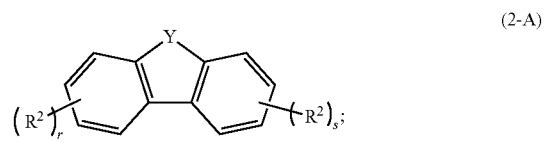

(2-A)

Y represents O, S, or C($R^{21}$)$_2$;

$R^2$ and $R^{21}$ represent the same as $R^2$ of the formula (2);

one of $R^2$ is a single bond to be bonded with $L^2$ in the formula (2);

when Y is C($R^{21}$)$_2$, a plurality of $R^{21}$ are mutually the same or different; and r and s are 4.

6. The organic electroluminescence device according to claim 1, wherein:

the second host material is represented by the formula (2) in which FA is represented by any one of formulae (2-1), (2-2) and (2-4):

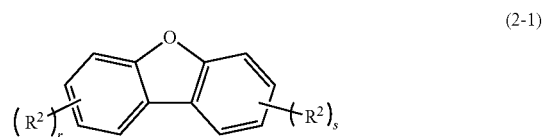

(2-1)

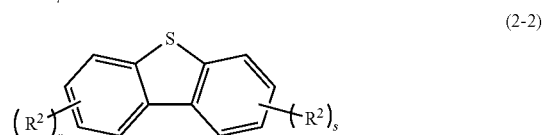

(2-2)

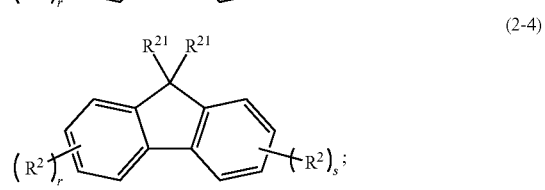

(2-4)

$R^2$ and $R^{21}$ represent the same as $R^2$ of the formula (2);
one of $R^2$ is a single bond to be bonded with $L^2$ in the formula (2); and
r and s are 4.

7. The organic electroluminescence device according to claim 6, wherein the second host material is represented by the formula (2) in which FA is represented by the formula (2-1) or the formula (2-2).

8. The organic electroluminescence device according to claim 1, wherein an emission peak wavelength of the phosphorescent dopant material is in a range of 490 nm to 700 nm.

9. A material for an organic electroluminescence device, comprising a compound represented by formula (3) and a compound represented by formula (2):

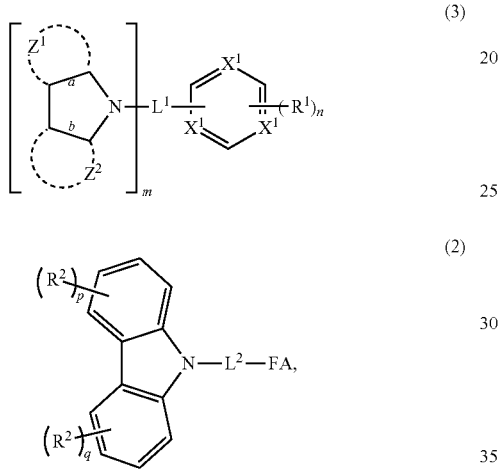

(3)

(2)

wherein:
$Z^1$ represents a cyclic structure fused at a of the formula (3) and represented by formula (1-1) or formula (1-2):

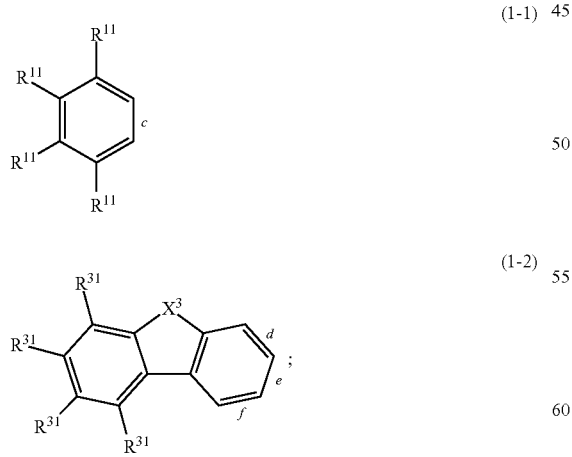

(1-1)

(1-2)

$Z^2$ represents a cyclic structure fused at b of the formula (3) and represented by the formula (1-1) or the formula (1-2);

at least one of $Z^1$ and $Z^2$ is represented by the formula (1-1);

$L^1$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms;

m is 1 or 2;

n is 2; c, d, e, f are fused at a or b in the formula (3);

$R^{11}$ and $R^{31}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

a plurality of $R^{11}$ are mutually the same or different;
a plurality of $R^{31}$ are mutually the same or different;
adjacent groups of $R^{11}$ are optionally bonded with each other to form a ring;

$X^1$ is a nitrogen atom or C—$R^{10}$ and at least one of a plurality of $X^1$ is a nitrogen atom;

$R^1$ each independently represent a hydrogen atom, a halogen atom, a cyano group, a substituted or unsubstituted aryl group having 6 to 30 ring carbon atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

a plurality of $R^1$ are mutually the same or different;
adjacent groups of $R^1$ are optionally bonded with each other to form a ring;

$R^{10}$ represent the same as $R^{11}$ of the formula (1-1);
$X^3$ is a sulfur atom, an oxygen atom, N—$R^{32}$ or C($R^{32}$)$_2$;
$R^{32}$ represents the same as $R^{11}$ and $R^{31}$, $R^2$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

at least one of $R^2$ at 2-position, 3-position, 4-position, 6-position, and 7-position represents a substituted or unsubstituted 1-carbazolyl, a substituted or unsubstituted 2-carbazolyl group, a substituted or unsubstituted 3-carbazolyl group, or a substituted or unsubstituted 4-carbazolyl group;

$R^2$ at 1-position and 8-position do not represent a substituted or unsubstituted carbazolyl group;

p and q are 4;

a plurality of $R^2$ are mutually the same or different;

$L^2$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms;

adjacent groups of $R^2$ are optionally bonded with each other to form a ring;

FA represents a substituted or unsubstituted fused aromatic cyclic group having 14 to 30 ring carbon atoms, and a substituted or unsubstituted fused aromatic heterocyclic group having 9 to 30 ring atoms except for a substituted or unsubstituted carbazolyl group.

10. The material for the organic electroluminescence device according to claim 9, wherein:

the compound represented by the formula (3) is represented by formula (4):

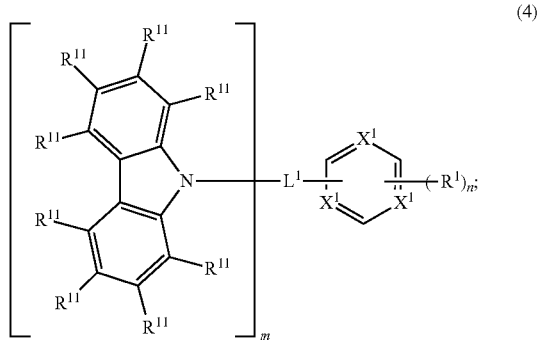

(4)

$L^1$ represents the same as $L^1$ of the formula (3);

$X^1$ is a nitrogen atom or C—$R^{10}$ and at least one of a plurality of $X^1$ is a nitrogen atom;

$R^1$ represents the same as $R^1$ of the formula (3);

$R^{10}$ and $R^{11}$ represent the same as $R^{11}$ of the formula (1-1);

m is 1 or 2; and n is 2.

11. The material for the organic electroluminescence device according to claim 9, wherein:

the compound represented by the formula (3) is represented by formula (5):

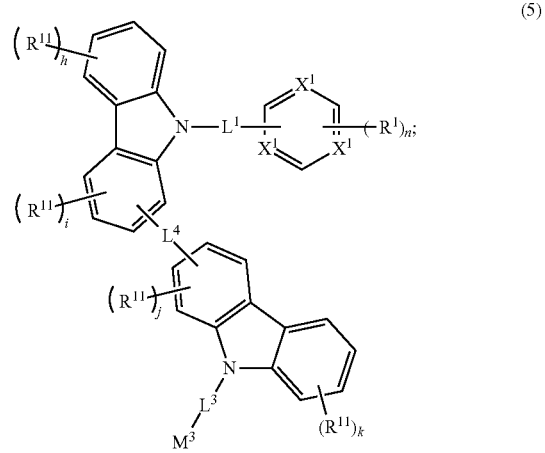

(5)

$L^1$ and $R^1$ respectively represent the same as $L^1$ and $R^1$ of the formula (3);

$R^{11}$ represents the same as $R^{11}$ of the formula (1-1);

$L^3$ and $L^4$ represent the same as $L^1$ of the formula (3);

$X^1$ is a nitrogen atom or C—$R^{10}$ and at least one of a plurality of $X^1$ is a nitrogen atom;

$R^{10}$ represents the same as $R^{11}$ of the formula (1-1);

n is 2;

$M^3$ represents a substituted or unsubstituted aryl group having 6 to 30 ring carbon atoms, or a substituted or unsubstituted heterocyclic group having 5 to 30 ring atoms;

h and k are 4; and i and j are 3.

12. The material for the organic electroluminescence device according to claim 9, wherein the second host material is represented by the formula (2) in which FA is a substituted or unsubstituted fused aromatic cyclic group having 2 to 5 fused rings, or a substituted or unsubstituted fused aromatic heterocyclic group having 2 to 5 fused rings.

13. The material for the organic electroluminescence device according to claim 9, wherein:

the second host material is represented by the formula (2) in which FA is represented by formula (2-A):

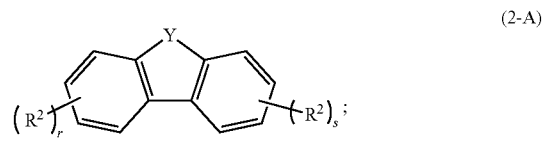

(2-A)

Y represents O, S or C($R^{21}$)$_2$;

$R^2$ and $R^{21}$ represent the same as $R^2$ of the formula (2);

one of $R^2$ is a single bond to be bonded with $L^2$ in the formula (2);

when Y is C($R^{21}$)$_2$, a plurality of $R^{21}$ are mutually the same or different; and r and s are 4.

14. The material for the organic electroluminescence device according to claim 9, wherein:

the second host material is represented by the formula (2) in which FA is represented by any one of formulae (2-1), (2-2) and (2-4):

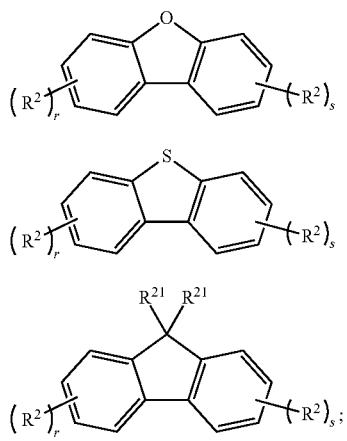

(2-1)

(2-2)

(2-4)

$R^2$ and $R^{21}$ represent the same as $R^2$ of the formula (2);
one of $R^2$ is a single bond to be bonded with $L^2$ in the formula (2); and
r and s are 4.

15. The material for the organic electroluminescence device according to claim 14, wherein the second host material is represented by the formula (2) in which FA is represented by the formula (2-1) or the formula (2-2).

16. The organic electroluminescence device according to claim 2, wherein $R^{10}$ do not represent a substituted or unsubstituted heterocyclic group having 5 to 30 ring atoms.

17. The organic electroluminescence device according to claim 1, wherein
  $Z^1$ is represented by formula (1-1);
  $Z^2$ is represented by formula (1-2);
  $R^{11}$ and $R^{31}$ each independently represent a hydrogen atom, an unsubstituted aryl group having 6 to 30 ring carbon atoms, or an unsubstituted alkyl group having 1 to 30 carbon atoms;
  $R^{32}$ each independently represent an unsubstituted aryl group having 6 to 30 ring carbon atoms, or an unsubstituted alkyl group having 1 to 30 carbon atoms;
  at least two of a plurality of $X^1$ are each a nitrogen atom;
  the rest of $X^1$ is C—$R^{10}$, wherein $R^{10}$ is a hydrogen atom;
  $R^1$ each independently represent an unsubstituted aryl group having 6 to 30 ring carbon atoms;
  $L^1$ represents a single bond or an unsubstituted aryl group having 6 to 30 ring carbon atoms;
  $L^2$ represents a single bond or an unsubstituted aryl group having 6 to 30 ring carbon atoms;
  one of $R^2$ at 2-position, 3-position, 4-position, 5-position, 6-position, and 7-position
  represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group;
  $R^2$ at 1-position and 8-position represent a hydrogen atom;
  the rest of $R^2$ each independently represent a hydrogen atom, an unsubstituted aryl group having 6 to 30 ring carbon atoms, or an unsubstituted alkyl group having 1 to 30 carbon atoms; and
  FA represents an unsubstituted fused aromatic cyclic group having 14 to 30 ring carbon atoms, or an unsubstituted fused aromatic heterocyclic group having 9 to 30 ring atoms.

18. The organic electroluminescence device according to claim 1, wherein
  $Z^1$ is represented by formula (1-1)
  $Z^2$ is represented by formula (1-2)
  $R^{11}$ and $R^{31}$ represent a hydrogen atom;
  $R^{32}$ each independently represent an unsubstituted phenyl group or an unsubstituted methyl group;
  all of $X^1$ are nitrogen atoms;
  $R^1$ each independently represent an unsubstituted phenyl group or an unsubstituted biphenyl group;
  $L^1$ represents a single bond or an unsubstituted phenyl group;
  m is 1;
  $L^2$ represents a single bond or an unsubstituted phenyl group;
  one of $R^2$ at 2-position, 3-position, 4-position, 5-position, 6-position, and 7-position
  represents a 1-carbazolyl group having a substituted or unsubstituted phenyl group, a 2-carbazolyl group having a substituted or unsubstituted phenyl group, a 3-carbazolyl group having a substituted or unsubstituted phenyl group, or a 4-carbazolyl group having a substituted or unsubstituted phenyl group;
  the rest of $R^2$ represent a hydrogen atom; and
  FA represents an unsubstituted fused aromatic cyclic group having 14 to 20 ring carbon atoms, or an unsubstituted fused aromatic heterocyclic group having 9 to 14 ring atoms.

19. The organic electroluminescence device according to claim 1, wherein
  $Z^1$ is represented by formula (1-1);
  $R^{11}$ each independently represent a hydrogen atom, an unsubstituted aryl group having 6 to 30 ring carbon atoms, an unsubstituted alkyl group having 1 to 30 carbon atoms, or a carbazolyl group having an unsubstituted phenyl group;
  $R^{31}$ each independently represent a hydrogen atom, an unsubstituted aryl group having 6 to 30 ring carbon atoms, or an unsubstituted alkyl group having 1 to 30 carbon atoms;
  $R^{32}$ each independently represent an unsubstituted aryl group having 6 to 30 ring carbon atoms, or an unsubstituted alkyl group having 1 to 30 carbon atoms;
  at least two of a plurality of $X^1$ are each a nitrogen atom;
  the rest of $X^1$ is C—$R^{10}$, wherein $R^{10}$ is a hydrogen atom;
  $R^1$ each independently represent an unsubstituted aryl group having 6 to 30 ring carbon atoms;
  $L^1$ represents a single bond or an unsubstituted aryl group having 6 to 30 ring carbon atoms;
  $L^2$ represents a single bond or an unsubstituted aryl group having 6 to 30 ring carbon atoms;
  one of $R^2$ at 2-position, 3-position, 4-position, 5-position, 6-position, and 7-position
  represents a substituted or unsubstituted 1-carbazolyl group, a substituted or unsubstituted 2-carbazolyl group, a substituted or unsubstituted 3-carbazolyl group or a substituted or unsubstituted 4-carbazolyl group;
  $R^2$ at 1-position and 8-position represent a hydrogen atom;
  the rest of $R^2$ each independently represent a hydrogen atom, an unsubstituted aryl group having 6 to 30 ring carbon atoms, or an unsubstituted alkyl group having 1 to 30 carbon atoms; and FA represents an unsubstituted fused aromatic cyclic group having 14 to 30 ring carbon atoms, or an unsubstituted fused aromatic heterocyclic group having 9 to 30 ring atoms.

20. The organic electroluminescence device according to claim 1, wherein
$Z^1$ is represented by formula (1-1)
$Z^2$ is represented by formula (1-2);
$R^{11}$ each independently represent a hydrogen atom, an unsubstituted aryl group having 6 to 30 ring carbon atoms, an unsubstituted alkyl group having 1 to 30 carbon atoms, or a carbazolyl group having an unsubstituted phenyl group;
$R^{31}$ represent a hydrogen atom;
$R^{32}$ each independently represent an unsubstituted phenyl group or an unsubstituted methyl group;
at least two of a plurality of $X^1$ are each a nitrogen atom;
the rest of $X^1$ is C—$R^{10}$, wherein $R^{10}$ is a hydrogen atom;
$R^1$ each independently represent an unsubstituted phenyl group or an unsubstituted biphenyl group;
$L^1$ represents a single bond or an unsubstituted phenyl group;
$L^2$ represents a single bond or an unsubstituted phenyl group;
one of $R^2$ at 2-position, 3-position, 4-position, 5-position, 6-position, and 7-position
represents a 1-carbazolyl group having a substituted or unsubstituted phenyl group, a 2-carbazolyl group having a substituted or unsubstituted phenyl group, a 3-carbazolyl group having a substituted or unsubstituted phenyl group, or a 4-carbazolyl group having a substituted or unsubstituted phenyl group;
the rest of $R^2$ represent a hydrogen atom; and
FA represents an unsubstituted fused aromatic cyclic group having 14 to 20 ring carbon atoms, or an unsubstituted fused aromatic heterocyclic group having 9 to 14 ring atoms.

21. The material for the organic electroluminescence device according to claim 9, wherein
$Z^1$ is represented by formula (1-1);
$Z^2$ is represented by formula (1-2);
$R^{11}$ and $R^{31}$ each independently represent a hydrogen atom, an unsubstituted aryl group having 6 to 30 ring carbon atoms, or an unsubstituted alkyl group having 1 to 30 carbon atoms:
$R^{32}$ each independently represent an unsubstituted aryl group having 6 to 30 ring carbon atoms, or an unsubstituted alkyl group having 1 to 30 carbon atoms;
at least two of a plurality of $X^1$ are each a nitrogen atom;
the rest of $X^1$ is C—$R^{10}$, wherein $R^{10}$ is a hydrogen atom;
$R^1$ each independently represent an unsubstituted aryl group having 6 to 30 ring carbon atoms;
$L^1$ represents a single bond or an unsubstituted aryl group having 6 to 30 ring carbon atoms;
$L^2$ represents a single bond or an unsubstituted aryl group having 6 to 30 ring carbon atoms;
one of $R^2$ at 2-position, 3-position, 4-position, 5-position, 6-position, and 7-position
represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group;
$R^2$ at 1-position and 8-position represent a hydrogen atom;

the rest of $R^2$ each independently represent a hydrogen atom, an unsubstituted aryl group having 6 to 30 ring carbon atoms, or an unsubstituted alkyl group having 1 to 30 carbon atoms; and
FA represents an unsubstituted fused aromatic cyclic group having 14 to 30 ring carbon atoms, or an unsubstituted fused aromatic heterocyclic group having 9 to 30 ring atoms.

22. The material for the organic electroluminescence device according to claim 9, wherein
$Z^1$ is represented by formula (1-1);
$Z^2$ is represented by formula (1-2);
$R^{11}$ and $R^{31}$ represent a hydrogen atom;
$R^{32}$ each independently represent an unsubstituted phenyl group or an unsubstituted methyl group;
all of $X^1$ are nitrogen atoms;
$R^1$ each independently represent an unsubstituted phenyl group or an unsubstituted biphenyl group;
$L^1$ represents a single bond or an unsubstituted phenyl group;
m is 1;
$L^2$ represents a single bond or an unsubstituted phenyl group;
one of $R^2$ at 2-position, 3-position, 4-position, 5-position, 6-position, and 7-position
represents a 1-carbazolyl group having a substituted or unsubstituted phenyl group, a 2-carbazolyl group having a substituted or unsubstituted phenyl group, a 3-carbazolyl group having a substituted or unsubstituted phenyl group, or a 4-carbazolyl group having a substituted or unsubstituted phenyl group;
the rest of $R^2$ represent a hydrogen atom; and
FA represents an unsubstituted fused aromatic cyclic group having 14 to 20 ring carbon atoms, or an unsubstituted fused aromatic heterocyclic group having 9 to 14 ring atoms.

23. The material for the organic electroluminescence device according to claim 9, wherein
$Z^1$ is represented by formula (1-1);
$R^{11}$ each independently represent a hydrogen atom, an unsubstituted aryl group having 6 to 30 ring carbon atoms, an unsubstituted alkyl group having 1 to 30 carbon atoms, or a carbazolyl group having an unsubstituted phenyl group;
$R^{31}$ each independently represent a hydrogen atom, an unsubstituted aryl group having 6 to 30 ring carbon atoms, or an unsubstituted alkyl group having 1 to 30 carbon atoms;
$R^{32}$ each independently represent an unsubstituted aryl group having 6 to 30 ring carbon atoms, or an unsubstituted alkyl group having 1 to 30 carbon atoms;
at least two of a plurality of $X^1$ are each a nitrogen atom;
the rest of $X^1$ is C—$R^{10}$, wherein $R^{10}$ is a hydrogen atom;
$R^1$ each independently represent an unsubstituted aryl group having 6 to 30 ring carbon atoms;
$L^1$ represents a single bond or an unsubstituted aryl group having 6 to 30 ring carbon atoms;
$L^2$ represents a single bond or an unsubstituted aryl group having 6 to 30 ring carbon atoms;
one of $R^2$ at 2-position, 3-position, 4-position, 5-position, 6-position, and 7-position
represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group;

$R^2$ at 1-position and 8-position represent a hydrogen atom;

the rest of $R^2$ each independently represent a hydrogen atom, an unsubstituted aryl group having 6 to 30 ring carbon atoms, or an unsubstituted alkyl group having 1 to 30 carbon atoms; and FA represents an unsubstituted fused aromatic cyclic group having 14 to 30 ring carbon atoms, or an unsubstituted fused aromatic heterocyclic group having 9 to 30 ring atoms.

24. The material for the organic electroluminescence device according to claim 9, wherein $Z^1$ is represented by formula (1-1);

$Z^2$ is represented by formula (1-2);

$R^{11}$ each independently represent a hydrogen atom, an unsubstituted aryl group having 6 to 30 ring carbon atoms, an unsubstituted alkyl group having 1 to 30 carbon atoms, or a carbazolyl group having an unsubstituted phenyl group;

$R^{31}$ represent a hydrogen atom;

$R^{32}$ each independently represent an unsubstituted phenyl group or an unsubstituted methyl group;

at least two of a plurality of $X^1$ are each a nitrogen atom;

the rest of $X^1$ is $C—R^{10}$, wherein $R^{10}$ is a hydrogen atom;

$R^1$ each independently represent an unsubstituted phenyl group or an unsubstituted biphenyl group;

$L^1$ represents a single bond or an unsubstituted phenyl group;

$L^2$ represents a single bond or an unsubstituted phenyl group;

one of $R^2$ at 2-position, 3-position, 4-position, 5-position, 6-position, and 7-position represents a 1-carbazolyl group having a substituted or unsubstituted phenyl group, a 2-carbazolyl group having a substituted or unsubstituted phenyl group, a 3-carbazolyl group having a substituted or unsubstituted phenyl group, or a 4-carbazolyl group having a substituted or unsubstituted phenyl group;

the rest of $R^2$ represent a hydrogen atom; and

FA represents an unsubstituted fused aromatic cyclic group having 14 to 20 ring carbon atoms, or an unsubstituted fused aromatic heterocyclic group having 9 to 14 ring atoms.

* * * * *